United States Patent
Anderson et al.

(10) Patent No.: US 7,214,518 B2
(45) Date of Patent: May 8, 2007

(54) CRYSTAL STRUCTURE OF AURORA A KINASE AND USES THEREOF

(75) Inventors: Malcom Anderson, Cheshire (GB); Nicholas John Keen, Cheshire (GB); Andrew David Bruce Pannifer, Cheshire (GB); Richard Alexander Pauptit, Cheshire (GB); Sian Rowsell, Cheshire (GB)

(73) Assignee: AstraZeneca AB, Sodertajle (SE)

( * ) Notice: Subject to any disclaimer, the term of this patent is extended or adjusted under 35 U.S.C. 154(b) by 0 days.

(21) Appl. No.: 10/491,854

(22) PCT Filed: Oct. 8, 2002

(86) PCT No.: PCT/GB02/04589

§ 371 (c)(1),
(2), (4) Date: Oct. 29, 2004

(87) PCT Pub. No.: WO03/031606

PCT Pub. Date: Apr. 17, 2003

(65) Prior Publication Data

US 2006/0078975 A1    Apr. 13, 2006

(30) Foreign Application Priority Data

Oct. 10, 2001   (GB)   ................................. 0124299.9

(51) Int. Cl.
    *C12N 9/00*   (2006.01)
(52) U.S. Cl. ..................................................... 435/183
(58) Field of Classification Search ................. 435/183
    See application file for complete search history.

(56) References Cited

U.S. PATENT DOCUMENTS

2005/0143402 A1*  6/2005  Cheetham et al. ..... 514/266.21

FOREIGN PATENT DOCUMENTS

EP           1522580 A1 *  4/2005

OTHER PUBLICATIONS

Owen et al. Two Structures of the Catalytic Domain of Phosphorylase Kinase: An Acitve Protein Kinase Complexed With Substrate Analogue and Product. Structure. 1995. vol. 3, No. 5, pp. 467-482.*
Pechkova et al. Protein nanocrystallography: a new approach to structural proteomics. Trends in Biotechnology. 2003. vol. 22, No. 3, pp. 117-122.*
Cudney, B. Protein Crystallization and Dumb Luck. Rigaku Journal. 1999. vol. 16, No. 1, pp. 1-7.*
Derewenda et al. Entropy and Surface Engineering in Protein Crystallization. Acta Crystallographica Section D. 2006. vol. D62, pp. 116-124.*
Clemente et al. 22 Space-group Changes. Acta Crystallographica Section B. 2003. vol. B59, pp. 43-50.*
Bischoff, J.R., et al., "The Aurora/lpl1p kinase family: regulators of chromosome segregation and cytokinesis," Trends in Cell Biology, 9:454-459 (1999).

(Continued)

*Primary Examiner*—Kathleen M. Kerri
*Assistant Examiner*—Suzanne M. Noakes

(57) ABSTRACT

The invention provides crystalline forms of a polypeptide corresponding to the catalytic domain of Aurora kinase. The active site ATP binding pocket is defined by its amino acid residues and their atomic coordinates. This structure may be used to select or design chemical modulators of Aurora kinase, particularly Aurora inhibitors. These modulators may be used to treat diseases of cell proliferation, e.g. cancer.

3 Claims, 4 Drawing Sheets

OTHER PUBLICATIONS

"Solutions for crystal growth," Hampton Research, retrieved from Internet: <URL: http://web.archieve.org/web/20010415205238/www.hamptonresearch.com/hrproducts/screens.html>, Apr. 15, 2001, XP002254573.

Mueller, U., et al., "Development of a technology for automation and miniaturization of protein crystallization," Journal of Biotechnology, 85:7-14 (2001).

Cheetham, G., et al., "Crystal Structure of Aurora-2, an Oncogenic Serine/Threonine Kinase," Journal of Biological Chemistry, 277(45):42419-42422 (2002).

Saridakis, E., et al., "Improving protein crystal quality by decoupling nucleation and growth in vapor diffusion," Protein Science, 9:755-757 (2000).

* cited by examiner

CRYSTAL STRUCTURE OF AURORA A KINASE AND USES THEREOF

This application is a national stage filing under 35 U.S.C. 371 of International Application No. PCT/GB02/04589, filed Oct. 8, 2002, which claims priority from United Kingdom Patent Application No. 0124299.9, filed Oct. 10, 2001, the specification of which is incorporated by reference herein. International Application No. PCT/GB02/04589 was published under PCT Article 21(2) in English.

FIELD OF THE INVENTION

This invention relates to crystallised Aurora A kinase and the use of its three-dimensional structure to investigate Aurora kinase homologues and to design Aurora kinase modulators.

BACKGROUND OF THE INVENTION

Proteins such as enzymes involved in physiological and pathological processes are important targets in the development of pharmaceutical compounds and treatments. Knowledge of the three dimensional (tertiary) structure of proteins allows the rational design of mimics or modulators of such proteins. By searching structural databases using structural parameters derived from the protein of interest, it is possible to select molecular structures that may mimic or interact with these parameters. It is then possible to synthesise the selected molecular structure and test its activity. Alternatively, the structural parameters derived from the protein of interest may be used to design and synthesise a mimic or modulator with the desired activity. Such mimics or modulators may be useful as therapeutic agents for treating certain diseases. For example, WO98/07835 discloses crystal structures of a protein tyrosine kinase optionally complexed with one or more compounds. The atomic coordinates of the enzyme structures and any of the bound compounds are used to determine the three-dimensional structures of kinases with unknown structure and to identify modulators of kinase functions. As another example, WO99/01476 discloses the crystal structures of anti-Factor IX Fab fragments (antibodies) and their use to identify and design new anticoagulant agents.

Knowledge of the three-dimensional structure of a protein is essential for the rational design of mimics or modulators of that protein. Lack of structural knowledge is a barrier to the development of new mimics or modulators that may have extremely useful pharmaceutical properties.

In Eukaryotes, the cell cycle is largely controlled by an ordered cascade of protein phosphorylation. Several families of protein kinases that play critical roles in this cascade have now been identified. The activity of many of these kinases is increased in human tumours when compared to normal tissue. This can occur by either increased levels of expression of the protein (as a result of gene amplification for example), or by changes in expression of co-activators or inhibitory proteins.

The first identified, and most widely studied of these cell cycle regulators have been the cyclin-dependent kinases (or CDKs). Activity of specific CDKs at specific times is essential for both initiation and coordinated progress through the cell cycle. For example, the CDK4 protein appears to control entry into the cell cycle (the G0-G1-S transition) by phosphorylating the retinoblastoma gene product pRb. This stimulates the release of the transcription factor E2F from pRb, which then acts to increase the transcription of genes necessary for entry into S phase. The catalytic activity of CDK4 is stimulated by binding to a partner protein, Cyclin D1. One of the first demonstrations of a direct link between cancer and the cell cycle was made with the observation that the Cyclin D1 gene was amplified and cyclin D1 protein levels increased (and hence the activity of CDK4 increased) in many human tumours (Reviewed in Sherr, 1996, Science 274: 1672–1677; Pines, 1995, Seminars in Cancer Biology 6: 63–72). Other studies have shown that negative regulators of CDK function are frequently down-regulated or deleted in human tumours, again leading to inappropriate activation of these kinases (Loda et al., 1997, Nature Medicine 3(2): 231–234; Gemma et al., 1996, International Journal of Cancer 68(5): 605–11; Elledge et al. 1996, Trends in Cell Biology 6; 388–392).

More recently, protein kinases that are structurally distinct from the CDK family have been identified which play critical roles in regulating the cell cycle and which also appear to be important in oncogenesis. These include the newly-identified human homologues of the *Drosophila* Aurora and *S. cerevisiae* Ipl1 proteins. *Drosophila* Aurora and *S. cerevisiae* Ipl1, which are highly homologous at the amino acid sequence level, encode serine/threonine protein kinases. Both Aurora and Ipl1 are known to be involved in controlling the transition from the G2 phase of the cell cycle through mitosis, centrosome function, formation of a mitotic spindle and proper chromosome separation/segregation into daughter cells. The three human homologues of these genes, termed Aurora A, B and C, encode cell cycle regulated protein kinases. These show a peak of expression and kinase activity at the G2/M boundary (Aurora A, C) and in mitosis and cytokinesis (Aurora B). Several observations implicate the involvement of human Aurora proteins, in particular Aurora A in cancer. The Aurora A gene maps to chromosome 20q13, a region that is frequently amplified in human tumours including both breast and colon tumours. Aurora A may be the major target gene of this amplicon, since Aurora A DNA is amplified and Aurora A mRNA over expressed in greater than 50% of primary human colorectal cancers. In these tumours Aurora A protein levels appear greatly elevated compared to adjacent normal tissue. In addition, transfection of rodent fibroblasts with human Aurora A leads to transformation, conferring the ability to grow in soft agar and form tumours in nude mice (Bischoff et al., 1998, The EMBO Journal. 117(11): 3052–3065). Other work has shown that artificial over expression of Aurora A leads to an increase in centrosome number and an increase in aneuploidy (Zhou et al., 1998, Nature Genetics. 20(2): 189–93).

Importantly, it has also been demonstrated that abrogation of Aurora A expression and function by antisense oligonucleotide treatment of human tumour cell lines (Bischoff and Ploughman, 1999, Trends in Cell Biology, 9(11): 454–459 or by a small molecule inhibitor of Aurora A kinase activity (Keen et al. 2001, poster #2455, American Association for Cancer Research annual meeting, New Orleans USA) leads to defects in mitosis, cell cycle arrest and exerts an antiproliferative effect in these tumour cell lines. This indicates that inhibition of the function of Aurora A will have an antiproliferative effect that may be useful in the treatment of human tumours and other hyperproliferative diseases.

In order to design inhibitors of Aurora A kinase, it is necessary to know the three-dimensional structure of Aurora A kinase, in complex with various lead compounds. To date, the three-dimensional structure of Aurora A kinase has not been available. Further, it has not been possible to obtain crystals of any part of Aurora of sufficient quality to allow determination of the structure of the kinase domain including the site of inhibition.

SUMMARY OF THE INVENTION

The present invention relates to the previously unknown three-dimensional structure of human Aurora A kinase. As described herein, the Applicants have overcome the difficulties encountered by others and have produced crystals of the Aurora A kinase catalytic domain that are of sufficient quality to determine the three-dimensional structure of the protein by X-ray diffraction methods. In addition, the Applicants have determined the three-dimensional crystal structure of the kinase catalytic domain of Aurora A kinase in a complex with the ATP analogue AMP-PNP, as well as the three-dimensional crystal structure of the Aurora A kinase catalytic domain in complex with a synthetic inhibitor. There is a clear need for this structural information to enable identification and structure-based design of new Aurora kinase modulators (particularly inhibitors) for the treatment of various diseases or conditions and in particular diseases of cell proliferation such as cancer. The methods described herein allow the determination of the three-dimensional structures of Aurora A kinase, as well as other Aurora kinases, in complex with numerous inhibitors of interest to aid in the rational design of modulators that will treat diseases of cell proliferation.

DETAILED DESCRIPTION OF THE INVENTION

Figure 1:
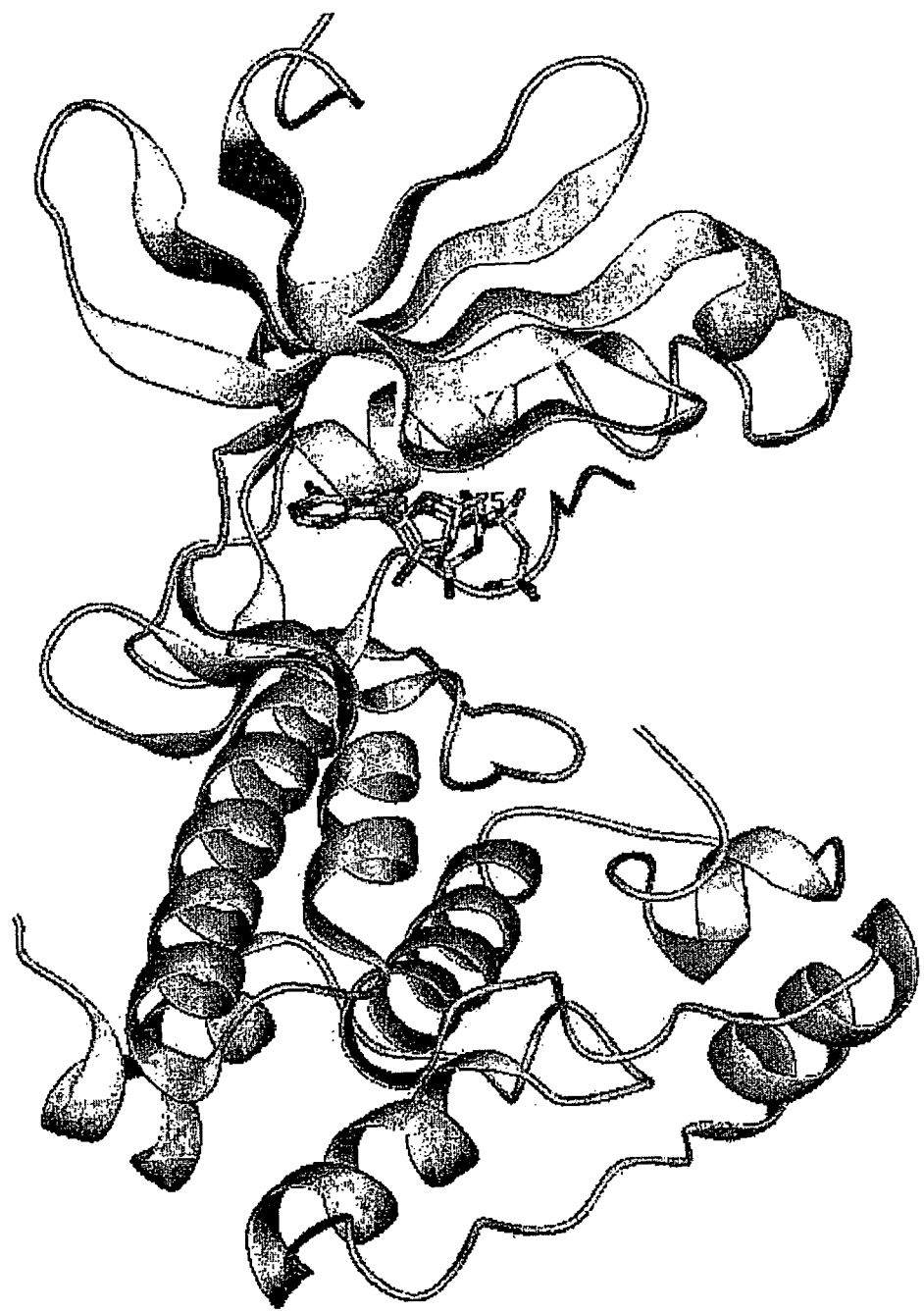
FIG. 1 is a schematic representation of the structure of the [T287D] Aurora A complex with AMP-PNP. The inhibitor has 2 conformations.

This invention relates to crystals of Aurora A kinase and the use of the three-dimensional structure to investigate Aurora kinase homologues and to design Aurora kinase modulators (preferably inhibitors). It further relates to crystals of Aurora kinase, particularly Aurora A kinase, or the catalytic portion thereof, complexed or uncomplexed as described, of sufficient quality to determine the three dimensional (tertiary) structure of the polypeptide by X-ray diffraction methods.

According to a first aspect of the invention, the Applicants provide two crystalline forms of a polypeptide comprising the catalytic domain of Aurora A kinase. One crystalline form is obtained when we crystallise [T287D]Aurora A(122–396) in the presence of the ATP-analogue AMP-PNP. The second crystalline form is obtained when we crystallise GSHM-[T287D]Aurora A(122–400) in the presence of a synthetic inhibitor. (Amino acid residues in Aurora A are numbered by taking the first amino acid immediately after the initial methionine as amino acid number one). In one embodiment, the first crystalline form has the space group P3$_2$21. In another embodiment, the first crystalline form has the unit cell dimensions a=b=86.55, c=78.34 Å, α=β=90 and γ=120°. In another embodiment, the second crystalline form has space group P2$_1$. In another embodiment, the second crystalline form has the unit cell dimensions a=52.6, b=88.4, c=67.8 Å, α=γ=90 and β=90.01°. In another embodiment, these crystalline forms are described by three-dimensional sets of x,y,z-coordinates (Tables 1 and 2) for each atom in the complex representing the unique repeating motif in the crystal. Table 1 contains the coordinates for the complex molecule in the first crystalline form; Table 2 contains the coordinates for two independent complex molecules in the asymmetric unit (smallest unique repeating unit) in the second crystalline form. In another embodiment, these crystalline forms contain a numerical definition of a binding site, approximated by the set of all residues within a 5 Å contact distance from any atom in either inhibitor. The binding site is defined by the x,y,z-coordinates of atoms in the set of amino acid residues (set A) given by the list Arg136, Leu138, Gly139, Lys140, Gly141, Val146, Ala 159, Lys161, Leu163, Val77, Glu180, Val181, Ile183, Gln184, Leu193, Leu195, Leu207, Leu209, Glu210, Tyr211, Ala212, Pro213, Leu214, Gly215, Thr216, Arg219, Glu259, Asn260, Leu262, Ala272, Asp273, Phe274, Gly275, Trp276, Ser277, Val278, and His279, the atomic coordinates being listed in Tables 1 and 2. The binding site is may be defined in any alternate crystalline form, homologue, variant or mutant wherein the binding site has a root mean square deviation from all atoms of the amino acid residues of not more than 1.0 Å from a least-flexible subset (set B) of the binding site that includes the amino acid residues Arg136, Leu138, Gly139, Val146, Ala159, Lys161, Leu163, Ile183, Gln184, Leu193, Leu195, Leu207, Leu209, Glu210, Tyr211, Ala212, Pro213, Leu214, Gly215, Thr216, Arg219, Glu259, Asn260 and Leu262, each having coordinates as described in Tables 1 and 2.

In another embodiment, the first crystalline form comprises a binding site defined by amino acid residues Leu138, Gly139, Val146, Lys161, Val177, Arg178, Arg179, Glu180, Val181, Glu182, Ile183, Gln184, Leu193, Leu209, Tyr211, Ala212, Gly215, Thr216, Glu259, Asn260, Leu262, Ala272, Asp273, Phe274, Gly275, Trp276, Ser277, Val278 and His 279, each having the coordinated listed in Table 1a. An alternative crystalline form, homologue, variant or mutant wherein the binding site has a root mean square deviation from the backbone atoms of the amino acid residues of not more than 1.5 Å, and preferably not more than 1.0 Å is also provided.

In another embodiment, the crystalline forms additionally comprise Aurora kinase inhibitors in complex with the catalytic domain of Aurora kinase including any of the above embodiments of the crystalline form.

Another aspect of the invention relates to a method of designing an Aurora chemical modulator using the atomic coordinates of a crystalline form according to any of the above embodiments.

Another aspect of the invention relates to a method of selecting an Aurora chemical modulator using the atomic coordinates of a crystalline form according to any of the above embodiments.

Another aspect of the invention relates to a method of designing or selecting an Aurora chemical modulator using the atomic coordinates of any other protein, e.g. PKA, which has been shown by this invention to have structural similarity to Aurora.

Another aspect of the invention relates to a method of designing an Aurora protein using the atomic coordinates of a crystalline form according to any of the above embodiments.

Another aspect of the invention relates to a method of designing or selecting an Aurora modulator comprising the steps of:

exploring the atomic coordinates of Aurora (Tables 1 and 2) for information on the three-dimensional characteristics of the protein surface;

arriving at an alternative overlapping or non-overlapping binding pocket to the active site ATP binding pocket; and selecting or designing an Aurora modulator using the binding pocket information.

Another aspect of the invention relates to a method of determining the three-dimensional structure of a crystal form of Aurora kinase, referred to as a second or new crystal or crystal form of Aurora kinase, comprising the step of applying difference Fourier or molecular replacement methods using the atomic coordinates of an original crystal of Aurora kinase (from Table 1 or 2) to model the structure of a new crystal, wherein the active site ATP binding pocket of the new crystal is equivalent to that in the first crystal. In a specific embodiment, the invention is a method of determining the three-dimensional structure of a crystal form of Aurora kinase A comprising the step of applying difference Fourier or molecular replacement methods using the atomic coordinates of an original (first) crystal of Aurora kinases (from Table 1 or 2) to model the structure of a new crystal or new crystal form of Aurora kinase A, wherein the active site ATP binding pocket of the new crystal is equivalent to that in the original (first) crystal.

In particular provided herein are crystalline forms of a polypeptide including the catalytic domain of an Aurora A protein. The catalytic domain may be found within the complete protein or within a fragment of the protein. The catalytic domain may be also derived from a wild-type Aurora A enzyme or from an Aurora A mutant, homologue or variant. A mutant is a wild type Aurora A protein having one or more changes in its amino acid sequence. An Aurora mutant may have the same activity as the wild type protein, may have modified activity or may be inactive. A variant is a wild type or mutant protein having one or more portions of its sequence removed, or an additional sequence or sequences added, so that the variant is a different length from the wild type or mutant protein. A variant usually has the same activity as the original wild type or mutant protein. A homologue is a related protein in which some parts of the amino acid sequence are the same as in the original protein. Aurora B and Aurora C, for example, are homologues of Aurora A.

The invention relates to crystals of sufficient quality to determine the three dimensional structure to high resolution of any portion, mutant, variant or homologue of Aurora A involving the catalytic domain.

According to a further aspect of the invention, we provide crystalline forms of a polypeptide containing the Aurora A catalytic domain in complex with small molecular weight inhibitor molecules. For example, the inhibitor molecule might be a non-hydrolysable analogue of ATP. Such analogues include, for example, formula I (AMP-PNP). As another example, the inhibitor might be a molecule synthesised chemically. Such molecules include, for example, formula II.

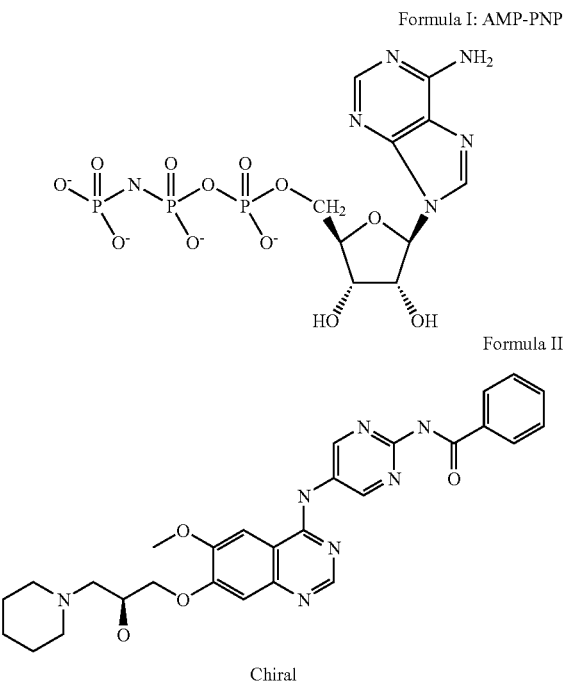

Another aspect of the invention is the unique shape of the active site ATP binding pocket in Aurora. Using X-ray crystallography, we have determined the three-dimensional molecular structure of an Aurora A catalytic domain. Resulting from this, we have determined the unique shape of an Aurora A active site ATP binding pocket (defined by the atomic coordinates of its constituent amino acids). Furthermore, we have determined the spatial arrangement of an Aurora A substrate analogue and an inhibitor molecule relative to the Aurora A active site binding pocket. This structural information can be stored on a computer-readable medium and may be used for rational drug design.

One of the difficulties in studying kinases in general is obtaining active protein. In order to be activated, certain kinases need to be phosphorylated at one or more key amino acid residues. It may be experimentally difficult to obtain 100% pure phosphorylated protein. Different phosphorylation states may have different conformations. Those in the art realise that such heterogeneities in the protein sample can severely impede the ability to form large well-ordered crystals. In Aurora A, phosphorylation of Thr 287 is necessary for activation of the kinase. Replacement of Thr-287 by Asp (an Aurora A mutant called [T287D] Aurora A) provides a mimic of the active protein which can be provided as a homogeneous sample. The [T287D]Aurora A mutant is constitutively active. Thus, preparation of this mutant conveniently addresses both issues of activity and crystallisability.

Figure 2A:
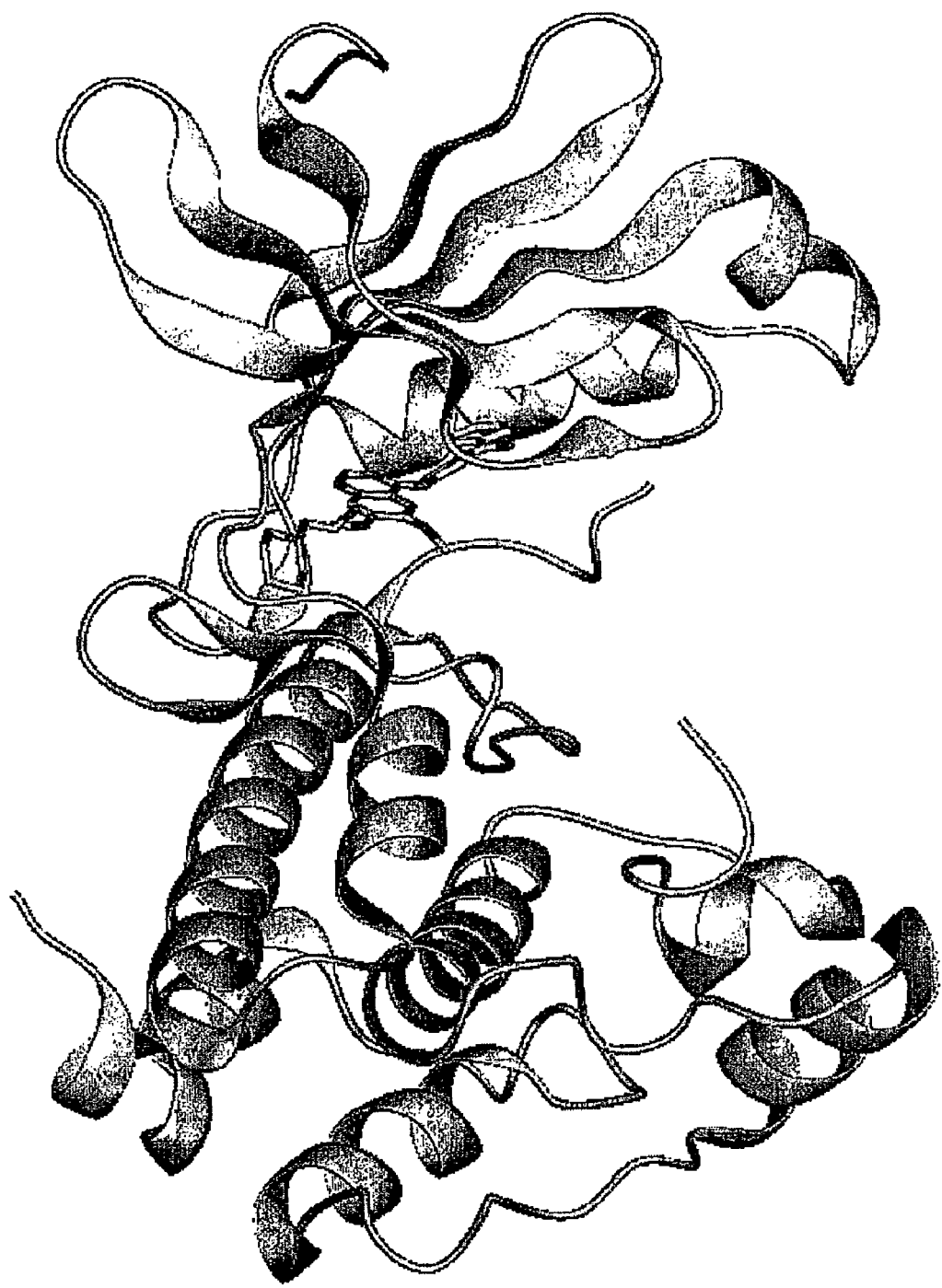
FIG. 2a is a schematic representation of the structure of Aurora A in complex with a synthetic inhibitor drawn in approximately the same orientation as FIG. 1.
Figure 2B:
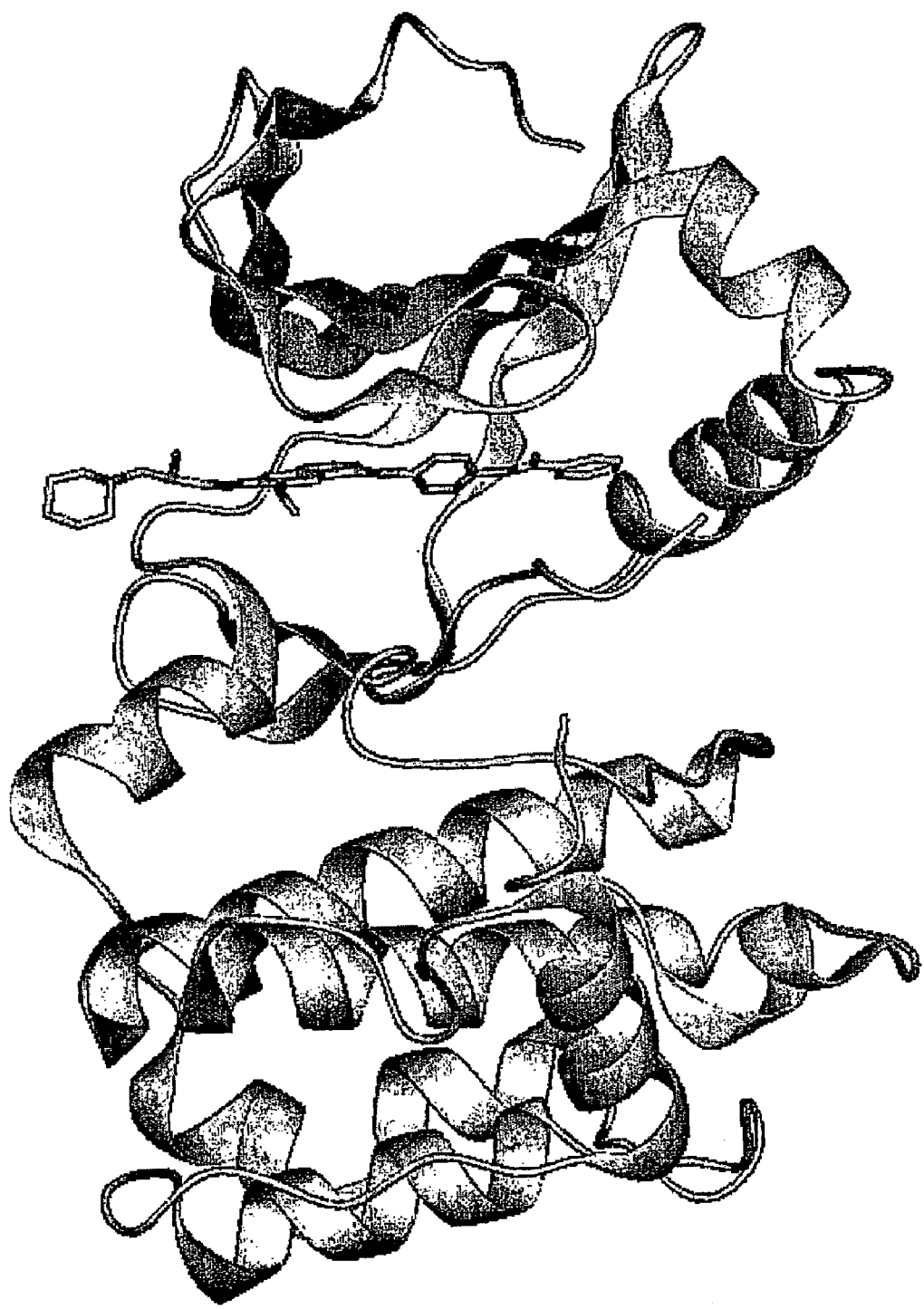
FIG. 2b is a schematic representation of Aurora A in complex with a synthetic inhibitor, rotated so as to show the extended inhibitor occupying a long active site binding pocket.

One of the major hurdles in the crystallisation of multi-domain proteins is their flexibility. To increase the chances of crystallising Aurora A, an enzyme construct limited to the catalytic domain was used. This provided a more rigid and compact domain. Catalytic domain constructs can be designed by comparing the amino acid sequence to other kinases of known structure, and defining start and end residues for the polypeptide encompassing the Aurora A catalytic domain by analogy. This gives numerous possible construct variants, which include the catalytic domain. In order to increase further the chances of crystallising Aurora A, experimental evidence was sought as to which catalytic domain construct would be the most compact while retaining integrity as a folding unit. Limited proteolysis was carried out using endoproteinase Glu-C from *Staphylococcus aureus* V8 on the catalytic domain. This defined the catalytic domain boundaries to be within residues 122 to 396. Other similar constructs may be obtained through similar procedures, using, for example, different proteases for the limited proteolysis experiment. Such a procedure is exemplified by our preparation, crystallisation and determination of the structure of two Aurora A catalytic domain polypeptides. The structure of [T287D]Aurora A(122–396) in complex with the non-hydrolysable ATP analogue AMP-PNP is shown in FIG. 1. The structure of GSHM-[T287D] Aurora A(122–400) in complex with the synthetic Aurora inhibitor of formula II is shown in FIGS. 2a and 2b.

The AMP-PNP molecule occupies a cleft between the N-terminal domain (residues 125 to 208) and the C-terminal domain (residues 215 to 374). Comparison with other kinases demonstrates that this cleft represents a portion of the ATP binding site. Therefore, we have identified the active site ATP binding pocket of Aurora. The electron density shows evidence for the AMP-PNP adopting a dual conformation. In both conformations, the adenine ring and ribose moiety occupy similar pockets with the adenine nitrogen atoms N1 and N6 making classical interactions with main chain atoms in the hinge region (residues 209 to 214) of the enzyme. N1 forms a hydrogen bond with the main chain nitrogen of Ala-212 while N6 forms a hydrogen bond to the peptide carbonyl group of Glu-210. However, torsion angle differences elsewhere in the molecule allow the alpha and beta phosphate groups to occupy alternative pockets. No electron density is apparent in either conformation for the gamma phosphate group of the AMP-PNP molecule. In conformation 1, the beta phosphate group makes polar interactions with the O oxygen atoms of Ser 277 and the side-chain of Asn260, while in conformation 2, the beta phosphate makes polar interactions with the amide carbonyl of -Glu-259 and with a water molecule (Wat-542 in this structure).

From the three-dimensional structure that we have determined for [T287D] Aurora A, we establish that the AMP-PNP binding pocket, which is the active site ATP binding pocket, is uniquely defined by the atomic co-ordinates of its constituent amino acid residues, the coordinates being listed in Tables 1 and 2. An equivalent ATP binding pocket may also be defined having the same co-ordinates as detailed in Table 1 and with the same constituent amino acid residues except that Lys140 and Gly 141 in Table 1 and replaced with Ala 140 and Ala 141, whereby such a table is referred to hereonin as Table 1a.

TABLE 1 coordinates of [T287D] Aurora A (122–396) in complex with AMP-PNP

REMARK coordinates from restrained individual B-factor refinement
REMARK refinement resolution: 500–2.2 A
REMARK starting r = 0.2325 free_r = 0.2841
REMARK final r = 0.2317 free_r = 0.2832
REMARK B rmsd for bonded mainchain atoms = 1.663 target = 1.5
REMARK B rmsd for bonded sidechain atoms = 2.408 target = 2.0
REMARK B rmsd for angle mainchain atoms = 2.759 target = 2.0
REMARK B rmsd for angle sidechain atoms = 3.575 target = 2.5
REMARK wa = 2.95383
REMARK rweight = 9.122374E−02
REMARK target = mlf steps = 40
REMARK sg = P3(2)21 a = 86.551 b = 86.551 c = 78.337 alpha = 90 beta = 90 gamma = 120
REMARK parameter file 1: MSI_CNX_TOPPAR:protein_rep.param
REMARK parameter file 2: anp.par
REMARK parameter file 3: fra.par
REMARK parameter file 4: MSI_CNX_TOPPAR:water_rep.param
REMARK parameter file 5: gly.par
REMARK molecular structure file: generate.mtf
REMARK input coordinates: minimize.pdb
REMARK reflection file = aurora-dl.cv
REMARK ncs = none
REMARK B-correction resolution: 6.0–2.2
REMARK initial B-factor correction applied to fobs:
REMARK B11 = −2.797 B22 = −2.797 B33 = 5.593
REMARK B12 = −2.312 B13 = 0.000 B23 = 0.000
REMARK B-factor correction applied to coordinate array B: 0.127
REMARK bulk solvent: (Mask)density level = 0.392672e/A^3, B-factor = 81.6283 A^2
REMARK reflections with |Fobs|/sigma_F < 0.0 rejected
REMARK reflections with |Fobs| > 1000 * rms(Fobs) rejected
REMARK theoretical total number of refl. in resol. range: 17604 (100.0%)
REMARK number of unobserved reflections (no entry or |F| = 0): 841 (4.8%)
REMARK number of reflections rejected:      0 (0.0%)
REMARK total number of reflections used:   16763 (95.2%)
REMARK number of reflections in working set:   15942 (90.6%)
REMARK number of reflections in test set:    821 (4.7%)
REMARK FILENAME = "bindividual.pdb"
REMARK DATE: Jun-18-2001 10:59:05 created by user: mar345
REMARK Written by CNX VERSION: 2000

| ATOM | 1 | CB | ALA | A | 125 | 45.635 | 59.219 | 11.462 | 1.00 | 79.31 | A | C |
|---|---|---|---|---|---|---|---|---|---|---|---|---|
| ATOM | 2 | C | ALA | A | 125 | 44.028 | 58.911 | 13.362 | 1.00 | 80.12 | A | C |
| ATOM | 3 | O | ALA | A | 125 | 45.008 | 59.073 | 14.092 | 1.00 | 81.57 | A | O |
| ATOM | 4 | N | ALA | A | 125 | 43.336 | 60.097 | 11.271 | 1.00 | 79.55 | A | N |
| ATOM | 5 | CA | ALA | A | 125 | 44.170 | 59.002 | 11.840 | 1.00 | 80.04 | A | C |

TABLE 1-continued coordinates of [T287D] Aurora A (122–396) in complex with AMP-PNP

| ATOM | 6 | N | GLN | A | 126 | 42.809 | 58.655 | 13.835 | 1.00 | 79.21 | A | N |
|---|---|---|---|---|---|---|---|---|---|---|---|---|
| ATOM | 7 | CA | GLN | A | 126 | 42.542 | 58.531 | 15.272 | 1.00 | 77.20 | A | C |
| ATOM | 8 | CB | GLN | A | 126 | 41.980 | 59.849 | 15.817 | 1.00 | 78.38 | A | C |
| ATOM | 9 | CG | GLN | A | 126 | 42.496 | 60.222 | 17.206 | 1.00 | 78.91 | A | C |
| ATOM | 10 | CD | GLN | A | 126 | 41.965 | 59.321 | 18.304 | 1.00 | 79.23 | A | C |
| ATOM | 11 | OE1 | GLN | A | 126 | 42.092 | 58.098 | 18.238 | 1.00 | 80.18 | A | O |
| ATOM | 12 | NE2 | GLN | A | 126 | 41.372 | 59.925 | 19.328 | 1.00 | 78.24 | A | N |
| ATOM | 13 | C | GLN | A | 126 | 41.550 | 57.382 | 15.510 | 1.00 | 74.64 | A | C |
| ATOM | 14 | O | GLN | A | 126 | 41.834 | 56.234 | 15.151 | 1.00 | 74.20 | A | O |
| ATOM | 15 | N | TRP | A | 127 | 40.402 | 57.676 | 16.121 | 1.00 | 70.19 | A | N |
| ATOM | 16 | CA | TRP | A | 127 | 39.395 | 56.640 | 16.358 | 1.00 | 65.92 | A | C |
| ATOM | 17 | CB | TRP | A | 127 | 38.110 | 57.242 | 16.943 | 1.00 | 67.39 | A | C |
| ATOM | 18 | CG | TRP | A | 127 | 38.032 | 57.327 | 18.449 | 1.00 | 68.91 | A | C |
| ATOM | 19 | CD2 | TRP | A | 127 | 38.438 | 56.330 | 19.399 | 1.00 | 69.52 | A | C |
| ATOM | 20 | CE2 | TRP | A | 127 | 38.137 | 56.832 | 20.686 | 1.00 | 69.28 | A | C |
| ATOM | 21 | CE3 | TRP | A | 127 | 39.028 | 55.062 | 19.288 | 1.00 | 70.75 | A | C |
| ATOM | 22 | CD1 | TRP | A | 127 | 37.515 | 58.361 | 19.182 | 1.00 | 68.38 | A | C |
| ATOM | 23 | NE1 | TRP | A | 127 | 37.575 | 58.070 | 20.523 | 1.00 | 68.76 | A | N |
| ATOM | 24 | CZ2 | TRP | A | 127 | 38.407 | 56.111 | 21.855 | 1.00 | 70.27 | A | C |
| ATOM | 25 | CZ3 | TRP | A | 127 | 39.299 | 54.343 | 20.455 | 1.00 | 70.56 | A | C |
| ATOM | 26 | CH2 | TRP | A | 127 | 38.987 | 54.873 | 21.719 | 1.00 | 71.20 | A | C |
| ATOM | 27 | C | TRP | A | 127 | 39.067 | 56.021 | 15.004 | 1.00 | 61.91 | A | C |
| ATOM | 28 | O | TRP | A | 127 | 39.034 | 56.724 | 14.001 | 1.00 | 62.11 | A | O |
| ATOM | 29 | N | ALA | A | 128 | 38.836 | 54.712 | 14.975 | 1.00 | 57.60 | A | N |
| ATOM | 30 | CA | ALA | A | 128 | 38.491 | 54.016 | 13.740 | 1.00 | 52.69 | A | C |
| ATOM | 31 | CB | ALA | A | 128 | 39.757 | 53.556 | 13.027 | 1.00 | 53.72 | A | C |
| ATOM | 32 | C | ALA | A | 128 | 37.597 | 52.820 | 14.075 | 1.00 | 50.40 | A | C |
| ATOM | 33 | O | ALA | A | 128 | 37.565 | 52.372 | 15.220 | 1.00 | 48.81 | A | O |
| ATOM | 34 | N | LEU | A | 129 | 36.875 | 52.308 | 13.082 | 1.00 | 47.90 | A | N |
| ATOM | 35 | CA | LEU | A | 129 | 35.975 | 51.176 | 13.293 | 1.00 | 47.52 | A | C |
| ATOM | 36 | CB | LEU | A | 129 | 35.235 | 50.836 | 11.991 | 1.00 | 46.25 | A | C |
| ATOM | 37 | CG | LEU | A | 129 | 34.125 | 49.775 | 12.047 | 1.00 | 47.39 | A | C |
| ATOM | 38 | CD1 | LEU | A | 129 | 33.068 | 50.164 | 13.079 | 1.00 | 45.16 | A | C |
| ATOM | 39 | CD2 | LEU | A | 129 | 33.488 | 49.630 | 10.671 | 1.00 | 48.56 | A | C |
| ATOM | 40 | C | LEU | A | 129 | 36.706 | 49.936 | 13.815 | 1.00 | 48.62 | A | C |
| ATOM | 41 | O | LEU | A | 129 | 36.170 | 49.199 | 14.645 | 1.00 | 46.32 | A | O |
| ATOM | 42 | N | ALA | A | 130 | 37.930 | 49.724 | 13.333 | 1.00 | 49.46 | A | N |
| ATOM | 43 | CA | ALA | A | 130 | 38.750 | 48.584 | 13.742 | 1.00 | 50.75 | A | C |
| ATOM | 44 | CB | ALA | A | 130 | 40.037 | 48.538 | 12.907 | 1.00 | 50.42 | A | C |
| ATOM | 45 | C | ALA | A | 130 | 39.098 | 48.610 | 15.233 | 1.00 | 51.11 | A | C |
| ATOM | 46 | O | ALA | A | 130 | 39.559 | 47.611 | 15.782 | 1.00 | 51.23 | A | O |
| ATOM | 47 | N | ASP | A | 131 | 38.896 | 49.752 | 15.883 | 1.00 | 51.02 | A | N |
| ATOM | 48 | CA | ASP | A | 131 | 39.183 | 49.863 | 17.310 | 1.00 | 51.74 | A | C |
| ATOM | 49 | CB | ASP | A | 131 | 39.353 | 51.328 | 17.735 | 1.00 | 55.51 | A | C |
| ATOM | 50 | CG | ASP | A | 131 | 40.539 | 52.012 | 17.080 | 1.00 | 57.37 | A | C |
| ATOM | 51 | OD1 | ASP | A | 131 | 40.515 | 52.230 | 15.852 | 1.00 | 60.16 | A | O |
| ATOM | 52 | OD2 | ASP | A | 131 | 41.496 | 52.344 | 17.804 | 1.00 | 60.43 | A | O |
| ATOM | 53 | C | ASP | A | 131 | 38.041 | 49.282 | 18.134 | 1.00 | 50.19 | A | C |
| ATOM | 54 | O | ASP | A | 131 | 38.147 | 49.195 | 19.352 | 1.00 | 51.36 | A | O |
| ATOM | 55 | N | PHE | A | 132 | 36.956 | 48.881 | 17.474 | 1.00 | 48.84 | A | N |
| ATOM | 56 | CA | PHE | A | 132 | 35.779 | 48.370 | 18.181 | 1.00 | 47.79 | A | C |
| ATOM | 57 | CB | PHE | A | 132 | 34.600 | 49.327 | 17.969 | 1.00 | 47.00 | A | C |
| ATOM | 58 | CG | PHE | A | 132 | 34.877 | 50.743 | 18.370 | 1.00 | 45.30 | A | C |
| ATOM | 59 | CD1 | PHE | A | 132 | 34.853 | 51.119 | 19.711 | 1.00 | 45.44 | A | C |
| ATOM | 60 | CD2 | PHE | A | 132 | 35.148 | 51.708 | 17.404 | 1.00 | 43.30 | A | C |
| ATOM | 61 | CE1 | PHE | A | 132 | 35.093 | 52.443 | 20.087 | 1.00 | 41.66 | A | C |
| ATOM | 62 | CE2 | PHE | A | 132 | 35.390 | 53.034 | 17.772 | 1.00 | 43.84 | A | C |
| ATOM | 63 | CZ | PHE | A | 132 | 35.361 | 53.399 | 19.115 | 1.00 | 42.35 | A | C |
| ATOM | 64 | C | PHE | A | 132 | 35.278 | 46.982 | 17.801 | 1.00 | 48.37 | A | C |
| ATOM | 65 | O | PHE | A | 132 | 35.501 | 46.505 | 16.689 | 1.00 | 49.60 | A | O |
| ATOM | 66 | N | GLU | A | 133 | 34.575 | 46.350 | 18.740 | 1.00 | 47.46 | A | N |
| ATOM | 67 | CA | GLU | A | 133 | 33.951 | 45.053 | 18.501 | 1.00 | 45.33 | A | C |
| ATOM | 68 | CB | GLU | A | 133 | 34.214 | 44.082 | 19.661 | 1.00 | 48.04 | A | C |
| ATOM | 69 | CG | GLU | A | 133 | 34.835 | 42.759 | 19.214 | 1.00 | 49.09 | A | C |
| ATOM | 70 | CD | GLU | A | 133 | 34.935 | 41.725 | 20.325 | 1.00 | 49.60 | A | C |
| ATOM | 71 | OE1 | GLU | A | 133 | 33.892 | 41.172 | 20.745 | 1.00 | 49.55 | A | O |
| ATOM | 72 | OE2 | GLU | A | 133 | 36.064 | 41.464 | 20.778 | 1.00 | 49.86 | A | O |
| ATOM | 73 | C | GLU | A | 133 | 32.460 | 45.384 | 18.418 | 1.00 | 44.56 | A | C |
| ATOM | 74 | O | GLU | A | 133 | 31.932 | 46.080 | 19.282 | 1.00 | 41.15 | A | O |
| ATOM | 75 | N | ILE | A | 134 | 31.785 | 44.899 | 17.380 | 1.00 | 44.52 | A | N |
| ATOM | 76 | CA | ILE | A | 134 | 30.364 | 45.180 | 17.194 | 1.00 | 44.87 | A | C |
| ATOM | 77 | CB | ILE | A | 134 | 30.033 | 45.362 | 15.700 | 1.00 | 43.36 | A | C |
| ATOM | 78 | CG2 | ILE | A | 134 | 28.567 | 45.739 | 15.540 | 1.00 | 44.27 | A | C |
| ATOM | 79 | CG1 | ILE | A | 134 | 30.968 | 46.409 | 15.080 | 1.00 | 45.76 | A | C |
| ATOM | 80 | CD1 | ILE | A | 134 | 30.975 | 47.777 | 15.776 | 1.00 | 43.59 | A | C |
| ATOM | 81 | C | ILE | A | 134 | 29.420 | 44.119 | 17.759 | 1.00 | 45.96 | A | C |
| ATOM | 82 | O | ILE | A | 134 | 29.603 | 42.927 | 17.514 | 1.00 | 46.32 | A | O |

TABLE 1-continued coordinates of [T287D] Aurora A (122–396) in complex with AMP-PNP

| ATOM | 83 | N | GLY | A | 135 | 28.396 | 44.571 | 18.487 | 1.00 | 44.99 | A | N |
|---|---|---|---|---|---|---|---|---|---|---|---|---|
| ATOM | 84 | CA | GLY | A | 135 | 27.425 | 43.661 | 19.083 | 1.00 | 45.95 | A | C |
| ATOM | 85 | C | GLY | A | 135 | 26.050 | 43.706 | 18.438 | 1.00 | 44.79 | A | C |
| ATOM | 86 | O | GLY | A | 135 | 25.918 | 44.096 | 17.281 | 1.00 | 45.37 | A | O |
| ATOM | 87 | N | ARG | A | 136 | 25.014 | 43.330 | 19.183 | 1.00 | 46.84 | A | N |
| ATOM | 88 | CA | ARG | A | 136 | 23.652 | 43.314 | 18.630 | 1.00 | 47.11 | A | C |
| ATOM | 89 | CB | ARG | A | 136 | 22.665 | 42.699 | 19.629 | 1.00 | 47.09 | A | C |
| ATOM | 90 | CG | ARG | A | 136 | 22.462 | 43.505 | 20.909 | 1.00 | 45.16 | A | C |
| ATOM | 91 | CD | ARG | A | 136 | 21.296 | 42.979 | 21.736 | 1.00 | 41.59 | A | C |
| ATOM | 92 | NE | ARG | A | 136 | 21.296 | 43.550 | 23.080 | 1.00 | 41.35 | A | N |
| ATOM | 93 | CZ | ARG | A | 136 | 20.457 | 44.490 | 23.507 | 1.00 | 41.75 | A | C |
| ATOM | 94 | NH1 | ARG | A | 136 | 19.527 | 44.978 | 22.701 | 1.00 | 41.10 | A | N |
| ATOM | 95 | NH2 | ARG | A | 136 | 20.553 | 44.949 | 24.745 | 1.00 | 41.12 | A | N |
| ATOM | 96 | C | ARG | A | 136 | 23.116 | 44.680 | 18.205 | 1.00 | 47.41 | A | C |
| ATOM | 97 | O | ARG | A | 136 | 23.482 | 45.710 | 18.770 | 1.00 | 46.21 | A | O |
| ATOM | 98 | N | PRO | A | 137 | 22.231 | 44.696 | 17.197 | 1.00 | 49.15 | A | N |
| ATOM | 99 | CD | PRO | A | 137 | 21.994 | 43.557 | 16.295 | 1.00 | 50.53 | A | C |
| ATOM | 100 | CA | PRO | A | 137 | 21.607 | 45.910 | 16.659 | 1.00 | 50.22 | A | C |
| ATOM | 101 | CB | PRO | A | 137 | 20.948 | 45.420 | 15.373 | 1.00 | 49.86 | A | C |
| ATOM | 102 | CG | PRO | A | 137 | 21.781 | 44.245 | 14.978 | 1.00 | 49.74 | A | C |
| ATOM | 103 | C | PRO | A | 137 | 20.580 | 46.507 | 17.620 | 1.00 | 51.56 | A | C |
| ATOM | 104 | O | PRO | A | 137 | 19.619 | 45.841 | 18.007 | 1.00 | 52.67 | A | O |
| ATOM | 105 | N | LEU | A | 138 | 20.783 | 47.760 | 18.005 | 1.00 | 51.44 | A | N |
| ATOM | 106 | CA | LEU | A | 138 | 19.851 | 48.430 | 18.908 | 1.00 | 52.81 | A | C |
| ATOM | 107 | CB | LEU | A | 138 | 20.589 | 49.498 | 19.721 | 1.00 | 52.13 | A | C |
| ATOM | 108 | CG | LEU | A | 138 | 21.156 | 49.087 | 21.086 | 1.00 | 51.35 | A | C |
| ATOM | 109 | CD1 | LEU | A | 138 | 21.737 | 47.694 | 21.033 | 1.00 | 54.20 | A | C |
| ATOM | 110 | CD2 | LEU | A | 138 | 22.201 | 50.093 | 21.516 | 1.00 | 50.21 | A | C |
| ATOM | 111 | C | LEU | A | 138 | 18.710 | 49.064 | 18.114 | 1.00 | 53.48 | A | C |
| ATOM | 112 | O | LEU | A | 138 | 17.604 | 49.235 | 18.620 | 1.00 | 53.15 | A | O |
| ATOM | 113 | N | GLY | A | 139 | 18.990 | 49.401 | 16.860 | 1.00 | 55.10 | A | N |
| ATOM | 114 | CA | GLY | A | 139 | 17.992 | 50.015 | 16.009 | 1.00 | 55.12 | A | C |
| ATOM | 115 | C | GLY | A | 139 | 18.494 | 50.122 | 14.586 | 1.00 | 57.30 | A | C |
| ATOM | 116 | O | GLY | A | 139 | 19.684 | 50.365 | 14.348 | 1.00 | 55.60 | A | O |
| ATOM | 117 | N | LYS | A | 140 | 17.585 | 49.930 | 13.636 | 1.00 | 57.79 | A | N |
| ATOM | 118 | CA | LYS | A | 140 | 17.920 | 50.004 | 12.222 | 1.00 | 59.68 | A | C |
| ATOM | 119 | CB | LYS | A | 140 | 17.898 | 48.612 | 11.604 | 1.00 | 60.43 | A | C |
| ATOM | 120 | C | LYS | A | 140 | 16.902 | 50.897 | 11.534 | 1.00 | 61.09 | A | C |
| ATOM | 121 | O | LYS | A | 140 | 15.735 | 50.910 | 11.912 | 1.00 | 61.20 | A | O |
| ATOM | 122 | N | GLY | A | 141 | 17.337 | 51.648 | 10.530 | 1.00 | 62.18 | A | N |
| ATOM | 123 | CA | GLY | A | 141 | 16.413 | 52.525 | 9.834 | 1.00 | 62.70 | A | C |
| ATOM | 124 | CB | GLY | A | 141 | 15.841 | 53.534 | 10.803 | 1.00 | 65.14 | A | C |
| ATOM | 125 | C | GLY | A | 141 | 17.012 | 53.241 | 8.640 | 1.00 | 62.45 | A | C |
| ATOM | 126 | O | GLY | A | 141 | 18.188 | 53.082 | 8.325 | 1.00 | 61.72 | A | O |
| ATOM | 127 | N | ALA | A | 142 | 16.171 | 54.048 | 7.999 | 1.00 | 62.55 | A | N |
| ATOM | 128 | CA | ALA | A | 142 | 16.522 | 54.811 | 6.806 | 1.00 | 61.63 | A | C |
| ATOM | 129 | CB | ALA | A | 142 | 15.351 | 55.713 | 6.416 | 1.00 | 62.21 | A | C |
| ATOM | 130 | C | ALA | A | 142 | 17.793 | 55.641 | 6.903 | 1.00 | 60.80 | A | C |
| ATOM | 131 | O | ALA | A | 142 | 18.502 | 55.816 | 5.910 | 1.00 | 59.56 | A | O |
| ATOM | 132 | N | PHE | A | 143 | 18.088 | 56.152 | 8.091 | 1.00 | 59.81 | A | N |
| ATOM | 133 | CA | PHE | A | 143 | 19.266 | 56.986 | 8.255 | 1.00 | 58.87 | A | C |
| ATOM | 134 | CB | PHE | A | 143 | 18.913 | 58.170 | 9.153 | 1.00 | 61.93 | A | C |
| ATOM | 135 | CG | PHE | A | 143 | 18.150 | 59.246 | 8.439 | 1.00 | 64.91 | A | C |
| ATOM | 136 | CD1 | PHE | A | 143 | 18.825 | 60.244 | 7.739 | 1.00 | 65.80 | A | C |
| ATOM | 137 | CD2 | PHE | A | 143 | 16.759 | 59.225 | 8.407 | 1.00 | 65.92 | A | C |
| ATOM | 138 | CE1 | PHE | A | 143 | 18.125 | 61.206 | 7.013 | 1.00 | 68.03 | A | C |
| ATOM | 139 | CE2 | PHE | A | 143 | 16.048 | 60.182 | 7.683 | 1.00 | 67.18 | A | C |
| ATOM | 140 | CZ | PHE | A | 143 | 16.732 | 61.173 | 6.984 | 1.00 | 67.45 | A | C |
| ATOM | 141 | C | PHE | A | 143 | 20.514 | 56.275 | 8.755 | 1.00 | 56.62 | A | C |
| ATOM | 142 | O | PHE | A | 143 | 21.614 | 56.822 | 8.694 | 1.00 | 56.81 | A | O |
| ATOM | 143 | N | GLY | A | 144 | 20.343 | 55.050 | 9.235 | 1.00 | 54.51 | A | N |
| ATOM | 144 | CA | GLY | A | 144 | 21.472 | 54.289 | 9.728 | 1.00 | 51.51 | A | C |
| ATOM | 145 | C | GLY | A | 144 | 21.046 | 53.257 | 10.748 | 1.00 | 50.01 | A | C |
| ATOM | 146 | O | GLY | A | 144 | 19.864 | 52.914 | 10.849 | 1.00 | 50.62 | A | O |
| ATOM | 147 | N | ASN | A | 145 | 22.011 | 52.763 | 11.512 | 1.00 | 47.13 | A | N |
| ATOM | 148 | CA | ASN | A | 145 | 21.731 | 51.769 | 12.535 | 1.00 | 43.41 | A | C |
| ATOM | 149 | CB | ASN | A | 145 | 22.164 | 50.372 | 12.065 | 1.00 | 44.40 | A | C |
| ATOM | 150 | CG | ASN | A | 145 | 21.861 | 50.117 | 10.598 | 1.00 | 44.65 | A | C |
| ATOM | 151 | OD1 | ASN | A | 145 | 22.761 | 50.118 | 9.761 | 1.00 | 46.61 | A | O |
| ATOM | 152 | ND2 | ASN | A | 145 | 20.591 | 49.900 | 10.281 | 1.00 | 45.75 | A | N |
| ATOM | 153 | C | ASN | A | 145 | 22.517 | 52.127 | 13.788 | 1.00 | 40.16 | A | C |
| ATOM | 154 | O | ASN | A | 145 | 23.491 | 52.874 | 13.722 | 1.00 | 38.46 | A | O |
| ATOM | 155 | N | VAL | A | 146 | 22.082 | 51.599 | 14.927 | 1.00 | 36.92 | A | N |
| ATOM | 156 | CA | VAL | A | 146 | 22.780 | 51.818 | 16.188 | 1.00 | 35.73 | A | C |
| ATOM | 157 | CB | VAL | A | 146 | 21.908 | 52.590 | 17.221 | 1.00 | 35.98 | A | C |
| ATOM | 158 | CG1 | VAL | A | 146 | 22.737 | 52.921 | 18.440 | 1.00 | 35.61 | A | C |
| ATOM | 159 | CG2 | VAL | A | 146 | 21.353 | 53.868 | 16.610 | 1.00 | 38.31 | A | C |

TABLE 1-continued coordinates of [T287D] Aurora A (122–396) in complex with AMP-PNP

| ATOM | 160 | C | VAL | A | 146 | 23.082 | 50.414 | 16.732 | 1.00 | 35.97 | A | C |
|---|---|---|---|---|---|---|---|---|---|---|---|---|
| ATOM | 161 | O | VAL | A | 146 | 22.224 | 49.537 | 16.688 | 1.00 | 35.59 | A | O |
| ATOM | 162 | N | TYR | A | 147 | 24.296 | 50.197 | 17.231 | 1.00 | 37.55 | A | N |
| ATOM | 163 | CA | TYR | A | 147 | 24.670 | 48.886 | 17.763 | 1.00 | 37.38 | A | C |
| ATOM | 164 | CB | TYR | A | 147 | 25.674 | 48.159 | 16.854 | 1.00 | 39.73 | A | C |
| ATOM | 165 | CG | TYR | A | 147 | 25.324 | 48.027 | 15.388 | 1.00 | 41.31 | A | C |
| ATOM | 166 | CD1 | TYR | A | 147 | 25.614 | 49.052 | 14.484 | 1.00 | 43.72 | A | C |
| ATOM | 167 | CE1 | TYR | A | 147 | 25.371 | 48.900 | 13.119 | 1.00 | 41.58 | A | C |
| ATOM | 168 | CD2 | TYR | A | 147 | 24.773 | 46.847 | 14.890 | 1.00 | 42.29 | A | C |
| ATOM | 169 | CE2 | TYR | A | 147 | 24.528 | 46.685 | 13.534 | 1.00 | 42.99 | A | C |
| ATOM | 170 | CZ | TYR | A | 147 | 24.832 | 47.712 | 12.656 | 1.00 | 43.10 | A | C |
| ATOM | 171 | OH | TYR | A | 147 | 24.619 | 47.533 | 11.312 | 1.00 | 43.57 | A | O |
| ATOM | 172 | C | TYR | A | 147 | 25.352 | 48.972 | 19.116 | 1.00 | 37.06 | A | C |
| ATOM | 173 | O | TYR | A | 147 | 25.950 | 49.985 | 19.466 | 1.00 | 36.75 | A | O |
| ATOM | 174 | N | LEU | A | 148 | 25.277 | 47.879 | 19.864 | 1.00 | 36.10 | A | N |
| ATOM | 175 | CA | LEU | A | 148 | 25.970 | 47.790 | 21.133 | 1.00 | 35.79 | A | C |
| ATOM | 176 | CB | LEU | A | 148 | 25.466 | 46.574 | 21.911 | 1.00 | 38.69 | A | C |
| ATOM | 177 | CG | LEU | A | 148 | 25.919 | 46.357 | 23.350 | 1.00 | 41.70 | A | C |
| ATOM | 178 | CD1 | LEU | A | 148 | 25.512 | 47.550 | 24.213 | 1.00 | 44.96 | A | C |
| ATOM | 179 | CD2 | LEU | A | 148 | 25.285 | 45.083 | 23.876 | 1.00 | 41.80 | A | C |
| ATOM | 180 | C | LEU | A | 148 | 27.407 | 47.562 | 20.655 | 1.00 | 35.72 | A | C |
| ATOM | 181 | O | LEU | A | 148 | 27.606 | 46.984 | 19.593 | 1.00 | 35.45 | A | O |
| ATOM | 182 | N | ALA | A | 149 | 28.404 | 48.033 | 21.395 | 1.00 | 36.28 | A | N |
| ATOM | 183 | CA | ALA | A | 149 | 29.791 | 47.829 | 20.989 | 1.00 | 37.35 | A | C |
| ATOM | 184 | CB | ALA | A | 149 | 30.211 | 48.870 | 19.943 | 1.00 | 35.81 | A | C |
| ATOM | 185 | C | ALA | A | 149 | 30.728 | 47.894 | 22.182 | 1.00 | 40.30 | A | C |
| ATOM | 186 | O | ALA | A | 149 | 30.341 | 48.301 | 23.278 | 1.00 | 39.46 | A | O |
| ATOM | 187 | N | ARG | A | 150 | 31.974 | 47.498 | 21.962 | 1.00 | 41.71 | A | N |
| ATOM | 188 | CA | ARG | A | 150 | 32.956 | 47.506 | 23.026 | 1.00 | 45.19 | A | C |
| ATOM | 189 | CB | ARG | A | 150 | 32.946 | 46.137 | 23.717 | 1.00 | 49.42 | A | C |
| ATOM | 190 | CG | ARG | A | 150 | 33.892 | 45.984 | 24.888 | 1.00 | 52.01 | A | C |
| ATOM | 191 | CD | ARG | A | 150 | 33.362 | 44.946 | 25.885 | 1.00 | 54.44 | A | C |
| ATOM | 192 | NE | ARG | A | 150 | 32.854 | 43.742 | 25.231 | 1.00 | 55.30 | A | N |
| ATOM | 193 | CZ | ARG | A | 150 | 32.082 | 42.837 | 25.828 | 1.00 | 53.68 | A | C |
| ATOM | 194 | NH1 | ARG | A | 150 | 31.729 | 42.996 | 27.095 | 1.00 | 54.04 | A | N |
| ATOM | 195 | NH2 | ARG | A | 150 | 31.652 | 41.781 | 25.154 | 1.00 | 52.52 | A | N |
| ATOM | 196 | C | ARG | A | 150 | 34.322 | 47.829 | 22.440 | 1.00 | 47.01 | A | C |
| ATOM | 197 | O | ARG | A | 150 | 34.703 | 47.296 | 21.397 | 1.00 | 47.88 | A | O |
| ATOM | 198 | N | GLU | A | 151 | 35.042 | 48.730 | 23.093 | 1.00 | 49.42 | A | N |
| ATOM | 199 | CA | GLU | A | 151 | 36.365 | 49.124 | 22.632 | 1.00 | 54.61 | A | C |
| ATOM | 200 | CB | GLU | A | 151 | 36.848 | 50.346 | 23.426 | 1.00 | 56.69 | A | C |
| ATOM | 201 | CG | GLU | A | 151 | 37.983 | 51.140 | 22.766 | 1.00 | 63.91 | A | C |
| ATOM | 202 | CD | GLU | A | 151 | 39.363 | 50.535 | 22.995 | 1.00 | 66.90 | A | C |
| ATOM | 203 | OE1 | GLU | A | 151 | 39.845 | 50.581 | 24.151 | 1.00 | 67.65 | A | O |
| ATOM | 204 | OE2 | GLU | A | 151 | 39.967 | 50.018 | 22.024 | 1.00 | 69.20 | A | O |
| ATOM | 205 | C | GLU | A | 151 | 37.265 | 47.917 | 22.871 | 1.00 | 56.41 | A | C |
| ATOM | 206 | O | GLU | A | 151 | 37.304 | 47.384 | 23.975 | 1.00 | 56.29 | A | O |
| ATOM | 207 | N | LYS | A | 152 | 37.963 | 47.471 | 21.830 | 1.00 | 59.00 | A | N |
| ATOM | 208 | CA | LYS | A | 152 | 38.842 | 46.305 | 21.934 | 1.00 | 60.50 | A | C |
| ATOM | 209 | CB | LYS | A | 152 | 39.626 | 46.114 | 20.630 | 1.00 | 61.26 | A | C |
| ATOM | 210 | CG | LYS | A | 152 | 38.765 | 45.794 | 19.402 | 1.00 | 61.58 | A | C |
| ATOM | 211 | CD | LYS | A | 152 | 39.643 | 45.531 | 18.171 | 1.00 | 62.51 | A | C |
| ATOM | 212 | CE | LYS | A | 152 | 38.831 | 45.211 | 16.916 | 1.00 | 61.68 | A | C |
| ATOM | 213 | NZ | LYS | A | 152 | 37.959 | 44.023 | 17.075 | 1.00 | 63.73 | A | N |
| ATOM | 214 | C | LYS | A | 152 | 39.816 | 46.390 | 23.111 | 1.00 | 61.70 | A | C |
| ATOM | 215 | O | LYS | A | 152 | 39.759 | 45.572 | 24.030 | 1.00 | 60.64 | A | O |
| ATOM | 216 | N | GLN | A | 153 | 40.702 | 47.381 | 23.083 | 1.00 | 63.23 | A | N |
| ATOM | 217 | CA | GLN | A | 153 | 41.689 | 47.562 | 24.145 | 1.00 | 66.35 | A | C |
| ATOM | 218 | CB | GLN | A | 153 | 42.477 | 48.859 | 23.916 | 1.00 | 68.76 | A | C |
| ATOM | 219 | CG | GLN | A | 153 | 43.247 | 48.912 | 22.597 | 1.00 | 72.76 | A | C |
| ATOM | 220 | CD | GLN | A | 153 | 44.497 | 48.038 | 22.595 | 1.00 | 75.69 | A | C |
| ATOM | 221 | OE1 | GLN | A | 153 | 44.438 | 46.835 | 22.872 | 1.00 | 75.15 | A | O |
| ATOM | 222 | NE2 | GLN | A | 153 | 45.639 | 48.644 | 22.273 | 1.00 | 76.04 | A | N |
| ATOM | 223 | C | GLN | A | 153 | 41.055 | 47.600 | 25.535 | 1.00 | 67.63 | A | C |
| ATOM | 224 | O | GLN | A | 153 | 41.276 | 46.709 | 26.360 | 1.00 | 67.71 | A | O |
| ATOM | 225 | N | SER | A | 154 | 40.265 | 48.642 | 25.776 | 1.00 | 67.64 | A | N |
| ATOM | 226 | CA | SER | A | 154 | 39.592 | 48.858 | 27.054 | 1.00 | 68.46 | A | C |
| ATOM | 227 | CB | SER | A | 154 | 38.963 | 50.253 | 27.067 | 1.00 | 68.69 | A | C |
| ATOM | 228 | OG | SER | A | 154 | 38.180 | 50.435 | 28.231 | 1.00 | 72.14 | A | O |
| ATOM | 229 | C | SER | A | 154 | 38.524 | 47.827 | 27.413 | 1.00 | 67.39 | A | C |
| ATOM | 230 | O | SER | A | 154 | 38.422 | 47.404 | 28.562 | 1.00 | 66.91 | A | O |
| ATOM | 231 | N | LYS | A | 155 | 37.722 | 47.447 | 26.426 | 1.00 | 66.94 | A | N |
| ATOM | 232 | CA | LYS | A | 155 | 36.645 | 46.479 | 26.602 | 1.00 | 65.83 | A | C |
| ATOM | 233 | CB | LYS | A | 155 | 37.166 | 45.229 | 27.310 | 1.00 | 66.50 | A | C |
| ATOM | 234 | CG | LYS | A | 155 | 38.159 | 44.456 | 26.452 | 1.00 | 69.74 | A | C |
| ATOM | 235 | CD | LYS | A | 155 | 38.437 | 43.070 | 26.992 | 1.00 | 70.98 | A | C |
| ATOM | 236 | CE | LYS | A | 155 | 39.396 | 42.318 | 26.080 | 1.00 | 72.81 | A | C |

TABLE 1-continued coordinates of [T287D] Aurora A (122–396) in complex with AMP-PNP

| ATOM | 237 | NZ | LYS | A | 155 | 39.663 | 40.936 | 26.573 | 1.00 | 75.35 | A | N |
|------|-----|-----|-----|---|-----|--------|--------|--------|------|-------|---|---|
| ATOM | 238 | C | LYS | A | 155 | 35.422 | 47.053 | 27.326 | 1.00 | 64.74 | A | C |
| ATOM | 239 | O | LYS | A | 155 | 34.608 | 46.318 | 27.891 | 1.00 | 63.21 | A | O |
| ATOM | 240 | N | PHE | A | 156 | 35.289 | 48.375 | 27.278 | 1.00 | 63.83 | A | N |
| ATOM | 241 | CA | PHE | A | 156 | 34.162 | 49.061 | 27.901 | 1.00 | 61.40 | A | C |
| ATOM | 242 | CB | PHE | A | 156 | 34.544 | 50.514 | 28.194 | 1.00 | 63.97 | A | C |
| ATOM | 243 | CG | PHE | A | 156 | 33.478 | 51.290 | 28.911 | 1.00 | 68.01 | A | C |
| ATOM | 244 | CD1 | PHE | A | 156 | 32.956 | 50.832 | 30.121 | 1.00 | 69.99 | A | C |
| ATOM | 245 | CD2 | PHE | A | 156 | 33.004 | 52.490 | 28.387 | 1.00 | 68.86 | A | C |
| ATOM | 246 | CE1 | PHE | A | 156 | 31.975 | 51.559 | 30.800 | 1.00 | 70.97 | A | C |
| ATOM | 247 | CE2 | PHE | A | 156 | 32.026 | 53.224 | 29.055 | 1.00 | 69.64 | A | C |
| ATOM | 248 | CZ | PHE | A | 156 | 31.510 | 52.759 | 30.264 | 1.00 | 70.88 | A | C |
| ATOM | 249 | C | PHE | A | 156 | 32.963 | 49.013 | 26.946 | 1.00 | 57.88 | A | C |
| ATOM | 250 | O | PHE | A | 156 | 33.127 | 49.157 | 25.732 | 1.00 | 55.27 | A | O |
| ATOM | 251 | N | ILE | A | 157 | 31.768 | 48.799 | 27.498 | 1.00 | 53.85 | A | N |
| ATOM | 252 | CA | ILE | A | 157 | 30.542 | 48.730 | 26.701 | 1.00 | 50.05 | A | C |
| ATOM | 253 | CB | ILE | A | 157 | 29.434 | 47.949 | 27.459 | 1.00 | 50.70 | A | C |
| ATOM | 254 | CG2 | ILE | A | 157 | 28.097 | 48.111 | 26.760 | 1.00 | 48.39 | A | C |
| ATOM | 255 | CG1 | ILE | A | 157 | 29.800 | 46.464 | 27.545 | 1.00 | 51.64 | A | C |
| ATOM | 256 | CD1 | ILE | A | 157 | 29.635 | 45.707 | 26.244 | 1.00 | 52.26 | A | C |
| ATOM | 257 | C | ILE | A | 157 | 30.020 | 50.130 | 26.353 | 1.00 | 47.74 | A | C |
| ATOM | 258 | O | ILE | A | 157 | 29.998 | 51.021 | 27.203 | 1.00 | 45.67 | A | O |
| ATOM | 259 | N | LEU | A | 158 | 29.609 | 50.308 | 25.097 | 1.00 | 44.24 | A | N |
| ATOM | 260 | CA | LEU | A | 158 | 29.079 | 51.586 | 24.618 | 1.00 | 43.05 | A | C |
| ATOM | 261 | CB | LEU | A | 158 | 30.229 | 52.539 | 24.251 | 1.00 | 42.08 | A | C |
| ATOM | 262 | CG | LEU | A | 158 | 31.339 | 52.029 | 23.327 | 1.00 | 45.57 | A | C |
| ATOM | 263 | CD1 | LEU | A | 158 | 30.844 | 51.994 | 21.901 | 1.00 | 46.09 | A | C |
| ATOM | 264 | CD2 | LEU | A | 158 | 32.566 | 52.940 | 23.435 | 1.00 | 46.27 | A | C |
| ATOM | 265 | C | LEU | A | 158 | 28.154 | 51.392 | 23.427 | 1.00 | 39.34 | A | C |
| ATOM | 266 | O | LEU | A | 158 | 27.861 | 50.269 | 23.036 | 1.00 | 38.00 | A | O |
| ATOM | 267 | N | ALA | A | 159 | 27.669 | 52.489 | 22.858 | 1.00 | 39.30 | A | N |
| ATOM | 268 | CA | ALA | A | 159 | 26.789 | 52.384 | 21.702 | 1.00 | 38.21 | A | C |
| ATOM | 269 | CB | ALA | A | 159 | 25.438 | 53.007 | 22.006 | 1.00 | 37.68 | A | C |
| ATOM | 270 | C | ALA | A | 159 | 27.443 | 53.082 | 20.525 | 1.00 | 38.81 | A | C |
| ATOM | 271 | O | ALA | A | 159 | 28.146 | 54.073 | 20.694 | 1.00 | 38.10 | A | O |
| ATOM | 272 | N | LEU | A | 160 | 27.221 | 52.556 | 19.329 | 1.00 | 39.75 | A | N |
| ATOM | 273 | CA | LEU | A | 160 | 27.806 | 53.152 | 18.145 | 1.00 | 39.68 | A | C |
| ATOM | 274 | CB | LEU | A | 160 | 28.793 | 52.175 | 17.503 | 1.00 | 41.87 | A | C |
| ATOM | 275 | CG | LEU | A | 160 | 29.841 | 52.748 | 16.543 | 1.00 | 44.90 | A | C |
| ATOM | 276 | CD1 | LEU | A | 160 | 30.807 | 53.651 | 17.305 | 1.00 | 43.49 | A | C |
| ATOM | 277 | CD2 | LEU | A | 160 | 30.602 | 51.604 | 15.885 | 1.00 | 44.40 | A | C |
| ATOM | 278 | C | LEU | A | 160 | 26.690 | 53.496 | 17.169 | 1.00 | 39.67 | A | C |
| ATOM | 279 | O | LEU | A | 160 | 26.005 | 52.610 | 16.666 | 1.00 | 39.99 | A | O |
| ATOM | 280 | N | LYS | A | 161 | 26.493 | 54.788 | 16.921 | 1.00 | 38.00 | A | N |
| ATOM | 281 | CA | LYS | A | 161 | 25.461 | 55.212 | 15.996 | 1.00 | 39.14 | A | C |
| ATOM | 282 | CB | LYS | A | 161 | 24.782 | 56.501 | 16.480 | 1.00 | 40.21 | A | C |
| ATOM | 283 | CG | LYS | A | 161 | 23.783 | 57.073 | 15.485 | 1.00 | 43.91 | A | C |
| ATOM | 284 | CD | LYS | A | 161 | 23.120 | 58.347 | 15.994 | 1.00 | 45.72 | A | C |
| ATOM | 285 | CE | LYS | A | 161 | 22.171 | 58.060 | 17.140 | 1.00 | 48.13 | A | C |
| ATOM | 286 | NZ | LYS | A | 161 | 21.511 | 59.299 | 17.670 | 1.00 | 52.12 | A | N |
| ATOM | 287 | C | LYS | A | 161 | 26.102 | 55.429 | 14.644 | 1.00 | 36.94 | A | C |
| ATOM | 288 | O | LYS | A | 161 | 26.961 | 56.294 | 14.485 | 1.00 | 35.11 | A | O |
| ATOM | 289 | N | VAL | A | 162 | 25.661 | 54.631 | 13.677 | 1.00 | 37.87 | A | N |
| ATOM | 290 | CA | VAL | A | 162 | 26.168 | 54.656 | 12.311 | 1.00 | 37.92 | A | C |
| ATOM | 291 | CB | VAL | A | 162 | 26.400 | 53.201 | 11.807 | 1.00 | 39.41 | A | C |
| ATOM | 292 | CG1 | VAL | A | 162 | 27.179 | 53.214 | 10.506 | 1.00 | 37.99 | A | C |
| ATOM | 293 | CG2 | VAL | A | 162 | 27.142 | 52.382 | 12.873 | 1.00 | 37.26 | A | C |
| ATOM | 294 | C | VAL | A | 162 | 25.180 | 55.362 | 11.368 | 1.00 | 39.49 | A | C |
| ATOM | 295 | O | VAL | A | 162 | 24.070 | 54.878 | 11.141 | 1.00 | 40.14 | A | O |
| ATOM | 296 | N | LEU | A | 163 | 25.595 | 56.500 | 10.817 | 1.00 | 39.18 | A | N |
| ATOM | 297 | CA | LEU | A | 163 | 24.757 | 57.277 | 9.907 | 1.00 | 42.61 | A | C |
| ATOM | 298 | CB | LEU | A | 163 | 24.659 | 58.726 | 10.400 | 1.00 | 43.27 | A | C |
| ATOM | 299 | CG | LEU | A | 163 | 23.621 | 59.124 | 11.457 | 1.00 | 42.79 | A | C |
| ATOM | 300 | CD1 | LEU | A | 163 | 23.227 | 57.944 | 12.311 | 1.00 | 43.48 | A | C |
| ATOM | 301 | CD2 | LEU | A | 163 | 24.201 | 60.246 | 12.313 | 1.00 | 43.16 | A | C |
| ATOM | 302 | C | LEU | A | 163 | 25.279 | 57.278 | 8.466 | 1.00 | 45.56 | A | C |
| ATOM | 303 | O | LEU | A | 163 | 26.462 | 57.515 | 8.228 | 1.00 | 43.94 | A | O |
| ATOM | 304 | N | PHE | A | 164 | 24.381 | 57.029 | 7.513 | 1.00 | 48.16 | A | N |
| ATOM | 305 | CA | PHE | A | 164 | 24.733 | 57.006 | 6.091 | 1.00 | 52.24 | A | C |
| ATOM | 306 | CB | PHE | A | 164 | 23.624 | 56.332 | 5.286 | 1.00 | 53.67 | A | C |
| ATOM | 307 | CG | PHE | A | 164 | 23.201 | 55.008 | 5.831 | 1.00 | 55.86 | A | C |
| ATOM | 308 | CD1 | PHE | A | 164 | 21.865 | 54.625 | 5.781 | 1.00 | 56.34 | A | C |
| ATOM | 309 | CD2 | PHE | A | 164 | 24.133 | 54.139 | 6.392 | 1.00 | 55.83 | A | C |
| ATOM | 310 | CE1 | PHE | A | 164 | 21.460 | 53.393 | 6.286 | 1.00 | 58.23 | A | C |
| ATOM | 311 | CE2 | PHE | A | 164 | 23.743 | 52.907 | 6.897 | 1.00 | 55.86 | A | C |
| ATOM | 312 | CZ | PHE | A | 164 | 22.404 | 52.530 | 6.846 | 1.00 | 58.79 | A | C |
| ATOM | 313 | C | PHE | A | 164 | 24.919 | 58.423 | 5.551 | 1.00 | 53.31 | A | C |

TABLE 1-continued coordinates of [T287D] Aurora A (122–396) in complex with AMP-PNP

| ATOM | 314 | O | PHE | A | 164 | 24.022 | 59.262 | 5.676 | 1.00 | 51.66 | A | O |
|---|---|---|---|---|---|---|---|---|---|---|---|---|
| ATOM | 315 | N | LYS | A | 165 | 26.072 | 58.682 | 4.940 | 1.00 | 55.24 | A | N |
| ATOM | 316 | CA | LYS | A | 165 | 26.355 | 60.000 | 4.372 | 1.00 | 57.91 | A | C |
| ATOM | 317 | CB | LYS | A | 165 | 27.751 | 60.033 | 3.754 | 1.00 | 57.31 | A | C |
| ATOM | 318 | CG | LYS | A | 165 | 28.881 | 60.126 | 4.756 | 1.00 | 57.21 | A | C |
| ATOM | 319 | CD | LYS | A | 165 | 30.201 | 60.338 | 4.040 | 1.00 | 57.36 | A | C |
| ATOM | 320 | CE | LYS | A | 165 | 31.340 | 60.528 | 5.018 | 1.00 | 58.00 | A | C |
| ATOM | 321 | NZ | LYS | A | 165 | 32.638 | 60.675 | 4.309 | 1.00 | 60.01 | A | N |
| ATOM | 322 | C | LYS | A | 165 | 25.340 | 60.392 | 3.306 | 1.00 | 59.50 | A | C |
| ATOM | 323 | O | LYS | A | 165 | 24.971 | 61.559 | 3.194 | 1.00 | 59.56 | A | O |
| ATOM | 324 | N | ALA | A | 166 | 24.894 | 59.407 | 2.534 | 1.00 | 62.03 | A | N |
| ATOM | 325 | CA | ALA | A | 166 | 23.931 | 59.628 | 1.462 | 1.00 | 66.28 | A | C |
| ATOM | 326 | CB | ALA | A | 166 | 23.673 | 58.319 | 0.728 | 1.00 | 65.88 | A | C |
| ATOM | 327 | C | ALA | A | 166 | 22.606 | 60.229 | 1.939 | 1.00 | 69.38 | A | C |
| ATOM | 328 | O | ALA | A | 166 | 21.706 | 60.485 | 1.132 | 1.00 | 69.73 | A | O |
| ATOM | 329 | N | GLN | A | 167 | 22.486 | 60.447 | 3.246 | 1.00 | 70.89 | A | N |
| ATOM | 330 | CA | GLN | A | 167 | 21.272 | 61.017 | 3.819 | 1.00 | 71.80 | A | C |
| ATOM | 331 | CB | GLN | A | 167 | 20.686 | 60.063 | 4.856 | 1.00 | 73.19 | A | C |
| ATOM | 332 | CG | GLN | A | 167 | 20.621 | 58.625 | 4.388 | 1.00 | 76.66 | A | C |
| ATOM | 333 | CD | GLN | A | 167 | 19.769 | 58.453 | 3.152 | 1.00 | 79.08 | A | C |
| ATOM | 334 | OE1 | GLN | A | 167 | 19.772 | 57.390 | 2.527 | 1.00 | 80.82 | A | O |
| ATOM | 335 | NE2 | GLN | A | 167 | 19.025 | 59.497 | 2.792 | 1.00 | 80.53 | A | N |
| ATOM | 336 | C | GLN | A | 167 | 21.597 | 62.352 | 4.477 | 1.00 | 72.50 | A | C |
| ATOM | 337 | O | GLN | A | 167 | 20.884 | 63.336 | 4.298 | 1.00 | 71.35 | A | O |
| ATOM | 338 | N | LEU | A | 168 | 22.676 | 62.379 | 5.247 | 1.00 | 73.59 | A | N |
| ATOM | 339 | CA | LEU | A | 168 | 23.082 | 63.602 | 5.912 | 1.00 | 76.12 | A | C |
| ATOM | 340 | CB | LEU | A | 168 | 24.460 | 63.421 | 6.552 | 1.00 | 74.15 | A | C |
| ATOM | 341 | CG | LEU | A | 168 | 24.547 | 62.317 | 7.612 | 1.00 | 73.50 | A | C |
| ATOM | 342 | CD1 | LEU | A | 168 | 25.979 | 62.150 | 8.066 | 1.00 | 72.46 | A | C |
| ATOM | 343 | CD2 | LEU | A | 168 | 23.656 | 62.665 | 8.789 | 1.00 | 72.72 | A | C |
| ATOM | 344 | C | LEU | A | 168 | 23.112 | 64.728 | 4.881 | 1.00 | 78.84 | A | C |
| ATOM | 345 | O | LEU | A | 168 | 22.254 | 65.610 | 4.896 | 1.00 | 79.50 | A | O |
| ATOM | 346 | N | GLU | A | 169 | 24.086 | 64.681 | 3.976 | 1.00 | 81.12 | A | N |
| ATOM | 347 | CA | GLU | A | 169 | 24.228 | 65.697 | 2.936 | 1.00 | 83.10 | A | C |
| ATOM | 348 | CB | GLU | A | 169 | 25.344 | 65.296 | 1.971 | 1.00 | 83.78 | A | C |
| ATOM | 349 | CG | GLU | A | 169 | 25.096 | 63.979 | 1.255 | 1.00 | 85.16 | A | C |
| ATOM | 350 | CD | GLU | A | 169 | 26.298 | 63.510 | 0.457 | 1.00 | 86.11 | A | C |
| ATOM | 351 | OE1 | GLU | A | 169 | 27.361 | 63.266 | 1.068 | 1.00 | 85.05 | A | O |
| ATOM | 352 | OE2 | GLU | A | 169 | 26.179 | 63.387 | −0.781 | 1.00 | 87.77 | A | O |
| ATOM | 353 | C | GLU | A | 169 | 22.924 | 65.891 | 2.164 | 1.00 | 83.83 | A | C |
| ATOM | 354 | O | GLU | A | 169 | 22.541 | 67.018 | 1.840 | 1.00 | 83.53 | A | O |
| ATOM | 355 | N | LYS | A | 170 | 22.250 | 64.782 | 1.878 | 1.00 | 84.15 | A | N |
| ATOM | 356 | CA | LYS | A | 170 | 20.985 | 64.794 | 1.149 | 1.00 | 85.24 | A | C |
| ATOM | 357 | CB | LYS | A | 170 | 20.809 | 63.467 | 0.411 | 1.00 | 84.77 | A | C |
| ATOM | 358 | CG | LYS | A | 170 | 19.407 | 63.207 | −0.112 | 1.00 | 84.91 | A | C |
| ATOM | 359 | CD | LYS | A | 170 | 19.271 | 61.764 | −0.560 | 1.00 | 84.46 | A | C |
| ATOM | 360 | CE | LYS | A | 170 | 17.863 | 61.447 | −1.022 | 1.00 | 84.75 | A | C |
| ATOM | 361 | NZ | LYS | A | 170 | 17.754 | 60.021 | −1.434 | 1.00 | 84.95 | A | N |
| ATOM | 362 | C | LYS | A | 170 | 19.797 | 65.020 | 2.085 | 1.00 | 86.98 | A | C |
| ATOM | 363 | O | LYS | A | 170 | 19.175 | 64.058 | 2.547 | 1.00 | 88.55 | A | O |
| ATOM | 364 | N | ALA | A | 171 | 19.495 | 66.291 | 2.353 | 1.00 | 86.65 | A | N |
| ATOM | 365 | CA | ALA | A | 171 | 18.388 | 66.702 | 3.222 | 1.00 | 86.88 | A | C |
| ATOM | 366 | CB | ALA | A | 171 | 17.388 | 65.561 | 3.418 | 1.00 | 86.71 | A | C |
| ATOM | 367 | C | ALA | A | 171 | 18.877 | 67.194 | 4.577 | 1.00 | 86.86 | A | C |
| ATOM | 368 | O | ALA | A | 171 | 19.133 | 68.386 | 4.754 | 1.00 | 86.68 | A | O |
| ATOM | 369 | N | GLY | A | 172 | 18.993 | 66.275 | 5.533 | 1.00 | 86.88 | A | N |
| ATOM | 370 | CA | GLY | A | 172 | 19.449 | 66.635 | 6.866 | 1.00 | 86.26 | A | C |
| ATOM | 371 | C | GLY | A | 172 | 20.858 | 67.190 | 6.837 | 1.00 | 86.14 | A | C |
| ATOM | 372 | O | GLY | A | 172 | 21.659 | 66.924 | 7.735 | 1.00 | 86.73 | A | O |
| ATOM | 373 | N | VAL | A | 173 | 21.141 | 67.967 | 5.793 | 1.00 | 85.19 | A | N |
| ATOM | 374 | CA | VAL | A | 173 | 22.437 | 68.593 | 5.564 | 1.00 | 83.10 | A | C |
| ATOM | 375 | CB | VAL | A | 173 | 22.280 | 70.107 | 5.336 | 1.00 | 82.25 | A | C |
| ATOM | 376 | CG1 | VAL | A | 173 | 23.622 | 70.720 | 4.988 | 1.00 | 79.89 | A | C |
| ATOM | 377 | CG2 | VAL | A | 173 | 21.276 | 70.355 | 4.223 | 1.00 | 82.16 | A | C |
| ATOM | 378 | C | VAL | A | 173 | 23.450 | 68.364 | 6.678 | 1.00 | 82.27 | A | C |
| ATOM | 379 | O | VAL | A | 173 | 23.174 | 68.599 | 7.857 | 1.00 | 82.63 | A | O |
| ATOM | 380 | N | GLU | A | 174 | 24.629 | 67.897 | 6.289 | 1.00 | 80.75 | A | N |
| ATOM | 381 | CA | GLU | A | 174 | 25.690 | 67.639 | 7.242 | 1.00 | 79.61 | A | C |
| ATOM | 382 | CB | GLU | A | 174 | 26.984 | 67.310 | 6.492 | 1.00 | 80.39 | A | C |
| ATOM | 383 | CG | GLU | A | 174 | 28.221 | 67.233 | 7.369 | 1.00 | 81.70 | A | C |
| ATOM | 384 | CD | GLU | A | 174 | 28.904 | 68.577 | 7.535 | 1.00 | 83.27 | A | C |
| ATOM | 385 | OE1 | GLU | A | 174 | 29.877 | 68.658 | 8.314 | 1.00 | 83.32 | A | O |
| ATOM | 386 | OE2 | GLU | A | 174 | 28.474 | 69.552 | 6.879 | 1.00 | 83.99 | A | O |
| ATOM | 387 | C | GLU | A | 174 | 25.886 | 68.848 | 8.151 | 1.00 | 78.82 | A | C |
| ATOM | 388 | O | GLU | A | 174 | 26.258 | 68.701 | 9.313 | 1.00 | 78.22 | A | O |
| ATOM | 389 | N | HIS | A | 175 | 25.618 | 70.038 | 7.615 | 1.00 | 78.24 | A | N |
| ATOM | 390 | CA | HIS | A | 175 | 25.770 | 71.285 | 8.363 | 1.00 | 77.47 | A | C |

TABLE 1-continued coordinates of [T287D] Aurora A (122–396) in complex with AMP-PNP

| ATOM | 391 | CB | HIS | A | 175 | 25.205 | 72.463 | 7.562 | 1.00 | 76.98 | A | C |
|------|-----|-----|-----|---|-----|--------|--------|--------|------|-------|---|---|
| ATOM | 392 | CG | HIS | A | 175 | 25.859 | 72.663 | 6.231 | 1.00 | 77.17 | A | C |
| ATOM | 393 | CD2 | HIS | A | 175 | 26.828 | 71.962 | 5.597 | 1.00 | 76.90 | A | C |
| ATOM | 394 | ND1 | HIS | A | 175 | 25.506 | 73.687 | 5.378 | 1.00 | 77.46 | A | N |
| ATOM | 395 | CE1 | HIS | A | 175 | 26.229 | 73.607 | 4.275 | 1.00 | 77.33 | A | C |
| ATOM | 396 | NE2 | HIS | A | 175 | 27.039 | 72.568 | 4.382 | 1.00 | 77.65 | A | N |
| ATOM | 397 | C | HIS | A | 175 | 25.073 | 71.223 | 9.716 | 1.00 | 76.86 | A | C |
| ATOM | 398 | O | HIS | A | 175 | 25.709 | 71.382 | 10.756 | 1.00 | 74.77 | A | O |
| ATOM | 399 | N | GLN | A | 176 | 23.761 | 70.998 | 9.684 | 1.00 | 77.67 | A | N |
| ATOM | 400 | CA | GLN | A | 176 | 22.946 | 70.907 | 10.893 | 1.00 | 79.14 | A | C |
| ATOM | 401 | CB | GLN | A | 176 | 21.495 | 70.583 | 10.517 | 1.00 | 79.88 | A | C |
| ATOM | 402 | CG | GLN | A | 176 | 20.643 | 70.082 | 11.673 | 1.00 | 81.72 | A | C |
| ATOM | 403 | CD | GLN | A | 176 | 19.203 | 69.804 | 11.272 | 1.00 | 83.00 | A | C |
| ATOM | 404 | OE1 | GLN | A | 176 | 18.444 | 69.197 | 12.028 | 1.00 | 82.78 | A | O |
| ATOM | 405 | NE2 | GLN | A | 176 | 18.818 | 70.257 | 10.081 | 1.00 | 83.25 | A | N |
| ATOM | 406 | C | GLN | A | 176 | 23.459 | 69.858 | 11.873 | 1.00 | 79.66 | A | C |
| ATOM | 407 | O | GLN | A | 176 | 23.533 | 70.103 | 13.079 | 1.00 | 78.29 | A | O |
| ATOM | 408 | N | ALA | A | 177 | 23.816 | 68.689 | 11.348 | 1.00 | 81.28 | A | N |
| ATOM | 409 | CA | ALA | A | 177 | 24.305 | 67.596 | 12.178 | 1.00 | 82.55 | A | C |
| ATOM | 410 | CB | ALA | A | 177 | 23.604 | 66.305 | 11.786 | 1.00 | 83.52 | A | C |
| ATOM | 411 | C | ALA | A | 177 | 25.814 | 67.399 | 12.113 | 1.00 | 83.96 | A | C |
| ATOM | 412 | O | ALA | A | 177 | 26.284 | 66.312 | 11.767 | 1.00 | 85.89 | A | O |
| ATOM | 413 | N | ARG | A | 178 | 26.575 | 68.438 | 12.447 | 1.00 | 84.10 | A | N |
| ATOM | 414 | CA | ARG | A | 178 | 28.029 | 68.327 | 12.426 | 1.00 | 84.25 | A | C |
| ATOM | 415 | CB | ARG | A | 178 | 28.612 | 68.952 | 11.160 | 1.00 | 83.50 | A | C |
| ATOM | 416 | CG | ARG | A | 178 | 30.132 | 69.065 | 11.216 | 1.00 | 84.36 | A | C |
| ATOM | 417 | CD | ARG | A | 178 | 30.782 | 67.748 | 11.659 | 1.00 | 83.46 | A | C |
| ATOM | 418 | NE | ARG | A | 178 | 32.208 | 67.902 | 11.948 | 1.00 | 81.99 | A | N |
| ATOM | 419 | CZ | ARG | A | 178 | 32.704 | 68.564 | 12.990 | 1.00 | 79.87 | A | C |
| ATOM | 420 | NH1 | ARG | A | 178 | 31.897 | 69.144 | 13.867 | 1.00 | 78.59 | A | N |
| ATOM | 421 | NH2 | ARG | A | 178 | 34.017 | 68.652 | 13.149 | 1.00 | 78.59 | A | N |
| ATOM | 422 | C | ARG | A | 178 | 28.735 | 68.923 | 13.639 | 1.00 | 83.89 | A | C |
| ATOM | 423 | O | ARG | A | 178 | 29.075 | 68.199 | 14.576 | 1.00 | 84.19 | A | O |
| ATOM | 424 | N | ALA | A | 179 | 28.971 | 70.234 | 13.610 | 1.00 | 83.02 | A | N |
| ATOM | 425 | CA | ALA | A | 179 | 29.657 | 70.913 | 14.711 | 1.00 | 81.63 | A | C |
| ATOM | 426 | CB | ALA | A | 179 | 29.708 | 72.420 | 14.457 | 1.00 | 82.10 | A | C |
| ATOM | 427 | C | ALA | A | 179 | 28.928 | 70.622 | 16.010 | 1.00 | 80.48 | A | C |
| ATOM | 428 | O | ALA | A | 179 | 29.497 | 70.733 | 17.102 | 1.00 | 79.55 | A | O |
| ATOM | 429 | N | GLU | A | 180 | 27.658 | 70.253 | 15.869 | 1.00 | 79.39 | A | N |
| ATOM | 430 | CA | GLU | A | 180 | 26.815 | 69.908 | 17.002 | 1.00 | 78.29 | A | C |
| ATOM | 431 | CB | GLU | A | 180 | 25.389 | 69.647 | 16.521 | 1.00 | 78.71 | A | C |
| ATOM | 432 | CG | GLU | A | 180 | 24.543 | 70.903 | 16.382 | 1.00 | 81.63 | A | C |
| ATOM | 433 | CD | GLU | A | 180 | 25.322 | 72.098 | 15.848 | 1.00 | 83.43 | A | C |
| ATOM | 434 | OE1 | GLU | A | 180 | 26.170 | 72.639 | 16.591 | 1.00 | 84.35 | A | O |
| ATOM | 435 | OE2 | GLU | A | 180 | 25.088 | 72.499 | 14.686 | 1.00 | 84.07 | A | O |
| ATOM | 436 | C | GLU | A | 180 | 27.382 | 68.681 | 17.713 | 1.00 | 75.99 | A | C |
| ATOM | 437 | O | GLU | A | 180 | 26.838 | 68.226 | 18.720 | 1.00 | 75.11 | A | O |
| ATOM | 438 | N | VAL | A | 181 | 28.471 | 68.146 | 17.165 | 1.00 | 73.03 | A | N |
| ATOM | 439 | CA | VAL | A | 181 | 29.148 | 66.999 | 17.757 | 1.00 | 70.84 | A | C |
| ATOM | 440 | CB | VAL | A | 181 | 29.938 | 66.175 | 16.706 | 1.00 | 70.79 | A | C |
| ATOM | 441 | CG1 | VAL | A | 181 | 30.861 | 65.180 | 17.409 | 1.00 | 69.55 | A | C |
| ATOM | 442 | CG2 | VAL | A | 181 | 28.973 | 65.433 | 15.791 | 1.00 | 69.51 | A | C |
| ATOM | 443 | C | VAL | A | 181 | 30.128 | 67.585 | 18.758 | 1.00 | 69.44 | A | C |
| ATOM | 444 | O | VAL | A | 181 | 30.351 | 67.026 | 19.831 | 1.00 | 69.27 | A | O |
| ATOM | 445 | N | ALA | A | 182 | 30.707 | 68.724 | 18.392 | 1.00 | 68.30 | A | N |
| ATOM | 446 | CA | ALA | A | 182 | 31.654 | 69.416 | 19.259 | 1.00 | 66.45 | A | C |
| ATOM | 447 | CB | ALA | A | 182 | 32.419 | 70.483 | 18.469 | 1.00 | 67.64 | A | C |
| ATOM | 448 | C | ALA | A | 182 | 30.900 | 70.057 | 20.425 | 1.00 | 64.52 | A | C |
| ATOM | 449 | O | ALA | A | 182 | 31.368 | 70.013 | 21.567 | 1.00 | 64.11 | A | O |
| ATOM | 450 | N | ILE | A | 183 | 29.737 | 70.649 | 20.146 | 1.00 | 59.92 | A | N |
| ATOM | 451 | CA | ILE | A | 183 | 28.969 | 71.262 | 21.222 | 1.00 | 59.47 | A | C |
| ATOM | 452 | CB | ILE | A | 183 | 27.772 | 72.131 | 20.710 | 1.00 | 60.11 | A | C |
| ATOM | 453 | CG2 | ILE | A | 183 | 28.277 | 73.193 | 19.744 | 1.00 | 60.37 | A | C |
| ATOM | 454 | CG1 | ILE | A | 183 | 26.705 | 71.251 | 20.053 | 1.00 | 60.21 | A | C |
| ATOM | 455 | CD1 | ILE | A | 183 | 25.391 | 71.971 | 19.783 | 1.00 | 60.28 | A | C |
| ATOM | 456 | C | ILE | A | 183 | 28.437 | 70.164 | 22.140 | 1.00 | 56.99 | A | C |
| ATOM | 457 | O | ILE | A | 183 | 28.617 | 70.229 | 23.350 | 1.00 | 56.38 | A | O |
| ATOM | 458 | N | GLN | A | 184 | 27.799 | 69.150 | 21.562 | 1.00 | 56.33 | A | N |
| ATOM | 459 | CA | GLN | A | 184 | 27.264 | 68.045 | 22.352 | 1.00 | 56.17 | A | C |
| ATOM | 460 | CB | GLN | A | 184 | 26.552 | 67.026 | 21.458 | 1.00 | 57.52 | A | C |
| ATOM | 461 | CG | GLN | A | 184 | 25.670 | 66.045 | 22.228 | 1.00 | 61.39 | A | C |
| ATOM | 462 | CD | GLN | A | 184 | 24.324 | 66.650 | 22.615 | 1.00 | 64.82 | A | C |
| ATOM | 463 | OE1 | GLN | A | 184 | 23.672 | 66.213 | 23.570 | 1.00 | 62.62 | A | O |
| ATOM | 464 | NE2 | GLN | A | 184 | 23.897 | 67.654 | 21.857 | 1.00 | 65.33 | A | N |
| ATOM | 465 | C | GLN | A | 184 | 28.381 | 67.342 | 23.124 | 1.00 | 54.27 | A | C |
| ATOM | 466 | O | GLN | A | 184 | 28.236 | 67.057 | 24.308 | 1.00 | 53.30 | A | O |
| ATOM | 467 | N | SER | A | 185 | 29.498 | 67.076 | 22.458 | 1.00 | 53.49 | A | N |

TABLE 1-continued coordinates of [T287D] Aurora A (122–396) in complex with AMP-PNP

| ATOM | 468 | CA | SER | A | 185 | 30.621 | 66.401 | 23.106 | 1.00 | 55.92 | A | C |
|------|-----|-----|-----|---|-----|--------|--------|--------|------|-------|---|---|
| ATOM | 469 | CB | SER | A | 185 | 31.786 | 66.247 | 22.128 | 1.00 | 56.01 | A | C |
| ATOM | 470 | OG | SER | A | 185 | 32.335 | 67.510 | 21.797 | 1.00 | 55.72 | A | O |
| ATOM | 471 | C | SER | A | 185 | 31.115 | 67.152 | 24.342 | 1.00 | 56.22 | A | C |
| ATOM | 472 | O | SER | A | 185 | 31.636 | 66.551 | 25.281 | 1.00 | 55.88 | A | O |
| ATOM | 473 | N | HIS | A | 186 | 30.945 | 68.467 | 24.341 | 1.00 | 56.92 | A | N |
| ATOM | 474 | CA | HIS | A | 186 | 31.399 | 69.281 | 25.460 | 1.00 | 58.35 | A | C |
| ATOM | 475 | CB | HIS | A | 186 | 31.765 | 70.676 | 24.953 | 1.00 | 61.17 | A | C |
| ATOM | 476 | CG | HIS | A | 186 | 32.936 | 70.683 | 24.017 | 1.00 | 64.95 | A | C |
| ATOM | 477 | CD2 | HIS | A | 186 | 33.986 | 69.834 | 23.898 | 1.00 | 65.77 | A | C |
| ATOM | 478 | ND1 | HIS | A | 186 | 33.120 | 71.656 | 23.056 | 1.00 | 66.54 | A | N |
| ATOM | 479 | CE1 | HIS | A | 186 | 34.231 | 71.404 | 22.386 | 1.00 | 66.45 | A | C |
| ATOM | 480 | NE2 | HIS | A | 186 | 34.775 | 70.305 | 22.877 | 1.00 | 66.45 | A | N |
| ATOM | 481 | C | HIS | A | 186 | 30.399 | 69.359 | 26.610 | 1.00 | 56.48 | A | C |
| ATOM | 482 | O | HIS | A | 186 | 30.615 | 70.079 | 27.583 | 1.00 | 57.86 | A | O |
| ATOM | 483 | N | LEU | A | 187 | 29.304 | 68.614 | 26.496 | 1.00 | 53.92 | A | N |
| ATOM | 484 | CA | LEU | A | 187 | 28.296 | 68.580 | 27.543 | 1.00 | 52.14 | A | C |
| ATOM | 485 | CB | LEU | A | 187 | 26.900 | 68.410 | 26.935 | 1.00 | 51.03 | A | C |
| ATOM | 486 | CG | LEU | A | 187 | 26.067 | 69.660 | 26.626 | 1.00 | 52.63 | A | C |
| ATOM | 487 | CD1 | LEU | A | 187 | 26.958 | 70.858 | 26.344 | 1.00 | 52.17 | A | C |
| ATOM | 488 | CD2 | LEU | A | 187 | 25.158 | 69.365 | 25.444 | 1.00 | 51.26 | A | C |
| ATOM | 489 | C | LEU | A | 187 | 28.619 | 67.401 | 28.454 | 1.00 | 51.97 | A | C |
| ATOM | 490 | O | LEU | A | 187 | 28.631 | 66.256 | 28.010 | 1.00 | 51.83 | A | O |
| ATOM | 491 | N | ARG | A | 188 | 28.891 | 67.682 | 29.724 | 1.00 | 50.85 | A | N |
| ATOM | 492 | CA | ARG | A | 188 | 29.213 | 66.626 | 30.676 | 1.00 | 49.45 | A | C |
| ATOM | 493 | CB | ARG | A | 188 | 30.703 | 66.670 | 31.026 | 1.00 | 52.24 | A | C |
| ATOM | 494 | CG | ARG | A | 188 | 31.595 | 66.327 | 29.838 | 1.00 | 56.65 | A | C |
| ATOM | 495 | CD | ARG | A | 188 | 33.042 | 66.111 | 30.252 | 1.00 | 61.31 | A | C |
| ATOM | 496 | NE | ARG | A | 188 | 33.881 | 65.699 | 29.126 | 1.00 | 64.86 | A | N |
| ATOM | 497 | CZ | ARG | A | 188 | 34.195 | 66.477 | 28.092 | 1.00 | 65.93 | A | C |
| ATOM | 498 | NH1 | ARG | A | 188 | 33.744 | 67.725 | 28.028 | 1.00 | 67.33 | A | N |
| ATOM | 499 | NH2 | ARG | A | 188 | 34.959 | 66.007 | 27.115 | 1.00 | 66.11 | A | N |
| ATOM | 500 | C | ARG | A | 188 | 28.356 | 66.746 | 31.923 | 1.00 | 47.99 | A | C |
| ATOM | 501 | O | ARG | A | 188 | 28.619 | 67.561 | 32.813 | 1.00 | 47.40 | A | O |
| ATOM | 502 | N | HIS | A | 189 | 27.323 | 65.913 | 31.981 | 1.00 | 46.41 | A | N |
| ATOM | 503 | CA | HIS | A | 189 | 26.387 | 65.939 | 33.095 | 1.00 | 43.42 | A | C |
| ATOM | 504 | CB | HIS | A | 189 | 25.288 | 66.961 | 32.775 | 1.00 | 39.93 | A | C |
| ATOM | 505 | CG | HIS | A | 189 | 24.371 | 67.255 | 33.918 | 1.00 | 37.78 | A | C |
| ATOM | 506 | CD2 | HIS | A | 189 | 24.342 | 68.289 | 34.793 | 1.00 | 37.18 | A | C |
| ATOM | 507 | ND1 | HIS | A | 189 | 23.322 | 66.431 | 34.261 | 1.00 | 38.04 | A | N |
| ATOM | 508 | CE1 | HIS | A | 189 | 22.681 | 66.948 | 35.296 | 1.00 | 40.74 | A | C |
| ATOM | 509 | NE2 | HIS | A | 189 | 23.281 | 68.076 | 35.637 | 1.00 | 38.70 | A | N |
| ATOM | 510 | C | HIS | A | 189 | 25.794 | 64.546 | 33.314 | 1.00 | 42.45 | A | C |
| ATOM | 511 | O | HIS | A | 189 | 25.585 | 63.799 | 32.367 | 1.00 | 43.83 | A | O |
| ATOM | 512 | N | PRO | A | 190 | 25.539 | 64.171 | 34.576 | 1.00 | 41.87 | A | N |
| ATOM | 513 | CD | PRO | A | 190 | 25.811 | 64.893 | 35.829 | 1.00 | 41.35 | A | C |
| ATOM | 514 | CA | PRO | A | 190 | 24.970 | 62.850 | 34.851 | 1.00 | 40.95 | A | C |
| ATOM | 515 | CB | PRO | A | 190 | 24.878 | 62.820 | 36.378 | 1.00 | 40.22 | A | C |
| ATOM | 516 | CG | PRO | A | 190 | 24.803 | 64.267 | 36.758 | 1.00 | 43.23 | A | C |
| ATOM | 517 | C | PRO | A | 190 | 23.626 | 62.591 | 34.178 | 1.00 | 40.60 | A | C |
| ATOM | 518 | O | PRO | A | 190 | 23.260 | 61.442 | 33.931 | 1.00 | 40.06 | A | O |
| ATOM | 519 | N | ASN | A | 191 | 22.886 | 63.650 | 33.865 | 1.00 | 39.67 | A | N |
| ATOM | 520 | CA | ASN | A | 191 | 21.594 | 63.451 | 33.237 | 1.00 | 37.85 | A | C |
| ATOM | 521 | CB | ASN | A | 191 | 20.532 | 64.244 | 34.003 | 1.00 | 39.49 | A | C |
| ATOM | 522 | CG | ASN | A | 191 | 20.373 | 63.762 | 35.446 | 1.00 | 37.64 | A | C |
| ATOM | 523 | OD1 | ASN | A | 191 | 20.013 | 62.606 | 35.695 | 1.00 | 38.24 | A | O |
| ATOM | 524 | ND2 | ASN | A | 191 | 20.647 | 64.645 | 36.397 | 1.00 | 35.93 | A | N |
| ATOM | 525 | C | ASN | A | 191 | 21.570 | 63.766 | 31.735 | 1.00 | 37.60 | A | C |
| ATOM | 526 | O | ASN | A | 191 | 20.518 | 64.003 | 31.150 | 1.00 | 36.22 | A | O |
| ATOM | 527 | N | ILE | A | 192 | 22.741 | 63.776 | 31.112 | 1.00 | 37.28 | A | N |
| ATOM | 528 | CA | ILE | A | 192 | 22.829 | 64.006 | 29.673 | 1.00 | 38.27 | A | C |
| ATOM | 529 | CB | ILE | A | 192 | 23.511 | 65.351 | 29.316 | 1.00 | 38.46 | A | C |
| ATOM | 530 | CG2 | ILE | A | 192 | 23.623 | 65.488 | 27.795 | 1.00 | 35.81 | A | C |
| ATOM | 531 | CG1 | ILE | A | 192 | 22.689 | 66.516 | 29.867 | 1.00 | 41.28 | A | C |
| ATOM | 532 | CD1 | ILE | A | 192 | 23.199 | 67.881 | 29.476 | 1.00 | 38.83 | A | C |
| ATOM | 533 | C | ILE | A | 192 | 23.672 | 62.881 | 29.108 | 1.00 | 38.70 | A | C |
| ATOM | 534 | O | ILE | A | 192 | 24.772 | 62.629 | 29.597 | 1.00 | 38.53 | A | O |
| ATOM | 535 | N | LEU | A | 193 | 23.153 | 62.195 | 28.095 | 1.00 | 40.02 | A | N |
| ATOM | 536 | CA | LEU | A | 193 | 23.884 | 61.094 | 27.477 | 1.00 | 39.54 | A | C |
| ATOM | 537 | CB | LEU | A | 193 | 23.099 | 60.525 | 26.299 | 1.00 | 38.70 | A | C |
| ATOM | 538 | CG | LEU | A | 193 | 23.577 | 59.164 | 25.775 | 1.00 | 38.41 | A | C |
| ATOM | 539 | CD1 | LEU | A | 193 | 23.122 | 58.073 | 26.751 | 1.00 | 35.03 | A | C |
| ATOM | 540 | CD2 | LEU | A | 193 | 22.995 | 58.913 | 24.380 | 1.00 | 34.30 | A | C |
| ATOM | 541 | C | LEU | A | 193 | 25.211 | 61.630 | 26.973 | 1.00 | 40.55 | A | C |
| ATOM | 542 | O | LEU | A | 193 | 25.245 | 62.660 | 26.302 | 1.00 | 42.56 | A | O |
| ATOM | 543 | N | ARG | A | 194 | 26.308 | 60.947 | 27.282 | 1.00 | 40.25 | A | N |
| ATOM | 544 | CA | ARG | A | 194 | 27.593 | 61.436 | 26.820 | 1.00 | 41.82 | A | C |

TABLE 1-continued coordinates of [T287D] Aurora A (122–396) in complex with AMP-PNP

| ATOM | 545 | CB | ARG | A | 194 | 28.728 | 61.018 | 27.756 | 1.00 | 43.59 | A | C |
|---|---|---|---|---|---|---|---|---|---|---|---|---|
| ATOM | 546 | CG | ARG | A | 194 | 30.023 | 61.749 | 27.418 | 1.00 | 49.64 | A | C |
| ATOM | 547 | CD | ARG | A | 194 | 31.216 | 61.273 | 28.217 | 1.00 | 56.35 | A | C |
| ATOM | 548 | NE | ARG | A | 194 | 32.436 | 62.006 | 27.871 | 1.00 | 60.72 | A | N |
| ATOM | 549 | CZ | ARG | A | 194 | 33.658 | 61.677 | 28.291 | 1.00 | 64.00 | A | C |
| ATOM | 550 | NH1 | ARG | A | 194 | 33.834 | 60.621 | 29.076 | 1.00 | 64.55 | A | N |
| ATOM | 551 | NH2 | ARG | A | 194 | 34.708 | 62.403 | 27.924 | 1.00 | 65.94 | A | N |
| ATOM | 552 | C | ARG | A | 194 | 27.957 | 61.023 | 25.401 | 1.00 | 42.36 | A | C |
| ATOM | 553 | O | ARG | A | 194 | 27.723 | 59.887 | 24.974 | 1.00 | 41.77 | A | O |
| ATOM | 554 | N | LEU | A | 195 | 28.517 | 61.981 | 24.671 | 1.00 | 41.98 | A | N |
| ATOM | 555 | CA | LEU | A | 195 | 28.981 | 61.763 | 23.308 | 1.00 | 43.72 | A | C |
| ATOM | 556 | CB | LEU | A | 195 | 28.538 | 62.912 | 22.395 | 1.00 | 42.46 | A | C |
| ATOM | 557 | CG | LEU | A | 195 | 28.545 | 62.694 | 20.878 | 1.00 | 46.89 | A | C |
| ATOM | 558 | CD1 | LEU | A | 195 | 28.063 | 63.967 | 20.193 | 1.00 | 48.66 | A | C |
| ATOM | 559 | CD2 | LEU | A | 195 | 29.926 | 62.338 | 20.395 | 1.00 | 45.85 | A | C |
| ATOM | 560 | C | LEU | A | 195 | 30.491 | 61.790 | 23.493 | 1.00 | 43.63 | A | C |
| ATOM | 561 | O | LEU | A | 195 | 31.061 | 62.851 | 23.722 | 1.00 | 45.28 | A | O |
| ATOM | 562 | N | TYR | A | 196 | 31.123 | 60.622 | 23.436 | 1.00 | 42.73 | A | N |
| ATOM | 563 | CA | TYR | A | 196 | 32.566 | 60.518 | 23.618 | 1.00 | 44.78 | A | C |
| ATOM | 564 | CB | TYR | A | 196 | 32.980 | 59.061 | 23.844 | 1.00 | 46.97 | A | C |
| ATOM | 565 | CG | TYR | A | 196 | 32.399 | 58.427 | 25.085 | 1.00 | 50.10 | A | C |
| ATOM | 566 | CD1 | TYR | A | 196 | 31.409 | 57.452 | 24.996 | 1.00 | 50.68 | A | C |
| ATOM | 567 | CE1 | TYR | A | 196 | 30.888 | 56.846 | 26.139 | 1.00 | 52.33 | A | C |
| ATOM | 568 | CD2 | TYR | A | 196 | 32.853 | 58.786 | 26.352 | 1.00 | 51.97 | A | C |
| ATOM | 569 | CE2 | TYR | A | 196 | 32.338 | 58.187 | 27.504 | 1.00 | 52.17 | A | C |
| ATOM | 570 | CZ | TYR | A | 196 | 31.358 | 57.220 | 27.389 | 1.00 | 54.59 | A | C |
| ATOM | 571 | OH | TYR | A | 196 | 30.844 | 56.626 | 28.525 | 1.00 | 57.15 | A | O |
| ATOM | 572 | C | TYR | A | 196 | 33.356 | 61.070 | 22.443 | 1.00 | 44.49 | A | C |
| ATOM | 573 | O | TYR | A | 196 | 34.445 | 61.604 | 22.622 | 1.00 | 45.61 | A | O |
| ATOM | 574 | N | GLY | A | 197 | 32.819 | 60.932 | 21.240 | 1.00 | 44.09 | A | N |
| ATOM | 575 | CA | GLY | A | 197 | 33.517 | 61.441 | 20.074 | 1.00 | 43.41 | A | C |
| ATOM | 576 | C | GLY | A | 197 | 32.913 | 60.907 | 18.797 | 1.00 | 43.77 | A | C |
| ATOM | 577 | O | GLY | A | 197 | 31.804 | 60.380 | 18.802 | 1.00 | 43.31 | A | O |
| ATOM | 578 | N | TYR | A | 198 | 33.633 | 61.044 | 17.694 | 1.00 | 44.25 | A | N |
| ATOM | 579 | CA | TYR | A | 198 | 33.127 | 60.551 | 16.425 | 1.00 | 45.18 | A | C |
| ATOM | 580 | CB | TYR | A | 198 | 32.041 | 61.491 | 15.889 | 1.00 | 49.33 | A | C |
| ATOM | 581 | CG | TYR | A | 198 | 32.571 | 62.592 | 14.997 | 1.00 | 55.20 | A | C |
| ATOM | 582 | CD1 | TYR | A | 198 | 33.310 | 63.653 | 15.520 | 1.00 | 57.66 | A | C |
| ATOM | 583 | CE1 | TYR | A | 198 | 33.845 | 64.638 | 14.688 | 1.00 | 59.20 | A | C |
| ATOM | 584 | CD2 | TYR | A | 198 | 32.375 | 62.543 | 13.618 | 1.00 | 58.31 | A | C |
| ATOM | 585 | CE2 | TYR | A | 198 | 32.904 | 63.521 | 12.775 | 1.00 | 60.71 | A | C |
| ATOM | 586 | CZ | TYR | A | 198 | 33.640 | 64.561 | 13.315 | 1.00 | 60.83 | A | C |
| ATOM | 587 | OH | TYR | A | 198 | 34.190 | 65.505 | 12.472 | 1.00 | 62.06 | A | O |
| ATOM | 588 | C | TYR | A | 198 | 34.235 | 60.408 | 15.382 | 1.00 | 43.11 | A | C |
| ATOM | 589 | O | TYR | A | 198 | 35.344 | 60.925 | 15.553 | 1.00 | 39.29 | A | O |
| ATOM | 590 | N | PHE | A | 199 | 33.913 | 59.695 | 14.307 | 1.00 | 41.05 | A | N |
| ATOM | 591 | CA | PHE | A | 199 | 34.834 | 59.483 | 13.194 | 1.00 | 42.76 | A | C |
| ATOM | 592 | CB | PHE | A | 199 | 35.884 | 58.405 | 13.540 | 1.00 | 41.19 | A | C |
| ATOM | 593 | CG | PHE | A | 199 | 35.308 | 57.040 | 13.853 | 1.00 | 42.02 | A | C |
| ATOM | 594 | CD1 | PHE | A | 199 | 35.100 | 56.105 | 12.842 | 1.00 | 42.90 | A | C |
| ATOM | 595 | CD2 | PHE | A | 199 | 35.025 | 56.677 | 15.162 | 1.00 | 40.34 | A | C |
| ATOM | 596 | CE1 | PHE | A | 199 | 34.623 | 54.822 | 13.129 | 1.00 | 40.61 | A | C |
| ATOM | 597 | CE2 | PHE | A | 199 | 34.545 | 55.394 | 15.465 | 1.00 | 43.97 | A | C |
| ATOM | 598 | CZ | PHE | A | 199 | 34.347 | 54.464 | 14.441 | 1.00 | 41.24 | A | C |
| ATOM | 599 | C | PHE | A | 199 | 34.012 | 59.104 | 11.964 | 1.00 | 42.14 | A | C |
| ATOM | 600 | O | PHE | A | 199 | 32.807 | 58.881 | 12.068 | 1.00 | 42.73 | A | O |
| ATOM | 601 | N | HIS | A | 200 | 34.647 | 59.068 | 10.800 | 1.00 | 42.87 | A | N |
| ATOM | 602 | CA | HIS | A | 200 | 33.946 | 58.732 | 9.570 | 1.00 | 44.89 | A | C |
| ATOM | 603 | CB | HIS | A | 200 | 33.493 | 60.002 | 8.856 | 1.00 | 46.96 | A | C |
| ATOM | 604 | CG | HIS | A | 200 | 34.610 | 60.727 | 8.170 | 1.00 | 51.07 | A | C |
| ATOM | 605 | CD2 | HIS | A | 200 | 34.913 | 60.863 | 6.856 | 1.00 | 52.59 | A | C |
| ATOM | 606 | ND1 | HIS | A | 200 | 35.616 | 61.370 | 8.862 | 1.00 | 53.07 | A | N |
| ATOM | 607 | CE1 | HIS | A | 200 | 36.489 | 61.870 | 8.005 | 1.00 | 53.71 | A | C |
| ATOM | 608 | NE2 | HIS | A | 200 | 36.087 | 61.576 | 6.781 | 1.00 | 52.64 | A | N |
| ATOM | 609 | C | HIS | A | 200 | 34.838 | 57.969 | 8.597 | 1.00 | 44.12 | A | C |
| ATOM | 610 | O | HIS | A | 200 | 36.041 | 57.819 | 8.813 | 1.00 | 43.09 | A | O |
| ATOM | 611 | N | ASP | A | 201 | 34.214 | 57.494 | 7.525 | 1.00 | 42.67 | A | N |
| ATOM | 612 | CA | ASP | A | 201 | 34.910 | 56.818 | 6.442 | 1.00 | 44.38 | A | C |
| ATOM | 613 | CB | ASP | A | 201 | 34.819 | 55.281 | 6.545 | 1.00 | 44.11 | A | C |
| ATOM | 614 | CG | ASP | A | 201 | 33.399 | 54.766 | 6.553 | 1.00 | 43.31 | A | C |
| ATOM | 615 | OD1 | ASP | A | 201 | 32.535 | 55.361 | 5.881 | 1.00 | 46.12 | A | O |
| ATOM | 616 | OD2 | ASP | A | 201 | 33.152 | 53.742 | 7.222 | 1.00 | 45.46 | A | O |
| ATOM | 617 | C | ASP | A | 201 | 34.260 | 57.325 | 5.153 | 1.00 | 44.18 | A | C |
| ATOM | 618 | O | ASP | A | 201 | 33.535 | 58.322 | 5.166 | 1.00 | 42.40 | A | O |
| ATOM | 619 | N | ALA | A | 202 | 34.515 | 56.642 | 4.049 | 1.00 | 44.77 | A | N |
| ATOM | 620 | CA | ALA | A | 202 | 33.981 | 57.044 | 2.755 | 1.00 | 45.80 | A | C |
| ATOM | 621 | CB | ALA | A | 202 | 34.409 | 56.028 | 1.687 | 1.00 | 44.78 | A | C |

TABLE 1-continued coordinates of [T287D] Aurora A (122–396) in complex with AMP-PNP

| ATOM | 622 | C | ALA | A | 202 | 32.470 | 57.227 | 2.696 | 1.00 | 46.73 | A | C |
|------|-----|-----|-----|---|-----|--------|--------|-------|------|-------|---|---|
| ATOM | 623 | O | ALA | A | 202 | 31.982 | 58.209 | 2.122 | 1.00 | 46.56 | A | O |
| ATOM | 624 | N | THR | A | 203 | 31.736 | 56.291 | 3.297 | 1.00 | 45.01 | A | N |
| ATOM | 625 | CA | THR | A | 203 | 30.282 | 56.318 | 3.245 | 1.00 | 45.70 | A | C |
| ATOM | 626 | CB | THR | A | 203 | 29.761 | 55.004 | 2.628 | 1.00 | 47.92 | A | C |
| ATOM | 627 | OG1 | THR | A | 203 | 29.962 | 53.934 | 3.565 | 1.00 | 50.55 | A | O |
| ATOM | 628 | CG2 | THR | A | 203 | 30.525 | 54.669 | 1.350 | 1.00 | 46.84 | A | C |
| ATOM | 629 | C | THR | A | 203 | 29.503 | 56.536 | 4.548 | 1.00 | 46.72 | A | C |
| ATOM | 630 | O | THR | A | 203 | 28.281 | 56.715 | 4.506 | 1.00 | 46.89 | A | O |
| ATOM | 631 | N | ARG | A | 204 | 30.170 | 56.528 | 5.699 | 1.00 | 43.86 | A | N |
| ATOM | 632 | CA | ARG | A | 204 | 29.424 | 56.680 | 6.948 | 1.00 | 41.61 | A | C |
| ATOM | 633 | CB | ARG | A | 204 | 29.167 | 55.300 | 7.577 | 1.00 | 42.57 | A | C |
| ATOM | 634 | CG | ARG | A | 204 | 28.645 | 54.199 | 6.646 | 1.00 | 45.37 | A | C |
| ATOM | 635 | CD | ARG | A | 204 | 28.299 | 52.983 | 7.491 | 1.00 | 52.00 | A | C |
| ATOM | 636 | NE | ARG | A | 204 | 28.122 | 51.719 | 6.769 | 1.00 | 59.45 | A | N |
| ATOM | 637 | CZ | ARG | A | 204 | 27.200 | 51.489 | 5.838 | 1.00 | 60.63 | A | C |
| ATOM | 638 | NH1 | ARG | A | 204 | 26.350 | 52.439 | 5.480 | 1.00 | 63.62 | A | N |
| ATOM | 639 | NH2 | ARG | A | 204 | 27.106 | 50.287 | 5.286 | 1.00 | 64.09 | A | N |
| ATOM | 640 | C | ARG | A | 204 | 30.073 | 57.564 | 8.010 | 1.00 | 39.60 | A | C |
| ATOM | 641 | O | ARG | A | 204 | 31.273 | 57.839 | 7.968 | 1.00 | 38.12 | A | O |
| ATOM | 642 | N | VAL | A | 205 | 29.249 | 57.993 | 8.967 | 1.00 | 38.69 | A | N |
| ATOM | 643 | CA | VAL | A | 205 | 29.684 | 58.807 | 10.098 | 1.00 | 36.15 | A | C |
| ATOM | 644 | CB | VAL | A | 205 | 28.872 | 60.127 | 10.202 | 1.00 | 39.01 | A | C |
| ATOM | 645 | CG1 | VAL | A | 205 | 29.345 | 60.924 | 11.406 | 1.00 | 37.93 | A | C |
| ATOM | 646 | CG2 | VAL | A | 205 | 29.031 | 60.957 | 8.919 | 1.00 | 36.49 | A | C |
| ATOM | 647 | C | VAL | A | 205 | 29.419 | 57.954 | 11.344 | 1.00 | 36.45 | A | C |
| ATOM | 648 | O | VAL | A | 205 | 28.365 | 57.331 | 11.457 | 1.00 | 36.62 | A | O |
| ATOM | 649 | N | TYR | A | 206 | 30.367 | 57.911 | 12.271 | 1.00 | 35.58 | A | N |
| ATOM | 650 | CA | TYR | A | 206 | 30.185 | 57.100 | 13.470 | 1.00 | 39.37 | A | C |
| ATOM | 651 | CB | TYR | A | 206 | 31.254 | 55.996 | 13.533 | 1.00 | 40.23 | A | C |
| ATOM | 652 | CG | TYR | A | 206 | 31.301 | 55.101 | 12.314 | 1.00 | 40.95 | A | C |
| ATOM | 653 | CD1 | TYR | A | 206 | 31.811 | 55.565 | 11.101 | 1.00 | 43.93 | A | C |
| ATOM | 654 | CE1 | TYR | A | 206 | 31.859 | 54.741 | 9.973 | 1.00 | 43.38 | A | C |
| ATOM | 655 | CD2 | TYR | A | 206 | 30.836 | 53.784 | 12.372 | 1.00 | 43.86 | A | C |
| ATOM | 656 | CE2 | TYR | A | 206 | 30.882 | 52.949 | 11.252 | 1.00 | 42.92 | A | C |
| ATOM | 657 | CZ | TYR | A | 206 | 31.394 | 53.436 | 10.057 | 1.00 | 43.76 | A | C |
| ATOM | 658 | OH | TYR | A | 206 | 31.433 | 52.623 | 8.946 | 1.00 | 45.92 | A | O |
| ATOM | 659 | C | TYR | A | 206 | 30.226 | 57.915 | 14.760 | 1.00 | 38.58 | A | C |
| ATOM | 660 | O | TYR | A | 206 | 31.200 | 58.604 | 15.045 | 1.00 | 40.46 | A | O |
| ATOM | 661 | N | LEU | A | 207 | 29.163 | 57.823 | 15.544 | 1.00 | 37.67 | A | N |
| ATOM | 662 | CA | LEU | A | 207 | 29.098 | 58.545 | 16.806 | 1.00 | 35.63 | A | C |
| ATOM | 663 | CB | LEU | A | 207 | 27.735 | 59.232 | 16.928 | 1.00 | 35.79 | A | C |
| ATOM | 664 | CG | LEU | A | 207 | 27.388 | 60.127 | 15.729 | 1.00 | 37.16 | A | C |
| ATOM | 665 | CD1 | LEU | A | 207 | 25.985 | 60.681 | 15.899 | 1.00 | 37.87 | A | C |
| ATOM | 666 | CD2 | LEU | A | 207 | 28.409 | 61.256 | 15.606 | 1.00 | 33.68 | A | C |
| ATOM | 667 | C | LEU | A | 207 | 29.314 | 57.561 | 17.955 | 1.00 | 33.49 | A | C |
| ATOM | 668 | O | LEU | A | 207 | 28.624 | 56.556 | 18.044 | 1.00 | 32.51 | A | O |
| ATOM | 669 | N | ILE | A | 208 | 30.276 | 57.858 | 18.826 | 1.00 | 31.11 | A | N |
| ATOM | 670 | CA | ILE | A | 208 | 30.592 | 56.997 | 19.961 | 1.00 | 32.62 | A | C |
| ATOM | 671 | CB | ILE | A | 208 | 32.094 | 57.029 | 20.266 | 1.00 | 31.85 | A | C |
| ATOM | 672 | CG2 | ILE | A | 208 | 32.423 | 55.991 | 21.298 | 1.00 | 29.97 | A | C |
| ATOM | 673 | CG1 | ILE | A | 208 | 32.889 | 56.759 | 18.983 | 1.00 | 34.87 | A | C |
| ATOM | 674 | CD1 | ILE | A | 208 | 34.370 | 57.064 | 19.111 | 1.00 | 34.66 | A | C |
| ATOM | 675 | C | ILE | A | 208 | 29.827 | 57.494 | 21.185 | 1.00 | 33.51 | A | C |
| ATOM | 676 | O | ILE | A | 208 | 30.226 | 58.470 | 21.823 | 1.00 | 33.57 | A | O |
| ATOM | 677 | N | LEU | A | 209 | 28.747 | 56.794 | 21.515 | 1.00 | 32.77 | A | N |
| ATOM | 678 | CA | LEU | A | 209 | 27.867 | 57.173 | 22.613 | 1.00 | 33.70 | A | C |
| ATOM | 679 | CB | LEU | A | 209 | 26.413 | 57.171 | 22.104 | 1.00 | 31.78 | A | C |
| ATOM | 680 | CG | LEU | A | 209 | 26.089 | 58.037 | 20.880 | 1.00 | 31.51 | A | C |
| ATOM | 681 | CD1 | LEU | A | 209 | 24.794 | 57.580 | 20.244 | 1.00 | 32.48 | A | C |
| ATOM | 682 | CD2 | LEU | A | 209 | 26.011 | 59.504 | 21.295 | 1.00 | 32.98 | A | C |
| ATOM | 683 | C | LEU | A | 209 | 27.933 | 56.314 | 23.878 | 1.00 | 34.77 | A | C |
| ATOM | 684 | O | LEU | A | 209 | 28.326 | 55.151 | 23.842 | 1.00 | 35.59 | A | O |
| ATOM | 685 | N | GLU | A | 210 | 27.529 | 56.917 | 24.993 | 1.00 | 35.23 | A | N |
| ATOM | 686 | CA | GLU | A | 210 | 27.443 | 56.237 | 26.282 | 1.00 | 34.76 | A | C |
| ATOM | 687 | CB | GLU | A | 210 | 27.107 | 57.260 | 27.371 | 1.00 | 36.80 | A | C |
| ATOM | 688 | CG | GLU | A | 210 | 26.610 | 56.678 | 28.686 | 1.00 | 37.86 | A | C |
| ATOM | 689 | CD | GLU | A | 210 | 26.086 | 57.752 | 29.637 | 1.00 | 39.64 | A | C |
| ATOM | 690 | OE1 | GLU | A | 210 | 25.525 | 57.394 | 30.691 | 1.00 | 38.77 | A | O |
| ATOM | 691 | OE2 | GLU | A | 210 | 26.237 | 58.957 | 29.334 | 1.00 | 41.10 | A | O |
| ATOM | 692 | C | GLU | A | 210 | 26.269 | 55.281 | 26.102 | 1.00 | 34.26 | A | C |
| ATOM | 693 | O | GLU | A | 210 | 25.304 | 55.624 | 25.417 | 1.00 | 33.07 | A | O |
| ATOM | 694 | N | TYR | A | 211 | 26.334 | 54.091 | 26.699 | 1.00 | 34.30 | A | N |
| ATOM | 695 | CA | TYR | A | 211 | 25.234 | 53.126 | 26.558 | 1.00 | 32.97 | A | C |
| ATOM | 696 | CB | TYR | A | 211 | 25.782 | 51.691 | 26.439 | 1.00 | 33.26 | A | C |
| ATOM | 697 | CG | TYR | A | 211 | 24.709 | 50.628 | 26.361 | 1.00 | 32.75 | A | C |
| ATOM | 698 | CD1 | TYR | A | 211 | 23.845 | 50.564 | 25.266 | 1.00 | 34.54 | A | C |

TABLE 1-continued coordinates of [T287D] Aurora A (122–396) in complex with AMP-PNP

| ATOM | 699 | CE1 | TYR | A | 211 | 22.802 | 49.649 | 25.223 | 1.00 | 35.34 | A | C |
|---|---|---|---|---|---|---|---|---|---|---|---|---|
| ATOM | 700 | CD2 | TYR | A | 211 | 24.507 | 49.732 | 27.414 | 1.00 | 34.61 | A | C |
| ATOM | 701 | CE2 | TYR | A | 211 | 23.461 | 48.807 | 27.385 | 1.00 | 35.43 | A | C |
| ATOM | 702 | CZ | TYR | A | 211 | 22.609 | 48.774 | 26.288 | 1.00 | 38.58 | A | C |
| ATOM | 703 | OH | TYR | A | 211 | 21.538 | 47.896 | 26.267 | 1.00 | 38.81 | A | O |
| ATOM | 704 | C | TYR | A | 211 | 24.260 | 53.213 | 27.735 | 1.00 | 33.39 | A | C |
| ATOM | 705 | O | TYR | A | 211 | 24.671 | 53.179 | 28.894 | 1.00 | 34.96 | A | O |
| ATOM | 706 | N | ALA | A | 212 | 22.972 | 53.352 | 27.425 | 1.00 | 33.87 | A | N |
| ATOM | 707 | CA | ALA | A | 212 | 21.920 | 53.438 | 28.441 | 1.00 | 35.11 | A | C |
| ATOM | 708 | CB | ALA | A | 212 | 20.919 | 54.559 | 28.080 | 1.00 | 34.05 | A | C |
| ATOM | 709 | C | ALA | A | 212 | 21.230 | 52.071 | 28.452 | 1.00 | 36.01 | A | C |
| ATOM | 710 | O | ALA | A | 212 | 20.408 | 51.757 | 27.578 | 1.00 | 36.24 | A | O |
| ATOM | 711 | N | PRO | A | 213 | 21.531 | 51.250 | 29.471 | 1.00 | 37.45 | A | N |
| ATOM | 712 | CD | PRO | A | 213 | 22.357 | 51.610 | 30.640 | 1.00 | 35.55 | A | C |
| ATOM | 713 | CA | PRO | A | 213 | 20.982 | 49.900 | 29.623 | 1.00 | 36.93 | A | C |
| ATOM | 714 | CB | PRO | A | 213 | 21.830 | 49.324 | 30.754 | 1.00 | 36.23 | A | C |
| ATOM | 715 | CG | PRO | A | 213 | 22.033 | 50.511 | 31.627 | 1.00 | 37.14 | A | C |
| ATOM | 716 | C | PRO | A | 213 | 19.493 | 49.694 | 29.857 | 1.00 | 37.75 | A | C |
| ATOM | 717 | O | PRO | A | 213 | 18.933 | 48.701 | 29.386 | 1.00 | 36.37 | A | O |
| ATOM | 718 | N | LEU | A | 214 | 18.837 | 50.612 | 30.560 | 1.00 | 36.70 | A | N |
| ATOM | 719 | CA | LEU | A | 214 | 17.418 | 50.415 | 30.846 | 1.00 | 37.91 | A | C |
| ATOM | 720 | CB | LEU | A | 214 | 17.104 | 50.906 | 32.266 | 1.00 | 36.60 | A | C |
| ATOM | 721 | CG | LEU | A | 214 | 17.399 | 49.897 | 33.394 | 1.00 | 37.61 | A | C |
| ATOM | 722 | CD1 | LEU | A | 214 | 18.858 | 49.506 | 33.397 | 1.00 | 37.59 | A | C |
| ATOM | 723 | CD2 | LEU | A | 214 | 17.028 | 50.497 | 34.736 | 1.00 | 36.22 | A | C |
| ATOM | 724 | C | LEU | A | 214 | 16.371 | 50.939 | 29.859 | 1.00 | 38.39 | A | C |
| ATOM | 725 | O | LEU | A | 214 | 15.182 | 50.954 | 30.173 | 1.00 | 38.54 | A | O |
| ATOM | 726 | N | GLY | A | 215 | 16.797 | 51.355 | 28.669 | 1.00 | 38.88 | A | N |
| ATOM | 727 | CA | GLY | A | 215 | 15.845 | 51.820 | 27.671 | 1.00 | 39.34 | A | C |
| ATOM | 728 | C | GLY | A | 215 | 15.322 | 53.244 | 27.782 | 1.00 | 37.48 | A | C |
| ATOM | 729 | O | GLY | A | 215 | 15.892 | 54.079 | 28.483 | 1.00 | 37.79 | A | O |
| ATOM | 730 | N | THR | A | 216 | 14.226 | 53.517 | 27.079 | 1.00 | 36.14 | A | N |
| ATOM | 731 | CA | THR | A | 216 | 13.642 | 54.862 | 27.066 | 1.00 | 36.67 | A | C |
| ATOM | 732 | CB | THR | A | 216 | 13.132 | 55.254 | 25.657 | 1.00 | 36.78 | A | C |
| ATOM | 733 | OG1 | THR | A | 216 | 11.980 | 54.461 | 25.327 | 1.00 | 37.06 | A | O |
| ATOM | 734 | CG2 | THR | A | 216 | 14.219 | 55.026 | 24.596 | 1.00 | 34.73 | A | C |
| ATOM | 735 | C | THR | A | 216 | 12.470 | 55.056 | 28.018 | 1.00 | 36.30 | A | C |
| ATOM | 736 | O | THR | A | 216 | 11.785 | 54.106 | 28.404 | 1.00 | 35.69 | A | O |
| ATOM | 737 | N | VAL | A | 217 | 12.254 | 56.311 | 28.391 | 1.00 | 38.14 | A | N |
| ATOM | 738 | CA | VAL | A | 217 | 11.147 | 56.686 | 29.258 | 1.00 | 38.24 | A | C |
| ATOM | 739 | CB | VAL | A | 217 | 11.180 | 58.209 | 29.559 | 1.00 | 38.38 | A | C |
| ATOM | 740 | CG1 | VAL | A | 217 | 9.903 | 58.642 | 30.269 | 1.00 | 38.16 | A | C |
| ATOM | 741 | CG2 | VAL | A | 217 | 12.394 | 58.532 | 30.418 | 1.00 | 34.69 | A | C |
| ATOM | 742 | C | VAL | A | 217 | 9.872 | 56.328 | 28.497 | 1.00 | 38.49 | A | C |
| ATOM | 743 | O | VAL | A | 217 | 8.865 | 55.949 | 29.087 | 1.00 | 38.84 | A | O |
| ATOM | 744 | N | TYR | A | 218 | 9.934 | 56.432 | 27.176 | 1.00 | 39.52 | A | N |
| ATOM | 745 | CA | TYR | A | 218 | 8.793 | 56.105 | 26.338 | 1.00 | 44.49 | A | C |
| ATOM | 746 | CB | TYR | A | 218 | 9.128 | 56.352 | 24.868 | 1.00 | 47.79 | A | C |
| ATOM | 747 | CG | TYR | A | 218 | 8.037 | 55.903 | 23.932 | 1.00 | 53.55 | A | C |
| ATOM | 748 | CD1 | TYR | A | 218 | 8.292 | 54.963 | 22.934 | 1.00 | 55.54 | A | C |
| ATOM | 749 | CE1 | TYR | A | 218 | 7.278 | 54.518 | 22.087 | 1.00 | 59.77 | A | C |
| ATOM | 750 | CD2 | TYR | A | 218 | 6.738 | 56.394 | 24.060 | 1.00 | 57.06 | A | C |
| ATOM | 751 | CE2 | TYR | A | 218 | 5.714 | 55.957 | 23.219 | 1.00 | 59.73 | A | C |
| ATOM | 752 | CZ | TYR | A | 218 | 5.993 | 55.018 | 22.235 | 1.00 | 61.61 | A | C |
| ATOM | 753 | OH | TYR | A | 218 | 4.986 | 54.575 | 21.402 | 1.00 | 65.83 | A | O |
| ATOM | 754 | C | TYR | A | 218 | 8.324 | 54.655 | 26.523 | 1.00 | 45.40 | A | C |
| ATOM | 755 | O | TYR | A | 218 | 7.131 | 54.409 | 26.740 | 1.00 | 44.19 | A | O |
| ATOM | 756 | N | ARG | A | 219 | 9.248 | 53.698 | 26.436 | 1.00 | 44.49 | A | N |
| ATOM | 757 | CA | ARG | A | 219 | 8.875 | 52.290 | 26.605 | 1.00 | 46.38 | A | C |
| ATOM | 758 | CB | ARG | A | 219 | 10.059 | 51.355 | 26.324 | 1.00 | 47.75 | A | C |
| ATOM | 759 | CG | ARG | A | 219 | 9.690 | 49.883 | 26.517 | 1.00 | 55.47 | A | C |
| ATOM | 760 | CD | ARG | A | 219 | 10.682 | 48.919 | 25.869 | 1.00 | 63.31 | A | C |
| ATOM | 761 | NE | ARG | A | 219 | 10.197 | 47.538 | 25.933 | 1.00 | 68.90 | A | N |
| ATOM | 762 | CZ | ARG | A | 219 | 10.723 | 46.518 | 25.260 | 1.00 | 70.39 | A | C |
| ATOM | 763 | NH1 | ARG | A | 219 | 11.766 | 46.714 | 24.460 | 1.00 | 71.45 | A | N |
| ATOM | 764 | NH2 | ARG | A | 219 | 10.199 | 45.301 | 25.382 | 1.00 | 70.62 | A | N |
| ATOM | 765 | C | ARG | A | 219 | 8.349 | 52.033 | 28.015 | 1.00 | 44.03 | A | C |
| ATOM | 766 | O | ARG | A | 219 | 7.381 | 51.297 | 28.202 | 1.00 | 41.33 | A | O |
| ATOM | 767 | N | GLU | A | 220 | 8.991 | 52.647 | 29.004 | 1.00 | 44.46 | A | N |
| ATOM | 768 | CA | GLU | A | 220 | 8.567 | 52.505 | 30.395 | 1.00 | 46.08 | A | C |
| ATOM | 769 | CB | GLU | A | 220 | 9.534 | 53.261 | 31.315 | 1.00 | 47.47 | A | C |
| ATOM | 770 | CG | GLU | A | 220 | 9.059 | 53.418 | 32.753 | 1.00 | 52.18 | A | C |
| ATOM | 771 | CD | GLU | A | 220 | 10.098 | 54.084 | 33.661 | 1.00 | 55.45 | A | C |
| ATOM | 772 | OE1 | GLU | A | 220 | 10.628 | 55.158 | 33.296 | 1.00 | 55.13 | A | O |
| ATOM | 773 | OE2 | GLU | A | 220 | 10.379 | 53.533 | 34.751 | 1.00 | 56.93 | A | O |
| ATOM | 774 | C | GLU | A | 220 | 7.144 | 53.050 | 30.550 | 1.00 | 45.87 | A | C |
| ATOM | 775 | O | GLU | A | 220 | 6.367 | 52.568 | 31.375 | 1.00 | 43.91 | A | O |

TABLE 1-continued coordinates of [T287D] Aurora A (122–396) in complex with AMP-PNP

| ATOM | 776 | N | LEU | A | 221 | 6.801 | 54.045 | 29.737 | 1.00 | 44.52 | A | N |
|------|-----|-----|-----|---|-----|--------|--------|--------|------|-------|---|---|
| ATOM | 777 | CA | LEU | A | 221 | 5.473 | 54.649 | 29.789 | 1.00 | 45.19 | A | C |
| ATOM | 778 | CB | LEU | A | 221 | 5.483 | 55.989 | 29.036 | 1.00 | 45.91 | A | C |
| ATOM | 779 | CG | LEU | A | 221 | 4.363 | 57.008 | 29.278 | 1.00 | 47.69 | A | C |
| ATOM | 780 | CD1 | LEU | A | 221 | 4.268 | 57.346 | 30.755 | 1.00 | 46.44 | A | C |
| ATOM | 781 | CD2 | LEU | A | 221 | 4.646 | 58.270 | 28.470 | 1.00 | 47.40 | A | C |
| ATOM | 782 | C | LEU | A | 221 | 4.465 | 53.674 | 29.170 | 1.00 | 46.08 | A | C |
| ATOM | 783 | O | LEU | A | 221 | 3.320 | 53.580 | 29.617 | 1.00 | 44.50 | A | O |
| ATOM | 784 | N | GLN | A | 222 | 4.893 | 52.949 | 28.139 | 1.00 | 46.94 | A | N |
| ATOM | 785 | CA | GLN | A | 222 | 4.024 | 51.960 | 27.505 | 1.00 | 50.56 | A | C |
| ATOM | 786 | CB | GLN | A | 222 | 4.715 | 51.299 | 26.313 | 1.00 | 52.06 | A | C |
| ATOM | 787 | CG | GLN | A | 222 | 4.828 | 52.143 | 25.069 | 1.00 | 56.98 | A | C |
| ATOM | 788 | CD | GLN | A | 222 | 5.281 | 51.318 | 23.882 | 1.00 | 61.40 | A | C |
| ATOM | 789 | OE1 | GLN | A | 222 | 6.287 | 50.607 | 23.958 | 1.00 | 64.80 | A | O |
| ATOM | 790 | NE2 | GLN | A | 222 | 4.542 | 51.403 | 22.776 | 1.00 | 61.65 | A | N |
| ATOM | 791 | C | GLN | A | 222 | 3.701 | 50.872 | 28.528 | 1.00 | 50.28 | A | C |
| ATOM | 792 | O | GLN | A | 222 | 2.572 | 50.385 | 28.609 | 1.00 | 48.43 | A | O |
| ATOM | 793 | N | LYS | A | 223 | 4.718 | 50.502 | 29.301 | 1.00 | 51.04 | A | N |
| ATOM | 794 | CA | LYS | A | 223 | 4.604 | 49.475 | 30.332 | 1.00 | 52.24 | A | C |
| ATOM | 795 | CB | LYS | A | 223 | 5.992 | 49.146 | 30.895 | 1.00 | 53.80 | A | C |
| ATOM | 796 | CG | LYS | A | 223 | 6.680 | 47.951 | 30.261 | 1.00 | 57.08 | A | C |
| ATOM | 797 | CD | LYS | A | 223 | 6.939 | 48.120 | 28.773 | 1.00 | 59.58 | A | C |
| ATOM | 798 | CE | LYS | A | 223 | 7.506 | 46.821 | 28.187 | 1.00 | 62.45 | A | C |
| ATOM | 799 | NZ | LYS | A | 223 | 7.723 | 46.877 | 26.711 | 1.00 | 65.10 | A | N |
| ATOM | 800 | C | LYS | A | 223 | 3.680 | 49.855 | 31.488 | 1.00 | 51.07 | A | C |
| ATOM | 801 | O | LYS | A | 223 | 2.678 | 49.188 | 31.731 | 1.00 | 51.74 | A | O |
| ATOM | 802 | N | LEU | A | 224 | 4.024 | 50.927 | 32.195 | 1.00 | 49.30 | A | N |
| ATOM | 803 | CA | LEU | A | 224 | 3.250 | 51.382 | 33.347 | 1.00 | 47.99 | A | C |
| ATOM | 804 | CB | LEU | A | 224 | 4.153 | 52.201 | 34.272 | 1.00 | 45.38 | A | C |
| ATOM | 805 | CG | LEU | A | 224 | 5.509 | 51.562 | 34.588 | 1.00 | 45.90 | A | C |
| ATOM | 806 | CD1 | LEU | A | 224 | 6.327 | 52.477 | 35.475 | 1.00 | 43.89 | A | C |
| ATOM | 807 | CD2 | LEU | A | 224 | 5.291 | 50.228 | 35.263 | 1.00 | 47.72 | A | C |
| ATOM | 808 | C | LEU | A | 224 | 1.979 | 52.183 | 33.067 | 1.00 | 47.57 | A | C |
| ATOM | 809 | O | LEU | A | 224 | 1.198 | 52.417 | 33.986 | 1.00 | 48.98 | A | O |
| ATOM | 810 | N | SER | A | 225 | 1.770 | 52.596 | 31.818 | 1.00 | 47.50 | A | N |
| ATOM | 811 | CA | SER | A | 225 | 0.602 | 53.397 | 31.432 | 1.00 | 46.59 | A | C |
| ATOM | 812 | CB | SER | A | 225 | −0.682 | 52.840 | 32.053 | 1.00 | 48.00 | A | C |
| ATOM | 813 | OG | SER | A | 225 | −1.018 | 51.593 | 31.477 | 1.00 | 51.00 | A | O |
| ATOM | 814 | C | SER | A | 225 | 0.790 | 54.850 | 31.862 | 1.00 | 46.78 | A | C |
| ATOM | 815 | O | SER | A | 225 | 0.652 | 55.771 | 31.056 | 1.00 | 46.17 | A | O |
| ATOM | 816 | N | LYS | A | 226 | 1.113 | 55.043 | 33.136 | 1.00 | 45.76 | A | N |
| ATOM | 817 | CA | LYS | A | 226 | 1.349 | 56.371 | 33.690 | 1.00 | 45.69 | A | C |
| ATOM | 818 | CB | LYS | A | 226 | 0.019 | 57.049 | 34.025 | 1.00 | 48.92 | A | C |
| ATOM | 819 | CG | LYS | A | 226 | −0.896 | 56.251 | 34.937 | 1.00 | 50.24 | A | C |
| ATOM | 820 | CD | LYS | A | 226 | −2.286 | 56.871 | 34.944 | 1.00 | 55.99 | A | C |
| ATOM | 821 | CE | LYS | A | 226 | −3.213 | 56.217 | 35.960 | 1.00 | 56.96 | A | C |
| ATOM | 822 | NZ | LYS | A | 226 | −4.577 | 56.820 | 35.924 | 1.00 | 58.58 | A | N |
| ATOM | 823 | C | LYS | A | 226 | 2.211 | 56.235 | 34.935 | 1.00 | 43.87 | A | C |
| ATOM | 824 | O | LYS | A | 226 | 2.219 | 55.180 | 35.563 | 1.00 | 43.31 | A | O |
| ATOM | 825 | N | PHE | A | 227 | 2.945 | 57.291 | 35.280 | 1.00 | 42.51 | A | N |
| ATOM | 826 | CA | PHE | A | 227 | 3.822 | 57.271 | 36.446 | 1.00 | 41.32 | A | C |
| ATOM | 827 | CB | PHE | A | 227 | 5.136 | 58.018 | 36.163 | 1.00 | 38.84 | A | C |
| ATOM | 828 | CG | PHE | A | 227 | 5.901 | 57.493 | 34.969 | 1.00 | 38.42 | A | C |
| ATOM | 829 | CD1 | PHE | A | 227 | 5.793 | 56.155 | 34.574 | 1.00 | 34.24 | A | C |
| ATOM | 830 | CD2 | PHE | A | 227 | 6.741 | 58.338 | 34.242 | 1.00 | 37.52 | A | C |
| ATOM | 831 | CE1 | PHE | A | 227 | 6.506 | 55.673 | 33.477 | 1.00 | 33.25 | A | C |
| ATOM | 832 | CE2 | PHE | A | 227 | 7.460 | 57.859 | 33.139 | 1.00 | 37.09 | A | C |
| ATOM | 833 | CZ | PHE | A | 227 | 7.340 | 56.525 | 32.760 | 1.00 | 31.91 | A | C |
| ATOM | 834 | C | PHE | A | 227 | 3.168 | 57.888 | 37.669 | 1.00 | 44.70 | A | C |
| ATOM | 835 | O | PHE | A | 227 | 2.199 | 58.644 | 37.554 | 1.00 | 45.27 | A | O |
| ATOM | 836 | N | ASP | A | 228 | 3.708 | 57.572 | 38.844 | 1.00 | 44.53 | A | N |
| ATOM | 837 | CA | ASP | A | 228 | 3.170 | 58.115 | 40.078 | 1.00 | 45.73 | A | C |
| ATOM | 838 | CB | ASP | A | 228 | 3.357 | 57.121 | 41.234 | 1.00 | 47.95 | A | C |
| ATOM | 839 | CG | ASP | A | 228 | 4.797 | 57.012 | 41.696 | 1.00 | 50.80 | A | C |
| ATOM | 840 | OD1 | ASP | A | 228 | 5.711 | 57.200 | 40.871 | 1.00 | 55.59 | A | O |
| ATOM | 841 | OD2 | ASP | A | 228 | 5.016 | 56.718 | 42.889 | 1.00 | 53.57 | A | O |
| ATOM | 842 | C | ASP | A | 228 | 3.873 | 59.435 | 40.363 | 1.00 | 44.84 | A | C |
| ATOM | 843 | O | ASP | A | 228 | 4.805 | 59.815 | 39.655 | 1.00 | 42.73 | A | O |
| ATOM | 844 | N | GLU | A | 229 | 3.419 | 60.130 | 41.400 | 1.00 | 44.06 | A | N |
| ATOM | 845 | CA | GLU | A | 229 | 3.986 | 61.419 | 41.769 | 1.00 | 44.15 | A | C |
| ATOM | 846 | CB | GLU | A | 229 | 3.176 | 62.046 | 42.914 | 1.00 | 46.01 | A | C |
| ATOM | 847 | CG | GLU | A | 229 | 1.732 | 62.358 | 42.554 | 1.00 | 49.15 | A | C |
| ATOM | 848 | CD | GLU | A | 229 | 1.149 | 63.475 | 43.398 | 1.00 | 53.31 | A | C |
| ATOM | 849 | OE1 | GLU | A | 229 | 1.055 | 63.311 | 44.633 | 1.00 | 54.33 | A | O |
| ATOM | 850 | OE2 | GLU | A | 229 | 0.785 | 64.525 | 42.823 | 1.00 | 57.15 | A | O |
| ATOM | 851 | C | GLU | A | 229 | 5.459 | 61.412 | 42.146 | 1.00 | 42.45 | A | C |
| ATOM | 852 | O | GLU | A | 229 | 6.189 | 62.330 | 41.778 | 1.00 | 42.84 | A | O |

TABLE 1-continued coordinates of [T287D] Aurora A (122–396) in complex with AMP-PNP

| ATOM | 853 | N | GLN | A | 230 | 5.904 | 60.399 | 42.889 | 1.00 | 42.42 | A | N |
|------|-----|------|-----|---|-----|--------|--------|--------|------|-------|---|---|
| ATOM | 854 | CA | GLN | A | 230 | 7.309 | 60.355 | 43.291 | 1.00 | 40.75 | A | C |
| ATOM | 855 | CB | GLN | A | 230 | 7.583 | 59.227 | 44.302 | 1.00 | 43.22 | A | C |
| ATOM | 856 | CG | GLN | A | 230 | 9.034 | 59.251 | 44.825 | 1.00 | 46.84 | A | C |
| ATOM | 857 | CD | GLN | A | 230 | 9.369 | 58.120 | 45.789 | 1.00 | 51.94 | A | C |
| ATOM | 858 | OE1 | GLN | A | 230 | 9.463 | 56.955 | 45.397 | 1.00 | 55.25 | A | O |
| ATOM | 859 | NE2 | GLN | A | 230 | 9.558 | 58.464 | 47.059 | 1.00 | 53.28 | A | N |
| ATOM | 860 | C | GLN | A | 230 | 8.233 | 60.171 | 42.095 | 1.00 | 38.22 | A | C |
| ATOM | 861 | O | GLN | A | 230 | 9.274 | 60.816 | 42.014 | 1.00 | 37.20 | A | O |
| ATOM | 862 | N | ARG | A | 231 | 7.851 | 59.286 | 41.176 | 1.00 | 36.78 | A | N |
| ATOM | 863 | CA | ARG | A | 231 | 8.663 | 59.017 | 39.997 | 1.00 | 39.10 | A | C |
| ATOM | 864 | CB | ARG | A | 231 | 8.186 | 57.749 | 39.284 | 1.00 | 37.47 | A | C |
| ATOM | 865 | CG | ARG | A | 231 | 9.122 | 57.330 | 38.158 | 1.00 | 39.31 | A | C |
| ATOM | 866 | CD | ARG | A | 231 | 8.420 | 56.555 | 37.057 | 1.00 | 41.69 | A | C |
| ATOM | 867 | NE | ARG | A | 231 | 8.185 | 55.146 | 37.380 | 1.00 | 47.47 | A | N |
| ATOM | 868 | CZ | ARG | A | 231 | 9.134 | 54.213 | 37.466 | 1.00 | 51.32 | A | C |
| ATOM | 869 | NH1 | ARG | A | 231 | 8.799 | 52.963 | 37.761 | 1.00 | 52.36 | A | N |
| ATOM | 870 | NH2 | ARG | A | 231 | 10.416 | 54.515 | 37.266 | 1.00 | 48.44 | A | N |
| ATOM | 871 | C | ARG | A | 231 | 8.635 | 60.192 | 39.013 | 1.00 | 38.58 | A | C |
| ATOM | 872 | O | ARG | A | 231 | 9.640 | 60.497 | 38.381 | 1.00 | 37.91 | A | O |
| ATOM | 873 | N | THR | A | 232 | 7.477 | 60.836 | 38.878 | 1.00 | 39.25 | A | N |
| ATOM | 874 | CA | THR | A | 232 | 7.336 | 61.980 | 37.980 | 1.00 | 36.38 | A | C |
| ATOM | 875 | CB | THR | A | 232 | 5.866 | 62.434 | 37.888 | 1.00 | 35.78 | A | C |
| ATOM | 876 | OG1 | THR | A | 232 | 5.077 | 61.377 | 37.327 | 1.00 | 33.52 | A | O |
| ATOM | 877 | CG2 | THR | A | 232 | 5.740 | 63.684 | 37.014 | 1.00 | 33.99 | A | C |
| ATOM | 878 | C | THR | A | 232 | 8.176 | 63.157 | 38.475 | 1.00 | 37.94 | A | C |
| ATOM | 879 | O | THR | A | 232 | 8.906 | 63.780 | 37.708 | 1.00 | 39.65 | A | O |
| ATOM | 880 | N | ALA | A | 233 | 8.085 | 63.445 | 39.769 | 1.00 | 38.61 | A | N |
| ATOM | 881 | CA | ALA | A | 233 | 8.820 | 64.556 | 40.364 | 1.00 | 39.65 | A | C |
| ATOM | 882 | CB | ALA | A | 233 | 8.374 | 64.757 | 41.810 | 1.00 | 39.86 | A | C |
| ATOM | 883 | C | ALA | A | 233 | 10.333 | 64.359 | 40.304 | 1.00 | 39.68 | A | C |
| ATOM | 884 | O | ALA | A | 233 | 11.085 | 65.318 | 40.118 | 1.00 | 39.18 | A | O |
| ATOM | 885 | N | THR | A | 234 | 10.783 | 63.120 | 40.474 | 1.00 | 39.91 | A | N |
| ATOM | 886 | CA | THR | A | 234 | 12.214 | 62.838 | 40.421 | 1.00 | 39.28 | A | C |
| ATOM | 887 | CB | THR | A | 234 | 12.517 | 61.360 | 40.828 | 1.00 | 39.65 | A | C |
| ATOM | 888 | OG1 | THR | A | 234 | 11.901 | 61.073 | 42.086 | 1.00 | 36.77 | A | O |
| ATOM | 889 | CG2 | THR | A | 234 | 14.006 | 61.131 | 40.978 | 1.00 | 39.65 | A | C |
| ATOM | 890 | C | THR | A | 234 | 12.687 | 63.096 | 38.991 | 1.00 | 38.18 | A | C |
| ATOM | 891 | O | THR | A | 234 | 13.685 | 63.780 | 38.775 | 1.00 | 41.05 | A | O |
| ATOM | 892 | N | TYR | A | 235 | 11.953 | 62.559 | 38.015 | 1.00 | 39.28 | A | N |
| ATOM | 893 | CA | TYR | A | 235 | 12.300 | 62.737 | 36.602 | 1.00 | 38.40 | A | C |
| ATOM | 894 | CB | TYR | A | 235 | 11.293 | 62.018 | 35.700 | 1.00 | 38.30 | A | C |
| ATOM | 895 | CG | TYR | A | 235 | 11.446 | 60.517 | 35.606 | 1.00 | 40.28 | A | C |
| ATOM | 896 | CD1 | TYR | A | 235 | 12.516 | 59.853 | 36.209 | 1.00 | 41.54 | A | C |
| ATOM | 897 | CE1 | TYR | A | 235 | 12.668 | 58.463 | 36.079 | 1.00 | 42.34 | A | C |
| ATOM | 898 | CD2 | TYR | A | 235 | 10.532 | 59.761 | 34.878 | 1.00 | 39.41 | A | C |
| ATOM | 899 | CE2 | TYR | A | 235 | 10.670 | 58.387 | 34.746 | 1.00 | 40.62 | A | C |
| ATOM | 900 | CZ | TYR | A | 235 | 11.737 | 57.738 | 35.344 | 1.00 | 42.31 | A | C |
| ATOM | 901 | OH | TYR | A | 235 | 11.866 | 56.370 | 35.191 | 1.00 | 40.25 | A | O |
| ATOM | 902 | C | TYR | A | 235 | 12.358 | 64.213 | 36.207 | 1.00 | 38.07 | A | C |
| ATOM | 903 | O | TYR | A | 235 | 13.259 | 64.629 | 35.482 | 1.00 | 36.19 | A | O |
| ATOM | 904 | N | ILE | A | 236 | 11.392 | 65.002 | 36.678 | 1.00 | 39.25 | A | N |
| ATOM | 905 | CA | ILE | A | 236 | 11.370 | 66.434 | 36.374 | 1.00 | 37.44 | A | C |
| ATOM | 906 | CB | ILE | A | 236 | 10.064 | 67.102 | 36.872 | 1.00 | 37.12 | A | C |
| ATOM | 907 | CG2 | ILE | A | 236 | 10.170 | 68.627 | 36.741 | 1.00 | 34.15 | A | C |
| ATOM | 908 | CG1 | ILE | A | 236 | 8.878 | 66.554 | 36.072 | 1.00 | 35.02 | A | C |
| ATOM | 909 | CD1 | ILE | A | 236 | 8.997 | 66.750 | 34.561 | 1.00 | 36.77 | A | C |
| ATOM | 910 | C | ILE | A | 236 | 12.574 | 67.115 | 37.012 | 1.00 | 37.57 | A | C |
| ATOM | 911 | O | ILE | A | 236 | 13.172 | 68.022 | 36.426 | 1.00 | 40.12 | A | O |
| ATOM | 912 | N | THR | A | 237 | 12.941 | 66.668 | 38.209 | 1.00 | 36.62 | A | N |
| ATOM | 913 | CA | THR | A | 237 | 14.114 | 67.215 | 38.891 | 1.00 | 36.77 | A | C |
| ATOM | 914 | CB | THR | A | 237 | 14.285 | 66.590 | 40.310 | 1.00 | 36.70 | A | C |
| ATOM | 915 | OG1 | THR | A | 237 | 13.174 | 66.970 | 41.134 | 1.00 | 39.88 | A | O |
| ATOM | 916 | CG2 | THR | A | 237 | 15.592 | 67.072 | 40.970 | 1.00 | 33.73 | A | C |
| ATOM | 917 | C | THR | A | 237 | 15.393 | 66.931 | 38.084 | 1.00 | 36.40 | A | C |
| ATOM | 918 | O | THR | A | 237 | 16.244 | 67.808 | 37.917 | 1.00 | 34.72 | A | O |
| ATOM | 919 | N | GLU | A | 238 | 15.531 | 65.703 | 37.589 | 1.00 | 35.89 | A | N |
| ATOM | 920 | CA | GLU | A | 238 | 16.724 | 65.343 | 36.826 | 1.00 | 36.31 | A | C |
| ATOM | 921 | CB | GLU | A | 238 | 16.743 | 63.831 | 36.584 | 1.00 | 37.43 | A | C |
| ATOM | 922 | CG | GLU | A | 238 | 16.699 | 63.014 | 37.882 | 1.00 | 39.75 | A | C |
| ATOM | 923 | CD | GLU | A | 238 | 16.579 | 61.516 | 37.652 | 1.00 | 42.37 | A | C |
| ATOM | 924 | OE1 | GLU | A | 238 | 16.240 | 61.106 | 36.526 | 1.00 | 46.02 | A | O |
| ATOM | 925 | OE2 | GLU | A | 238 | 16.804 | 60.739 | 38.605 | 1.00 | 44.16 | A | O |
| ATOM | 926 | C | GLU | A | 238 | 16.792 | 66.124 | 35.508 | 1.00 | 36.97 | A | C |
| ATOM | 927 | O | GLU | A | 238 | 17.875 | 66.515 | 35.068 | 1.00 | 38.41 | A | O |
| ATOM | 928 | N | LEU | A | 239 | 15.634 | 66.371 | 34.898 | 1.00 | 37.50 | A | N |
| ATOM | 929 | CA | LEU | A | 239 | 15.551 | 67.133 | 33.646 | 1.00 | 36.81 | A | C |

TABLE 1-continued coordinates of [T287D] Aurora A (122–396) in complex with AMP-PNP

| ATOM | 930 | CB | LEU | A | 239 | 14.142 | 67.020 | 33.063 | 1.00 | 35.68 | A | C |
|---|---|---|---|---|---|---|---|---|---|---|---|---|
| ATOM | 931 | CG | LEU | A | 239 | 13.804 | 65.710 | 32.362 | 1.00 | 39.17 | A | C |
| ATOM | 932 | CD1 | LEU | A | 239 | 12.292 | 65.600 | 32.137 | 1.00 | 37.66 | A | C |
| ATOM | 933 | CD2 | LEU | A | 239 | 14.575 | 65.663 | 31.041 | 1.00 | 37.84 | A | C |
| ATOM | 934 | C | LEU | A | 239 | 15.875 | 68.613 | 33.852 | 1.00 | 35.88 | A | C |
| ATOM | 935 | O | LEU | A | 239 | 16.629 | 69.219 | 33.085 | 1.00 | 34.18 | A | O |
| ATOM | 936 | N | ALA | A | 240 | 15.294 | 69.198 | 34.892 | 1.00 | 37.08 | A | N |
| ATOM | 937 | CA | ALA | A | 240 | 15.526 | 70.613 | 35.171 | 1.00 | 37.40 | A | C |
| ATOM | 938 | CB | ALA | A | 240 | 14.677 | 71.059 | 36.375 | 1.00 | 35.91 | A | C |
| ATOM | 939 | C | ALA | A | 240 | 17.011 | 70.863 | 35.426 | 1.00 | 37.09 | A | C |
| ATOM | 940 | O | ALA | A | 240 | 17.558 | 71.896 | 35.024 | 1.00 | 35.00 | A | O |
| ATOM | 941 | N | ASN | A | 241 | 17.661 | 69.909 | 36.092 | 1.00 | 38.15 | A | N |
| ATOM | 942 | CA | ASN | A | 241 | 19.092 | 70.010 | 36.387 | 1.00 | 37.31 | A | C |
| ATOM | 943 | CB | ASN | A | 241 | 19.562 | 68.864 | 37.294 | 1.00 | 39.88 | A | C |
| ATOM | 944 | CG | ASN | A | 241 | 19.152 | 69.053 | 38.733 | 1.00 | 44.02 | A | C |
| ATOM | 945 | OD1 | ASN | A | 241 | 19.346 | 70.125 | 39.308 | 1.00 | 47.57 | A | O |
| ATOM | 946 | ND2 | ASN | A | 241 | 18.588 | 68.006 | 39.331 | 1.00 | 46.92 | A | N |
| ATOM | 947 | C | ASN | A | 241 | 19.920 | 69.962 | 35.119 | 1.00 | 36.22 | A | C |
| ATOM | 948 | O | ASN | A | 241 | 20.871 | 70.724 | 34.975 | 1.00 | 36.76 | A | O |
| ATOM | 949 | N | ALA | A | 242 | 19.585 | 69.041 | 34.217 | 1.00 | 33.89 | A | N |
| ATOM | 950 | CA | ALA | A | 242 | 20.328 | 68.916 | 32.963 | 1.00 | 34.20 | A | C |
| ATOM | 951 | CB | ALA | A | 242 | 19.869 | 67.669 | 32.178 | 1.00 | 31.75 | A | C |
| ATOM | 952 | C | ALA | A | 242 | 20.121 | 70.173 | 32.125 | 1.00 | 33.01 | A | C |
| ATOM | 953 | O | ALA | A | 242 | 21.073 | 70.719 | 31.574 | 1.00 | 33.65 | A | O |
| ATOM | 954 | N | LEU | A | 243 | 18.875 | 70.630 | 32.043 | 1.00 | 33.50 | A | N |
| ATOM | 955 | CA | LEU | A | 243 | 18.554 | 71.830 | 31.279 | 1.00 | 36.89 | A | C |
| ATOM | 956 | CB | LEU | A | 243 | 17.031 | 71.999 | 31.183 | 1.00 | 34.36 | A | C |
| ATOM | 957 | CG | LEU | A | 243 | 16.331 | 70.888 | 30.385 | 1.00 | 35.75 | A | C |
| ATOM | 958 | CD1 | LEU | A | 243 | 14.827 | 71.111 | 30.357 | 1.00 | 36.43 | A | C |
| ATOM | 959 | CD2 | LEU | A | 243 | 16.884 | 70.867 | 28.965 | 1.00 | 34.93 | A | C |
| ATOM | 960 | C | LEU | A | 243 | 19.218 | 73.098 | 31.848 | 1.00 | 38.16 | A | C |
| ATOM | 961 | O | LEU | A | 243 | 19.666 | 73.956 | 31.083 | 1.00 | 38.31 | A | O |
| ATOM | 962 | N | SER | A | 244 | 19.296 | 73.219 | 33.175 | 1.00 | 39.80 | A | N |
| ATOM | 963 | CA | SER | A | 244 | 19.945 | 74.391 | 33.778 | 1.00 | 40.44 | A | C |
| ATOM | 964 | CB | SER | A | 244 | 19.861 | 74.357 | 35.308 | 1.00 | 43.11 | A | C |
| ATOM | 965 | OG | SER | A | 244 | 18.521 | 74.198 | 35.743 | 1.00 | 47.97 | A | O |
| ATOM | 966 | C | SER | A | 244 | 21.411 | 74.365 | 33.369 | 1.00 | 40.05 | A | C |
| ATOM | 967 | O | SER | A | 244 | 22.001 | 75.396 | 33.021 | 1.00 | 40.00 | A | O |
| ATOM | 968 | N | TYR | A | 245 | 22.005 | 73.177 | 33.413 | 1.00 | 37.27 | A | N |
| ATOM | 969 | CA | TYR | A | 245 | 23.400 | 73.053 | 33.021 | 1.00 | 35.82 | A | C |
| ATOM | 970 | CB | TYR | A | 245 | 23.897 | 71.622 | 33.252 | 1.00 | 35.21 | A | C |
| ATOM | 971 | CG | TYR | A | 245 | 25.202 | 71.317 | 32.555 | 1.00 | 37.03 | A | C |
| ATOM | 972 | CD1 | TYR | A | 245 | 25.215 | 70.770 | 31.274 | 1.00 | 36.51 | A | C |
| ATOM | 973 | CE1 | TYR | A | 245 | 26.410 | 70.511 | 30.613 | 1.00 | 40.47 | A | C |
| ATOM | 974 | CD2 | TYR | A | 245 | 26.426 | 71.603 | 33.163 | 1.00 | 38.38 | A | C |
| ATOM | 975 | CE2 | TYR | A | 245 | 27.630 | 71.350 | 32.507 | 1.00 | 41.25 | A | C |
| ATOM | 976 | CZ | TYR | A | 245 | 27.612 | 70.800 | 31.231 | 1.00 | 40.43 | A | C |
| ATOM | 977 | OH | TYR | A | 245 | 28.788 | 70.527 | 30.576 | 1.00 | 43.84 | A | O |
| ATOM | 978 | C | TYR | A | 245 | 23.561 | 73.448 | 31.550 | 1.00 | 35.32 | A | C |
| ATOM | 979 | O | TYR | A | 245 | 24.479 | 74.176 | 31.200 | 1.00 | 35.27 | A | O |
| ATOM | 980 | N | CYS | A | 246 | 22.661 | 72.971 | 30.694 | 1.00 | 36.27 | A | N |
| ATOM | 981 | CA | CYS | A | 246 | 22.721 | 73.295 | 29.267 | 1.00 | 38.83 | A | C |
| ATOM | 982 | CB | CYS | A | 246 | 21.609 | 72.568 | 28.498 | 1.00 | 38.59 | A | C |
| ATOM | 983 | SG | CYS | A | 246 | 21.897 | 70.797 | 28.263 | 1.00 | 44.30 | A | S |
| ATOM | 984 | C | CYS | A | 246 | 22.606 | 74.802 | 29.031 | 1.00 | 39.39 | A | C |
| ATOM | 985 | O | CYS | A | 246 | 23.322 | 75.358 | 28.200 | 1.00 | 37.11 | A | O |
| ATOM | 986 | N | HIS | A | 247 | 21.704 | 75.461 | 29.756 | 1.00 | 40.65 | A | N |
| ATOM | 987 | CA | HIS | A | 247 | 21.542 | 76.903 | 29.603 | 1.00 | 43.91 | A | C |
| ATOM | 988 | CB | HIS | A | 247 | 20.403 | 77.414 | 30.493 | 1.00 | 44.23 | A | C |
| ATOM | 989 | CG | HIS | A | 247 | 19.038 | 77.074 | 29.978 | 1.00 | 45.59 | A | C |
| ATOM | 990 | CD2 | HIS | A | 247 | 18.645 | 76.412 | 28.862 | 1.00 | 45.56 | A | C |
| ATOM | 991 | ND1 | HIS | A | 247 | 17.881 | 77.447 | 30.628 | 1.00 | 45.85 | A | N |
| ATOM | 992 | CE1 | HIS | A | 247 | 16.834 | 77.033 | 29.937 | 1.00 | 46.13 | A | C |
| ATOM | 993 | NE2 | HIS | A | 247 | 17.270 | 76.402 | 28.861 | 1.00 | 48.11 | A | N |
| ATOM | 994 | C | HIS | A | 247 | 22.840 | 77.642 | 29.931 | 1.00 | 46.24 | A | C |
| ATOM | 995 | O | HIS | A | 247 | 23.223 | 78.581 | 29.231 | 1.00 | 46.66 | A | O |
| ATOM | 996 | N | SER | A | 248 | 23.527 | 77.213 | 30.985 | 1.00 | 46.80 | A | N |
| ATOM | 997 | CA | SER | A | 248 | 24.780 | 77.858 | 31.359 | 1.00 | 47.62 | A | C |
| ATOM | 998 | CB | SER | A | 248 | 25.344 | 77.247 | 32.653 | 1.00 | 46.92 | A | C |
| ATOM | 999 | OG | SER | A | 248 | 25.872 | 75.950 | 32.432 | 1.00 | 48.53 | A | O |
| ATOM | 1000 | C | SER | A | 248 | 25.799 | 77.716 | 30.223 | 1.00 | 47.38 | A | C |
| ATOM | 1001 | O | SER | A | 248 | 26.774 | 78.469 | 30.152 | 1.00 | 48.22 | A | O |
| ATOM | 1002 | N | LYS | A | 249 | 25.566 | 76.761 | 29.328 | 1.00 | 45.39 | A | N |
| ATOM | 1003 | CA | LYS | A | 249 | 26.473 | 76.541 | 28.209 | 1.00 | 46.59 | A | C |
| ATOM | 1004 | CB | LYS | A | 249 | 26.731 | 75.047 | 28.021 | 1.00 | 44.79 | A | C |
| ATOM | 1005 | CG | LYS | A | 249 | 27.091 | 74.323 | 29.300 | 1.00 | 49.43 | A | C |
| ATOM | 1006 | CD | LYS | A | 249 | 28.337 | 74.902 | 29.951 | 1.00 | 52.06 | A | C |

TABLE 1-continued coordinates of [T287D] Aurora A (122–396) in complex with AMP-PNP

| ATOM | 1007 | CE | LYS | A | 249 | 29.587 | 74.520 | 29.183 | 1.00 | 56.23 | A | C |
|------|------|-----|-----|---|-----|--------|--------|--------|------|-------|---|---|
| ATOM | 1008 | NZ | LYS | A | 249 | 29.806 | 73.040 | 29.150 | 1.00 | 58.63 | A | N |
| ATOM | 1009 | C | LYS | A | 249 | 25.909 | 77.131 | 26.919 | 1.00 | 48.59 | A | C |
| ATOM | 1010 | O | LYS | A | 249 | 26.490 | 76.966 | 25.847 | 1.00 | 47.53 | A | O |
| ATOM | 1011 | N | ARG | A | 250 | 24.769 | 77.808 | 27.032 | 1.00 | 51.35 | A | N |
| ATOM | 1012 | CA | ARG | A | 250 | 24.117 | 78.434 | 25.884 | 1.00 | 55.46 | A | C |
| ATOM | 1013 | CB | ARG | A | 250 | 25.079 | 79.425 | 25.204 | 1.00 | 58.41 | A | C |
| ATOM | 1014 | CG | ARG | A | 250 | 25.543 | 80.543 | 26.151 | 1.00 | 64.68 | A | C |
| ATOM | 1015 | CD | ARG | A | 250 | 26.350 | 81.658 | 25.464 | 1.00 | 69.77 | A | C |
| ATOM | 1016 | NE | ARG | A | 250 | 27.615 | 81.204 | 24.886 | 1.00 | 72.33 | A | N |
| ATOM | 1017 | CZ | ARG | A | 250 | 28.584 | 82.020 | 24.473 | 1.00 | 74.30 | A | C |
| ATOM | 1018 | NH1 | ARG | A | 250 | 28.439 | 83.338 | 24.574 | 1.00 | 73.90 | A | N |
| ATOM | 1019 | NH2 | ARG | A | 250 | 29.699 | 81.520 | 23.951 | 1.00 | 74.27 | A | N |
| ATOM | 1020 | C | ARG | A | 250 | 23.606 | 77.401 | 24.884 | 1.00 | 54.89 | A | C |
| ATOM | 1021 | O | ARG | A | 250 | 23.589 | 77.635 | 23.671 | 1.00 | 55.10 | A | O |
| ATOM | 1022 | N | VAL | A | 251 | 23.196 | 76.252 | 25.413 | 1.00 | 53.65 | A | N |
| ATOM | 1023 | CA | VAL | A | 251 | 22.658 | 75.169 | 24.605 | 1.00 | 51.49 | A | C |
| ATOM | 1024 | CB | VAL | A | 251 | 23.343 | 73.815 | 24.924 | 1.00 | 51.47 | A | C |
| ATOM | 1025 | CG1 | VAL | A | 251 | 22.550 | 72.664 | 24.310 | 1.00 | 47.16 | A | C |
| ATOM | 1026 | CG2 | VAL | A | 251 | 24.761 | 73.809 | 24.378 | 1.00 | 51.44 | A | C |
| ATOM | 1027 | C | VAL | A | 251 | 21.175 | 75.052 | 24.927 | 1.00 | 52.04 | A | C |
| ATOM | 1028 | O | VAL | A | 251 | 20.793 | 74.885 | 26.090 | 1.00 | 50.43 | A | O |
| ATOM | 1029 | N | ILE | A | 252 | 20.348 | 75.158 | 23.894 | 1.00 | 51.36 | A | N |
| ATOM | 1030 | CA | ILE | A | 252 | 18.908 | 75.050 | 24.049 | 1.00 | 52.79 | A | C |
| ATOM | 1031 | CB | ILE | A | 252 | 18.205 | 76.372 | 23.690 | 1.00 | 54.02 | A | C |
| ATOM | 1032 | CG2 | ILE | A | 252 | 16.696 | 76.214 | 23.823 | 1.00 | 54.66 | A | C |
| ATOM | 1033 | CG1 | ILE | A | 252 | 18.709 | 77.490 | 24.611 | 1.00 | 54.46 | A | C |
| ATOM | 1034 | CD1 | ILE | A | 252 | 18.176 | 78.868 | 24.259 | 1.00 | 55.53 | A | C |
| ATOM | 1035 | C | ILE | A | 252 | 18.434 | 73.950 | 23.113 | 1.00 | 53.85 | A | C |
| ATOM | 1036 | O | ILE | A | 252 | 18.911 | 73.841 | 21.984 | 1.00 | 54.35 | A | O |
| ATOM | 1037 | N | HIS | A | 253 | 17.515 | 73.124 | 23.602 | 1.00 | 54.36 | A | N |
| ATOM | 1038 | CA | HIS | A | 253 | 16.964 | 72.021 | 22.824 | 1.00 | 54.56 | A | C |
| ATOM | 1039 | CB | HIS | A | 253 | 16.590 | 70.840 | 23.736 | 1.00 | 52.75 | A | C |
| ATOM | 1040 | CG | HIS | A | 253 | 17.757 | 70.216 | 24.438 | 1.00 | 52.00 | A | C |
| ATOM | 1041 | CD2 | HIS | A | 253 | 18.281 | 68.970 | 24.359 | 1.00 | 52.22 | A | C |
| ATOM | 1042 | ND1 | HIS | A | 253 | 18.546 | 70.907 | 25.334 | 1.00 | 50.80 | A | N |
| ATOM | 1043 | CE1 | HIS | A | 253 | 19.509 | 70.115 | 25.771 | 1.00 | 50.65 | A | C |
| ATOM | 1044 | NE2 | HIS | A | 253 | 19.372 | 68.934 | 25.195 | 1.00 | 52.67 | A | N |
| ATOM | 1045 | C | HIS | A | 253 | 15.715 | 72.509 | 22.115 | 1.00 | 55.98 | A | C |
| ATOM | 1046 | O | HIS | A | 253 | 15.189 | 73.579 | 22.423 | 1.00 | 53.17 | A | O |
| ATOM | 1047 | N | ARG | A | 254 | 15.247 | 71.716 | 21.161 | 1.00 | 59.64 | A | N |
| ATOM | 1048 | CA | ARG | A | 254 | 14.046 | 72.048 | 20.412 | 1.00 | 63.55 | A | C |
| ATOM | 1049 | CB | ARG | A | 254 | 14.391 | 72.384 | 18.956 | 1.00 | 67.04 | A | C |
| ATOM | 1050 | CG | ARG | A | 254 | 15.314 | 73.592 | 18.803 | 1.00 | 72.33 | A | C |
| ATOM | 1051 | CD | ARG | A | 254 | 15.366 | 74.081 | 17.357 | 1.00 | 76.66 | A | C |
| ATOM | 1052 | NE | ARG | A | 254 | 16.348 | 75.148 | 17.165 | 1.00 | 79.26 | A | N |
| ATOM | 1053 | CZ | ARG | A | 254 | 16.488 | 75.840 | 16.037 | 1.00 | 80.83 | A | C |
| ATOM | 1054 | NH1 | ARG | A | 254 | 15.706 | 75.581 | 14.997 | 1.00 | 81.15 | A | N |
| ATOM | 1055 | NH2 | ARG | A | 254 | 17.413 | 76.787 | 15.944 | 1.00 | 81.58 | A | N |
| ATOM | 1056 | C | ARG | A | 254 | 13.133 | 70.831 | 20.476 | 1.00 | 63.27 | A | C |
| ATOM | 1057 | O | ARG | A | 254 | 13.176 | 69.967 | 19.607 | 1.00 | 65.67 | A | O |
| ATOM | 1058 | N | ASP | A | 255 | 12.327 | 70.776 | 21.531 | 1.00 | 60.76 | A | N |
| ATOM | 1059 | CA | ASP | A | 255 | 11.391 | 69.686 | 21.786 | 1.00 | 59.10 | A | C |
| ATOM | 1060 | CB | ASP | A | 255 | 10.512 | 69.404 | 20.549 | 1.00 | 59.56 | A | C |
| ATOM | 1061 | CG | ASP | A | 255 | 11.108 | 68.366 | 19.606 | 1.00 | 60.20 | A | C |
| ATOM | 1062 | OD1 | ASP | A | 255 | 11.300 | 67.208 | 20.026 | 1.00 | 62.58 | A | O |
| ATOM | 1063 | OD2 | ASP | A | 255 | 11.372 | 68.702 | 18.433 | 1.00 | 60.34 | A | O |
| ATOM | 1064 | C | ASP | A | 255 | 12.099 | 68.411 | 22.256 | 1.00 | 57.58 | A | C |
| ATOM | 1065 | O | ASP | A | 255 | 13.017 | 67.901 | 21.596 | 1.00 | 55.18 | A | O |
| ATOM | 1066 | N | ILE | A | 256 | 11.698 | 67.920 | 23.426 | 1.00 | 54.14 | A | N |
| ATOM | 1067 | CA | ILE | A | 256 | 12.285 | 66.695 | 23.948 | 1.00 | 52.47 | A | C |
| ATOM | 1068 | CB | ILE | A | 256 | 13.115 | 66.949 | 25.237 | 1.00 | 54.35 | A | C |
| ATOM | 1069 | CG2 | ILE | A | 256 | 13.581 | 68.397 | 25.271 | 1.00 | 54.91 | A | C |
| ATOM | 1070 | CG1 | ILE | A | 256 | 12.298 | 66.652 | 26.487 | 1.00 | 56.23 | A | C |
| ATOM | 1071 | CD1 | ILE | A | 256 | 13.151 | 66.501 | 27.717 | 1.00 | 58.73 | A | C |
| ATOM | 1072 | C | ILE | A | 256 | 11.150 | 65.705 | 24.193 | 1.00 | 48.66 | A | C |
| ATOM | 1073 | O | ILE | A | 256 | 10.242 | 65.957 | 24.989 | 1.00 | 48.97 | A | O |
| ATOM | 1074 | N | LYS | A | 257 | 11.190 | 64.598 | 23.461 | 1.00 | 44.04 | A | N |
| ATOM | 1075 | CA | LYS | A | 257 | 10.164 | 63.569 | 23.551 | 1.00 | 42.42 | A | C |
| ATOM | 1076 | CB | LYS | A | 257 | 9.837 | 63.053 | 22.146 | 1.00 | 42.94 | A | C |
| ATOM | 1077 | CG | LYS | A | 257 | 9.671 | 64.158 | 21.119 | 1.00 | 47.60 | A | C |
| ATOM | 1078 | CD | LYS | A | 257 | 8.714 | 63.758 | 20.008 | 1.00 | 50.15 | A | C |
| ATOM | 1079 | CE | LYS | A | 257 | 9.278 | 62.672 | 19.115 | 1.00 | 54.00 | A | C |
| ATOM | 1080 | NZ | LYS | A | 257 | 8.244 | 62.166 | 18.147 | 1.00 | 55.95 | A | N |
| ATOM | 1081 | C | LYS | A | 257 | 10.575 | 62.395 | 24.446 | 1.00 | 40.38 | A | C |
| ATOM | 1082 | O | LYS | A | 257 | 11.761 | 62.170 | 24.688 | 1.00 | 40.25 | A | O |
| ATOM | 1083 | N | PRO | A | 258 | 9.592 | 61.631 | 24.944 | 1.00 | 38.26 | A | N |

TABLE 1-continued coordinates of [T287D] Aurora A (122–396) in complex with AMP-PNP

| ATOM | 1084 | CD  | PRO | A | 258 | 8.141  | 61.822 | 24.769 | 1.00 | 35.77 | A | C |
| --- | --- | --- | --- | --- | --- | --- | --- | --- | --- | --- | --- | --- |
| ATOM | 1085 | CA  | PRO | A | 258 | 9.866  | 60.479 | 25.809 | 1.00 | 39.42 | A | C |
| ATOM | 1086 | CB  | PRO | A | 258 | 8.478  | 59.868 | 26.026 | 1.00 | 38.99 | A | C |
| ATOM | 1087 | CG  | PRO | A | 258 | 7.571  | 61.051 | 25.941 | 1.00 | 38.85 | A | C |
| ATOM | 1088 | C   | PRO | A | 258 | 10.838 | 59.483 | 25.173 | 1.00 | 38.24 | A | C |
| ATOM | 1089 | O   | PRO | A | 258 | 11.621 | 58.855 | 25.876 | 1.00 | 37.93 | A | O |
| ATOM | 1090 | N   | GLU | A | 259 | 10.795 | 59.352 | 23.848 | 1.00 | 39.21 | A | N |
| ATOM | 1091 | CA  | GLU | A | 259 | 11.682 | 58.421 | 23.142 | 1.00 | 39.84 | A | C |
| ATOM | 1092 | CB  | GLU | A | 259 | 11.188 | 58.155 | 21.716 | 1.00 | 40.55 | A | C |
| ATOM | 1093 | CG  | GLU | A | 259 | 9.688  | 58.072 | 21.594 | 1.00 | 48.83 | A | C |
| ATOM | 1094 | CD  | GLU | A | 259 | 9.081  | 59.411 | 21.225 | 1.00 | 50.31 | A | C |
| ATOM | 1095 | OE1 | GLU | A | 259 | 7.919  | 59.679 | 21.604 | 1.00 | 51.19 | A | O |
| ATOM | 1096 | OE2 | GLU | A | 259 | 9.776  | 60.190 | 20.536 | 1.00 | 54.44 | A | O |
| ATOM | 1097 | C   | GLU | A | 259 | 13.121 | 58.909 | 23.070 | 1.00 | 38.93 | A | C |
| ATOM | 1098 | O   | GLU | A | 259 | 14.011 | 58.149 | 22.694 | 1.00 | 36.58 | A | O |
| ATOM | 1099 | N   | ASN | A | 260 | 13.347 | 60.176 | 23.413 | 1.00 | 38.55 | A | N |
| ATOM | 1100 | CA  | ASN | A | 260 | 14.690 | 60.746 | 23.391 | 1.00 | 37.69 | A | C |
| ATOM | 1101 | CB  | ASN | A | 260 | 14.694 | 62.115 | 22.702 | 1.00 | 42.07 | A | C |
| ATOM | 1102 | CG  | ASN | A | 260 | 13.986 | 62.096 | 21.362 | 1.00 | 45.98 | A | C |
| ATOM | 1103 | OD1 | ASN | A | 260 | 14.267 | 61.258 | 20.507 | 1.00 | 50.60 | A | O |
| ATOM | 1104 | ND2 | ASN | A | 260 | 13.062 | 63.032 | 21.171 | 1.00 | 50.14 | A | N |
| ATOM | 1105 | C   | ASN | A | 260 | 15.222 | 60.883 | 24.818 | 1.00 | 35.15 | A | C |
| ATOM | 1106 | O   | ASN | A | 260 | 16.206 | 61.578 | 25.071 | 1.00 | 33.57 | A | O |
| ATOM | 1107 | N   | LEU | A | 261 | 14.548 | 60.236 | 25.754 | 1.00 | 32.79 | A | N |
| ATOM | 1108 | CA  | LEU | A | 261 | 14.995 | 60.242 | 27.146 | 1.00 | 35.15 | A | C |
| ATOM | 1109 | CB  | LEU | A | 261 | 13.875 | 60.737 | 28.075 | 1.00 | 30.11 | A | C |
| ATOM | 1110 | CG  | LEU | A | 261 | 13.410 | 62.179 | 27.822 | 1.00 | 29.12 | A | C |
| ATOM | 1111 | CD1 | LEU | A | 261 | 12.459 | 62.616 | 28.925 | 1.00 | 21.95 | A | C |
| ATOM | 1112 | CD2 | LEU | A | 261 | 14.624 | 63.110 | 27.765 | 1.00 | 29.74 | A | C |
| ATOM | 1113 | C   | LEU | A | 261 | 15.366 | 58.785 | 27.462 | 1.00 | 35.15 | A | C |
| ATOM | 1114 | O   | LEU | A | 261 | 14.499 | 57.911 | 27.498 | 1.00 | 34.65 | A | O |
| ATOM | 1115 | N   | LEU | A | 262 | 16.656 | 58.528 | 27.657 | 1.00 | 35.80 | A | N |
| ATOM | 1116 | CA  | LEU | A | 262 | 17.140 | 57.180 | 27.934 | 1.00 | 36.00 | A | C |
| ATOM | 1117 | CB  | LEU | A | 262 | 18.439 | 56.923 | 27.167 | 1.00 | 36.54 | A | C |
| ATOM | 1118 | CG  | LEU | A | 262 | 18.311 | 56.713 | 25.654 | 1.00 | 39.58 | A | C |
| ATOM | 1119 | CD1 | LEU | A | 262 | 19.676 | 56.811 | 25.001 | 1.00 | 37.56 | A | C |
| ATOM | 1120 | CD2 | LEU | A | 262 | 17.678 | 55.352 | 25.377 | 1.00 | 41.77 | A | C |
| ATOM | 1121 | C   | LEU | A | 262 | 17.355 | 56.958 | 29.421 | 1.00 | 36.91 | A | C |
| ATOM | 1122 | O   | LEU | A | 262 | 17.428 | 57.915 | 30.189 | 1.00 | 38.50 | A | O |
| ATOM | 1123 | N   | LEU | A | 263 | 17.467 | 55.694 | 29.828 | 1.00 | 36.14 | A | N |
| ATOM | 1124 | CA  | LEU | A | 263 | 17.640 | 55.364 | 31.246 | 1.00 | 35.96 | A | C |
| ATOM | 1125 | CB  | LEU | A | 263 | 16.472 | 54.488 | 31.709 | 1.00 | 37.11 | A | C |
| ATOM | 1126 | CG  | LEU | A | 263 | 15.116 | 55.210 | 31.748 | 1.00 | 36.12 | A | C |
| ATOM | 1127 | CD1 | LEU | A | 263 | 14.003 | 54.231 | 32.073 | 1.00 | 36.15 | A | C |
| ATOM | 1128 | CD2 | LEU | A | 263 | 15.168 | 56.321 | 32.782 | 1.00 | 32.38 | A | C |
| ATOM | 1129 | C   | LEU | A | 263 | 18.965 | 54.690 | 31.584 | 1.00 | 36.75 | A | C |
| ATOM | 1130 | O   | LEU | A | 263 | 19.305 | 53.648 | 31.022 | 1.00 | 35.94 | A | O |
| ATOM | 1131 | N   | GLY | A | 264 | 19.700 | 55.301 | 32.512 | 1.00 | 36.23 | A | N |
| ATOM | 1132 | CA  | GLY | A | 264 | 20.990 | 54.788 | 32.933 | 1.00 | 38.00 | A | C |
| ATOM | 1133 | C   | GLY | A | 264 | 20.941 | 53.534 | 33.796 | 1.00 | 38.80 | A | C |
| ATOM | 1134 | O   | GLY | A | 264 | 19.864 | 53.026 | 34.113 | 1.00 | 36.95 | A | O |
| ATOM | 1135 | N   | SER | A | 265 | 22.122 | 53.060 | 34.193 | 1.00 | 39.31 | A | N |
| ATOM | 1136 | CA  | SER | A | 265 | 22.271 | 51.844 | 34.999 | 1.00 | 40.86 | A | C |
| ATOM | 1137 | CB  | SER | A | 265 | 23.758 | 51.555 | 35.232 | 1.00 | 40.25 | A | C |
| ATOM | 1138 | OG  | SER | A | 265 | 23.942 | 50.288 | 35.847 | 1.00 | 45.33 | A | O |
| ATOM | 1139 | C   | SER | A | 265 | 21.544 | 51.876 | 36.337 | 1.00 | 41.82 | A | C |
| ATOM | 1140 | O   | SER | A | 265 | 21.030 | 50.852 | 36.800 | 1.00 | 43.16 | A | O |
| ATOM | 1141 | N   | ALA | A | 266 | 21.506 | 53.048 | 36.962 | 1.00 | 43.56 | A | N |
| ATOM | 1142 | CA  | ALA | A | 266 | 20.833 | 53.213 | 38.248 | 1.00 | 43.39 | A | C |
| ATOM | 1143 | CB  | ALA | A | 266 | 21.603 | 54.213 | 39.126 | 1.00 | 41.16 | A | C |
| ATOM | 1144 | C   | ALA | A | 266 | 19.402 | 53.701 | 38.037 | 1.00 | 42.96 | A | C |
| ATOM | 1145 | O   | ALA | A | 266 | 18.709 | 54.053 | 38.987 | 1.00 | 44.36 | A | O |
| ATOM | 1146 | N   | GLY | A | 267 | 18.960 | 53.722 | 36.787 | 1.00 | 43.26 | A | N |
| ATOM | 1147 | CA  | GLY | A | 267 | 17.613 | 54.176 | 36.510 | 1.00 | 43.62 | A | C |
| ATOM | 1148 | C   | GLY | A | 267 | 17.464 | 55.678 | 36.307 | 1.00 | 43.28 | A | C |
| ATOM | 1149 | O   | GLY | A | 267 | 16.346 | 56.156 | 36.114 | 1.00 | 46.43 | A | O |
| ATOM | 1150 | N   | GLU | A | 268 | 18.557 | 56.433 | 36.350 | 1.00 | 42.29 | A | N |
| ATOM | 1151 | CA  | GLU | A | 268 | 18.456 | 57.881 | 36.147 | 1.00 | 42.87 | A | C |
| ATOM | 1152 | CB  | GLU | A | 268 | 19.725 | 58.627 | 36.592 | 1.00 | 44.50 | A | C |
| ATOM | 1153 | CG  | GLU | A | 268 | 20.796 | 57.769 | 37.220 | 1.00 | 50.35 | A | C |
| ATOM | 1154 | CD  | GLU | A | 268 | 21.520 | 56.919 | 36.204 | 1.00 | 49.75 | A | C |
| ATOM | 1155 | OE1 | GLU | A | 268 | 22.583 | 57.358 | 35.701 | 1.00 | 49.51 | A | O |
| ATOM | 1156 | OE2 | GLU | A | 268 | 21.012 | 55.817 | 35.904 | 1.00 | 48.21 | A | O |
| ATOM | 1157 | C   | GLU | A | 268 | 18.175 | 58.231 | 34.689 | 1.00 | 41.51 | A | C |
| ATOM | 1158 | O   | GLU | A | 268 | 18.505 | 57.484 | 33.764 | 1.00 | 39.67 | A | O |
| ATOM | 1159 | N   | LEU | A | 269 | 17.563 | 59.390 | 34.502 | 1.00 | 39.23 | A | N |
| ATOM | 1160 | CA  | LEU | A | 269 | 17.206 | 59.881 | 33.185 | 1.00 | 38.66 | A | C |

TABLE 1-continued coordinates of [T287D] Aurora A (122–396) in complex with AMP-PNP

| ATOM | 1161 | CB | LEU | A | 269 | 16.091 | 60.912 | 33.371 | 1.00 | 37.44 | A | C |
|------|------|------|-----|---|-----|--------|--------|--------|------|-------|---|---|
| ATOM | 1162 | CG | LEU | A | 269 | 15.367 | 61.562 | 32.205 | 1.00 | 38.26 | A | C |
| ATOM | 1163 | CD1 | LEU | A | 269 | 13.995 | 62.029 | 32.680 | 1.00 | 32.98 | A | C |
| ATOM | 1164 | CD2 | LEU | A | 269 | 16.203 | 62.718 | 31.665 | 1.00 | 40.16 | A | C |
| ATOM | 1165 | C | LEU | A | 269 | 18.418 | 60.480 | 32.447 | 1.00 | 36.13 | A | C |
| ATOM | 1166 | O | LEU | A | 269 | 19.255 | 61.153 | 33.050 | 1.00 | 34.63 | A | O |
| ATOM | 1167 | N | LYS | A | 270 | 18.507 | 60.215 | 31.145 | 1.00 | 38.12 | A | N |
| ATOM | 1168 | CA | LYS | A | 270 | 19.589 | 60.740 | 30.302 | 1.00 | 38.51 | A | C |
| ATOM | 1169 | CB | LYS | A | 270 | 20.511 | 59.616 | 29.811 | 1.00 | 38.16 | A | C |
| ATOM | 1170 | CG | LYS | A | 270 | 21.125 | 58.721 | 30.874 | 1.00 | 41.06 | A | C |
| ATOM | 1171 | CD | LYS | A | 270 | 22.288 | 59.391 | 31.567 | 1.00 | 38.38 | A | C |
| ATOM | 1172 | CE | LYS | A | 270 | 23.088 | 58.381 | 32.379 | 1.00 | 36.07 | A | C |
| ATOM | 1173 | NZ | LYS | A | 270 | 24.297 | 59.001 | 32.993 | 1.00 | 29.99 | A | N |
| ATOM | 1174 | C | LYS | A | 270 | 18.977 | 61.397 | 29.054 | 1.00 | 38.60 | A | C |
| ATOM | 1175 | O | LYS | A | 270 | 18.327 | 60.714 | 28.265 | 1.00 | 38.86 | A | O |
| ATOM | 1176 | N | ILE | A | 271 | 19.168 | 62.702 | 28.870 | 1.00 | 36.85 | A | N |
| ATOM | 1177 | CA | ILE | A | 271 | 18.641 | 63.351 | 27.671 | 1.00 | 38.69 | A | C |
| ATOM | 1178 | CB | ILE | A | 271 | 18.652 | 64.906 | 27.752 | 1.00 | 38.48 | A | C |
| ATOM | 1179 | CG2 | ILE | A | 271 | 18.141 | 65.498 | 26.426 | 1.00 | 38.13 | A | C |
| ATOM | 1180 | CG1 | ILE | A | 271 | 17.739 | 65.390 | 28.872 | 1.00 | 37.28 | A | C |
| ATOM | 1181 | CD1 | ILE | A | 271 | 17.641 | 66.894 | 28.965 | 1.00 | 41.06 | A | C |
| ATOM | 1182 | C | ILE | A | 271 | 19.579 | 62.934 | 26.547 | 1.00 | 39.33 | A | C |
| ATOM | 1183 | O | ILE | A | 271 | 20.761 | 63.273 | 26.562 | 1.00 | 33.34 | A | O |
| ATOM | 1184 | N | ALA | A | 272 | 19.053 | 62.203 | 25.575 | 1.00 | 43.07 | A | N |
| ATOM | 1185 | CA | ALA | A | 272 | 19.873 | 61.721 | 24.474 | 1.00 | 50.47 | A | C |
| ATOM | 1186 | CB | ALA | A | 272 | 19.121 | 60.654 | 23.687 | 1.00 | 46.47 | A | C |
| ATOM | 1187 | C | ALA | A | 272 | 20.320 | 62.829 | 23.539 | 1.00 | 56.66 | A | C |
| ATOM | 1188 | O | ALA | A | 272 | 19.630 | 63.837 | 23.379 | 1.00 | 57.25 | A | O |
| ATOM | 1189 | N | ASP | A | 273 | 21.490 | 62.625 | 22.935 | 1.00 | 61.74 | A | N |
| ATOM | 1190 | CA | ASP | A | 273 | 22.062 | 63.562 | 21.979 | 1.00 | 65.85 | A | C |
| ATOM | 1191 | CB | ASP | A | 273 | 23.107 | 62.837 | 21.120 | 1.00 | 66.61 | A | C |
| ATOM | 1192 | CG | ASP | A | 273 | 22.680 | 61.413 | 20.754 | 1.00 | 65.34 | A | C |
| ATOM | 1193 | OD1 | ASP | A | 273 | 22.571 | 60.579 | 21.679 | 1.00 | 66.75 | A | O |
| ATOM | 1194 | OD2 | ASP | A | 273 | 22.457 | 61.118 | 19.561 | 1.00 | 64.24 | A | O |
| ATOM | 1195 | C | ASP | A | 273 | 20.934 | 64.078 | 21.095 | 1.00 | 69.02 | A | C |
| ATOM | 1196 | O | ASP | A | 273 | 20.500 | 63.379 | 20.175 | 1.00 | 69.51 | A | O |
| ATOM | 1197 | N | PHE | A | 274 | 20.444 | 65.287 | 21.365 | 1.00 | 72.26 | A | N |
| ATOM | 1198 | CA | PHE | A | 274 | 19.359 | 65.784 | 20.535 | 1.00 | 74.92 | A | C |
| ATOM | 1199 | CB | PHE | A | 274 | 18.873 | 67.185 | 20.973 | 1.00 | 77.06 | A | C |
| ATOM | 1200 | CG | PHE | A | 274 | 19.908 | 68.278 | 20.889 | 1.00 | 78.54 | A | C |
| ATOM | 1201 | CD1 | PHE | A | 274 | 20.908 | 68.397 | 21.850 | 1.00 | 78.95 | A | C |
| ATOM | 1202 | CD2 | PHE | A | 274 | 19.819 | 69.250 | 19.896 | 1.00 | 79.45 | A | C |
| ATOM | 1203 | CE1 | PHE | A | 274 | 21.797 | 69.480 | 21.823 | 1.00 | 79.11 | A | C |
| ATOM | 1204 | CE2 | PHE | A | 274 | 20.700 | 70.330 | 19.861 | 1.00 | 80.03 | A | C |
| ATOM | 1205 | CZ | PHE | A | 274 | 21.691 | 70.448 | 20.828 | 1.00 | 79.54 | A | C |
| ATOM | 1206 | C | PHE | A | 274 | 19.759 | 65.753 | 19.067 | 1.00 | 76.11 | A | C |
| ATOM | 1207 | O | PHE | A | 274 | 20.857 | 66.162 | 18.688 | 1.00 | 75.92 | A | O |
| ATOM | 1208 | N | GLY | A | 275 | 18.860 | 65.208 | 18.257 | 1.00 | 77.26 | A | N |
| ATOM | 1209 | CA | GLY | A | 275 | 19.106 | 65.096 | 16.836 | 1.00 | 77.96 | A | C |
| ATOM | 1210 | C | GLY | A | 275 | 19.590 | 63.710 | 16.471 | 1.00 | 79.01 | A | C |
| ATOM | 1211 | O | GLY | A | 275 | 19.492 | 62.770 | 17.261 | 1.00 | 78.98 | A | O |
| ATOM | 1212 | N | TRP | A | 276 | 20.137 | 63.595 | 15.268 | 1.00 | 78.75 | A | N |
| ATOM | 1213 | CA | TRP | A | 276 | 20.659 | 62.336 | 14.751 | 1.00 | 77.92 | A | C |
| ATOM | 1214 | CB | TRP | A | 276 | 21.944 | 61.930 | 15.489 | 1.00 | 80.84 | A | C |
| ATOM | 1215 | CG | TRP | A | 276 | 22.633 | 63.003 | 16.308 | 1.00 | 83.68 | A | C |
| ATOM | 1216 | CD2 | TRP | A | 276 | 23.693 | 63.869 | 15.877 | 1.00 | 84.50 | A | C |
| ATOM | 1217 | CE2 | TRP | A | 276 | 24.079 | 64.647 | 16.994 | 1.00 | 84.93 | A | C |
| ATOM | 1218 | CE3 | TRP | A | 276 | 24.355 | 64.063 | 14.656 | 1.00 | 85.10 | A | C |
| ATOM | 1219 | CD1 | TRP | A | 276 | 22.420 | 63.289 | 17.627 | 1.00 | 84.53 | A | C |
| ATOM | 1220 | NE1 | TRP | A | 276 | 23.287 | 64.271 | 18.047 | 1.00 | 85.71 | A | N |
| ATOM | 1221 | CZ2 | TRP | A | 276 | 25.100 | 65.604 | 16.928 | 1.00 | 85.38 | A | C |
| ATOM | 1222 | CZ3 | TRP | A | 276 | 25.373 | 65.018 | 14.592 | 1.00 | 85.86 | A | C |
| ATOM | 1223 | CH2 | TRP | A | 276 | 25.732 | 65.774 | 15.723 | 1.00 | 85.40 | A | C |
| ATOM | 1224 | C | TRP | A | 276 | 19.696 | 61.138 | 14.777 | 1.00 | 75.88 | A | C |
| ATOM | 1225 | O | TRP | A | 276 | 20.148 | 60.001 | 14.873 | 1.00 | 75.31 | A | O |
| ATOM | 1226 | N | SER | A | 277 | 18.386 | 61.363 | 14.692 | 1.00 | 73.54 | A | N |
| ATOM | 1227 | CA | SER | A | 277 | 17.470 | 60.218 | 14.706 | 1.00 | 69.92 | A | C |
| ATOM | 1228 | CB | SER | A | 277 | 16.009 | 60.656 | 14.626 | 1.00 | 69.39 | A | C |
| ATOM | 1229 | OG | SER | A | 277 | 15.145 | 59.528 | 14.690 | 1.00 | 68.26 | A | O |
| ATOM | 1230 | C | SER | A | 277 | 17.795 | 59.324 | 13.518 | 1.00 | 68.61 | A | C |
| ATOM | 1231 | O | SER | A | 277 | 18.330 | 59.791 | 12.514 | 1.00 | 66.97 | A | O |
| ATOM | 1232 | N | VAL | A | 278 | 17.460 | 58.042 | 13.624 | 1.00 | 67.80 | A | N |
| ATOM | 1233 | CA | VAL | A | 278 | 17.764 | 57.094 | 12.560 | 1.00 | 67.75 | A | C |
| ATOM | 1234 | CB | VAL | A | 278 | 18.452 | 55.830 | 13.161 | 1.00 | 67.67 | A | C |
| ATOM | 1235 | CG1 | VAL | A | 278 | 17.429 | 54.748 | 13.454 | 1.00 | 66.50 | A | C |
| ATOM | 1236 | CG2 | VAL | A | 278 | 19.530 | 55.338 | 12.245 | 1.00 | 67.32 | A | C |
| ATOM | 1237 | C | VAL | A | 278 | 16.554 | 56.679 | 11.713 | 1.00 | 68.01 | A | C |

TABLE 1-continued coordinates of [T287D] Aurora A (122–396) in complex with AMP-PNP

| ATOM | 1238 | O   | VAL | A | 278 | 16.722 | 56.161 | 10.606 | 1.00 | 66.68 | A | O |
|------|------|-----|-----|---|-----|--------|--------|--------|------|-------|---|---|
| ATOM | 1239 | N   | ALA | A | 279 | 15.351 | 56.918 | 12.240 | 1.00 | 69.17 | A | N |
| ATOM | 1240 | CA  | ALA | A | 279 | 14.076 | 56.586 | 11.584 | 1.00 | 69.86 | A | C |
| ATOM | 1241 | CB  | ALA | A | 279 | 14.174 | 56.772 | 10.063 | 1.00 | 69.92 | A | C |
| ATOM | 1242 | C   | ALA | A | 279 | 13.607 | 55.167 | 11.904 | 1.00 | 68.92 | A | C |
| ATOM | 1243 | O   | ALA | A | 279 | 13.970 | 54.593 | 12.929 | 1.00 | 69.04 | A | O |
| ATOM | 1244 | N   | GLY | A | 290 | 10.838 | 65.378 | 16.485 | 1.00 | 60.42 | A | N |
| ATOM | 1245 | CA  | GLY | A | 290 | 9.748  | 65.485 | 17.442 | 1.00 | 58.73 | A | C |
| ATOM | 1246 | C   | GLY | A | 290 | 8.433  | 65.948 | 16.835 | 1.00 | 57.18 | A | C |
| ATOM | 1247 | O   | GLY | A | 290 | 8.400  | 66.907 | 16.063 | 1.00 | 56.04 | A | O |
| ATOM | 1248 | N   | THR | A | 291 | 7.341  | 65.281 | 17.198 | 1.00 | 54.45 | A | N |
| ATOM | 1249 | CA  | THR | A | 291 | 6.039  | 65.646 | 16.665 | 1.00 | 49.75 | A | C |
| ATOM | 1250 | CB  | THR | A | 291 | 4.985  | 64.552 | 16.910 | 1.00 | 49.00 | A | C |
| ATOM | 1251 | OG1 | THR | A | 291 | 4.825  | 64.330 | 18.315 | 1.00 | 49.86 | A | O |
| ATOM | 1252 | CG2 | THR | A | 291 | 5.388  | 63.284 | 16.227 | 1.00 | 51.10 | A | C |
| ATOM | 1253 | C   | THR | A | 291 | 5.471  | 66.956 | 17.194 | 1.00 | 46.23 | A | C |
| ATOM | 1254 | O   | THR | A | 291 | 5.959  | 67.548 | 18.163 | 1.00 | 42.68 | A | O |
| ATOM | 1255 | N   | LEU | A | 292 | 4.419  | 67.386 | 16.514 | 1.00 | 43.51 | A | N |
| ATOM | 1256 | CA  | LEU | A | 292 | 3.696  | 68.601 | 16.819 | 1.00 | 38.04 | A | C |
| ATOM | 1257 | CB  | LEU | A | 292 | 2.460  | 68.662 | 15.927 | 1.00 | 35.68 | A | C |
| ATOM | 1258 | CG  | LEU | A | 292 | 1.624  | 69.937 | 15.948 | 1.00 | 33.83 | A | C |
| ATOM | 1259 | CD1 | LEU | A | 292 | 2.511  | 71.150 | 15.696 | 1.00 | 33.10 | A | C |
| ATOM | 1260 | CD2 | LEU | A | 292 | 0.550  | 69.821 | 14.881 | 1.00 | 35.15 | A | C |
| ATOM | 1261 | C   | LEU | A | 292 | 3.275  | 68.691 | 18.280 | 1.00 | 36.84 | A | C |
| ATOM | 1262 | O   | LEU | A | 292 | 3.286  | 69.771 | 18.862 | 1.00 | 36.40 | A | O |
| ATOM | 1263 | N   | ASP | A | 293 | 2.910  | 67.558 | 18.878 | 1.00 | 36.26 | A | N |
| ATOM | 1264 | CA  | ASP | A | 293 | 2.464  | 67.545 | 20.270 | 1.00 | 33.20 | A | C |
| ATOM | 1265 | CB  | ASP | A | 293 | 2.067  | 66.132 | 20.701 | 1.00 | 36.86 | A | C |
| ATOM | 1266 | CG  | ASP | A | 293 | 0.647  | 65.790 | 20.328 | 1.00 | 37.14 | A | C |
| ATOM | 1267 | OD1 | ASP | A | 293 | 0.417  | 65.413 | 19.166 | 1.00 | 41.08 | A | O |
| ATOM | 1268 | OD2 | ASP | A | 293 | −0.240 | 65.910 | 21.198 | 1.00 | 39.86 | A | O |
| ATOM | 1269 | C   | ASP | A | 293 | 3.447  | 68.091 | 21.279 | 1.00 | 32.18 | A | C |
| ATOM | 1270 | O   | ASP | A | 293 | 3.060  | 68.442 | 22.388 | 1.00 | 32.05 | A | O |
| ATOM | 1271 | N   | TYR | A | 294 | 4.719  | 68.170 | 20.920 | 1.00 | 33.09 | A | N |
| ATOM | 1272 | CA  | TYR | A | 294 | 5.692  | 68.669 | 21.880 | 1.00 | 35.14 | A | C |
| ATOM | 1273 | CB  | TYR | A | 294 | 6.837  | 67.653 | 22.027 | 1.00 | 36.03 | A | C |
| ATOM | 1274 | CG  | TYR | A | 294 | 6.352  | 66.274 | 22.443 | 1.00 | 35.56 | A | C |
| ATOM | 1275 | CD1 | TYR | A | 294 | 5.804  | 65.389 | 21.509 | 1.00 | 35.20 | A | C |
| ATOM | 1276 | CE1 | TYR | A | 294 | 5.310  | 64.131 | 21.905 | 1.00 | 37.12 | A | C |
| ATOM | 1277 | CD2 | TYR | A | 294 | 6.397  | 65.872 | 23.783 | 1.00 | 35.96 | A | C |
| ATOM | 1278 | CE2 | TYR | A | 294 | 5.908  | 64.628 | 24.184 | 1.00 | 34.99 | A | C |
| ATOM | 1279 | CZ  | TYR | A | 294 | 5.369  | 63.762 | 23.244 | 1.00 | 35.56 | A | C |
| ATOM | 1280 | OH  | TYR | A | 294 | 4.917  | 62.521 | 23.644 | 1.00 | 35.68 | A | O |
| ATOM | 1281 | C   | TYR | A | 294 | 6.245  | 70.064 | 21.566 | 1.00 | 37.52 | A | C |
| ATOM | 1282 | O   | TYR | A | 294 | 7.079  | 70.590 | 22.303 | 1.00 | 39.14 | A | O |
| ATOM | 1283 | N   | LEU | A | 295 | 5.758  | 70.674 | 20.493 | 1.00 | 36.26 | A | N |
| ATOM | 1284 | CA  | LEU | A | 295 | 6.232  | 72.005 | 20.102 | 1.00 | 36.64 | A | C |
| ATOM | 1285 | CB  | LEU | A | 295 | 6.135  | 72.154 | 18.587 | 1.00 | 35.17 | A | C |
| ATOM | 1286 | CG  | LEU | A | 295 | 6.953  | 71.141 | 17.781 | 1.00 | 36.95 | A | C |
| ATOM | 1287 | CD1 | LEU | A | 295 | 6.675  | 71.328 | 16.282 | 1.00 | 37.45 | A | C |
| ATOM | 1288 | CD2 | LEU | A | 295 | 8.440  | 71.326 | 18.097 | 1.00 | 36.23 | A | C |
| ATOM | 1289 | C   | LEU | A | 295 | 5.480  | 73.161 | 20.765 | 1.00 | 34.99 | A | C |
| ATOM | 1290 | O   | LEU | A | 295 | 4.256  | 73.170 | 20.811 | 1.00 | 34.10 | A | O |
| ATOM | 1291 | N   | PRO | A | 296 | 6.215  | 74.154 | 21.293 | 1.00 | 35.03 | A | N |
| ATOM | 1292 | CD  | PRO | A | 296 | 7.683  | 74.244 | 21.374 | 1.00 | 32.23 | A | C |
| ATOM | 1293 | CA  | PRO | A | 296 | 5.583  | 75.306 | 21.939 | 1.00 | 34.56 | A | C |
| ATOM | 1294 | CB  | PRO | A | 296 | 6.743  | 75.963 | 22.686 | 1.00 | 32.65 | A | C |
| ATOM | 1295 | CG  | PRO | A | 296 | 7.897  | 75.677 | 21.801 | 1.00 | 35.00 | A | C |
| ATOM | 1296 | C   | PRO | A | 296 | 4.980  | 76.216 | 20.865 | 1.00 | 35.38 | A | C |
| ATOM | 1297 | O   | PRO | A | 296 | 5.423  | 76.210 | 19.715 | 1.00 | 31.51 | A | O |
| ATOM | 1298 | N   | PRO | A | 297 | 3.964  | 77.009 | 21.231 | 1.00 | 35.66 | A | N |
| ATOM | 1299 | CD  | PRO | A | 297 | 3.432  | 77.146 | 22.597 | 1.00 | 35.54 | A | C |
| ATOM | 1300 | CA  | PRO | A | 297 | 3.283  | 77.927 | 20.313 | 1.00 | 36.80 | A | C |
| ATOM | 1301 | CB  | PRO | A | 297 | 2.400  | 78.758 | 21.245 | 1.00 | 37.34 | A | C |
| ATOM | 1302 | CG  | PRO | A | 297 | 2.100  | 77.819 | 22.358 | 1.00 | 38.15 | A | C |
| ATOM | 1303 | C   | PRO | A | 297 | 4.182  | 78.818 | 19.458 | 1.00 | 37.23 | A | C |
| ATOM | 1304 | O   | PRO | A | 297 | 3.991  | 78.920 | 18.235 | 1.00 | 33.75 | A | O |
| ATOM | 1305 | N   | GLU | A | 298 | 5.158  | 79.461 | 20.095 | 1.00 | 37.28 | A | N |
| ATOM | 1306 | CA  | GLU | A | 298 | 6.040  | 80.368 | 19.375 | 1.00 | 39.04 | A | C |
| ATOM | 1307 | CB  | GLU | A | 298 | 7.016  | 81.072 | 20.335 | 1.00 | 40.64 | A | C |
| ATOM | 1308 | CG  | GLU | A | 298 | 7.969  | 80.146 | 21.080 | 1.00 | 41.60 | A | C |
| ATOM | 1309 | CD  | GLU | A | 298 | 7.456  | 79.749 | 22.453 | 1.00 | 41.95 | A | C |
| ATOM | 1310 | OE1 | GLU | A | 298 | 6.216  | 79.639 | 22.633 | 1.00 | 37.64 | A | O |
| ATOM | 1311 | OE2 | GLU | A | 298 | 8.304  | 79.536 | 23.352 | 1.00 | 42.68 | A | O |
| ATOM | 1312 | C   | GLU | A | 298 | 6.805  | 79.668 | 18.266 | 1.00 | 40.93 | A | C |
| ATOM | 1313 | O   | GLU | A | 298 | 7.175  | 80.297 | 17.272 | 1.00 | 40.31 | A | O |
| ATOM | 1314 | N   | MET | A | 299 | 7.029  | 78.366 | 18.415 | 1.00 | 41.73 | A | N |

TABLE 1-continued coordinates of [T287D] Aurora A (122–396) in complex with AMP-PNP

| ATOM | 1315 | CA | MET | A | 299 | 7.759 | 77.624 | 17.395 | 1.00 | 43.83 | A | C |
|---|---|---|---|---|---|---|---|---|---|---|---|---|
| ATOM | 1316 | CB | MET | A | 299 | 8.495 | 76.437 | 18.017 | 1.00 | 47.01 | A | C |
| ATOM | 1317 | CG | MET | A | 299 | 9.916 | 76.769 | 18.440 | 1.00 | 50.51 | A | C |
| ATOM | 1318 | SD | MET | A | 299 | 10.859 | 75.322 | 18.989 | 1.00 | 56.33 | A | S |
| ATOM | 1319 | CE | MET | A | 299 | 10.979 | 74.398 | 17.460 | 1.00 | 57.30 | A | C |
| ATOM | 1320 | C | MET | A | 299 | 6.907 | 77.157 | 16.222 | 1.00 | 45.51 | A | C |
| ATOM | 1321 | O | MET | A | 299 | 7.357 | 77.219 | 15.078 | 1.00 | 46.23 | A | O |
| ATOM | 1322 | N | ILE | A | 300 | 5.686 | 76.691 | 16.473 | 1.00 | 46.41 | A | N |
| ATOM | 1323 | CA | ILE | A | 300 | 4.857 | 76.256 | 15.354 | 1.00 | 49.69 | A | C |
| ATOM | 1324 | CB | ILE | A | 300 | 3.667 | 75.376 | 15.798 | 1.00 | 48.42 | A | C |
| ATOM | 1325 | CG2 | ILE | A | 300 | 4.178 | 74.162 | 16.561 | 1.00 | 47.80 | A | C |
| ATOM | 1326 | CG1 | ILE | A | 300 | 2.709 | 76.179 | 16.675 | 1.00 | 49.64 | A | C |
| ATOM | 1327 | CD1 | ILE | A | 300 | 1.559 | 75.360 | 17.234 | 1.00 | 47.41 | A | C |
| ATOM | 1328 | C | ILE | A | 300 | 4.322 | 77.478 | 14.610 | 1.00 | 54.06 | A | C |
| ATOM | 1329 | O | ILE | A | 300 | 4.079 | 77.416 | 13.399 | 1.00 | 54.63 | A | O |
| ATOM | 1330 | N | GLU | A | 301 | 4.153 | 78.590 | 15.332 | 1.00 | 55.66 | A | N |
| ATOM | 1331 | CA | GLU | A | 301 | 3.646 | 79.827 | 14.733 | 1.00 | 56.31 | A | C |
| ATOM | 1332 | CB | GLU | A | 301 | 3.129 | 80.780 | 15.815 | 1.00 | 54.96 | A | C |
| ATOM | 1333 | CG | GLU | A | 301 | 1.744 | 80.422 | 16.350 | 1.00 | 54.86 | A | C |
| ATOM | 1334 | CD | GLU | A | 301 | 1.408 | 81.163 | 17.629 | 1.00 | 57.37 | A | C |
| ATOM | 1335 | OE1 | GLU | A | 301 | 2.017 | 82.225 | 17.865 | 1.00 | 61.01 | A | O |
| ATOM | 1336 | OE2 | GLU | A | 301 | 0.535 | 80.701 | 18.397 | 1.00 | 57.95 | A | O |
| ATOM | 1337 | C | GLU | A | 301 | 4.684 | 80.533 | 13.875 | 1.00 | 56.92 | A | C |
| ATOM | 1338 | O | GLU | A | 301 | 4.345 | 81.438 | 13.120 | 1.00 | 60.15 | A | O |
| ATOM | 1339 | N | GLY | A | 302 | 5.943 | 80.119 | 13.988 | 1.00 | 58.80 | A | N |
| ATOM | 1340 | CA | GLY | A | 302 | 6.998 | 80.729 | 13.191 | 1.00 | 59.94 | A | C |
| ATOM | 1341 | C | GLY | A | 302 | 7.683 | 81.921 | 13.838 | 1.00 | 61.59 | A | C |
| ATOM | 1342 | O | GLY | A | 302 | 8.681 | 82.429 | 13.322 | 1.00 | 60.55 | A | O |
| ATOM | 1343 | N | ARG | A | 303 | 7.149 | 82.359 | 14.974 | 1.00 | 62.63 | A | N |
| ATOM | 1344 | CA | ARG | A | 303 | 7.688 | 83.497 | 15.712 | 1.00 | 63.82 | A | C |
| ATOM | 1345 | CB | ARG | A | 303 | 6.674 | 83.913 | 16.778 | 1.00 | 64.15 | A | C |
| ATOM | 1346 | CG | ARG | A | 303 | 5.352 | 84.320 | 16.161 | 1.00 | 65.61 | A | C |
| ATOM | 1347 | CD | ARG | A | 303 | 4.180 | 84.153 | 17.100 | 1.00 | 69.14 | A | C |
| ATOM | 1348 | NE | ARG | A | 303 | 3.933 | 85.328 | 17.925 | 1.00 | 72.61 | A | N |
| ATOM | 1349 | CZ | ARG | A | 303 | 2.797 | 85.543 | 18.585 | 1.00 | 75.65 | A | C |
| ATOM | 1350 | NH1 | ARG | A | 303 | 2.644 | 86.641 | 19.318 | 1.00 | 75.84 | A | N |
| ATOM | 1351 | NH2 | ARG | A | 303 | 1.806 | 84.660 | 18.509 | 1.00 | 75.29 | A | N |
| ATOM | 1352 | C | ARG | A | 303 | 9.056 | 83.212 | 16.339 | 1.00 | 64.35 | A | C |
| ATOM | 1353 | O | ARG | A | 303 | 9.637 | 82.148 | 16.122 | 1.00 | 65.12 | A | O |
| ATOM | 1354 | N | MET | A | 304 | 9.572 | 84.173 | 17.099 | 1.00 | 65.05 | A | N |
| ATOM | 1355 | CA | MET | A | 304 | 10.871 | 84.038 | 17.756 | 1.00 | 66.24 | A | C |
| ATOM | 1356 | CB | MET | A | 304 | 11.377 | 85.403 | 18.216 | 1.00 | 69.81 | A | C |
| ATOM | 1357 | CG | MET | A | 304 | 11.911 | 86.312 | 17.135 | 1.00 | 74.75 | A | C |
| ATOM | 1358 | SD | MET | A | 304 | 12.200 | 87.972 | 17.807 | 1.00 | 80.86 | A | S |
| ATOM | 1359 | CE | MET | A | 304 | 13.387 | 87.618 | 19.128 | 1.00 | 78.52 | A | C |
| ATOM | 1360 | C | MET | A | 304 | 10.792 | 83.139 | 18.981 | 1.00 | 65.57 | A | C |
| ATOM | 1361 | O | MET | A | 304 | 9.798 | 83.164 | 19.710 | 1.00 | 66.01 | A | O |
| ATOM | 1362 | N | HIS | A | 305 | 11.847 | 82.361 | 19.216 | 1.00 | 64.22 | A | N |
| ATOM | 1363 | CA | HIS | A | 305 | 11.900 | 81.478 | 20.381 | 1.00 | 63.54 | A | C |
| ATOM | 1364 | CB | HIS | A | 305 | 11.502 | 80.047 | 20.005 | 1.00 | 62.59 | A | C |
| ATOM | 1365 | CG | HIS | A | 305 | 12.372 | 79.428 | 18.958 | 1.00 | 63.59 | A | C |
| ATOM | 1366 | CD2 | HIS | A | 305 | 13.509 | 78.699 | 19.062 | 1.00 | 63.03 | A | C |
| ATOM | 1367 | ND1 | HIS | A | 305 | 12.100 | 79.524 | 17.611 | 1.00 | 64.03 | A | N |
| ATOM | 1368 | CE1 | HIS | A | 305 | 13.031 | 78.878 | 16.930 | 1.00 | 64.73 | A | C |
| ATOM | 1369 | NE2 | HIS | A | 305 | 13.897 | 78.369 | 17.787 | 1.00 | 63.15 | A | N |
| ATOM | 1370 | C | HIS | A | 305 | 13.284 | 81.470 | 21.031 | 1.00 | 62.77 | A | C |
| ATOM | 1371 | O | HIS | A | 305 | 14.303 | 81.665 | 20.359 | 1.00 | 61.65 | A | O |
| ATOM | 1372 | N | ASP | A | 306 | 13.307 | 81.235 | 22.342 | 1.00 | 61.87 | A | N |
| ATOM | 1373 | CA | ASP | A | 306 | 14.553 | 81.211 | 23.109 | 1.00 | 59.72 | A | C |
| ATOM | 1374 | CB | ASP | A | 306 | 14.722 | 82.543 | 23.838 | 1.00 | 61.31 | A | C |
| ATOM | 1375 | CG | ASP | A | 306 | 13.804 | 82.668 | 25.035 | 1.00 | 63.77 | A | C |
| ATOM | 1376 | OD1 | ASP | A | 306 | 12.597 | 82.368 | 24.903 | 1.00 | 63.61 | A | O |
| ATOM | 1377 | OD2 | ASP | A | 306 | 14.293 | 83.073 | 26.111 | 1.00 | 67.22 | A | O |
| ATOM | 1378 | C | ASP | A | 306 | 14.614 | 80.058 | 24.128 | 1.00 | 57.12 | A | C |
| ATOM | 1379 | O | ASP | A | 306 | 13.984 | 79.014 | 23.944 | 1.00 | 55.04 | A | O |
| ATOM | 1380 | N | GLU | A | 307 | 15.372 | 80.269 | 25.202 | 1.00 | 53.44 | A | N |
| ATOM | 1381 | CA | GLU | A | 307 | 15.552 | 79.274 | 26.253 | 1.00 | 50.60 | A | C |
| ATOM | 1382 | CB | GLU | A | 307 | 16.547 | 79.793 | 27.298 | 1.00 | 52.86 | A | C |
| ATOM | 1383 | CG | GLU | A | 307 | 16.215 | 81.169 | 27.862 | 1.00 | 56.28 | A | C |
| ATOM | 1384 | CD | GLU | A | 307 | 15.453 | 81.128 | 29.175 | 1.00 | 58.72 | A | C |
| ATOM | 1385 | OE1 | GLU | A | 307 | 15.048 | 82.215 | 29.646 | 1.00 | 62.07 | A | O |
| ATOM | 1386 | OE2 | GLU | A | 307 | 15.264 | 80.027 | 29.742 | 1.00 | 58.85 | A | O |
| ATOM | 1387 | C | GLU | A | 307 | 14.259 | 78.861 | 26.935 | 1.00 | 48.53 | A | C |
| ATOM | 1388 | O | GLU | A | 307 | 14.153 | 77.745 | 27.450 | 1.00 | 45.98 | A | O |
| ATOM | 1389 | N | LYS | A | 308 | 13.275 | 79.756 | 26.935 | 1.00 | 44.46 | A | N |
| ATOM | 1390 | CA | LYS | A | 308 | 11.990 | 79.460 | 27.555 | 1.00 | 42.65 | A | C |
| ATOM | 1391 | CB | LYS | A | 308 | 11.099 | 80.706 | 27.556 | 1.00 | 43.53 | A | C |

TABLE 1-continued coordinates of [T287D] Aurora A (122–396) in complex with AMP-PNP

| ATOM | 1392 | CG | LYS | A | 308 | 11.596 | 81.812 | 28.477 | 1.00 | 46.71 | A | C |
|---|---|---|---|---|---|---|---|---|---|---|---|---|
| ATOM | 1393 | CD | LYS | A | 308 | 11.642 | 81.330 | 29.916 | 1.00 | 46.09 | A | C |
| ATOM | 1394 | CE | LYS | A | 308 | 12.011 | 82.458 | 30.861 | 1.00 | 50.52 | A | C |
| ATOM | 1395 | NZ | LYS | A | 308 | 11.941 | 82.037 | 32.292 | 1.00 | 48.95 | A | N |
| ATOM | 1396 | C | LYS | A | 308 | 11.254 | 78.301 | 26.881 | 1.00 | 39.37 | A | C |
| ATOM | 1397 | O | LYS | A | 308 | 10.288 | 77.784 | 27.439 | 1.00 | 38.96 | A | O |
| ATOM | 1398 | N | VAL | A | 309 | 11.691 | 77.904 | 25.685 | 1.00 | 37.85 | A | N |
| ATOM | 1399 | CA | VAL | A | 309 | 11.055 | 76.781 | 24.999 | 1.00 | 36.62 | A | C |
| ATOM | 1400 | CB | VAL | A | 309 | 11.665 | 76.507 | 23.582 | 1.00 | 36.29 | A | C |
| ATOM | 1401 | CG1 | VAL | A | 309 | 11.361 | 77.654 | 22.638 | 1.00 | 36.56 | A | C |
| ATOM | 1402 | CG2 | VAL | A | 309 | 13.162 | 76.294 | 23.680 | 1.00 | 36.29 | A | C |
| ATOM | 1403 | C | VAL | A | 309 | 11.238 | 75.533 | 25.873 | 1.00 | 36.76 | A | C |
| ATOM | 1404 | O | VAL | A | 309 | 10.374 | 74.666 | 25.902 | 1.00 | 37.91 | A | O |
| ATOM | 1405 | N | ASP | A | 310 | 12.359 | 75.455 | 26.594 | 1.00 | 36.49 | A | N |
| ATOM | 1406 | CA | ASP | A | 310 | 12.616 | 74.311 | 27.467 | 1.00 | 37.02 | A | C |
| ATOM | 1407 | CB | ASP | A | 310 | 14.048 | 74.340 | 28.005 | 1.00 | 36.24 | A | C |
| ATOM | 1408 | CG | ASP | A | 310 | 15.080 | 74.031 | 26.947 | 1.00 | 39.49 | A | C |
| ATOM | 1409 | OD1 | ASP | A | 310 | 14.820 | 73.177 | 26.074 | 1.00 | 42.74 | A | O |
| ATOM | 1410 | OD2 | ASP | A | 310 | 16.172 | 74.629 | 26.994 | 1.00 | 43.52 | A | O |
| ATOM | 1411 | C | ASP | A | 310 | 11.633 | 74.227 | 28.645 | 1.00 | 36.95 | A | C |
| ATOM | 1412 | O | ASP | A | 310 | 11.342 | 73.133 | 29.140 | 1.00 | 37.49 | A | O |
| ATOM | 1413 | N | LEU | A | 311 | 11.122 | 75.365 | 29.109 | 1.00 | 35.08 | A | N |
| ATOM | 1414 | CA | LEU | A | 311 | 10.166 | 75.333 | 30.211 | 1.00 | 32.22 | A | C |
| ATOM | 1415 | CB | LEU | A | 311 | 9.951 | 76.736 | 30.790 | 1.00 | 34.39 | A | C |
| ATOM | 1416 | CG | LEU | A | 311 | 10.913 | 77.158 | 31.909 | 1.00 | 33.96 | A | C |
| ATOM | 1417 | CD1 | LEU | A | 311 | 10.809 | 76.178 | 33.064 | 1.00 | 35.22 | A | C |
| ATOM | 1418 | CD2 | LEU | A | 311 | 12.334 | 77.210 | 31.389 | 1.00 | 33.80 | A | C |
| ATOM | 1419 | C | LEU | A | 311 | 8.833 | 74.752 | 29.743 | 1.00 | 31.56 | A | C |
| ATOM | 1420 | O | LEU | A | 311 | 8.139 | 74.050 | 30.488 | 1.00 | 31.74 | A | O |
| ATOM | 1421 | N | TRP | A | 312 | 8.466 | 75.048 | 28.503 | 1.00 | 30.35 | A | N |
| ATOM | 1422 | CA | TRP | A | 312 | 7.220 | 74.520 | 27.960 | 1.00 | 29.50 | A | C |
| ATOM | 1423 | CB | TRP | A | 312 | 6.948 | 75.139 | 26.585 | 1.00 | 28.53 | A | C |
| ATOM | 1424 | CG | TRP | A | 312 | 5.759 | 74.557 | 25.875 | 1.00 | 28.80 | A | C |
| ATOM | 1425 | CD2 | TRP | A | 312 | 4.431 | 75.100 | 25.843 | 1.00 | 30.03 | A | C |
| ATOM | 1426 | CE2 | TRP | A | 312 | 3.648 | 74.251 | 25.027 | 1.00 | 29.38 | A | C |
| ATOM | 1427 | CE3 | TRP | A | 312 | 3.830 | 76.225 | 26.421 | 1.00 | 29.90 | A | C |
| ATOM | 1428 | CD1 | TRP | A | 312 | 5.730 | 73.429 | 25.103 | 1.00 | 26.36 | A | C |
| ATOM | 1429 | NE1 | TRP | A | 312 | 4.460 | 73.237 | 24.589 | 1.00 | 30.47 | A | N |
| ATOM | 1430 | CZ2 | TRP | A | 312 | 2.299 | 74.495 | 24.775 | 1.00 | 32.48 | A | C |
| ATOM | 1431 | CZ3 | TRP | A | 312 | 2.488 | 76.465 | 26.171 | 1.00 | 31.78 | A | C |
| ATOM | 1432 | CH2 | TRP | A | 312 | 1.739 | 75.604 | 25.354 | 1.00 | 33.00 | A | C |
| ATOM | 1433 | C | TRP | A | 312 | 7.319 | 72.991 | 27.855 | 1.00 | 28.16 | A | C |
| ATOM | 1434 | O | TRP | A | 312 | 6.371 | 72.272 | 28.190 | 1.00 | 30.23 | A | O |
| ATOM | 1435 | N | SER | A | 313 | 8.467 | 72.503 | 27.389 | 1.00 | 27.71 | A | N |
| ATOM | 1436 | CA | SER | A | 313 | 8.699 | 71.066 | 27.248 | 1.00 | 29.31 | A | C |
| ATOM | 1437 | CB | SER | A | 313 | 10.120 | 70.803 | 26.715 | 1.00 | 30.43 | A | C |
| ATOM | 1438 | OG | SER | A | 313 | 10.265 | 71.217 | 25.364 | 1.00 | 31.34 | A | O |
| ATOM | 1439 | C | SER | A | 313 | 8.540 | 70.373 | 28.605 | 1.00 | 30.79 | A | C |
| ATOM | 1440 | O | SER | A | 313 | 7.926 | 69.314 | 28.729 | 1.00 | 31.14 | A | O |
| ATOM | 1441 | N | LEU | A | 314 | 9.101 | 70.994 | 29.628 | 1.00 | 32.96 | A | N |
| ATOM | 1442 | CA | LEU | A | 314 | 9.026 | 70.455 | 30.966 | 1.00 | 33.68 | A | C |
| ATOM | 1443 | CB | LEU | A | 314 | 9.746 | 71.412 | 31.921 | 1.00 | 35.73 | A | C |
| ATOM | 1444 | CG | LEU | A | 314 | 10.693 | 70.816 | 32.958 | 1.00 | 39.36 | A | C |
| ATOM | 1445 | CD1 | LEU | A | 314 | 11.611 | 69.795 | 32.312 | 1.00 | 37.79 | A | C |
| ATOM | 1446 | CD2 | LEU | A | 314 | 11.494 | 71.940 | 33.611 | 1.00 | 39.93 | A | C |
| ATOM | 1447 | C | LEU | A | 314 | 7.567 | 70.265 | 31.368 | 1.00 | 34.08 | A | C |
| ATOM | 1448 | O | LEU | A | 314 | 7.213 | 69.270 | 32.002 | 1.00 | 35.54 | A | O |
| ATOM | 1449 | N | GLY | A | 315 | 6.715 | 71.212 | 30.974 | 1.00 | 34.46 | A | N |
| ATOM | 1450 | CA | GLY | A | 315 | 5.302 | 71.129 | 31.311 | 1.00 | 32.61 | A | C |
| ATOM | 1451 | C | GLY | A | 315 | 4.533 | 70.037 | 30.580 | 1.00 | 32.40 | A | C |
| ATOM | 1452 | O | GLY | A | 315 | 3.653 | 69.393 | 31.156 | 1.00 | 31.59 | A | O |
| ATOM | 1453 | N | VAL | A | 316 | 4.848 | 69.839 | 29.305 | 1.00 | 30.85 | A | N |
| ATOM | 1454 | CA | VAL | A | 316 | 4.191 | 68.812 | 28.500 | 1.00 | 30.81 | A | C |
| ATOM | 1455 | CB | VAL | A | 316 | 4.675 | 68.870 | 27.019 | 1.00 | 31.13 | A | C |
| ATOM | 1456 | CG1 | VAL | A | 316 | 4.091 | 67.703 | 26.225 | 1.00 | 31.52 | A | C |
| ATOM | 1457 | CG2 | VAL | A | 316 | 4.268 | 70.206 | 26.381 | 1.00 | 31.54 | A | C |
| ATOM | 1458 | C | VAL | A | 316 | 4.541 | 67.431 | 29.076 | 1.00 | 30.12 | A | C |
| ATOM | 1459 | O | VAL | A | 316 | 3.694 | 66.547 | 29.151 | 1.00 | 28.42 | A | O |
| ATOM | 1460 | N | LEU | A | 317 | 5.800 | 67.269 | 29.472 | 1.00 | 30.58 | A | N |
| ATOM | 1461 | CA | LEU | A | 317 | 6.307 | 66.018 | 30.041 | 1.00 | 32.76 | A | C |
| ATOM | 1462 | CB | LEU | A | 317 | 7.834 | 66.091 | 30.182 | 1.00 | 33.36 | A | C |
| ATOM | 1463 | CG | LEU | A | 317 | 8.741 | 65.504 | 29.091 | 1.00 | 37.19 | A | C |
| ATOM | 1464 | CD1 | LEU | A | 317 | 7.959 | 65.186 | 27.838 | 1.00 | 34.20 | A | C |
| ATOM | 1465 | CD2 | LEU | A | 317 | 9.868 | 66.471 | 28.805 | 1.00 | 29.92 | A | C |
| ATOM | 1466 | C | LEU | A | 317 | 5.700 | 65.710 | 31.408 | 1.00 | 32.08 | A | C |
| ATOM | 1467 | O | LEU | A | 317 | 5.249 | 64.587 | 31.656 | 1.00 | 34.68 | A | O |
| ATOM | 1468 | N | CYS | A | 318 | 5.702 | 66.697 | 32.298 | 1.00 | 31.11 | A | N |

TABLE 1-continued coordinates of [T287D] Aurora A (122–396) in complex with AMP-PNP

| ATOM | 1469 | CA  | CYS | A | 318 | 5.151  | 66.491 | 33.629 | 1.00 | 33.57 | A | C |
| ---- | ---- | --- | --- | - | --- | ------ | ------ | ------ | ---- | ----- | - | - |
| ATOM | 1470 | CB  | CYS | A | 318 | 5.156  | 67.798 | 34.432 | 1.00 | 33.30 | A | C |
| ATOM | 1471 | SG  | CYS | A | 318 | 4.864  | 67.562 | 36.226 | 1.00 | 37.22 | A | S |
| ATOM | 1472 | C   | CYS | A | 318 | 3.725  | 65.973 | 33.468 | 1.00 | 35.37 | A | C |
| ATOM | 1473 | O   | CYS | A | 318 | 3.326  | 64.971 | 34.075 | 1.00 | 33.70 | A | O |
| ATOM | 1474 | N   | TYR | A | 319 | 2.969  | 66.645 | 32.613 | 1.00 | 32.86 | A | N |
| ATOM | 1475 | CA  | TYR | A | 319 | 1.598  | 66.244 | 32.364 | 1.00 | 33.70 | A | C |
| ATOM | 1476 | CB  | TYR | A | 319 | 0.927  | 67.239 | 31.395 | 1.00 | 29.85 | A | C |
| ATOM | 1477 | CG  | TYR | A | 319 | −0.525 | 66.932 | 31.098 | 1.00 | 30.41 | A | C |
| ATOM | 1478 | CD1 | TYR | A | 319 | −0.877 | 65.857 | 30.276 | 1.00 | 28.02 | A | C |
| ATOM | 1479 | CE1 | TYR | A | 319 | −2.207 | 65.545 | 30.022 | 1.00 | 29.18 | A | C |
| ATOM | 1480 | CD2 | TYR | A | 319 | −1.557 | 67.696 | 31.667 | 1.00 | 28.95 | A | C |
| ATOM | 1481 | CE2 | TYR | A | 319 | −2.902 | 67.387 | 31.424 | 1.00 | 27.56 | A | C |
| ATOM | 1482 | CZ  | TYR | A | 319 | −3.217 | 66.318 | 30.599 | 1.00 | 30.05 | A | C |
| ATOM | 1483 | OH  | TYR | A | 319 | −4.530 | 66.032 | 30.309 | 1.00 | 30.26 | A | O |
| ATOM | 1484 | C   | TYR | A | 319 | 1.550  | 64.825 | 31.796 | 1.00 | 33.79 | A | C |
| ATOM | 1485 | O   | TYR | A | 319 | 0.804  | 63.970 | 32.286 | 1.00 | 34.68 | A | O |
| ATOM | 1486 | N   | GLU | A | 320 | 2.343  | 64.562 | 30.764 | 1.00 | 34.53 | A | N |
| ATOM | 1487 | CA  | GLU | A | 320 | 2.317  | 63.236 | 30.153 | 1.00 | 34.32 | A | C |
| ATOM | 1488 | CB  | GLU | A | 320 | 3.228  | 63.166 | 28.927 | 1.00 | 31.06 | A | C |
| ATOM | 1489 | CG  | GLU | A | 320 | 3.005  | 61.857 | 28.188 | 1.00 | 40.04 | A | C |
| ATOM | 1490 | CD  | GLU | A | 320 | 3.781  | 61.719 | 26.906 | 1.00 | 42.41 | A | C |
| ATOM | 1491 | OE1 | GLU | A | 320 | 3.546  | 60.713 | 26.203 | 1.00 | 44.86 | A | O |
| ATOM | 1492 | OE2 | GLU | A | 320 | 4.618  | 62.591 | 26.600 | 1.00 | 43.17 | A | O |
| ATOM | 1493 | C   | GLU | A | 320 | 2.688  | 62.104 | 31.116 | 1.00 | 32.80 | A | C |
| ATOM | 1494 | O   | GLU | A | 320 | 2.109  | 61.018 | 31.045 | 1.00 | 32.14 | A | O |
| ATOM | 1495 | N   | PHE | A | 321 | 3.651  | 62.357 | 32.003 | 1.00 | 32.51 | A | N |
| ATOM | 1496 | CA  | PHE | A | 321 | 4.071  | 61.343 | 32.973 | 1.00 | 33.85 | A | C |
| ATOM | 1497 | CB  | PHE | A | 321 | 5.235  | 61.833 | 33.829 | 1.00 | 29.43 | A | C |
| ATOM | 1498 | CG  | PHE | A | 321 | 6.517  | 62.054 | 33.070 | 1.00 | 30.26 | A | C |
| ATOM | 1499 | CD1 | PHE | A | 321 | 6.711  | 61.505 | 31.816 | 1.00 | 28.99 | A | C |
| ATOM | 1500 | CD2 | PHE | A | 321 | 7.556  | 62.764 | 33.655 | 1.00 | 25.23 | A | C |
| ATOM | 1501 | CE1 | PHE | A | 321 | 7.932  | 61.654 | 31.156 | 1.00 | 32.51 | A | C |
| ATOM | 1502 | CE2 | PHE | A | 321 | 8.782  | 62.919 | 33.007 | 1.00 | 30.02 | A | C |
| ATOM | 1503 | CZ  | PHE | A | 321 | 8.969  | 62.356 | 31.750 | 1.00 | 28.27 | A | C |
| ATOM | 1504 | C   | PHE | A | 321 | 2.933  | 60.969 | 33.916 | 1.00 | 36.33 | A | C |
| ATOM | 1505 | O   | PHE | A | 321 | 2.740  | 59.800 | 34.239 | 1.00 | 34.14 | A | O |
| ATOM | 1506 | N   | LEU | A | 322 | 2.191  | 61.976 | 34.367 | 1.00 | 37.42 | A | N |
| ATOM | 1507 | CA  | LEU | A | 322 | 1.085  | 61.755 | 35.296 | 1.00 | 37.42 | A | C |
| ATOM | 1508 | CB  | LEU | A | 322 | 0.811  | 63.030 | 36.085 | 1.00 | 38.07 | A | C |
| ATOM | 1509 | CG  | LEU | A | 322 | 1.884  | 63.502 | 37.050 | 1.00 | 37.46 | A | C |
| ATOM | 1510 | CD1 | LEU | A | 322 | 1.563  | 64.921 | 37.490 | 1.00 | 41.27 | A | C |
| ATOM | 1511 | CD2 | LEU | A | 322 | 1.939  | 62.557 | 38.246 | 1.00 | 40.08 | A | C |
| ATOM | 1512 | C   | LEU | A | 322 | −0.214 | 61.302 | 34.658 | 1.00 | 37.12 | A | C |
| ATOM | 1513 | O   | LEU | A | 322 | −1.004 | 60.596 | 35.281 | 1.00 | 38.55 | A | O |
| ATOM | 1514 | N   | VAL | A | 323 | −0.435 | 61.692 | 33.410 | 1.00 | 38.25 | A | N |
| ATOM | 1515 | CA  | VAL | A | 323 | −1.686 | 61.356 | 32.743 | 1.00 | 37.24 | A | C |
| ATOM | 1516 | CB  | VAL | A | 323 | −2.283 | 62.634 | 32.058 | 1.00 | 35.89 | A | C |
| ATOM | 1517 | CG1 | VAL | A | 323 | −3.556 | 62.300 | 31.285 | 1.00 | 35.08 | A | C |
| ATOM | 1518 | CG2 | VAL | A | 323 | −2.587 | 63.683 | 33.123 | 1.00 | 33.83 | A | C |
| ATOM | 1519 | C   | VAL | A | 323 | −1.609 | 60.209 | 31.746 | 1.00 | 37.69 | A | C |
| ATOM | 1520 | O   | VAL | A | 323 | −2.620 | 59.538 | 31.493 | 1.00 | 38.39 | A | O |
| ATOM | 1521 | N   | GLY | A | 324 | −0.429 | 59.972 | 31.177 | 1.00 | 36.52 | A | N |
| ATOM | 1522 | CA  | GLY | A | 324 | −0.310 | 58.887 | 30.215 | 1.00 | 38.42 | A | C |
| ATOM | 1523 | C   | GLY | A | 324 | −0.333 | 59.333 | 28.759 | 1.00 | 39.62 | A | C |
| ATOM | 1524 | O   | GLY | A | 324 | −0.077 | 58.536 | 27.855 | 1.00 | 36.81 | A | O |
| ATOM | 1525 | N   | LYS | A | 325 | −0.652 | 60.606 | 28.527 | 1.00 | 40.00 | A | N |
| ATOM | 1526 | CA  | LYS | A | 325 | −0.682 | 61.165 | 27.173 | 1.00 | 37.45 | A | C |
| ATOM | 1527 | CB  | LYS | A | 325 | −2.002 | 60.824 | 26.477 | 1.00 | 39.47 | A | C |
| ATOM | 1528 | CG  | LYS | A | 325 | −3.252 | 61.105 | 27.288 | 1.00 | 42.40 | A | C |
| ATOM | 1529 | CD  | LYS | A | 325 | −4.497 | 60.695 | 26.509 | 1.00 | 45.48 | A | C |
| ATOM | 1530 | CE  | LYS | A | 325 | −5.785 | 61.028 | 27.265 | 1.00 | 49.79 | A | C |
| ATOM | 1531 | NZ  | LYS | A | 325 | −5.968 | 60.179 | 28.489 | 1.00 | 55.16 | A | N |
| ATOM | 1532 | C   | LYS | A | 325 | −0.449 | 62.675 | 27.230 | 1.00 | 33.68 | A | C |
| ATOM | 1533 | O   | LYS | A | 325 | −0.751 | 63.318 | 28.236 | 1.00 | 31.87 | A | O |
| ATOM | 1534 | N   | PRO | A | 326 | 0.121  | 63.256 | 26.158 | 1.00 | 31.60 | A | N |
| ATOM | 1535 | CD  | PRO | A | 326 | 0.475  | 62.618 | 24.876 | 1.00 | 32.20 | A | C |
| ATOM | 1536 | CA  | PRO | A | 326 | 0.390  | 64.697 | 26.133 | 1.00 | 31.72 | A | C |
| ATOM | 1537 | CB  | PRO | A | 326 | 1.174  | 64.879 | 24.832 | 1.00 | 31.00 | A | C |
| ATOM | 1538 | CG  | PRO | A | 326 | 0.629  | 63.796 | 23.948 | 1.00 | 32.88 | A | C |
| ATOM | 1539 | C   | PRO | A | 326 | −0.903 | 65.527 | 26.234 | 1.00 | 29.94 | A | C |
| ATOM | 1540 | O   | PRO | A | 326 | −1.946 | 65.112 | 25.753 | 1.00 | 30.57 | A | O |
| ATOM | 1541 | N   | PRO | A | 327 | −0.836 | 66.715 | 26.857 | 1.00 | 27.73 | A | N |
| ATOM | 1542 | CD  | PRO | A | 327 | 0.377  | 67.360 | 27.400 | 1.00 | 27.90 | A | C |
| ATOM | 1543 | CA  | PRO | A | 327 | −2.024 | 67.570 | 27.025 | 1.00 | 29.32 | A | C |
| ATOM | 1544 | CB  | PRO | A | 327 | −1.517 | 68.695 | 27.933 | 1.00 | 25.30 | A | C |
| ATOM | 1545 | CG  | PRO | A | 327 | −0.039 | 68.828 | 27.530 | 1.00 | 27.21 | A | C |

TABLE 1-continued coordinates of [T287D] Aurora A (122–396) in complex with AMP-PNP

| ATOM | 1546 | C   | PRO | A | 327 | −2.821  | 68.110 | 25.831 | 1.00 | 30.82 | A | C |
|------|------|-----|-----|---|-----|---------|--------|--------|------|-------|---|---|
| ATOM | 1547 | O   | PRO | A | 327 | −3.998  | 68.441 | 25.988 | 1.00 | 33.12 | A | O |
| ATOM | 1548 | N   | PHE | A | 328 | −2.218  | 68.177 | 24.649 | 1.00 | 31.39 | A | N |
| ATOM | 1549 | CA  | PHE | A | 328 | −2.901  | 68.742 | 23.486 | 1.00 | 33.88 | A | C |
| ATOM | 1550 | CB  | PHE | A | 328 | −2.041  | 69.869 | 22.890 | 1.00 | 33.58 | A | C |
| ATOM | 1551 | CG  | PHE | A | 328 | −1.601  | 70.894 | 23.899 | 1.00 | 33.55 | A | C |
| ATOM | 1552 | CD1 | PHE | A | 328 | −2.531  | 71.726 | 24.522 | 1.00 | 33.79 | A | C |
| ATOM | 1553 | CD2 | PHE | A | 328 | −0.257  | 71.002 | 24.256 | 1.00 | 33.06 | A | C |
| ATOM | 1554 | CE1 | PHE | A | 328 | −2.133  | 72.647 | 25.490 | 1.00 | 33.48 | A | C |
| ATOM | 1555 | CE2 | PHE | A | 328 | 0.160   | 71.923 | 25.226 | 1.00 | 34.56 | A | C |
| ATOM | 1556 | CZ  | PHE | A | 328 | −0.781  | 72.748 | 25.846 | 1.00 | 36.22 | A | C |
| ATOM | 1557 | C   | PHE | A | 328 | −3.240  | 67.739 | 22.390 | 1.00 | 36.41 | A | C |
| ATOM | 1558 | O   | PHE | A | 328 | −3.555  | 68.125 | 21.260 | 1.00 | 36.68 | A | O |
| ATOM | 1559 | N   | GLU | A | 329 | −3.189  | 66.457 | 22.728 | 1.00 | 39.55 | A | N |
| ATOM | 1560 | CA  | GLU | A | 329 | −3.457  | 65.388 | 21.771 | 1.00 | 42.10 | A | C |
| ATOM | 1561 | CB  | GLU | A | 329 | −3.331  | 64.037 | 22.474 | 1.00 | 44.65 | A | C |
| ATOM | 1562 | CG  | GLU | A | 329 | −3.295  | 62.852 | 21.537 | 1.00 | 51.26 | A | C |
| ATOM | 1563 | CD  | GLU | A | 329 | −2.954  | 61.571 | 22.264 | 1.00 | 54.01 | A | C |
| ATOM | 1564 | OE1 | GLU | A | 329 | −3.729  | 61.174 | 23.160 | 1.00 | 56.26 | A | O |
| ATOM | 1565 | OE2 | GLU | A | 329 | −1.907  | 60.966 | 21.943 | 1.00 | 57.24 | A | O |
| ATOM | 1566 | C   | GLU | A | 329 | −4.820  | 65.498 | 21.089 | 1.00 | 41.21 | A | C |
| ATOM | 1567 | O   | GLU | A | 329 | −5.827  | 65.795 | 21.731 | 1.00 | 38.95 | A | O |
| ATOM | 1568 | N   | ALA | A | 330 | −4.842  | 65.248 | 19.783 | 1.00 | 41.49 | A | N |
| ATOM | 1569 | CA  | ALA | A | 330 | −6.077  | 65.330 | 19.014 | 1.00 | 44.78 | A | C |
| ATOM | 1570 | CB  | ALA | A | 330 | −6.345  | 66.782 | 18.609 | 1.00 | 45.23 | A | C |
| ATOM | 1571 | C   | ALA | A | 330 | −6.059  | 64.438 | 17.775 | 1.00 | 45.72 | A | C |
| ATOM | 1572 | O   | ALA | A | 330 | −5.013  | 63.941 | 17.363 | 1.00 | 45.07 | A | O |
| ATOM | 1573 | N   | ASN | A | 331 | −7.234  | 64.252 | 17.185 | 1.00 | 47.77 | A | N |
| ATOM | 1574 | CA  | ASN | A | 331 | −7.386  | 63.413 | 16.006 | 1.00 | 50.88 | A | C |
| ATOM | 1575 | CB  | ASN | A | 331 | −8.875  | 63.131 | 15.755 | 1.00 | 54.96 | A | C |
| ATOM | 1576 | CG  | ASN | A | 331 | −9.508  | 62.298 | 16.865 | 1.00 | 60.45 | A | C |
| ATOM | 1577 | OD1 | ASN | A | 331 | −9.016  | 61.216 | 17.202 | 1.00 | 64.11 | A | O |
| ATOM | 1578 | ND2 | ASN | A | 331 | −10.608 | 62.795 | 17.433 | 1.00 | 63.29 | A | N |
| ATOM | 1579 | C   | ASN | A | 331 | −6.749  | 63.980 | 14.741 | 1.00 | 49.91 | A | C |
| ATOM | 1580 | O   | ASN | A | 331 | −6.409  | 63.229 | 13.833 | 1.00 | 51.49 | A | O |
| ATOM | 1581 | N   | THR | A | 332 | −6.586  | 65.296 | 14.675 | 1.00 | 48.66 | A | N |
| ATOM | 1582 | CA  | THR | A | 332 | −5.982  | 65.917 | 13.496 | 1.00 | 46.76 | A | C |
| ATOM | 1583 | CB  | THR | A | 332 | −7.050  | 66.648 | 12.650 | 1.00 | 47.96 | A | C |
| ATOM | 1584 | OG1 | THR | A | 332 | −7.648  | 67.696 | 13.424 | 1.00 | 45.93 | A | O |
| ATOM | 1585 | CG2 | THR | A | 332 | −8.131  | 65.675 | 12.217 | 1.00 | 46.55 | A | C |
| ATOM | 1586 | C   | THR | A | 332 | −4.886  | 66.914 | 13.864 | 1.00 | 44.80 | A | C |
| ATOM | 1587 | O   | THR | A | 332 | −4.875  | 67.444 | 14.973 | 1.00 | 41.95 | A | O |
| ATOM | 1588 | N   | TYR | A | 333 | −3.954  | 67.155 | 12.940 | 1.00 | 43.86 | A | N |
| ATOM | 1589 | CA  | TYR | A | 333 | −2.885  | 68.115 | 13.199 | 1.00 | 43.43 | A | C |
| ATOM | 1590 | CB  | TYR | A | 333 | −1.938  | 68.232 | 11.999 | 1.00 | 47.91 | A | C |
| ATOM | 1591 | CG  | TYR | A | 333 | −1.084  | 67.015 | 11.710 | 1.00 | 50.72 | A | C |
| ATOM | 1592 | CD1 | TYR | A | 333 | −1.606  | 65.916 | 11.033 | 1.00 | 53.76 | A | C |
| ATOM | 1593 | CE1 | TYR | A | 333 | −0.816  | 64.803 | 10.748 | 1.00 | 54.63 | A | C |
| ATOM | 1594 | CD2 | TYR | A | 333 | 0.254   | 66.973 | 12.099 | 1.00 | 50.61 | A | C |
| ATOM | 1595 | CE2 | TYR | A | 333 | 1.053   | 65.868 | 11.821 | 1.00 | 51.32 | A | C |
| ATOM | 1596 | CZ  | TYR | A | 333 | 0.515   | 64.786 | 11.142 | 1.00 | 53.90 | A | C |
| ATOM | 1597 | OH  | TYR | A | 333 | 1.305   | 63.696 | 10.836 | 1.00 | 52.72 | A | O |
| ATOM | 1598 | C   | TYR | A | 333 | −3.561  | 69.470 | 13.416 | 1.00 | 42.37 | A | C |
| ATOM | 1599 | O   | TYR | A | 333 | −3.083  | 70.317 | 14.169 | 1.00 | 39.21 | A | O |
| ATOM | 1600 | N   | GLN | A | 334 | −4.688  | 69.643 | 12.734 | 1.00 | 41.68 | A | N |
| ATOM | 1601 | CA  | GLN | A | 334 | −5.479  | 70.865 | 12.790 | 1.00 | 41.47 | A | C |
| ATOM | 1602 | CB  | GLN | A | 334 | −6.709  | 70.733 | 11.885 | 1.00 | 42.29 | A | C |
| ATOM | 1603 | CG  | GLN | A | 334 | −7.485  | 72.011 | 11.777 | 1.00 | 45.81 | A | C |
| ATOM | 1604 | CD  | GLN | A | 334 | −6.550  | 73.173 | 11.567 | 1.00 | 51.49 | A | C |
| ATOM | 1605 | OE1 | GLN | A | 334 | −5.725  | 73.152 | 10.653 | 1.00 | 52.23 | A | O |
| ATOM | 1606 | NE2 | GLN | A | 334 | −6.655  | 74.192 | 12.420 | 1.00 | 52.56 | A | N |
| ATOM | 1607 | C   | GLN | A | 334 | −5.933  | 71.195 | 14.202 | 1.00 | 37.45 | A | C |
| ATOM | 1608 | O   | GLN | A | 334 | −5.690  | 72.291 | 14.706 | 1.00 | 33.84 | A | O |
| ATOM | 1609 | N   | GLU | A | 335 | −6.599  | 70.231 | 14.821 | 1.00 | 35.59 | A | N |
| ATOM | 1610 | CA  | GLU | A | 335 | −7.113  | 70.385 | 16.164 | 1.00 | 37.26 | A | C |
| ATOM | 1611 | CB  | GLU | A | 335 | −8.091  | 69.243 | 16.458 | 1.00 | 39.04 | A | C |
| ATOM | 1612 | CG  | GLU | A | 335 | −8.854  | 69.370 | 17.767 | 1.00 | 44.38 | A | C |
| ATOM | 1613 | CD  | GLU | A | 335 | −9.901  | 70.478 | 17.746 | 1.00 | 49.56 | A | C |
| ATOM | 1614 | OE1 | GLU | A | 335 | −10.579 | 70.666 | 18.784 | 1.00 | 48.54 | A | O |
| ATOM | 1615 | OE2 | GLU | A | 335 | −10.042 | 71.159 | 16.699 | 1.00 | 49.52 | A | O |
| ATOM | 1616 | C   | GLU | A | 335 | −5.967  | 70.416 | 17.189 | 1.00 | 36.13 | A | C |
| ATOM | 1617 | O   | GLU | A | 335 | −6.083  | 71.062 | 18.232 | 1.00 | 35.59 | A | O |
| ATOM | 1618 | N   | THR | A | 336 | −4.864  | 69.723 | 16.900 | 1.00 | 33.83 | A | N |
| ATOM | 1619 | CA  | THR | A | 336 | −3.721  | 69.727 | 17.819 | 1.00 | 32.60 | A | C |
| ATOM | 1620 | CB  | THR | A | 336 | −2.606  | 68.755 | 17.357 | 1.00 | 31.68 | A | C |
| ATOM | 1621 | OG1 | THR | A | 336 | −3.126  | 67.422 | 17.292 | 1.00 | 34.29 | A | O |
| ATOM | 1622 | CG2 | THR | A | 336 | −1.443  | 68.771 | 18.331 | 1.00 | 29.91 | A | C |

TABLE 1-continued coordinates of [T287D] Aurora A (122–396) in complex with AMP-PNP

| ATOM | 1623 | C   | THR | A | 336 | −3.143  | 71.145 | 17.889 | 1.00 | 31.31 | A | C |
|------|------|-----|-----|---|-----|---------|--------|--------|------|-------|---|---|
| ATOM | 1624 | O   | THR | A | 336 | −2.914  | 71.686 | 18.971 | 1.00 | 28.38 | A | O |
| ATOM | 1625 | N   | TYR | A | 337 | −2.911  | 71.732 | 16.717 | 1.00 | 31.54 | A | N |
| ATOM | 1626 | CA  | TYR | A | 337 | −2.381  | 73.094 | 16.597 | 1.00 | 33.23 | A | C |
| ATOM | 1627 | CB  | TYR | A | 337 | −2.339  | 73.489 | 15.120 | 1.00 | 38.97 | A | C |
| ATOM | 1628 | CG  | TYR | A | 337 | −1.770  | 74.861 | 14.855 | 1.00 | 43.55 | A | C |
| ATOM | 1629 | CD1 | TYR | A | 337 | −0.414  | 75.030 | 14.589 | 1.00 | 50.62 | A | C |
| ATOM | 1630 | CE1 | TYR | A | 337 | 0.123   | 76.290 | 14.343 | 1.00 | 53.16 | A | C |
| ATOM | 1631 | CD2 | TYR | A | 337 | −2.584  | 75.991 | 14.872 | 1.00 | 43.59 | A | C |
| ATOM | 1632 | CE2 | TYR | A | 337 | −2.062  | 77.254 | 14.632 | 1.00 | 47.84 | A | C |
| ATOM | 1633 | CZ  | TYR | A | 337 | −0.704  | 77.397 | 14.364 | 1.00 | 53.57 | A | C |
| ATOM | 1634 | OH  | TYR | A | 337 | −0.170  | 78.637 | 14.096 | 1.00 | 56.75 | A | O |
| ATOM | 1635 | C   | TYR | A | 337 | −3.290  | 74.070 | 17.359 | 1.00 | 32.20 | A | C |
| ATOM | 1636 | O   | TYR | A | 337 | −2.823  | 74.890 | 18.159 | 1.00 | 30.91 | A | O |
| ATOM | 1637 | N   | LYS | A | 338 | −4.592  | 73.966 | 17.103 | 1.00 | 30.03 | A | N |
| ATOM | 1638 | CA  | LYS | A | 338 | −5.580  | 74.809 | 17.771 | 1.00 | 30.11 | A | C |
| ATOM | 1639 | CB  | LYS | A | 338 | −7.008  | 74.344 | 17.421 | 1.00 | 31.44 | A | C |
| ATOM | 1640 | CG  | LYS | A | 338 | −8.107  | 75.329 | 17.852 | 1.00 | 34.97 | A | C |
| ATOM | 1641 | CD  | LYS | A | 338 | −9.521  | 74.720 | 17.889 | 1.00 | 38.62 | A | C |
| ATOM | 1642 | CE  | LYS | A | 338 | −10.082 | 74.415 | 16.504 | 1.00 | 43.83 | A | C |
| ATOM | 1643 | NZ  | LYS | A | 338 | −11.532 | 74.025 | 16.552 | 1.00 | 43.82 | A | N |
| ATOM | 1644 | C   | LYS | A | 338 | −5.387  | 74.764 | 19.289 | 1.00 | 30.09 | A | C |
| ATOM | 1645 | O   | LYS | A | 338 | −5.257  | 75.804 | 19.942 | 1.00 | 29.38 | A | O |
| ATOM | 1646 | N   | ARG | A | 339 | −5.356  | 73.554 | 19.846 | 1.00 | 29.91 | A | N |
| ATOM | 1647 | CA  | ARG | A | 339 | −5.200  | 73.370 | 21.288 | 1.00 | 29.88 | A | C |
| ATOM | 1648 | CB  | ARG | A | 339 | −5.376  | 71.880 | 21.642 | 1.00 | 32.35 | A | C |
| ATOM | 1649 | CG  | ARG | A | 339 | −6.790  | 71.364 | 21.347 | 1.00 | 37.87 | A | C |
| ATOM | 1650 | CD  | ARG | A | 339 | −6.962  | 69.849 | 21.524 | 1.00 | 43.23 | A | C |
| ATOM | 1651 | NE  | ARG | A | 339 | −8.337  | 69.455 | 21.193 | 1.00 | 48.20 | A | N |
| ATOM | 1652 | CZ  | ARG | A | 339 | −8.845  | 68.223 | 21.287 | 1.00 | 50.25 | A | C |
| ATOM | 1653 | NH1 | ARG | A | 339 | −8.107  | 67.202 | 21.712 | 1.00 | 48.72 | A | N |
| ATOM | 1654 | NH2 | ARG | A | 339 | −10.111 | 68.010 | 20.940 | 1.00 | 51.23 | A | N |
| ATOM | 1655 | C   | ARG | A | 339 | −3.883  | 73.906 | 21.850 | 1.00 | 28.91 | A | C |
| ATOM | 1656 | O   | ARG | A | 339 | −3.853  | 74.491 | 22.930 | 1.00 | 31.71 | A | O |
| ATOM | 1657 | N   | ILE | A | 340 | −2.792  | 73.700 | 21.125 | 1.00 | 28.62 | A | N |
| ATOM | 1658 | CA  | ILE | A | 340 | −1.487  | 74.180 | 21.565 | 1.00 | 30.14 | A | C |
| ATOM | 1659 | CB  | ILE | A | 340 | −0.366  | 73.660 | 20.631 | 1.00 | 28.04 | A | C |
| ATOM | 1660 | CG2 | ILE | A | 340 | 0.932   | 74.397 | 20.925 | 1.00 | 25.58 | A | C |
| ATOM | 1661 | CG1 | ILE | A | 340 | −0.190  | 72.142 | 20.807 | 1.00 | 26.16 | A | C |
| ATOM | 1662 | CD1 | ILE | A | 340 | 0.830   | 71.531 | 19.845 | 1.00 | 27.76 | A | C |
| ATOM | 1663 | C   | ILE | A | 340 | −1.462  | 75.712 | 21.526 | 1.00 | 32.65 | A | C |
| ATOM | 1664 | O   | ILE | A | 340 | −1.024  | 76.377 | 22.470 | 1.00 | 33.37 | A | O |
| ATOM | 1665 | N   | SER | A | 341 | −1.935  | 76.243 | 20.404 | 1.00 | 33.83 | A | N |
| ATOM | 1666 | CA  | SER | A | 341 | −2.000  | 77.676 | 20.138 | 1.00 | 35.56 | A | C |
| ATOM | 1667 | CB  | SER | A | 341 | −2.644  | 77.892 | 18.772 | 1.00 | 35.09 | A | C |
| ATOM | 1668 | OG  | SER | A | 341 | −1.991  | 78.931 | 18.084 | 1.00 | 39.44 | A | O |
| ATOM | 1669 | C   | SER | A | 341 | −2.794  | 78.436 | 21.185 | 1.00 | 35.59 | A | C |
| ATOM | 1670 | O   | SER | A | 341 | −2.367  | 79.478 | 21.673 | 1.00 | 37.28 | A | O |
| ATOM | 1671 | N   | ARG | A | 342 | −3.952  | 77.893 | 21.530 | 1.00 | 34.73 | A | N |
| ATOM | 1672 | CA  | ARG | A | 342 | −4.851  | 78.508 | 22.493 | 1.00 | 34.53 | A | C |
| ATOM | 1673 | CB  | ARG | A | 342 | −6.296  | 78.295 | 22.016 | 1.00 | 35.36 | A | C |
| ATOM | 1674 | CG  | ARG | A | 342 | −6.539  | 78.913 | 20.641 | 1.00 | 33.27 | A | C |
| ATOM | 1675 | CD  | ARG | A | 342 | −7.836  | 78.460 | 19.969 | 1.00 | 38.01 | A | C |
| ATOM | 1676 | NE  | ARG | A | 342 | −8.038  | 79.214 | 18.730 | 1.00 | 41.54 | A | N |
| ATOM | 1677 | CZ  | ARG | A | 342 | −9.135  | 79.184 | 17.974 | 1.00 | 41.67 | A | C |
| ATOM | 1678 | NH1 | ARG | A | 342 | −9.187  | 79.922 | 16.870 | 1.00 | 44.15 | A | N |
| ATOM | 1679 | NH2 | ARG | A | 342 | −10.176 | 78.435 | 18.315 | 1.00 | 37.28 | A | N |
| ATOM | 1680 | C   | ARG | A | 342 | −4.652  | 77.962 | 23.900 | 1.00 | 36.18 | A | C |
| ATOM | 1681 | O   | ARG | A | 342 | −5.446  | 78.252 | 24.802 | 1.00 | 34.08 | A | O |
| ATOM | 1682 | N   | VAL | A | 343 | −3.582  | 77.178 | 24.072 | 1.00 | 35.22 | A | N |
| ATOM | 1683 | CA  | VAL | A | 343 | −3.221  | 76.575 | 25.355 | 1.00 | 34.16 | A | C |
| ATOM | 1684 | CB  | VAL | A | 343 | −2.613  | 77.622 | 26.315 | 1.00 | 34.38 | A | C |
| ATOM | 1685 | CG1 | VAL | A | 343 | −2.081  | 76.935 | 27.561 | 1.00 | 36.51 | A | C |
| ATOM | 1686 | CG2 | VAL | A | 343 | −1.500  | 78.391 | 25.632 | 1.00 | 31.25 | A | C |
| ATOM | 1687 | C   | VAL | A | 343 | −4.441  | 75.952 | 26.018 | 1.00 | 34.20 | A | C |
| ATOM | 1688 | O   | VAL | A | 343 | −4.782  | 76.284 | 27.153 | 1.00 | 31.68 | A | O |
| ATOM | 1689 | N   | GLU | A | 344 | −5.097  | 75.050 | 25.294 | 1.00 | 33.81 | A | N |
| ATOM | 1690 | CA  | GLU | A | 344 | −6.292  | 74.369 | 25.783 | 1.00 | 34.08 | A | C |
| ATOM | 1691 | CB  | GLU | A | 344 | −7.340  | 74.265 | 24.658 | 1.00 | 34.89 | A | C |
| ATOM | 1692 | CG  | GLU | A | 344 | −8.047  | 75.572 | 24.334 | 1.00 | 38.33 | A | C |
| ATOM | 1693 | CD  | GLU | A | 344 | −8.665  | 75.594 | 22.944 | 1.00 | 40.26 | A | C |
| ATOM | 1694 | OE1 | GLU | A | 344 | −9.402  | 76.553 | 22.636 | 1.00 | 39.02 | A | O |
| ATOM | 1695 | OE2 | GLU | A | 344 | −8.406  | 74.665 | 22.154 | 1.00 | 41.41 | A | O |
| ATOM | 1696 | C   | GLU | A | 344 | −6.022  | 72.972 | 26.337 | 1.00 | 33.90 | A | C |
| ATOM | 1697 | O   | GLU | A | 344 | −5.887  | 72.020 | 25.575 | 1.00 | 35.23 | A | O |
| ATOM | 1698 | N   | PHE | A | 345 | −5.958  | 72.851 | 27.661 | 1.00 | 35.80 | A | N |
| ATOM | 1699 | CA  | PHE | A | 345 | −5.736  | 71.558 | 28.314 | 1.00 | 37.65 | A | C |

TABLE 1-continued coordinates of [T287D] Aurora A (122–396) in complex with AMP-PNP

| ATOM | 1700 | CB | PHE | A | 345 | −4.247 | 71.370 | 28.643 | 1.00 | 35.66 | A | C |
|---|---|---|---|---|---|---|---|---|---|---|---|---|
| ATOM | 1701 | CG | PHE | A | 345 | −3.731 | 72.296 | 29.714 | 1.00 | 38.52 | A | C |
| ATOM | 1702 | CD1 | PHE | A | 345 | −3.768 | 71.924 | 31.052 | 1.00 | 40.34 | A | C |
| ATOM | 1703 | CD2 | PHE | A | 345 | −3.212 | 73.545 | 29.382 | 1.00 | 38.83 | A | C |
| ATOM | 1704 | CE1 | PHE | A | 345 | −3.294 | 72.786 | 32.049 | 1.00 | 41.72 | A | C |
| ATOM | 1705 | CE2 | PHE | A | 345 | −2.737 | 74.414 | 30.361 | 1.00 | 39.94 | A | C |
| ATOM | 1706 | CZ | PHE | A | 345 | −2.778 | 74.034 | 31.701 | 1.00 | 43.18 | A | C |
| ATOM | 1707 | C | PHE | A | 345 | −6.559 | 71.455 | 29.595 | 1.00 | 39.42 | A | C |
| ATOM | 1708 | O | PHE | A | 345 | −6.876 | 72.478 | 30.211 | 1.00 | 40.64 | A | O |
| ATOM | 1709 | N | THR | A | 346 | −6.905 | 70.225 | 29.985 | 1.00 | 38.79 | A | N |
| ATOM | 1710 | CA | THR | A | 346 | −7.669 | 69.967 | 31.209 | 1.00 | 38.83 | A | C |
| ATOM | 1711 | CB | THR | A | 346 | −9.177 | 69.732 | 30.906 | 1.00 | 38.24 | A | C |
| ATOM | 1712 | OG1 | THR | A | 346 | −9.324 | 68.712 | 29.912 | 1.00 | 35.72 | A | O |
| ATOM | 1713 | CG2 | THR | A | 346 | −9.831 | 71.024 | 30.411 | 1.00 | 38.59 | A | C |
| ATOM | 1714 | C | THR | A | 346 | −7.103 | 68.743 | 31.957 | 1.00 | 40.45 | A | C |
| ATOM | 1715 | O | THR | A | 346 | −6.477 | 67.872 | 31.350 | 1.00 | 40.52 | A | O |
| ATOM | 1716 | N | PHE | A | 347 | −7.337 | 68.684 | 33.267 | 1.00 | 38.41 | A | N |
| ATOM | 1717 | CA | PHE | A | 347 | −6.832 | 67.602 | 34.117 | 1.00 | 38.01 | A | C |
| ATOM | 1718 | CB | PHE | A | 347 | −6.299 | 68.175 | 35.430 | 1.00 | 33.25 | A | C |
| ATOM | 1719 | CG | PHE | A | 347 | −5.179 | 69.157 | 35.272 | 1.00 | 37.35 | A | C |
| ATOM | 1720 | CD1 | PHE | A | 347 | −3.910 | 68.736 | 34.870 | 1.00 | 36.75 | A | C |
| ATOM | 1721 | CD2 | PHE | A | 347 | −5.377 | 70.507 | 35.570 | 1.00 | 35.58 | A | C |
| ATOM | 1722 | CE1 | PHE | A | 347 | −2.854 | 69.647 | 34.773 | 1.00 | 37.99 | A | C |
| ATOM | 1723 | CE2 | PHE | A | 347 | −4.334 | 71.420 | 35.477 | 1.00 | 36.58 | A | C |
| ATOM | 1724 | CZ | PHE | A | 347 | −3.064 | 70.993 | 35.077 | 1.00 | 36.04 | A | C |
| ATOM | 1725 | C | PHE | A | 347 | −7.829 | 66.501 | 34.502 | 1.00 | 40.55 | A | C |
| ATOM | 1726 | O | PHE | A | 347 | −8.996 | 66.775 | 34.800 | 1.00 | 40.32 | A | O |
| ATOM | 1727 | N | PRO | A | 348 | −7.381 | 65.230 | 34.493 | 1.00 | 42.22 | A | N |
| ATOM | 1728 | CD | PRO | A | 348 | −6.184 | 64.654 | 33.855 | 1.00 | 40.80 | A | C |
| ATOM | 1729 | CA | PRO | A | 348 | −8.326 | 64.177 | 34.887 | 1.00 | 43.29 | A | C |
| ATOM | 1730 | CB | PRO | A | 348 | −7.552 | 62.888 | 34.612 | 1.00 | 41.59 | A | C |
| ATOM | 1731 | CG | PRO | A | 348 | −6.671 | 63.267 | 33.455 | 1.00 | 41.69 | A | C |
| ATOM | 1732 | C | PRO | A | 348 | −8.540 | 64.420 | 36.380 | 1.00 | 43.20 | A | C |
| ATOM | 1733 | O | PRO | A | 348 | −7.758 | 65.136 | 37.003 | 1.00 | 42.10 | A | O |
| ATOM | 1734 | N | ASP | A | 349 | −9.574 | 63.832 | 36.963 | 1.00 | 46.66 | A | N |
| ATOM | 1735 | CA | ASP | A | 349 | −9.842 | 64.058 | 38.380 | 1.00 | 49.33 | A | C |
| ATOM | 1736 | CB | ASP | A | 349 | −11.171 | 63.396 | 38.774 | 1.00 | 52.46 | A | C |
| ATOM | 1737 | CG | ASP | A | 349 | −12.363 | 64.001 | 38.043 | 1.00 | 56.47 | A | C |
| ATOM | 1738 | OD1 | ASP | A | 349 | −12.403 | 65.242 | 37.898 | 1.00 | 56.97 | A | O |
| ATOM | 1739 | OD2 | ASP | A | 349 | −13.265 | 63.240 | 37.623 | 1.00 | 59.92 | A | O |
| ATOM | 1740 | C | ASP | A | 349 | −8.747 | 63.646 | 39.375 | 1.00 | 49.27 | A | C |
| ATOM | 1741 | O | ASP | A | 349 | −8.651 | 64.225 | 40.454 | 1.00 | 48.92 | A | O |
| ATOM | 1742 | N | PHE | A | 350 | −7.908 | 62.675 | 39.020 | 1.00 | 49.30 | A | N |
| ATOM | 1743 | CA | PHE | A | 350 | −6.863 | 62.219 | 39.946 | 1.00 | 47.22 | A | C |
| ATOM | 1744 | CB | PHE | A | 350 | −6.440 | 60.781 | 39.598 | 1.00 | 46.74 | A | C |
| ATOM | 1745 | CG | PHE | A | 350 | −5.715 | 60.649 | 38.287 | 1.00 | 43.91 | A | C |
| ATOM | 1746 | CD1 | PHE | A | 350 | −4.417 | 61.141 | 38.135 | 1.00 | 44.25 | A | C |
| ATOM | 1747 | CD2 | PHE | A | 350 | −6.330 | 60.039 | 37.202 | 1.00 | 40.16 | A | C |
| ATOM | 1748 | CE1 | PHE | A | 350 | −3.748 | 61.025 | 36.915 | 1.00 | 42.32 | A | C |
| ATOM | 1749 | CE2 | PHE | A | 350 | −5.674 | 59.919 | 35.984 | 1.00 | 39.67 | A | C |
| ATOM | 1750 | CZ | PHE | A | 350 | −4.382 | 60.413 | 35.839 | 1.00 | 40.57 | A | C |
| ATOM | 1751 | C | PHE | A | 350 | −5.614 | 63.085 | 40.109 | 1.00 | 47.01 | A | C |
| ATOM | 1752 | O | PHE | A | 350 | −4.843 | 62.876 | 41.041 | 1.00 | 46.65 | A | O |
| ATOM | 1753 | N | VAL | A | 351 | −5.395 | 64.051 | 39.222 | 1.00 | 46.50 | A | N |
| ATOM | 1754 | CA | VAL | A | 351 | −4.211 | 64.893 | 39.355 | 1.00 | 45.42 | A | C |
| ATOM | 1755 | CB | VAL | A | 351 | −3.936 | 65.695 | 38.057 | 1.00 | 44.39 | A | C |
| ATOM | 1756 | CG1 | VAL | A | 351 | −2.726 | 66.586 | 38.236 | 1.00 | 40.46 | A | C |
| ATOM | 1757 | CG2 | VAL | A | 351 | −3.705 | 64.745 | 36.909 | 1.00 | 42.44 | A | C |
| ATOM | 1758 | C | VAL | A | 351 | −4.356 | 65.847 | 40.542 | 1.00 | 48.95 | A | C |
| ATOM | 1759 | O | VAL | A | 351 | −5.391 | 66.498 | 40.709 | 1.00 | 49.11 | A | O |
| ATOM | 1760 | N | THR | A | 352 | −3.304 | 65.913 | 41.355 | 1.00 | 48.97 | A | N |
| ATOM | 1761 | CA | THR | A | 352 | −3.246 | 66.739 | 42.557 | 1.00 | 50.49 | A | C |
| ATOM | 1762 | CB | THR | A | 352 | −2.058 | 66.288 | 43.442 | 1.00 | 51.76 | A | C |
| ATOM | 1763 | OG1 | THR | A | 352 | −2.329 | 64.978 | 43.962 | 1.00 | 54.65 | A | O |
| ATOM | 1764 | CG2 | THR | A | 352 | −1.839 | 67.249 | 44.600 | 1.00 | 55.96 | A | C |
| ATOM | 1765 | C | THR | A | 352 | −3.127 | 68.239 | 42.291 | 1.00 | 51.36 | A | C |
| ATOM | 1766 | O | THR | A | 352 | −2.633 | 68.655 | 41.240 | 1.00 | 51.12 | A | O |
| ATOM | 1767 | N | GLU | A | 353 | −3.574 | 69.044 | 43.256 | 1.00 | 49.74 | A | N |
| ATOM | 1768 | CA | GLU | A | 353 | −3.519 | 70.499 | 43.132 | 1.00 | 51.27 | A | C |
| ATOM | 1769 | CB | GLU | A | 353 | −4.131 | 71.177 | 44.363 | 1.00 | 53.88 | A | C |
| ATOM | 1770 | CG | GLU | A | 353 | −5.636 | 70.993 | 44.533 | 1.00 | 60.04 | A | C |
| ATOM | 1771 | CD | GLU | A | 353 | −6.446 | 71.598 | 43.397 | 1.00 | 64.09 | A | C |
| ATOM | 1772 | OE1 | GLU | A | 353 | −6.082 | 72.700 | 42.921 | 1.00 | 64.63 | A | O |
| ATOM | 1773 | OE2 | GLU | A | 353 | −7.457 | 70.975 | 42.991 | 1.00 | 65.02 | A | O |
| ATOM | 1774 | C | GLU | A | 353 | −2.088 | 70.989 | 42.969 | 1.00 | 49.88 | A | C |
| ATOM | 1775 | O | GLU | A | 353 | −1.838 | 71.970 | 42.268 | 1.00 | 50.18 | A | O |
| ATOM | 1776 | N | GLY | A | 354 | −1.154 | 70.319 | 43.635 | 1.00 | 47.30 | A | N |

TABLE 1-continued coordinates of [T287D] Aurora A (122–396) in complex with AMP-PNP

| ATOM | 1777 | CA | GLY | A | 354 | 0.238 | 70.709 | 43.529 | 1.00 | 47.27 | A | C |
|---|---|---|---|---|---|---|---|---|---|---|---|---|
| ATOM | 1778 | C | GLY | A | 354 | 0.764 | 70.481 | 42.123 | 1.00 | 46.09 | A | C |
| ATOM | 1779 | O | GLY | A | 354 | 1.525 | 71.292 | 41.594 | 1.00 | 46.49 | A | O |
| ATOM | 1780 | N | ALA | A | 355 | 0.360 | 69.367 | 41.523 | 1.00 | 45.69 | A | N |
| ATOM | 1781 | CA | ALA | A | 355 | 0.764 | 69.018 | 40.164 | 1.00 | 45.85 | A | C |
| ATOM | 1782 | CB | ALA | A | 355 | 0.304 | 67.604 | 39.841 | 1.00 | 43.96 | A | C |
| ATOM | 1783 | C | ALA | A | 355 | 0.115 | 70.011 | 39.194 | 1.00 | 45.34 | A | C |
| ATOM | 1784 | O | ALA | A | 355 | 0.774 | 70.582 | 38.318 | 1.00 | 43.69 | A | O |
| ATOM | 1785 | N | ARG | A | 356 | −1.188 | 70.210 | 39.374 | 1.00 | 44.80 | A | N |
| ATOM | 1786 | CA | ARG | A | 356 | −1.964 | 71.121 | 38.547 | 1.00 | 43.64 | A | C |
| ATOM | 1787 | CB | ARG | A | 356 | −3.429 | 71.110 | 39.008 | 1.00 | 43.97 | A | C |
| ATOM | 1788 | CG | ARG | A | 356 | −4.084 | 69.742 | 38.844 | 1.00 | 44.00 | A | C |
| ATOM | 1789 | CD | ARG | A | 356 | −5.299 | 69.539 | 39.760 | 1.00 | 46.78 | A | C |
| ATOM | 1790 | NE | ARG | A | 356 | −6.562 | 69.930 | 39.146 | 1.00 | 46.50 | A | N |
| ATOM | 1791 | CZ | ARG | A | 356 | −7.545 | 69.088 | 38.835 | 1.00 | 48.09 | A | C |
| ATOM | 1792 | NH1 | ARG | A | 356 | −7.423 | 67.793 | 39.078 | 1.00 | 45.87 | A | N |
| ATOM | 1793 | NH2 | ARG | A | 356 | −8.660 | 69.545 | 38.276 | 1.00 | 47.73 | A | N |
| ATOM | 1794 | C | ARG | A | 356 | −1.387 | 72.534 | 38.584 | 1.00 | 42.30 | A | C |
| ATOM | 1795 | O | ARG | A | 356 | −1.404 | 73.242 | 37.579 | 1.00 | 42.77 | A | O |
| ATOM | 1796 | N | ASP | A | 357 | −0.850 | 72.938 | 39.728 | 1.00 | 39.68 | A | N |
| ATOM | 1797 | CA | ASP | A | 357 | −0.273 | 74.267 | 39.836 | 1.00 | 41.20 | A | C |
| ATOM | 1798 | CB | ASP | A | 357 | −0.047 | 74.645 | 41.305 | 1.00 | 45.03 | A | C |
| ATOM | 1799 | CG | ASP | A | 357 | 0.628 | 76.002 | 41.454 | 1.00 | 45.48 | A | C |
| ATOM | 1800 | OD1 | ASP | A | 357 | −0.080 | 77.030 | 41.454 | 1.00 | 49.20 | A | O |
| ATOM | 1801 | OD2 | ASP | A | 357 | 1.872 | 76.046 | 41.544 | 1.00 | 46.68 | A | O |
| ATOM | 1802 | C | ASP | A | 357 | 1.054 | 74.381 | 39.081 | 1.00 | 41.64 | A | C |
| ATOM | 1803 | O | ASP | A | 357 | 1.326 | 75.406 | 38.448 | 1.00 | 41.73 | A | O |
| ATOM | 1804 | N | LEU | A | 358 | 1.888 | 73.343 | 39.153 | 1.00 | 41.39 | A | N |
| ATOM | 1805 | CA | LEU | A | 358 | 3.179 | 73.381 | 38.461 | 1.00 | 40.21 | A | C |
| ATOM | 1806 | CB | LEU | A | 358 | 4.060 | 72.189 | 38.858 | 1.00 | 40.82 | A | C |
| ATOM | 1807 | CG | LEU | A | 358 | 5.351 | 71.990 | 38.038 | 1.00 | 39.19 | A | C |
| ATOM | 1808 | CD1 | LEU | A | 358 | 6.262 | 73.211 | 38.156 | 1.00 | 35.41 | A | C |
| ATOM | 1809 | CD2 | LEU | A | 358 | 6.082 | 70.757 | 38.534 | 1.00 | 35.10 | A | C |
| ATOM | 1810 | C | LEU | A | 358 | 2.989 | 73.376 | 36.949 | 1.00 | 38.71 | A | C |
| ATOM | 1811 | O | LEU | A | 358 | 3.548 | 74.210 | 36.240 | 1.00 | 36.97 | A | O |
| ATOM | 1812 | N | ILE | A | 359 | 2.205 | 72.425 | 36.463 | 1.00 | 37.63 | A | N |
| ATOM | 1813 | CA | ILE | A | 359 | 1.958 | 72.318 | 35.036 | 1.00 | 37.27 | A | C |
| ATOM | 1814 | CB | ILE | A | 359 | 1.024 | 71.129 | 34.739 | 1.00 | 35.58 | A | C |
| ATOM | 1815 | CG2 | ILE | A | 359 | 0.616 | 71.125 | 33.257 | 1.00 | 33.52 | A | C |
| ATOM | 1816 | CG1 | ILE | A | 359 | 1.740 | 69.822 | 35.123 | 1.00 | 33.71 | A | C |
| ATOM | 1817 | CD1 | ILE | A | 359 | 0.904 | 68.556 | 34.965 | 1.00 | 27.32 | A | C |
| ATOM | 1818 | C | ILE | A | 359 | 1.367 | 73.619 | 34.490 | 1.00 | 39.28 | A | C |
| ATOM | 1819 | O | ILE | A | 359 | 1.756 | 74.080 | 33.419 | 1.00 | 40.17 | A | O |
| ATOM | 1820 | N | SER | A | 360 | 0.448 | 74.219 | 35.243 | 1.00 | 39.65 | A | N |
| ATOM | 1821 | CA | SER | A | 360 | −0.178 | 75.468 | 34.828 | 1.00 | 39.78 | A | C |
| ATOM | 1822 | CB | SER | A | 360 | −1.326 | 75.824 | 35.774 | 1.00 | 38.05 | A | C |
| ATOM | 1823 | OG | SER | A | 360 | −2.421 | 74.949 | 35.570 | 1.00 | 41.59 | A | O |
| ATOM | 1824 | C | SER | A | 360 | 0.803 | 76.634 | 34.732 | 1.00 | 38.08 | A | C |
| ATOM | 1825 | O | SER | A | 360 | 0.648 | 77.505 | 33.881 | 1.00 | 37.97 | A | O |
| ATOM | 1826 | N | ARG | A | 361 | 1.809 | 76.655 | 35.600 | 1.00 | 37.99 | A | N |
| ATOM | 1827 | CA | ARG | A | 361 | 2.809 | 77.722 | 35.568 | 1.00 | 38.96 | A | C |
| ATOM | 1828 | CB | ARG | A | 361 | 3.667 | 77.702 | 36.834 | 1.00 | 42.54 | A | C |
| ATOM | 1829 | CG | ARG | A | 361 | 2.988 | 78.154 | 38.121 | 1.00 | 50.26 | A | C |
| ATOM | 1830 | CD | ARG | A | 361 | 3.971 | 78.022 | 39.287 | 1.00 | 54.77 | A | C |
| ATOM | 1831 | NE | ARG | A | 361 | 3.358 | 78.286 | 40.586 | 1.00 | 60.68 | A | N |
| ATOM | 1832 | CZ | ARG | A | 361 | 2.987 | 79.490 | 41.010 | 1.00 | 63.56 | A | C |
| ATOM | 1833 | NH1 | ARG | A | 361 | 2.435 | 79.631 | 42.211 | 1.00 | 65.68 | A | N |
| ATOM | 1834 | NH2 | ARG | A | 361 | 3.171 | 80.554 | 40.238 | 1.00 | 63.46 | A | N |
| ATOM | 1835 | C | ARG | A | 361 | 3.745 | 77.560 | 34.371 | 1.00 | 36.65 | A | C |
| ATOM | 1836 | O | ARG | A | 361 | 4.273 | 78.537 | 33.838 | 1.00 | 34.66 | A | O |
| ATOM | 1837 | N | LEU | A | 362 | 3.956 | 76.314 | 33.966 | 1.00 | 34.75 | A | N |
| ATOM | 1838 | CA | LEU | A | 362 | 4.865 | 76.004 | 32.871 | 1.00 | 33.58 | A | C |
| ATOM | 1839 | CB | LEU | A | 362 | 5.370 | 74.563 | 33.019 | 1.00 | 33.55 | A | C |
| ATOM | 1840 | CG | LEU | A | 362 | 6.321 | 74.331 | 34.198 | 1.00 | 33.17 | A | C |
| ATOM | 1841 | CD1 | LEU | A | 362 | 6.561 | 72.852 | 34.402 | 1.00 | 32.66 | A | C |
| ATOM | 1842 | CD2 | LEU | A | 362 | 7.624 | 75.058 | 33.936 | 1.00 | 28.23 | A | C |
| ATOM | 1843 | C | LEU | A | 362 | 4.275 | 76.199 | 31.479 | 1.00 | 32.52 | A | C |
| ATOM | 1844 | O | LEU | A | 362 | 4.965 | 76.657 | 30.580 | 1.00 | 33.69 | A | O |
| ATOM | 1845 | N | LEU | A | 363 | 3.010 | 75.848 | 31.302 | 1.00 | 29.78 | A | N |
| ATOM | 1846 | CA | LEU | A | 363 | 2.369 | 75.985 | 29.997 | 1.00 | 33.86 | A | C |
| ATOM | 1847 | CB | LEU | A | 363 | 1.323 | 74.870 | 29.814 | 1.00 | 29.15 | A | C |
| ATOM | 1848 | CG | LEU | A | 363 | 1.817 | 73.401 | 29.868 | 1.00 | 31.05 | A | C |
| ATOM | 1849 | CD1 | LEU | A | 363 | 0.631 | 72.468 | 29.746 | 1.00 | 24.51 | A | C |
| ATOM | 1850 | CD2 | LEU | A | 363 | 2.837 | 73.123 | 28.748 | 1.00 | 24.89 | A | C |
| ATOM | 1851 | C | LEU | A | 363 | 1.726 | 77.371 | 29.798 | 1.00 | 34.25 | A | C |
| ATOM | 1852 | O | LEU | A | 363 | 0.508 | 77.505 | 29.740 | 1.00 | 36.86 | A | O |
| ATOM | 1853 | N | LYS | A | 364 | 2.565 | 78.396 | 29.710 | 1.00 | 38.02 | A | N |

TABLE 1-continued coordinates of [T287D] Aurora A (122–396) in complex with AMP-PNP

| ATOM | 1854 | CA  | LYS | A | 364 | 2.117  | 79.773 | 29.510 | 1.00 | 39.26 | A | C |
|------|------|-----|-----|---|-----|--------|--------|--------|------|-------|---|---|
| ATOM | 1855 | CB  | LYS | A | 364 | 2.907  | 80.735 | 30.407 | 1.00 | 40.63 | A | C |
| ATOM | 1856 | CG  | LYS | A | 364 | 2.650  | 80.605 | 31.901 | 1.00 | 42.73 | A | C |
| ATOM | 1857 | CD  | LYS | A | 364 | 1.227  | 81.004 | 32.237 | 1.00 | 45.77 | A | C |
| ATOM | 1858 | CE  | LYS | A | 364 | 1.046  | 81.228 | 33.725 | 1.00 | 50.52 | A | C |
| ATOM | 1859 | NZ  | LYS | A | 364 | -0.323 | 81.742 | 34.024 | 1.00 | 54.71 | A | N |
| ATOM | 1860 | C   | LYS | A | 364 | 2.372  | 80.145 | 28.057 | 1.00 | 39.30 | A | C |
| ATOM | 1861 | O   | LYS | A | 364 | 3.496  | 79.997 | 27.569 | 1.00 | 38.57 | A | O |
| ATOM | 1862 | N   | HIS | A | 365 | 1.335  | 80.616 | 27.368 | 1.00 | 39.57 | A | N |
| ATOM | 1863 | CA  | HIS | A | 365 | 1.476  | 81.020 | 25.970 | 1.00 | 40.20 | A | C |
| ATOM | 1864 | CB  | HIS | A | 365 | 0.187  | 81.659 | 25.451 | 1.00 | 40.44 | A | C |
| ATOM | 1865 | CG  | HIS | A | 365 | 0.276  | 82.111 | 24.027 | 1.00 | 37.64 | A | C |
| ATOM | 1866 | CD2 | HIS | A | 365 | 0.827  | 83.219 | 23.477 | 1.00 | 40.32 | A | C |
| ATOM | 1867 | ND1 | HIS | A | 365 | -0.179 | 81.349 | 22.974 | 1.00 | 38.59 | A | N |
| ATOM | 1868 | CE1 | HIS | A | 365 | 0.088  | 81.963 | 21.836 | 1.00 | 36.60 | A | C |
| ATOM | 1869 | NE2 | HIS | A | 365 | 0.699  | 83.101 | 22.113 | 1.00 | 41.15 | A | N |
| ATOM | 1870 | C   | HIS | A | 365 | 2.606  | 82.031 | 25.839 | 1.00 | 40.73 | A | C |
| ATOM | 1871 | O   | HIS | A | 365 | 3.430  | 81.948 | 24.925 | 1.00 | 41.73 | A | O |
| ATOM | 1872 | N   | ASN | A | 366 | 2.637  | 82.997 | 26.753 | 1.00 | 42.45 | A | N |
| ATOM | 1873 | CA  | ASN | A | 366 | 3.681  | 84.024 | 26.737 | 1.00 | 44.24 | A | C |
| ATOM | 1874 | CB  | ASN | A | 366 | 3.183  | 85.272 | 27.477 | 1.00 | 44.55 | A | C |
| ATOM | 1875 | CG  | ASN | A | 366 | 4.149  | 86.454 | 27.384 | 1.00 | 47.76 | A | C |
| ATOM | 1876 | OD1 | ASN | A | 366 | 3.772  | 87.591 | 27.682 | 1.00 | 51.08 | A | O |
| ATOM | 1877 | ND2 | ASN | A | 366 | 5.388  | 86.194 | 26.985 | 1.00 | 43.49 | A | N |
| ATOM | 1878 | C   | ASN | A | 366 | 4.922  | 83.443 | 27.415 | 1.00 | 42.19 | A | C |
| ATOM | 1879 | O   | ASN | A | 366 | 4.885  | 83.105 | 28.594 | 1.00 | 39.81 | A | O |
| ATOM | 1880 | N   | PRO | A | 367 | 6.036  | 83.321 | 26.668 | 1.00 | 44.23 | A | N |
| ATOM | 1881 | CD  | PRO | A | 367 | 6.151  | 83.761 | 25.267 | 1.00 | 43.04 | A | C |
| ATOM | 1882 | CA  | PRO | A | 367 | 7.319  | 82.778 | 27.145 | 1.00 | 45.24 | A | C |
| ATOM | 1883 | CB  | PRO | A | 367 | 8.252  | 82.989 | 25.953 | 1.00 | 44.30 | A | C |
| ATOM | 1884 | CG  | PRO | A | 367 | 7.320  | 82.944 | 24.778 | 1.00 | 45.18 | A | C |
| ATOM | 1885 | C   | PRO | A | 367 | 7.851  | 83.444 | 28.413 | 1.00 | 47.56 | A | C |
| ATOM | 1886 | O   | PRO | A | 367 | 8.370  | 82.764 | 29.312 | 1.00 | 46.80 | A | O |
| ATOM | 1887 | N   | SER | A | 368 | 7.716  | 84.770 | 28.470 | 1.00 | 47.18 | A | N |
| ATOM | 1888 | CA  | SER | A | 368 | 8.162  | 85.579 | 29.607 | 1.00 | 47.72 | A | C |
| ATOM | 1889 | CB  | SER | A | 368 | 7.926  | 87.076 | 29.334 | 1.00 | 48.23 | A | C |
| ATOM | 1890 | OG  | SER | A | 368 | 8.681  | 87.537 | 28.227 | 1.00 | 51.49 | A | O |
| ATOM | 1891 | C   | SER | A | 368 | 7.447  | 85.211 | 30.897 | 1.00 | 46.18 | A | C |
| ATOM | 1892 | O   | SER | A | 368 | 7.988  | 85.406 | 31.989 | 1.00 | 48.13 | A | O |
| ATOM | 1893 | N   | GLN | A | 369 | 6.228  | 84.699 | 30.787 | 1.00 | 45.87 | A | N |
| ATOM | 1894 | CA  | GLN | A | 369 | 5.481  | 84.329 | 31.984 | 1.00 | 47.80 | A | C |
| ATOM | 1895 | CB  | GLN | A | 369 | 3.973  | 84.295 | 31.697 | 1.00 | 51.34 | A | C |
| ATOM | 1896 | CG  | GLN | A | 369 | 3.343  | 85.642 | 31.358 | 1.00 | 53.45 | A | C |
| ATOM | 1897 | CD  | GLN | A | 369 | 1.840  | 85.530 | 31.120 | 1.00 | 57.46 | A | C |
| ATOM | 1898 | OE1 | GLN | A | 369 | 1.061  | 85.287 | 32.048 | 1.00 | 60.02 | A | O |
| ATOM | 1899 | NE2 | GLN | A | 369 | 1.430  | 85.698 | 29.872 | 1.00 | 58.61 | A | N |
| ATOM | 1900 | C   | GLN | A | 369 | 5.916  | 82.983 | 32.561 | 1.00 | 47.67 | A | C |
| ATOM | 1901 | O   | GLN | A | 369 | 5.606  | 82.668 | 33.715 | 1.00 | 46.25 | A | O |
| ATOM | 1902 | N   | ARG | A | 370 | 6.628  | 82.188 | 31.765 | 1.00 | 46.58 | A | N |
| ATOM | 1903 | CA  | ARG | A | 370 | 7.095  | 80.881 | 32.229 | 1.00 | 47.27 | A | C |
| ATOM | 1904 | CB  | ARG | A | 370 | 7.596  | 80.040 | 31.042 | 1.00 | 43.84 | A | C |
| ATOM | 1905 | CG  | ARG | A | 370 | 6.520  | 79.778 | 29.989 | 1.00 | 41.08 | A | C |
| ATOM | 1906 | CD  | ARG | A | 370 | 7.094  | 79.136 | 28.732 | 1.00 | 42.55 | A | C |
| ATOM | 1907 | NE  | ARG | A | 370 | 6.191  | 79.264 | 27.585 | 1.00 | 38.83 | A | N |
| ATOM | 1908 | CZ  | ARG | A | 370 | 6.563  | 79.083 | 26.324 | 1.00 | 36.60 | A | C |
| ATOM | 1909 | NH1 | ARG | A | 370 | 7.816  | 78.757 | 26.039 | 1.00 | 35.02 | A | N |
| ATOM | 1910 | NH2 | ARG | A | 370 | 5.692  | 79.264 | 25.343 | 1.00 | 37.82 | A | N |
| ATOM | 1911 | C   | ARG | A | 370 | 8.209  | 81.119 | 33.247 | 1.00 | 47.29 | A | C |
| ATOM | 1912 | O   | ARG | A | 370 | 8.995  | 82.057 | 33.102 | 1.00 | 48.42 | A | O |
| ATOM | 1913 | N   | PRO | A | 371 | 8.284  | 80.277 | 34.296 | 1.00 | 47.54 | A | N |
| ATOM | 1914 | CD  | PRO | A | 371 | 7.383  | 79.135 | 34.552 | 1.00 | 46.07 | A | C |
| ATOM | 1915 | CA  | PRO | A | 371 | 9.291  | 80.382 | 35.359 | 1.00 | 46.72 | A | C |
| ATOM | 1916 | CB  | PRO | A | 371 | 8.772  | 79.410 | 36.415 | 1.00 | 45.48 | A | C |
| ATOM | 1917 | CG  | PRO | A | 371 | 8.160  | 78.338 | 35.581 | 1.00 | 47.78 | A | C |
| ATOM | 1918 | C   | PRO | A | 371 | 10.734 | 80.076 | 34.980 | 1.00 | 47.35 | A | C |
| ATOM | 1919 | O   | PRO | A | 371 | 11.026 | 79.618 | 33.877 | 1.00 | 47.37 | A | O |
| ATOM | 1920 | N   | MET | A | 372 | 11.642 | 80.357 | 35.911 | 1.00 | 48.69 | A | N |
| ATOM | 1921 | CA  | MET | A | 372 | 13.055 | 80.067 | 35.713 | 1.00 | 47.91 | A | C |
| ATOM | 1922 | CB  | MET | A | 372 | 13.923 | 80.961 | 36.598 | 1.00 | 51.73 | A | C |
| ATOM | 1923 | CG  | MET | A | 372 | 13.788 | 82.444 | 36.324 | 1.00 | 56.54 | A | C |
| ATOM | 1924 | SD  | MET | A | 372 | 14.948 | 83.405 | 37.339 | 1.00 | 60.67 | A | S |
| ATOM | 1925 | CE  | MET | A | 372 | 16.321 | 83.556 | 36.190 | 1.00 | 59.45 | A | C |
| ATOM | 1926 | C   | MET | A | 372 | 13.178 | 78.618 | 36.164 | 1.00 | 45.14 | A | C |
| ATOM | 1927 | O   | MET | A | 372 | 12.344 | 78.139 | 36.929 | 1.00 | 44.11 | A | O |
| ATOM | 1928 | N   | LEU | A | 373 | 14.204 | 77.917 | 35.703 | 1.00 | 44.75 | A | N |
| ATOM | 1929 | CA  | LEU | A | 373 | 14.354 | 76.522 | 36.086 | 1.00 | 44.46 | A | C |
| ATOM | 1930 | CB  | LEU | A | 373 | 15.526 | 75.893 | 35.325 | 1.00 | 42.40 | A | C |

TABLE 1-continued coordinates of [T287D] Aurora A (122–396) in complex with AMP-PNP

| ATOM | 1931 | CG | LEU | A | 373 | 15.209 | 75.530 | 33.861 | 1.00 | 41.97 | A | C |
|---|---|---|---|---|---|---|---|---|---|---|---|---|
| ATOM | 1932 | CD1 | LEU | A | 373 | 16.493 | 75.194 | 33.117 | 1.00 | 37.82 | A | C |
| ATOM | 1933 | CD2 | LEU | A | 373 | 14.223 | 74.352 | 33.808 | 1.00 | 38.88 | A | C |
| ATOM | 1934 | C | LEU | A | 373 | 14.507 | 76.353 | 37.597 | 1.00 | 44.43 | A | C |
| ATOM | 1935 | O | LEU | A | 373 | 14.051 | 75.364 | 38.164 | 1.00 | 43.69 | A | O |
| ATOM | 1936 | N | ALA | A | 374 | 15.121 | 77.336 | 38.249 | 1.00 | 47.31 | A | N |
| ATOM | 1937 | CA | ALA | A | 374 | 15.310 | 77.289 | 39.699 | 1.00 | 48.80 | A | C |
| ATOM | 1938 | CB | ALA | A | 374 | 16.126 | 78.496 | 40.152 | 1.00 | 49.01 | A | C |
| ATOM | 1939 | C | ALA | A | 374 | 13.967 | 77.239 | 40.446 | 1.00 | 49.34 | A | C |
| ATOM | 1940 | O | ALA | A | 374 | 13.825 | 76.527 | 41.444 | 1.00 | 50.65 | A | O |
| ATOM | 1941 | N | GLU | A | 375 | 12.981 | 77.986 | 39.960 | 1.00 | 50.02 | A | N |
| ATOM | 1942 | CA | GLU | A | 375 | 11.662 | 78.006 | 40.582 | 1.00 | 50.79 | A | C |
| ATOM | 1943 | CB | GLU | A | 375 | 10.785 | 79.070 | 39.925 | 1.00 | 53.29 | A | C |
| ATOM | 1944 | CG | GLU | A | 375 | 11.341 | 80.477 | 39.993 | 1.00 | 58.36 | A | C |
| ATOM | 1945 | CD | GLU | A | 375 | 10.491 | 81.460 | 39.207 | 1.00 | 60.16 | A | C |
| ATOM | 1946 | OE1 | GLU | A | 375 | 9.294 | 81.606 | 39.540 | 1.00 | 62.91 | A | O |
| ATOM | 1947 | OE2 | GLU | A | 375 | 11.015 | 82.078 | 38.255 | 1.00 | 59.36 | A | O |
| ATOM | 1948 | C | GLU | A | 375 | 10.954 | 76.653 | 40.485 | 1.00 | 50.97 | A | C |
| ATOM | 1949 | O | GLU | A | 375 | 10.032 | 76.373 | 41.253 | 1.00 | 50.08 | A | O |
| ATOM | 1950 | N | VAL | A | 376 | 11.363 | 75.826 | 39.526 | 1.00 | 50.81 | A | N |
| ATOM | 1951 | CA | VAL | A | 376 | 10.765 | 74.502 | 39.358 | 1.00 | 50.86 | A | C |
| ATOM | 1952 | CB | VAL | A | 376 | 10.995 | 73.942 | 37.927 | 1.00 | 51.95 | A | C |
| ATOM | 1953 | CG1 | VAL | A | 376 | 10.460 | 72.511 | 37.836 | 1.00 | 49.77 | A | C |
| ATOM | 1954 | CG2 | VAL | A | 376 | 10.306 | 74.834 | 36.895 | 1.00 | 50.95 | A | C |
| ATOM | 1955 | C | VAL | A | 376 | 11.379 | 73.524 | 40.360 | 1.00 | 50.64 | A | C |
| ATOM | 1956 | O | VAL | A | 376 | 10.682 | 72.682 | 40.928 | 1.00 | 51.15 | A | O |
| ATOM | 1957 | N | LEU | A | 377 | 12.687 | 73.642 | 40.564 | 1.00 | 50.28 | A | N |
| ATOM | 1958 | CA | LEU | A | 377 | 13.413 | 72.782 | 41.492 | 1.00 | 52.39 | A | C |
| ATOM | 1959 | CB | LEU | A | 377 | 14.921 | 72.951 | 41.294 | 1.00 | 50.30 | A | C |
| ATOM | 1960 | CG | LEU | A | 377 | 15.497 | 72.434 | 39.973 | 1.00 | 49.77 | A | C |
| ATOM | 1961 | CD1 | LEU | A | 377 | 16.942 | 72.875 | 39.830 | 1.00 | 47.65 | A | C |
| ATOM | 1962 | CD2 | LEU | A | 377 | 15.393 | 70.919 | 39.931 | 1.00 | 48.67 | A | C |
| ATOM | 1963 | C | LEU | A | 377 | 13.054 | 73.091 | 42.944 | 1.00 | 54.42 | A | C |
| ATOM | 1964 | O | LEU | A | 377 | 13.302 | 72.283 | 43.841 | 1.00 | 55.25 | A | O |
| ATOM | 1965 | N | GLU | A | 378 | 12.467 | 74.263 | 43.169 | 1.00 | 55.92 | A | N |
| ATOM | 1966 | CA | GLU | A | 378 | 12.075 | 74.676 | 44.510 | 1.00 | 56.51 | A | C |
| ATOM | 1967 | CB | GLU | A | 378 | 12.597 | 76.079 | 44.791 | 1.00 | 57.88 | A | C |
| ATOM | 1968 | CG | GLU | A | 378 | 14.102 | 76.137 | 44.929 | 1.00 | 61.78 | A | C |
| ATOM | 1969 | CD | GLU | A | 378 | 14.631 | 77.545 | 44.819 | 1.00 | 65.68 | A | C |
| ATOM | 1970 | OE1 | GLU | A | 378 | 15.846 | 77.741 | 45.039 | 1.00 | 68.31 | A | O |
| ATOM | 1971 | OE2 | GLU | A | 378 | 13.834 | 78.456 | 44.502 | 1.00 | 67.56 | A | O |
| ATOM | 1972 | C | GLU | A | 378 | 10.569 | 74.639 | 44.721 | 1.00 | 55.69 | A | C |
| ATOM | 1973 | O | GLU | A | 378 | 10.081 | 75.016 | 45.784 | 1.00 | 57.50 | A | O |
| ATOM | 1974 | N | HIS | A | 379 | 9.832 | 74.183 | 43.715 | 1.00 | 52.52 | A | N |
| ATOM | 1975 | CA | HIS | A | 379 | 8.381 | 74.103 | 43.824 | 1.00 | 50.30 | A | C |
| ATOM | 1976 | CB | HIS | A | 379 | 7.773 | 73.684 | 42.484 | 1.00 | 46.98 | A | C |
| ATOM | 1977 | CG | HIS | A | 379 | 6.276 | 73.759 | 42.441 | 1.00 | 45.89 | A | C |
| ATOM | 1978 | CD2 | HIS | A | 379 | 5.446 | 74.721 | 41.969 | 1.00 | 43.25 | A | C |
| ATOM | 1979 | ND1 | HIS | A | 379 | 5.463 | 72.753 | 42.922 | 1.00 | 44.60 | A | N |
| ATOM | 1980 | CE1 | HIS | A | 379 | 4.197 | 73.090 | 42.746 | 1.00 | 42.55 | A | C |
| ATOM | 1981 | NE2 | HIS | A | 379 | 4.159 | 74.279 | 42.170 | 1.00 | 45.42 | A | N |
| ATOM | 1982 | C | HIS | A | 379 | 8.002 | 73.108 | 44.918 | 1.00 | 51.08 | A | C |
| ATOM | 1983 | O | HIS | A | 379 | 8.526 | 71.992 | 44.975 | 1.00 | 50.77 | A | O |
| ATOM | 1984 | N | PRO | A | 380 | 7.076 | 73.506 | 45.804 | 1.00 | 52.09 | A | N |
| ATOM | 1985 | CD | PRO | A | 380 | 6.283 | 74.747 | 45.721 | 1.00 | 52.19 | A | C |
| ATOM | 1986 | CA | PRO | A | 380 | 6.612 | 72.669 | 46.913 | 1.00 | 50.97 | A | C |
| ATOM | 1987 | CB | PRO | A | 380 | 5.502 | 73.519 | 47.546 | 1.00 | 51.57 | A | C |
| ATOM | 1988 | CG | PRO | A | 380 | 5.003 | 74.343 | 46.401 | 1.00 | 53.46 | A | C |
| ATOM | 1989 | C | PRO | A | 380 | 6.146 | 71.257 | 46.549 | 1.00 | 49.66 | A | C |
| ATOM | 1990 | O | PRO | A | 380 | 6.253 | 70.340 | 47.361 | 1.00 | 48.94 | A | O |
| ATOM | 1991 | N | TRP | A | 381 | 5.626 | 71.074 | 45.341 | 1.00 | 47.98 | A | N |
| ATOM | 1992 | CA | TRP | A | 381 | 5.169 | 69.751 | 44.936 | 1.00 | 46.47 | A | C |
| ATOM | 1993 | CB | TRP | A | 381 | 4.188 | 69.854 | 43.774 | 1.00 | 45.54 | A | C |
| ATOM | 1994 | CG | TRP | A | 381 | 3.631 | 68.527 | 43.346 | 1.00 | 40.93 | A | C |
| ATOM | 1995 | CD2 | TRP | A | 381 | 4.049 | 67.743 | 42.222 | 1.00 | 40.08 | A | C |
| ATOM | 1996 | CE2 | TRP | A | 381 | 3.226 | 66.595 | 42.185 | 1.00 | 38.42 | A | C |
| ATOM | 1997 | CE3 | TRP | A | 381 | 5.036 | 67.900 | 41.238 | 1.00 | 40.44 | A | C |
| ATOM | 1998 | CD1 | TRP | A | 381 | 2.606 | 67.840 | 43.932 | 1.00 | 41.28 | A | C |
| ATOM | 1999 | NE1 | TRP | A | 381 | 2.356 | 66.681 | 43.240 | 1.00 | 40.02 | A | N |
| ATOM | 2000 | CZ2 | TRP | A | 381 | 3.359 | 65.605 | 41.200 | 1.00 | 38.16 | A | C |
| ATOM | 2001 | CZ3 | TRP | A | 381 | 5.167 | 66.914 | 40.257 | 1.00 | 39.27 | A | C |
| ATOM | 2002 | CH2 | TRP | A | 381 | 4.332 | 65.783 | 40.248 | 1.00 | 35.86 | A | C |
| ATOM | 2003 | C | TRP | A | 381 | 6.362 | 68.898 | 44.516 | 1.00 | 46.87 | A | C |
| ATOM | 2004 | O | TRP | A | 381 | 6.373 | 67.683 | 44.718 | 1.00 | 46.53 | A | O |
| ATOM | 2005 | N | ILE | A | 382 | 7.362 | 69.539 | 43.917 | 1.00 | 48.95 | A | N |
| ATOM | 2006 | CA | ILE | A | 382 | 8.566 | 68.835 | 43.485 | 1.00 | 50.95 | A | C |
| ATOM | 2007 | CB | ILE | A | 382 | 9.489 | 69.749 | 42.634 | 1.00 | 49.30 | A | C |

TABLE 1-continued coordinates of [T287D] Aurora A (122–396) in complex with AMP-PNP

| ATOM | 2008 | CG2 | ILE | A | 382 | 10.821 | 69.053 | 42.398 | 1.00 | 48.74 | A | C |
|---|---|---|---|---|---|---|---|---|---|---|---|---|
| ATOM | 2009 | CG1 | ILE | A | 382 | 8.822 | 70.098 | 41.294 | 1.00 | 49.61 | A | C |
| ATOM | 2010 | CD1 | ILE | A | 382 | 8.619 | 68.907 | 40.358 | 1.00 | 42.81 | A | C |
| ATOM | 2011 | C | ILE | A | 382 | 9.341 | 68.384 | 44.725 | 1.00 | 53.01 | A | C |
| ATOM | 2012 | O | ILE | A | 382 | 9.651 | 67.203 | 44.889 | 1.00 | 51.75 | A | O |
| ATOM | 2013 | N | THR | A | 383 | 9.643 | 69.340 | 45.596 | 1.00 | 56.54 | A | N |
| ATOM | 2014 | CA | THR | A | 383 | 10.384 | 69.069 | 46.827 | 1.00 | 60.42 | A | C |
| ATOM | 2015 | CB | THR | A | 383 | 10.615 | 70.364 | 47.629 | 1.00 | 60.63 | A | C |
| ATOM | 2016 | OG1 | THR | A | 383 | 11.390 | 71.279 | 46.844 | 1.00 | 62.34 | A | O |
| ATOM | 2017 | CG2 | THR | A | 383 | 11.360 | 70.067 | 48.923 | 1.00 | 64.67 | A | C |
| ATOM | 2018 | C | THR | A | 383 | 9.667 | 68.070 | 47.726 | 1.00 | 61.26 | A | C |
| ATOM | 2019 | O | THR | A | 383 | 10.303 | 67.355 | 48.501 | 1.00 | 62.87 | A | O |
| ATOM | 2020 | N | ALA | A | 384 | 8.346 | 68.010 | 47.609 | 1.00 | 61.81 | A | N |
| ATOM | 2021 | CA | ALA | A | 384 | 7.554 | 67.104 | 48.427 | 1.00 | 62.66 | A | C |
| ATOM | 2022 | CB | ALA | A | 384 | 6.140 | 67.656 | 48.585 | 1.00 | 63.07 | A | C |
| ATOM | 2023 | C | ALA | A | 384 | 7.493 | 65.668 | 47.909 | 1.00 | 63.07 | A | C |
| ATOM | 2024 | O | ALA | A | 384 | 7.337 | 64.735 | 48.695 | 1.00 | 63.72 | A | O |
| ATOM | 2025 | N | ASN | A | 385 | 7.612 | 65.482 | 46.597 | 1.00 | 62.18 | A | N |
| ATOM | 2026 | CA | ASN | A | 385 | 7.550 | 64.140 | 46.025 | 1.00 | 62.42 | A | C |
| ATOM | 2027 | CB | ASN | A | 385 | 6.466 | 64.083 | 44.946 | 1.00 | 61.14 | A | C |
| ATOM | 2028 | CG | ASN | A | 385 | 5.078 | 64.372 | 45.491 | 1.00 | 60.33 | A | C |
| ATOM | 2029 | OD1 | ASN | A | 385 | 4.427 | 63.499 | 46.065 | 1.00 | 57.45 | A | O |
| ATOM | 2030 | ND2 | ASN | A | 385 | 4.623 | 65.610 | 45.317 | 1.00 | 56.76 | A | N |
| ATOM | 2031 | C | ASN | A | 385 | 8.871 | 63.653 | 45.430 | 1.00 | 63.75 | A | C |
| ATOM | 2032 | O | ASN | A | 385 | 9.030 | 62.466 | 45.154 | 1.00 | 63.17 | A | O |
| ATOM | 2033 | N | SER | A | 386 | 9.814 | 64.565 | 45.234 | 1.00 | 66.08 | A | N |
| ATOM | 2034 | CA | SER | A | 386 | 11.103 | 64.211 | 44.651 | 1.00 | 69.04 | A | C |
| ATOM | 2035 | CB | SER | A | 386 | 11.731 | 65.441 | 43.990 | 1.00 | 70.22 | A | C |
| ATOM | 2036 | OG | SER | A | 386 | 13.032 | 65.159 | 43.503 | 1.00 | 70.59 | A | O |
| ATOM | 2037 | C | SER | A | 386 | 12.093 | 63.626 | 45.654 | 1.00 | 72.01 | A | C |
| ATOM | 2038 | O | SER | A | 386 | 12.098 | 63.989 | 46.833 | 1.00 | 73.11 | A | O |
| ATOM | 2039 | N | SER | A | 387 | 12.931 | 62.717 | 45.169 | 1.00 | 73.40 | A | N |
| ATOM | 2040 | CA | SER | A | 387 | 13.951 | 62.088 | 45.995 | 1.00 | 75.94 | A | C |
| ATOM | 2041 | CB | SER | A | 387 | 14.024 | 60.589 | 45.695 | 1.00 | 75.91 | A | C |
| ATOM | 2042 | OG | SER | A | 387 | 12.754 | 59.981 | 45.840 | 1.00 | 76.94 | A | O |
| ATOM | 2043 | C | SER | A | 387 | 15.284 | 62.751 | 45.650 | 1.00 | 77.73 | A | C |
| ATOM | 2044 | O | SER | A | 387 | 16.348 | 62.280 | 46.058 | 1.00 | 78.06 | A | O |
| ATOM | 2045 | N | LYS | A | 388 | 15.194 | 63.843 | 44.886 | 1.00 | 78.26 | A | N |
| ATOM | 2046 | CA | LYS | A | 388 | 16.339 | 64.635 | 44.428 | 1.00 | 79.08 | A | C |
| ATOM | 2047 | CB | LYS | A | 388 | 17.409 | 64.724 | 45.525 | 1.00 | 79.44 | A | C |
| ATOM | 2048 | CG | LYS | A | 388 | 16.974 | 65.500 | 46.763 | 1.00 | 79.33 | A | C |
| ATOM | 2049 | CD | LYS | A | 388 | 18.062 | 65.484 | 47.824 | 1.00 | 79.09 | A | C |
| ATOM | 2050 | CE | LYS | A | 388 | 17.695 | 66.350 | 49.018 | 1.00 | 79.02 | A | C |
| ATOM | 2051 | NZ | LYS | A | 388 | 17.530 | 67.782 | 48.641 | 1.00 | 78.19 | A | N |
| ATOM | 2052 | C | LYS | A | 388 | 16.959 | 64.102 | 43.130 | 1.00 | 78.82 | A | C |
| ATOM | 2053 | O | LYS | A | 388 | 16.481 | 63.074 | 42.619 | 1.00 | 78.44 | A | O |
| ATOM | 2054 | OXT | LYS | A | 388 | 17.916 | 64.723 | 42.618 | 1.00 | 79.61 | A | O |
| ATOM | 2056 | PB | AANP | Z | 379 | 15.037 | 57.738 | 17.969 | 0.50 | 47.69 | Z | P |
| ATOM | 2057 | PB | BANP | Z | 379 | 17.785 | 58.350 | 20.389 | 0.50 | 50.58 | Z | P |
| ATOM | 2058 | O1B | AANP | Z | 379 | 15.506 | 57.453 | 19.308 | 0.50 | 49.57 | Z | O |
| ATOM | 2059 | O1B | BANP | Z | 379 | 18.803 | 57.539 | 21.023 | 0.50 | 51.23 | Z | O |
| ATOM | 2060 | O2B | AANP | Z | 379 | 14.617 | 59.160 | 17.829 | 0.50 | 48.87 | Z | O |
| ATOM | 2061 | O2B | BANP | Z | 379 | 18.020 | 59.811 | 20.601 | 0.50 | 52.85 | Z | O |
| ATOM | 2062 | O3B | AANP | Z | 379 | 13.854 | 56.738 | 17.611 | 0.50 | 47.44 | Z | O |
| ATOM | 2063 | O3B | BANP | Z | 379 | 16.375 | 57.916 | 20.971 | 0.50 | 53.88 | Z | O |
| ATOM | 2064 | PA | AANP | Z | 379 | 17.533 | 56.644 | 17.115 | 0.50 | 51.30 | Z | P |
| ATOM | 2065 | PA | BANP | Z | 379 | 18.302 | 56.815 | 17.978 | 0.50 | 49.99 | Z | P |
| ATOM | 2066 | O1A | AANP | Z | 379 | 18.137 | 56.443 | 15.785 | 0.50 | 52.19 | Z | O |
| ATOM | 2067 | O1A | BANP | Z | 379 | 17.740 | 56.898 | 16.602 | 0.50 | 51.27 | Z | O |
| ATOM | 2068 | O2A | AANP | Z | 379 | 18.354 | 57.484 | 18.041 | 0.50 | 51.52 | Z | O |
| ATOM | 2069 | O2A | BANP | Z | 379 | 19.779 | 56.935 | 18.073 | 0.50 | 51.64 | Z | O |
| ATOM | 2070 | O3A | AANP | Z | 379 | 16.105 | 57.302 | 16.924 | 0.50 | 51.44 | Z | O |
| ATOM | 2071 | O3A | BANP | Z | 379 | 17.600 | 57.938 | 18.878 | 0.50 | 50.89 | Z | O |
| ATOM | 2072 | O5* | AANP | Z | 379 | 17.177 | 55.295 | 17.877 | 0.50 | 50.92 | Z | O |
| ATOM | 2073 | O5* | BANP | Z | 379 | 17.867 | 55.497 | 18.751 | 0.50 | 47.15 | Z | O |
| ATOM | 2074 | C5* | AANP | Z | 379 | 17.877 | 54.090 | 17.490 | 0.50 | 47.94 | Z | C |
| ATOM | 2075 | C5* | BANP | Z | 379 | 17.722 | 54.257 | 18.009 | 0.50 | 40.88 | Z | C |
| ATOM | 2076 | C4* | AANP | Z | 379 | 17.460 | 52.862 | 18.318 | 0.50 | 47.92 | Z | C |
| ATOM | 2077 | C4* | BANP | Z | 379 | 17.263 | 53.099 | 18.926 | 0.50 | 36.96 | Z | C |
| ATOM | 2078 | O4* | AANP | Z | 379 | 18.576 | 52.400 | 19.179 | 0.50 | 47.21 | Z | O |
| ATOM | 2079 | O4* | BANP | Z | 379 | 18.369 | 52.549 | 19.752 | 0.50 | 33.82 | Z | O |
| ATOM | 2080 | C3* | AANP | Z | 379 | 16.328 | 53.019 | 19.359 | 0.50 | 47.98 | Z | C |
| ATOM | 2081 | C3* | BANP | Z | 379 | 16.203 | 53.417 | 20.009 | 0.50 | 33.98 | Z | C |
| ATOM | 2082 | O3* | AANP | Z | 379 | 15.560 | 51.846 | 19.588 | 0.50 | 48.47 | Z | O |
| ATOM | 2083 | O3* | BANP | Z | 379 | 15.320 | 52.350 | 20.339 | 0.50 | 32.96 | Z | O |
| ATOM | 2084 | C2* | AANP | Z | 379 | 17.076 | 53.566 | 20.584 | 0.50 | 47.21 | Z | C |
| ATOM | 2085 | C2* | BANP | Z | 379 | 17.064 | 53.934 | 21.164 | 0.50 | 32.17 | Z | C |

TABLE 1-continued coordinates of [T287D] Aurora A (122–396) in complex with AMP-PNP

| ATOM | 2086 | O2* | AANP | Z | 379 | 16.398 | 53.519 | 21.825 | 0.50 | 48.99 | Z | O |
|---|---|---|---|---|---|---|---|---|---|---|---|---|
| ATOM | 2087 | O2* | BANP | Z | 379 | 16.446 | 54.056 | 22.437 | 0.50 | 30.71 | Z | O |
| ATOM | 2088 | C1* | AANP | Z | 379 | 18.369 | 52.807 | 20.558 | 0.50 | 46.20 | Z | C |
| ATOM | 2089 | C1* | BANP | Z | 379 | 18.273 | 53.024 | 21.121 | 0.50 | 31.00 | Z | C |
| ATOM | 2090 | N9 | AANP | Z | 379 | 19.533 | 53.632 | 21.081 | 0.50 | 44.22 | Z | N |
| ATOM | 2091 | N9 | BANP | Z | 379 | 19.537 | 53.738 | 21.552 | 0.50 | 27.84 | Z | N |
| ATOM | 2092 | C8 | AANP | Z | 379 | 20.137 | 54.688 | 20.410 | 0.50 | 43.51 | Z | C |
| ATOM | 2093 | C8 | BANP | Z | 379 | 20.190 | 54.721 | 20.820 | 0.50 | 26.21 | Z | C |
| ATOM | 2094 | N7 | AANP | Z | 379 | 21.138 | 55.258 | 21.064 | 0.50 | 43.16 | Z | N |
| ATOM | 2095 | N7 | BANP | Z | 379 | 21.273 | 55.211 | 21.389 | 0.50 | 27.05 | Z | N |
| ATOM | 2096 | C5 | AANP | Z | 379 | 21.222 | 54.563 | 22.228 | 0.50 | 43.37 | Z | C |
| ATOM | 2097 | C5 | BANP | Z | 379 | 21.372 | 54.538 | 22.561 | 0.50 | 27.46 | Z | C |
| ATOM | 2098 | C6 | AANP | Z | 379 | 22.077 | 54.630 | 23.408 | 0.50 | 41.80 | Z | C |
| ATOM | 2099 | C6 | BANP | Z | 379 | 22.300 | 54.555 | 23.675 | 0.50 | 26.76 | Z | C |
| ATOM | 2100 | N6 | AANP | Z | 379 | 23.058 | 55.506 | 23.571 | 0.50 | 41.70 | Z | N |
| ATOM | 2101 | N6 | BANP | Z | 379 | 23.356 | 55.348 | 23.750 | 0.50 | 26.20 | Z | N |
| ATOM | 2102 | N1 | AANP | Z | 379 | 21.858 | 53.706 | 24.460 | 0.50 | 43.30 | Z | N |
| ATOM | 2103 | N1 | BANP | Z | 379 | 22.075 | 53.675 | 24.765 | 0.50 | 29.25 | Z | N |
| ATOM | 2104 | C2 | AANP | Z | 379 | 20.844 | 52.746 | 24.372 | 0.50 | 42.75 | Z | C |
| ATOM | 2105 | C2 | BANP | Z | 379 | 20.979 | 52.806 | 24.765 | 0.50 | 27.75 | Z | C |
| ATOM | 2106 | N3 | AANP | Z | 379 | 19.992 | 52.607 | 23.302 | 0.50 | 43.98 | Z | N |
| ATOM | 2107 | N3 | BANP | Z | 379 | 20.052 | 52.720 | 23.761 | 0.50 | 28.35 | Z | N |
| ATOM | 2108 | C4 | AANP | Z | 379 | 20.223 | 53.538 | 22.258 | 0.50 | 43.59 | Z | C |
| ATOM | 2109 | C4 | BANP | Z | 379 | 20.292 | 53.604 | 22.682 | 0.50 | 27.97 | Z | C |
| ATOM | 2110 | P1 | FRA | Z | 379 | 26.094 | 48.843 | 31.713 | 1.00 | 52.95 | Z | P |
| ATOM | 2111 | O2 | FRA | Z | 379 | 27.446 | 48.301 | 31.747 | 1.00 | 53.45 | Z | O |
| ATOM | 2112 | O3 | FRA | Z | 379 | 25.842 | 49.670 | 32.927 | 1.00 | 57.52 | Z | O |
| ATOM | 2113 | O4 | FRA | Z | 379 | 25.079 | 47.640 | 31.660 | 1.00 | 53.32 | Z | O |
| ATOM | 2114 | O5 | FRA | Z | 379 | 25.925 | 49.788 | 30.418 | 1.00 | 54.94 | Z | O |
| TER | 2115 | | FRAG | Z | 1 | | | | | | Z | |
| ATOM | 2116 | O | HOH | W | 379 | 0.331 | 67.542 | 23.164 | 1.00 | 33.20 | W | O |
| ATOM | 2117 | O | HOH | W | 380 | 28.844 | 46.119 | 11.651 | 1.00 | 48.79 | W | O |
| ATOM | 2118 | O | HOH | W | 381 | 23.007 | 73.689 | 19.317 | 1.00 | 39.02 | W | O |
| ATOM | 2119 | O | HOH | W | 382 | 10.568 | 41.141 | 28.154 | 1.00 | 49.97 | W | O |
| ATOM | 2120 | O | HOH | W | 383 | 12.722 | 71.913 | 24.732 | 1.00 | 38.33 | W | O |
| ATOM | 2121 | O | HOH | W | 384 | 27.119 | 63.991 | 29.594 | 1.00 | 34.78 | W | O |
| ATOM | 2122 | O | HOH | W | 385 | 25.822 | 60.889 | 31.761 | 1.00 | 35.64 | W | O |
| ATOM | 2123 | O | HOH | W | 386 | 12.649 | 51.436 | 29.438 | 1.00 | 30.54 | W | O |
| ATOM | 2124 | O | HOH | W | 387 | −1.136 | 77.886 | 32.084 | 1.00 | 58.06 | W | O |
| ATOM | 2125 | O | HOH | W | 388 | −5.994 | 68.177 | 27.794 | 1.00 | 32.43 | W | O |
| ATOM | 2126 | O | HOH | W | 389 | 30.025 | 50.004 | 9.061 | 1.00 | 46.99 | W | O |
| ATOM | 2127 | O | HOH | W | 390 | −3.566 | 81.854 | 26.459 | 1.00 | 55.28 | W | O |
| ATOM | 2128 | O | HOH | W | 391 | 30.646 | 47.521 | 34.093 | 1.00 | 60.01 | W | O |
| ATOM | 2129 | O | HOH | W | 392 | −1.097 | 85.911 | 26.783 | 1.00 | 47.89 | W | O |
| ATOM | 2130 | O | HOH | W | 393 | 0.595 | 65.227 | 46.406 | 1.00 | 53.88 | W | O |
| ATOM | 2131 | O | HOH | W | 394 | 6.207 | 71.002 | 50.031 | 1.00 | 52.47 | W | O |
| ATOM | 2132 | O | HOH | W | 395 | 5.278 | 55.170 | 38.782 | 1.00 | 41.90 | W | O |
| ATOM | 2133 | O | HOH | W | 396 | −12.360 | 69.423 | 40.011 | 1.00 | 62.19 | W | O |
| ATOM | 2134 | O | HOH | W | 397 | 10.584 | 80.817 | 23.752 | 1.00 | 42.95 | W | O |
| ATOM | 2135 | O | HOH | W | 398 | 20.285 | 61.152 | 38.189 | 1.00 | 57.76 | W | O |
| ATOM | 2136 | O | HOH | W | 399 | 38.138 | 63.320 | 28.926 | 1.00 | 63.01 | W | O |
| ATOM | 2137 | O | HOH | W | 400 | 36.205 | 63.417 | 18.017 | 1.00 | 42.85 | W | O |
| ATOM | 2138 | O | HOH | W | 401 | 10.940 | 46.826 | 29.244 | 1.00 | 66.42 | W | O |
| ATOM | 2139 | O | HOH | W | 402 | 28.740 | 45.402 | 31.083 | 1.00 | 57.98 | W | O |
| ATOM | 2140 | O | HOH | W | 403 | 16.667 | 51.609 | 23.943 | 1.00 | 49.28 | W | O |
| ATOM | 2141 | O | HOH | W | 404 | 0.650 | 83.566 | 28.516 | 1.00 | 48.67 | W | O |
| ATOM | 2142 | O | HOH | W | 405 | 23.052 | 81.277 | 32.597 | 1.00 | 79.68 | W | O |
| ATOM | 2143 | O | HOH | W | 406 | 21.015 | 66.488 | 25.190 | 1.00 | 51.11 | W | O |
| ATOM | 2144 | O | HOH | W | 407 | 29.555 | 78.569 | 17.681 | 1.00 | 72.97 | W | O |
| ATOM | 2145 | O | HOH | W | 408 | 23.196 | 68.069 | 19.434 | 1.00 | 38.38 | W | O |
| ATOM | 2146 | O | HOH | W | 409 | −7.313 | 65.296 | 29.334 | 1.00 | 66.68 | W | O |
| ATOM | 2147 | O | HOH | W | 410 | 24.377 | 54.450 | 33.733 | 1.00 | 39.04 | W | O |
| ATOM | 2148 | O | HOH | W | 411 | 18.676 | 56.503 | 40.201 | 1.00 | 43.61 | W | O |
| ATOM | 2149 | O | HOH | W | 412 | 19.799 | 63.234 | 10.818 | 1.00 | 60.37 | W | O |
| ATOM | 2150 | O | HOH | W | 413 | 4.227 | 81.623 | 22.473 | 1.00 | 45.07 | W | O |
| ATOM | 2151 | O | HOH | W | 414 | 35.586 | 63.256 | 25.029 | 1.00 | 58.40 | W | O |
| ATOM | 2152 | O | HOH | W | 415 | 26.042 | 47.904 | 6.604 | 1.00 | 63.98 | W | O |
| ATOM | 2153 | O | HOH | W | 416 | 0.125 | 61.540 | 20.664 | 1.00 | 58.49 | W | O |
| ATOM | 2154 | O | HOH | W | 417 | 15.750 | 58.426 | 38.595 | 1.00 | 51.37 | W | O |
| ATOM | 2155 | O | HOH | W | 418 | 8.114 | 48.760 | 24.263 | 1.00 | 66.46 | W | O |
| ATOM | 2156 | O | HOH | W | 419 | −13.534 | 60.538 | 36.389 | 1.00 | 56.48 | W | O |
| ATOM | 2157 | O | HOH | W | 420 | 37.492 | 60.906 | 4.499 | 1.00 | 56.53 | W | O |
| ATOM | 2158 | O | HOH | W | 421 | 11.597 | 49.198 | 40.125 | 1.00 | 55.46 | W | O |
| ATOM | 2159 | O | HOH | W | 422 | 29.535 | 40.480 | 27.301 | 1.00 | 39.07 | W | O |
| ATOM | 2160 | O | HOH | W | 423 | −9.419 | 60.202 | 32.744 | 1.00 | 49.49 | W | O |
| ATOM | 2161 | O | HOH | W | 424 | −3.387 | 80.285 | 33.001 | 1.00 | 53.18 | W | O |
| ATOM | 2162 | O | HOH | W | 425 | 22.854 | 68.702 | 38.913 | 1.00 | 56.31 | W | O |

TABLE 1-continued coordinates of [T287D] Aurora A (122–396) in complex with AMP-PNP

| ATOM | 2163 | O | HOH | W | 426 | 5.516 | 90.168 | 27.801 | 1.00 | 57.26 | W | O |
|---|---|---|---|---|---|---|---|---|---|---|---|---|
| ATOM | 2164 | O | HOH | W | 427 | 42.341 | 62.424 | 13.295 | 1.00 | 70.57 | W | O |
| ATOM | 2165 | O | HOH | W | 428 | 50.104 | 46.432 | 21.896 | 1.00 | 59.70 | W | O |
| ATOM | 2166 | O | HOH | W | 429 | 19.133 | 50.530 | 8.236 | 1.00 | 38.20 | W | O |
| ATOM | 2167 | O | HOH | W | 430 | 14.218 | 90.460 | 15.295 | 1.00 | 59.43 | W | O |
| ATOM | 2168 | O | HOH | W | 431 | 20.996 | 76.724 | 18.128 | 1.00 | 68.02 | W | O |
| ATOM | 2169 | O | HOH | W | 432 | 28.748 | 65.408 | 11.519 | 1.00 | 55.89 | W | O |
| ATOM | 2170 | O | HOH | W | 433 | 33.109 | 52.617 | 3.045 | 1.00 | 66.13 | W | O |
| ATOM | 2171 | O | HOH | W | 434 | −0.097 | 51.530 | 27.181 | 1.00 | 62.48 | W | O |
| ATOM | 2172 | O | HOH | W | 435 | 34.328 | 49.913 | 33.453 | 1.00 | 80.02 | W | O |
| ATOM | 2173 | O | HOH | W | 436 | 16.321 | 46.597 | 36.609 | 1.00 | 55.74 | W | O |
| ATOM | 2174 | O | HOH | W | 437 | 15.506 | 88.823 | 36.550 | 1.00 | 60.31 | W | O |
| ATOM | 2175 | O | HOH | W | 438 | −10.288 | 68.090 | 36.659 | 1.00 | 43.23 | W | O |
| ATOM | 2176 | O | HOH | W | 439 | 35.236 | 49.316 | 7.956 | 1.00 | 47.01 | W | O |
| ATOM | 2177 | O | HOH | W | 440 | −2.382 | 64.267 | 14.669 | 1.00 | 54.31 | W | O |
| ATOM | 2178 | O | HOH | W | 441 | 3.145 | 71.184 | 22.878 | 1.00 | 32.15 | W | O |
| ATOM | 2179 | O | HOH | W | 442 | 13.920 | 51.205 | 25.014 | 1.00 | 47.83 | W | O |
| ATOM | 2180 | O | HOH | W | 443 | −0.162 | 59.596 | 37.808 | 1.00 | 46.99 | W | O |
| ATOM | 2181 | O | HOH | W | 444 | 21.993 | 67.937 | 15.891 | 1.00 | 41.38 | W | O |
| ATOM | 2182 | O | HOH | W | 445 | 18.406 | 49.826 | 26.693 | 1.00 | 48.92 | W | O |
| ATOM | 2183 | O | HOH | W | 446 | 27.317 | 49.713 | 35.324 | 1.00 | 50.93 | W | O |
| ATOM | 2184 | O | HOH | W | 447 | 32.044 | 55.554 | 32.480 | 1.00 | 59.20 | W | O |
| ATOM | 2185 | O | HOH | W | 448 | 15.585 | 66.847 | 22.965 | 1.00 | 66.60 | W | O |
| ATOM | 2186 | O | HOH | W | 449 | 28.577 | 85.371 | 20.089 | 1.00 | 61.69 | W | O |
| ATOM | 2187 | O | HOH | W | 450 | 19.255 | 74.406 | 43.569 | 1.00 | 78.23 | W | O |
| ATOM | 2188 | O | HOH | W | 451 | 46.877 | 44.566 | 20.648 | 1.00 | 63.82 | W | O |
| ATOM | 2189 | O | HOH | W | 452 | 18.724 | 77.353 | 37.945 | 1.00 | 74.74 | W | O |
| ATOM | 2190 | O | HOH | W | 453 | 32.145 | 68.599 | 9.155 | 1.00 | 80.54 | W | O |
| ATOM | 2191 | O | HOH | W | 454 | 4.355 | 81.219 | 35.183 | 1.00 | 34.92 | W | O |
| ATOM | 2192 | O | HOH | W | 455 | 25.635 | 56.901 | 34.614 | 1.00 | 47.34 | W | O |
| ATOM | 2193 | O | HOH | W | 456 | 42.338 | 49.434 | 11.100 | 1.00 | 72.43 | W | O |
| ATOM | 2194 | O | HOH | W | 457 | −2.051 | 65.103 | 18.494 | 1.00 | 39.83 | W | O |
| ATOM | 2195 | O | HOH | W | 458 | −9.591 | 72.598 | 44.168 | 1.00 | 64.69 | W | O |
| ATOM | 2196 | O | HOH | W | 459 | 20.373 | 46.614 | 27.914 | 1.00 | 38.68 | W | O |
| ATOM | 2197 | O | HOH | W | 460 | 0.659 | 55.516 | 18.515 | 1.00 | 58.39 | W | O |
| ATOM | 2198 | O | HOH | W | 461 | 21.076 | 80.510 | 26.713 | 1.00 | 61.17 | W | O |
| ATOM | 2199 | O | HOH | W | 462 | 32.155 | 47.583 | 8.094 | 1.00 | 70.56 | W | O |
| ATOM | 2200 | O | HOH | W | 463 | 4.044 | 58.878 | 44.996 | 1.00 | 51.08 | W | O |
| ATOM | 2201 | O | HOH | W | 464 | 41.005 | 53.749 | 30.770 | 1.00 | 75.59 | W | O |
| ATOM | 2202 | O | HOH | W | 465 | 26.371 | 63.533 | −4.679 | 1.00 | 74.46 | W | O |
| ATOM | 2203 | O | HOH | W | 466 | 18.683 | 73.320 | 26.848 | 1.00 | 53.79 | W | O |
| ATOM | 2204 | O | HOH | W | 467 | 31.520 | 71.009 | 32.011 | 1.00 | 56.96 | W | O |
| ATOM | 2205 | O | HOH | W | 468 | 17.101 | 44.021 | 28.295 | 1.00 | 65.42 | W | O |
| ATOM | 2206 | O | HOH | W | 469 | 39.280 | 50.487 | 10.873 | 1.00 | 71.08 | W | O |
| ATOM | 2207 | O | HOH | W | 470 | 37.290 | 42.352 | 23.513 | 1.00 | 70.13 | W | O |
| ATOM | 2208 | O | HOH | W | 471 | 5.578 | 77.441 | 49.897 | 1.00 | 69.56 | W | O |
| ATOM | 2209 | O | HOH | W | 472 | 7.437 | 83.010 | 37.688 | 1.00 | 69.84 | W | O |
| ATOM | 2210 | O | HOH | W | 473 | 26.352 | 64.806 | 24.911 | 1.00 | 54.06 | W | O |
| ATOM | 2211 | O | HOH | W | 474 | 11.127 | 50.403 | 42.491 | 1.00 | 74.19 | W | O |
| ATOM | 2212 | O | HOH | W | 475 | 13.078 | 66.605 | 47.781 | 1.00 | 64.41 | W | O |
| ATOM | 2213 | O | HOH | W | 476 | 33.069 | 47.485 | 4.075 | 1.00 | 73.62 | W | O |
| ATOM | 2214 | O | HOH | W | 477 | 16.310 | 47.636 | 28.660 | 1.00 | 60.28 | W | O |
| ATOM | 2215 | O | HOH | W | 478 | 10.526 | 56.684 | 48.949 | 1.00 | 65.54 | W | O |
| ATOM | 2216 | O | HOH | W | 479 | 8.120 | 87.653 | 17.142 | 1.00 | 54.25 | W | O |
| ATOM | 2217 | O | HOH | W | 480 | 8.395 | 84.399 | 35.638 | 1.00 | 53.58 | W | O |
| ATOM | 2218 | O | HOH | W | 481 | 37.470 | 55.653 | 9.464 | 1.00 | 46.07 | W | O |
| ATOM | 2219 | O | HOH | W | 482 | 26.702 | 61.295 | 39.749 | 1.00 | 63.14 | W | O |
| ATOM | 2220 | O | HOH | W | 483 | 45.743 | 51.322 | 22.505 | 1.00 | 64.82 | W | O |
| ATOM | 2221 | O | HOH | W | 484 | 26.243 | 53.676 | 32.375 | 1.00 | 76.35 | W | O |
| ATOM | 2222 | O | HOH | W | 485 | 28.613 | 53.324 | 28.097 | 1.00 | 38.88 | W | O |
| ATOM | 2223 | O | HOH | W | 486 | 4.244 | 65.989 | 13.927 | 1.00 | 36.47 | W | O |
| ATOM | 2224 | O | HOH | W | 487 | 24.103 | 54.829 | 31.073 | 1.00 | 48.23 | W | O |
| ATOM | 2225 | O | HOH | W | 488 | 16.440 | 64.104 | 14.517 | 1.00 | 46.59 | W | O |
| ATOM | 2226 | O | HOH | W | 489 | 37.058 | 53.211 | 10.107 | 1.00 | 41.19 | W | O |
| ATOM | 2227 | O | HOH | W | 490 | 1.626 | 58.930 | 43.465 | 1.00 | 56.15 | W | O |
| ATOM | 2228 | O | HOH | W | 491 | 5.404 | 80.824 | 37.937 | 1.00 | 49.30 | W | O |
| ATOM | 2229 | O | HOH | W | 492 | 3.696 | 83.191 | 19.871 | 1.00 | 55.84 | W | O |
| ATOM | 2230 | O | HOH | W | 493 | 9.216 | 69.339 | 23.781 | 1.00 | 49.12 | W | O |
| ATOM | 2231 | O | HOH | W | 494 | 36.460 | 55.040 | 25.386 | 1.00 | 61.90 | W | O |
| ATOM | 2232 | O | HOH | W | 495 | 29.035 | 64.618 | 25.993 | 1.00 | 44.19 | W | O |
| ATOM | 2233 | O | HOH | W | 496 | −1.211 | 81.253 | 28.481 | 1.00 | 49.42 | W | O |
| ATOM | 2234 | O | HOH | W | 497 | −13.349 | 74.056 | 40.995 | 1.00 | 57.64 | W | O |
| ATOM | 2235 | O | HOH | W | 498 | 22.952 | 75.394 | 20.894 | 1.00 | 54.51 | W | O |
| ATOM | 2236 | O | HOH | W | 499 | 8.061 | 54.650 | 41.586 | 1.00 | 49.70 | W | O |
| ATOM | 2237 | O | HOH | W | 500 | −4.078 | 73.918 | 41.599 | 1.00 | 51.57 | W | O |
| ATOM | 2238 | O | HOH | W | 501 | 26.284 | 56.747 | 2.127 | 1.00 | 52.08 | W | O |
| ATOM | 2239 | O | HOH | W | 502 | 30.005 | 48.619 | 30.666 | 1.00 | 72.19 | W | O |

TABLE 1-continued coordinates of [T287D] Aurora A (122–396) in complex with AMP-PNP

| ATOM | 2240 | O | HOH | W | 503 | 20.159 | 65.366 | 13.420 | 1.00 | 51.24 | W | O |
|---|---|---|---|---|---|---|---|---|---|---|---|---|
| ATOM | 2241 | O | HOH | W | 504 | −5.361 | 63.850 | 28.736 | 1.00 | 60.73 | W | O |
| ATOM | 2242 | O | HOH | W | 505 | 26.955 | 52.505 | 30.145 | 1.00 | 52.17 | W | O |
| ATOM | 2243 | O | HOH | W | 506 | 0.745 | 55.925 | 28.349 | 1.00 | 47.50 | W | O |
| ATOM | 2244 | O | HOH | W | 507 | 13.465 | 63.276 | 17.023 | 1.00 | 63.56 | W | O |
| ATOM | 2245 | O | HOH | W | 508 | −0.920 | 64.629 | 40.572 | 1.00 | 40.57 | W | O |
| ATOM | 2246 | O | HOH | W | 509 | −8.382 | 72.769 | 39.661 | 1.00 | 58.85 | W | O |
| ATOM | 2247 | O | HOH | W | 510 | 19.488 | 70.756 | 41.864 | 1.00 | 49.15 | W | O |
| ATOM | 2248 | O | HOH | W | 511 | 14.101 | 54.714 | 36.057 | 1.00 | 57.27 | W | O |
| ATOM | 2249 | O | HOH | W | 512 | 31.885 | 61.378 | 38.523 | 1.00 | 62.27 | W | O |
| ATOM | 2250 | O | HOH | W | 513 | 35.755 | 51.839 | 8.257 | 1.00 | 47.13 | W | O |
| ATOM | 2251 | O | HOH | W | 514 | 17.069 | 82.457 | 25.470 | 1.00 | 55.98 | W | O |
| ATOM | 2252 | O | HOH | W | 515 | −4.640 | 64.734 | 26.208 | 1.00 | 35.90 | W | O |
| ATOM | 2253 | O | HOH | W | 516 | 28.342 | 79.720 | 28.289 | 1.00 | 51.97 | W | O |
| ATOM | 2254 | O | HOH | W | 517 | 28.930 | 63.693 | 33.886 | 1.00 | 47.21 | W | O |
| ATOM | 2255 | O | HOH | W | 518 | 14.019 | 51.336 | 17.356 | 1.00 | 74.59 | W | O |
| ATOM | 2256 | O | HOH | W | 519 | 16.446 | 79.651 | 42.696 | 1.00 | 66.23 | W | O |
| ATOM | 2257 | O | HOH | W | 520 | 32.520 | 63.699 | 25.738 | 1.00 | 57.23 | W | O |
| ATOM | 2258 | O | HOH | W | 521 | −11.168 | 62.126 | 35.907 | 1.00 | 65.36 | W | O |
| ATOM | 2259 | O | HOH | W | 522 | 13.702 | 76.196 | 48.300 | 1.00 | 61.59 | W | O |
| ATOM | 2260 | O | HOH | W | 523 | 1.241 | 58.718 | 25.331 | 1.00 | 64.44 | W | O |
| ATOM | 2261 | O | HOH | W | 524 | 14.477 | 78.178 | 21.588 | 1.00 | 64.83 | W | O |
| ATOM | 2262 | O | HOH | W | 525 | 12.372 | 54.887 | 20.646 | 1.00 | 60.88 | W | O |
| ATOM | 2263 | O | HOH | W | 526 | 7.266 | 74.256 | 14.263 | 1.00 | 39.73 | W | O |
| ATOM | 2264 | O | HOH | W | 527 | 20.091 | 44.006 | 35.105 | 1.00 | 50.82 | W | O |
| ATOM | 2265 | O | HOH | W | 528 | 1.165 | 69.375 | 46.475 | 1.00 | 57.89 | W | O |
| ATOM | 2266 | O | HOH | W | 529 | 19.142 | 46.127 | 35.660 | 1.00 | 45.19 | W | O |
| ATOM | 2267 | O | HOH | W | 530 | 42.086 | 55.304 | 19.791 | 1.00 | 71.79 | W | O |
| ATOM | 2268 | O | HOH | W | 531 | 25.087 | 50.111 | 39.148 | 1.00 | 63.76 | W | O |
| ATOM | 2269 | O | HOH | W | 532 | 5.318 | 61.373 | 18.508 | 1.00 | 62.59 | W | O |
| ATOM | 2270 | O | HOH | W | 533 | 29.675 | 78.586 | 23.627 | 1.00 | 58.56 | W | O |
| ATOM | 2271 | O | HOH | W | 534 | 19.557 | 76.701 | 12.869 | 1.00 | 68.72 | W | O |
| ATOM | 2272 | O | HOH | W | 535 | 42.115 | 57.119 | 21.522 | 1.00 | 71.32 | W | O |
| ATOM | 2273 | O | HOH | W | 536 | 0.634 | 77.003 | 19.831 | 1.00 | 100.00 | W | O |
| ATOM | 2274 | O | HOH | W | 537 | 19.709 | 88.994 | 42.992 | 1.00 | 58.23 | W | O |
| ATOM | 2275 | O | HOH | W | 538 | 13.524 | 50.624 | 47.508 | 1.00 | 75.63 | W | O |
| ATOM | 2276 | O | HOH | W | 539 | 11.617 | 86.001 | 30.094 | 1.00 | 68.80 | W | O |
| ATOM | 2277 | O | HOH | W | 540 | −7.680 | 59.135 | 43.088 | 1.00 | 61.92 | W | O |
| TER | 2278 | | HOH | W | 205 | | | | | | W | |
| ATOM | 2279 | C1 | FRA | V | 541 | 18.019 | 80.374 | 32.848 | 1.00 | 57.37 | V | C |
| ATOM | 2280 | C2 | FRA | V | 541 | 17.378 | 79.416 | 33.865 | 1.00 | 55.67 | V | C |
| ATOM | 2281 | C3 | FRA | V | 541 | 17.724 | 79.837 | 35.320 | 1.00 | 57.54 | V | C |
| ATOM | 2282 | O4 | FRA | V | 541 | 17.702 | 79.994 | 31.523 | 1.00 | 54.83 | V | O |
| ATOM | 2283 | O5 | FRA | V | 541 | 15.964 | 79.445 | 33.671 | 1.00 | 53.75 | V | O |
| ATOM | 2284 | O6 | FRA | V | 541 | 16.818 | 79.285 | 36.284 | 1.00 | 58.10 | V | O |
| ATOM | 2285 | O | HOH | V | 542 | 21.116 | 58.251 | 20.758 | 1.00 | 34.64 | V | O |
| TER | 2286 | | HOH | V | 2 | | | | | | V | |
| END | | | | | | | | | | | | |

TABLE 2 coordinates for the two molecules in the asymmetric unit of [T287] Aurora A (122–396) in complex with an inhibitor of formula II in space group $P2_1$ REMARK [No title given]
REMARK [No title given]
REMARK [No title given]
REMARK Aurora complex with M535136. Refined structure. Solved by
REMARK molecular replacement using a partly refined aurora structure
REMARK from the trigonal crystal form. Original MR model derived
REMARK from a PKA alignment. Inhibitor occupies much of active site
REMARK cleft and usual interactions at adenine site. Superposition
REMARK with PKA shows a very wide, open active site cleft.
REMARK coordinates from restrained individual B-factor refinement
REMARK refinement resolution: 500.0–2.1 A
REMARK starting r = 0.2306 free_r = 0.2716
REMARK final r = 0.2256 free_r = 0.2677
REMARK B rmsd for bonded mainchain atoms = 1.521 target = 1.5
REMARK B rmsd for bonded sidechain atoms = 2.205 target = 2.0
REMARK B rmsd for angle mainchain atoms = 2.492 target = 2.0
REMARK B rmsd for angle sidechain atoms = 3.350 target = 2.5
REMARK rweight = 0.1000 (with wa = 3.00741)
REMARK target = mlf steps = 30

TABLE 2-continued coordinates for the two molecules in the asymmetric unit of [T287] Aurora
A (122–396) in complex with an inhibitor of formula II in space group P2₁

REMARK sg = P2(1)a = 52.603 b = 88.421 c = 67.832 alpha = 90 beta = 90.013 gamma = 90
REMARK parameter file 1: MSI_CNX_TOPPAR:protein_rep.param
REMARK parameter file 2: fra.par
REMARK parameter file 3: MSI_CNX_TOPPAR:water_rep.param
REMARK molecular structure file: reb9.mtf
REMARK input coordinates: anneal_reb_1.pdb
REMARK reflection file = aurora-p21.cv
REMARK ncs = none
REMARK B-correction resolution: 6.0–2.1
REMARK initial B-factor correction applied to fobs:
REMARK B11 = 1.629 B22 = −1.218 B33 = −0.411
REMARK B12 = 0.000 B13 = 0.000 B23 = 0.000
REMARK B-factor correction applied to coordinate array B: −0.233
REMARK bulk solvent: (Mask)density level = 0.31769 e/A^3, B-factor = 51.8227 A^2
REMARK reflections with |Fobs|/sigma_F < 0.0 rejected
REMARK reflections with |Fobs| > 10000 * rms(Fobs) rejected
REMARK theoretical total number of refl. in resol. range:   36279(100.0%)
REMARK number of unobserved reflections (no entry or |F| = 0): 9992 (27.5%)
REMARK number of reflections rejected:       0 (0.0%)
REMARK total number of reflections used:    26287 (72.5%)
REMARK number of reflections in working set:     25018 (69.0%)
REMARK number of reflections in test set:     1269 (3.5%)
REMARK FILENAME = "bindividual.pdb"
REMARK DATE: Feb-12-2001 13:11:17   created by user: mar345
REMARK Written by CNX VERSION: 2000.1
CRYST1 52.603 88.421 67.832 90.00 90.01 90.00 P 1 21 1
SCALE1    0.019010 0.000000 0.000003    0.00000
SCALE2    0.000000 0.011310 0.000000    0.00000
SCALE3    0.000000 0.000000 0.014742    0.00000

| | | | | | | | | | | | |
|---|---|---|---|---|---|---|---|---|---|---|---|
| ATOM | 1 | CB | GLN | A | 126 | 32.162 | 112.290 | 73.232 | 1.00 | 49.44 A | C |
| ATOM | 2 | CG | GLN | A | 126 | 32.015 | 113.484 | 72.284 | 1.00 | 51.02 A | C |
| ATOM | 3 | CD | GLN | A | 126 | 32.563 | 113.219 | 70.887 | 1.00 | 51.57 A | C |
| ATOM | 4 | OE1 | GLN | A | 126 | 31.961 | 112.499 | 70.089 | 1.00 | 51.89 A | O |
| ATOM | 5 | NE2 | GLN | A | 126 | 33.717 | 113.803 | 70.589 | 1.00 | 52.45 A | N |
| ATOM | 6 | C | GLN | A | 126 | 31.499 | 110.010 | 73.975 | 1.00 | 46.32 A | C |
| ATOM | 7 | O | GLN | A | 126 | 31.745 | 110.223 | 75.161 | 1.00 | 48.00 A | O |
| ATOM | 8 | N | GLN | A | 126 | 29.765 | 111.655 | 73.328 | 1.00 | 47.98 A | N |
| ATOM | 9 | CA | GLN | A | 126 | 31.143 | 111.162 | 73.040 | 1.00 | 47.45 A | C |
| ATOM | 10 | N | TRP | A | 127 | 31.523 | 108.792 | 73.443 | 1.00 | 43.51 A | N |
| ATOM | 11 | CA | TRP | A | 127 | 31.864 | 107.618 | 74.238 | 1.00 | 40.38 A | C |
| ATOM | 12 | CB | TRP | A | 127 | 30.998 | 106.418 | 73.836 | 1.00 | 40.28 A | C |
| ATOM | 13 | CG | TRP | A | 127 | 29.528 | 106.692 | 73.786 | 1.00 | 37.53 A | C |
| ATOM | 14 | CD2 | TRP | A | 127 | 28.575 | 106.442 | 74.826 | 1.00 | 36.46 A | C |
| ATOM | 15 | CE2 | TRP | A | 127 | 27.309 | 106.835 | 74.335 | 1.00 | 36.39 A | C |
| ATOM | 16 | CE3 | TRP | A | 127 | 28.669 | 105.924 | 76.123 | 1.00 | 34.75 A | C |
| ATOM | 17 | CD1 | TRP | A | 127 | 28.827 | 107.215 | 72.740 | 1.00 | 37.84 A | C |
| ATOM | 18 | NE1 | TRP | A | 127 | 27.490 | 107.302 | 73.060 | 1.00 | 36.81 A | N |
| ATOM | 19 | CZ2 | TRP | A | 127 | 26.142 | 106.725 | 75.097 | 1.00 | 36.10 A | C |
| ATOM | 20 | CZ3 | TRP | A | 127 | 27.507 | 105.814 | 76.884 | 1.00 | 37.35 A | C |
| ATOM | 21 | CH2 | TRP | A | 127 | 26.260 | 106.214 | 76.366 | 1.00 | 37.47 A | C |
| ATOM | 22 | C | TRP | A | 127 | 33.329 | 107.249 | 74.024 | 1.00 | 38.84 A | C |
| ATOM | 23 | O | TRP | A | 127 | 33.984 | 107.765 | 73.117 | 1.00 | 37.85 A | O |
| ATOM | 24 | N | ALA | A | 128 | 33.835 | 106.349 | 74.858 | 1.00 | 36.22 A | N |
| ATOM | 25 | CA | ALA | A | 128 | 35.212 | 105.891 | 74.741 | 1.00 | 35.97 A | C |
| ATOM | 26 | CB | ALA | A | 128 | 36.136 | 106.763 | 75.582 | 1.00 | 35.91 A | C |
| ATOM | 27 | C | ALA | A | 128 | 35.289 | 104.441 | 75.200 | 1.00 | 35.31 A | C |
| ATOM | 28 | O | ALA | A | 128 | 34.514 | 104.015 | 76.056 | 1.00 | 34.64 A | O |
| ATOM | 29 | N | LEU | A | 129 | 36.221 | 103.688 | 74.626 | 1.00 | 33.98 A | N |
| ATOM | 30 | CA | LEU | A | 129 | 36.385 | 102.283 | 74.976 | 1.00 | 34.14 A | C |
| ATOM | 31 | CB | LEU | A | 129 | 37.556 | 101.681 | 74.191 | 1.00 | 33.48 A | C |
| ATOM | 32 | CG | LEU | A | 129 | 37.816 | 100.175 | 74.339 | 1.00 | 35.39 A | C |
| ATOM | 33 | CD1 | LEU | A | 129 | 36.514 | 99.396 | 74.175 | 1.00 | 34.09 A | C |
| ATOM | 34 | CD2 | LEU | A | 129 | 38.841 | 99.729 | 73.300 | 1.00 | 33.75 A | C |
| ATOM | 35 | C | LEU | A | 129 | 36.596 | 102.092 | 76.476 | 1.00 | 33.77 A | C |
| ATOM | 36 | O | LEU | A | 129 | 36.028 | 101.182 | 77.083 | 1.00 | 33.18 A | O |
| ATOM | 37 | N | ALA | A | 130 | 37.389 | 102.974 | 77.072 | 1.00 | 34.08 A | N |
| ATOM | 38 | CA | ALA | A | 130 | 37.691 | 102.918 | 78.500 | 1.00 | 33.53 A | C |
| ATOM | 39 | CB | ALA | A | 130 | 38.757 | 103.954 | 78.836 | 1.00 | 33.52 A | C |
| ATOM | 40 | C | ALA | A | 130 | 36.483 | 103.112 | 79.415 | 1.00 | 33.70 A | C |
| ATOM | 41 | O | ALA | A | 130 | 36.615 | 103.026 | 80.633 | 1.00 | 35.42 A | O |
| ATOM | 42 | N | ASP | A | 131 | 35.315 | 103.380 | 78.841 | 1.00 | 33.03 A | N |
| ATOM | 43 | CA | ASP | A | 131 | 34.092 | 103.588 | 79.632 | 1.00 | 31.53 A | C |
| ATOM | 44 | CB | ASP | A | 131 | 33.094 | 104.444 | 78.849 | 1.00 | 35.30 A | C |
| ATOM | 45 | CG | ASP | A | 131 | 33.415 | 105.919 | 78.898 | 1.00 | 37.25 A | C |
| ATOM | 46 | OD1 | ASP | A | 131 | 32.854 | 106.665 | 78.066 | 1.00 | 40.43 A | O |
| ATOM | 47 | OD2 | ASP | A | 131 | 34.209 | 106.335 | 79.770 | 1.00 | 39.65 A | O |

TABLE 2-continued coordinates for the two molecules in the asymmetric unit of [T287] Aurora
A (122–396) in complex with an inhibitor of formula II in space group P2₁

| ATOM | 48 | C | ASP | A | 131 | 33.404 | 102.274 | 79.970 | 1.00 | 29.88 | A | C |
|------|----|----|-----|---|-----|--------|---------|--------|------|-------|---|---|
| ATOM | 49 | O | ASP | A | 131 | 32.510 | 102.223 | 80.816 | 1.00 | 27.49 | A | O |
| ATOM | 50 | N | PHE | A | 132 | 33.836 | 101.211 | 79.305 | 1.00 | 28.87 | A | N |
| ATOM | 51 | CA | PHE | A | 132 | 33.232 | 99.906 | 79.487 | 1.00 | 27.75 | A | C |
| ATOM | 52 | CB | PHE | A | 132 | 32.617 | 99.450 | 78.168 | 1.00 | 25.08 | A | C |
| ATOM | 53 | CG | PHE | A | 132 | 31.820 | 100.504 | 77.478 | 1.00 | 24.75 | A | C |
| ATOM | 54 | CD1 | PHE | A | 132 | 30.535 | 100.808 | 77.899 | 1.00 | 22.62 | A | C |
| ATOM | 55 | CD2 | PHE | A | 132 | 32.356 | 101.195 | 76.403 | 1.00 | 22.91 | A | C |
| ATOM | 56 | CE1 | PHE | A | 132 | 29.794 | 101.788 | 77.249 | 1.00 | 26.12 | A | C |
| ATOM | 57 | CE2 | PHE | A | 132 | 31.626 | 102.174 | 75.749 | 1.00 | 25.55 | A | C |
| ATOM | 58 | CZ | PHE | A | 132 | 30.340 | 102.471 | 76.173 | 1.00 | 23.27 | A | C |
| ATOM | 59 | C | PHE | A | 132 | 34.164 | 98.801 | 79.947 | 1.00 | 27.73 | A | C |
| ATOM | 60 | O | PHE | A | 132 | 35.375 | 98.852 | 79.736 | 1.00 | 27.55 | A | O |
| ATOM | 61 | N | GLU | A | 133 | 33.560 | 97.798 | 80.575 | 1.00 | 27.29 | A | N |
| ATOM | 62 | CA | GLU | A | 133 | 34.254 | 96.596 | 81.004 | 1.00 | 26.91 | A | C |
| ATOM | 63 | CB | GLU | A | 133 | 33.863 | 96.187 | 82.415 | 1.00 | 29.96 | A | C |
| ATOM | 64 | CG | GLU | A | 133 | 34.290 | 97.120 | 83.506 | 1.00 | 35.88 | A | C |
| ATOM | 65 | CD | GLU | A | 133 | 33.945 | 96.546 | 84.858 | 1.00 | 39.31 | A | C |
| ATOM | 66 | OE1 | GLU | A | 133 | 34.491 | 95.469 | 85.189 | 1.00 | 40.33 | A | O |
| ATOM | 67 | OE2 | GLU | A | 133 | 33.120 | 97.153 | 85.576 | 1.00 | 40.57 | A | O |
| ATOM | 68 | C | GLU | A | 133 | 33.665 | 95.582 | 80.034 | 1.00 | 24.82 | A | C |
| ATOM | 69 | O | GLU | A | 133 | 32.444 | 95.536 | 79.854 | 1.00 | 21.66 | A | O |
| ATOM | 70 | N | ILE | A | 134 | 34.523 | 94.787 | 79.410 | 1.00 | 22.94 | A | N |
| ATOM | 71 | CA | ILE | A | 134 | 34.091 | 93.784 | 78.443 | 1.00 | 22.52 | A | C |
| ATOM | 72 | CB | ILE | A | 134 | 35.115 | 93.688 | 77.286 | 1.00 | 23.20 | A | C |
| ATOM | 73 | CG2 | ILE | A | 134 | 34.652 | 92.704 | 76.240 | 1.00 | 23.57 | A | C |
| ATOM | 74 | CG1 | ILE | A | 134 | 35.317 | 95.073 | 76.668 | 1.00 | 26.34 | A | C |
| ATOM | 75 | CD1 | ILE | A | 134 | 34.059 | 95.709 | 76.121 | 1.00 | 27.45 | A | C |
| ATOM | 76 | C | ILE | A | 134 | 33.935 | 92.413 | 79.093 | 1.00 | 23.10 | A | C |
| ATOM | 77 | O | ILE | A | 134 | 34.737 | 92.024 | 79.941 | 1.00 | 24.84 | A | O |
| ATOM | 78 | N | GLY | A | 135 | 32.904 | 91.679 | 78.681 | 1.00 | 24.78 | A | N |
| ATOM | 79 | CA | GLY | A | 135 | 32.648 | 90.355 | 79.231 | 1.00 | 22.02 | A | C |
| ATOM | 80 | C | GLY | A | 135 | 32.677 | 89.246 | 78.193 | 1.00 | 20.46 | A | C |
| ATOM | 81 | O | GLY | A | 135 | 33.404 | 89.330 | 77.212 | 1.00 | 18.06 | A | O |
| ATOM | 82 | N | ARG | A | 136 | 31.867 | 88.212 | 78.391 | 1.00 | 23.35 | A | N |
| ATOM | 83 | CA | ARG | A | 136 | 31.852 | 87.077 | 77.464 | 1.00 | 25.21 | A | C |
| ATOM | 84 | CB | ARG | A | 136 | 31.078 | 85.902 | 78.064 | 1.00 | 26.99 | A | C |
| ATOM | 85 | CG | ARG | A | 136 | 29.601 | 86.174 | 78.284 | 1.00 | 28.67 | A | C |
| ATOM | 86 | CD | ARG | A | 136 | 28.870 | 84.914 | 78.725 | 1.00 | 29.20 | A | C |
| ATOM | 87 | NE | ARG | A | 136 | 27.497 | 85.201 | 79.121 | 1.00 | 31.23 | A | N |
| ATOM | 88 | CZ | ARG | A | 136 | 26.417 | 84.687 | 78.532 | 1.00 | 34.58 | A | C |
| ATOM | 89 | NH1 | ARG | A | 136 | 26.546 | 83.847 | 77.512 | 1.00 | 33.49 | A | N |
| ATOM | 90 | NH2 | ARG | A | 136 | 25.204 | 85.028 | 78.958 | 1.00 | 34.12 | A | N |
| ATOM | 91 | C | ARG | A | 136 | 31.285 | 87.369 | 76.084 | 1.00 | 26.22 | A | C |
| ATOM | 92 | O | ARG | A | 136 | 30.450 | 88.260 | 75.916 | 1.00 | 24.47 | A | O |
| ATOM | 93 | N | PRO | A | 137 | 31.749 | 86.620 | 75.070 | 1.00 | 26.55 | A | N |
| ATOM | 94 | CD | PRO | A | 137 | 32.907 | 85.714 | 75.122 | 1.00 | 27.27 | A | C |
| ATOM | 95 | CA | PRO | A | 137 | 31.285 | 86.786 | 73.690 | 1.00 | 26.49 | A | C |
| ATOM | 96 | CB | PRO | A | 137 | 32.236 | 85.898 | 72.887 | 1.00 | 25.92 | A | C |
| ATOM | 97 | CG | PRO | A | 137 | 33.477 | 85.858 | 73.729 | 1.00 | 25.14 | A | C |
| ATOM | 98 | C | PRO | A | 137 | 29.856 | 86.276 | 73.609 | 1.00 | 27.01 | A | C |
| ATOM | 99 | O | PRO | A | 137 | 29.538 | 85.226 | 74.169 | 1.00 | 26.92 | A | O |
| ATOM | 100 | N | LEU | A | 138 | 28.995 | 87.018 | 72.924 | 1.00 | 27.88 | A | N |
| ATOM | 101 | CA | LEU | A | 138 | 27.602 | 86.615 | 72.779 | 1.00 | 29.09 | A | C |
| ATOM | 102 | CB | LEU | A | 138 | 26.691 | 87.843 | 72.865 | 1.00 | 27.78 | A | C |
| ATOM | 103 | CG | LEU | A | 138 | 26.450 | 88.473 | 74.240 | 1.00 | 26.22 | A | C |
| ATOM | 104 | CD1 | LEU | A | 138 | 27.758 | 88.636 | 74.965 | 1.00 | 29.17 | A | C |
| ATOM | 105 | CD2 | LEU | A | 138 | 25.771 | 89.816 | 74.075 | 1.00 | 20.07 | A | C |
| ATOM | 106 | C | LEU | A | 138 | 27.403 | 85.907 | 71.438 | 1.00 | 30.81 | A | C |
| ATOM | 107 | O | LEU | A | 138 | 26.619 | 84.964 | 71.329 | 1.00 | 32.24 | A | O |
| ATOM | 108 | N | GLY | A | 139 | 28.124 | 86.367 | 70.424 | 1.00 | 32.34 | A | N |
| ATOM | 109 | CA | GLY | A | 139 | 28.014 | 85.773 | 69.109 | 1.00 | 35.00 | A | C |
| ATOM | 110 | C | GLY | A | 139 | 29.136 | 86.215 | 68.190 | 1.00 | 38.07 | A | C |
| ATOM | 111 | O | GLY | A | 139 | 29.859 | 87.166 | 68.488 | 1.00 | 38.60 | A | O |
| ATOM | 112 | N | LYS | A | 140 | 29.281 | 85.519 | 67.066 | 1.00 | 41.32 | A | N |
| ATOM | 113 | CA | LYS | A | 140 | 30.320 | 85.831 | 66.092 | 1.00 | 43.10 | A | C |
| ATOM | 114 | CB | LYS | A | 140 | 31.244 | 84.633 | 65.917 | 1.00 | 44.15 | A | C |
| ATOM | 115 | C | LYS | A | 140 | 29.703 | 86.216 | 64.751 | 1.00 | 44.25 | A | C |
| ATOM | 116 | O | LYS | A | 140 | 28.615 | 85.755 | 64.403 | 1.00 | 43.38 | A | O |
| ATOM | 117 | N | GLY | A | 141 | 30.406 | 87.066 | 64.007 | 1.00 | 45.98 | A | N |
| ATOM | 118 | CA | GLY | A | 141 | 29.939 | 87.527 | 62.705 | 1.00 | 47.85 | A | C |
| ATOM | 119 | CB | GLY | A | 141 | 29.270 | 88.895 | 62.842 | 1.00 | 49.28 | A | C |
| ATOM | 120 | C | GLY | A | 141 | 31.109 | 87.613 | 61.731 | 1.00 | 48.68 | A | C |
| ATOM | 121 | O | GLY | A | 141 | 32.235 | 87.245 | 62.073 | 1.00 | 48.92 | A | O |
| ATOM | 122 | N | ALA | A | 142 | 30.842 | 88.111 | 60.525 | 1.00 | 48.78 | A | N |
| ATOM | 123 | CA | ALA | A | 142 | 31.877 | 88.226 | 59.502 | 1.00 | 47.65 | A | C |

TABLE 2-continued coordinates for the two molecules in the asymmetric unit of [T287] Aurora
A (122–396) in complex with an inhibitor of formula II in space group P2$_1$

| ATOM | 124 | CB | ALA | A | 142 | 31.247 | 88.156 | 58.115 | 1.00 | 48.08 A | C |
|---|---|---|---|---|---|---|---|---|---|---|---|
| ATOM | 125 | C | ALA | A | 142 | 32.730 | 89.488 | 59.620 | 1.00 | 46.86 A | C |
| ATOM | 126 | O | ALA | A | 142 | 33.828 | 89.550 | 59.063 | 1.00 | 46.94 A | O |
| ATOM | 127 | N | PHE | A | 143 | 32.242 | 90.492 | 60.343 | 1.00 | 45.34 A | N |
| ATOM | 128 | CA | PHE | A | 143 | 33.004 | 91.731 | 60.477 | 1.00 | 43.93 A | C |
| ATOM | 129 | CB | PHE | A | 143 | 32.193 | 92.907 | 59.920 | 1.00 | 43.56 A | C |
| ATOM | 130 | CG | PHE | A | 143 | 31.628 | 92.653 | 58.550 | 1.00 | 43.95 A | C |
| ATOM | 131 | CD1 | PHE | A | 143 | 30.352 | 92.118 | 58.397 | 1.00 | 44.56 A | C |
| ATOM | 132 | CD2 | PHE | A | 143 | 32.385 | 92.915 | 57.413 | 1.00 | 44.21 A | C |
| ATOM | 133 | CE1 | PHE | A | 143 | 29.836 | 91.845 | 57.129 | 1.00 | 44.68 A | C |
| ATOM | 134 | CE2 | PHE | A | 143 | 31.881 | 92.645 | 56.141 | 1.00 | 44.72 A | C |
| ATOM | 135 | CZ | PHE | A | 143 | 30.604 | 92.109 | 55.999 | 1.00 | 44.72 A | C |
| ATOM | 136 | C | PHE | A | 143 | 33.456 | 92.045 | 61.901 | 1.00 | 42.13 A | C |
| ATOM | 137 | O | PHE | A | 143 | 34.137 | 93.043 | 62.132 | 1.00 | 41.48 A | O |
| ATOM | 138 | N | GLY | A | 144 | 33.085 | 91.183 | 62.846 | 1.00 | 40.73 A | N |
| ATOM | 139 | CA | GLY | A | 144 | 33.452 | 91.396 | 64.235 | 1.00 | 37.57 A | C |
| ATOM | 140 | C | GLY | A | 144 | 32.537 | 90.631 | 65.171 | 1.00 | 36.23 A | C |
| ATOM | 141 | O | GLY | A | 144 | 31.625 | 89.938 | 64.721 | 1.00 | 35.58 A | O |
| ATOM | 142 | N | ASN | A | 145 | 32.763 | 90.763 | 66.474 | 1.00 | 34.55 A | N |
| ATOM | 143 | CA | ASN | A | 145 | 31.947 | 90.052 | 67.453 | 1.00 | 32.65 A | C |
| ATOM | 144 | CB | ASN | A | 145 | 32.842 | 89.187 | 68.341 | 1.00 | 34.14 A | C |
| ATOM | 145 | CG | ASN | A | 145 | 33.913 | 88.458 | 67.549 | 1.00 | 36.27 A | C |
| ATOM | 146 | OD1 | ASN | A | 145 | 35.068 | 88.893 | 67.489 | 1.00 | 36.74 A | O |
| ATOM | 147 | ND2 | ASN | A | 145 | 33.531 | 87.352 | 66.924 | 1.00 | 35.73 A | N |
| ATOM | 148 | C | ASN | A | 145 | 31.096 | 90.959 | 68.331 | 1.00 | 30.37 A | C |
| ATOM | 149 | O | ASN | A | 145 | 31.232 | 92.183 | 68.308 | 1.00 | 31.36 A | O |
| ATOM | 150 | N | VAL | A | 146 | 30.214 | 90.337 | 69.107 | 1.00 | 27.53 A | N |
| ATOM | 151 | CA | VAL | A | 146 | 29.326 | 91.051 | 70.013 | 1.00 | 24.74 A | C |
| ATOM | 152 | CB | VAL | A | 146 | 27.836 | 90.769 | 69.684 | 1.00 | 26.28 A | C |
| ATOM | 153 | CG1 | VAL | A | 146 | 26.932 | 91.644 | 70.548 | 1.00 | 24.90 A | C |
| ATOM | 154 | CG2 | VAL | A | 146 | 27.573 | 91.006 | 68.211 | 1.00 | 28.46 A | C |
| ATOM | 155 | C | VAL | A | 146 | 29.605 | 90.546 | 71.424 | 1.00 | 22.82 A | C |
| ATOM | 156 | O | VAL | A | 146 | 29.599 | 89.341 | 71.660 | 1.00 | 24.33 A | O |
| ATOM | 157 | N | TYR | A | 147 | 29.836 | 91.461 | 72.357 | 1.00 | 20.11 A | N |
| ATOM | 158 | CA | TYR | A | 147 | 30.125 | 91.081 | 73.738 | 1.00 | 18.69 A | C |
| ATOM | 159 | CB | TYR | A | 147 | 31.530 | 91.523 | 74.145 | 1.00 | 16.30 A | C |
| ATOM | 160 | CG | TYR | A | 147 | 32.646 | 91.083 | 73.231 | 1.00 | 20.13 A | C |
| ATOM | 161 | CD1 | TYR | A | 147 | 32.849 | 91.701 | 71.997 | 1.00 | 19.62 A | C |
| ATOM | 162 | CE1 | TYR | A | 147 | 33.898 | 91.318 | 71.162 | 1.00 | 22.76 A | C |
| ATOM | 163 | CD2 | TYR | A | 147 | 33.519 | 90.059 | 73.610 | 1.00 | 19.37 A | C |
| ATOM | 164 | CE2 | TYR | A | 147 | 34.574 | 89.661 | 72.777 | 1.00 | 20.22 A | C |
| ATOM | 165 | CZ | TYR | A | 147 | 34.755 | 90.298 | 71.559 | 1.00 | 23.88 A | C |
| ATOM | 166 | OH | TYR | A | 147 | 35.788 | 89.925 | 70.727 | 1.00 | 27.07 A | O |
| ATOM | 167 | C | TYR | A | 147 | 29.177 | 91.690 | 74.757 | 1.00 | 17.31 A | C |
| ATOM | 168 | O | TYR | A | 147 | 28.568 | 92.731 | 74.521 | 1.00 | 16.25 A | O |
| ATOM | 169 | N | LEU | A | 148 | 29.071 | 91.026 | 75.903 | 1.00 | 17.91 A | N |
| ATOM | 170 | CA | LEU | A | 148 | 28.283 | 91.544 | 76.996 | 1.00 | 16.28 A | C |
| ATOM | 171 | CB | LEU | A | 148 | 28.040 | 90.472 | 78.054 | 1.00 | 19.47 A | C |
| ATOM | 172 | CG | LEU | A | 148 | 27.148 | 90.939 | 79.205 | 1.00 | 19.54 A | C |
| ATOM | 173 | CD1 | LEU | A | 148 | 25.844 | 90.198 | 79.117 | 1.00 | 23.07 A | C |
| ATOM | 174 | CD2 | LEU | A | 148 | 27.809 | 90.695 | 80.561 | 1.00 | 21.88 A | C |
| ATOM | 175 | C | LEU | A | 148 | 29.230 | 92.599 | 77.555 | 1.00 | 16.81 A | C |
| ATOM | 176 | O | LEU | A | 148 | 30.449 | 92.387 | 77.604 | 1.00 | 17.66 A | O |
| ATOM | 177 | N | ALA | A | 149 | 28.693 | 93.740 | 77.962 | 1.00 | 17.06 A | N |
| ATOM | 178 | CA | ALA | A | 149 | 29.529 | 94.794 | 78.504 | 1.00 | 15.77 A | C |
| ATOM | 179 | CB | ALA | A | 149 | 29.953 | 95.744 | 77.400 | 1.00 | 16.74 A | C |
| ATOM | 180 | C | ALA | A | 149 | 28.778 | 95.540 | 79.591 | 1.00 | 19.32 A | C |
| ATOM | 181 | O | ALA | A | 149 | 27.585 | 95.302 | 79.815 | 1.00 | 17.25 A | O |
| ATOM | 182 | N | ARG | A | 150 | 29.483 | 96.442 | 80.262 | 1.00 | 18.18 A | N |
| ATOM | 183 | CA | ARG | A | 150 | 28.903 | 97.215 | 81.338 | 1.00 | 20.87 A | C |
| ATOM | 184 | CB | ARG | A | 150 | 29.073 | 96.435 | 82.651 | 1.00 | 24.33 A | C |
| ATOM | 185 | CG | ARG | A | 150 | 28.543 | 97.119 | 83.890 | 1.00 | 30.19 A | C |
| ATOM | 186 | CD | ARG | A | 150 | 28.265 | 96.096 | 84.995 | 1.00 | 32.40 A | C |
| ATOM | 187 | NE | ARG | A | 150 | 29.370 | 95.162 | 85.167 | 1.00 | 33.70 A | N |
| ATOM | 188 | CZ | ARG | A | 150 | 29.308 | 94.053 | 85.897 | 1.00 | 35.11 A | C |
| ATOM | 189 | NH1 | ARG | A | 150 | 28.186 | 93.735 | 86.533 | 1.00 | 36.02 A | N |
| ATOM | 190 | NH2 | ARG | A | 150 | 30.365 | 93.252 | 85.983 | 1.00 | 32.01 A | N |
| ATOM | 191 | C | ARG | A | 150 | 29.593 | 98.574 | 81.422 | 1.00 | 22.84 A | C |
| ATOM | 192 | O | ARG | A | 150 | 30.808 | 98.675 | 81.180 | 1.00 | 18.77 A | O |
| ATOM | 193 | N | GLU | A | 151 | 28.819 | 99.618 | 81.727 | 1.00 | 23.89 A | N |
| ATOM | 194 | CA | GLU | A | 151 | 29.383 | 100.958 | 81.874 | 1.00 | 26.53 A | C |
| ATOM | 195 | CB | GLU | A | 151 | 28.286 | 102.033 | 81.883 | 1.00 | 26.52 A | C |
| ATOM | 196 | CG | GLU | A | 151 | 27.420 | 102.099 | 80.629 | 1.00 | 28.40 A | C |
| ATOM | 197 | CD | GLU | A | 151 | 26.365 | 103.198 | 80.704 | 1.00 | 29.97 A | C |
| ATOM | 198 | OE1 | GLU | A | 151 | 25.724 | 103.337 | 81.765 | 1.00 | 29.43 A | O |
| ATOM | 199 | OE2 | GLU | A | 151 | 26.164 | 103.917 | 79.704 | 1.00 | 31.53 A | O |

TABLE 2-continued coordinates for the two molecules in the asymmetric unit of [T287] Aurora
A (122–396) in complex with an inhibitor of formula II in space group P2₁

| ATOM | 200 | C | GLU | A | 151 | 30.049 | 100.897 | 83.242 | 1.00 | 27.68 | A | C |
|---|---|---|---|---|---|---|---|---|---|---|---|---|
| ATOM | 201 | O | GLU | A | 151 | 29.390 | 100.577 | 84.230 | 1.00 | 28.40 | A | O |
| ATOM | 202 | N | LYS | A | 152 | 31.346 | 101.195 | 83.288 | 1.00 | 30.73 | A | N |
| ATOM | 203 | CA | LYS | A | 152 | 32.135 | 101.140 | 84.523 | 1.00 | 33.53 | A | C |
| ATOM | 204 | CB | LYS | A | 152 | 33.545 | 101.691 | 84.288 | 1.00 | 34.64 | A | C |
| ATOM | 205 | CG | LYS | A | 152 | 34.458 | 100.758 | 83.531 | 1.00 | 37.25 | A | C |
| ATOM | 206 | CD | LYS | A | 152 | 35.836 | 101.367 | 83.353 | 1.00 | 39.94 | A | C |
| ATOM | 207 | CE | LYS | A | 152 | 36.759 | 100.408 | 82.629 | 1.00 | 40.54 | A | C |
| ATOM | 208 | NZ | LYS | A | 152 | 38.093 | 101.012 | 82.399 | 1.00 | 41.98 | A | N |
| ATOM | 209 | C | LYS | A | 152 | 31.548 | 101.842 | 85.727 | 1.00 | 33.54 | A | C |
| ATOM | 210 | O | LYS | A | 152 | 31.401 | 101.239 | 86.790 | 1.00 | 35.42 | A | O |
| ATOM | 211 | N | GLN | A | 153 | 31.222 | 103.117 | 85.564 | 1.00 | 33.48 | A | N |
| ATOM | 212 | CA | GLN | A | 153 | 30.669 | 103.904 | 86.655 | 1.00 | 34.22 | A | C |
| ATOM | 213 | CB | GLN | A | 153 | 30.568 | 105.370 | 86.231 | 1.00 | 36.43 | A | C |
| ATOM | 214 | CG | GLN | A | 153 | 31.890 | 105.975 | 85.797 | 1.00 | 39.77 | A | C |
| ATOM | 215 | CD | GLN | A | 153 | 32.954 | 105.939 | 86.889 | 1.00 | 42.68 | A | C |
| ATOM | 216 | OE1 | GLN | A | 153 | 34.107 | 106.304 | 86.657 | 1.00 | 46.22 | A | O |
| ATOM | 217 | NE2 | GLN | A | 153 | 32.572 | 105.503 | 88.082 | 1.00 | 43.83 | A | N |
| ATOM | 218 | C | GLN | A | 153 | 29.316 | 103.424 | 87.182 | 1.00 | 33.78 | A | C |
| ATOM | 219 | O | GLN | A | 153 | 29.226 | 102.938 | 88.314 | 1.00 | 34.62 | A | O |
| ATOM | 220 | N | SER | A | 154 | 28.268 | 103.555 | 86.371 | 1.00 | 32.03 | A | N |
| ATOM | 221 | CA | SER | A | 154 | 26.929 | 103.156 | 86.794 | 1.00 | 29.99 | A | C |
| ATOM | 222 | CB | SER | A | 154 | 25.868 | 103.831 | 85.914 | 1.00 | 29.69 | A | C |
| ATOM | 223 | OG | SER | A | 154 | 26.050 | 103.510 | 84.551 | 1.00 | 29.28 | A | O |
| ATOM | 224 | C | SER | A | 154 | 26.661 | 101.657 | 86.845 | 1.00 | 29.81 | A | C |
| ATOM | 225 | O | SER | A | 154 | 25.646 | 101.236 | 87.398 | 1.00 | 29.38 | A | O |
| ATOM | 226 | N | LYS | A | 155 | 27.550 | 100.855 | 86.261 | 1.00 | 29.05 | A | N |
| ATOM | 227 | CA | LYS | A | 155 | 27.389 | 99.401 | 86.276 | 1.00 | 30.67 | A | C |
| ATOM | 228 | CB | LYS | A | 155 | 27.185 | 98.936 | 87.725 | 1.00 | 32.82 | A | C |
| ATOM | 229 | CG | LYS | A | 155 | 27.059 | 97.435 | 87.912 | 1.00 | 39.02 | A | C |
| ATOM | 230 | CD | LYS | A | 155 | 26.671 | 97.066 | 89.342 | 1.00 | 43.54 | A | C |
| ATOM | 231 | CE | LYS | A | 155 | 25.205 | 97.386 | 89.669 | 1.00 | 47.18 | A | C |
| ATOM | 232 | NZ | LYS | A | 155 | 24.902 | 98.848 | 89.800 | 1.00 | 49.30 | A | N |
| ATOM | 233 | C | LYS | A | 155 | 26.223 | 98.913 | 85.398 | 1.00 | 28.46 | A | C |
| ATOM | 234 | O | LYS | A | 155 | 25.706 | 97.812 | 85.590 | 1.00 | 27.89 | A | O |
| ATOM | 235 | N | PHE | A | 156 | 25.831 | 99.727 | 84.424 | 1.00 | 26.49 | A | N |
| ATOM | 236 | CA | PHE | A | 156 | 24.716 | 99.403 | 83.536 | 1.00 | 23.82 | A | C |
| ATOM | 237 | CB | PHE | A | 156 | 24.185 | 100.698 | 82.905 | 1.00 | 24.31 | A | C |
| ATOM | 238 | CG | PHE | A | 156 | 23.043 | 100.492 | 81.955 | 1.00 | 24.97 | A | C |
| ATOM | 239 | CD1 | PHE | A | 156 | 21.771 | 100.187 | 82.428 | 1.00 | 24.81 | A | C |
| ATOM | 240 | CD2 | PHE | A | 156 | 23.244 | 100.592 | 80.580 | 1.00 | 24.41 | A | C |
| ATOM | 241 | CE1 | PHE | A | 156 | 20.705 | 99.982 | 81.537 | 1.00 | 27.89 | A | C |
| ATOM | 242 | CE2 | PHE | A | 156 | 22.195 | 100.390 | 79.685 | 1.00 | 24.55 | A | C |
| ATOM | 243 | CZ | PHE | A | 156 | 20.920 | 100.084 | 80.163 | 1.00 | 25.32 | A | C |
| ATOM | 244 | C | PHE | A | 156 | 25.082 | 98.381 | 82.445 | 1.00 | 21.90 | A | C |
| ATOM | 245 | O | PHE | A | 156 | 26.019 | 98.582 | 81.676 | 1.00 | 21.26 | A | O |
| ATOM | 246 | N | ILE | A | 157 | 24.321 | 97.294 | 82.388 | 1.00 | 19.42 | A | N |
| ATOM | 247 | CA | ILE | A | 157 | 24.535 | 96.219 | 81.418 | 1.00 | 19.66 | A | C |
| ATOM | 248 | CB | ILE | A | 157 | 23.863 | 94.906 | 81.878 | 1.00 | 20.30 | A | C |
| ATOM | 249 | CG2 | ILE | A | 157 | 23.931 | 93.876 | 80.759 | 1.00 | 18.66 | A | C |
| ATOM | 250 | CG1 | ILE | A | 157 | 24.541 | 94.373 | 83.143 | 1.00 | 20.54 | A | C |
| ATOM | 251 | CD1 | ILE | A | 157 | 25.994 | 93.979 | 82.929 | 1.00 | 23.70 | A | C |
| ATOM | 252 | C | ILE | A | 157 | 23.996 | 96.515 | 80.018 | 1.00 | 20.08 | A | C |
| ATOM | 253 | O | ILE | A | 157 | 22.851 | 96.955 | 79.859 | 1.00 | 18.61 | A | O |
| ATOM | 254 | N | LEU | A | 158 | 24.819 | 96.239 | 79.011 | 1.00 | 18.01 | A | N |
| ATOM | 255 | CA | LEU | A | 158 | 24.445 | 96.436 | 77.616 | 1.00 | 19.34 | A | C |
| ATOM | 256 | CB | LEU | A | 158 | 24.651 | 97.900 | 77.220 | 1.00 | 20.73 | A | C |
| ATOM | 257 | CG | LEU | A | 158 | 25.882 | 98.644 | 77.734 | 1.00 | 22.83 | A | C |
| ATOM | 258 | CD1 | LEU | A | 158 | 27.125 | 98.226 | 76.965 | 1.00 | 23.65 | A | C |
| ATOM | 259 | CD2 | LEU | A | 158 | 25.633 | 100.139 | 77.576 | 1.00 | 24.53 | A | C |
| ATOM | 260 | C | LEU | A | 158 | 25.231 | 95.498 | 76.688 | 1.00 | 19.24 | A | C |
| ATOM | 261 | O | LEU | A | 158 | 25.944 | 94.623 | 77.153 | 1.00 | 20.32 | A | O |
| ATOM | 262 | N | ALA | A | 159 | 25.077 | 95.654 | 75.379 | 1.00 | 19.56 | A | N |
| ATOM | 263 | CA | ALA | A | 159 | 25.790 | 94.803 | 74.431 | 1.00 | 19.83 | A | C |
| ATOM | 264 | CB | ALA | A | 159 | 24.809 | 94.009 | 73.579 | 1.00 | 19.54 | A | C |
| ATOM | 265 | C | ALA | A | 159 | 26.673 | 95.672 | 73.553 | 1.00 | 20.25 | A | C |
| ATOM | 266 | O | ALA | A | 159 | 26.274 | 96.766 | 73.143 | 1.00 | 19.23 | A | O |
| ATOM | 267 | N | LEU | A | 160 | 27.878 | 95.190 | 73.274 | 1.00 | 20.17 | A | N |
| ATOM | 268 | CA | LEU | A | 160 | 28.820 | 95.944 | 72.459 | 1.00 | 22.21 | A | C |
| ATOM | 269 | CB | LEU | A | 160 | 30.019 | 96.360 | 73.326 | 1.00 | 23.33 | A | C |
| ATOM | 270 | CG | LEU | A | 160 | 31.194 | 97.129 | 72.715 | 1.00 | 27.33 | A | C |
| ATOM | 271 | CD1 | LEU | A | 160 | 30.789 | 98.572 | 72.410 | 1.00 | 27.43 | A | C |
| ATOM | 272 | CD2 | LEU | A | 160 | 32.359 | 97.112 | 73.699 | 1.00 | 26.63 | A | C |
| ATOM | 273 | C | LEU | A | 160 | 29.298 | 95.146 | 71.249 | 1.00 | 22.33 | A | C |
| ATOM | 274 | O | LEU | A | 160 | 29.772 | 94.021 | 71.379 | 1.00 | 21.48 | A | O |
| ATOM | 275 | N | LYS | A | 161 | 29.170 | 95.738 | 70.067 | 1.00 | 23.83 | A | N |

TABLE 2-continued coordinates for the two molecules in the asymmetric unit of [T287] Aurora A (122–396) in complex with an inhibitor of formula II in space group P2$_1$

| ATOM | 276 | CA | LYS | A | 161 | 29.612 | 95.082 | 68.840 | 1.00 | 24.70 | A | C |
|---|---|---|---|---|---|---|---|---|---|---|---|---|
| ATOM | 277 | CB | LYS | A | 161 | 28.502 | 95.107 | 67.792 | 1.00 | 24.56 | A | C |
| ATOM | 278 | CG | LYS | A | 161 | 28.735 | 94.154 | 66.635 | 1.00 | 26.78 | A | C |
| ATOM | 279 | CD | LYS | A | 161 | 27.431 | 93.891 | 65.887 | 1.00 | 25.97 | A | C |
| ATOM | 280 | CE | LYS | A | 161 | 27.612 | 92.863 | 64.792 | 1.00 | 23.17 | A | C |
| ATOM | 281 | NZ | LYS | A | 161 | 26.293 | 92.377 | 64.315 | 1.00 | 22.83 | A | N |
| ATOM | 282 | C | LYS | A | 161 | 30.850 | 95.798 | 68.314 | 1.00 | 25.61 | A | C |
| ATOM | 283 | O | LYS | A | 161 | 30.850 | 97.014 | 68.146 | 1.00 | 25.29 | A | O |
| ATOM | 284 | N | VAL | A | 162 | 31.907 | 95.031 | 68.072 | 1.00 | 27.06 | A | N |
| ATOM | 285 | CA | VAL | A | 162 | 33.172 | 95.568 | 67.585 | 1.00 | 28.41 | A | C |
| ATOM | 286 | CB | VAL | A | 162 | 34.346 | 95.050 | 68.456 | 1.00 | 31.04 | A | C |
| ATOM | 287 | CG1 | VAL | A | 162 | 35.678 | 95.617 | 67.957 | 1.00 | 31.63 | A | C |
| ATOM | 288 | CG2 | VAL | A | 162 | 34.113 | 95.427 | 69.914 | 1.00 | 30.41 | A | C |
| ATOM | 289 | C | VAL | A | 162 | 33.387 | 95.132 | 66.139 | 1.00 | 28.72 | A | C |
| ATOM | 290 | O | VAL | A | 162 | 33.387 | 93.942 | 65.844 | 1.00 | 28.91 | A | O |
| ATOM | 291 | N | LEU | A | 163 | 33.561 | 96.096 | 65.241 | 1.00 | 30.09 | A | N |
| ATOM | 292 | CA | LEU | A | 163 | 33.760 | 95.801 | 63.823 | 1.00 | 31.38 | A | C |
| ATOM | 293 | CB | LEU | A | 163 | 32.670 | 96.479 | 62.987 | 1.00 | 30.68 | A | C |
| ATOM | 294 | CG | LEU | A | 163 | 31.207 | 96.151 | 63.295 | 1.00 | 31.65 | A | C |
| ATOM | 295 | CD1 | LEU | A | 163 | 30.343 | 97.379 | 63.035 | 1.00 | 33.15 | A | C |
| ATOM | 296 | CD2 | LEU | A | 163 | 30.747 | 94.985 | 62.452 | 1.00 | 31.46 | A | C |
| ATOM | 297 | C | LEU | A | 163 | 35.116 | 96.333 | 63.393 | 1.00 | 32.77 | A | C |
| ATOM | 298 | O | LEU | A | 163 | 35.541 | 97.386 | 63.865 | 1.00 | 33.03 | A | O |
| ATOM | 299 | N | PHE | A | 164 | 35.793 | 95.610 | 62.503 | 1.00 | 34.61 | A | N |
| ATOM | 300 | CA | PHE | A | 164 | 37.107 | 96.043 | 62.018 | 1.00 | 36.93 | A | C |
| ATOM | 301 | CB | PHE | A | 164 | 38.068 | 94.849 | 61.878 | 1.00 | 38.68 | A | C |
| ATOM | 302 | CG | PHE | A | 164 | 38.406 | 94.181 | 63.180 | 1.00 | 40.41 | A | C |
| ATOM | 303 | CD1 | PHE | A | 164 | 37.659 | 93.101 | 63.639 | 1.00 | 41.41 | A | C |
| ATOM | 304 | CD2 | PHE | A | 164 | 39.464 | 94.645 | 63.960 | 1.00 | 41.14 | A | C |
| ATOM | 305 | CE1 | PHE | A | 164 | 37.959 | 92.489 | 64.857 | 1.00 | 41.57 | A | C |
| ATOM | 306 | CE2 | PHE | A | 164 | 39.774 | 94.041 | 65.182 | 1.00 | 42.28 | A | C |
| ATOM | 307 | CZ | PHE | A | 164 | 39.020 | 92.960 | 65.630 | 1.00 | 41.55 | A | C |
| ATOM | 308 | C | PHE | A | 164 | 37.000 | 96.759 | 60.674 | 1.00 | 36.27 | A | C |
| ATOM | 309 | O | PHE | A | 164 | 36.489 | 96.203 | 59.701 | 1.00 | 34.52 | A | O |
| ATOM | 310 | N | LYS | A | 165 | 37.495 | 97.993 | 60.632 | 1.00 | 37.51 | A | N |
| ATOM | 311 | CA | LYS | A | 165 | 37.461 | 98.809 | 59.422 | 1.00 | 39.00 | A | C |
| ATOM | 312 | CB | LYS | A | 165 | 38.248 | 100.103 | 59.635 | 1.00 | 39.41 | A | C |
| ATOM | 313 | CG | LYS | A | 165 | 37.700 | 100.988 | 60.738 | 1.00 | 41.43 | A | C |
| ATOM | 314 | CD | LYS | A | 165 | 38.473 | 102.292 | 60.820 | 1.00 | 43.19 | A | C |
| ATOM | 315 | CE | LYS | A | 165 | 37.957 | 103.175 | 61.941 | 1.00 | 43.06 | A | C |
| ATOM | 316 | NZ | LYS | A | 165 | 38.712 | 104.452 | 62.007 | 1.00 | 45.01 | A | N |
| ATOM | 317 | C | LYS | A | 165 | 38.016 | 98.092 | 58.200 | 1.00 | 39.84 | A | C |
| ATOM | 318 | O | LYS | A | 165 | 37.332 | 97.966 | 57.183 | 1.00 | 40.35 | A | O |
| ATOM | 319 | N | ALA | A | 166 | 39.259 | 97.629 | 58.309 | 1.00 | 40.50 | A | N |
| ATOM | 320 | CA | ALA | A | 166 | 39.930 | 96.930 | 57.218 | 1.00 | 41.24 | A | C |
| ATOM | 321 | CB | ALA | A | 166 | 41.230 | 96.314 | 57.717 | 1.00 | 40.66 | A | C |
| ATOM | 322 | C | ALA | A | 166 | 39.039 | 95.850 | 56.622 | 1.00 | 42.45 | A | C |
| ATOM | 323 | O | ALA | A | 166 | 39.143 | 95.524 | 55.439 | 1.00 | 42.34 | A | O |
| ATOM | 324 | N | GLN | A | 167 | 38.160 | 95.298 | 57.448 | 1.00 | 42.58 | A | N |
| ATOM | 325 | CA | GLN | A | 167 | 37.256 | 94.255 | 56.995 | 1.00 | 44.47 | A | C |
| ATOM | 326 | CB | GLN | A | 167 | 36.814 | 93.405 | 58.189 | 1.00 | 47.08 | A | C |
| ATOM | 327 | CG | GLN | A | 167 | 36.076 | 92.133 | 57.818 | 1.00 | 49.82 | A | C |
| ATOM | 328 | CD | GLN | A | 167 | 36.382 | 90.991 | 58.772 | 1.00 | 51.86 | A | C |
| ATOM | 329 | OE1 | GLN | A | 167 | 36.182 | 91.105 | 59.985 | 1.00 | 52.31 | A | O |
| ATOM | 330 | NE2 | GLN | A | 167 | 36.873 | 89.880 | 58.226 | 1.00 | 52.20 | A | N |
| ATOM | 331 | C | GLN | A | 167 | 36.044 | 94.856 | 56.288 | 1.00 | 44.78 | A | C |
| ATOM | 332 | O | GLN | A | 167 | 35.580 | 94.329 | 55.277 | 1.00 | 44.92 | A | O |
| ATOM | 333 | N | LEU | A | 168 | 35.539 | 95.965 | 56.818 | 1.00 | 45.62 | A | N |
| ATOM | 334 | CA | LEU | A | 168 | 34.379 | 96.635 | 56.232 | 1.00 | 47.56 | A | C |
| ATOM | 335 | CB | LEU | A | 168 | 33.899 | 97.775 | 57.146 | 1.00 | 46.01 | A | C |
| ATOM | 336 | CG | LEU | A | 168 | 33.222 | 97.423 | 58.476 | 1.00 | 43.92 | A | C |
| ATOM | 337 | CD1 | LEU | A | 168 | 33.079 | 98.664 | 59.335 | 1.00 | 42.28 | A | C |
| ATOM | 338 | CD2 | LEU | A | 168 | 31.866 | 96.802 | 58.209 | 1.00 | 44.54 | A | C |
| ATOM | 339 | C | LEU | A | 168 | 34.702 | 97.200 | 54.851 | 1.00 | 49.49 | A | C |
| ATOM | 340 | O | LEU | A | 168 | 33.974 | 96.973 | 53.884 | 1.00 | 49.80 | A | O |
| ATOM | 341 | N | GLU | A | 169 | 35.806 | 97.930 | 54.756 | 1.00 | 51.68 | A | N |
| ATOM | 342 | CA | GLU | A | 169 | 36.185 | 98.536 | 53.490 | 1.00 | 53.42 | A | C |
| ATOM | 343 | CB | GLU | A | 169 | 37.063 | 99.751 | 53.749 | 1.00 | 53.84 | A | C |
| ATOM | 344 | CG | GLU | A | 169 | 38.381 | 99.423 | 54.394 | 1.00 | 54.96 | A | C |
| ATOM | 345 | CD | GLU | A | 169 | 39.178 | 100.665 | 54.697 | 1.00 | 55.82 | A | C |
| ATOM | 346 | OE1 | GLU | A | 169 | 38.781 | 101.410 | 55.619 | 1.00 | 55.83 | A | O |
| ATOM | 347 | OE2 | GLU | A | 169 | 40.193 | 100.901 | 54.006 | 1.00 | 57.62 | A | O |
| ATOM | 348 | C | GLU | A | 169 | 36.886 | 97.589 | 52.523 | 1.00 | 53.75 | A | C |
| ATOM | 349 | O | GLU | A | 169 | 37.892 | 97.947 | 51.922 | 1.00 | 54.54 | A | O |
| ATOM | 350 | N | LYS | A | 170 | 36.352 | 96.382 | 52.375 | 1.00 | 54.68 | A | N |
| ATOM | 351 | CA | LYS | A | 170 | 36.923 | 95.398 | 51.464 | 1.00 | 55.27 | A | C |

TABLE 2-continued coordinates for the two molecules in the asymmetric unit of [T287] Aurora A (122–396) in complex with an inhibitor of formula II in space group P2₁

| ATOM | 352 | CB | LYS | A | 170 | 38.040 | 94.603 | 52.151 | 1.00 | 56.80 | A | C |
|------|-----|-----|-----|---|-----|--------|--------|--------|------|-------|---|---|
| ATOM | 353 | CG | LYS | A | 170 | 37.588 | 93.641 | 53.249 | 1.00 | 59.09 | A | C |
| ATOM | 354 | CD | LYS | A | 170 | 37.396 | 92.216 | 52.725 | 1.00 | 59.63 | A | C |
| ATOM | 355 | CE | LYS | A | 170 | 37.133 | 91.239 | 53.873 | 1.00 | 60.14 | A | C |
| ATOM | 356 | NZ | LYS | A | 170 | 37.117 | 89.809 | 53.437 | 1.00 | 59.19 | A | N |
| ATOM | 357 | C | LYS | A | 170 | 35.815 | 94.469 | 50.997 | 1.00 | 55.75 | A | C |
| ATOM | 358 | O | LYS | A | 170 | 35.765 | 94.086 | 49.830 | 1.00 | 56.27 | A | O |
| ATOM | 359 | N | ALA | A | 171 | 34.921 | 94.116 | 51.915 | 1.00 | 55.93 | A | N |
| ATOM | 360 | CA | ALA | A | 171 | 33.792 | 93.250 | 51.590 | 1.00 | 56.64 | A | C |
| ATOM | 361 | CB | ALA | A | 171 | 33.064 | 92.823 | 52.866 | 1.00 | 56.68 | A | C |
| ATOM | 362 | C | ALA | A | 171 | 32.872 | 94.088 | 50.719 | 1.00 | 56.98 | A | C |
| ATOM | 363 | O | ALA | A | 171 | 31.899 | 93.599 | 50.139 | 1.00 | 55.93 | A | O |
| ATOM | 364 | N | GLY | A | 172 | 33.207 | 95.369 | 50.642 | 1.00 | 56.93 | A | N |
| ATOM | 365 | CA | GLY | A | 172 | 32.429 | 96.297 | 49.856 | 1.00 | 58.46 | A | C |
| ATOM | 366 | C | GLY | A | 172 | 32.681 | 97.681 | 50.397 | 1.00 | 59.30 | A | C |
| ATOM | 367 | O | GLY | A | 172 | 33.629 | 97.892 | 51.156 | 1.00 | 60.21 | A | O |
| ATOM | 368 | N | VAL | A | 173 | 31.840 | 98.626 | 50.003 | 1.00 | 59.95 | A | N |
| ATOM | 369 | CA | VAL | A | 173 | 31.970 | 99.998 | 50.459 | 1.00 | 60.15 | A | C |
| ATOM | 370 | CB | VAL | A | 173 | 31.642 | 100.992 | 49.328 | 1.00 | 61.54 | A | C |
| ATOM | 371 | CG1 | VAL | A | 173 | 31.817 | 102.420 | 49.825 | 1.00 | 62.43 | A | C |
| ATOM | 372 | CG2 | VAL | A | 173 | 32.538 | 100.720 | 48.118 | 1.00 | 61.17 | A | C |
| ATOM | 373 | C | VAL | A | 173 | 30.955 | 100.142 | 51.574 | 1.00 | 59.92 | A | C |
| ATOM | 374 | O | VAL | A | 173 | 29.860 | 100.673 | 51.369 | 1.00 | 60.94 | A | O |
| ATOM | 375 | N | GLU | A | 174 | 31.327 | 99.652 | 52.756 | 1.00 | 58.81 | A | N |
| ATOM | 376 | CA | GLU | A | 174 | 30.452 | 99.681 | 53.921 | 1.00 | 55.71 | A | C |
| ATOM | 377 | CB | GLU | A | 174 | 31.091 | 98.900 | 55.067 | 1.00 | 56.69 | A | C |
| ATOM | 378 | CG | GLU | A | 174 | 31.360 | 97.440 | 54.731 | 1.00 | 57.20 | A | C |
| ATOM | 379 | CD | GLU | A | 174 | 30.135 | 96.717 | 54.197 | 1.00 | 57.78 | A | C |
| ATOM | 380 | OE1 | GLU | A | 174 | 29.580 | 97.156 | 53.166 | 1.00 | 56.65 | A | O |
| ATOM | 381 | OE2 | GLU | A | 174 | 29.733 | 95.705 | 54.808 | 1.00 | 57.97 | A | O |
| ATOM | 382 | C | GLU | A | 174 | 29.985 | 101.040 | 54.428 | 1.00 | 54.20 | A | C |
| ATOM | 383 | O | GLU | A | 174 | 29.998 | 101.302 | 55.634 | 1.00 | 53.74 | A | O |
| ATOM | 384 | N | HIS | A | 175 | 29.587 | 101.913 | 53.506 | 1.00 | 51.35 | A | N |
| ATOM | 385 | CA | HIS | A | 175 | 29.040 | 103.199 | 53.896 | 1.00 | 47.97 | A | C |
| ATOM | 386 | CB | HIS | A | 175 | 29.047 | 104.184 | 52.726 | 1.00 | 50.39 | A | C |
| ATOM | 387 | CG | HIS | A | 175 | 30.391 | 104.788 | 52.460 | 1.00 | 54.57 | A | C |
| ATOM | 388 | CD2 | HIS | A | 175 | 30.998 | 105.144 | 51.303 | 1.00 | 55.04 | A | C |
| ATOM | 389 | ND1 | HIS | A | 175 | 31.266 | 105.127 | 53.472 | 1.00 | 55.47 | A | N |
| ATOM | 390 | CE1 | HIS | A | 175 | 32.354 | 105.664 | 52.949 | 1.00 | 55.64 | A | C |
| ATOM | 391 | NE2 | HIS | A | 175 | 32.216 | 105.687 | 51.635 | 1.00 | 55.68 | A | N |
| ATOM | 392 | C | HIS | A | 175 | 27.615 | 102.794 | 54.253 | 1.00 | 44.77 | A | C |
| ATOM | 393 | O | HIS | A | 175 | 26.842 | 103.562 | 54.817 | 1.00 | 43.37 | A | O |
| ATOM | 394 | N | GLN | A | 176 | 27.299 | 101.550 | 53.902 | 1.00 | 41.61 | A | N |
| ATOM | 395 | CA | GLN | A | 176 | 26.010 | 100.942 | 54.178 | 1.00 | 39.54 | A | C |
| ATOM | 396 | CB | GLN | A | 176 | 25.982 | 99.524 | 53.604 | 1.00 | 40.25 | A | C |
| ATOM | 397 | CG | GLN | A | 176 | 24.822 | 98.672 | 54.086 | 1.00 | 42.14 | A | C |
| ATOM | 398 | CD | GLN | A | 176 | 23.480 | 99.184 | 53.606 | 1.00 | 44.16 | A | C |
| ATOM | 399 | OE1 | GLN | A | 176 | 22.431 | 98.673 | 54.002 | 1.00 | 45.91 | A | O |
| ATOM | 400 | NE2 | GLN | A | 176 | 23.505 | 100.193 | 52.745 | 1.00 | 43.65 | A | N |
| ATOM | 401 | C | GLN | A | 176 | 25.817 | 100.891 | 55.696 | 1.00 | 37.68 | A | C |
| ATOM | 402 | O | GLN | A | 176 | 24.727 | 101.142 | 56.205 | 1.00 | 36.70 | A | O |
| ATOM | 403 | N | LEU | A | 177 | 26.887 | 100.559 | 56.408 | 1.00 | 34.73 | A | N |
| ATOM | 404 | CA | LEU | A | 177 | 26.842 | 100.495 | 57.862 | 1.00 | 33.53 | A | C |
| ATOM | 405 | CB | LEU | A | 177 | 28.236 | 100.230 | 58.427 | 1.00 | 32.47 | A | C |
| ATOM | 406 | CG | LEU | A | 177 | 28.307 | 100.187 | 59.957 | 1.00 | 32.80 | A | C |
| ATOM | 407 | CD1 | LEU | A | 177 | 27.773 | 98.844 | 60.439 | 1.00 | 33.65 | A | C |
| ATOM | 408 | CD2 | LEU | A | 177 | 29.742 | 100.380 | 60.431 | 1.00 | 31.75 | A | C |
| ATOM | 409 | C | LEU | A | 177 | 26.357 | 101.842 | 58.380 | 1.00 | 33.15 | A | C |
| ATOM | 410 | O | LEU | A | 177 | 25.411 | 101.920 | 59.168 | 1.00 | 30.88 | A | O |
| ATOM | 411 | N | ARG | A | 178 | 27.021 | 102.898 | 57.916 | 1.00 | 31.91 | A | N |
| ATOM | 412 | CA | ARG | A | 178 | 26.709 | 104.261 | 58.317 | 1.00 | 31.40 | A | C |
| ATOM | 413 | CB | ARG | A | 178 | 27.661 | 105.238 | 57.618 | 1.00 | 33.75 | A | C |
| ATOM | 414 | CG | ARG | A | 178 | 27.658 | 106.625 | 58.226 | 1.00 | 36.73 | A | C |
| ATOM | 415 | CD | ARG | A | 178 | 28.681 | 107.531 | 57.562 | 1.00 | 43.53 | A | C |
| ATOM | 416 | NE | ARG | A | 178 | 28.822 | 108.809 | 58.262 | 1.00 | 46.96 | A | N |
| ATOM | 417 | CZ | ARG | A | 178 | 29.674 | 109.770 | 57.909 | 1.00 | 48.25 | A | C |
| ATOM | 418 | NH1 | ARG | A | 178 | 30.466 | 109.604 | 56.857 | 1.00 | 48.99 | A | N |
| ATOM | 419 | NH2 | ARG | A | 178 | 29.741 | 110.895 | 58.613 | 1.00 | 47.98 | A | N |
| ATOM | 420 | C | ARG | A | 178 | 25.254 | 104.669 | 58.065 | 1.00 | 29.09 | A | C |
| ATOM | 421 | O | ARG | A | 178 | 24.642 | 105.327 | 58.902 | 1.00 | 28.32 | A | O |
| ATOM | 422 | N | ARG | A | 179 | 24.694 | 104.289 | 56.924 | 1.00 | 28.97 | A | N |
| ATOM | 423 | CA | ARG | A | 179 | 23.301 | 104.633 | 56.624 | 1.00 | 27.69 | A | C |
| ATOM | 424 | CB | ARG | A | 179 | 22.927 | 104.220 | 55.194 | 1.00 | 29.53 | A | C |
| ATOM | 425 | CG | ARG | A | 179 | 23.091 | 105.294 | 54.131 | 1.00 | 33.34 | A | C |
| ATOM | 426 | CD | ARG | A | 179 | 22.514 | 104.813 | 52.800 | 1.00 | 34.69 | A | C |
| ATOM | 427 | NE | ARG | A | 179 | 21.091 | 104.473 | 52.896 | 1.00 | 38.29 | A | N |

TABLE 2-continued coordinates for the two molecules in the asymmetric unit of [T287] Aurora
A (122–396) in complex with an inhibitor of formula II in space group P2₁

| ATOM | 428 | CZ | ARG | A | 179 | 20.103 | 105.367 | 52.916 | 1.00 | 39.89 | A | C |
|------|-----|-----|-----|---|-----|--------|---------|--------|------|-------|---|---|
| ATOM | 429 | NH1 | ARG | A | 179 | 20.377 | 106.665 | 52.842 | 1.00 | 41.81 | A | N |
| ATOM | 430 | NH2 | ARG | A | 179 | 18.840 | 104.966 | 53.011 | 1.00 | 39.44 | A | N |
| ATOM | 431 | C | ARG | A | 179 | 22.377 | 103.900 | 57.589 | 1.00 | 25.80 | A | C |
| ATOM | 432 | O | ARG | A | 179 | 21.421 | 104.465 | 58.121 | 1.00 | 24.65 | A | O |
| ATOM | 433 | N | GLU | A | 180 | 22.689 | 102.628 | 57.795 | 1.00 | 24.97 | A | N |
| ATOM | 434 | CA | GLU | A | 180 | 21.924 | 101.746 | 58.655 | 1.00 | 24.64 | A | C |
| ATOM | 435 | CB | GLU | A | 180 | 22.475 | 100.329 | 58.512 | 1.00 | 25.95 | A | C |
| ATOM | 436 | CG | GLU | A | 180 | 21.507 | 99.239 | 58.900 | 1.00 | 30.77 | A | C |
| ATOM | 437 | CD | GLU | A | 180 | 20.238 | 99.256 | 58.073 | 1.00 | 32.75 | A | C |
| ATOM | 438 | OE1 | GLU | A | 180 | 20.336 | 99.283 | 56.830 | 1.00 | 33.51 | A | O |
| ATOM | 439 | OE2 | GLU | A | 180 | 19.138 | 99.233 | 58.669 | 1.00 | 36.77 | A | O |
| ATOM | 440 | C | GLU | A | 180 | 21.962 | 102.206 | 60.110 | 1.00 | 24.56 | A | C |
| ATOM | 441 | O | GLU | A | 180 | 20.965 | 102.116 | 60.831 | 1.00 | 23.69 | A | O |
| ATOM | 442 | N | VAL | A | 181 | 23.109 | 102.715 | 60.541 | 1.00 | 23.97 | A | N |
| ATOM | 443 | CA | VAL | A | 181 | 23.235 | 103.191 | 61.905 | 1.00 | 25.68 | A | C |
| ATOM | 444 | CB | VAL | A | 181 | 24.709 | 103.469 | 62.244 | 1.00 | 24.65 | A | C |
| ATOM | 445 | CG1 | VAL | A | 181 | 24.806 | 104.314 | 63.499 | 1.00 | 21.02 | A | C |
| ATOM | 446 | CG2 | VAL | A | 181 | 25.440 | 102.142 | 62.440 | 1.00 | 23.99 | A | C |
| ATOM | 447 | C | VAL | A | 181 | 22.403 | 104.459 | 62.100 | 1.00 | 27.42 | A | C |
| ATOM | 448 | O | VAL | A | 181 | 21.771 | 104.653 | 63.144 | 1.00 | 28.13 | A | O |
| ATOM | 449 | N | GLU | A | 182 | 22.406 | 105.307 | 61.079 | 1.00 | 28.83 | A | N |
| ATOM | 450 | CA | GLU | A | 182 | 21.667 | 106.563 | 61.092 | 1.00 | 31.06 | A | C |
| ATOM | 451 | CB | GLU | A | 182 | 21.938 | 107.314 | 59.779 | 1.00 | 34.99 | A | C |
| ATOM | 452 | CG | GLU | A | 182 | 21.403 | 108.753 | 59.671 | 1.00 | 41.26 | A | C |
| ATOM | 453 | CD | GLU | A | 182 | 21.846 | 109.429 | 58.359 | 1.00 | 45.14 | A | C |
| ATOM | 454 | OE1 | GLU | A | 182 | 21.502 | 110.617 | 58.122 | 1.00 | 42.54 | A | O |
| ATOM | 455 | OE2 | GLU | A | 182 | 22.548 | 108.757 | 57.561 | 1.00 | 46.92 | A | O |
| ATOM | 456 | C | GLU | A | 182 | 20.182 | 106.239 | 61.235 | 1.00 | 29.45 | A | C |
| ATOM | 457 | O | GLU | A | 182 | 19.488 | 106.798 | 62.080 | 1.00 | 26.72 | A | O |
| ATOM | 458 | N | ILE | A | 183 | 19.717 | 105.306 | 60.412 | 1.00 | 28.76 | A | N |
| ATOM | 459 | CA | ILE | A | 183 | 18.323 | 104.890 | 60.411 | 1.00 | 28.45 | A | C |
| ATOM | 460 | CB | ILE | A | 183 | 18.055 | 103.892 | 59.265 | 1.00 | 28.73 | A | C |
| ATOM | 461 | CG2 | ILE | A | 183 | 16.618 | 103.413 | 59.318 | 1.00 | 28.72 | A | C |
| ATOM | 462 | CG1 | ILE | A | 183 | 18.344 | 104.554 | 57.916 | 1.00 | 27.67 | A | C |
| ATOM | 463 | CD1 | ILE | A | 183 | 18.250 | 103.605 | 56.728 | 1.00 | 26.58 | A | C |
| ATOM | 464 | C | ILE | A | 183 | 17.886 | 104.235 | 61.716 | 1.00 | 29.83 | A | C |
| ATOM | 465 | O | ILE | A | 183 | 16.870 | 104.605 | 62.302 | 1.00 | 27.93 | A | O |
| ATOM | 466 | N | GLN | A | 184 | 18.668 | 103.261 | 62.168 | 1.00 | 29.56 | A | N |
| ATOM | 467 | CA | GLN | A | 184 | 18.349 | 102.519 | 63.373 | 1.00 | 30.04 | A | C |
| ATOM | 468 | CB | GLN | A | 184 | 19.315 | 101.345 | 63.495 | 1.00 | 30.32 | A | C |
| ATOM | 469 | CG | GLN | A | 184 | 18.801 | 100.235 | 64.369 | 1.00 | 34.52 | A | C |
| ATOM | 470 | CD | GLN | A | 184 | 17.721 | 99.403 | 63.709 | 1.00 | 32.90 | A | C |
| ATOM | 471 | OE1 | GLN | A | 184 | 16.988 | 98.695 | 64.388 | 1.00 | 36.44 | A | O |
| ATOM | 472 | NE2 | GLN | A | 184 | 17.628 | 99.470 | 62.386 | 1.00 | 32.19 | A | N |
| ATOM | 473 | C | GLN | A | 184 | 18.335 | 103.318 | 64.679 | 1.00 | 31.00 | A | C |
| ATOM | 474 | O | GLN | A | 184 | 17.593 | 102.988 | 65.606 | 1.00 | 29.21 | A | O |
| ATOM | 475 | N | SER | A | 185 | 19.139 | 104.375 | 64.752 | 1.00 | 32.70 | A | N |
| ATOM | 476 | CA | SER | A | 185 | 19.219 | 105.179 | 65.968 | 1.00 | 33.38 | A | C |
| ATOM | 477 | CB | SER | A | 185 | 20.512 | 105.985 | 65.976 | 1.00 | 34.25 | A | C |
| ATOM | 478 | OG | SER | A | 185 | 20.460 | 107.001 | 64.996 | 1.00 | 35.32 | A | O |
| ATOM | 479 | C | SER | A | 185 | 18.051 | 106.134 | 66.192 | 1.00 | 34.71 | A | C |
| ATOM | 480 | O | SER | A | 185 | 17.989 | 106.797 | 67.221 | 1.00 | 34.82 | A | O |
| ATOM | 481 | N | HIS | A | 186 | 17.131 | 106.212 | 65.237 | 1.00 | 35.78 | A | N |
| ATOM | 482 | CA | HIS | A | 186 | 15.974 | 107.098 | 65.366 | 1.00 | 36.17 | A | C |
| ATOM | 483 | CB | HIS | A | 186 | 15.875 | 108.002 | 64.133 | 1.00 | 38.62 | A | C |
| ATOM | 484 | CG | HIS | A | 186 | 17.044 | 108.925 | 63.970 | 1.00 | 42.07 | A | C |
| ATOM | 485 | CD2 | HIS | A | 186 | 17.816 | 109.557 | 64.886 | 1.00 | 42.75 | A | C |
| ATOM | 486 | ND1 | HIS | A | 186 | 17.538 | 109.290 | 62.736 | 1.00 | 42.17 | A | N |
| ATOM | 487 | CE1 | HIS | A | 186 | 18.566 | 110.104 | 62.899 | 1.00 | 42.82 | A | C |
| ATOM | 488 | NE2 | HIS | A | 186 | 18.755 | 110.283 | 64.194 | 1.00 | 43.03 | A | N |
| ATOM | 489 | C | HIS | A | 186 | 14.673 | 106.310 | 65.545 | 1.00 | 35.02 | A | C |
| ATOM | 490 | O | HIS | A | 186 | 13.580 | 106.868 | 65.449 | 1.00 | 36.65 | A | O |
| ATOM | 491 | N | LEU | A | 187 | 14.796 | 105.011 | 65.793 | 1.00 | 31.62 | A | N |
| ATOM | 492 | CA | LEU | A | 187 | 13.631 | 104.161 | 65.994 | 1.00 | 29.84 | A | C |
| ATOM | 493 | CB | LEU | A | 187 | 13.791 | 102.828 | 65.253 | 1.00 | 28.15 | A | C |
| ATOM | 494 | CG | LEU | A | 187 | 13.577 | 102.778 | 63.743 | 1.00 | 28.01 | A | C |
| ATOM | 495 | CD1 | LEU | A | 187 | 14.398 | 103.855 | 63.066 | 1.00 | 31.70 | A | C |
| ATOM | 496 | CD2 | LEU | A | 187 | 13.973 | 101.410 | 63.226 | 1.00 | 25.23 | A | C |
| ATOM | 497 | C | LEU | A | 187 | 13.480 | 103.886 | 67.479 | 1.00 | 28.25 | A | C |
| ATOM | 498 | O | LEU | A | 187 | 14.397 | 103.359 | 68.110 | 1.00 | 28.90 | A | O |
| ATOM | 499 | N | ALA | A | 188 | 12.333 | 104.254 | 68.038 | 1.00 | 25.67 | A | N |
| ATOM | 500 | CA | ALA | A | 188 | 12.074 | 104.024 | 69.451 | 1.00 | 23.28 | A | C |
| ATOM | 501 | CB | ALA | A | 188 | 11.981 | 105.355 | 70.201 | 1.00 | 22.40 | A | C |
| ATOM | 502 | C | ALA | A | 188 | 10.782 | 103.241 | 69.612 | 1.00 | 21.56 | A | C |
| ATOM | 503 | O | ALA | A | 188 | 9.695 | 103.793 | 69.488 | 1.00 | 21.09 | A | O |

TABLE 2-continued coordinates for the two molecules in the asymmetric unit of [T287] Aurora
A (122–396) in complex with an inhibitor of formula II in space group P2$_1$

| ATOM | 504 | N | HIS | A | 189 | 10.906 | 101.944 | 69.859 | 1.00 | 21.04 | A | N |
|------|-----|-----|-----|---|-----|--------|---------|--------|------|-------|---|---|
| ATOM | 505 | CA | HIS | A | 189 | 9.736 | 101.088 | 70.048 | 1.00 | 22.71 | A | C |
| ATOM | 506 | CB | HIS | A | 189 | 9.299 | 100.458 | 68.720 | 1.00 | 22.11 | A | C |
| ATOM | 507 | CG | HIS | A | 189 | 7.961 | 99.784 | 68.774 | 1.00 | 23.56 | A | C |
| ATOM | 508 | CD2 | HIS | A | 189 | 7.621 | 98.494 | 69.014 | 1.00 | 23.56 | A | C |
| ATOM | 509 | ND1 | HIS | A | 189 | 6.775 | 100.456 | 68.562 | 1.00 | 26.00 | A | N |
| ATOM | 510 | CE1 | HIS | A | 189 | 5.765 | 99.612 | 68.666 | 1.00 | 23.68 | A | C |
| ATOM | 511 | NE2 | HIS | A | 189 | 6.251 | 98.414 | 68.941 | 1.00 | 25.80 | A | N |
| ATOM | 512 | C | HIS | A | 189 | 10.122 | 99.999 | 71.045 | 1.00 | 22.46 | A | C |
| ATOM | 513 | O | HIS | A | 189 | 11.254 | 99.509 | 71.041 | 1.00 | 22.66 | A | O |
| ATOM | 514 | N | PRO | A | 190 | 9.185 | 99.615 | 71.919 | 1.00 | 22.08 | A | N |
| ATOM | 515 | CD | PRO | A | 190 | 7.823 | 100.159 | 72.076 | 1.00 | 22.50 | A | C |
| ATOM | 516 | CA | PRO | A | 190 | 9.458 | 98.584 | 72.915 | 1.00 | 22.42 | A | C |
| ATOM | 517 | CB | PRO | A | 190 | 8.238 | 98.659 | 73.837 | 1.00 | 22.67 | A | C |
| ATOM | 518 | CG | PRO | A | 190 | 7.149 | 99.106 | 72.925 | 1.00 | 23.94 | A | C |
| ATOM | 519 | C | PRO | A | 190 | 9.688 | 97.190 | 72.341 | 1.00 | 23.17 | A | C |
| ATOM | 520 | O | PRO | A | 190 | 10.091 | 96.282 | 73.070 | 1.00 | 21.69 | A | O |
| ATOM | 521 | N | ASN | A | 191 | 9.445 | 97.015 | 71.043 | 1.00 | 21.27 | A | N |
| ATOM | 522 | CA | ASN | A | 191 | 9.657 | 95.711 | 70.422 | 1.00 | 19.49 | A | C |
| ATOM | 523 | CB | ASN | A | 191 | 8.361 | 95.170 | 69.831 | 1.00 | 19.45 | A | C |
| ATOM | 524 | CG | ASN | A | 191 | 7.320 | 94.880 | 70.884 | 1.00 | 19.61 | A | C |
| ATOM | 525 | OD1 | ASN | A | 191 | 7.495 | 93.995 | 71.715 | 1.00 | 22.06 | A | O |
| ATOM | 526 | ND2 | ASN | A | 191 | 6.227 | 95.628 | 70.855 | 1.00 | 20.03 | A | N |
| ATOM | 527 | C | ASN | A | 191 | 10.732 | 95.753 | 69.345 | 1.00 | 19.88 | A | C |
| ATOM | 528 | O | ASN | A | 191 | 10.813 | 94.857 | 68.497 | 1.00 | 19.36 | A | O |
| ATOM | 529 | N | ILE | A | 192 | 11.542 | 96.807 | 69.380 | 1.00 | 18.73 | A | N |
| ATOM | 530 | CA | ILE | A | 192 | 12.652 | 96.973 | 68.454 | 1.00 | 18.72 | A | C |
| ATOM | 531 | CB | ILE | A | 192 | 12.412 | 98.160 | 67.491 | 1.00 | 18.58 | A | C |
| ATOM | 532 | CG2 | ILE | A | 192 | 13.676 | 98.453 | 66.697 | 1.00 | 15.53 | A | C |
| ATOM | 533 | CG1 | ILE | A | 192 | 11.252 | 97.824 | 66.543 | 1.00 | 20.81 | A | C |
| ATOM | 534 | CD1 | ILE | A | 192 | 10.965 | 98.892 | 65.507 | 1.00 | 22.29 | A | C |
| ATOM | 535 | C | ILE | A | 192 | 13.904 | 97.224 | 69.300 | 1.00 | 19.43 | A | C |
| ATOM | 536 | O | ILE | A | 192 | 13.909 | 98.111 | 70.157 | 1.00 | 21.71 | A | O |
| ATOM | 537 | N | LEU | A | 193 | 14.957 | 96.441 | 69.075 | 1.00 | 18.98 | A | N |
| ATOM | 538 | CA | LEU | A | 193 | 16.188 | 96.588 | 69.860 | 1.00 | 20.69 | A | C |
| ATOM | 539 | CB | LEU | A | 193 | 17.214 | 95.514 | 69.467 | 1.00 | 19.99 | A | C |
| ATOM | 540 | CG | LEU | A | 193 | 18.234 | 95.145 | 70.558 | 1.00 | 21.41 | A | C |
| ATOM | 541 | CD1 | LEU | A | 193 | 17.560 | 94.248 | 71.601 | 1.00 | 18.84 | A | C |
| ATOM | 542 | CD2 | LEU | A | 193 | 19.431 | 94.424 | 69.942 | 1.00 | 20.29 | A | C |
| ATOM | 543 | C | LEU | A | 193 | 16.799 | 97.985 | 69.693 | 1.00 | 19.95 | A | C |
| ATOM | 544 | O | LEU | A | 193 | 17.020 | 98.455 | 68.578 | 1.00 | 21.40 | A | O |
| ATOM | 545 | N | ARG | A | 194 | 17.060 | 98.647 | 70.811 | 1.00 | 19.34 | A | N |
| ATOM | 546 | CA | ARG | A | 194 | 17.628 | 99.988 | 70.805 | 1.00 | 18.88 | A | C |
| ATOM | 547 | CB | ARG | A | 194 | 17.376 | 100.662 | 72.154 | 1.00 | 23.30 | A | C |
| ATOM | 548 | CG | ARG | A | 194 | 16.092 | 101.460 | 72.259 | 1.00 | 29.13 | A | C |
| ATOM | 549 | CD | ARG | A | 194 | 16.164 | 102.728 | 71.425 | 1.00 | 36.10 | A | C |
| ATOM | 550 | NE | ARG | A | 194 | 15.089 | 103.659 | 71.763 | 1.00 | 41.78 | A | N |
| ATOM | 551 | CZ | ARG | A | 194 | 14.999 | 104.308 | 72.922 | 1.00 | 44.56 | A | C |
| ATOM | 552 | NH1 | ARG | A | 194 | 15.925 | 104.131 | 73.860 | 1.00 | 45.72 | A | N |
| ATOM | 553 | NH2 | ARG | A | 194 | 13.983 | 105.132 | 73.147 | 1.00 | 45.18 | A | N |
| ATOM | 554 | C | ARG | A | 194 | 19.126 | 100.073 | 70.513 | 1.00 | 18.39 | A | C |
| ATOM | 555 | O | ARG | A | 194 | 19.919 | 99.292 | 71.031 | 1.00 | 15.95 | A | O |
| ATOM | 556 | N | LEU | A | 195 | 19.493 | 101.035 | 69.673 | 1.00 | 18.46 | A | N |
| ATOM | 557 | CA | LEU | A | 195 | 20.887 | 101.311 | 69.355 | 1.00 | 22.13 | A | C |
| ATOM | 558 | CB | LEU | A | 195 | 21.056 | 101.650 | 67.869 | 1.00 | 23.02 | A | C |
| ATOM | 559 | CG | LEU | A | 195 | 22.400 | 101.369 | 67.180 | 1.00 | 25.45 | A | C |
| ATOM | 560 | CD1 | LEU | A | 195 | 22.513 | 102.259 | 65.948 | 1.00 | 24.91 | A | C |
| ATOM | 561 | CD2 | LEU | A | 195 | 23.570 | 101.636 | 68.111 | 1.00 | 25.90 | A | C |
| ATOM | 562 | C | LEU | A | 195 | 21.116 | 102.573 | 70.196 | 1.00 | 22.63 | A | C |
| ATOM | 563 | O | LEU | A | 195 | 20.599 | 103.633 | 69.862 | 1.00 | 24.54 | A | O |
| ATOM | 564 | N | TYR | A | 196 | 21.851 | 102.456 | 71.294 | 1.00 | 22.66 | A | N |
| ATOM | 565 | CA | TYR | A | 196 | 22.095 | 103.605 | 72.168 | 1.00 | 23.33 | A | C |
| ATOM | 566 | CB | TYR | A | 196 | 22.619 | 103.141 | 73.534 | 1.00 | 22.65 | A | C |
| ATOM | 567 | CG | TYR | A | 196 | 21.702 | 102.221 | 74.310 | 1.00 | 21.37 | A | C |
| ATOM | 568 | CD1 | TYR | A | 196 | 22.190 | 101.040 | 74.879 | 1.00 | 22.83 | A | C |
| ATOM | 569 | CE1 | TYR | A | 196 | 21.387 | 100.235 | 75.677 | 1.00 | 22.12 | A | C |
| ATOM | 570 | CD2 | TYR | A | 196 | 20.379 | 102.565 | 74.551 | 1.00 | 22.29 | A | C |
| ATOM | 571 | CE2 | TYR | A | 196 | 19.561 | 101.765 | 75.348 | 1.00 | 23.98 | A | C |
| ATOM | 572 | CZ | TYR | A | 196 | 20.075 | 100.603 | 75.911 | 1.00 | 25.61 | A | C |
| ATOM | 573 | OH | TYR | A | 196 | 19.277 | 99.825 | 76.725 | 1.00 | 27.32 | A | O |
| ATOM | 574 | C | TYR | A | 196 | 23.088 | 104.603 | 71.574 | 1.00 | 23.97 | A | C |
| ATOM | 575 | O | TYR | A | 196 | 23.028 | 105.794 | 71.867 | 1.00 | 24.83 | A | O |
| ATOM | 576 | N | GLY | A | 197 | 24.008 | 104.114 | 70.750 | 1.00 | 25.27 | A | N |
| ATOM | 577 | CA | GLY | A | 197 | 24.985 | 104.999 | 70.141 | 1.00 | 23.65 | A | C |
| ATOM | 578 | C | GLY | A | 197 | 26.091 | 104.230 | 69.457 | 1.00 | 24.59 | A | C |
| ATOM | 579 | O | GLY | A | 197 | 25.990 | 103.019 | 69.276 | 1.00 | 24.07 | A | O |

TABLE 2-continued coordinates for the two molecules in the asymmetric unit of [T287] Aurora
A (122–396) in complex with an inhibitor of formula II in space group P2$_1$

| ATOM | 580 | N | TYR | A | 198 | 27.147 | 104.934 | 69.070 | 1.00 | 26.73 | A | N |
|------|-----|-----|-----|---|-----|--------|---------|--------|------|-------|---|---|
| ATOM | 581 | CA | TYR | A | 198 | 28.282 | 104.307 | 68.413 | 1.00 | 29.46 | A | C |
| ATOM | 582 | CB | TYR | A | 198 | 27.894 | 103.881 | 66.994 | 1.00 | 33.22 | A | C |
| ATOM | 583 | CG | TYR | A | 198 | 27.914 | 104.997 | 65.981 | 1.00 | 38.83 | A | C |
| ATOM | 584 | CD1 | TYR | A | 198 | 29.029 | 105.197 | 65.165 | 1.00 | 40.36 | A | C |
| ATOM | 585 | CE1 | TYR | A | 198 | 29.066 | 106.235 | 64.237 | 1.00 | 44.11 | A | C |
| ATOM | 586 | CD2 | TYR | A | 198 | 26.830 | 105.865 | 65.846 | 1.00 | 41.61 | A | C |
| ATOM | 587 | CE2 | TYR | A | 198 | 26.856 | 106.912 | 64.917 | 1.00 | 44.45 | A | C |
| ATOM | 588 | CZ | TYR | A | 198 | 27.978 | 107.088 | 64.118 | 1.00 | 45.02 | A | C |
| ATOM | 589 | OH | TYR | A | 198 | 28.016 | 108.112 | 63.195 | 1.00 | 48.52 | A | O |
| ATOM | 590 | C | TYR | A | 198 | 29.462 | 105.272 | 68.366 | 1.00 | 29.09 | A | C |
| ATOM | 591 | O | TYR | A | 198 | 29.286 | 106.475 | 68.477 | 1.00 | 28.17 | A | O |
| ATOM | 592 | N | PHE | A | 199 | 30.664 | 104.729 | 68.218 | 1.00 | 30.25 | A | N |
| ATOM | 593 | CA | PHE | A | 199 | 31.880 | 105.533 | 68.134 | 1.00 | 31.17 | A | C |
| ATOM | 594 | CB | PHE | A | 199 | 32.356 | 105.961 | 69.529 | 1.00 | 29.63 | A | C |
| ATOM | 595 | CG | PHE | A | 199 | 32.650 | 104.819 | 70.462 | 1.00 | 28.60 | A | C |
| ATOM | 596 | CD1 | PHE | A | 199 | 33.957 | 104.372 | 70.648 | 1.00 | 29.19 | A | C |
| ATOM | 597 | CD2 | PHE | A | 199 | 31.624 | 104.210 | 71.181 | 1.00 | 27.35 | A | C |
| ATOM | 598 | CE1 | PHE | A | 199 | 34.242 | 103.335 | 71.541 | 1.00 | 28.83 | A | C |
| ATOM | 599 | CE2 | PHE | A | 199 | 31.894 | 103.171 | 72.076 | 1.00 | 28.14 | A | C |
| ATOM | 600 | CZ | PHE | A | 199 | 33.208 | 102.732 | 72.258 | 1.00 | 28.52 | A | C |
| ATOM | 601 | C | PHE | A | 199 | 32.946 | 104.707 | 67.435 | 1.00 | 32.80 | A | C |
| ATOM | 602 | O | PHE | A | 199 | 32.689 | 103.574 | 67.032 | 1.00 | 31.66 | A | O |
| ATOM | 603 | N | HIS | A | 200 | 34.137 | 105.269 | 67.277 | 1.00 | 35.04 | A | N |
| ATOM | 604 | CA | HIS | A | 200 | 35.204 | 104.542 | 66.604 | 1.00 | 37.23 | A | C |
| ATOM | 605 | CB | HIS | A | 200 | 35.033 | 104.644 | 65.082 | 1.00 | 38.99 | A | C |
| ATOM | 606 | CG | HIS | A | 200 | 35.193 | 106.036 | 64.552 | 1.00 | 41.96 | A | C |
| ATOM | 607 | CD2 | HIS | A | 200 | 36.210 | 106.620 | 63.875 | 1.00 | 43.26 | A | C |
| ATOM | 608 | ND1 | HIS | A | 200 | 34.257 | 107.027 | 64.763 | 1.00 | 44.18 | A | N |
| ATOM | 609 | CE1 | HIS | A | 200 | 34.691 | 108.160 | 64.240 | 1.00 | 43.73 | A | C |
| ATOM | 610 | NE2 | HIS | A | 200 | 35.875 | 107.940 | 63.697 | 1.00 | 43.65 | A | N |
| ATOM | 611 | C | HIS | A | 200 | 36.570 | 105.083 | 66.987 | 1.00 | 36.48 | A | C |
| ATOM | 612 | O | HIS | A | 200 | 36.679 | 106.156 | 67.574 | 1.00 | 37.25 | A | O |
| ATOM | 613 | N | ASP | A | 201 | 37.607 | 104.315 | 66.673 | 1.00 | 36.48 | A | N |
| ATOM | 614 | CA | ASP | A | 201 | 38.981 | 104.730 | 66.930 | 1.00 | 35.68 | A | C |
| ATOM | 615 | CB | ASP | A | 201 | 39.662 | 103.861 | 68.007 | 1.00 | 34.18 | A | C |
| ATOM | 616 | CG | ASP | A | 201 | 39.533 | 102.371 | 67.745 | 1.00 | 33.78 | A | C |
| ATOM | 617 | OD1 | ASP | A | 201 | 39.597 | 101.946 | 66.574 | 1.00 | 33.96 | A | O |
| ATOM | 618 | OD2 | ASP | A | 201 | 39.386 | 101.616 | 68.731 | 1.00 | 35.77 | A | O |
| ATOM | 619 | C | ASP | A | 201 | 39.717 | 104.633 | 65.599 | 1.00 | 35.73 | A | C |
| ATOM | 620 | O | ASP | A | 201 | 39.136 | 104.924 | 64.556 | 1.00 | 36.16 | A | O |
| ATOM | 621 | N | ALA | A | 202 | 40.977 | 104.215 | 65.614 | 1.00 | 36.60 | A | N |
| ATOM | 622 | CA | ALA | A | 202 | 41.738 | 104.124 | 64.372 | 1.00 | 35.67 | A | C |
| ATOM | 623 | CB | ALA | A | 202 | 43.228 | 104.205 | 64.676 | 1.00 | 34.98 | A | C |
| ATOM | 624 | C | ALA | A | 202 | 41.444 | 102.881 | 63.530 | 1.00 | 36.02 | A | C |
| ATOM | 625 | O | ALA | A | 202 | 41.396 | 102.960 | 62.302 | 1.00 | 36.18 | A | O |
| ATOM | 626 | N | ALA | A | 203 | 41.234 | 101.741 | 64.182 | 1.00 | 35.91 | A | N |
| ATOM | 627 | CA | ALA | A | 203 | 40.983 | 100.499 | 63.455 | 1.00 | 35.99 | A | C |
| ATOM | 628 | CB | ALA | A | 203 | 42.056 | 99.474 | 63.822 | 1.00 | 35.92 | A | C |
| ATOM | 629 | C | ALA | A | 203 | 39.599 | 99.881 | 63.642 | 1.00 | 35.06 | A | C |
| ATOM | 630 | O | ALA | A | 203 | 39.167 | 99.058 | 62.833 | 1.00 | 35.70 | A | O |
| ATOM | 631 | N | ARG | A | 204 | 38.896 | 100.275 | 64.697 | 1.00 | 34.43 | A | N |
| ATOM | 632 | CA | ARG | A | 204 | 37.580 | 99.700 | 64.962 | 1.00 | 32.43 | A | C |
| ATOM | 633 | CB | ARG | A | 204 | 37.648 | 98.895 | 66.267 | 1.00 | 32.75 | A | C |
| ATOM | 634 | CG | ARG | A | 204 | 38.506 | 97.632 | 66.175 | 1.00 | 35.06 | A | C |
| ATOM | 635 | CD | ARG | A | 204 | 39.131 | 97.280 | 67.516 | 1.00 | 35.42 | A | C |
| ATOM | 636 | NE | ARG | A | 204 | 40.124 | 98.281 | 67.891 | 1.00 | 39.37 | A | N |
| ATOM | 637 | CZ | ARG | A | 204 | 40.829 | 98.271 | 69.020 | 1.00 | 39.97 | A | C |
| ATOM | 638 | NH1 | ARG | A | 204 | 40.664 | 97.303 | 69.915 | 1.00 | 41.24 | A | N |
| ATOM | 639 | NH2 | ARG | A | 204 | 41.691 | 99.249 | 69.259 | 1.00 | 42.09 | A | N |
| ATOM | 640 | C | ARG | A | 204 | 36.397 | 100.675 | 65.019 | 1.00 | 29.51 | A | C |
| ATOM | 641 | O | ARG | A | 204 | 36.563 | 101.873 | 65.235 | 1.00 | 27.71 | A | O |
| ATOM | 642 | N | VAL | A | 205 | 35.203 | 100.124 | 64.810 | 1.00 | 27.67 | A | N |
| ATOM | 643 | CA | VAL | A | 205 | 33.945 | 100.864 | 64.873 | 1.00 | 26.35 | A | C |
| ATOM | 644 | CB | VAL | A | 205 | 33.203 | 100.843 | 63.514 | 1.00 | 27.17 | A | C |
| ATOM | 645 | CG1 | VAL | A | 205 | 31.863 | 101.555 | 63.639 | 1.00 | 28.86 | A | C |
| ATOM | 646 | CG2 | VAL | A | 205 | 34.049 | 101.521 | 62.446 | 1.00 | 28.26 | A | C |
| ATOM | 647 | C | VAL | A | 205 | 33.103 | 100.127 | 65.919 | 1.00 | 24.01 | A | C |
| ATOM | 648 | O | VAL | A | 205 | 32.992 | 98.892 | 65.876 | 1.00 | 22.92 | A | O |
| ATOM | 649 | N | TYR | A | 206 | 32.516 | 100.868 | 66.852 | 1.00 | 22.11 | A | N |
| ATOM | 650 | CA | TYR | A | 206 | 31.723 | 100.254 | 67.919 | 1.00 | 21.58 | A | C |
| ATOM | 651 | CB | TYR | A | 206 | 32.341 | 100.574 | 69.286 | 1.00 | 24.51 | A | C |
| ATOM | 652 | CG | TYR | A | 206 | 33.832 | 100.308 | 69.398 | 1.00 | 28.74 | A | C |
| ATOM | 653 | CD1 | TYR | A | 206 | 34.768 | 101.282 | 69.043 | 1.00 | 30.43 | A | C |
| ATOM | 654 | CE1 | TYR | A | 206 | 36.148 | 101.040 | 69.156 | 1.00 | 33.31 | A | C |
| ATOM | 655 | CD2 | TYR | A | 206 | 34.304 | 99.084 | 69.862 | 1.00 | 30.70 | A | C |

TABLE 2-continued coordinates for the two molecules in the asymmetric unit of [T287] Aurora
A (122–396) in complex with an inhibitor of formula II in space group P2₁

| ATOM | 656 | CE2 | TYR | A | 206 | 35.672 | 98.832 | 69.974 | 1.00 | 33.27 | A | C |
|------|-----|-----|-----|---|-----|--------|--------|--------|------|-------|---|---|
| ATOM | 657 | CZ  | TYR | A | 206 | 36.587 | 99.810 | 69.624 | 1.00 | 33.23 | A | C |
| ATOM | 658 | OH  | TYR | A | 206 | 37.934 | 99.555 | 69.755 | 1.00 | 33.76 | A | O |
| ATOM | 659 | C   | TYR | A | 206 | 30.245 | 100.650| 67.964 | 1.00 | 20.45 | A | C |
| ATOM | 660 | O   | TYR | A | 206 | 29.898 | 101.825| 67.828 | 1.00 | 20.51 | A | O |
| ATOM | 661 | N   | LEU | A | 207 | 29.385 | 99.659 | 68.179 | 1.00 | 19.23 | A | N |
| ATOM | 662 | CA  | LEU | A | 207 | 27.943 | 99.883 | 68.290 | 1.00 | 20.53 | A | C |
| ATOM | 663 | CB  | LEU | A | 207 | 27.183 | 99.001 | 67.288 | 1.00 | 21.53 | A | C |
| ATOM | 664 | CG  | LEU | A | 207 | 27.574 | 99.160 | 65.814 | 1.00 | 21.15 | A | C |
| ATOM | 665 | CD1 | LEU | A | 207 | 26.675 | 98.309 | 64.950 | 1.00 | 23.10 | A | C |
| ATOM | 666 | CD2 | LEU | A | 207 | 27.462 | 100.624| 65.412 | 1.00 | 23.96 | A | C |
| ATOM | 667 | C   | LEU | A | 207 | 27.495 | 99.542 | 69.712 | 1.00 | 20.27 | A | C |
| ATOM | 668 | O   | LEU | A | 207 | 27.760 | 98.443 | 70.204 | 1.00 | 22.20 | A | O |
| ATOM | 669 | N   | ILE | A | 208 | 26.825 | 100.480| 70.375 | 1.00 | 18.68 | A | N |
| ATOM | 670 | CA  | ILE | A | 208 | 26.350 | 100.256| 71.736 | 1.00 | 18.33 | A | C |
| ATOM | 671 | CB  | ILE | A | 208 | 26.514 | 101.518| 72.599 | 1.00 | 17.78 | A | C |
| ATOM | 672 | CG2 | ILE | A | 208 | 26.331 | 101.161| 74.075 | 1.00 | 18.29 | A | C |
| ATOM | 673 | CG1 | ILE | A | 208 | 27.896 | 102.138| 72.365 | 1.00 | 21.18 | A | C |
| ATOM | 674 | CD1 | ILE | A | 208 | 28.100 | 103.468| 73.086 | 1.00 | 19.74 | A | C |
| ATOM | 675 | C   | ILE | A | 208 | 24.864 | 99.895 | 71.650 | 1.00 | 19.02 | A | C |
| ATOM | 676 | O   | ILE | A | 208 | 24.025 | 100.749| 71.332 | 1.00 | 20.96 | A | O |
| ATOM | 677 | N   | LEU | A | 209 | 24.554 | 98.639 | 71.963 | 1.00 | 18.23 | A | N |
| ATOM | 678 | CA  | LEU | A | 209 | 23.200 | 98.100 | 71.868 | 1.00 | 17.67 | A | C |
| ATOM | 679 | CB  | LEU | A | 209 | 23.216 | 96.893 | 70.941 | 1.00 | 17.32 | A | C |
| ATOM | 680 | CG  | LEU | A | 209 | 23.871 | 97.022 | 69.564 | 1.00 | 19.38 | A | C |
| ATOM | 681 | CD1 | LEU | A | 209 | 24.381 | 95.647 | 69.117 | 1.00 | 20.09 | A | C |
| ATOM | 682 | CD2 | LEU | A | 209 | 22.877 | 97.587 | 68.571 | 1.00 | 19.54 | A | C |
| ATOM | 683 | C   | LEU | A | 209 | 22.519 | 97.668 | 73.160 | 1.00 | 19.32 | A | C |
| ATOM | 684 | O   | LEU | A | 209 | 23.169 | 97.322 | 74.149 | 1.00 | 18.62 | A | O |
| ATOM | 685 | N   | GLU | A | 210 | 21.190 | 97.682 | 73.124 | 1.00 | 17.29 | A | N |
| ATOM | 686 | CA  | GLU | A | 210 | 20.373 | 97.235 | 74.240 | 1.00 | 17.08 | A | C |
| ATOM | 687 | CB  | GLU | A | 210 | 18.892 | 97.490 | 73.922 | 1.00 | 17.25 | A | C |
| ATOM | 688 | CG  | GLU | A | 210 | 17.915 | 97.005 | 74.971 | 1.00 | 14.08 | A | C |
| ATOM | 689 | CD  | GLU | A | 210 | 16.466 | 97.056 | 74.493 | 1.00 | 16.64 | A | C |
| ATOM | 690 | OE1 | GLU | A | 210 | 15.579 | 96.672 | 75.275 | 1.00 | 16.48 | A | O |
| ATOM | 691 | OE2 | GLU | A | 210 | 16.210 | 97.470 | 73.338 | 1.00 | 18.70 | A | O |
| ATOM | 692 | C   | GLU | A | 210 | 20.625 | 95.724 | 74.369 | 1.00 | 17.70 | A | C |
| ATOM | 693 | O   | GLU | A | 210 | 20.722 | 95.018 | 73.367 | 1.00 | 16.33 | A | O |
| ATOM | 694 | N   | TYR | A | 211 | 20.737 | 95.230 | 75.596 | 1.00 | 18.29 | A | N |
| ATOM | 695 | CA  | TYR | A | 211 | 20.992 | 93.811 | 75.817 | 1.00 | 18.22 | A | C |
| ATOM | 696 | CB  | TYR | A | 211 | 21.889 | 93.644 | 77.045 | 1.00 | 21.03 | A | C |
| ATOM | 697 | CG  | TYR | A | 211 | 22.150 | 92.216 | 77.474 | 1.00 | 21.77 | A | C |
| ATOM | 698 | CD1 | TYR | A | 211 | 22.898 | 91.347 | 76.681 | 1.00 | 22.50 | A | C |
| ATOM | 699 | CE1 | TYR | A | 211 | 23.160 | 90.036 | 77.103 | 1.00 | 23.40 | A | C |
| ATOM | 700 | CD2 | TYR | A | 211 | 21.671 | 91.743 | 78.696 | 1.00 | 22.56 | A | C |
| ATOM | 701 | CE2 | TYR | A | 211 | 21.928 | 90.443 | 79.124 | 1.00 | 21.84 | A | C |
| ATOM | 702 | CZ  | TYR | A | 211 | 22.666 | 89.598 | 78.328 | 1.00 | 22.93 | A | C |
| ATOM | 703 | OH  | TYR | A | 211 | 22.902 | 88.314 | 78.757 | 1.00 | 24.56 | A | O |
| ATOM | 704 | C   | TYR | A | 211 | 19.704 | 93.011 | 75.996 | 1.00 | 17.77 | A | C |
| ATOM | 705 | O   | TYR | A | 211 | 18.791 | 93.444 | 76.694 | 1.00 | 16.95 | A | O |
| ATOM | 706 | N   | ALA | A | 212 | 19.642 | 91.845 | 75.353 | 1.00 | 18.77 | A | N |
| ATOM | 707 | CA  | ALA | A | 212 | 18.477 | 90.952 | 75.439 | 1.00 | 18.90 | A | C |
| ATOM | 708 | CB  | ALA | A | 212 | 18.090 | 90.485 | 74.040 | 1.00 | 16.75 | A | C |
| ATOM | 709 | C   | ALA | A | 212 | 18.873 | 89.755 | 76.325 | 1.00 | 19.85 | A | C |
| ATOM | 710 | O   | ALA | A | 212 | 19.551 | 88.837 | 75.872 | 1.00 | 20.40 | A | O |
| ATOM | 711 | N   | PRO | A | 213 | 18.444 | 89.757 | 77.602 | 1.00 | 21.83 | A | N |
| ATOM | 712 | CD  | PRO | A | 213 | 17.600 | 90.806 | 78.190 | 1.00 | 22.17 | A | C |
| ATOM | 713 | CA  | PRO | A | 213 | 18.727 | 88.726 | 78.609 | 1.00 | 22.10 | A | C |
| ATOM | 714 | CB  | PRO | A | 213 | 18.026 | 89.258 | 79.865 | 1.00 | 23.45 | A | C |
| ATOM | 715 | CG  | PRO | A | 213 | 17.976 | 90.713 | 79.651 | 1.00 | 24.12 | A | C |
| ATOM | 716 | C   | PRO | A | 213 | 18.318 | 87.295 | 78.320 | 1.00 | 22.31 | A | C |
| ATOM | 717 | O   | PRO | A | 213 | 19.019 | 86.360 | 78.703 | 1.00 | 22.54 | A | O |
| ATOM | 718 | N   | LEU | A | 214 | 17.184 | 87.111 | 77.656 | 1.00 | 22.59 | A | N |
| ATOM | 719 | CA  | LEU | A | 214 | 16.715 | 85.765 | 77.375 | 1.00 | 20.79 | A | C |
| ATOM | 720 | CB  | LEU | A | 214 | 15.181 | 85.716 | 77.499 | 1.00 | 21.06 | A | C |
| ATOM | 721 | CG  | LEU | A | 214 | 14.680 | 85.611 | 78.950 | 1.00 | 22.27 | A | C |
| ATOM | 722 | CD1 | LEU | A | 214 | 15.249 | 86.752 | 79.769 | 1.00 | 25.21 | A | C |
| ATOM | 723 | CD2 | LEU | A | 214 | 13.160 | 85.633 | 79.001 | 1.00 | 21.90 | A | C |
| ATOM | 724 | C   | LEU | A | 214 | 17.189 | 85.117 | 76.075 | 1.00 | 20.41 | A | C |
| ATOM | 725 | O   | LEU | A | 214 | 16.846 | 83.975 | 75.805 | 1.00 | 21.99 | A | O |
| ATOM | 726 | N   | GLY | A | 215 | 17.986 | 85.823 | 75.276 | 1.00 | 20.34 | A | N |
| ATOM | 727 | CA  | GLY | A | 215 | 18.503 | 85.227 | 74.047 | 1.00 | 22.43 | A | C |
| ATOM | 728 | C   | GLY | A | 215 | 17.611 | 85.190 | 72.813 | 1.00 | 21.59 | A | C |
| ATOM | 729 | O   | GLY | A | 215 | 16.679 | 85.976 | 72.696 | 1.00 | 23.24 | A | O |
| ATOM | 730 | N   | THR | A | 216 | 17.892 | 84.273 | 71.889 | 1.00 | 22.02 | A | N |
| ATOM | 731 | CA  | THR | A | 216 | 17.112 | 84.172 | 70.652 | 1.00 | 23.73 | A | C |

TABLE 2-continued coordinates for the two molecules in the asymmetric unit of [T287] Aurora
A (122–396) in complex with an inhibitor of formula II in space group P2₁

| ATOM | 732 | CB | THR | A | 216 | 17.960 | 83.626 | 69.487 | 1.00 | 24.78 | A | C |
|------|-----|-----|-----|---|-----|--------|--------|--------|------|-------|---|---|
| ATOM | 733 | OG1 | THR | A | 216 | 18.233 | 82.238 | 69.706 | 1.00 | 25.51 | A | O |
| ATOM | 734 | CG2 | THR | A | 216 | 19.270 | 84.397 | 69.369 | 1.00 | 25.01 | A | C |
| ATOM | 735 | C | THR | A | 216 | 15.851 | 83.314 | 70.720 | 1.00 | 23.31 | A | C |
| ATOM | 736 | O | THR | A | 216 | 15.750 | 82.382 | 71.513 | 1.00 | 21.80 | A | O |
| ATOM | 737 | N | VAL | A | 217 | 14.886 | 83.645 | 69.867 | 1.00 | 25.09 | A | N |
| ATOM | 738 | CA | VAL | A | 217 | 13.626 | 82.904 | 69.797 | 1.00 | 25.79 | A | C |
| ATOM | 739 | CB | VAL | A | 217 | 12.604 | 83.633 | 68.902 | 1.00 | 23.02 | A | C |
| ATOM | 740 | CG1 | VAL | A | 217 | 11.368 | 82.773 | 68.703 | 1.00 | 24.17 | A | C |
| ATOM | 741 | CG2 | VAL | A | 217 | 12.234 | 84.961 | 69.533 | 1.00 | 22.94 | A | C |
| ATOM | 742 | C | VAL | A | 217 | 13.921 | 81.530 | 69.196 | 1.00 | 26.14 | A | C |
| ATOM | 743 | O | VAL | A | 217 | 13.278 | 80.534 | 69.525 | 1.00 | 25.55 | A | O |
| ATOM | 744 | N | TYR | A | 218 | 14.909 | 81.501 | 68.314 | 1.00 | 26.45 | A | N |
| ATOM | 745 | CA | TYR | A | 218 | 15.327 | 80.283 | 67.655 | 1.00 | 30.04 | A | C |
| ATOM | 746 | CB | TYR | A | 218 | 16.464 | 80.624 | 66.690 | 1.00 | 34.58 | A | C |
| ATOM | 747 | CG | TYR | A | 218 | 17.201 | 79.443 | 66.113 | 1.00 | 40.28 | A | C |
| ATOM | 748 | CD1 | TYR | A | 218 | 18.240 | 78.834 | 66.818 | 1.00 | 43.24 | A | C |
| ATOM | 749 | CE1 | TYR | A | 218 | 18.945 | 77.765 | 66.277 | 1.00 | 44.89 | A | C |
| ATOM | 750 | CD2 | TYR | A | 218 | 16.882 | 78.949 | 64.854 | 1.00 | 42.24 | A | C |
| ATOM | 751 | CE2 | TYR | A | 218 | 17.579 | 77.879 | 64.304 | 1.00 | 44.73 | A | C |
| ATOM | 752 | CZ | TYR | A | 218 | 18.608 | 77.292 | 65.019 | 1.00 | 46.29 | A | C |
| ATOM | 753 | OH | TYR | A | 218 | 19.304 | 76.235 | 64.475 | 1.00 | 48.71 | A | O |
| ATOM | 754 | C | TYR | A | 218 | 15.759 | 79.241 | 68.684 | 1.00 | 30.04 | A | C |
| ATOM | 755 | O | TYR | A | 218 | 15.383 | 78.075 | 68.607 | 1.00 | 29.65 | A | O |
| ATOM | 756 | N | ARG | A | 219 | 16.534 | 79.675 | 69.668 | 1.00 | 31.08 | A | N |
| ATOM | 757 | CA | ARG | A | 219 | 17.011 | 78.778 | 70.702 | 1.00 | 30.24 | A | C |
| ATOM | 758 | CB | ARG | A | 219 | 18.047 | 79.502 | 71.555 | 1.00 | 34.57 | A | C |
| ATOM | 759 | CG | ARG | A | 219 | 18.660 | 78.657 | 72.634 | 1.00 | 39.81 | A | C |
| ATOM | 760 | CD | ARG | A | 219 | 19.723 | 79.443 | 73.374 | 1.00 | 45.90 | A | C |
| ATOM | 761 | NE | ARG | A | 219 | 20.255 | 78.683 | 74.501 | 1.00 | 51.60 | A | N |
| ATOM | 762 | CZ | ARG | A | 219 | 21.250 | 79.097 | 75.276 | 1.00 | 52.82 | A | C |
| ATOM | 763 | NH1 | ARG | A | 219 | 21.826 | 80.273 | 75.041 | 1.00 | 53.30 | A | N |
| ATOM | 764 | NH2 | ARG | A | 219 | 21.658 | 78.338 | 76.289 | 1.00 | 53.23 | A | N |
| ATOM | 765 | C | ARG | A | 219 | 15.855 | 78.267 | 71.556 | 1.00 | 29.44 | A | C |
| ATOM | 766 | O | ARG | A | 219 | 15.829 | 77.101 | 71.941 | 1.00 | 28.48 | A | O |
| ATOM | 767 | N | GLU | A | 220 | 14.892 | 79.138 | 71.840 | 1.00 | 29.18 | A | N |
| ATOM | 768 | CA | GLU | A | 220 | 13.721 | 78.765 | 72.627 | 1.00 | 29.90 | A | C |
| ATOM | 769 | CB | GLU | A | 220 | 12.873 | 80.011 | 72.924 | 1.00 | 30.93 | A | C |
| ATOM | 770 | CG | GLU | A | 220 | 11.570 | 79.737 | 73.653 | 1.00 | 35.19 | A | C |
| ATOM | 771 | CD | GLU | A | 220 | 10.684 | 80.975 | 73.765 | 1.00 | 38.55 | A | C |
| ATOM | 772 | OE1 | GLU | A | 220 | 10.619 | 81.754 | 72.789 | 1.00 | 41.41 | A | O |
| ATOM | 773 | OE2 | GLU | A | 220 | 10.036 | 81.165 | 74.816 | 1.00 | 38.75 | A | O |
| ATOM | 774 | C | GLU | A | 220 | 12.890 | 77.730 | 71.852 | 1.00 | 29.28 | A | C |
| ATOM | 775 | O | GLU | A | 220 | 12.319 | 76.813 | 72.434 | 1.00 | 29.27 | A | O |
| ATOM | 776 | N | LEU | A | 221 | 12.846 | 77.882 | 70.533 | 1.00 | 29.01 | A | N |
| ATOM | 777 | CA | LEU | A | 221 | 12.096 | 76.981 | 69.661 | 1.00 | 29.41 | A | C |
| ATOM | 778 | CB | LEU | A | 221 | 12.087 | 77.547 | 68.234 | 1.00 | 29.75 | A | C |
| ATOM | 779 | CG | LEU | A | 221 | 11.135 | 76.947 | 67.198 | 1.00 | 27.34 | A | C |
| ATOM | 780 | CD1 | LEU | A | 221 | 9.691 | 77.040 | 67.681 | 1.00 | 26.36 | A | C |
| ATOM | 781 | CD2 | LEU | A | 221 | 11.298 | 77.707 | 65.902 | 1.00 | 28.29 | A | C |
| ATOM | 782 | C | LEU | A | 221 | 12.691 | 75.570 | 69.655 | 1.00 | 31.02 | A | C |
| ATOM | 783 | O | LEU | A | 221 | 11.958 | 74.579 | 69.659 | 1.00 | 30.54 | A | O |
| ATOM | 784 | N | GLN | A | 222 | 14.022 | 75.487 | 69.636 | 1.00 | 32.15 | A | N |
| ATOM | 785 | CA | GLN | A | 222 | 14.718 | 74.204 | 69.644 | 1.00 | 33.38 | A | C |
| ATOM | 786 | CB | GLN | A | 222 | 16.224 | 74.405 | 69.478 | 1.00 | 36.12 | A | C |
| ATOM | 787 | CG | GLN | A | 222 | 16.624 | 75.120 | 68.206 | 1.00 | 40.81 | A | C |
| ATOM | 788 | CD | GLN | A | 222 | 18.126 | 75.279 | 68.092 | 1.00 | 44.96 | A | C |
| ATOM | 789 | OE1 | GLN | A | 222 | 18.787 | 75.722 | 69.033 | 1.00 | 46.46 | A | O |
| ATOM | 790 | NE2 | GLN | A | 222 | 18.675 | 74.924 | 66.933 | 1.00 | 47.81 | A | N |
| ATOM | 791 | C | GLN | A | 222 | 14.467 | 73.437 | 70.937 | 1.00 | 33.08 | A | C |
| ATOM | 792 | O | GLN | A | 222 | 14.435 | 72.212 | 70.933 | 1.00 | 33.65 | A | O |
| ATOM | 793 | N | LYS | A | 223 | 14.288 | 74.160 | 72.038 | 1.00 | 32.99 | A | N |
| ATOM | 794 | CA | LYS | A | 223 | 14.045 | 73.539 | 73.336 | 1.00 | 32.56 | A | C |
| ATOM | 795 | CB | LYS | A | 223 | 14.314 | 74.541 | 74.464 | 1.00 | 35.07 | A | C |
| ATOM | 796 | CG | LYS | A | 223 | 15.780 | 74.660 | 74.873 | 1.00 | 38.94 | A | C |
| ATOM | 797 | CD | LYS | A | 223 | 16.682 | 74.938 | 73.680 | 1.00 | 42.58 | A | C |
| ATOM | 798 | CE | LYS | A | 223 | 18.143 | 75.049 | 74.084 | 1.00 | 45.75 | A | C |
| ATOM | 799 | NZ | LYS | A | 223 | 19.012 | 75.377 | 72.910 | 1.00 | 47.32 | A | N |
| ATOM | 800 | C | LYS | A | 223 | 12.629 | 72.992 | 73.480 | 1.00 | 31.92 | A | C |
| ATOM | 801 | O | LYS | A | 223 | 12.444 | 71.840 | 73.869 | 1.00 | 31.63 | A | O |
| ATOM | 802 | N | LEU | A | 224 | 11.635 | 73.815 | 73.159 | 1.00 | 29.58 | A | N |
| ATOM | 803 | CA | LEU | A | 224 | 10.235 | 73.413 | 73.272 | 1.00 | 27.04 | A | C |
| ATOM | 804 | CB | LEU | A | 224 | 9.355 | 74.651 | 73.488 | 1.00 | 27.41 | A | C |
| ATOM | 805 | CG | LEU | A | 224 | 9.626 | 75.554 | 74.703 | 1.00 | 26.07 | A | C |
| ATOM | 806 | CD1 | LEU | A | 224 | 8.545 | 76.626 | 74.805 | 1.00 | 23.48 | A | C |
| ATOM | 807 | CD2 | LEU | A | 224 | 9.632 | 74.717 | 75.968 | 1.00 | 26.95 | A | C |

TABLE 2-continued coordinates for the two molecules in the asymmetric unit of [T287] Aurora A (122–396) in complex with an inhibitor of formula II in space group P2₁

| ATOM | 808 | C | LEU | A | 224 | 9.698 | 72.613 | 72.080 | 1.00 | 26.87 | A | C |
|------|-----|-----|-----|---|-----|-------|--------|--------|------|-------|---|---|
| ATOM | 809 | O | LEU | A | 224 | 8.653 | 71.977 | 72.187 | 1.00 | 27.46 | A | O |
| ATOM | 810 | N | SER | A | 225 | 10.410 | 72.650 | 70.954 | 1.00 | 26.55 | A | N |
| ATOM | 811 | CA | SER | A | 225 | 10.009 | 71.944 | 69.730 | 1.00 | 28.34 | A | C |
| ATOM | 812 | CB | SER | A | 225 | 9.473 | 70.549 | 70.062 | 1.00 | 30.23 | A | C |
| ATOM | 813 | OG | SER | A | 225 | 9.605 | 69.698 | 68.941 | 1.00 | 33.93 | A | O |
| ATOM | 814 | C | SER | A | 225 | 8.964 | 72.732 | 68.920 | 1.00 | 26.55 | A | C |
| ATOM | 815 | O | SER | A | 225 | 9.046 | 72.810 | 67.697 | 1.00 | 26.63 | A | O |
| ATOM | 816 | N | LYS | A | 226 | 7.977 | 73.296 | 69.607 | 1.00 | 25.84 | A | N |
| ATOM | 817 | CA | LYS | A | 226 | 6.958 | 74.129 | 68.976 | 1.00 | 25.88 | A | C |
| ATOM | 818 | CB | LYS | A | 226 | 6.012 | 73.304 | 68.087 | 1.00 | 28.21 | A | C |
| ATOM | 819 | CG | LYS | A | 226 | 5.184 | 72.259 | 68.790 | 1.00 | 28.88 | A | C |
| ATOM | 820 | CD | LYS | A | 226 | 4.409 | 71.443 | 67.770 | 1.00 | 34.11 | A | C |
| ATOM | 821 | CE | LYS | A | 226 | 3.483 | 70.427 | 68.435 | 1.00 | 34.70 | A | C |
| ATOM | 822 | NZ | LYS | A | 226 | 4.240 | 69.444 | 69.261 | 1.00 | 37.81 | A | N |
| ATOM | 823 | C | LYS | A | 226 | 6.191 | 74.851 | 70.073 | 1.00 | 25.27 | A | C |
| ATOM | 824 | O | LYS | A | 226 | 6.124 | 74.373 | 71.202 | 1.00 | 26.71 | A | O |
| ATOM | 825 | N | PHE | A | 227 | 5.637 | 76.016 | 69.749 | 1.00 | 24.65 | A | N |
| ATOM | 826 | CA | PHE | A | 227 | 4.891 | 76.808 | 70.722 | 1.00 | 22.54 | A | C |
| ATOM | 827 | CB | PHE | A | 227 | 5.085 | 78.312 | 70.463 | 1.00 | 23.44 | A | C |
| ATOM | 828 | CG | PHE | A | 227 | 6.527 | 78.753 | 70.359 | 1.00 | 20.95 | A | C |
| ATOM | 829 | CD1 | PHE | A | 227 | 7.523 | 78.135 | 71.106 | 1.00 | 21.88 | A | C |
| ATOM | 830 | CD2 | PHE | A | 227 | 6.868 | 79.847 | 69.561 | 1.00 | 19.95 | A | C |
| ATOM | 831 | CE1 | PHE | A | 227 | 8.850 | 78.606 | 71.065 | 1.00 | 23.78 | A | C |
| ATOM | 832 | CE2 | PHE | A | 227 | 8.183 | 80.326 | 69.511 | 1.00 | 21.33 | A | C |
| ATOM | 833 | CZ | PHE | A | 227 | 9.176 | 79.706 | 70.265 | 1.00 | 21.20 | A | C |
| ATOM | 834 | C | PHE | A | 227 | 3.397 | 76.514 | 70.673 | 1.00 | 22.04 | A | C |
| ATOM | 835 | O | PHE | A | 227 | 2.882 | 76.035 | 69.660 | 1.00 | 21.17 | A | O |
| ATOM | 836 | N | ASP | A | 228 | 2.707 | 76.813 | 71.768 | 1.00 | 19.93 | A | N |
| ATOM | 837 | CA | ASP | A | 228 | 1.269 | 76.617 | 71.842 | 1.00 | 21.17 | A | C |
| ATOM | 838 | CB | ASP | A | 228 | 0.840 | 76.388 | 73.294 | 1.00 | 22.28 | A | C |
| ATOM | 839 | CG | ASP | A | 228 | 1.204 | 77.547 | 74.203 | 1.00 | 24.14 | A | C |
| ATOM | 840 | OD1 | ASP | A | 228 | 1.715 | 77.288 | 75.307 | 1.00 | 25.83 | A | O |
| ATOM | 841 | OD2 | ASP | A | 228 | 0.968 | 78.718 | 73.829 | 1.00 | 24.66 | A | O |
| ATOM | 842 | C | ASP | A | 228 | 0.607 | 77.876 | 71.259 | 1.00 | 21.29 | A | C |
| ATOM | 843 | O | ASP | A | 228 | 1.287 | 78.878 | 70.977 | 1.00 | 20.58 | A | O |
| ATOM | 844 | N | GLU | A | 229 | −0.707 | 77.829 | 71.086 | 1.00 | 19.93 | A | N |
| ATOM | 845 | CA | GLU | A | 229 | −1.441 | 78.947 | 70.498 | 1.00 | 20.43 | A | C |
| ATOM | 846 | CB | GLU | A | 229 | −2.919 | 78.586 | 70.333 | 1.00 | 22.25 | A | C |
| ATOM | 847 | CG | GLU | A | 229 | −3.177 | 77.435 | 69.383 | 1.00 | 22.96 | A | C |
| ATOM | 848 | CD | GLU | A | 229 | −4.657 | 77.151 | 69.227 | 1.00 | 23.72 | A | C |
| ATOM | 849 | OE1 | GLU | A | 229 | −5.276 | 76.655 | 70.185 | 1.00 | 27.47 | A | O |
| ATOM | 850 | OE2 | GLU | A | 229 | −5.203 | 77.437 | 68.152 | 1.00 | 23.78 | A | O |
| ATOM | 851 | C | GLU | A | 229 | −1.330 | 80.270 | 71.237 | 1.00 | 20.15 | A | C |
| ATOM | 852 | O | GLU | A | 229 | −1.247 | 81.320 | 70.598 | 1.00 | 19.16 | A | O |
| ATOM | 853 | N | GLN | A | 230 | −1.337 | 80.238 | 72.569 | 1.00 | 17.98 | A | N |
| ATOM | 854 | CA | GLN | A | 230 | −1.233 | 81.480 | 73.319 | 1.00 | 17.46 | A | C |
| ATOM | 855 | CB | GLN | A | 230 | −1.412 | 81.246 | 74.833 | 1.00 | 16.42 | A | C |
| ATOM | 856 | CG | GLN | A | 230 | −1.448 | 82.560 | 75.641 | 1.00 | 18.34 | A | C |
| ATOM | 857 | CD | GLN | A | 230 | −1.683 | 82.377 | 77.140 | 1.00 | 18.98 | A | C |
| ATOM | 858 | OE1 | GLN | A | 230 | −0.744 | 82.430 | 77.933 | 1.00 | 21.19 | A | O |
| ATOM | 859 | NE2 | GLN | A | 230 | −2.932 | 82.167 | 77.529 | 1.00 | 16.82 | A | N |
| ATOM | 860 | C | GLN | A | 230 | 0.107 | 82.173 | 73.040 | 1.00 | 16.75 | A | C |
| ATOM | 861 | O | GLN | A | 230 | 0.136 | 83.359 | 72.679 | 1.00 | 17.29 | A | O |
| ATOM | 862 | N | ARG | A | 231 | 1.210 | 81.443 | 73.179 | 1.00 | 14.85 | A | N |
| ATOM | 863 | CA | ARG | A | 231 | 2.519 | 82.045 | 72.939 | 1.00 | 16.59 | A | C |
| ATOM | 864 | CB | ARG | A | 231 | 3.657 | 81.051 | 73.227 | 1.00 | 18.36 | A | C |
| ATOM | 865 | CG | ARG | A | 231 | 5.042 | 81.728 | 73.190 | 1.00 | 22.57 | A | C |
| ATOM | 866 | CD | ARG | A | 231 | 6.185 | 80.747 | 73.258 | 1.00 | 27.11 | A | C |
| ATOM | 867 | NE | ARG | A | 231 | 6.191 | 79.991 | 74.503 | 1.00 | 33.40 | A | N |
| ATOM | 868 | CZ | ARG | A | 231 | 6.654 | 80.446 | 75.664 | 1.00 | 35.76 | A | C |
| ATOM | 869 | NH1 | ARG | A | 231 | 6.605 | 79.675 | 76.738 | 1.00 | 36.21 | A | N |
| ATOM | 870 | NH2 | ARG | A | 231 | 7.176 | 81.660 | 75.752 | 1.00 | 38.74 | A | N |
| ATOM | 871 | C | ARG | A | 231 | 2.671 | 82.581 | 71.513 | 1.00 | 14.93 | A | C |
| ATOM | 872 | O | ARG | A | 231 | 3.151 | 83.700 | 71.311 | 1.00 | 14.16 | A | O |
| ATOM | 873 | N | THR | A | 232 | 2.276 | 81.776 | 70.531 | 1.00 | 15.57 | A | N |
| ATOM | 874 | CA | THR | A | 232 | 2.366 | 82.160 | 69.121 | 1.00 | 17.08 | A | C |
| ATOM | 875 | CB | THR | A | 232 | 1.859 | 81.030 | 68.188 | 1.00 | 18.02 | A | C |
| ATOM | 876 | OG1 | THR | A | 232 | 2.656 | 79.856 | 68.382 | 1.00 | 18.40 | A | O |
| ATOM | 877 | CG2 | THR | A | 232 | 1.953 | 81.451 | 66.718 | 1.00 | 15.83 | A | C |
| ATOM | 878 | C | THR | A | 232 | 1.553 | 83.420 | 68.821 | 1.00 | 17.13 | A | C |
| ATOM | 879 | O | THR | A | 232 | 2.061 | 84.359 | 68.204 | 1.00 | 18.70 | A | O |
| ATOM | 880 | N | ALA | A | 233 | 0.296 | 83.433 | 69.258 | 1.00 | 16.14 | A | N |
| ATOM | 881 | CA | ALA | A | 233 | −0.590 | 84.568 | 69.025 | 1.00 | 16.30 | A | C |
| ATOM | 882 | CB | ALA | A | 233 | −1.982 | 84.246 | 69.529 | 1.00 | 16.62 | A | C |
| ATOM | 883 | C | ALA | A | 233 | −0.076 | 85.846 | 69.687 | 1.00 | 17.07 | A | C |

TABLE 2-continued coordinates for the two molecules in the asymmetric unit of [T287] Aurora A (122–396) in complex with an inhibitor of formula II in space group P2$_1$

| ATOM | 884 | O | ALA | A | 233 | −0.259 | 86.944 | 69.166 | 1.00 | 16.10 | A | O |
|---|---|---|---|---|---|---|---|---|---|---|---|---|
| ATOM | 885 | N | THR | A | 234 | 0.552 | 85.699 | 70.849 | 1.00 | 17.52 | A | N |
| ATOM | 886 | CA | THR | A | 234 | 1.092 | 86.845 | 71.552 | 1.00 | 16.78 | A | C |
| ATOM | 887 | CB | THR | A | 234 | 1.494 | 86.467 | 73.014 | 1.00 | 17.54 | A | C |
| ATOM | 888 | OG1 | THR | A | 234 | 0.314 | 86.125 | 73.759 | 1.00 | 12.72 | A | O |
| ATOM | 889 | CG2 | THR | A | 234 | 2.184 | 87.633 | 73.706 | 1.00 | 17.21 | A | C |
| ATOM | 890 | C | THR | A | 234 | 2.297 | 87.362 | 70.766 | 1.00 | 16.02 | A | C |
| ATOM | 891 | O | THR | A | 234 | 2.471 | 88.564 | 70.621 | 1.00 | 18.24 | A | O |
| ATOM | 892 | N | TYR | A | 235 | 3.116 | 86.459 | 70.239 | 1.00 | 15.74 | A | N |
| ATOM | 893 | CA | TYR | A | 235 | 4.275 | 86.879 | 69.456 | 1.00 | 18.00 | A | C |
| ATOM | 894 | CB | TYR | A | 235 | 5.180 | 85.694 | 69.117 | 1.00 | 18.40 | A | C |
| ATOM | 895 | CG | TYR | A | 235 | 6.016 | 85.167 | 70.264 | 1.00 | 22.59 | A | C |
| ATOM | 896 | CD1 | TYR | A | 235 | 6.142 | 85.880 | 71.459 | 1.00 | 19.60 | A | C |
| ATOM | 897 | CE1 | TYR | A | 235 | 6.943 | 85.413 | 72.490 | 1.00 | 23.79 | A | C |
| ATOM | 898 | CD2 | TYR | A | 235 | 6.718 | 83.968 | 70.133 | 1.00 | 22.03 | A | C |
| ATOM | 899 | CE2 | TYR | A | 235 | 7.530 | 83.492 | 71.158 | 1.00 | 25.06 | A | C |
| ATOM | 900 | CZ | TYR | A | 235 | 7.639 | 84.217 | 72.331 | 1.00 | 24.79 | A | C |
| ATOM | 901 | OH | TYR | A | 235 | 8.449 | 83.748 | 73.332 | 1.00 | 27.52 | A | O |
| ATOM | 902 | C | TYR | A | 235 | 3.882 | 87.574 | 68.148 | 1.00 | 17.48 | A | C |
| ATOM | 903 | O | TYR | A | 235 | 4.498 | 88.570 | 67.760 | 1.00 | 18.14 | A | O |
| ATOM | 904 | N | ILE | A | 236 | 2.869 | 87.050 | 67.463 | 1.00 | 15.10 | A | N |
| ATOM | 905 | CA | ILE | A | 236 | 2.443 | 87.655 | 66.207 | 1.00 | 15.95 | A | C |
| ATOM | 906 | CB | ILE | A | 236 | 1.374 | 86.784 | 65.505 | 1.00 | 15.91 | A | C |
| ATOM | 907 | CG2 | ILE | A | 236 | 0.944 | 87.425 | 64.184 | 1.00 | 14.22 | A | C |
| ATOM | 908 | CG1 | ILE | A | 236 | 1.950 | 85.393 | 65.225 | 1.00 | 13.58 | A | C |
| ATOM | 909 | CD1 | ILE | A | 236 | 3.140 | 85.396 | 64.289 | 1.00 | 15.33 | A | C |
| ATOM | 910 | C | ILE | A | 236 | 1.905 | 89.070 | 66.425 | 1.00 | 16.93 | A | C |
| ATOM | 911 | O | ILE | A | 236 | 2.064 | 89.935 | 65.560 | 1.00 | 16.24 | A | O |
| ATOM | 912 | N | THR | A | 237 | 1.281 | 89.301 | 67.584 | 1.00 | 18.11 | A | N |
| ATOM | 913 | CA | THR | A | 237 | 0.727 | 90.613 | 67.937 | 1.00 | 19.28 | A | C |
| ATOM | 914 | CB | THR | A | 237 | −0.107 | 90.545 | 69.255 | 1.00 | 22.99 | A | C |
| ATOM | 915 | OG1 | THR | A | 237 | −1.306 | 89.787 | 69.035 | 1.00 | 23.64 | A | O |
| ATOM | 916 | CG2 | THR | A | 237 | −0.470 | 91.953 | 69.741 | 1.00 | 21.39 | A | C |
| ATOM | 917 | C | THR | A | 237 | 1.863 | 91.610 | 68.152 | 1.00 | 19.31 | A | C |
| ATOM | 918 | O | THR | A | 237 | 1.787 | 92.763 | 67.726 | 1.00 | 20.31 | A | O |
| ATOM | 919 | N | GLU | A | 238 | 2.912 | 91.164 | 68.836 | 1.00 | 18.54 | A | N |
| ATOM | 920 | CA | GLU | A | 238 | 4.063 | 92.011 | 69.097 | 1.00 | 18.15 | A | C |
| ATOM | 921 | CB | GLU | A | 238 | 5.052 | 91.280 | 70.025 | 1.00 | 20.31 | A | C |
| ATOM | 922 | CG | GLU | A | 238 | 4.684 | 91.396 | 71.511 | 1.00 | 23.11 | A | C |
| ATOM | 923 | CD1 | GLU | A | 238 | 5.394 | 90.392 | 72.410 | 1.00 | 24.67 | A | C |
| ATOM | 924 | OE1 | GLU | A | 238 | 6.516 | 89.946 | 72.079 | 1.00 | 24.03 | A | O |
| ATOM | 925 | OE2 | GLU | A | 238 | 4.825 | 90.057 | 73.473 | 1.00 | 28.40 | A | O |
| ATOM | 926 | C | GLU | A | 238 | 4.746 | 92.432 | 67.794 | 1.00 | 17.67 | A | C |
| ATOM | 927 | O | GLU | A | 238 | 5.101 | 93.601 | 67.629 | 1.00 | 16.64 | A | O |
| ATOM | 928 | N | LEU | A | 239 | 4.917 | 91.487 | 66.869 | 1.00 | 18.93 | A | N |
| ATOM | 929 | CA | LEU | A | 239 | 5.555 | 91.769 | 65.573 | 1.00 | 19.50 | A | C |
| ATOM | 930 | CB | LEU | A | 239 | 5.822 | 90.469 | 64.813 | 1.00 | 18.18 | A | C |
| ATOM | 931 | CG | LEU | A | 239 | 6.841 | 89.501 | 65.407 | 1.00 | 23.44 | A | C |
| ATOM | 932 | CD1 | LEU | A | 239 | 6.766 | 88.159 | 64.674 | 1.00 | 22.23 | A | C |
| ATOM | 933 | CD2 | LEU | A | 239 | 8.236 | 90.107 | 65.314 | 1.00 | 21.26 | A | C |
| ATOM | 934 | C | LEU | A | 239 | 4.727 | 92.703 | 64.675 | 1.00 | 19.61 | A | C |
| ATOM | 935 | O | LEU | A | 239 | 5.279 | 93.583 | 64.024 | 1.00 | 17.80 | A | O |
| ATOM | 936 | N | ALA | A | 240 | 3.412 | 92.502 | 64.631 | 1.00 | 18.94 | A | N |
| ATOM | 937 | CA | ALA | A | 240 | 2.548 | 93.351 | 63.802 | 1.00 | 19.51 | A | C |
| ATOM | 938 | CB | ALA | A | 240 | 1.079 | 92.853 | 63.841 | 1.00 | 18.09 | A | C |
| ATOM | 939 | C | ALA | A | 240 | 2.633 | 94.787 | 64.288 | 1.00 | 18.99 | A | C |
| ATOM | 940 | O | ALA | A | 240 | 2.721 | 95.706 | 63.482 | 1.00 | 22.48 | A | O |
| ATOM | 941 | N | ASN | A | 241 | 2.610 | 94.992 | 65.603 | 1.00 | 21.18 | A | N |
| ATOM | 942 | CA | ASN | A | 241 | 2.736 | 96.347 | 66.135 | 1.00 | 21.65 | A | C |
| ATOM | 943 | CB | ASN | A | 241 | 2.687 | 96.365 | 67.663 | 1.00 | 23.20 | A | C |
| ATOM | 944 | CG | ASN | A | 241 | 1.299 | 96.153 | 68.203 | 1.00 | 24.44 | A | C |
| ATOM | 945 | OD1 | ASN | A | 241 | 0.325 | 96.621 | 67.626 | 1.00 | 27.47 | A | O |
| ATOM | 946 | ND2 | ASN | A | 241 | 1.198 | 95.462 | 69.326 | 1.00 | 27.36 | A | N |
| ATOM | 947 | C | ASN | A | 241 | 4.069 | 96.935 | 65.685 | 1.00 | 22.55 | A | C |
| ATOM | 948 | O | ASN | A | 241 | 4.111 | 98.035 | 65.129 | 1.00 | 24.99 | A | O |
| ATOM | 949 | N | ALA | A | 242 | 5.159 | 96.200 | 65.909 | 1.00 | 21.61 | A | N |
| ATOM | 950 | CA | ALA | A | 242 | 6.483 | 96.684 | 65.525 | 1.00 | 20.55 | A | C |
| ATOM | 951 | CB | ALA | A | 242 | 7.557 | 95.687 | 65.959 | 1.00 | 20.38 | A | C |
| ATOM | 952 | C | ALA | A | 242 | 6.607 | 96.967 | 64.026 | 1.00 | 21.10 | A | C |
| ATOM | 953 | O | ALA | A | 242 | 7.207 | 97.969 | 63.627 | 1.00 | 20.03 | A | O |
| ATOM | 954 | N | LEU | A | 243 | 6.050 | 96.088 | 63.195 | 1.00 | 21.54 | A | N |
| ATOM | 955 | CA | LEU | A | 243 | 6.111 | 96.281 | 61.742 | 1.00 | 23.33 | A | C |
| ATOM | 956 | CB | LEU | A | 243 | 5.617 | 95.029 | 61.014 | 1.00 | 21.31 | A | C |
| ATOM | 957 | CG | LEU | A | 243 | 6.556 | 93.828 | 61.128 | 1.00 | 21.88 | A | C |
| ATOM | 958 | CD1 | LEU | A | 243 | 5.843 | 92.565 | 60.657 | 1.00 | 20.10 | A | C |
| ATOM | 959 | CD2 | LEU | A | 243 | 7.802 | 94.085 | 60.305 | 1.00 | 18.75 | A | C |

TABLE 2-continued coordinates for the two molecules in the asymmetric unit of [T287] Aurora A (122–396) in complex with an inhibitor of formula II in space group P2$_1$

| ATOM | 960 | C | LEU | A | 243 | 5.284 | 97.489 | 61.306 | 1.00 | 23.69 | A | C |
|---|---|---|---|---|---|---|---|---|---|---|---|---|
| ATOM | 961 | O | LEU | A | 243 | 5.627 | 98.171 | 60.344 | 1.00 | 22.16 | A | O |
| ATOM | 962 | N | SER | A | 244 | 4.191 | 97.741 | 62.021 | 1.00 | 25.47 | A | N |
| ATOM | 963 | CA | SER | A | 244 | 3.315 | 98.872 | 61.724 | 1.00 | 27.54 | A | C |
| ATOM | 964 | CB | SER | A | 244 | 2.053 | 98.784 | 62.584 | 1.00 | 28.75 | A | C |
| ATOM | 965 | OG | SER | A | 244 | 1.177 | 99.856 | 62.312 | 1.00 | 33.33 | A | O |
| ATOM | 966 | C | SER | A | 244 | 4.053 | 100.190 | 61.992 | 1.00 | 27.13 | A | C |
| ATOM | 967 | O | SER | A | 244 | 3.987 | 101.131 | 61.197 | 1.00 | 25.34 | A | O |
| ATOM | 968 | N | TYR | A | 245 | 4.757 | 100.253 | 63.117 | 1.00 | 27.39 | A | N |
| ATOM | 969 | CA | TYR | A | 245 | 5.518 | 101.444 | 63.455 | 1.00 | 26.91 | A | C |
| ATOM | 970 | CB | TYR | A | 245 | 6.122 | 101.303 | 64.862 | 1.00 | 26.66 | A | C |
| ATOM | 971 | CG | TYR | A | 245 | 7.181 | 102.328 | 65.192 | 1.00 | 26.43 | A | C |
| ATOM | 972 | CD1 | TYR | A | 245 | 8.530 | 102.058 | 64.966 | 1.00 | 26.18 | A | C |
| ATOM | 973 | CE1 | TYR | A | 245 | 9.517 | 103.008 | 65.248 | 1.00 | 27.41 | A | C |
| ATOM | 974 | CD2 | TYR | A | 245 | 6.836 | 103.580 | 65.709 | 1.00 | 28.15 | A | C |
| ATOM | 975 | CE2 | TYR | A | 245 | 7.815 | 104.539 | 65.994 | 1.00 | 27.61 | A | C |
| ATOM | 976 | CZ | TYR | A | 245 | 9.153 | 104.243 | 65.762 | 1.00 | 28.05 | A | C |
| ATOM | 977 | OH | TYR | A | 245 | 10.130 | 105.171 | 66.056 | 1.00 | 29.74 | A | O |
| ATOM | 978 | C | TYR | A | 245 | 6.612 | 101.653 | 62.402 | 1.00 | 26.52 | A | C |
| ATOM | 979 | O | TYR | A | 245 | 6.864 | 102.780 | 61.975 | 1.00 | 28.22 | A | O |
| ATOM | 980 | N | CYS | A | 246 | 7.254 | 100.573 | 61.970 | 1.00 | 26.10 | A | N |
| ATOM | 981 | CA | CYS | A | 246 | 8.305 | 100.683 | 60.957 | 1.00 | 27.26 | A | C |
| ATOM | 982 | CB | CYS | A | 246 | 8.973 | 99.320 | 60.703 | 1.00 | 25.76 | A | C |
| ATOM | 983 | SG | CYS | A | 246 | 10.111 | 98.729 | 62.011 | 1.00 | 25.61 | A | S |
| ATOM | 984 | C | CYS | A | 246 | 7.766 | 101.234 | 59.630 | 1.00 | 28.04 | A | C |
| ATOM | 985 | O | CYS | A | 246 | 8.357 | 102.139 | 59.041 | 1.00 | 28.18 | A | O |
| ATOM | 986 | N | HIS | A | 247 | 6.649 | 100.685 | 59.159 | 1.00 | 28.72 | A | N |
| ATOM | 987 | CA | HIS | A | 247 | 6.063 | 101.135 | 57.900 | 1.00 | 28.83 | A | C |
| ATOM | 988 | CB | HIS | A | 247 | 4.807 | 100.321 | 57.565 | 1.00 | 27.01 | A | C |
| ATOM | 989 | CG | HIS | A | 247 | 5.100 | 98.935 | 57.074 | 1.00 | 28.45 | A | C |
| ATOM | 990 | CD2 | HIS | A | 247 | 6.274 | 98.296 | 56.851 | 1.00 | 29.49 | A | C |
| ATOM | 991 | ND1 | HIS | A | 247 | 4.108 | 98.032 | 56.751 | 1.00 | 28.49 | A | N |
| ATOM | 992 | CE1 | HIS | A | 247 | 4.658 | 96.898 | 56.354 | 1.00 | 27.81 | A | C |
| ATOM | 993 | NE2 | HIS | A | 247 | 5.971 | 97.032 | 56.404 | 1.00 | 27.61 | A | N |
| ATOM | 994 | C | HIS | A | 247 | 5.757 | 102.627 | 57.921 | 1.00 | 28.03 | A | C |
| ATOM | 995 | O | HIS | A | 247 | 5.962 | 103.312 | 56.926 | 1.00 | 27.03 | A | O |
| ATOM | 996 | N | SER | A | 248 | 5.289 | 103.135 | 59.055 | 1.00 | 29.96 | A | N |
| ATOM | 997 | CA | SER | A | 248 | 4.996 | 104.568 | 59.172 | 1.00 | 31.71 | A | C |
| ATOM | 998 | CB | SER | A | 248 | 4.209 | 104.862 | 60.460 | 1.00 | 31.45 | A | C |
| ATOM | 999 | OG | SER | A | 248 | 4.988 | 104.617 | 61.622 | 1.00 | 32.11 | A | O |
| ATOM | 1000 | C | SER | A | 248 | 6.296 | 105.381 | 59.167 | 1.00 | 32.32 | A | C |
| ATOM | 1001 | O | SER | A | 248 | 6.276 | 106.604 | 59.039 | 1.00 | 33.26 | A | O |
| ATOM | 1002 | N | LYS | A | 249 | 7.426 | 104.694 | 59.310 | 1.00 | 33.45 | A | N |
| ATOM | 1003 | CA | LYS | A | 249 | 8.727 | 105.351 | 59.312 | 1.00 | 34.06 | A | C |
| ATOM | 1004 | CB | LYS | A | 249 | 9.572 | 104.883 | 60.506 | 1.00 | 35.23 | A | C |
| ATOM | 1005 | CG | LYS | A | 249 | 9.108 | 105.420 | 61.849 | 1.00 | 36.16 | A | C |
| ATOM | 1006 | CD | LYS | A | 249 | 9.142 | 106.947 | 61.870 | 1.00 | 38.50 | A | C |
| ATOM | 1007 | CE | LYS | A | 249 | 8.754 | 107.506 | 63.231 | 1.00 | 39.69 | A | C |
| ATOM | 1008 | NZ | LYS | A | 249 | 7.384 | 107.080 | 63.656 | 1.00 | 42.72 | A | N |
| ATOM | 1009 | C | LYS | A | 249 | 9.457 | 105.048 | 58.012 | 1.00 | 34.43 | A | C |
| ATOM | 1010 | O | LYS | A | 249 | 10.640 | 105.364 | 57.861 | 1.00 | 32.18 | A | O |
| ATOM | 1011 | N | ARG | A | 250 | 8.738 | 104.430 | 57.078 | 1.00 | 35.69 | A | N |
| ATOM | 1012 | CA | ARG | A | 250 | 9.288 | 104.081 | 55.778 | 1.00 | 37.56 | A | C |
| ATOM | 1013 | CB | ARG | A | 250 | 9.696 | 105.359 | 55.038 | 1.00 | 39.76 | A | C |
| ATOM | 1014 | CG | ARG | A | 250 | 8.501 | 106.132 | 54.453 | 1.00 | 41.59 | A | C |
| ATOM | 1015 | CD | ARG | A | 250 | 8.894 | 107.524 | 53.945 | 1.00 | 45.10 | A | C |
| ATOM | 1016 | NE | ARG | A | 250 | 8.232 | 107.855 | 52.679 | 1.00 | 47.20 | A | N |
| ATOM | 1017 | CZ | ARG | A | 250 | 8.713 | 107.536 | 51.478 | 1.00 | 47.18 | A | C |
| ATOM | 1018 | NH1 | ARG | A | 250 | 9.865 | 106.884 | 51.374 | 1.00 | 46.33 | A | N |
| ATOM | 1019 | NH2 | ARG | A | 250 | 8.042 | 107.863 | 50.381 | 1.00 | 45.77 | A | N |
| ATOM | 1020 | C | ARG | A | 250 | 10.465 | 103.118 | 55.890 | 1.00 | 39.53 | A | C |
| ATOM | 1021 | O | ARG | A | 250 | 11.451 | 103.225 | 55.162 | 1.00 | 38.88 | A | O |
| ATOM | 1022 | N | VAL | A | 251 | 10.348 | 102.169 | 56.813 | 1.00 | 41.36 | A | N |
| ATOM | 1023 | CA | VAL | A | 251 | 11.384 | 101.171 | 57.031 | 1.00 | 43.61 | A | C |
| ATOM | 1024 | CB | VAL | A | 251 | 11.846 | 101.171 | 58.500 | 1.00 | 43.34 | A | C |
| ATOM | 1025 | CG1 | VAL | A | 251 | 12.834 | 100.031 | 58.745 | 1.00 | 42.55 | A | C |
| ATOM | 1026 | CG2 | VAL | A | 251 | 12.479 | 102.512 | 58.834 | 1.00 | 41.90 | A | C |
| ATOM | 1027 | C | VAL | A | 251 | 10.864 | 99.782 | 56.672 | 1.00 | 45.77 | A | C |
| ATOM | 1028 | O | VAL | A | 251 | 9.773 | 99.393 | 57.087 | 1.00 | 45.19 | A | O |
| ATOM | 1029 | N | ILE | A | 252 | 11.013 | 98.979 | 55.608 | 1.00 | 48.92 | A | N |
| ATOM | 1030 | CA | ILE | A | 252 | 10.490 | 97.678 | 55.184 | 1.00 | 51.87 | A | C |
| ATOM | 1031 | CB | ILE | A | 252 | 10.035 | 97.701 | 53.702 | 1.00 | 51.65 | A | C |
| ATOM | 1032 | CG2 | ILE | A | 252 | 9.532 | 96.322 | 53.292 | 1.00 | 52.57 | A | C |
| ATOM | 1033 | CG1 | ILE | A | 252 | 8.929 | 98.741 | 53.511 | 1.00 | 50.23 | A | C |
| ATOM | 1034 | CD1 | ILE | A | 252 | 9.375 | 100.169 | 53.722 | 1.00 | 48.71 | A | C |
| ATOM | 1035 | C | ILE | A | 252 | 11.630 | 96.682 | 55.358 | 1.00 | 53.81 | A | C |

TABLE 2-continued coordinates for the two molecules in the asymmetric unit of [T287] Aurora A (122–396) in complex with an inhibitor of formula II in space group P2$_1$

| ATOM | 1036 | O   | ILE | A | 252 | 12.743 | 96.924 | 54.895 | 1.00 | 53.23 | A | O |
|------|------|-----|-----|---|-----|--------|--------|--------|------|-------|---|---|
| ATOM | 1037 | N   | HIS | A | 253 | 11.359 | 95.564 | 56.019 | 1.00 | 57.15 | A | N |
| ATOM | 1038 | CA  | HIS | A | 253 | 12.415 | 94.593 | 56.281 | 1.00 | 60.73 | A | C |
| ATOM | 1039 | CB  | HIS | A | 253 | 12.150 | 93.878 | 57.606 | 1.00 | 61.57 | A | C |
| ATOM | 1040 | CG  | HIS | A | 253 | 12.383 | 94.743 | 58.805 | 1.00 | 63.18 | A | C |
| ATOM | 1041 | CD2 | HIS | A | 253 | 11.736 | 94.819 | 59.992 | 1.00 | 62.71 | A | C |
| ATOM | 1042 | ND1 | HIS | A | 253 | 13.419 | 95.651 | 58.873 | 1.00 | 63.35 | A | N |
| ATOM | 1043 | CE1 | HIS | A | 253 | 13.400 | 96.248 | 60.051 | 1.00 | 63.74 | A | C |
| ATOM | 1044 | NE2 | HIS | A | 253 | 12.389 | 95.762 | 60.749 | 1.00 | 63.77 | A | N |
| ATOM | 1045 | C   | HIS | A | 253 | 12.749 | 93.565 | 55.217 | 1.00 | 62.30 | A | C |
| ATOM | 1046 | O   | HIS | A | 253 | 13.885 | 93.514 | 54.744 | 1.00 | 61.97 | A | O |
| ATOM | 1047 | N   | ARG | A | 254 | 11.774 | 92.742 | 54.849 | 1.00 | 64.77 | A | N |
| ATOM | 1048 | CA  | ARG | A | 254 | 12.004 | 91.700 | 53.855 | 1.00 | 66.63 | A | C |
| ATOM | 1049 | CB  | ARG | A | 254 | 12.719 | 92.304 | 52.639 | 1.00 | 67.76 | A | C |
| ATOM | 1050 | CG  | ARG | A | 254 | 11.948 | 93.473 | 52.021 | 1.00 | 69.83 | A | C |
| ATOM | 1051 | CD  | ARG | A | 254 | 12.846 | 94.466 | 51.288 | 1.00 | 71.13 | A | C |
| ATOM | 1052 | NE  | ARG | A | 254 | 13.615 | 93.863 | 50.203 | 1.00 | 71.83 | A | N |
| ATOM | 1053 | CZ  | ARG | A | 254 | 14.438 | 94.543 | 49.410 | 1.00 | 72.27 | A | C |
| ATOM | 1054 | NH1 | ARG | A | 254 | 14.596 | 95.850 | 49.580 | 1.00 | 72.84 | A | N |
| ATOM | 1055 | NH2 | ARG | A | 254 | 15.107 | 93.917 | 48.450 | 1.00 | 72.64 | A | N |
| ATOM | 1056 | C   | ARG | A | 254 | 12.858 | 90.603 | 54.507 | 1.00 | 67.14 | A | C |
| ATOM | 1057 | O   | ARG | A | 254 | 13.356 | 89.699 | 53.830 | 1.00 | 67.13 | A | O |
| ATOM | 1058 | N   | ASP | A | 255 | 13.002 | 90.694 | 55.832 | 1.00 | 67.58 | A | N |
| ATOM | 1059 | CA  | ASP | A | 255 | 13.789 | 89.744 | 56.630 | 1.00 | 66.56 | A | C |
| ATOM | 1060 | CB  | ASP | A | 255 | 15.286 | 90.046 | 56.458 | 1.00 | 67.69 | A | C |
| ATOM | 1061 | CG  | ASP | A | 255 | 16.113 | 89.642 | 57.669 | 1.00 | 68.95 | A | C |
| ATOM | 1062 | OD1 | ASP | A | 255 | 16.108 | 88.448 | 58.041 | 1.00 | 69.89 | A | O |
| ATOM | 1063 | OD2 | ASP | A | 255 | 16.772 | 90.529 | 58.249 | 1.00 | 69.16 | A | O |
| ATOM | 1064 | C   | ASP | A | 255 | 13.413 | 89.809 | 58.122 | 1.00 | 64.41 | A | C |
| ATOM | 1065 | O   | ASP | A | 255 | 13.261 | 90.904 | 58.674 | 1.00 | 64.57 | A | O |
| ATOM | 1066 | N   | ILE | A | 256 | 13.265 | 88.644 | 58.763 | 1.00 | 60.26 | A | N |
| ATOM | 1067 | CA  | ILE | A | 256 | 12.918 | 88.587 | 60.186 | 1.00 | 56.43 | A | C |
| ATOM | 1068 | CB  | ILE | A | 256 | 11.560 | 89.297 | 60.443 | 1.00 | 56.10 | A | C |
| ATOM | 1069 | CG2 | ILE | A | 256 | 10.406 | 88.449 | 59.934 | 1.00 | 55.25 | A | C |
| ATOM | 1070 | CG1 | ILE | A | 256 | 11.386 | 89.571 | 61.931 | 1.00 | 55.17 | A | C |
| ATOM | 1071 | CD1 | ILE | A | 256 | 10.193 | 90.444 | 62.235 | 1.00 | 56.51 | A | C |
| ATOM | 1072 | C   | ILE | A | 256 | 12.877 | 87.163 | 60.782 | 1.00 | 53.68 | A | C |
| ATOM | 1073 | O   | ILE | A | 256 | 11.950 | 86.803 | 61.505 | 1.00 | 53.90 | A | O |
| ATOM | 1074 | N   | LYS | A | 257 | 13.904 | 86.370 | 60.492 | 1.00 | 49.81 | A | N |
| ATOM | 1075 | CA  | LYS | A | 257 | 14.008 | 84.992 | 60.975 | 1.00 | 46.01 | A | C |
| ATOM | 1076 | CB  | LYS | A | 257 | 15.248 | 84.327 | 60.369 | 1.00 | 45.90 | A | C |
| ATOM | 1077 | CG  | LYS | A | 257 | 15.162 | 84.086 | 58.880 | 1.00 | 48.40 | A | C |
| ATOM | 1078 | CD  | LYS | A | 257 | 16.403 | 83.366 | 58.365 | 1.00 | 49.60 | A | C |
| ATOM | 1079 | CE  | LYS | A | 257 | 17.628 | 84.250 | 58.442 | 1.00 | 49.74 | A | C |
| ATOM | 1080 | NZ  | LYS | A | 257 | 17.476 | 85.429 | 57.544 | 1.00 | 51.45 | A | N |
| ATOM | 1081 | C   | LYS | A | 257 | 14.070 | 84.838 | 62.498 | 1.00 | 42.23 | A | C |
| ATOM | 1082 | O   | LYS | A | 257 | 14.379 | 85.783 | 63.218 | 1.00 | 42.43 | A | O |
| ATOM | 1083 | N   | PRO | A | 258 | 13.822 | 84.410 | 63.074 | 1.00 | 38.37 | A | N |
| ATOM | 1084 | CD  | PRO | A | 258 | 13.620 | 83.540 | 61.908 | 1.00 | 37.81 | A | C |
| ATOM | 1085 | CA  | PRO | A | 258 | 13.838 | 83.621 | 64.315 | 1.00 | 36.58 | A | C |
| ATOM | 1086 | CB  | PRO | A | 258 | 13.569 | 82.193 | 63.834 | 1.00 | 35.41 | A | C |
| ATOM | 1087 | CG  | PRO | A | 258 | 12.869 | 82.383 | 62.514 | 1.00 | 35.75 | A | C |
| ATOM | 1088 | C   | PRO | A | 258 | 15.216 | 83.756 | 64.962 | 1.00 | 35.92 | A | C |
| ATOM | 1089 | O   | PRO | A | 258 | 15.333 | 84.057 | 66.151 | 1.00 | 32.14 | A | O |
| ATOM | 1090 | N   | GLU | A | 259 | 16.249 | 83.523 | 64.155 | 1.00 | 35.08 | A | N |
| ATOM | 1091 | CA  | GLU | A | 259 | 17.626 | 83.652 | 64.601 | 1.00 | 36.22 | A | C |
| ATOM | 1092 | CB  | GLU | A | 259 | 18.607 | 83.198 | 63.506 | 1.00 | 37.23 | A | C |
| ATOM | 1093 | CG  | GLU | A | 259 | 18.795 | 81.688 | 63.340 | 1.00 | 40.19 | A | C |
| ATOM | 1094 | CD  | GLU | A | 259 | 17.713 | 81.010 | 62.496 | 1.00 | 42.23 | A | C |
| ATOM | 1095 | OE1 | GLU | A | 259 | 17.915 | 79.827 | 62.142 | 1.00 | 41.52 | A | O |
| ATOM | 1096 | OE2 | GLU | A | 259 | 16.670 | 81.642 | 62.192 | 1.00 | 40.30 | A | O |
| ATOM | 1097 | C   | GLU | A | 259 | 17.863 | 85.132 | 64.870 | 1.00 | 35.71 | A | C |
| ATOM | 1098 | O   | GLU | A | 259 | 18.700 | 85.499 | 65.688 | 1.00 | 35.67 | A | O |
| ATOM | 1099 | N   | ASN | A | 260 | 17.114 | 85.980 | 64.171 | 1.00 | 35.37 | A | N |
| ATOM | 1100 | CA  | ASN | A | 260 | 17.264 | 87.423 | 64.308 | 1.00 | 33.13 | A | C |
| ATOM | 1101 | CB  | ASN | A | 260 | 17.209 | 88.081 | 62.927 | 1.00 | 34.73 | A | C |
| ATOM | 1102 | CG  | ASN | A | 260 | 18.037 | 87.335 | 61.893 | 1.00 | 35.58 | A | C |
| ATOM | 1103 | OD1 | ASN | A | 260 | 19.087 | 86.773 | 62.205 | 1.00 | 37.11 | A | O |
| ATOM | 1104 | ND2 | ASN | A | 260 | 17.573 | 87.340 | 60.653 | 1.00 | 37.65 | A | N |
| ATOM | 1105 | C   | ASN | A | 260 | 16.236 | 88.073 | 65.229 | 1.00 | 31.26 | A | C |
| ATOM | 1106 | O   | ASN | A | 260 | 16.106 | 89.300 | 65.261 | 1.00 | 34.44 | A | O |
| ATOM | 1107 | N   | LEU | A | 261 | 15.494 | 87.255 | 65.963 | 1.00 | 27.11 | A | N |
| ATOM | 1108 | CA  | LEU | A | 261 | 14.501 | 87.762 | 66.902 | 1.00 | 24.52 | A | C |
| ATOM | 1109 | CB  | LEU | A | 261 | 13.147 | 87.089 | 66.648 | 1.00 | 24.18 | A | C |
| ATOM | 1110 | CG  | LEU | A | 261 | 12.432 | 87.443 | 65.340 | 1.00 | 22.90 | A | C |
| ATOM | 1111 | CD1 | LEU | A | 261 | 11.116 | 86.685 | 65.252 | 1.00 | 24.50 | A | C |

TABLE 2-continued coordinates for the two molecules in the asymmetric unit of [T287] Aurora
A (122–396) in complex with an inhibitor of formula II in space group P2₁

| ATOM | 1112 | CD2 | LEU | A | 261 | 12.172 | 88.923 | 65.296 | 1.00 | 21.37 | A | C |
|---|---|---|---|---|---|---|---|---|---|---|---|---|
| ATOM | 1113 | C | LEU | A | 261 | 14.986 | 87.476 | 68.329 | 1.00 | 22.38 | A | C |
| ATOM | 1114 | O | LEU | A | 261 | 15.179 | 86.321 | 68.694 | 1.00 | 23.95 | A | O |
| ATOM | 1115 | N | LEU | A | 262 | 15.182 | 88.524 | 69.126 | 1.00 | 20.79 | A | N |
| ATOM | 1116 | CA | LEU | A | 262 | 15.670 | 88.370 | 70.499 | 1.00 | 20.67 | A | C |
| ATOM | 1117 | CB | LEU | A | 262 | 16.810 | 89.376 | 70.758 | 1.00 | 18.51 | A | C |
| ATOM | 1118 | CG | LEU | A | 262 | 17.955 | 89.381 | 69.723 | 1.00 | 21.77 | A | C |
| ATOM | 1119 | CD1 | LEU | A | 262 | 18.955 | 90.499 | 70.035 | 1.00 | 21.55 | A | C |
| ATOM | 1120 | CD2 | LEU | A | 262 | 18.672 | 88.033 | 69.723 | 1.00 | 20.67 | A | C |
| ATOM | 1121 | C | LEU | A | 262 | 14.556 | 88.538 | 71.543 | 1.00 | 20.45 | A | C |
| ATOM | 1122 | O | LEU | A | 262 | 13.484 | 89.054 | 71.232 | 1.00 | 21.30 | A | O |
| ATOM | 1123 | N | LEU | A | 263 | 14.820 | 88.095 | 72.775 | 1.00 | 19.96 | A | N |
| ATOM | 1124 | CA | LEU | A | 263 | 13.855 | 88.172 | 73.875 | 1.00 | 20.52 | A | C |
| ATOM | 1125 | CB | LEU | A | 263 | 13.556 | 86.769 | 74.407 | 1.00 | 20.43 | A | C |
| ATOM | 1126 | CG | LEU | A | 263 | 12.804 | 85.816 | 73.471 | 1.00 | 22.66 | A | C |
| ATOM | 1127 | CD1 | LEU | A | 263 | 12.979 | 84.366 | 73.956 | 1.00 | 21.47 | A | C |
| ATOM | 1128 | CD2 | LEU | A | 263 | 11.330 | 86.219 | 73.415 | 1.00 | 19.52 | A | C |
| ATOM | 1129 | C | LEU | A | 263 | 14.307 | 89.045 | 75.046 | 1.00 | 22.38 | A | C |
| ATOM | 1130 | O | LEU | A | 263 | 15.389 | 88.848 | 75.603 | 1.00 | 22.70 | A | O |
| ATOM | 1131 | N | GLY | A | 264 | 13.456 | 89.992 | 75.429 | 1.00 | 21.30 | A | N |
| ATOM | 1132 | CA | GLY | A | 264 | 13.765 | 90.882 | 76.530 | 1.00 | 23.34 | A | C |
| ATOM | 1133 | C | GLY | A | 264 | 13.574 | 90.251 | 77.902 | 1.00 | 25.78 | A | C |
| ATOM | 1134 | O | GLY | A | 264 | 13.277 | 89.061 | 78.025 | 1.00 | 24.77 | A | O |
| ATOM | 1135 | N | SER | A | 265 | 13.732 | 91.067 | 78.939 | 1.00 | 27.28 | A | N |
| ATOM | 1136 | CA | SER | A | 265 | 13.618 | 90.609 | 80.321 | 1.00 | 28.82 | A | C |
| ATOM | 1137 | CB | SER | A | 265 | 13.959 | 91.758 | 81.270 | 1.00 | 29.98 | A | C |
| ATOM | 1138 | OG | SER | A | 265 | 14.174 | 91.285 | 82.583 | 1.00 | 31.27 | A | O |
| ATOM | 1139 | C | SER | A | 265 | 12.253 | 90.039 | 80.684 | 1.00 | 29.23 | A | C |
| ATOM | 1140 | O | SER | A | 265 | 12.158 | 89.086 | 81.449 | 1.00 | 30.53 | A | O |
| ATOM | 1141 | N | ALA | A | 266 | 11.193 | 90.623 | 80.140 | 1.00 | 29.57 | A | N |
| ATOM | 1142 | CA | ALA | A | 266 | 9.845 | 90.156 | 80.432 | 1.00 | 28.18 | A | C |
| ATOM | 1143 | CB | ALA | A | 266 | 8.889 | 91.338 | 80.475 | 1.00 | 28.62 | A | C |
| ATOM | 1144 | C | ALA | A | 266 | 9.373 | 89.141 | 79.399 | 1.00 | 27.11 | A | C |
| ATOM | 1145 | O | ALA | A | 266 | 8.211 | 88.749 | 79.393 | 1.00 | 29.47 | A | O |
| ATOM | 1146 | N | GLY | A | 267 | 10.274 | 88.717 | 78.524 | 1.00 | 25.83 | A | N |
| ATOM | 1147 | CA | GLY | A | 267 | 9.900 | 87.759 | 77.502 | 1.00 | 24.74 | A | C |
| ATOM | 1148 | C | GLY | A | 267 | 9.343 | 88.414 | 76.249 | 1.00 | 24.20 | A | C |
| ATOM | 1149 | O | GLY | A | 267 | 8.829 | 87.729 | 75.365 | 1.00 | 22.75 | A | O |
| ATOM | 1150 | N | GLU | A | 268 | 9.435 | 89.740 | 76.167 | 1.00 | 24.05 | A | N |
| ATOM | 1151 | CA | GLU | A | 268 | 8.942 | 90.468 | 74.993 | 1.00 | 25.88 | A | C |
| ATOM | 1152 | CB | GLU | A | 268 | 8.748 | 91.951 | 75.328 | 1.00 | 27.62 | A | C |
| ATOM | 1153 | CG | GLU | A | 268 | 8.880 | 92.266 | 76.803 | 1.00 | 33.71 | A | C |
| ATOM | 1154 | CD | GLU | A | 268 | 10.323 | 92.434 | 77.243 | 1.00 | 35.40 | A | C |
| ATOM | 1155 | OE1 | GLU | A | 268 | 10.874 | 93.537 | 77.049 | 1.00 | 36.57 | A | O |
| ATOM | 1156 | OE2 | GLU | A | 268 | 10.909 | 91.465 | 77.773 | 1.00 | 36.25 | A | O |
| ATOM | 1157 | C | GLU | A | 268 | 9.920 | 90.327 | 73.820 | 1.00 | 24.17 | A | C |
| ATOM | 1158 | O | GLU | A | 268 | 11.138 | 90.213 | 74.021 | 1.00 | 23.37 | A | O |
| ATOM | 1159 | N | LEU | A | 269 | 9.380 | 90.317 | 72.603 | 1.00 | 22.43 | A | N |
| ATOM | 1160 | CA | LEU | A | 269 | 10.185 | 90.189 | 71.388 | 1.00 | 22.74 | A | C |
| ATOM | 1161 | CB | LEU | A | 269 | 9.291 | 89.793 | 70.204 | 1.00 | 27.41 | A | C |
| ATOM | 1162 | CG | LEU | A | 269 | 8.740 | 88.370 | 70.198 | 1.00 | 30.77 | A | C |
| ATOM | 1163 | CD1 | LEU | A | 269 | 7.689 | 88.219 | 69.115 | 1.00 | 32.33 | A | C |
| ATOM | 1164 | CD2 | LEU | A | 269 | 9.893 | 87.387 | 69.981 | 1.00 | 30.69 | A | C |
| ATOM | 1165 | C | LEU | A | 269 | 10.941 | 91.466 | 71.024 | 1.00 | 20.79 | A | C |
| ATOM | 1166 | O | LEU | A | 269 | 10.427 | 92.569 | 71.176 | 1.00 | 20.86 | A | O |
| ATOM | 1167 | N | LYS | A | 270 | 12.164 | 91.310 | 70.536 | 1.00 | 19.07 | A | N |
| ATOM | 1168 | CA | LYS | A | 270 | 12.968 | 92.453 | 70.123 | 1.00 | 19.86 | A | C |
| ATOM | 1169 | CB | LYS | A | 270 | 14.179 | 92.628 | 71.046 | 1.00 | 19.41 | A | C |
| ATOM | 1170 | CG | LYS | A | 270 | 13.839 | 92.907 | 72.512 | 1.00 | 21.56 | A | C |
| ATOM | 1171 | CD | LYS | A | 270 | 13.368 | 94.336 | 72.739 | 1.00 | 21.90 | A | C |
| ATOM | 1172 | CE | LYS | A | 270 | 13.083 | 94.578 | 74.222 | 1.00 | 19.95 | A | C |
| ATOM | 1173 | NZ | LYS | A | 270 | 12.812 | 96.006 | 74.509 | 1.00 | 19.75 | A | N |
| ATOM | 1174 | C | LYS | A | 270 | 13.459 | 92.201 | 68.703 | 1.00 | 19.52 | A | C |
| ATOM | 1175 | O | LYS | A | 270 | 14.126 | 91.199 | 68.458 | 1.00 | 19.94 | A | O |
| ATOM | 1176 | N | ILE | A | 271 | 13.122 | 93.092 | 67.768 | 1.00 | 20.30 | A | N |
| ATOM | 1177 | CA | ILE | A | 271 | 13.581 | 92.946 | 66.388 | 1.00 | 19.95 | A | C |
| ATOM | 1178 | CB | ILE | A | 271 | 12.637 | 93.645 | 65.375 | 1.00 | 21.57 | A | C |
| ATOM | 1179 | CG2 | ILE | A | 271 | 13.245 | 93.602 | 63.959 | 1.00 | 22.31 | A | C |
| ATOM | 1180 | CG1 | ILE | A | 271 | 11.275 | 92.952 | 65.349 | 1.00 | 23.31 | A | C |
| ATOM | 1181 | CD1 | ILE | A | 271 | 10.313 | 93.557 | 64.325 | 1.00 | 23.77 | A | C |
| ATOM | 1182 | C | ILE | A | 271 | 14.966 | 93.584 | 66.273 | 1.00 | 20.17 | A | C |
| ATOM | 1183 | O | ILE | A | 271 | 15.139 | 94.761 | 66.590 | 1.00 | 19.60 | A | O |
| ATOM | 1184 | N | ALA | A | 272 | 15.945 | 92.805 | 65.822 | 1.00 | 20.80 | A | N |
| ATOM | 1185 | CA | ALA | A | 272 | 17.318 | 93.291 | 65.675 | 1.00 | 22.55 | A | C |
| ATOM | 1186 | CB | ALA | A | 272 | 18.278 | 92.307 | 66.319 | 1.00 | 22.63 | A | C |
| ATOM | 1187 | C | ALA | A | 272 | 17.671 | 93.477 | 64.199 | 1.00 | 23.77 | A | C |

TABLE 2-continued coordinates for the two molecules in the asymmetric unit of [T287] Aurora A (122–396) in complex with an inhibitor of formula II in space group P2₁

| ATOM | 1188 | O | ALA | A | 272 | 16.967 | 92.985 | 63.335 | 1.00 | 27.69 | A | O |
|---|---|---|---|---|---|---|---|---|---|---|---|---|
| ATOM | 1189 | N | ASP | A | 273 | 18.770 | 94.166 | 63.914 | 1.00 | 25.21 | A | N |
| ATOM | 1190 | CA | ASP | A | 273 | 19.179 | 94.423 | 62.535 | 1.00 | 26.15 | A | C |
| ATOM | 1191 | CB | ASP | A | 273 | 19.470 | 95.919 | 62.371 | 1.00 | 26.59 | A | C |
| ATOM | 1192 | CG | ASP | A | 273 | 19.481 | 96.364 | 60.922 | 1.00 | 28.71 | A | C |
| ATOM | 1193 | OD1 | ASP | A | 273 | 19.921 | 97.503 | 60.662 | 1.00 | 27.94 | A | O |
| ATOM | 1194 | OD2 | ASP | A | 273 | 19.042 | 95.587 | 60.048 | 1.00 | 26.80 | A | O |
| ATOM | 1195 | C | ASP | A | 273 | 20.409 | 93.608 | 62.114 | 1.00 | 28.69 | A | C |
| ATOM | 1196 | O | ASP | A | 273 | 21.513 | 94.134 | 62.036 | 1.00 | 31.16 | A | O |
| ATOM | 1197 | N | PHE | A | 274 | 20.212 | 92.325 | 61.825 | 1.00 | 31.46 | A | N |
| ATOM | 1198 | CA | PHE | A | 274 | 21.309 | 91.445 | 61.410 | 1.00 | 34.17 | A | C |
| ATOM | 1199 | CB | PHE | A | 274 | 21.014 | 90.005 | 61.826 | 1.00 | 34.86 | A | C |
| ATOM | 1200 | CG | PHE | A | 274 | 21.126 | 89.762 | 63.298 | 1.00 | 34.01 | A | C |
| ATOM | 1201 | CD1 | PHE | A | 274 | 22.369 | 89.593 | 63.891 | 1.00 | 35.57 | A | C |
| ATOM | 1202 | CD2 | PHE | A | 274 | 19.986 | 89.690 | 64.091 | 1.00 | 33.84 | A | C |
| ATOM | 1203 | CE1 | PHE | A | 274 | 22.478 | 89.352 | 65.255 | 1.00 | 34.13 | A | C |
| ATOM | 1204 | CE2 | PHE | A | 274 | 20.075 | 89.449 | 65.458 | 1.00 | 33.04 | A | C |
| ATOM | 1205 | CZ | PHE | A | 274 | 21.315 | 89.279 | 66.043 | 1.00 | 35.67 | A | C |
| ATOM | 1206 | C | PHE | A | 274 | 21.610 | 91.465 | 59.908 | 1.00 | 35.98 | A | C |
| ATOM | 1207 | O | PHE | A | 274 | 22.769 | 91.357 | 59.508 | 1.00 | 37.36 | A | O |
| ATOM | 1208 | N | GLY | A | 275 | 20.591 | 91.607 | 59.065 | 1.00 | 36.77 | A | N |
| ATOM | 1209 | CA | GLY | A | 275 | 20.872 | 91.613 | 57.640 | 1.00 | 38.21 | A | C |
| ATOM | 1210 | C | GLY | A | 275 | 21.125 | 93.012 | 57.108 | 1.00 | 39.96 | A | C |
| ATOM | 1211 | O | GLY | A | 275 | 20.645 | 93.371 | 56.030 | 1.00 | 40.54 | A | O |
| ATOM | 1212 | N | TRP | A | 276 | 21.894 | 93.801 | 57.850 | 1.00 | 40.99 | A | N |
| ATOM | 1213 | CA | TRP | A | 276 | 22.180 | 95.178 | 57.454 | 1.00 | 41.46 | A | C |
| ATOM | 1214 | CB | TRP | A | 276 | 22.767 | 95.958 | 58.633 | 1.00 | 39.82 | A | C |
| ATOM | 1215 | CG | TRP | A | 276 | 24.099 | 95.435 | 59.065 | 1.00 | 39.01 | A | C |
| ATOM | 1216 | CD2 | TRP | A | 276 | 25.376 | 95.801 | 58.523 | 1.00 | 38.81 | A | C |
| ATOM | 1217 | CE2 | TRP | A | 276 | 26.350 | 95.024 | 59.190 | 1.00 | 38.69 | A | C |
| ATOM | 1218 | CE3 | TRP | A | 276 | 25.790 | 96.707 | 57.538 | 1.00 | 38.86 | A | C |
| ATOM | 1219 | CD1 | TRP | A | 276 | 24.344 | 94.481 | 60.014 | 1.00 | 37.17 | A | C |
| ATOM | 1220 | NE1 | TRP | A | 276 | 25.692 | 94.231 | 60.092 | 1.00 | 36.72 | A | N |
| ATOM | 1221 | CZ2 | TRP | A | 276 | 27.717 | 95.125 | 58.905 | 1.00 | 39.22 | A | C |
| ATOM | 1222 | CZ3 | TRP | A | 276 | 27.154 | 96.809 | 57.249 | 1.00 | 40.49 | A | C |
| ATOM | 1223 | CH2 | TRP | A | 276 | 28.101 | 96.018 | 57.934 | 1.00 | 39.41 | A | C |
| ATOM | 1224 | C | TRP | A | 276 | 23.152 | 95.244 | 56.289 | 1.00 | 42.15 | A | C |
| ATOM | 1225 | O | TRP | A | 276 | 23.334 | 96.307 | 55.686 | 1.00 | 43.44 | A | O |
| ATOM | 1226 | N | SER | A | 277 | 23.790 | 94.119 | 55.982 | 1.00 | 42.35 | A | N |
| ATOM | 1227 | CA | SER | A | 277 | 24.750 | 94.058 | 54.887 | 1.00 | 43.23 | A | C |
| ATOM | 1228 | CB | SER | A | 277 | 26.063 | 93.415 | 55.360 | 1.00 | 42.06 | A | C |
| ATOM | 1229 | OG | SER | A | 277 | 25.810 | 92.188 | 56.032 | 1.00 | 41.30 | A | O |
| ATOM | 1230 | C | SER | A | 277 | 24.171 | 93.244 | 53.736 | 1.00 | 44.99 | A | C |
| ATOM | 1231 | O | SER | A | 277 | 24.709 | 93.259 | 52.619 | 1.00 | 46.90 | A | O |
| ATOM | 1232 | N | GLY | A | 290 | 19.559 | 85.906 | 54.593 | 1.00 | 50.58 | A | N |
| ATOM | 1233 | CA | GLY | A | 290 | 18.167 | 85.530 | 54.418 | 1.00 | 50.41 | A | C |
| ATOM | 1234 | C | GLY | A | 290 | 17.976 | 84.405 | 53.413 | 1.00 | 49.78 | A | C |
| ATOM | 1235 | O | GLY | A | 290 | 17.787 | 84.652 | 52.215 | 1.00 | 49.58 | A | O |
| ATOM | 1236 | N | THR | A | 291 | 18.024 | 83.166 | 53.899 | 1.00 | 47.99 | A | N |
| ATOM | 1237 | CA | THR | A | 291 | 17.855 | 82.001 | 53.036 | 1.00 | 45.67 | A | C |
| ATOM | 1238 | CB | THR | A | 291 | 17.993 | 80.671 | 53.833 | 1.00 | 46.93 | A | C |
| ATOM | 1239 | OG1 | THR | A | 291 | 17.389 | 80.818 | 55.127 | 1.00 | 47.18 | A | O |
| ATOM | 1240 | CG2 | THR | A | 291 | 19.460 | 80.279 | 53.988 | 1.00 | 45.73 | A | C |
| ATOM | 1241 | C | THR | A | 291 | 16.504 | 82.009 | 52.318 | 1.00 | 43.16 | A | C |
| ATOM | 1242 | O | THR | A | 291 | 15.604 | 82.783 | 52.650 | 1.00 | 42.03 | A | O |
| ATOM | 1243 | N | LEU | A | 292 | 16.385 | 81.119 | 51.340 | 1.00 | 41.25 | A | N |
| ATOM | 1244 | CA | LEU | A | 292 | 15.194 | 80.972 | 50.514 | 1.00 | 39.15 | A | C |
| ATOM | 1245 | CB | LEU | A | 292 | 15.417 | 79.814 | 49.540 | 1.00 | 41.13 | A | C |
| ATOM | 1246 | CG | LEU | A | 292 | 14.653 | 79.815 | 48.220 | 1.00 | 41.33 | A | C |
| ATOM | 1247 | CD1 | LEU | A | 292 | 14.961 | 81.085 | 47.436 | 1.00 | 40.19 | A | C |
| ATOM | 1248 | CD2 | LEU | A | 292 | 15.069 | 78.592 | 47.423 | 1.00 | 43.53 | A | C |
| ATOM | 1249 | C | LEU | A | 292 | 13.887 | 80.750 | 51.280 | 1.00 | 36.22 | A | C |
| ATOM | 1250 | O | LEU | A | 292 | 12.847 | 81.287 | 50.909 | 1.00 | 35.72 | A | O |
| ATOM | 1251 | N | ASP | A | 293 | 13.949 | 79.964 | 52.346 | 1.00 | 32.89 | A | N |
| ATOM | 1252 | CA | ASP | A | 293 | 12.771 | 79.647 | 53.150 | 1.00 | 31.62 | A | C |
| ATOM | 1253 | CB | ASP | A | 293 | 13.211 | 78.945 | 54.437 | 1.00 | 31.49 | A | C |
| ATOM | 1254 | CG | ASP | A | 293 | 13.399 | 77.452 | 54.253 | 1.00 | 33.23 | A | C |
| ATOM | 1255 | OD1 | ASP | A | 293 | 14.114 | 76.838 | 55.076 | 1.00 | 35.49 | A | O |
| ATOM | 1256 | OD2 | ASP | A | 293 | 12.818 | 76.886 | 53.299 | 1.00 | 31.43 | A | O |
| ATOM | 1257 | C | ASP | A | 293 | 11.805 | 80.779 | 53.503 | 1.00 | 29.72 | A | C |
| ATOM | 1258 | O | ASP | A | 293 | 10.595 | 80.563 | 53.556 | 1.00 | 28.20 | A | O |
| ATOM | 1259 | N | TYR | A | 294 | 12.327 | 81.977 | 53.748 | 1.00 | 28.61 | A | N |
| ATOM | 1260 | CA | TYR | A | 294 | 11.476 | 83.101 | 54.128 | 1.00 | 27.28 | A | C |
| ATOM | 1261 | CB | TYR | A | 294 | 12.064 | 83.814 | 55.357 | 1.00 | 28.14 | A | C |
| ATOM | 1262 | CG | TYR | A | 294 | 12.451 | 82.871 | 56.472 | 1.00 | 29.60 | A | C |
| ATOM | 1263 | CD1 | TYR | A | 294 | 13.669 | 82.192 | 56.442 | 1.00 | 31.65 | A | C |

TABLE 2-continued coordinates for the two molecules in the asymmetric unit of [T287] Aurora A (122–396) in complex with an inhibitor of formula II in space group P2$_1$

| ATOM | 1264 | CE1 | TYR | A | 294 | 14.003 | 81.264 | 57.423 | 1.00 | 33.54 A | C |
|---|---|---|---|---|---|---|---|---|---|---|---|
| ATOM | 1265 | CD2 | TYR | A | 294 | 11.574 | 82.601 | 57.522 | 1.00 | 31.90 A | C |
| ATOM | 1266 | CE2 | TYR | A | 294 | 11.897 | 81.669 | 58.514 | 1.00 | 32.48 A | C |
| ATOM | 1267 | CZ | TYR | A | 294 | 13.112 | 81.005 | 58.454 | 1.00 | 35.17 A | C |
| ATOM | 1268 | OH | TYR | A | 294 | 13.437 | 80.065 | 59.406 | 1.00 | 37.45 A | O |
| ATOM | 1269 | C | TYR | A | 294 | 11.211 | 84.126 | 53.032 | 1.00 | 26.29 A | C |
| ATOM | 1270 | O | TYR | A | 294 | 10.530 | 85.117 | 53.276 | 1.00 | 27.19 A | O |
| ATOM | 1271 | N | LEU | A | 295 | 11.732 | 83.888 | 51.830 | 1.00 | 25.16 A | N |
| ATOM | 1272 | CA | LEU | A | 295 | 11.540 | 84.809 | 50.709 | 1.00 | 24.82 A | C |
| ATOM | 1273 | CB | LEU | A | 295 | 12.643 | 84.607 | 49.669 | 1.00 | 24.50 A | C |
| ATOM | 1274 | CG | LEU | A | 295 | 14.052 | 85.044 | 50.075 | 1.00 | 25.62 A | C |
| ATOM | 1275 | CD1 | LEU | A | 295 | 15.019 | 84.731 | 48.952 | 1.00 | 21.99 A | C |
| ATOM | 1276 | CD2 | LEU | A | 295 | 14.053 | 86.535 | 50.391 | 1.00 | 25.81 A | C |
| ATOM | 1277 | C | LEU | A | 295 | 10.181 | 84.671 | 50.019 | 1.00 | 22.65 A | C |
| ATOM | 1278 | O | LEU | A | 295 | 9.736 | 83.565 | 49.730 | 1.00 | 22.45 A | O |
| ATOM | 1279 | N | PRO | A | 296 | 9.515 | 85.800 | 49.730 | 1.00 | 21.47 A | N |
| ATOM | 1280 | CD | PRO | A | 296 | 9.864 | 87.159 | 50.187 | 1.00 | 22.06 A | C |
| ATOM | 1281 | CA | PRO | A | 296 | 8.202 | 85.782 | 49.066 | 1.00 | 21.33 A | C |
| ATOM | 1282 | CB | PRO | A | 296 | 7.634 | 87.169 | 49.380 | 1.00 | 20.33 A | C |
| ATOM | 1283 | CG | PRO | A | 296 | 8.848 | 88.033 | 49.450 | 1.00 | 21.76 A | C |
| ATOM | 1284 | C | PRO | A | 296 | 8.260 | 85.479 | 47.561 | 1.00 | 22.16 A | C |
| ATOM | 1285 | O | PRO | A | 296 | 9.292 | 85.652 | 46.917 | 1.00 | 19.11 A | O |
| ATOM | 1286 | N | PRO | A | 297 | 7.137 | 85.032 | 46.976 | 1.00 | 23.42 A | N |
| ATOM | 1287 | CD | PRO | A | 297 | 5.799 | 84.826 | 47.557 | 1.00 | 21.93 A | C |
| ATOM | 1288 | CA | PRO | A | 297 | 7.141 | 84.720 | 45.542 | 1.00 | 24.58 A | C |
| ATOM | 1289 | CB | PRO | A | 297 | 5.693 | 84.315 | 45.271 | 1.00 | 24.85 A | C |
| ATOM | 1290 | CG | PRO | A | 297 | 5.220 | 83.791 | 46.629 | 1.00 | 22.35 A | C |
| ATOM | 1291 | C | PRO | A | 297 | 7.602 | 85.869 | 44.641 | 1.00 | 26.51 A | C |
| ATOM | 1292 | O | PRO | A | 297 | 8.425 | 85.667 | 43.749 | 1.00 | 24.25 A | O |
| ATOM | 1293 | N | GLU | A | 298 | 7.081 | 87.070 | 44.884 | 1.00 | 28.74 A | N |
| ATOM | 1294 | CA | GLU | A | 298 | 7.435 | 88.231 | 44.070 | 1.00 | 32.43 A | C |
| ATOM | 1295 | CB | GLU | A | 298 | 6.792 | 89.508 | 44.625 | 1.00 | 31.92 A | C |
| ATOM | 1296 | CG | GLU | A | 298 | 7.073 | 89.780 | 46.093 | 1.00 | 31.41 A | C |
| ATOM | 1297 | CD | GLU | A | 298 | 5.970 | 89.259 | 46.993 | 1.00 | 31.60 A | C |
| ATOM | 1298 | OE1 | GLU | A | 298 | 5.566 | 88.089 | 46.835 | 1.00 | 32.77 A | O |
| ATOM | 1299 | OE2 | GLU | A | 298 | 5.504 | 90.017 | 47.864 | 1.00 | 32.41 A | O |
| ATOM | 1300 | C | GLU | A | 298 | 8.937 | 88.440 | 43.934 | 1.00 | 34.76 A | C |
| ATOM | 1301 | O | GLU | A | 298 | 9.420 | 88.836 | 42.872 | 1.00 | 34.79 A | O |
| ATOM | 1302 | N | MET | A | 299 | 9.679 | 88.167 | 45.003 | 1.00 | 37.58 A | N |
| ATOM | 1303 | CA | MET | A | 299 | 11.121 | 88.348 | 44.966 | 1.00 | 39.94 A | C |
| ATOM | 1304 | CB | MET | A | 299 | 11.676 | 88.481 | 46.391 | 1.00 | 40.17 A | C |
| ATOM | 1305 | CG | MET | A | 299 | 11.251 | 89.800 | 47.055 | 1.00 | 40.44 A | C |
| ATOM | 1306 | SD | MET | A | 299 | 11.866 | 90.123 | 48.737 | 1.00 | 42.44 A | S |
| ATOM | 1307 | CE | MET | A | 299 | 13.408 | 90.986 | 48.365 | 1.00 | 41.54 A | C |
| ATOM | 1308 | C | MET | A | 299 | 11.857 | 87.268 | 44.179 | 1.00 | 41.00 A | C |
| ATOM | 1309 | O | MET | A | 299 | 12.582 | 87.589 | 43.237 | 1.00 | 42.71 A | O |
| ATOM | 1310 | N | ILE | A | 300 | 11.674 | 85.998 | 44.525 | 1.00 | 42.03 A | N |
| ATOM | 1311 | CA | ILE | A | 300 | 12.363 | 84.941 | 43.784 | 1.00 | 43.81 A | C |
| ATOM | 1312 | CB | ILE | A | 300 | 12.140 | 83.535 | 44.407 | 1.00 | 44.39 A | C |
| ATOM | 1313 | CG2 | ILE | A | 300 | 12.690 | 83.497 | 45.829 | 1.00 | 45.06 A | C |
| ATOM | 1314 | CG1 | ILE | A | 300 | 10.656 | 83.172 | 44.378 | 1.00 | 44.10 A | C |
| ATOM | 1315 | CD1 | ILE | A | 300 | 10.379 | 81.745 | 44.804 | 1.00 | 44.41 A | C |
| ATOM | 1316 | C | ILE | A | 300 | 11.906 | 84.908 | 42.323 | 1.00 | 44.98 A | C |
| ATOM | 1317 | O | ILE | A | 300 | 12.573 | 84.322 | 41.472 | 1.00 | 45.46 A | O |
| ATOM | 1318 | N | GLU | A | 301 | 10.762 | 85.529 | 42.042 | 1.00 | 45.85 A | N |
| ATOM | 1319 | CA | GLU | A | 301 | 10.232 | 85.592 | 40.682 | 1.00 | 46.66 A | C |
| ATOM | 1320 | CB | GLU | A | 301 | 8.709 | 85.477 | 40.687 | 1.00 | 47.45 A | C |
| ATOM | 1321 | CG | GLU | A | 301 | 8.189 | 84.054 | 40.721 | 1.00 | 48.05 A | C |
| ATOM | 1322 | CD | GLU | A | 301 | 6.688 | 83.997 | 40.916 | 1.00 | 49.14 A | C |
| ATOM | 1323 | OE1 | GLU | A | 301 | 5.979 | 84.782 | 40.253 | 1.00 | 50.01 A | O |
| ATOM | 1324 | OE2 | GLU | A | 301 | 6.218 | 83.166 | 41.724 | 1.00 | 48.90 A | O |
| ATOM | 1325 | C | GLU | A | 301 | 10.643 | 86.904 | 40.026 | 1.00 | 47.81 A | C |
| ATOM | 1326 | O | GLU | A | 301 | 10.048 | 87.326 | 39.035 | 1.00 | 47.15 A | O |
| ATOM | 1327 | N | GLY | A | 302 | 11.650 | 87.547 | 40.613 | 1.00 | 49.04 A | N |
| ATOM | 1328 | CA | GLY | A | 302 | 12.193 | 88.792 | 40.094 | 1.00 | 50.61 A | C |
| ATOM | 1329 | C | GLY | A | 302 | 11.296 | 89.991 | 39.844 | 1.00 | 51.92 A | C |
| ATOM | 1330 | O | GLY | A | 302 | 11.642 | 90.841 | 39.025 | 1.00 | 52.54 A | O |
| ATOM | 1331 | N | ARG | A | 303 | 10.167 | 90.087 | 40.542 | 1.00 | 52.91 A | N |
| ATOM | 1332 | CA | ARG | A | 303 | 9.259 | 91.219 | 40.356 | 1.00 | 53.57 A | C |
| ATOM | 1333 | CB | ARG | A | 303 | 7.812 | 90.753 | 40.529 | 1.00 | 55.04 A | C |
| ATOM | 1334 | CG | ARG | A | 303 | 7.494 | 89.500 | 39.724 | 1.00 | 58.17 A | C |
| ATOM | 1335 | CD | ARG | A | 303 | 6.011 | 89.149 | 39.750 | 1.00 | 60.28 A | C |
| ATOM | 1336 | NE | ARG | A | 303 | 5.212 | 90.072 | 38.947 | 1.00 | 62.73 A | N |
| ATOM | 1337 | CZ | ARG | A | 303 | 3.919 | 89.903 | 38.680 | 1.00 | 63.00 A | C |
| ATOM | 1338 | NH1 | ARG | A | 303 | 3.271 | 90.794 | 37.941 | 1.00 | 62.86 A | N |
| ATOM | 1339 | NH2 | ARG | A | 303 | 3.275 | 88.842 | 39.150 | 1.00 | 62.02 A | N |

TABLE 2-continued coordinates for the two molecules in the asymmetric unit of [T287] Aurora
A (122–396) in complex with an inhibitor of formula II in space group P2$_1$

| ATOM | 1340 | C   | ARG | A | 303 | 9.571  | 92.371 | 41.320 | 1.00 | 52.69 | A | C |
|------|------|-----|-----|---|-----|--------|--------|--------|------|-------|---|---|
| ATOM | 1341 | O   | ARG | A | 303 | 10.582 | 92.344 | 42.020 | 1.00 | 52.06 | A | O |
| ATOM | 1342 | N   | MET | A | 304 | 8.710  | 93.385 | 41.344 | 1.00 | 52.57 | A | N |
| ATOM | 1343 | CA  | MET | A | 304 | 8.907  | 94.539 | 42.223 | 1.00 | 52.97 | A | C |
| ATOM | 1344 | CB  | MET | A | 304 | 8.395  | 95.820 | 41.542 | 1.00 | 55.47 | A | C |
| ATOM | 1345 | CG  | MET | A | 304 | 8.972  | 97.135 | 42.103 | 1.00 | 59.08 | A | C |
| ATOM | 1346 | SD  | MET | A | 304 | 7.948  | 98.022 | 43.326 | 1.00 | 62.23 | A | S |
| ATOM | 1347 | CE  | MET | A | 304 | 7.208  | 99.317 | 42.301 | 1.00 | 60.78 | A | C |
| ATOM | 1348 | C   | MET | A | 304 | 8.153  | 94.299 | 43.526 | 1.00 | 51.89 | A | C |
| ATOM | 1349 | O   | MET | A | 304 | 7.026  | 93.809 | 43.511 | 1.00 | 51.02 | A | O |
| ATOM | 1350 | N   | HIS | A | 305 | 8.775  | 94.645 | 44.651 | 1.00 | 50.91 | A | N |
| ATOM | 1351 | CA  | HIS | A | 305 | 8.149  | 94.441 | 45.953 | 1.00 | 49.66 | A | C |
| ATOM | 1352 | CB  | HIS | A | 305 | 8.944  | 93.415 | 46.762 | 1.00 | 51.52 | A | C |
| ATOM | 1353 | CG  | HIS | A | 305 | 10.392 | 93.763 | 46.926 | 1.00 | 54.62 | A | C |
| ATOM | 1354 | CD2 | HIS | A | 305 | 11.085 | 94.211 | 48.000 | 1.00 | 54.89 | A | C |
| ATOM | 1355 | ND1 | HIS | A | 305 | 11.304 | 93.665 | 45.897 | 1.00 | 55.05 | A | N |
| ATOM | 1356 | CE1 | HIS | A | 305 | 12.496 | 94.034 | 46.330 | 1.00 | 55.54 | A | C |
| ATOM | 1357 | NE2 | HIS | A | 305 | 12.391 | 94.371 | 47.603 | 1.00 | 55.94 | A | N |
| ATOM | 1358 | C   | HIS | A | 305 | 7.996  | 95.712 | 46.778 | 1.00 | 47.80 | A | C |
| ATOM | 1359 | O   | HIS | A | 305 | 8.620  | 96.730 | 46.491 | 1.00 | 47.81 | A | O |
| ATOM | 1360 | N   | ASP | A | 306 | 7.150  | 95.635 | 47.802 | 1.00 | 45.38 | A | N |
| ATOM | 1361 | CA  | ASP | A | 306 | 6.903  | 96.746 | 48.713 | 1.00 | 43.84 | A | C |
| ATOM | 1362 | CB  | ASP | A | 306 | 5.667  | 97.548 | 48.278 | 1.00 | 44.46 | A | C |
| ATOM | 1363 | CG  | ASP | A | 306 | 4.424  | 96.691 | 48.154 | 1.00 | 45.21 | A | C |
| ATOM | 1364 | OD1 | ASP | A | 306 | 4.281  | 95.727 | 48.935 | 1.00 | 45.61 | A | O |
| ATOM | 1365 | OD2 | ASP | A | 306 | 3.579  | 96.992 | 47.285 | 1.00 | 45.96 | A | O |
| ATOM | 1366 | C   | ASP | A | 306 | 6.714  | 96.213 | 50.141 | 1.00 | 42.01 | A | C |
| ATOM | 1367 | O   | ASP | A | 306 | 7.276  | 95.181 | 50.498 | 1.00 | 40.43 | A | O |
| ATOM | 1368 | N   | GLU | A | 307 | 5.917  | 96.910 | 50.948 | 1.00 | 41.41 | A | N |
| ATOM | 1369 | CA  | GLU | A | 307 | 5.684  | 96.503 | 52.334 | 1.00 | 40.47 | A | C |
| ATOM | 1370 | CB  | GLU | A | 307 | 5.047  | 97.658 | 53.116 | 1.00 | 43.34 | A | C |
| ATOM | 1371 | CG  | GLU | A | 307 | 3.673  | 98.084 | 52.624 | 1.00 | 49.09 | A | C |
| ATOM | 1372 | CD  | GLU | A | 307 | 2.543  | 97.317 | 53.287 | 1.00 | 53.33 | A | C |
| ATOM | 1373 | OE1 | GLU | A | 307 | 1.369  | 97.561 | 52.933 | 1.00 | 56.15 | A | O |
| ATOM | 1374 | OE2 | GLU | A | 307 | 2.822  | 96.475 | 54.168 | 1.00 | 56.15 | A | O |
| ATOM | 1375 | C   | GLU | A | 307 | 4.838  | 95.236 | 52.486 | 1.00 | 37.15 | A | C |
| ATOM | 1376 | O   | GLU | A | 307 | 4.595  | 94.774 | 53.603 | 1.00 | 36.77 | A | O |
| ATOM | 1377 | N   | LYS | A | 308 | 4.402  | 94.668 | 51.367 | 1.00 | 33.66 | A | N |
| ATOM | 1378 | CA  | LYS | A | 308 | 3.599  | 93.455 | 51.411 | 1.00 | 29.96 | A | C |
| ATOM | 1379 | CB  | LYS | A | 308 | 2.842  | 93.262 | 50.095 | 1.00 | 31.75 | A | C |
| ATOM | 1380 | CG  | LYS | A | 308 | 1.668  | 94.214 | 49.908 | 1.00 | 30.26 | A | C |
| ATOM | 1381 | CD  | LYS | A | 308 | 0.631  | 94.005 | 50.994 | 1.00 | 30.93 | A | C |
| ATOM | 1382 | CE  | LYS | A | 308 | −0.590 | 94.881 | 50.766 | 1.00 | 33.18 | A | C |
| ATOM | 1383 | NZ  | LYS | A | 308 | −1.687 | 94.574 | 51.722 | 1.00 | 31.42 | A | N |
| ATOM | 1384 | C   | LYS | A | 308 | 4.452  | 92.227 | 51.704 | 1.00 | 28.16 | A | C |
| ATOM | 1385 | O   | LYS | A | 308 | 3.918  | 91.178 | 52.055 | 1.00 | 26.90 | A | O |
| ATOM | 1386 | N   | VAL | A | 309 | 5.772  | 92.354 | 51.566 | 1.00 | 26.12 | A | N |
| ATOM | 1387 | CA  | VAL | A | 309 | 6.666  | 91.230 | 51.849 | 1.00 | 27.15 | A | C |
| ATOM | 1388 | CB  | VAL | A | 309 | 8.147  | 91.546 | 51.483 | 1.00 | 28.50 | A | C |
| ATOM | 1389 | CG1 | VAL | A | 309 | 8.273  | 91.828 | 49.988 | 1.00 | 28.82 | A | C |
| ATOM | 1390 | CG2 | VAL | A | 309 | 8.648  | 92.728 | 52.299 | 1.00 | 28.83 | A | C |
| ATOM | 1391 | C   | VAL | A | 309 | 6.608  | 90.885 | 53.339 | 1.00 | 27.51 | A | C |
| ATOM | 1392 | O   | VAL | A | 309 | 6.748  | 89.720 | 53.725 | 1.00 | 28.44 | A | O |
| ATOM | 1393 | N   | ASP | A | 310 | 6.382  | 91.905 | 54.167 | 1.00 | 25.49 | A | N |
| ATOM | 1394 | CA  | ASP | A | 310 | 6.308  | 91.715 | 55.607 | 1.00 | 23.57 | A | C |
| ATOM | 1395 | CB  | ASP | A | 310 | 6.281  | 93.069 | 56.332 | 1.00 | 23.42 | A | C |
| ATOM | 1396 | CG  | ASP | A | 310 | 7.564  | 93.858 | 56.139 | 1.00 | 26.52 | A | C |
| ATOM | 1397 | OD1 | ASP | A | 310 | 8.657  | 93.249 | 56.164 | 1.00 | 26.12 | A | O |
| ATOM | 1398 | OD2 | ASP | A | 310 | 7.489  | 95.095 | 55.974 | 1.00 | 28.59 | A | O |
| ATOM | 1399 | C   | ASP | A | 310 | 5.106  | 90.878 | 56.012 | 1.00 | 21.40 | A | C |
| ATOM | 1400 | O   | ASP | A | 310 | 5.147  | 90.193 | 57.038 | 1.00 | 21.03 | A | O |
| ATOM | 1401 | N   | LEU | A | 311 | 4.032  | 90.932 | 55.228 | 1.00 | 20.72 | A | N |
| ATOM | 1402 | CA  | LEU | A | 311 | 2.848  | 90.126 | 55.541 | 1.00 | 20.20 | A | C |
| ATOM | 1403 | CB  | LEU | A | 311 | 1.628  | 90.564 | 54.713 | 1.00 | 19.65 | A | C |
| ATOM | 1404 | CG  | LEU | A | 311 | 0.794  | 91.785 | 55.141 | 1.00 | 21.99 | A | C |
| ATOM | 1405 | CD1 | LEU | A | 311 | 0.255  | 91.575 | 56.547 | 1.00 | 23.33 | A | C |
| ATOM | 1406 | CD2 | LEU | A | 311 | 1.635  | 93.047 | 55.092 | 1.00 | 23.76 | A | C |
| ATOM | 1407 | C   | LEU | A | 311 | 3.171  | 88.658 | 55.238 | 1.00 | 18.99 | A | C |
| ATOM | 1408 | O   | LEU | A | 311 | 2.764  | 87.760 | 55.960 | 1.00 | 16.87 | A | O |
| ATOM | 1409 | N   | TRP | A | 312 | 3.892  | 88.424 | 54.148 | 1.00 | 19.04 | A | N |
| ATOM | 1410 | CA  | TRP | A | 312 | 4.284  | 87.069 | 53.786 | 1.00 | 19.16 | A | C |
| ATOM | 1411 | CB  | TRP | A | 312 | 5.094  | 87.083 | 52.482 | 1.00 | 19.35 | A | C |
| ATOM | 1412 | CG  | TRP | A | 312 | 5.628  | 85.742 | 52.102 | 1.00 | 18.58 | A | C |
| ATOM | 1413 | CD2 | TRP | A | 312 | 4.970  | 84.762 | 51.294 | 1.00 | 17.19 | A | C |
| ATOM | 1414 | CE2 | TRP | A | 312 | 5.813  | 83.629 | 51.242 | 1.00 | 16.50 | A | C |
| ATOM | 1415 | CE3 | TRP | A | 312 | 3.747  | 84.730 | 50.607 | 1.00 | 17.90 | A | C |

TABLE 2-continued coordinates for the two molecules in the asymmetric unit of [T287] Aurora A (122–396) in complex with an inhibitor of formula II in space group P2₁

| ATOM | 1416 | CD1 | TRP | A | 312 | 6.815 | 85.184 | 52.496 | 1.00 | 19.08 | A | C |
|---|---|---|---|---|---|---|---|---|---|---|---|---|
| ATOM | 1417 | NE1 | TRP | A | 312 | 6.933 | 83.911 | 51.983 | 1.00 | 18.08 | A | N |
| ATOM | 1418 | CZ2 | TRP | A | 312 | 5.473 | 82.478 | 50.533 | 1.00 | 17.00 | A | C |
| ATOM | 1419 | CZ3 | TRP | A | 312 | 3.409 | 83.580 | 49.899 | 1.00 | 14.87 | A | C |
| ATOM | 1420 | CH2 | TRP | A | 312 | 4.271 | 82.470 | 49.870 | 1.00 | 19.28 | A | C |
| ATOM | 1421 | C | TRP | A | 312 | 5.142 | 86.497 | 54.923 | 1.00 | 18.64 | A | C |
| ATOM | 1422 | O | TRP | A | 312 | 4.883 | 85.396 | 55.424 | 1.00 | 16.66 | A | O |
| ATOM | 1423 | N | SER | A | 313 | 6.154 | 87.259 | 55.333 | 1.00 | 15.99 | A | N |
| ATOM | 1424 | CA | SER | A | 313 | 7.043 | 86.823 | 56.408 | 1.00 | 18.14 | A | C |
| ATOM | 1425 | CB | SER | A | 313 | 8.034 | 87.931 | 56.760 | 1.00 | 18.03 | A | C |
| ATOM | 1426 | OG | SER | A | 313 | 8.746 | 88.320 | 55.604 | 1.00 | 20.11 | A | O |
| ATOM | 1427 | C | SER | A | 313 | 6.254 | 86.450 | 57.650 | 1.00 | 15.82 | A | C |
| ATOM | 1428 | O | SER | A | 313 | 6.538 | 85.460 | 58.303 | 1.00 | 16.33 | A | O |
| ATOM | 1429 | N | LEU | A | 314 | 5.251 | 87.249 | 57.967 | 1.00 | 17.05 | A | N |
| ATOM | 1430 | CA | LEU | A | 314 | 4.429 | 86.997 | 59.137 | 1.00 | 18.31 | A | C |
| ATOM | 1431 | CB | LEU | A | 314 | 3.408 | 88.136 | 59.273 | 1.00 | 21.36 | A | C |
| ATOM | 1432 | CG | LEU | A | 314 | 3.115 | 88.707 | 60.664 | 1.00 | 25.08 | A | C |
| ATOM | 1433 | CD1 | LEU | A | 314 | 4.403 | 89.035 | 61.393 | 1.00 | 26.53 | A | C |
| ATOM | 1434 | CD2 | LEU | A | 314 | 2.258 | 89.954 | 60.524 | 1.00 | 26.95 | A | C |
| ATOM | 1435 | C | LEU | A | 314 | 3.736 | 85.627 | 59.044 | 1.00 | 17.43 | A | C |
| ATOM | 1436 | O | LEU | A | 314 | 3.565 | 84.928 | 60.046 | 1.00 | 16.65 | A | O |
| ATOM | 1437 | N | GLY | A | 315 | 3.348 | 85.242 | 57.835 | 1.00 | 17.42 | A | N |
| ATOM | 1438 | CA | GLY | A | 315 | 2.682 | 83.961 | 57.646 | 1.00 | 16.42 | A | C |
| ATOM | 1439 | C | GLY | A | 315 | 3.623 | 82.781 | 57.799 | 1.00 | 13.19 | A | C |
| ATOM | 1440 | O | GLY | A | 315 | 3.275 | 81.775 | 58.411 | 1.00 | 12.24 | A | O |
| ATOM | 1441 | N | VAL | A | 316 | 4.816 | 82.900 | 57.231 | 1.00 | 11.93 | A | N |
| ATOM | 1442 | CA | VAL | A | 316 | 5.810 | 81.844 | 57.322 | 1.00 | 12.52 | A | C |
| ATOM | 1443 | CB | VAL | A | 316 | 7.085 | 82.225 | 56.521 | 1.00 | 14.29 | A | C |
| ATOM | 1444 | CG1 | VAL | A | 316 | 8.233 | 81.270 | 56.858 | 1.00 | 9.03 | A | C |
| ATOM | 1445 | CG2 | VAL | A | 316 | 6.779 | 82.186 | 55.011 | 1.00 | 11.86 | A | C |
| ATOM | 1446 | C | VAL | A | 316 | 6.182 | 81.591 | 58.784 | 1.00 | 15.03 | A | C |
| ATOM | 1447 | O | VAL | A | 316 | 6.310 | 80.446 | 59.213 | 1.00 | 17.62 | A | O |
| ATOM | 1448 | N | LEU | A | 317 | 6.343 | 82.679 | 59.534 | 1.00 | 14.58 | A | N |
| ATOM | 1449 | CA | LEU | A | 317 | 6.709 | 82.651 | 60.945 | 1.00 | 16.47 | A | C |
| ATOM | 1450 | CB | LEU | A | 317 | 7.011 | 84.077 | 61.402 | 1.00 | 19.62 | A | C |
| ATOM | 1451 | CG | LEU | A | 317 | 8.077 | 84.260 | 62.478 | 1.00 | 23.94 | A | C |
| ATOM | 1452 | CD1 | LEU | A | 317 | 9.386 | 83.649 | 61.992 | 1.00 | 23.88 | A | C |
| ATOM | 1453 | CD2 | LEU | A | 317 | 8.256 | 85.742 | 62.782 | 1.00 | 25.46 | A | C |
| ATOM | 1454 | C | LEU | A | 317 | 5.618 | 82.058 | 61.837 | 1.00 | 17.53 | A | C |
| ATOM | 1455 | O | LEU | A | 317 | 5.897 | 81.270 | 62.752 | 1.00 | 16.69 | A | O |
| ATOM | 1456 | N | CYS | A | 318 | 4.371 | 82.444 | 61.578 | 1.00 | 15.98 | A | N |
| ATOM | 1457 | CA | CYS | A | 318 | 3.272 | 81.937 | 62.380 | 1.00 | 15.13 | A | C |
| ATOM | 1458 | CB | CYS | A | 318 | 1.940 | 82.520 | 61.898 | 1.00 | 13.25 | A | C |
| ATOM | 1459 | SG | CYS | A | 318 | 0.563 | 82.056 | 62.970 | 1.00 | 20.95 | A | S |
| ATOM | 1460 | C | CYS | A | 318 | 3.253 | 80.420 | 62.263 | 1.00 | 14.70 | A | C |
| ATOM | 1461 | O | CYS | A | 318 | 3.087 | 79.710 | 63.245 | 1.00 | 13.83 | A | O |
| ATOM | 1462 | N | TYR | A | 319 | 3.421 | 79.942 | 61.038 | 1.00 | 15.03 | A | N |
| ATOM | 1463 | CA | TYR | A | 319 | 3.444 | 78.518 | 60.742 | 1.00 | 15.40 | A | C |
| ATOM | 1464 | CB | TYR | A | 319 | 3.583 | 78.317 | 59.226 | 1.00 | 14.02 | A | C |
| ATOM | 1465 | CG | TYR | A | 319 | 3.545 | 76.875 | 58.766 | 1.00 | 14.42 | A | C |
| ATOM | 1466 | CD1 | TYR | A | 319 | 4.651 | 76.036 | 58.902 | 1.00 | 13.77 | A | C |
| ATOM | 1467 | CE1 | TYR | A | 319 | 4.612 | 74.713 | 58.446 | 1.00 | 16.09 | A | C |
| ATOM | 1468 | CD2 | TYR | A | 319 | 2.396 | 76.357 | 58.167 | 1.00 | 17.16 | A | C |
| ATOM | 1469 | CE2 | TYR | A | 319 | 2.345 | 75.047 | 57.710 | 1.00 | 15.61 | A | C |
| ATOM | 1470 | CZ | TYR | A | 319 | 3.445 | 74.231 | 57.849 | 1.00 | 16.40 | A | C |
| ATOM | 1471 | OH | TYR | A | 319 | 3.363 | 72.937 | 57.385 | 1.00 | 15.59 | A | O |
| ATOM | 1472 | C | TYR | A | 319 | 4.610 | 77.831 | 61.462 | 1.00 | 15.16 | A | C |
| ATOM | 1473 | O | TYR | A | 319 | 4.407 | 76.869 | 62.193 | 1.00 | 14.51 | A | O |
| ATOM | 1474 | N | GLU | A | 320 | 5.828 | 78.330 | 61.246 | 1.00 | 17.29 | A | N |
| ATOM | 1475 | CA | GLU | A | 320 | 7.000 | 77.734 | 61.880 | 1.00 | 17.27 | A | C |
| ATOM | 1476 | CB | GLU | A | 320 | 8.281 | 78.487 | 61.507 | 1.00 | 18.78 | A | C |
| ATOM | 1477 | CG | GLU | A | 320 | 9.537 | 77.819 | 62.068 | 1.00 | 22.31 | A | C |
| ATOM | 1478 | CD | GLU | A | 320 | 10.838 | 78.346 | 61.469 | 1.00 | 26.99 | A | C |
| ATOM | 1479 | OE1 | GLU | A | 320 | 11.904 | 77.777 | 61.784 | 1.00 | 27.38 | A | O |
| ATOM | 1480 | OE2 | GLU | A | 320 | 10.807 | 79.319 | 60.692 | 1.00 | 26.89 | A | O |
| ATOM | 1481 | C | GLU | A | 320 | 6.845 | 77.672 | 63.404 | 1.00 | 17.31 | A | C |
| ATOM | 1482 | O | GLU | A | 320 | 7.234 | 76.689 | 64.019 | 1.00 | 16.67 | A | O |
| ATOM | 1483 | N | PHE | A | 321 | 6.259 | 78.702 | 64.006 | 1.00 | 17.96 | A | N |
| ATOM | 1484 | CA | PHE | A | 321 | 6.057 | 78.697 | 65.458 | 1.00 | 18.82 | A | C |
| ATOM | 1485 | CB | PHE | A | 321 | 5.387 | 79.993 | 65.948 | 1.00 | 18.10 | A | C |
| ATOM | 1486 | CG | PHE | A | 321 | 6.318 | 81.180 | 66.061 | 1.00 | 20.78 | A | C |
| ATOM | 1487 | CD1 | PHE | A | 321 | 7.705 | 81.017 | 66.064 | 1.00 | 21.45 | A | C |
| ATOM | 1488 | CD2 | PHE | A | 321 | 5.796 | 82.472 | 66.152 | 1.00 | 20.42 | A | C |
| ATOM | 1489 | CE1 | PHE | A | 321 | 8.554 | 82.127 | 66.150 | 1.00 | 21.67 | A | C |
| ATOM | 1490 | CE2 | PHE | A | 321 | 6.632 | 83.587 | 66.238 | 1.00 | 21.82 | A | C |
| ATOM | 1491 | CZ | PHE | A | 321 | 8.013 | 83.417 | 66.236 | 1.00 | 21.08 | A | C |

TABLE 2-continued coordinates for the two molecules in the asymmetric unit of [T287] Aurora A (122–396) in complex with an inhibitor of formula II in space group P2$_1$

| ATOM | 1492 | C   | PHE | A | 321 | 5.174  | 77.530 | 65.896 | 1.00 | 19.26 | A | C |
|------|------|-----|-----|---|-----|--------|--------|--------|------|-------|---|---|
| ATOM | 1493 | O   | PHE | A | 321 | 5.466  | 76.848 | 66.878 | 1.00 | 18.07 | A | O |
| ATOM | 1494 | N   | LEU | A | 322 | 4.089  | 77.309 | 65.159 | 1.00 | 18.30 | A | N |
| ATOM | 1495 | CA  | LEU | A | 322 | 3.134  | 76.258 | 65.498 | 1.00 | 18.16 | A | C |
| ATOM | 1496 | CB  | LEU | A | 322 | 1.777  | 76.572 | 64.859 | 1.00 | 17.23 | A | C |
| ATOM | 1497 | CG  | LEU | A | 322 | 1.016  | 77.755 | 65.455 | 1.00 | 16.28 | A | C |
| ATOM | 1498 | CD1 | LEU | A | 322 | −0.128 | 78.162 | 64.528 | 1.00 | 20.13 | A | C |
| ATOM | 1499 | CD2 | LEU | A | 322 | 0.490  | 77.372 | 66.833 | 1.00 | 14.25 | A | C |
| ATOM | 1500 | C   | LEU | A | 322 | 3.530  | 74.833 | 65.136 | 1.00 | 17.66 | A | C |
| ATOM | 1501 | O   | LEU | A | 322 | 3.286  | 73.908 | 65.908 | 1.00 | 15.88 | A | O |
| ATOM | 1502 | N   | VAL | A | 323 | 4.138  | 74.670 | 63.963 | 1.00 | 17.86 | A | N |
| ATOM | 1503 | CA  | VAL | A | 323 | 4.531  | 73.360 | 63.462 | 1.00 | 19.30 | A | C |
| ATOM | 1504 | CB  | VAL | A | 323 | 4.441  | 73.318 | 61.909 | 1.00 | 19.49 | A | C |
| ATOM | 1505 | CG1 | VAL | A | 323 | 4.742  | 71.915 | 61.399 | 1.00 | 21.44 | A | C |
| ATOM | 1506 | CG2 | VAL | A | 323 | 3.069  | 73.746 | 61.462 | 1.00 | 18.47 | A | C |
| ATOM | 1507 | C   | VAL | A | 323 | 5.934  | 72.926 | 63.890 | 1.00 | 19.76 | A | C |
| ATOM | 1508 | O   | VAL | A | 323 | 6.164  | 71.746 | 64.148 | 1.00 | 18.74 | A | O |
| ATOM | 1509 | N   | GLY | A | 324 | 6.865  | 73.873 | 63.975 | 1.00 | 18.78 | A | N |
| ATOM | 1510 | CA  | GLY | A | 324 | 8.218  | 73.524 | 64.380 | 1.00 | 19.81 | A | C |
| ATOM | 1511 | C   | GLY | A | 324 | 9.219  | 73.717 | 63.257 | 1.00 | 21.90 | A | C |
| ATOM | 1512 | O   | GLY | A | 324 | 10.429 | 73.731 | 63.486 | 1.00 | 23.85 | A | O |
| ATOM | 1513 | N   | LYS | A | 325 | 8.715  | 73.851 | 62.034 | 1.00 | 23.08 | A | N |
| ATOM | 1514 | CA  | LYS | A | 325 | 9.560  | 74.078 | 60.873 | 1.00 | 23.18 | A | C |
| ATOM | 1515 | CB  | LYS | A | 325 | 10.035 | 72.748 | 60.282 | 1.00 | 25.82 | A | C |
| ATOM | 1516 | CG  | LYS | A | 325 | 8.940  | 71.860 | 59.738 | 1.00 | 28.72 | A | C |
| ATOM | 1517 | CD  | LYS | A | 325 | 9.550  | 70.690 | 58.988 | 1.00 | 31.14 | A | C |
| ATOM | 1518 | CE  | LYS | A | 325 | 8.492  | 69.716 | 58.508 | 1.00 | 32.54 | A | C |
| ATOM | 1519 | NZ  | LYS | A | 325 | 7.811  | 69.057 | 59.655 | 1.00 | 36.73 | A | N |
| ATOM | 1520 | C   | LYS | A | 325 | 8.775  | 74.886 | 59.838 | 1.00 | 22.65 | A | C |
| ATOM | 1521 | O   | LYS | A | 325 | 7.546  | 74.928 | 59.884 | 1.00 | 20.82 | A | O |
| ATOM | 1522 | N   | PRO | A | 326 | 9.480  | 75.543 | 58.897 | 1.00 | 21.36 | A | N |
| ATOM | 1523 | CD  | PRO | A | 326 | 10.936 | 75.420 | 58.702 | 1.00 | 22.88 | A | C |
| ATOM | 1524 | CA  | PRO | A | 326 | 8.891  | 76.368 | 57.836 | 1.00 | 21.28 | A | C |
| ATOM | 1525 | CB  | PRO | A | 326 | 10.118 | 76.980 | 57.165 | 1.00 | 23.22 | A | C |
| ATOM | 1526 | CG  | PRO | A | 326 | 11.115 | 75.882 | 57.275 | 1.00 | 22.99 | A | C |
| ATOM | 1527 | C   | PRO | A | 326 | 8.000  | 75.589 | 56.865 | 1.00 | 19.59 | A | C |
| ATOM | 1528 | O   | PRO | A | 326 | 8.191  | 74.391 | 56.637 | 1.00 | 17.62 | A | O |
| ATOM | 1529 | N   | PRO | A | 327 | 7.015  | 76.272 | 56.266 | 1.00 | 19.54 | A | N |
| ATOM | 1530 | CD  | PRO | A | 327 | 6.590  | 77.659 | 56.535 | 1.00 | 18.59 | A | C |
| ATOM | 1531 | CA  | PRO | A | 327 | 6.105  | 75.600 | 55.336 | 1.00 | 19.17 | A | C |
| ATOM | 1532 | CB  | PRO | A | 327 | 4.946  | 76.594 | 55.212 | 1.00 | 19.31 | A | C |
| ATOM | 1533 | CG  | PRO | A | 327 | 5.603  | 77.918 | 55.424 | 1.00 | 21.80 | A | C |
| ATOM | 1534 | C   | PRO | A | 327 | 6.612  | 75.105 | 53.976 | 1.00 | 20.25 | A | C |
| ATOM | 1535 | O   | PRO | A | 327 | 6.025  | 74.185 | 53.412 | 1.00 | 22.68 | A | O |
| ATOM | 1536 | N   | PHE | A | 328 | 7.692  | 75.672 | 53.449 | 1.00 | 19.21 | A | N |
| ATOM | 1537 | CA  | PHE | A | 328 | 8.179  | 75.244 | 52.134 | 1.00 | 21.50 | A | C |
| ATOM | 1538 | CB  | PHE | A | 328 | 8.344  | 76.469 | 51.220 | 1.00 | 20.17 | A | C |
| ATOM | 1539 | CG  | PHE | A | 328 | 7.108  | 77.331 | 51.119 | 1.00 | 19.02 | A | C |
| ATOM | 1540 | CD1 | PHE | A | 328 | 5.995  | 76.903 | 50.385 | 1.00 | 19.37 | A | C |
| ATOM | 1541 | CD2 | PHE | A | 328 | 7.048  | 78.561 | 51.776 | 1.00 | 17.08 | A | C |
| ATOM | 1542 | CE1 | PHE | A | 328 | 4.840  | 77.688 | 50.307 | 1.00 | 16.91 | A | C |
| ATOM | 1543 | CE2 | PHE | A | 328 | 5.900  | 79.354 | 51.709 | 1.00 | 20.03 | A | C |
| ATOM | 1544 | CZ  | PHE | A | 328 | 4.788  | 78.912 | 50.967 | 1.00 | 18.39 | A | C |
| ATOM | 1545 | C   | PHE | A | 328 | 9.501  | 74.466 | 52.163 | 1.00 | 24.45 | A | C |
| ATOM | 1546 | O   | PHE | A | 328 | 10.149 | 74.296 | 51.131 | 1.00 | 24.06 | A | O |
| ATOM | 1547 | N   | GLU | A | 329 | 9.902  | 73.992 | 53.337 | 1.00 | 26.19 | A | N |
| ATOM | 1548 | CA  | GLU | A | 329 | 11.159 | 73.255 | 53.465 | 1.00 | 28.35 | A | C |
| ATOM | 1549 | CB  | GLU | A | 329 | 11.410 | 72.938 | 54.936 | 1.00 | 31.29 | A | C |
| ATOM | 1550 | CG  | GLU | A | 329 | 12.815 | 72.478 | 55.236 | 1.00 | 37.80 | A | C |
| ATOM | 1551 | CD  | GLU | A | 329 | 12.954 | 71.963 | 56.648 | 1.00 | 41.63 | A | C |
| ATOM | 1552 | OE1 | GLU | A | 329 | 12.396 | 70.880 | 56.938 | 1.00 | 41.71 | A | O |
| ATOM | 1553 | OE2 | GLU | A | 329 | 13.614 | 72.646 | 57.468 | 1.00 | 44.04 | A | O |
| ATOM | 1554 | C   | GLU | A | 329 | 11.195 | 71.955 | 52.647 | 1.00 | 27.64 | A | C |
| ATOM | 1555 | O   | GLU | A | 329 | 10.230 | 71.193 | 52.639 | 1.00 | 25.94 | A | O |
| ATOM | 1556 | N   | ALA | A | 330 | 12.313 | 71.714 | 51.962 | 1.00 | 26.33 | A | N |
| ATOM | 1557 | CA  | ALA | A | 330 | 12.498 | 70.507 | 51.149 | 1.00 | 28.04 | A | C |
| ATOM | 1558 | CB  | ALA | A | 330 | 11.948 | 70.731 | 49.731 | 1.00 | 25.92 | A | C |
| ATOM | 1559 | C   | ALA | A | 330 | 13.982 | 70.099 | 51.084 | 1.00 | 28.74 | A | C |
| ATOM | 1560 | O   | ALA | A | 330 | 14.856 | 70.838 | 51.537 | 1.00 | 29.37 | A | O |
| ATOM | 1561 | N   | ASN | A | 331 | 14.259 | 68.930 | 50.513 | 1.00 | 30.23 | A | N |
| ATOM | 1562 | CA  | ASN | A | 331 | 15.627 | 68.421 | 50.411 | 1.00 | 31.60 | A | C |
| ATOM | 1563 | CB  | ASN | A | 331 | 15.610 | 66.949 | 50.002 | 1.00 | 34.66 | A | C |
| ATOM | 1564 | CG  | ASN | A | 331 | 14.955 | 66.069 | 51.041 | 1.00 | 38.24 | A | C |
| ATOM | 1565 | OD1 | ASN | A | 331 | 15.440 | 65.949 | 52.165 | 1.00 | 39.85 | A | O |
| ATOM | 1566 | ND2 | ASN | A | 331 | 13.841 | 65.449 | 50.672 | 1.00 | 42.35 | A | N |
| ATOM | 1567 | C   | ASN | A | 331 | 16.532 | 69.189 | 49.459 | 1.00 | 31.72 | A | C |

TABLE 2-continued coordinates for the two molecules in the asymmetric unit of [T287] Aurora
A (122–396) in complex with an inhibitor of formula II in space group P2₁

| ATOM | 1568 | O | ASN | A | 331 | 17.757 | 69.115 | 49.572 | 1.00 | 31.03 | A | O |
|---|---|---|---|---|---|---|---|---|---|---|---|---|
| ATOM | 1569 | N | THR | A | 332 | 15.946 | 69.918 | 48.512 | 1.00 | 31.48 | A | N |
| ATOM | 1570 | CA | THR | A | 332 | 16.756 | 70.684 | 47.566 | 1.00 | 29.77 | A | C |
| ATOM | 1571 | CB | THR | A | 332 | 16.799 | 70.011 | 46.173 | 1.00 | 28.89 | A | C |
| ATOM | 1572 | OG1 | THR | A | 332 | 15.487 | 70.003 | 45.606 | 1.00 | 29.21 | A | O |
| ATOM | 1573 | CG2 | THR | A | 332 | 17.308 | 68.580 | 46.279 | 1.00 | 27.84 | A | C |
| ATOM | 1574 | C | THR | A | 332 | 16.270 | 72.118 | 47.383 | 1.00 | 31.57 | A | C |
| ATOM | 1575 | O | THR | A | 332 | 15.093 | 72.433 | 47.603 | 1.00 | 30.47 | A | O |
| ATOM | 1576 | N | TYR | A | 333 | 17.200 | 72.981 | 46.990 | 1.00 | 30.46 | A | N |
| ATOM | 1577 | CA | TYR | A | 333 | 16.918 | 74.386 | 46.744 | 1.00 | 32.40 | A | C |
| ATOM | 1578 | CB | TYR | A | 333 | 18.187 | 75.094 | 46.254 | 1.00 | 35.27 | A | C |
| ATOM | 1579 | CG | TYR | A | 333 | 19.283 | 75.216 | 47.286 | 1.00 | 39.94 | A | C |
| ATOM | 1580 | CD1 | TYR | A | 333 | 20.620 | 75.025 | 46.934 | 1.00 | 41.64 | A | C |
| ATOM | 1581 | CE1 | TYR | A | 333 | 21.640 | 75.157 | 47.874 | 1.00 | 43.08 | A | C |
| ATOM | 1582 | CD2 | TYR | A | 333 | 18.992 | 75.542 | 48.608 | 1.00 | 40.76 | A | C |
| ATOM | 1583 | CE2 | TYR | A | 333 | 20.007 | 75.677 | 49.555 | 1.00 | 43.70 | A | C |
| ATOM | 1584 | CZ | TYR | A | 333 | 21.323 | 75.483 | 49.178 | 1.00 | 43.66 | A | C |
| ATOM | 1585 | OH | TYR | A | 333 | 22.323 | 75.613 | 50.107 | 1.00 | 47.82 | A | O |
| ATOM | 1586 | C | TYR | A | 333 | 15.842 | 74.529 | 45.671 | 1.00 | 31.07 | A | C |
| ATOM | 1587 | O | TYR | A | 333 | 14.916 | 75.327 | 45.807 | 1.00 | 31.04 | A | O |
| ATOM | 1588 | N | GLN | A | 334 | 15.991 | 73.754 | 44.601 | 1.00 | 29.99 | A | N |
| ATOM | 1589 | CA | GLN | A | 334 | 15.069 | 73.778 | 43.471 | 1.00 | 30.74 | A | C |
| ATOM | 1590 | CB | GLN | A | 334 | 15.526 | 72.779 | 42.403 | 1.00 | 33.77 | A | C |
| ATOM | 1591 | CG | GLN | A | 334 | 14.434 | 72.304 | 41.439 | 1.00 | 41.43 | A | C |
| ATOM | 1592 | CD | GLN | A | 334 | 13.963 | 73.367 | 40.443 | 1.00 | 46.44 | A | C |
| ATOM | 1593 | OE1 | GLN | A | 334 | 13.366 | 74.388 | 40.820 | 1.00 | 47.38 | A | O |
| ATOM | 1594 | NE2 | GLN | A | 334 | 14.222 | 73.120 | 39.156 | 1.00 | 47.54 | A | N |
| ATOM | 1595 | C | GLN | A | 334 | 13.639 | 73.480 | 43.878 | 1.00 | 27.78 | A | C |
| ATOM | 1596 | O | GLN | A | 334 | 12.725 | 74.204 | 43.504 | 1.00 | 26.99 | A | O |
| ATOM | 1597 | N | GLU | A | 335 | 13.448 | 72.412 | 44.641 | 1.00 | 26.65 | A | N |
| ATOM | 1598 | CA | GLU | A | 335 | 12.114 | 72.041 | 45.085 | 1.00 | 26.25 | A | C |
| ATOM | 1599 | CB | GLU | A | 335 | 12.158 | 70.678 | 45.785 | 1.00 | 29.22 | A | C |
| ATOM | 1600 | CG | GLU | A | 335 | 10.814 | 70.193 | 46.294 | 1.00 | 34.80 | A | C |
| ATOM | 1601 | CD | GLU | A | 335 | 9.755 | 70.092 | 45.197 | 1.00 | 39.80 | A | C |
| ATOM | 1602 | OE1 | GLU | A | 335 | 8.569 | 69.866 | 45.539 | 1.00 | 41.99 | A | O |
| ATOM | 1603 | OE2 | GLU | A | 335 | 10.101 | 70.231 | 43.999 | 1.00 | 40.49 | A | O |
| ATOM | 1604 | C | GLU | A | 335 | 11.502 | 73.108 | 46.005 | 1.00 | 23.81 | A | C |
| ATOM | 1605 | O | GLU | A | 335 | 10.295 | 73.333 | 45.969 | 1.00 | 22.15 | A | O |
| ATOM | 1606 | N | THR | A | 336 | 12.332 | 73.781 | 46.802 | 1.00 | 21.23 | A | N |
| ATOM | 1607 | CA | THR | A | 336 | 11.835 | 74.821 | 47.710 | 1.00 | 21.06 | A | C |
| ATOM | 1608 | CB | THR | A | 336 | 12.911 | 75.253 | 48.723 | 1.00 | 20.94 | A | C |
| ATOM | 1609 | OG1 | THR | A | 336 | 13.207 | 74.155 | 49.593 | 1.00 | 21.30 | A | O |
| ATOM | 1610 | CG2 | THR | A | 336 | 12.418 | 76.430 | 49.561 | 1.00 | 19.68 | A | C |
| ATOM | 1611 | C | THR | A | 336 | 11.375 | 76.036 | 46.920 | 1.00 | 21.05 | A | C |
| ATOM | 1612 | O | THR | A | 336 | 10.317 | 76.634 | 47.204 | 1.00 | 19.51 | A | O |
| ATOM | 1613 | N | TYR | A | 337 | 12.177 | 76.386 | 45.921 | 1.00 | 22.32 | A | N |
| ATOM | 1614 | CA | TYR | A | 337 | 11.888 | 77.500 | 45.026 | 1.00 | 23.61 | A | C |
| ATOM | 1615 | CB | TYR | A | 337 | 12.987 | 77.601 | 43.959 | 1.00 | 28.60 | A | C |
| ATOM | 1616 | CG | TYR | A | 337 | 12.727 | 78.643 | 42.890 | 1.00 | 35.53 | A | C |
| ATOM | 1617 | CD1 | TYR | A | 337 | 13.096 | 79.978 | 43.076 | 1.00 | 38.47 | A | C |
| ATOM | 1618 | CE1 | TYR | A | 337 | 12.825 | 80.947 | 42.100 | 1.00 | 41.00 | A | C |
| ATOM | 1619 | CD2 | TYR | A | 337 | 12.081 | 78.298 | 41.700 | 1.00 | 38.75 | A | C |
| ATOM | 1620 | CE2 | TYR | A | 337 | 11.803 | 79.251 | 40.722 | 1.00 | 41.63 | A | C |
| ATOM | 1621 | CZ | TYR | A | 337 | 12.177 | 80.573 | 40.927 | 1.00 | 43.73 | A | C |
| ATOM | 1622 | OH | TYR | A | 337 | 11.890 | 81.513 | 39.958 | 1.00 | 46.53 | A | O |
| ATOM | 1623 | C | TYR | A | 337 | 10.546 | 77.221 | 44.346 | 1.00 | 22.77 | A | C |
| ATOM | 1624 | O | TYR | A | 337 | 9.680 | 78.096 | 44.261 | 1.00 | 20.90 | A | O |
| ATOM | 1625 | N | LYS | A | 338 | 10.384 | 75.988 | 43.870 | 1.00 | 22.05 | A | N |
| ATOM | 1626 | CA | LYS | A | 338 | 9.163 | 75.578 | 43.183 | 1.00 | 24.06 | A | C |
| ATOM | 1627 | CB | LYS | A | 338 | 9.314 | 74.153 | 42.633 | 1.00 | 28.55 | A | C |
| ATOM | 1628 | CG | LYS | A | 338 | 8.183 | 73.729 | 41.703 | 1.00 | 35.30 | A | C |
| ATOM | 1629 | CD | LYS | A | 338 | 8.152 | 72.221 | 41.440 | 1.00 | 41.29 | A | C |
| ATOM | 1630 | CE | LYS | A | 338 | 9.451 | 71.691 | 40.831 | 1.00 | 42.96 | A | C |
| ATOM | 1631 | NZ | LYS | A | 338 | 10.551 | 71.612 | 41.836 | 1.00 | 45.52 | A | N |
| ATOM | 1632 | C | LYS | A | 338 | 7.934 | 75.656 | 44.094 | 1.00 | 22.36 | A | C |
| ATOM | 1633 | O | LYS | A | 338 | 6.894 | 76.160 | 43.686 | 1.00 | 22.23 | A | O |
| ATOM | 1634 | N | ARG | A | 339 | 8.056 | 75.174 | 45.328 | 1.00 | 20.86 | A | N |
| ATOM | 1635 | CA | ARG | A | 339 | 6.936 | 75.214 | 46.263 | 1.00 | 19.98 | A | C |
| ATOM | 1636 | CB | ARG | A | 339 | 7.252 | 74.388 | 47.506 | 1.00 | 21.06 | A | C |
| ATOM | 1637 | CG | ARG | A | 339 | 7.288 | 72.892 | 47.250 | 1.00 | 24.15 | A | C |
| ATOM | 1638 | CD | ARG | A | 339 | 7.637 | 72.141 | 48.504 | 1.00 | 25.25 | A | C |
| ATOM | 1639 | NE | ARG | A | 339 | 7.821 | 70.720 | 48.241 | 1.00 | 30.16 | A | N |
| ATOM | 1640 | CZ | ARG | A | 339 | 8.053 | 69.811 | 49.182 | 1.00 | 30.16 | A | C |
| ATOM | 1641 | NH1 | ARG | A | 339 | 8.126 | 70.173 | 50.456 | 1.00 | 31.69 | A | N |
| ATOM | 1642 | NH2 | ARG | A | 339 | 8.217 | 68.541 | 48.848 | 1.00 | 32.15 | A | N |
| ATOM | 1643 | C | ARG | A | 339 | 6.516 | 76.626 | 46.685 | 1.00 | 17.94 | A | C |

TABLE 2-continued coordinates for the two molecules in the asymmetric unit of [T287] Aurora A (122–396) in complex with an inhibitor of formula II in space group P2$_1$

| | | | | | | | | | | | |
|---|---|---|---|---|---|---|---|---|---|---|---|
| ATOM | 1644 | O | ARG | A | 339 | 5.339 | 76.878 | 46.919 | 1.00 | 14.93 A | O |
| ATOM | 1645 | N | ILE | A | 340 | 7.478 | 77.536 | 46.788 | 1.00 | 17.04 A | N |
| ATOM | 1646 | CA | ILE | A | 340 | 7.187 | 78.908 | 47.175 | 1.00 | 16.76 A | C |
| ATOM | 1647 | CB | ILE | A | 340 | 8.497 | 79.705 | 47.480 | 1.00 | 14.52 A | C |
| ATOM | 1648 | CG2 | ILE | A | 340 | 8.203 | 81.199 | 47.598 | 1.00 | 14.90 A | C |
| ATOM | 1649 | CG1 | ILE | A | 340 | 9.127 | 79.209 | 48.786 | 1.00 | 14.96 A | C |
| ATOM | 1650 | CD1 | ILE | A | 340 | 10.491 | 79.833 | 49.095 | 1.00 | 16.04 A | C |
| ATOM | 1651 | C | ILE | A | 340 | 6.433 | 79.573 | 46.030 | 1.00 | 16.16 A | C |
| ATOM | 1652 | O | ILE | A | 340 | 5.369 | 80.139 | 46.225 | 1.00 | 16.78 A | O |
| ATOM | 1653 | N | SER | A | 341 | 6.988 | 79.469 | 44.829 | 1.00 | 18.02 A | N |
| ATOM | 1654 | CA | SER | A | 341 | 6.397 | 80.061 | 43.636 | 1.00 | 19.89 A | C |
| ATOM | 1655 | CB | SER | A | 341 | 7.302 | 79.792 | 42.423 | 1.00 | 22.71 A | C |
| ATOM | 1656 | OG | SER | A | 341 | 6.820 | 80.457 | 41.269 | 1.00 | 27.61 A | O |
| ATOM | 1657 | C | SER | A | 341 | 4.982 | 79.552 | 43.360 | 1.00 | 19.31 A | C |
| ATOM | 1658 | O | SER | A | 341 | 4.118 | 80.318 | 42.946 | 1.00 | 18.97 A | O |
| ATOM | 1659 | N | ARG | A | 342 | 4.753 | 78.262 | 43.594 | 1.00 | 19.76 A | N |
| ATOM | 1660 | CA | ARG | A | 342 | 3.443 | 77.658 | 43.382 | 1.00 | 21.30 A | C |
| ATOM | 1661 | CB | ARG | A | 342 | 3.597 | 76.214 | 42.911 | 1.00 | 24.17 A | C |
| ATOM | 1662 | CG | ARG | A | 342 | 4.204 | 76.121 | 41.531 | 1.00 | 26.81 A | C |
| ATOM | 1663 | CD | ARG | A | 342 | 4.268 | 74.702 | 41.017 | 1.00 | 31.06 A | C |
| ATOM | 1664 | NE | ARG | A | 342 | 4.686 | 74.692 | 39.617 | 1.00 | 35.62 A | N |
| ATOM | 1665 | CZ | ARG | A | 342 | 4.769 | 73.601 | 38.868 | 1.00 | 36.48 A | C |
| ATOM | 1666 | NH1 | ARG | A | 342 | 5.157 | 73.700 | 37.606 | 1.00 | 40.12 A | N |
| ATOM | 1667 | NH2 | ARG | A | 342 | 4.471 | 72.414 | 39.382 | 1.00 | 38.88 A | N |
| ATOM | 1668 | C | ARG | A | 342 | 2.580 | 77.690 | 44.634 | 1.00 | 21.34 A | C |
| ATOM | 1669 | O | ARG | A | 342 | 1.403 | 77.298 | 44.600 | 1.00 | 21.22 A | O |
| ATOM | 1670 | N | VAL | A | 343 | 3.173 | 78.165 | 45.729 | 1.00 | 19.64 A | N |
| ATOM | 1671 | CA | VAL | A | 343 | 2.499 | 78.260 | 47.022 | 1.00 | 19.20 A | C |
| ATOM | 1672 | CB | VAL | A | 343 | 1.386 | 79.323 | 47.000 | 1.00 | 18.65 A | C |
| ATOM | 1673 | CG1 | VAL | A | 343 | 0.848 | 79.534 | 48.417 | 1.00 | 15.93 A | C |
| ATOM | 1674 | CG2 | VAL | A | 343 | 1.920 | 80.622 | 46.410 | 1.00 | 17.93 A | C |
| ATOM | 1675 | C | VAL | A | 343 | 1.887 | 76.917 | 47.403 | 1.00 | 19.26 A | C |
| ATOM | 1676 | O | VAL | A | 343 | 0.667 | 76.793 | 47.569 | 1.00 | 19.70 A | O |
| ATOM | 1677 | N | GLU | A | 344 | 2.747 | 75.916 | 47.544 | 1.00 | 17.68 A | N |
| ATOM | 1678 | CA | GLU | A | 344 | 2.311 | 74.568 | 47.879 | 1.00 | 19.81 A | C |
| ATOM | 1679 | CB | GLU | A | 344 | 2.860 | 73.584 | 46.830 | 1.00 | 19.99 A | C |
| ATOM | 1680 | CG | GLU | A | 344 | 2.339 | 73.871 | 45.426 | 1.00 | 26.77 A | C |
| ATOM | 1681 | CD | GLU | A | 344 | 3.088 | 73.125 | 44.328 | 1.00 | 29.54 A | C |
| ATOM | 1682 | OE1 | GLU | A | 344 | 2.646 | 73.198 | 43.163 | 1.00 | 33.31 A | O |
| ATOM | 1683 | OE2 | GLU | A | 344 | 4.115 | 72.476 | 44.619 | 1.00 | 30.95 A | O |
| ATOM | 1684 | C | GLU | A | 344 | 2.738 | 74.142 | 49.277 | 1.00 | 19.23 A | C |
| ATOM | 1685 | O | GLU | A | 344 | 3.928 | 73.915 | 49.529 | 1.00 | 17.01 A | O |
| ATOM | 1686 | N | PHE | A | 345 | 1.763 | 74.038 | 50.184 | 1.00 | 18.09 A | N |
| ATOM | 1687 | CA | PHE | A | 345 | 2.030 | 73.621 | 51.555 | 1.00 | 19.56 A | C |
| ATOM | 1688 | CB | PHE | A | 345 | 2.529 | 74.811 | 52.410 | 1.00 | 18.38 A | C |
| ATOM | 1689 | CG | PHE | A | 345 | 1.461 | 75.833 | 52.734 | 1.00 | 18.52 A | C |
| ATOM | 1690 | CD1 | PHE | A | 345 | 0.592 | 75.644 | 53.810 | 1.00 | 21.05 A | C |
| ATOM | 1691 | CD2 | PHE | A | 345 | 1.313 | 76.982 | 51.951 | 1.00 | 18.65 A | C |
| ATOM | 1692 | CE1 | PHE | A | 345 | −0.415 | 76.584 | 54.102 | 1.00 | 16.74 A | C |
| ATOM | 1693 | CE2 | PHE | A | 345 | 0.310 | 77.925 | 52.235 | 1.00 | 19.55 A | C |
| ATOM | 1694 | CZ | PHE | A | 345 | −0.553 | 77.720 | 53.317 | 1.00 | 18.36 A | C |
| ATOM | 1695 | C | PHE | A | 345 | 0.779 | 73.033 | 52.185 | 1.00 | 20.33 A | C |
| ATOM | 1696 | O | PHE | A | 345 | −0.332 | 73.277 | 51.708 | 1.00 | 20.11 A | O |
| ATOM | 1697 | N | THR | A | 346 | 0.969 | 72.260 | 53.255 | 1.00 | 19.73 A | N |
| ATOM | 1698 | CA | THR | A | 346 | −0.136 | 71.655 | 53.985 | 1.00 | 19.58 A | C |
| ATOM | 1699 | CB | THR | A | 346 | −0.326 | 70.158 | 53.615 | 1.00 | 20.72 A | C |
| ATOM | 1700 | OG1 | THR | A | 346 | 0.916 | 69.459 | 53.746 | 1.00 | 20.60 A | O |
| ATOM | 1701 | CG2 | THR | A | 346 | −0.821 | 70.023 | 52.177 | 1.00 | 20.25 A | C |
| ATOM | 1702 | C | THR | A | 346 | 0.116 | 71.792 | 55.487 | 1.00 | 20.13 A | C |
| ATOM | 1703 | O | THR | A | 346 | 1.232 | 72.103 | 55.902 | 1.00 | 18.25 A | O |
| ATOM | 1704 | N | PHE | A | 347 | −0.932 | 71.567 | 56.282 | 1.00 | 20.15 A | N |
| ATOM | 1705 | CA | PHE | A | 347 | −0.887 | 71.673 | 57.746 | 1.00 | 20.73 A | C |
| ATOM | 1706 | CB | PHE | A | 347 | −2.084 | 72.476 | 58.280 | 1.00 | 19.55 A | C |
| ATOM | 1707 | CG | PHE | A | 347 | −2.217 | 73.870 | 57.720 | 1.00 | 20.41 A | C |
| ATOM | 1708 | CD1 | PHE | A | 347 | −1.433 | 74.909 | 58.201 | 1.00 | 17.74 A | C |
| ATOM | 1709 | CD2 | PHE | A | 347 | −3.178 | 74.150 | 56.744 | 1.00 | 20.45 A | C |
| ATOM | 1710 | CE1 | PHE | A | 347 | −1.597 | 76.204 | 57.732 | 1.00 | 18.97 A | C |
| ATOM | 1711 | CE2 | PHE | A | 347 | −3.354 | 75.449 | 56.264 | 1.00 | 19.38 A | C |
| ATOM | 1712 | CZ | PHE | A | 347 | −2.566 | 76.476 | 56.757 | 1.00 | 20.54 A | C |
| ATOM | 1713 | C | PHE | A | 347 | −0.983 | 70.309 | 58.430 | 1.00 | 22.46 A | C |
| ATOM | 1714 | O | PHE | A | 347 | −1.685 | 69.416 | 57.952 | 1.00 | 21.99 A | O |
| ATOM | 1715 | N | PRO | A | 348 | −0.285 | 70.133 | 59.565 | 1.00 | 24.54 A | N |
| ATOM | 1716 | CD | PRO | A | 348 | 0.801 | 70.979 | 60.093 | 1.00 | 25.31 A | C |
| ATOM | 1717 | CA | PRO | A | 348 | −0.354 | 68.854 | 60.286 | 1.00 | 23.76 A | C |
| ATOM | 1718 | CB | PRO | A | 348 | 0.728 | 68.991 | 61.354 | 1.00 | 24.65 A | C |
| ATOM | 1719 | CG | PRO | A | 348 | 1.715 | 69.961 | 60.728 | 1.00 | 26.35 A | C |

TABLE 2-continued coordinates for the two molecules in the asymmetric unit of [T287] Aurora
A (122–396) in complex with an inhibitor of formula II in space group P2₁

| ATOM | 1720 | C   | PRO | A | 348 | −1.756  | 68.822 | 60.910 | 1.00 | 24.94 A | C |
|------|------|-----|-----|---|-----|---------|--------|--------|------|---------|---|
| ATOM | 1721 | O   | PRO | A | 348 | −2.389  | 69.868 | 61.056 | 1.00 | 22.13 A | O |
| ATOM | 1722 | N   | ASP | A | 349 | −2.231  | 67.640 | 61.286 | 1.00 | 27.34 A | N |
| ATOM | 1723 | CA  | ASP | A | 349 | −3.568  | 67.503 | 61.870 | 1.00 | 30.19 A | C |
| ATOM | 1724 | CB  | ASP | A | 349 | −3.856  | 66.047 | 62.234 | 1.00 | 33.25 A | C |
| ATOM | 1725 | CG  | ASP | A | 349 | −3.804  | 65.139 | 61.045 | 1.00 | 37.28 A | C |
| ATOM | 1726 | OD1 | ASP | A | 349 | −4.341  | 65.526 | 59.987 | 1.00 | 39.75 A | O |
| ATOM | 1727 | OD2 | ASP | A | 349 | −3.232  | 64.034 | 61.172 | 1.00 | 41.94 A | O |
| ATOM | 1728 | C   | ASP | A | 349 | −3.856  | 68.342 | 63.103 | 1.00 | 30.17 A | C |
| ATOM | 1729 | O   | ASP | A | 349 | −4.987  | 68.777 | 63.293 | 1.00 | 29.70 A | O |
| ATOM | 1730 | N   | PHE | A | 350 | −2.855  | 68.565 | 63.949 | 1.00 | 28.31 A | N |
| ATOM | 1731 | CA  | PHE | A | 350 | −3.100  | 69.334 | 65.160 | 1.00 | 26.49 A | C |
| ATOM | 1732 | CB  | PHE | A | 350 | −1.977  | 69.094 | 66.184 | 1.00 | 25.79 A | C |
| ATOM | 1733 | CG  | PHE | A | 350 | −0.600  | 69.470 | 65.705 | 1.00 | 24.86 A | C |
| ATOM | 1734 | CD1 | PHE | A | 350 | −0.183  | 70.798 | 65.703 | 1.00 | 27.41 A | C |
| ATOM | 1735 | CD2 | PHE | A | 350 | 0.294   | 68.492 | 65.296 | 1.00 | 22.65 A | C |
| ATOM | 1736 | CE1 | PHE | A | 350 | 1.112   | 71.143 | 65.302 | 1.00 | 23.41 A | C |
| ATOM | 1737 | CE2 | PHE | A | 350 | 1.586   | 68.824 | 64.895 | 1.00 | 22.60 A | C |
| ATOM | 1738 | CZ  | PHE | A | 350 | 1.995   | 70.153 | 64.899 | 1.00 | 23.36 A | C |
| ATOM | 1739 | C   | PHE | A | 350 | −3.349  | 70.830 | 64.963 | 1.00 | 26.28 A | C |
| ATOM | 1740 | O   | PHE | A | 350 | −3.926  | 71.482 | 65.833 | 1.00 | 26.14 A | O |
| ATOM | 1741 | N   | VAL | A | 351 | −2.957  | 71.380 | 63.820 | 1.00 | 24.56 A | N |
| ATOM | 1742 | CA  | VAL | A | 351 | −3.174  | 72.809 | 63.600 | 1.00 | 23.91 A | C |
| ATOM | 1743 | CB  | VAL | A | 351 | −2.429  | 73.304 | 62.341 | 1.00 | 21.91 A | C |
| ATOM | 1744 | CG1 | VAL | A | 351 | −2.624  | 74.803 | 62.184 | 1.00 | 22.59 A | C |
| ATOM | 1745 | CG2 | VAL | A | 351 | −0.943  | 72.989 | 62.459 | 1.00 | 19.79 A | C |
| ATOM | 1746 | C   | VAL | A | 351 | −4.666  | 73.183 | 63.510 | 1.00 | 23.38 A | C |
| ATOM | 1747 | O   | VAL | A | 351 | −5.408  | 72.635 | 62.707 | 1.00 | 23.52 A | O |
| ATOM | 1748 | N   | THR | A | 352 | −5.076  | 74.123 | 64.358 | 1.00 | 23.53 A | N |
| ATOM | 1749 | CA  | THR | A | 352 | −6.454  | 74.618 | 64.463 | 1.00 | 24.90 A | C |
| ATOM | 1750 | CB  | THR | A | 352 | −6.561  | 75.531 | 65.724 | 1.00 | 26.17 A | C |
| ATOM | 1751 | OG1 | THR | A | 352 | −6.461  | 74.713 | 66.893 | 1.00 | 29.32 A | O |
| ATOM | 1752 | CG2 | THR | A | 352 | −7.872  | 76.284 | 65.769 | 1.00 | 31.36 A | C |
| ATOM | 1753 | C   | THR | A | 352 | −7.013  | 75.350 | 63.230 | 1.00 | 23.73 A | C |
| ATOM | 1754 | O   | THR | A | 352 | −6.270  | 75.946 | 62.447 | 1.00 | 23.43 A | O |
| ATOM | 1755 | N   | GLU | A | 353 | −8.335  | 75.306 | 63.059 | 1.00 | 24.62 A | N |
| ATOM | 1756 | CA  | GLU | A | 353 | −8.967  | 75.954 | 61.909 | 1.00 | 24.68 A | C |
| ATOM | 1757 | CB  | GLU | A | 353 | −10.468 | 75.643 | 61.869 | 1.00 | 29.50 A | C |
| ATOM | 1758 | CG  | GLU | A | 353 | −10.797 | 74.232 | 61.368 | 1.00 | 35.19 A | C |
| ATOM | 1759 | CD  | GLU | A | 353 | −10.272 | 73.983 | 59.966 | 1.00 | 38.71 A | C |
| ATOM | 1760 | OE1 | GLU | A | 353 | −10.401 | 74.895 | 59.117 | 1.00 | 40.65 A | O |
| ATOM | 1761 | OE2 | GLU | A | 353 | −9.739  | 72.879 | 59.703 | 1.00 | 40.38 A | O |
| ATOM | 1762 | C   | GLU | A | 353 | −8.752  | 77.464 | 61.858 | 1.00 | 21.70 A | C |
| ATOM | 1763 | O   | GLU | A | 353 | −8.583  | 78.041 | 60.782 | 1.00 | 19.58 A | O |
| ATOM | 1764 | N   | GLY | A | 354 | −8.755  | 78.106 | 63.017 | 1.00 | 19.06 A | N |
| ATOM | 1765 | CA  | GLY | A | 354 | −8.551  | 79.542 | 63.035 | 1.00 | 17.79 A | C |
| ATOM | 1766 | C   | GLY | A | 354 | −7.128  | 79.867 | 62.603 | 1.00 | 18.40 A | C |
| ATOM | 1767 | O   | GLY | A | 354 | −6.878  | 80.874 | 61.930 | 1.00 | 16.97 A | O |
| ATOM | 1768 | N   | ALA | A | 355 | −6.191  | 79.009 | 62.993 | 1.00 | 14.57 A | N |
| ATOM | 1769 | CA  | ALA | A | 355 | −4.794  | 79.210 | 62.648 | 1.00 | 15.46 A | C |
| ATOM | 1770 | CB  | ALA | A | 355 | −3.919  | 78.229 | 63.439 | 1.00 | 16.64 A | C |
| ATOM | 1771 | C   | ALA | A | 355 | −4.589  | 79.038 | 61.136 | 1.00 | 14.00 A | C |
| ATOM | 1772 | O   | ALA | A | 355 | −3.846  | 79.800 | 60.508 | 1.00 | 10.53 A | O |
| ATOM | 1773 | N   | ARG | A | 356 | −5.269  | 78.043 | 60.565 | 1.00 | 15.01 A | N |
| ATOM | 1774 | CA  | ARG | A | 356 | −5.199  | 77.759 | 59.133 | 1.00 | 16.46 A | C |
| ATOM | 1775 | CB  | ARG | A | 356 | −6.010  | 76.503 | 58.799 | 1.00 | 16.70 A | C |
| ATOM | 1776 | CG  | ARG | A | 356 | −5.460  | 75.229 | 59.389 | 1.00 | 18.49 A | C |
| ATOM | 1777 | CD  | ARG | A | 356 | −6.495  | 74.120 | 59.378 | 1.00 | 22.62 A | C |
| ATOM | 1778 | NE  | ARG | A | 356 | −6.108  | 73.006 | 58.518 | 1.00 | 28.84 A | N |
| ATOM | 1779 | CZ  | ARG | A | 356 | −5.911  | 71.762 | 58.945 | 1.00 | 29.04 A | C |
| ATOM | 1780 | NH1 | ARG | A | 356 | −6.058  | 71.463 | 60.224 | 1.00 | 27.32 A | N |
| ATOM | 1781 | NH2 | ARG | A | 356 | −5.577  | 70.811 | 58.086 | 1.00 | 31.07 A | N |
| ATOM | 1782 | C   | ARG | A | 356 | −5.758  | 78.941 | 58.350 | 1.00 | 15.08 A | C |
| ATOM | 1783 | O   | ARG | A | 356 | −5.225  | 79.335 | 57.319 | 1.00 | 14.99 A | O |
| ATOM | 1784 | N   | ASP | A | 357 | −6.841  | 79.508 | 58.860 | 1.00 | 18.02 A | N |
| ATOM | 1785 | CA  | ASP | A | 357 | −7.466  | 80.646 | 58.214 | 1.00 | 18.90 A | C |
| ATOM | 1786 | CB  | ASP | A | 357 | −8.694  | 81.096 | 58.994 | 1.00 | 18.88 A | C |
| ATOM | 1787 | CG  | ASP | A | 357 | −9.406  | 82.240 | 58.312 | 1.00 | 22.28 A | C |
| ATOM | 1788 | OD1 | ASP | A | 357 | −9.966  | 81.992 | 57.235 | 1.00 | 22.61 A | O |
| ATOM | 1789 | OD2 | ASP | A | 357 | −9.388  | 83.381 | 58.830 | 1.00 | 24.45 A | O |
| ATOM | 1790 | C   | ASP | A | 357 | −6.494  | 81.824 | 58.092 | 1.00 | 19.94 A | C |
| ATOM | 1791 | O   | ASP | A | 357 | −6.289  | 82.342 | 56.998 | 1.00 | 20.32 A | O |
| ATOM | 1792 | N   | LEU | A | 358 | −5.900  | 82.238 | 59.211 | 1.00 | 18.05 A | N |
| ATOM | 1793 | CA  | LEU | A | 358 | −4.942  | 83.358 | 59.219 | 1.00 | 18.23 A | C |
| ATOM | 1794 | CB  | LEU | A | 358 | −4.411  | 83.613 | 60.638 | 1.00 | 18.23 A | C |
| ATOM | 1795 | CG  | LEU | A | 358 | −3.394  | 84.760 | 60.758 | 1.00 | 20.75 A | C |

TABLE 2-continued coordinates for the two molecules in the asymmetric unit of [T287] Aurora
A (122–396) in complex with an inhibitor of formula II in space group P2₁

| ATOM | 1796 | CD1 | LEU | A | 358 | −4.012 | 86.056 | 60.216 | 1.00 | 19.09 | A | C |
|------|------|-----|-----|---|-----|--------|--------|--------|------|-------|---|---|
| ATOM | 1797 | CD2 | LEU | A | 358 | −2.964 | 84.934 | 62.208 | 1.00 | 17.47 | A | C |
| ATOM | 1798 | C | LEU | A | 358 | −3.749 | 83.145 | 58.290 | 1.00 | 16.19 | A | C |
| ATOM | 1799 | O | LEU | A | 358 | −3.413 | 84.021 | 57.481 | 1.00 | 16.52 | A | O |
| ATOM | 1800 | N | ILE | A | 359 | −3.119 | 81.983 | 58.415 | 1.00 | 15.38 | A | N |
| ATOM | 1801 | CA | ILE | A | 359 | −1.956 | 81.629 | 57.613 | 1.00 | 16.57 | A | C |
| ATOM | 1802 | CB | ILE | A | 359 | −1.329 | 80.296 | 58.114 | 1.00 | 16.35 | A | C |
| ATOM | 1803 | CG2 | ILE | A | 359 | −0.186 | 79.879 | 57.193 | 1.00 | 13.83 | A | C |
| ATOM | 1804 | CG1 | ILE | A | 359 | −0.825 | 80.469 | 59.553 | 1.00 | 17.25 | A | C |
| ATOM | 1805 | CD1 | ILE | A | 359 | −0.321 | 79.200 | 60.220 | 1.00 | 14.18 | A | C |
| ATOM | 1806 | C | ILE | A | 359 | −2.255 | 81.518 | 56.112 | 1.00 | 17.80 | A | C |
| ATOM | 1807 | O | ILE | A | 359 | −1.398 | 81.829 | 55.294 | 1.00 | 18.14 | A | O |
| ATOM | 1808 | N | SER | A | 360 | −3.464 | 81.079 | 55.759 | 1.00 | 19.68 | A | N |
| ATOM | 1809 | CA | SER | A | 360 | −3.867 | 80.938 | 54.354 | 1.00 | 21.20 | A | C |
| ATOM | 1810 | CB | SER | A | 360 | −5.153 | 80.099 | 54.233 | 1.00 | 19.64 | A | C |
| ATOM | 1811 | OG | SER | A | 360 | −4.950 | 78.757 | 54.649 | 1.00 | 20.82 | A | O |
| ATOM | 1812 | C | SER | A | 360 | −4.105 | 82.303 | 53.714 | 1.00 | 22.33 | A | C |
| ATOM | 1813 | O | SER | A | 360 | −3.958 | 82.467 | 52.501 | 1.00 | 20.61 | A | O |
| ATOM | 1814 | N | ARG | A | 361 | −4.500 | 83.274 | 54.533 | 1.00 | 23.60 | A | N |
| ATOM | 1815 | CA | ARG | A | 361 | −4.741 | 84.633 | 54.059 | 1.00 | 23.75 | A | C |
| ATOM | 1816 | CB | ARG | A | 361 | −5.587 | 85.410 | 55.072 | 1.00 | 28.01 | A | C |
| ATOM | 1817 | CG | ARG | A | 361 | −7.078 | 85.081 | 55.087 | 1.00 | 32.71 | A | C |
| ATOM | 1818 | CD | ARG | A | 361 | −7.726 | 85.333 | 53.723 | 1.00 | 39.20 | A | C |
| ATOM | 1819 | NE | ARG | A | 361 | −7.187 | 86.514 | 53.042 | 1.00 | 44.85 | A | N |
| ATOM | 1820 | CZ | ARG | A | 361 | −7.332 | 87.772 | 53.456 | 1.00 | 46.87 | A | C |
| ATOM | 1821 | NH1 | ARG | A | 361 | −8.012 | 88.048 | 54.562 | 1.00 | 45.54 | A | N |
| ATOM | 1822 | NH2 | ARG | A | 361 | −6.772 | 88.759 | 52.767 | 1.00 | 47.53 | A | N |
| ATOM | 1823 | C | ARG | A | 361 | −3.414 | 85.369 | 53.863 | 1.00 | 21.60 | A | C |
| ATOM | 1824 | O | ARG | A | 361 | −3.268 | 86.174 | 52.941 | 1.00 | 24.02 | A | O |
| ATOM | 1825 | N | LEU | A | 362 | −2.450 | 85.078 | 54.730 | 1.00 | 19.99 | A | N |
| ATOM | 1826 | CA | LEU | A | 362 | −1.139 | 85.730 | 54.683 | 1.00 | 18.01 | A | C |
| ATOM | 1827 | CB | LEU | A | 362 | −0.431 | 85.627 | 56.042 | 1.00 | 15.49 | A | C |
| ATOM | 1828 | CG | LEU | A | 362 | −0.993 | 86.459 | 57.207 | 1.00 | 15.69 | A | C |
| ATOM | 1829 | CD1 | LEU | A | 362 | −0.312 | 86.063 | 58.496 | 1.00 | 10.97 | A | C |
| ATOM | 1830 | CD2 | LEU | A | 362 | −0.801 | 87.948 | 56.941 | 1.00 | 15.65 | A | C |
| ATOM | 1831 | C | LEU | A | 362 | −0.225 | 85.192 | 53.603 | 1.00 | 18.43 | A | C |
| ATOM | 1832 | O | LEU | A | 362 | 0.608 | 85.930 | 53.080 | 1.00 | 18.21 | A | O |
| ATOM | 1833 | N | LEU | A | 363 | −0.362 | 83.911 | 53.271 | 1.00 | 19.92 | A | N |
| ATOM | 1834 | CA | LEU | A | 363 | 0.483 | 83.328 | 52.235 | 1.00 | 21.77 | A | C |
| ATOM | 1835 | CB | LEU | A | 363 | 0.918 | 81.910 | 52.623 | 1.00 | 21.94 | A | C |
| ATOM | 1836 | CG | LEU | A | 363 | 1.412 | 81.704 | 54.065 | 1.00 | 26.68 | A | C |
| ATOM | 1837 | CD1 | LEU | A | 363 | 2.276 | 80.444 | 54.158 | 1.00 | 23.94 | A | C |
| ATOM | 1838 | CD2 | LEU | A | 363 | 2.215 | 82.925 | 54.518 | 1.00 | 26.76 | A | C |
| ATOM | 1839 | C | LEU | A | 363 | −0.243 | 83.314 | 50.892 | 1.00 | 22.91 | A | C |
| ATOM | 1840 | O | LEU | A | 363 | −0.570 | 82.261 | 50.359 | 1.00 | 24.15 | A | O |
| ATOM | 1841 | N | LYS | A | 364 | −0.505 | 84.508 | 50.370 | 1.00 | 23.56 | A | N |
| ATOM | 1842 | CA | LYS | A | 364 | −1.180 | 84.691 | 49.090 | 1.00 | 23.34 | A | C |
| ATOM | 1843 | CB | LYS | A | 364 | −2.211 | 85.818 | 49.181 | 1.00 | 24.62 | A | C |
| ATOM | 1844 | CG | LYS | A | 364 | −3.545 | 85.423 | 49.806 | 1.00 | 26.87 | A | C |
| ATOM | 1845 | CD | LYS | A | 364 | −4.289 | 84.446 | 48.912 | 1.00 | 29.10 | A | C |
| ATOM | 1846 | CE | LYS | A | 364 | −5.713 | 84.208 | 49.392 | 1.00 | 32.69 | A | C |
| ATOM | 1847 | NZ | LYS | A | 364 | −6.503 | 83.427 | 48.391 | 1.00 | 32.47 | A | N |
| ATOM | 1848 | C | LYS | A | 364 | −0.144 | 85.052 | 48.032 | 1.00 | 22.89 | A | C |
| ATOM | 1849 | O | LYS | A | 364 | 0.696 | 85.929 | 48.247 | 1.00 | 23.81 | A | O |
| ATOM | 1850 | N | HIS | A | 365 | −0.210 | 84.375 | 46.893 | 1.00 | 22.71 | A | N |
| ATOM | 1851 | CA | HIS | A | 365 | 0.717 | 84.624 | 45.797 | 1.00 | 23.97 | A | C |
| ATOM | 1852 | CB | HIS | A | 365 | 0.380 | 83.734 | 44.602 | 1.00 | 24.15 | A | C |
| ATOM | 1853 | CG | HIS | A | 365 | 1.275 | 83.955 | 43.426 | 1.00 | 25.26 | A | C |
| ATOM | 1854 | CD2 | HIS | A | 365 | 1.097 | 84.673 | 42.293 | 1.00 | 26.54 | A | C |
| ATOM | 1855 | ND1 | HIS | A | 365 | 2.563 | 83.470 | 43.372 | 1.00 | 27.83 | A | N |
| ATOM | 1856 | CE1 | HIS | A | 365 | 3.142 | 83.883 | 42.258 | 1.00 | 26.33 | A | C |
| ATOM | 1857 | NE2 | HIS | A | 365 | 2.274 | 84.617 | 41.588 | 1.00 | 26.94 | A | N |
| ATOM | 1858 | C | HIS | A | 365 | 0.703 | 86.085 | 45.354 | 1.00 | 23.66 | A | C |
| ATOM | 1859 | O | HIS | A | 365 | 1.757 | 86.695 | 45.187 | 1.00 | 24.80 | A | O |
| ATOM | 1860 | N | ASN | A | 366 | −0.491 | 86.631 | 45.144 | 1.00 | 25.39 | A | N |
| ATOM | 1861 | CA | ASN | A | 366 | −0.667 | 88.027 | 44.729 | 1.00 | 28.27 | A | C |
| ATOM | 1862 | CB | ASN | A | 366 | −2.058 | 88.197 | 44.101 | 1.00 | 30.44 | A | C |
| ATOM | 1863 | CG | ASN | A | 366 | −2.331 | 89.620 | 43.624 | 1.00 | 33.56 | A | C |
| ATOM | 1864 | OD1 | ASN | A | 366 | −3.386 | 89.895 | 43.051 | 1.00 | 36.17 | A | O |
| ATOM | 1865 | ND2 | ASN | A | 366 | −1.390 | 90.525 | 43.857 | 1.00 | 32.69 | A | N |
| ATOM | 1866 | C | ASN | A | 366 | −0.526 | 88.926 | 45.965 | 1.00 | 28.67 | A | C |
| ATOM | 1867 | O | ASN | A | 366 | −1.389 | 88.928 | 46.843 | 1.00 | 29.64 | A | O |
| ATOM | 1868 | N | PRO | A | 367 | 0.562 | 89.706 | 46.044 | 1.00 | 29.87 | A | N |
| ATOM | 1869 | CD | PRO | A | 367 | 1.612 | 89.829 | 45.019 | 1.00 | 28.83 | A | C |
| ATOM | 1870 | CA | PRO | A | 367 | 0.832 | 90.611 | 47.172 | 1.00 | 31.07 | A | C |
| ATOM | 1871 | CB | PRO | A | 367 | 2.013 | 91.437 | 46.675 | 1.00 | 30.37 | A | C |

TABLE 2-continued coordinates for the two molecules in the asymmetric unit of [T287] Aurora
A (122–396) in complex with an inhibitor of formula II in space group P2₁

| ATOM | 1872 | CG | PRO | A | 367 | 2.734 | 90.479 | 45.790 | 1.00 | 30.85 | A | C |
|---|---|---|---|---|---|---|---|---|---|---|---|---|
| ATOM | 1873 | C | PRO | A | 367 | −0.328 | 91.496 | 47.624 | 1.00 | 32.07 | A | C |
| ATOM | 1874 | O | PRO | A | 367 | −0.483 | 91.754 | 48.820 | 1.00 | 32.30 | A | O |
| ATOM | 1875 | N | SER | A | 368 | −1.131 | 91.966 | 46.671 | 1.00 | 32.61 | A | N |
| ATOM | 1876 | CA | SER | A | 368 | −2.261 | 92.834 | 46.987 | 1.00 | 34.50 | A | C |
| ATOM | 1877 | CB | SER | A | 368 | −2.760 | 93.547 | 45.720 | 1.00 | 35.81 | A | C |
| ATOM | 1878 | OG | SER | A | 368 | −3.206 | 92.623 | 44.736 | 1.00 | 36.05 | A | O |
| ATOM | 1879 | C | SER | A | 368 | −3.413 | 92.088 | 47.656 | 1.00 | 35.02 | A | C |
| ATOM | 1880 | O | SER | A | 368 | −4.290 | 92.706 | 48.258 | 1.00 | 37.52 | A | O |
| ATOM | 1881 | N | GLN | A | 369 | −3.418 | 90.763 | 47.554 | 1.00 | 34.24 | A | N |
| ATOM | 1882 | CA | GLN | A | 369 | −4.475 | 89.975 | 48.176 | 1.00 | 33.87 | A | C |
| ATOM | 1883 | CB | GLN | A | 369 | −4.644 | 88.637 | 47.463 | 1.00 | 36.07 | A | C |
| ATOM | 1884 | CG | GLN | A | 369 | −5.499 | 88.695 | 46.218 | 1.00 | 40.88 | A | C |
| ATOM | 1885 | CD | GLN | A | 369 | −5.478 | 87.382 | 45.463 | 1.00 | 44.11 | A | C |
| ATOM | 1886 | OE1 | GLN | A | 369 | −5.619 | 86.308 | 46.059 | 1.00 | 45.39 | A | O |
| ATOM | 1887 | NE2 | GLN | A | 369 | −5.303 | 87.457 | 44.145 | 1.00 | 45.10 | A | N |
| ATOM | 1888 | C | GLN | A | 369 | −4.214 | 89.721 | 49.653 | 1.00 | 32.42 | A | C |
| ATOM | 1889 | O | GLN | A | 369 | −5.045 | 89.136 | 50.336 | 1.00 | 31.67 | A | O |
| ATOM | 1890 | N | ARG | A | 370 | −3.053 | 90.149 | 50.141 | 1.00 | 31.86 | A | N |
| ATOM | 1891 | CA | ARG | A | 370 | −2.714 | 89.968 | 51.549 | 1.00 | 30.59 | A | C |
| ATOM | 1892 | CB | ARG | A | 370 | −1.193 | 89.979 | 51.741 | 1.00 | 27.86 | A | C |
| ATOM | 1893 | CG | ARG | A | 370 | −0.498 | 88.834 | 51.047 | 1.00 | 27.06 | A | C |
| ATOM | 1894 | CD | ARG | A | 370 | 1.015 | 89.020 | 50.987 | 1.00 | 25.62 | A | C |
| ATOM | 1895 | NE | ARG | A | 370 | 1.552 | 88.214 | 49.901 | 1.00 | 23.24 | A | N |
| ATOM | 1896 | CZ | ARG | A | 370 | 2.744 | 88.385 | 49.344 | 1.00 | 22.14 | A | C |
| ATOM | 1897 | NH1 | ARG | A | 370 | 3.557 | 89.340 | 49.777 | 1.00 | 19.46 | A | N |
| ATOM | 1898 | NH2 | ARG | A | 370 | 3.098 | 87.618 | 48.314 | 1.00 | 20.24 | A | N |
| ATOM | 1899 | C | ARG | A | 370 | −3.349 | 91.103 | 52.344 | 1.00 | 30.03 | A | C |
| ATOM | 1900 | O | ARG | A | 370 | −3.380 | 92.244 | 51.887 | 1.00 | 30.03 | A | O |
| ATOM | 1901 | N | PRO | A | 371 | −3.861 | 90.801 | 53.549 | 1.00 | 29.42 | A | N |
| ATOM | 1902 | CD | PRO | A | 371 | −3.861 | 89.468 | 54.180 | 1.00 | 28.61 | A | C |
| ATOM | 1903 | CA | PRO | A | 371 | −4.506 | 91.783 | 54.426 | 1.00 | 29.38 | A | C |
| ATOM | 1904 | CB | PRO | A | 371 | −5.105 | 90.911 | 55.524 | 1.00 | 28.93 | A | C |
| ATOM | 1905 | CG | PRO | A | 371 | −4.130 | 89.800 | 55.626 | 1.00 | 27.39 | A | C |
| ATOM | 1906 | C | PRO | A | 371 | −3.579 | 92.856 | 54.995 | 1.00 | 30.07 | A | C |
| ATOM | 1907 | O | PRO | A | 371 | −2.356 | 92.719 | 54.979 | 1.00 | 30.66 | A | O |
| ATOM | 1908 | N | MET | A | 372 | −4.179 | 93.932 | 55.489 | 1.00 | 29.01 | A | N |
| ATOM | 1909 | CA | MET | A | 372 | −3.422 | 95.014 | 56.095 | 1.00 | 28.79 | A | C |
| ATOM | 1910 | CB | MET | A | 372 | −4.297 | 96.255 | 56.209 | 1.00 | 32.05 | A | C |
| ATOM | 1911 | CG | MET | A | 372 | −4.983 | 96.641 | 54.909 | 1.00 | 38.91 | A | C |
| ATOM | 1912 | SD | MET | A | 372 | −6.339 | 97.820 | 55.165 | 1.00 | 45.86 | A | S |
| ATOM | 1913 | CE | MET | A | 372 | −5.396 | 99.295 | 55.623 | 1.00 | 43.73 | A | C |
| ATOM | 1914 | C | MET | A | 372 | −3.050 | 94.511 | 57.484 | 1.00 | 27.02 | A | C |
| ATOM | 1915 | O | MET | A | 372 | −3.635 | 93.542 | 57.965 | 1.00 | 25.83 | A | O |
| ATOM | 1916 | N | LEU | A | 373 | −2.084 | 95.160 | 58.126 | 1.00 | 26.03 | A | N |
| ATOM | 1917 | CA | LEU | A | 373 | −1.650 | 94.759 | 59.462 | 1.00 | 24.32 | A | C |
| ATOM | 1918 | CB | LEU | A | 373 | −0.422 | 95.570 | 59.886 | 1.00 | 24.26 | A | C |
| ATOM | 1919 | CG | LEU | A | 373 | 0.874 | 95.259 | 59.134 | 1.00 | 24.53 | A | C |
| ATOM | 1920 | CD1 | LEU | A | 373 | 1.971 | 96.239 | 59.545 | 1.00 | 22.42 | A | C |
| ATOM | 1921 | CD2 | LEU | A | 373 | 1.291 | 93.821 | 59.422 | 1.00 | 22.22 | A | C |
| ATOM | 1922 | C | LEU | A | 373 | −2.756 | 94.910 | 60.504 | 1.00 | 23.93 | A | C |
| ATOM | 1923 | O | LEU | A | 373 | −2.789 | 94.181 | 61.488 | 1.00 | 24.38 | A | O |
| ATOM | 1924 | N | ALA | A | 374 | −3.666 | 95.852 | 60.281 | 1.00 | 24.38 | A | N |
| ATOM | 1925 | CA | ALA | A | 374 | −4.772 | 96.080 | 61.203 | 1.00 | 22.71 | A | C |
| ATOM | 1926 | CB | ALA | A | 374 | −5.503 | 97.370 | 60.836 | 1.00 | 26.79 | A | C |
| ATOM | 1927 | C | ALA | A | 374 | −5.741 | 94.911 | 61.164 | 1.00 | 23.14 | A | C |
| ATOM | 1928 | O | ALA | A | 374 | −6.432 | 94.637 | 62.150 | 1.00 | 22.46 | A | O |
| ATOM | 1929 | N | GLU | A | 375 | −5.798 | 94.227 | 60.022 | 1.00 | 23.02 | A | N |
| ATOM | 1930 | CA | GLU | A | 375 | −6.694 | 93.084 | 59.875 | 1.00 | 25.10 | A | C |
| ATOM | 1931 | CB | GLU | A | 375 | −6.908 | 92.745 | 58.398 | 1.00 | 25.81 | A | C |
| ATOM | 1932 | CG | GLU | A | 375 | −7.552 | 93.858 | 57.593 | 1.00 | 30.24 | A | C |
| ATOM | 1933 | CD | GLU | A | 375 | −7.814 | 93.459 | 56.151 | 1.00 | 30.04 | A | C |
| ATOM | 1934 | OE1 | GLU | A | 375 | −8.843 | 92.800 | 55.883 | 1.00 | 33.09 | A | O |
| ATOM | 1935 | OE2 | GLU | A | 375 | −6.984 | 93.796 | 55.289 | 1.00 | 29.56 | A | O |
| ATOM | 1936 | C | GLU | A | 375 | −6.143 | 91.864 | 60.612 | 1.00 | 25.25 | A | C |
| ATOM | 1937 | O | GLU | A | 375 | −6.910 | 91.011 | 61.063 | 1.00 | 27.99 | A | O |
| ATOM | 1938 | N | VAL | A | 376 | −4.820 | 91.785 | 60.727 | 1.00 | 22.91 | A | N |
| ATOM | 1939 | CA | VAL | A | 376 | −4.175 | 90.687 | 61.439 | 1.00 | 21.50 | A | C |
| ATOM | 1940 | CB | VAL | A | 376 | −2.643 | 90.662 | 61.187 | 1.00 | 21.90 | A | C |
| ATOM | 1941 | CG1 | VAL | A | 376 | −1.976 | 89.654 | 62.125 | 1.00 | 19.51 | A | C |
| ATOM | 1942 | CG2 | VAL | A | 376 | −2.355 | 90.313 | 59.729 | 1.00 | 22.63 | A | C |
| ATOM | 1943 | C | VAL | A | 376 | −4.405 | 90.862 | 62.944 | 1.00 | 21.43 | A | C |
| ATOM | 1944 | O | VAL | A | 376 | −4.725 | 89.906 | 63.653 | 1.00 | 19.70 | A | O |
| ATOM | 1945 | N | LEU | A | 377 | −4.241 | 92.090 | 63.422 | 1.00 | 19.23 | A | N |
| ATOM | 1946 | CA | LEU | A | 377 | −4.426 | 92.375 | 64.837 | 1.00 | 22.49 | A | C |
| ATOM | 1947 | CB | LEU | A | 377 | −4.002 | 93.815 | 65.142 | 1.00 | 22.58 | A | C |

TABLE 2-continued coordinates for the two molecules in the asymmetric unit of [T287] Aurora
A (122–396) in complex with an inhibitor of formula II in space group P2$_1$

| ATOM | 1948 | CG | LEU | A | 377 | −2.498 | 94.047 | 64.962 | 1.00 | 22.54 | A | C |
|------|------|-----|-----|---|-----|--------|--------|--------|------|-------|---|---|
| ATOM | 1949 | CD1 | LEU | A | 377 | −2.172 | 95.525 | 64.951 | 1.00 | 22.51 | A | C |
| ATOM | 1950 | CD2 | LEU | A | 377 | −1.753 | 93.341 | 66.092 | 1.00 | 22.08 | A | C |
| ATOM | 1951 | C | LEU | A | 377 | −5.869 | 92.143 | 65.269 | 1.00 | 25.05 | A | C |
| ATOM | 1952 | O | LEU | A | 377 | −6.141 | 91.905 | 66.443 | 1.00 | 26.04 | A | O |
| ATOM | 1953 | N | GLU | A | 378 | −6.787 | 92.177 | 64.308 | 1.00 | 24.26 | A | N |
| ATOM | 1954 | CA | GLU | A | 378 | −8.193 | 91.983 | 64.611 | 1.00 | 25.18 | A | C |
| ATOM | 1955 | CB | GLU | A | 378 | −9.032 | 93.046 | 63.890 | 1.00 | 27.95 | A | C |
| ATOM | 1956 | CG | GLU | A | 378 | −8.848 | 94.444 | 64.452 | 1.00 | 31.63 | A | C |
| ATOM | 1957 | CD | GLU | A | 378 | −9.693 | 95.484 | 63.743 | 1.00 | 33.54 | A | C |
| ATOM | 1958 | OE1 | GLU | A | 378 | −9.894 | 96.568 | 64.334 | 1.00 | 35.00 | A | O |
| ATOM | 1959 | OE2 | GLU | A | 378 | −10.147 | 95.220 | 62.605 | 1.00 | 31.59 | A | O |
| ATOM | 1960 | C | GLU | A | 378 | −8.713 | 90.597 | 64.251 | 1.00 | 24.15 | A | C |
| ATOM | 1961 | O | GLU | A | 378 | −9.883 | 90.301 | 64.473 | 1.00 | 21.88 | A | O |
| ATOM | 1962 | N | HIS | A | 379 | −7.860 | 89.742 | 63.702 | 1.00 | 22.41 | A | N |
| ATOM | 1963 | CA | HIS | A | 379 | −8.322 | 88.410 | 63.337 | 1.00 | 22.38 | A | C |
| ATOM | 1964 | CB | HIS | A | 379 | −7.200 | 87.624 | 62.665 | 1.00 | 18.92 | A | C |
| ATOM | 1965 | CG | HIS | A | 379 | −7.650 | 86.333 | 62.050 | 1.00 | 16.62 | A | C |
| ATOM | 1966 | CD2 | HIS | A | 379 | −7.936 | 86.009 | 60.767 | 1.00 | 15.24 | A | C |
| ATOM | 1967 | ND1 | HIS | A | 379 | −7.834 | 85.181 | 62.786 | 1.00 | 15.11 | A | N |
| ATOM | 1968 | CE1 | HIS | A | 379 | −8.208 | 84.202 | 61.982 | 1.00 | 16.55 | A | C |
| ATOM | 1969 | NE2 | HIS | A | 379 | −8.278 | 84.678 | 60.751 | 1.00 | 17.07 | A | N |
| ATOM | 1970 | C | HIS | A | 379 | −8.818 | 87.695 | 64.595 | 1.00 | 22.89 | A | C |
| ATOM | 1971 | O | HIS | A | 379 | −8.211 | 87.802 | 65.659 | 1.00 | 24.73 | A | O |
| ATOM | 1972 | N | PRO | A | 380 | −9.948 | 86.978 | 64.489 | 1.00 | 22.77 | A | N |
| ATOM | 1973 | CD | PRO | A | 380 | −10.751 | 86.800 | 63.266 | 1.00 | 22.48 | A | C |
| ATOM | 1974 | CA | PRO | A | 380 | −10.544 | 86.247 | 65.614 | 1.00 | 22.16 | A | C |
| ATOM | 1975 | CB | PRO | A | 380 | −11.777 | 85.580 | 64.984 | 1.00 | 22.20 | A | C |
| ATOM | 1976 | CG | PRO | A | 380 | −11.422 | 85.482 | 63.529 | 1.00 | 24.64 | A | C |
| ATOM | 1977 | C | PRO | A | 380 | −9.633 | 85.256 | 66.351 | 1.00 | 21.00 | A | C |
| ATOM | 1978 | O | PRO | A | 380 | −9.762 | 85.078 | 67.563 | 1.00 | 19.68 | A | O |
| ATOM | 1979 | N | TRP | A | 381 | −8.722 | 84.613 | 65.627 | 1.00 | 19.43 | A | N |
| ATOM | 1980 | CA | TRP | A | 381 | −7.801 | 83.666 | 66.246 | 1.00 | 18.47 | A | C |
| ATOM | 1981 | CB | TRP | A | 381 | −7.098 | 82.827 | 65.172 | 1.00 | 17.30 | A | C |
| ATOM | 1982 | CG | TRP | A | 381 | −6.164 | 81.805 | 65.737 | 1.00 | 19.05 | A | C |
| ATOM | 1983 | CD2 | TRP | A | 381 | −4.733 | 81.895 | 65.800 | 1.00 | 18.83 | A | C |
| ATOM | 1984 | CE2 | TRP | A | 381 | −4.270 | 80.732 | 66.456 | 1.00 | 19.95 | A | C |
| ATOM | 1985 | CE3 | TRP | A | 381 | −3.800 | 82.846 | 65.366 | 1.00 | 19.48 | A | C |
| ATOM | 1986 | CD1 | TRP | A | 381 | −6.499 | 80.628 | 66.336 | 1.00 | 18.42 | A | C |
| ATOM | 1987 | NE1 | TRP | A | 381 | −5.368 | 79.975 | 66.771 | 1.00 | 18.35 | A | N |
| ATOM | 1988 | CZ2 | TRP | A | 381 | −2.907 | 80.493 | 66.690 | 1.00 | 18.02 | A | C |
| ATOM | 1989 | CZ3 | TRP | A | 381 | −2.440 | 82.609 | 65.597 | 1.00 | 19.48 | A | C |
| ATOM | 1990 | CH2 | TRP | A | 381 | −2.011 | 81.439 | 66.254 | 1.00 | 19.82 | A | C |
| ATOM | 1991 | C | TRP | A | 381 | −6.764 | 84.430 | 67.088 | 1.00 | 18.12 | A | C |
| ATOM | 1992 | O | TRP | A | 381 | −6.385 | 83.991 | 68.176 | 1.00 | 18.12 | A | O |
| ATOM | 1993 | N | ILE | A | 382 | −6.324 | 85.579 | 66.587 | 1.00 | 18.20 | A | N |
| ATOM | 1994 | CA | ILE | A | 382 | −5.347 | 86.410 | 67.296 | 1.00 | 19.68 | A | C |
| ATOM | 1995 | CB | ILE | A | 382 | −4.875 | 87.569 | 66.394 | 1.00 | 17.49 | A | C |
| ATOM | 1996 | CG2 | ILE | A | 382 | −4.118 | 88.599 | 67.213 | 1.00 | 20.81 | A | C |
| ATOM | 1997 | CG1 | ILE | A | 382 | −4.020 | 87.021 | 65.243 | 1.00 | 18.99 | A | C |
| ATOM | 1998 | CD1 | ILE | A | 382 | −2.653 | 86.493 | 65.655 | 1.00 | 19.59 | A | C |
| ATOM | 1999 | C | ILE | A | 382 | −5.932 | 86.997 | 68.592 | 1.00 | 22.60 | A | C |
| ATOM | 2000 | O | ILE | A | 382 | −5.271 | 87.019 | 69.642 | 1.00 | 21.36 | A | O |
| ATOM | 2001 | N | THR | A | 383 | −7.174 | 87.469 | 68.504 | 1.00 | 21.35 | A | N |
| ATOM | 2002 | CA | THR | A | 383 | −7.886 | 88.068 | 69.632 | 1.00 | 22.03 | A | C |
| ATOM | 2003 | CB | THR | A | 383 | −9.213 | 88.734 | 69.143 | 1.00 | 24.29 | A | C |
| ATOM | 2004 | OG1 | THR | A | 383 | −8.912 | 89.957 | 68.457 | 1.00 | 28.50 | A | O |
| ATOM | 2005 | CG2 | THR | A | 383 | −10.140 | 89.028 | 70.312 | 1.00 | 28.56 | A | C |
| ATOM | 2006 | C | THR | A | 383 | −8.225 | 87.040 | 70.713 | 1.00 | 21.21 | A | C |
| ATOM | 2007 | O | THR | A | 383 | −8.139 | 87.316 | 71.904 | 1.00 | 19.20 | A | O |
| ATOM | 2008 | N | ALA | A | 384 | −8.622 | 85.849 | 70.285 | 1.00 | 21.12 | A | N |
| ATOM | 2009 | CA | ALA | A | 384 | −8.986 | 84.788 | 71.217 | 1.00 | 19.34 | A | C |
| ATOM | 2010 | CB | ALA | A | 384 | −9.661 | 83.649 | 70.448 | 1.00 | 16.55 | A | C |
| ATOM | 2011 | C | ALA | A | 384 | −7.822 | 84.231 | 72.049 | 1.00 | 21.30 | A | C |
| ATOM | 2012 | O | ALA | A | 384 | −7.980 | 83.995 | 73.259 | 1.00 | 22.43 | A | O |
| ATOM | 2013 | N | ASN | A | 385 | −6.661 | 84.040 | 71.416 | 1.00 | 20.05 | A | N |
| ATOM | 2014 | CA | ASN | A | 385 | −5.503 | 83.449 | 72.091 | 1.00 | 22.78 | A | C |
| ATOM | 2015 | CB | ASN | A | 385 | −4.883 | 82.377 | 71.195 | 1.00 | 20.49 | A | C |
| ATOM | 2016 | CG | ASN | A | 385 | −5.871 | 81.286 | 70.817 | 1.00 | 21.65 | A | C |
| ATOM | 2017 | OD1 | ASN | A | 385 | −6.380 | 80.569 | 71.674 | 1.00 | 21.14 | A | O |
| ATOM | 2018 | ND2 | ASN | A | 385 | −6.148 | 81.160 | 69.525 | 1.00 | 19.14 | A | N |
| ATOM | 2019 | C | ASN | A | 385 | −4.385 | 84.356 | 72.593 | 1.00 | 25.16 | A | C |
| ATOM | 2020 | O | ASN | A | 385 | −3.472 | 83.883 | 73.267 | 1.00 | 27.83 | A | O |
| ATOM | 2021 | N | SER | A | 386 | −4.426 | 85.642 | 72.274 | 1.00 | 26.88 | A | N |
| ATOM | 2022 | CA | SER | A | 386 | −3.375 | 86.536 | 72.739 | 1.00 | 29.74 | A | C |
| ATOM | 2023 | CB | SER | A | 386 | −3.385 | 87.834 | 71.940 | 1.00 | 30.28 | A | C |

TABLE 2-continued coordinates for the two molecules in the asymmetric unit of [T287] Aurora
A (122–396) in complex with an inhibitor of formula II in space group P2$_1$

| ATOM | 2024 | OG | SER | A | 386 | −2.391 | 88.717 | 72.419 | 1.00 | 33.08 | A | O |
|---|---|---|---|---|---|---|---|---|---|---|---|---|
| ATOM | 2025 | C | SER | A | 386 | −3.559 | 86.851 | 74.218 | 1.00 | 32.93 | A | C |
| ATOM | 2026 | O | SER | A | 386 | −4.677 | 87.088 | 74.676 | 1.00 | 32.42 | A | O |
| ATOM | 2027 | N | SER | A | 387 | −2.461 | 86.844 | 74.967 | 1.00 | 34.64 | A | N |
| ATOM | 2028 | CA | SER | A | 387 | −2.524 | 87.144 | 76.393 | 1.00 | 37.99 | A | C |
| ATOM | 2029 | CB | SER | A | 387 | −1.376 | 86.454 | 77.141 | 1.00 | 38.92 | A | C |
| ATOM | 2030 | OG | SER | A | 387 | −0.112 | 86.876 | 76.662 | 1.00 | 37.92 | A | O |
| ATOM | 2031 | C | SER | A | 387 | −2.451 | 88.652 | 76.599 | 1.00 | 39.48 | A | C |
| ATOM | 2032 | O | SER | A | 387 | −2.459 | 89.135 | 77.728 | 1.00 | 40.65 | A | O |
| ATOM | 2033 | N | LYS | A | 388 | −2.387 | 89.383 | 75.489 | 1.00 | 41.58 | A | N |
| ATOM | 2034 | CA | LYS | A | 388 | −2.320 | 90.844 | 75.487 | 1.00 | 43.93 | A | C |
| ATOM | 2035 | CB | LYS | A | 388 | −3.340 | 91.441 | 76.466 | 1.00 | 43.62 | A | C |
| ATOM | 2036 | CG | LYS | A | 388 | −4.758 | 90.887 | 76.316 | 1.00 | 43.37 | A | C |
| ATOM | 2037 | CD | LYS | A | 388 | −5.787 | 91.767 | 77.016 | 1.00 | 43.10 | A | C |
| ATOM | 2038 | CE | LYS | A | 388 | −6.533 | 92.633 | 75.989 | 1.00 | 43.79 | A | C |
| ATOM | 2039 | NZ | LYS | A | 388 | −5.609 | 93.345 | 75.045 | 1.00 | 42.84 | A | N |
| ATOM | 2040 | C | LYS | A | 388 | −0.918 | 91.354 | 75.822 | 1.00 | 45.61 | A | C |
| ATOM | 2041 | O | LYS | A | 388 | −0.649 | 91.581 | 77.023 | 1.00 | 46.51 | A | O |
| ATOM | 2042 | OXT | LYS | A | 388 | −0.100 | 91.503 | 74.881 | 1.00 | 46.24 | A | O |
| TER | 2043 |  | LYS | A | 388 |  |  |  |  |  |  |  |
| ATOM | 2044 | CB | GLN | B | 126 | 10.213 | 7.246 | 17.228 | 1.00 | 52.35 | B | C |
| ATOM | 2045 | CG | GLN | B | 126 | 11.292 | 7.078 | 16.169 | 1.00 | 53.31 | B | C |
| ATOM | 2046 | CD | GLN | B | 126 | 12.534 | 6.382 | 16.706 | 1.00 | 54.51 | B | C |
| ATOM | 2047 | OE1 | GLN | B | 126 | 13.488 | 6.131 | 15.966 | 1.00 | 55.84 | B | O |
| ATOM | 2048 | NE2 | GLN | B | 126 | 12.526 | 6.065 | 17.999 | 1.00 | 53.41 | B | N |
| ATOM | 2049 | C | GLN | B | 126 | 8.987 | 9.170 | 16.193 | 1.00 | 50.24 | B | C |
| ATOM | 2050 | O | GLN | B | 126 | 8.930 | 9.438 | 14.994 | 1.00 | 50.75 | B | O |
| ATOM | 2051 | N | GLN | B | 126 | 8.388 | 6.816 | 15.605 | 1.00 | 51.32 | B | N |
| ATOM | 2052 | CA | GLN | B | 126 | 8.864 | 7.730 | 16.685 | 1.00 | 51.36 | B | C |
| ATOM | 2053 | N | TRP | B | 127 | 9.168 | 10.087 | 17.137 | 1.00 | 48.65 | B | N |
| ATOM | 2054 | CA | TRP | B | 127 | 9.279 | 11.516 | 16.855 | 1.00 | 45.05 | B | C |
| ATOM | 2055 | CB | TRP | B | 127 | 9.752 | 12.240 | 18.112 | 1.00 | 45.82 | B | C |
| ATOM | 2056 | CG | TRP | B | 127 | 8.716 | 12.256 | 19.197 | 1.00 | 48.91 | B | C |
| ATOM | 2057 | CD2 | TRP | B | 127 | 7.325 | 12.583 | 19.052 | 1.00 | 49.46 | B | C |
| ATOM | 2058 | CE2 | TRP | B | 127 | 6.741 | 12.502 | 20.336 | 1.00 | 50.15 | B | C |
| ATOM | 2059 | CE3 | TRP | B | 127 | 6.517 | 12.937 | 17.962 | 1.00 | 50.60 | B | C |
| ATOM | 2060 | CD1 | TRP | B | 127 | 8.911 | 11.997 | 20.523 | 1.00 | 49.18 | B | C |
| ATOM | 2061 | NE1 | TRP | B | 127 | 7.730 | 12.143 | 21.214 | 1.00 | 50.57 | B | N |
| ATOM | 2062 | CZ2 | TRP | B | 127 | 5.384 | 12.764 | 20.563 | 1.00 | 51.76 | B | C |
| ATOM | 2063 | CZ3 | TRP | B | 127 | 5.163 | 13.197 | 18.186 | 1.00 | 51.62 | B | C |
| ATOM | 2064 | CH2 | TRP | B | 127 | 4.613 | 13.108 | 19.479 | 1.00 | 51.32 | B | C |
| ATOM | 2065 | C | TRP | B | 127 | 10.131 | 11.952 | 15.671 | 1.00 | 42.62 | B | C |
| ATOM | 2066 | O | TRP | B | 127 | 11.322 | 11.660 | 15.593 | 1.00 | 42.25 | B | O |
| ATOM | 2067 | N | ALA | B | 128 | 9.488 | 12.664 | 14.749 | 1.00 | 39.75 | B | N |
| ATOM | 2068 | CA | ALA | B | 128 | 10.141 | 13.206 | 13.564 | 1.00 | 36.83 | B | C |
| ATOM | 2069 | CB | ALA | B | 128 | 9.858 | 12.342 | 12.342 | 1.00 | 37.27 | B | C |
| ATOM | 2070 | C | ALA | B | 128 | 9.533 | 14.584 | 13.386 | 1.00 | 33.84 | B | C |
| ATOM | 2071 | O | ALA | B | 128 | 8.469 | 14.862 | 13.929 | 1.00 | 33.46 | B | O |
| ATOM | 2072 | N | LEU | B | 129 | 10.201 | 15.443 | 12.630 | 1.00 | 32.37 | B | N |
| ATOM | 2073 | CA | LEU | B | 129 | 9.718 | 16.798 | 12.419 | 1.00 | 32.04 | B | C |
| ATOM | 2074 | CB | LEU | B | 129 | 10.708 | 17.570 | 11.548 | 1.00 | 31.51 | B | C |
| ATOM | 2075 | CG | LEU | B | 129 | 10.548 | 19.091 | 11.537 | 1.00 | 33.77 | B | C |
| ATOM | 2076 | CD1 | LEU | B | 129 | 10.560 | 19.625 | 12.968 | 1.00 | 33.40 | B | C |
| ATOM | 2077 | CD2 | LEU | B | 129 | 11.673 | 19.708 | 10.731 | 1.00 | 32.31 | B | C |
| ATOM | 2078 | C | LEU | B | 129 | 8.321 | 16.854 | 11.796 | 1.00 | 31.97 | B | C |
| ATOM | 2079 | O | LEU | B | 129 | 7.479 | 17.645 | 12.226 | 1.00 | 31.99 | B | O |
| ATOM | 2080 | N | ALA | B | 130 | 8.082 | 16.007 | 10.797 | 1.00 | 31.30 | B | N |
| ATOM | 2081 | CA | ALA | B | 130 | 6.803 | 15.951 | 10.091 | 1.00 | 31.88 | B | C |
| ATOM | 2082 | CB | ALA | B | 130 | 6.866 | 14.898 | 8.983 | 1.00 | 31.86 | B | C |
| ATOM | 2083 | C | ALA | B | 130 | 5.609 | 15.677 | 10.995 | 1.00 | 31.10 | B | C |
| ATOM | 2084 | O | ALA | B | 130 | 4.465 | 15.794 | 10.568 | 1.00 | 32.53 | B | O |
| ATOM | 2085 | N | ASP | B | 131 | 5.871 | 15.312 | 12.243 | 1.00 | 30.37 | B | N |
| ATOM | 2086 | CA | ASP | B | 131 | 4.800 | 15.038 | 13.193 | 1.00 | 30.59 | B | C |
| ATOM | 2087 | CB | ASP | B | 131 | 5.329 | 14.156 | 14.328 | 1.00 | 32.68 | B | C |
| ATOM | 2088 | CG | ASP | B | 131 | 5.607 | 12.727 | 13.884 | 1.00 | 36.29 | B | C |
| ATOM | 2089 | OD1 | ASP | B | 131 | 6.370 | 12.025 | 14.582 | 1.00 | 36.01 | B | O |
| ATOM | 2090 | OD2 | ASP | B | 131 | 5.053 | 12.302 | 12.847 | 1.00 | 36.71 | B | O |
| ATOM | 2091 | C | ASP | B | 131 | 4.197 | 16.309 | 13.796 | 1.00 | 29.73 | B | C |
| ATOM | 2092 | O | ASP | B | 131 | 3.185 | 16.242 | 14.492 | 1.00 | 30.13 | B | O |
| ATOM | 2093 | N | PHE | B | 132 | 4.800 | 17.462 | 13.512 | 1.00 | 28.26 | B | N |
| ATOM | 2094 | CA | PHE | B | 132 | 4.344 | 18.725 | 14.092 | 1.00 | 25.47 | B | C |
| ATOM | 2095 | CB | PHE | B | 132 | 5.417 | 19.272 | 15.039 | 1.00 | 25.53 | B | C |
| ATOM | 2096 | CG | PHE | B | 132 | 5.944 | 18.268 | 16.020 | 1.00 | 25.89 | B | C |
| ATOM | 2097 | CD1 | PHE | B | 132 | 5.301 | 18.056 | 17.234 | 1.00 | 27.37 | B | C |
| ATOM | 2098 | CD2 | PHE | B | 132 | 7.087 | 17.536 | 15.732 | 1.00 | 26.04 | B | C |
| ATOM | 2099 | CE1 | PHE | B | 132 | 5.791 | 17.130 | 18.144 | 1.00 | 28.04 | B | C |

TABLE 2-continued coordinates for the two molecules in the asymmetric unit of [T287] Aurora
A (122–396) in complex with an inhibitor of formula II in space group P2₁

| ATOM | 2100 | CE2 | PHE | B | 132 | 7.584 | 16.608 | 16.633 | 1.00 | 26.31 | B | C |
|---|---|---|---|---|---|---|---|---|---|---|---|---|
| ATOM | 2101 | CZ | PHE | B | 132 | 6.937 | 16.403 | 17.839 | 1.00 | 27.54 | B | C |
| ATOM | 2102 | C | PHE | B | 132 | 4.020 | 19.855 | 13.127 | 1.00 | 25.28 | B | C |
| ATOM | 2103 | O | PHE | B | 132 | 4.581 | 19.946 | 12.039 | 1.00 | 23.06 | B | O |
| ATOM | 2104 | N | GLU | B | 133 | 3.113 | 20.724 | 13.567 | 1.00 | 24.47 | B | N |
| ATOM | 2105 | CA | GLU | B | 133 | 2.751 | 21.929 | 12.835 | 1.00 | 24.02 | B | C |
| ATOM | 2106 | CB | GLU | B | 133 | 1.234 | 22.125 | 12.779 | 1.00 | 26.65 | B | C |
| ATOM | 2107 | CG | GLU | B | 133 | 0.586 | 21.444 | 11.597 | 1.00 | 32.34 | B | C |
| ATOM | 2108 | CD | GLU | B | 133 | −0.806 | 21.962 | 11.312 | 1.00 | 36.67 | B | C |
| ATOM | 2109 | OE1 | GLU | B | 133 | −1.355 | 21.615 | 10.245 | 1.00 | 38.29 | B | O |
| ATOM | 2110 | OE2 | GLU | B | 133 | −1.348 | 22.715 | 12.151 | 1.00 | 38.65 | B | O |
| ATOM | 2111 | C | GLU | B | 133 | 3.387 | 23.029 | 13.678 | 1.00 | 22.07 | B | C |
| ATOM | 2112 | O | GLU | B | 133 | 3.123 | 23.122 | 14.873 | 1.00 | 19.84 | B | O |
| ATOM | 2113 | N | ILE | B | 134 | 4.228 | 23.842 | 13.051 | 1.00 | 22.05 | B | N |
| ATOM | 2114 | CA | ILE | B | 134 | 4.957 | 24.924 | 13.718 | 1.00 | 20.74 | B | C |
| ATOM | 2115 | CB | ILE | B | 134 | 6.356 | 25.077 | 13.065 | 1.00 | 22.02 | B | C |
| ATOM | 2116 | CG2 | ILE | B | 134 | 7.127 | 26.232 | 13.692 | 1.00 | 19.99 | B | C |
| ATOM | 2117 | CG1 | ILE | B | 134 | 7.121 | 23.758 | 13.219 | 1.00 | 22.38 | B | C |
| ATOM | 2118 | CD1 | ILE | B | 134 | 8.451 | 23.728 | 12.488 | 1.00 | 26.58 | B | C |
| ATOM | 2119 | C | ILE | B | 134 | 4.226 | 26.259 | 13.661 | 1.00 | 20.52 | B | C |
| ATOM | 2120 | O | ILE | B | 134 | 3.688 | 26.621 | 12.618 | 1.00 | 21.50 | B | O |
| ATOM | 2121 | N | GLY | B | 135 | 4.222 | 26.989 | 14.778 | 1.00 | 19.55 | B | N |
| ATOM | 2122 | CA | GLY | B | 135 | 3.547 | 28.282 | 14.846 | 1.00 | 19.33 | B | C |
| ATOM | 2123 | C | GLY | B | 135 | 4.485 | 29.464 | 15.035 | 1.00 | 19.91 | B | C |
| ATOM | 2124 | O | GLY | B | 135 | 5.614 | 29.435 | 14.563 | 1.00 | 18.49 | B | O |
| ATOM | 2125 | N | ARG | B | 136 | 4.034 | 30.499 | 15.739 | 1.00 | 21.61 | B | N |
| ATOM | 2126 | CA | ARG | B | 136 | 4.857 | 31.695 | 15.970 | 1.00 | 23.20 | B | C |
| ATOM | 2127 | CB | ARG | B | 136 | 4.014 | 32.824 | 16.570 | 1.00 | 24.31 | B | C |
| ATOM | 2128 | CG | ARG | B | 136 | 3.656 | 32.619 | 18.042 | 1.00 | 27.58 | B | C |
| ATOM | 2129 | CD | ARG | B | 136 | 2.652 | 33.652 | 18.548 | 1.00 | 28.19 | B | C |
| ATOM | 2130 | NE | ARG | B | 136 | 2.162 | 33.295 | 19.877 | 1.00 | 29.58 | B | N |
| ATOM | 2131 | CZ | ARG | B | 136 | 2.671 | 33.747 | 21.023 | 1.00 | 30.89 | B | C |
| ATOM | 2132 | NH1 | ARG | B | 136 | 3.692 | 34.598 | 21.016 | 1.00 | 28.09 | B | N |
| ATOM | 2133 | NH2 | ARG | B | 136 | 2.167 | 33.326 | 22.182 | 1.00 | 29.68 | B | N |
| ATOM | 2134 | C | ARG | B | 136 | 6.049 | 31.460 | 16.895 | 1.00 | 22.61 | B | C |
| ATOM | 2135 | O | ARG | B | 136 | 6.019 | 30.597 | 17.762 | 1.00 | 22.20 | B | O |
| ATOM | 2136 | N | PRO | B | 137 | 7.126 | 32.231 | 16.709 | 1.00 | 24.01 | B | N |
| ATOM | 2137 | CD | PRO | B | 137 | 7.425 | 33.170 | 15.611 | 1.00 | 24.72 | B | C |
| ATOM | 2138 | CA | PRO | B | 137 | 8.287 | 32.047 | 17.581 | 1.00 | 23.55 | B | C |
| ATOM | 2139 | CB | PRO | B | 137 | 9.393 | 32.798 | 16.840 | 1.00 | 26.09 | B | C |
| ATOM | 2140 | CG | PRO | B | 137 | 8.637 | 33.905 | 16.144 | 1.00 | 26.11 | B | C |
| ATOM | 2141 | C | PRO | B | 137 | 7.976 | 32.627 | 18.965 | 1.00 | 23.34 | B | C |
| ATOM | 2142 | O | PRO | B | 137 | 7.350 | 33.682 | 19.088 | 1.00 | 22.43 | B | O |
| ATOM | 2143 | N | LEU | B | 138 | 8.390 | 31.909 | 20.000 | 1.00 | 22.77 | B | N |
| ATOM | 2144 | CA | LEU | B | 138 | 8.153 | 32.316 | 21.383 | 1.00 | 25.08 | B | C |
| ATOM | 2145 | CB | LEU | B | 138 | 7.909 | 31.077 | 22.247 | 1.00 | 23.93 | B | C |
| ATOM | 2146 | CG | LEU | B | 138 | 6.501 | 30.564 | 22.574 | 1.00 | 25.09 | B | C |
| ATOM | 2147 | CD1 | LEU | B | 138 | 5.475 | 30.991 | 21.532 | 1.00 | 21.71 | B | C |
| ATOM | 2148 | CD2 | LEU | B | 138 | 6.575 | 29.054 | 22.715 | 1.00 | 22.09 | B | C |
| ATOM | 2149 | C | LEU | B | 138 | 9.361 | 33.076 | 21.908 | 1.00 | 27.37 | B | C |
| ATOM | 2150 | O | LEU | B | 138 | 9.253 | 33.860 | 22.842 | 1.00 | 29.02 | B | O |
| ATOM | 2151 | N | GLY | B | 139 | 10.511 | 32.831 | 21.292 | 1.00 | 30.52 | B | N |
| ATOM | 2152 | CA | GLY | B | 139 | 11.736 | 33.487 | 21.701 | 1.00 | 33.40 | B | C |
| ATOM | 2153 | C | GLY | B | 139 | 12.887 | 33.087 | 20.796 | 1.00 | 36.61 | B | C |
| ATOM | 2154 | O | GLY | B | 139 | 12.829 | 32.049 | 20.125 | 1.00 | 34.75 | B | O |
| ATOM | 2155 | N | ALA | B | 140 | 13.931 | 33.917 | 20.775 | 1.00 | 38.80 | B | N |
| ATOM | 2156 | CA | ALA | B | 140 | 15.111 | 33.669 | 19.952 | 1.00 | 41.45 | B | C |
| ATOM | 2157 | CB | ALA | B | 140 | 15.197 | 34.703 | 18.839 | 1.00 | 41.02 | B | C |
| ATOM | 2158 | C | ALA | B | 140 | 16.348 | 33.742 | 20.833 | 1.00 | 42.68 | B | C |
| ATOM | 2159 | O | ALA | B | 140 | 16.614 | 34.774 | 21.443 | 1.00 | 44.14 | B | O |
| ATOM | 2160 | N | ALA | B | 141 | 17.091 | 32.640 | 20.905 | 1.00 | 43.65 | B | N |
| ATOM | 2161 | CA | ALA | B | 141 | 18.295 | 32.567 | 21.728 | 1.00 | 43.81 | B | C |
| ATOM | 2162 | CB | ALA | B | 141 | 18.233 | 31.342 | 22.638 | 1.00 | 45.73 | B | C |
| ATOM | 2163 | C | ALA | B | 141 | 19.553 | 32.515 | 20.872 | 1.00 | 43.24 | B | C |
| ATOM | 2164 | O | ALA | B | 141 | 19.501 | 32.748 | 19.669 | 1.00 | 41.60 | B | O |
| ATOM | 2165 | N | ALA | B | 142 | 20.682 | 32.203 | 21.502 | 1.00 | 43.17 | B | N |
| ATOM | 2166 | CA | ALA | B | 142 | 21.956 | 32.136 | 20.794 | 1.00 | 43.89 | B | C |
| ATOM | 2167 | CB | ALA | B | 142 | 23.107 | 32.336 | 21.774 | 1.00 | 43.83 | B | C |
| ATOM | 2168 | C | ALA | B | 142 | 22.146 | 30.826 | 20.032 | 1.00 | 44.12 | B | C |
| ATOM | 2169 | O | ALA | B | 142 | 22.701 | 30.817 | 18.932 | 1.00 | 45.04 | B | O |
| ATOM | 2170 | N | PHE | B | 143 | 21.682 | 29.723 | 20.612 | 1.00 | 43.15 | B | N |
| ATOM | 2171 | CA | PHE | B | 143 | 21.829 | 28.421 | 19.973 | 1.00 | 41.85 | B | C |
| ATOM | 2172 | CB | PHE | B | 143 | 22.102 | 27.350 | 21.025 | 1.00 | 43.72 | B | C |
| ATOM | 2173 | CG | PHE | B | 143 | 23.254 | 27.671 | 21.931 | 1.00 | 47.41 | B | C |
| ATOM | 2174 | CD1 | PHE | B | 143 | 23.098 | 28.563 | 22.986 | 1.00 | 48.28 | B | C |
| ATOM | 2175 | CD2 | PHE | B | 143 | 24.496 | 27.079 | 21.733 | 1.00 | 47.70 | B | C |

TABLE 2-continued coordinates for the two molecules in the asymmetric unit of [T287] Aurora A (122–396) in complex with an inhibitor of formula II in space group P2$_1$

| ATOM | 2176 | CE1 | PHE | B | 143 | 24.162 | 28.858 | 23.832 | 1.00 | 49.52 | B | C |
|------|------|-----|-----|---|-----|--------|--------|--------|------|-------|---|---|
| ATOM | 2177 | CE2 | PHE | B | 143 | 25.564 | 27.368 | 22.572 | 1.00 | 48.56 | B | C |
| ATOM | 2178 | CZ | PHE | B | 143 | 25.398 | 28.259 | 23.624 | 1.00 | 48.11 | B | C |
| ATOM | 2179 | C | PHE | B | 143 | 20.625 | 28.002 | 19.127 | 1.00 | 39.85 | B | C |
| ATOM | 2180 | O | PHE | B | 143 | 20.673 | 26.972 | 18.453 | 1.00 | 37.97 | B | O |
| ATOM | 2181 | N | GLY | B | 144 | 19.554 | 28.792 | 19.164 | 1.00 | 37.20 | B | N |
| ATOM | 2182 | CA | GLY | B | 144 | 18.374 | 28.461 | 18.386 | 1.00 | 35.94 | B | C |
| ATOM | 2183 | C | GLY | B | 144 | 17.111 | 29.160 | 18.851 | 1.00 | 35.06 | B | C |
| ATOM | 2184 | O | GLY | B | 144 | 17.172 | 30.161 | 19.565 | 1.00 | 34.22 | B | O |
| ATOM | 2185 | N | ASN | B | 145 | 15.959 | 28.628 | 18.449 | 1.00 | 33.13 | B | N |
| ATOM | 2186 | CA | ASN | B | 145 | 14.682 | 29.228 | 18.826 | 1.00 | 31.01 | B | C |
| ATOM | 2187 | CB | ASN | B | 145 | 14.082 | 29.980 | 17.639 | 1.00 | 33.45 | B | C |
| ATOM | 2188 | CG | ASN | B | 145 | 15.124 | 30.694 | 16.824 | 1.00 | 36.83 | B | C |
| ATOM | 2189 | OD1 | ASN | B | 145 | 15.849 | 30.072 | 16.051 | 1.00 | 39.85 | B | O |
| ATOM | 2190 | ND2 | ASN | B | 145 | 15.220 | 32.010 | 16.999 | 1.00 | 39.53 | B | N |
| ATOM | 2191 | C | ASN | B | 145 | 13.654 | 28.225 | 19.318 | 1.00 | 27.19 | B | C |
| ATOM | 2192 | O | ASN | B | 145 | 13.751 | 27.026 | 19.053 | 1.00 | 26.12 | B | O |
| ATOM | 2193 | N | VAL | B | 146 | 12.663 | 28.745 | 20.030 | 1.00 | 23.46 | B | N |
| ATOM | 2194 | CA | VAL | B | 146 | 11.568 | 27.951 | 20.568 | 1.00 | 21.53 | B | C |
| ATOM | 2195 | CB | VAL | B | 146 | 11.382 | 28.182 | 22.086 | 1.00 | 21.61 | B | C |
| ATOM | 2196 | CG1 | VAL | B | 146 | 10.329 | 27.242 | 22.623 | 1.00 | 22.87 | B | C |
| ATOM | 2197 | CG2 | VAL | B | 146 | 12.688 | 27.990 | 22.807 | 1.00 | 26.97 | B | C |
| ATOM | 2198 | C | VAL | B | 146 | 10.307 | 28.447 | 19.865 | 1.00 | 20.89 | B | C |
| ATOM | 2199 | O | VAL | B | 146 | 10.087 | 29.657 | 19.774 | 1.00 | 18.61 | B | O |
| ATOM | 2200 | N | TYR | B | 147 | 9.489 | 27.518 | 19.379 | 1.00 | 18.85 | B | N |
| ATOM | 2201 | CA | TYR | B | 147 | 8.254 | 27.866 | 18.688 | 1.00 | 18.39 | B | C |
| ATOM | 2202 | CB | TYR | B | 147 | 8.273 | 27.362 | 17.239 | 1.00 | 17.65 | B | C |
| ATOM | 2203 | CG | TYR | B | 147 | 9.420 | 27.846 | 16.400 | 1.00 | 17.80 | B | C |
| ATOM | 2204 | CD1 | TYR | B | 147 | 10.654 | 27.186 | 16.409 | 1.00 | 19.71 | B | C |
| ATOM | 2205 | CE1 | TYR | B | 147 | 11.726 | 27.653 | 15.629 | 1.00 | 20.17 | B | C |
| ATOM | 2206 | CD2 | TYR | B | 147 | 9.281 | 28.976 | 15.598 | 1.00 | 17.79 | B | C |
| ATOM | 2207 | CE2 | TYR | B | 147 | 10.336 | 29.447 | 14.823 | 1.00 | 16.88 | B | C |
| ATOM | 2208 | CZ | TYR | B | 147 | 11.550 | 28.791 | 14.840 | 1.00 | 17.99 | B | C |
| ATOM | 2209 | OH | TYR | B | 147 | 12.582 | 29.292 | 14.078 | 1.00 | 21.66 | B | O |
| ATOM | 2210 | C | TYR | B | 147 | 7.050 | 27.218 | 19.349 | 1.00 | 17.88 | B | C |
| ATOM | 2211 | O | TYR | B | 147 | 7.180 | 26.186 | 20.000 | 1.00 | 17.17 | B | O |
| ATOM | 2212 | N | LEU | B | 148 | 5.880 | 27.829 | 19.188 | 1.00 | 17.80 | B | N |
| ATOM | 2213 | CA | LEU | B | 148 | 4.661 | 27.208 | 19.688 | 1.00 | 18.36 | B | C |
| ATOM | 2214 | CB | LEU | B | 148 | 3.478 | 28.172 | 19.616 | 1.00 | 22.50 | B | C |
| ATOM | 2215 | CG | LEU | B | 148 | 2.102 | 27.595 | 19.990 | 1.00 | 23.22 | B | C |
| ATOM | 2216 | CD1 | LEU | B | 148 | 2.017 | 27.353 | 21.494 | 1.00 | 24.62 | B | C |
| ATOM | 2217 | CD2 | LEU | B | 148 | 1.016 | 28.563 | 19.559 | 1.00 | 25.28 | B | C |
| ATOM | 2218 | C | LEU | B | 148 | 4.475 | 26.107 | 18.641 | 1.00 | 19.19 | B | C |
| ATOM | 2219 | O | LEU | B | 148 | 4.849 | 26.289 | 17.476 | 1.00 | 18.41 | B | O |
| ATOM | 2220 | N | ALA | B | 149 | 3.941 | 24.959 | 19.034 | 1.00 | 18.74 | B | N |
| ATOM | 2221 | CA | ALA | B | 149 | 3.734 | 23.900 | 18.063 | 1.00 | 21.02 | B | C |
| ATOM | 2222 | CB | ALA | B | 149 | 5.005 | 23.057 | 17.907 | 1.00 | 22.54 | B | C |
| ATOM | 2223 | C | ALA | B | 149 | 2.560 | 23.018 | 18.429 | 1.00 | 22.53 | B | C |
| ATOM | 2224 | O | ALA | B | 149 | 2.109 | 23.002 | 19.573 | 1.00 | 22.04 | B | O |
| ATOM | 2225 | N | ARG | B | 150 | 2.060 | 22.286 | 17.444 | 1.00 | 23.48 | B | N |
| ATOM | 2226 | CA | ARG | B | 150 | 0.932 | 21.402 | 17.667 | 1.00 | 26.45 | B | C |
| ATOM | 2227 | CB | ARG | B | 150 | −0.349 | 22.081 | 17.176 | 1.00 | 27.56 | B | C |
| ATOM | 2228 | CG | ARG | B | 150 | −1.626 | 21.299 | 17.419 | 1.00 | 31.39 | B | C |
| ATOM | 2229 | CD | ARG | B | 150 | −2.817 | 22.249 | 17.534 | 1.00 | 33.89 | B | C |
| ATOM | 2230 | NE | ARG | B | 150 | −2.772 | 23.313 | 16.534 | 1.00 | 37.25 | B | N |
| ATOM | 2231 | CZ | ARG | B | 150 | −3.463 | 24.447 | 16.616 | 1.00 | 38.06 | B | C |
| ATOM | 2232 | NH1 | ARG | B | 150 | −4.258 | 24.669 | 17.655 | 1.00 | 39.33 | B | N |
| ATOM | 2233 | NH2 | ARG | B | 150 | −3.350 | 25.367 | 15.664 | 1.00 | 37.88 | B | N |
| ATOM | 2234 | C | ARG | B | 150 | 1.157 | 20.075 | 16.957 | 1.00 | 27.39 | B | C |
| ATOM | 2235 | O | ARG | B | 150 | 1.540 | 20.044 | 15.785 | 1.00 | 26.15 | B | O |
| ATOM | 2236 | N | GLU | B | 151 | 0.953 | 18.978 | 17.680 | 1.00 | 28.95 | B | N |
| ATOM | 2237 | CA | GLU | B | 151 | 1.130 | 17.657 | 17.092 | 1.00 | 33.02 | B | C |
| ATOM | 2238 | CB | GLU | B | 151 | 1.153 | 16.597 | 18.186 | 1.00 | 34.21 | B | C |
| ATOM | 2239 | CG | GLU | B | 151 | 1.901 | 15.344 | 17.795 | 1.00 | 39.51 | B | C |
| ATOM | 2240 | CD | GLU | B | 151 | 1.687 | 14.213 | 18.781 | 1.00 | 43.41 | B | C |
| ATOM | 2241 | OE1 | GLU | B | 151 | 1.948 | 14.412 | 19.991 | 1.00 | 44.45 | B | O |
| ATOM | 2242 | OE2 | GLU | B | 151 | 1.257 | 13.122 | 18.342 | 1.00 | 46.66 | B | O |
| ATOM | 2243 | C | GLU | B | 151 | −0.031 | 17.402 | 16.123 | 1.00 | 33.90 | B | C |
| ATOM | 2244 | O | GLU | B | 151 | −1.187 | 17.611 | 16.470 | 1.00 | 31.69 | B | O |
| ATOM | 2245 | N | LYS | B | 152 | 0.281 | 16.958 | 14.911 | 1.00 | 36.17 | B | N |
| ATOM | 2246 | CA | LYS | B | 152 | −0.747 | 16.718 | 13.901 | 1.00 | 39.16 | B | C |
| ATOM | 2247 | CB | LYS | B | 152 | −0.103 | 16.292 | 12.579 | 1.00 | 38.11 | B | C |
| ATOM | 2248 | CG | LYS | B | 152 | 0.598 | 17.422 | 11.855 | 1.00 | 37.99 | B | C |
| ATOM | 2249 | CD | LYS | B | 152 | 1.208 | 16.952 | 10.554 | 1.00 | 39.08 | B | C |
| ATOM | 2250 | CE | LYS | B | 152 | 1.924 | 18.091 | 9.855 | 1.00 | 40.02 | B | C |
| ATOM | 2251 | NZ | LYS | B | 152 | 2.654 | 17.635 | 8.642 | 1.00 | 41.02 | B | N |

TABLE 2-continued coordinates for the two molecules in the asymmetric unit of [T287] Aurora
A (122–396) in complex with an inhibitor of formula II in space group P2$_1$

| ATOM | 2252 | C   | LYS | B | 152 | −1.845 | 15.725 | 14.270 | 1.00 | 41.64 | B | C |
|------|------|-----|-----|---|-----|--------|--------|--------|------|-------|---|---|
| ATOM | 2253 | O   | LYS | B | 152 | −3.033 | 16.047 | 14.171 | 1.00 | 41.11 | B | O |
| ATOM | 2254 | N   | GLN | B | 153 | −1.459 | 14.523 | 14.688 | 1.00 | 44.21 | B | N |
| ATOM | 2255 | CA  | GLN | B | 153 | −2.445 | 13.505 | 15.040 | 1.00 | 46.53 | B | C |
| ATOM | 2256 | CB  | GLN | B | 153 | −1.756 | 12.244 | 15.553 | 1.00 | 48.92 | B | C |
| ATOM | 2257 | CG  | GLN | B | 153 | −2.672 | 11.035 | 15.561 | 1.00 | 53.13 | B | C |
| ATOM | 2258 | CD  | GLN | B | 153 | −3.378 | 10.842 | 14.226 | 1.00 | 55.60 | B | C |
| ATOM | 2259 | OE1 | GLN | B | 153 | −2.735 | 10.731 | 13.177 | 1.00 | 56.44 | B | O |
| ATOM | 2260 | NE2 | GLN | B | 153 | −4.708 | 10.807 | 14.260 | 1.00 | 55.73 | B | N |
| ATOM | 2261 | C   | GLN | B | 153 | −3.427 | 14.022 | 16.082 | 1.00 | 46.20 | B | C |
| ATOM | 2262 | O   | GLN | B | 153 | −4.626 | 14.116 | 15.825 | 1.00 | 47.04 | B | O |
| ATOM | 2263 | N   | SER | B | 154 | −2.926 | 14.344 | 17.265 | 1.00 | 46.37 | B | N |
| ATOM | 2264 | CA  | SER | B | 154 | −3.791 | 14.879 | 18.305 | 1.00 | 46.19 | B | C |
| ATOM | 2265 | CB  | SER | B | 154 | −3.206 | 14.591 | 19.690 | 1.00 | 45.90 | B | C |
| ATOM | 2266 | OG  | SER | B | 154 | −1.871 | 15.057 | 19.798 | 1.00 | 45.56 | B | O |
| ATOM | 2267 | C   | SER | B | 154 | −3.847 | 16.379 | 18.046 | 1.00 | 46.16 | B | C |
| ATOM | 2268 | O   | SER | B | 154 | −3.415 | 16.846 | 16.995 | 1.00 | 47.31 | B | O |
| ATOM | 2269 | N   | LYS | B | 155 | −4.387 | 17.139 | 18.981 | 1.00 | 45.67 | B | N |
| ATOM | 2270 | CA  | LYS | B | 155 | −4.450 | 18.582 | 18.806 | 1.00 | 45.70 | B | C |
| ATOM | 2271 | CB  | LYS | B | 155 | −5.916 | 19.031 | 18.799 | 1.00 | 48.89 | B | C |
| ATOM | 2272 | CG  | LYS | B | 155 | −6.128 | 20.540 | 18.761 | 1.00 | 52.40 | B | C |
| ATOM | 2273 | CD  | LYS | B | 155 | −6.349 | 21.108 | 20.159 | 1.00 | 53.23 | B | C |
| ATOM | 2274 | CE  | LYS | B | 155 | −6.084 | 22.601 | 20.182 | 1.00 | 54.16 | B | C |
| ATOM | 2275 | NZ  | LYS | B | 155 | −4.697 | 22.904 | 19.726 | 1.00 | 53.54 | B | N |
| ATOM | 2276 | C   | LYS | B | 155 | −3.677 | 19.222 | 19.959 | 1.00 | 42.90 | B | C |
| ATOM | 2277 | O   | LYS | B | 155 | −3.770 | 20.423 | 20.207 | 1.00 | 43.52 | B | O |
| ATOM | 2278 | N   | PHE | B | 156 | −2.892 | 18.397 | 20.644 | 1.00 | 39.07 | B | N |
| ATOM | 2279 | CA  | PHE | B | 156 | −2.108 | 18.824 | 21.796 | 1.00 | 35.93 | B | C |
| ATOM | 2280 | CB  | PHE | B | 156 | −1.375 | 17.615 | 22.377 | 1.00 | 37.42 | B | C |
| ATOM | 2281 | CG  | PHE | B | 156 | −0.841 | 17.834 | 23.761 | 1.00 | 39.54 | B | C |
| ATOM | 2282 | CD1 | PHE | B | 156 | −1.699 | 18.157 | 24.806 | 1.00 | 39.40 | B | C |
| ATOM | 2283 | CD2 | PHE | B | 156 | 0.521  | 17.705 | 24.024 | 1.00 | 40.10 | B | C |
| ATOM | 2284 | CE1 | PHE | B | 156 | −1.209 | 18.351 | 26.099 | 1.00 | 40.25 | B | C |
| ATOM | 2285 | CE2 | PHE | B | 156 | 1.024  | 17.897 | 25.316 | 1.00 | 40.40 | B | C |
| ATOM | 2286 | CZ  | PHE | B | 156 | 0.156  | 18.220 | 26.354 | 1.00 | 40.47 | B | C |
| ATOM | 2287 | C   | PHE | B | 156 | −1.111 | 19.943 | 21.487 | 1.00 | 32.41 | B | C |
| ATOM | 2288 | O   | PHE | B | 156 | −0.328 | 19.846 | 20.544 | 1.00 | 31.99 | B | O |
| ATOM | 2289 | N   | ILE | B | 157 | −1.153 | 20.999 | 22.294 | 1.00 | 28.30 | B | N |
| ATOM | 2290 | CA  | ILE | B | 157 | −0.270 | 22.153 | 22.146 | 1.00 | 27.01 | B | C |
| ATOM | 2291 | CB  | ILE | B | 157 | −0.933 | 23.445 | 22.684 | 1.00 | 28.09 | B | C |
| ATOM | 2292 | CG2 | ILE | B | 157 | 0.042  | 24.608 | 22.590 | 1.00 | 29.72 | B | C |
| ATOM | 2293 | CG1 | ILE | B | 157 | −2.212 | 23.754 | 21.899 | 1.00 | 29.62 | B | C |
| ATOM | 2294 | CD1 | ILE | B | 157 | −1.977 | 24.215 | 20.480 | 1.00 | 32.78 | B | C |
| ATOM | 2295 | C   | ILE | B | 157 | 1.016  | 21.934 | 22.936 | 1.00 | 24.58 | B | C |
| ATOM | 2296 | O   | ILE | B | 157 | 0.990  | 21.436 | 24.060 | 1.00 | 23.83 | B | O |
| ATOM | 2297 | N   | LEU | B | 158 | 2.141  | 22.320 | 22.353 | 1.00 | 23.27 | B | N |
| ATOM | 2298 | CA  | LEU | B | 158 | 3.426  | 22.158 | 23.020 | 1.00 | 22.00 | B | C |
| ATOM | 2299 | CB  | LEU | B | 158 | 3.933  | 20.721 | 22.832 | 1.00 | 22.79 | B | C |
| ATOM | 2300 | CG  | LEU | B | 158 | 3.978  | 20.154 | 21.407 | 1.00 | 26.19 | B | C |
| ATOM | 2301 | CD1 | LEU | B | 158 | 5.220  | 20.663 | 20.676 | 1.00 | 25.77 | B | C |
| ATOM | 2302 | CD2 | LEU | B | 158 | 3.991  | 18.632 | 21.463 | 1.00 | 24.53 | B | C |
| ATOM | 2303 | C   | LEU | B | 158 | 4.438  | 23.165 | 22.491 | 1.00 | 20.27 | B | C |
| ATOM | 2304 | O   | LEU | B | 158 | 4.118  | 24.000 | 21.648 | 1.00 | 19.23 | B | O |
| ATOM | 2305 | N   | ALA | B | 159 | 5.660  | 23.106 | 23.005 | 1.00 | 18.97 | B | N |
| ATOM | 2306 | CA  | ALA | B | 159 | 6.695  | 24.016 | 22.552 | 1.00 | 16.46 | B | C |
| ATOM | 2307 | CB  | ALA | B | 159 | 7.183  | 24.864 | 23.705 | 1.00 | 13.97 | B | C |
| ATOM | 2308 | C   | ALA | B | 159 | 7.826  | 23.189 | 21.967 | 1.00 | 16.51 | B | C |
| ATOM | 2309 | O   | ALA | B | 159 | 8.214  | 22.169 | 22.536 | 1.00 | 16.62 | B | O |
| ATOM | 2310 | N   | LEU | B | 160 | 8.330  | 23.614 | 20.813 | 1.00 | 16.01 | B | N |
| ATOM | 2311 | CA  | LEU | B | 160 | 9.419  | 22.914 | 20.143 | 1.00 | 17.40 | B | C |
| ATOM | 2312 | CB  | LEU | B | 160 | 9.002  | 22.524 | 18.712 | 1.00 | 19.02 | B | C |
| ATOM | 2313 | CG  | LEU | B | 160 | 10.016 | 21.678 | 17.928 | 1.00 | 20.39 | B | C |
| ATOM | 2314 | CD1 | LEU | B | 160 | 10.062 | 20.269 | 18.520 | 1.00 | 21.64 | B | C |
| ATOM | 2315 | CD2 | LEU | B | 160 | 9.628  | 21.606 | 16.459 | 1.00 | 21.97 | B | C |
| ATOM | 2316 | C   | LEU | B | 160 | 10.648 | 23.821 | 20.092 | 1.00 | 16.96 | B | C |
| ATOM | 2317 | O   | LEU | B | 160 | 10.582 | 24.930 | 19.581 | 1.00 | 17.75 | B | O |
| ATOM | 2318 | N   | LYS | B | 161 | 11.766 | 23.351 | 20.629 | 1.00 | 18.51 | B | N |
| ATOM | 2319 | CA  | LYS | B | 161 | 13.002 | 24.136 | 20.624 | 1.00 | 19.34 | B | C |
| ATOM | 2320 | CB  | LYS | B | 161 | 13.612 | 24.188 | 22.039 | 1.00 | 19.45 | B | C |
| ATOM | 2321 | CG  | LYS | B | 161 | 14.832 | 25.113 | 22.166 | 1.00 | 20.17 | B | C |
| ATOM | 2322 | CD  | LYS | B | 161 | 15.129 | 25.442 | 23.625 | 1.00 | 20.81 | B | C |
| ATOM | 2323 | CE  | LYS | B | 161 | 16.291 | 26.407 | 23.767 | 1.00 | 22.49 | B | C |
| ATOM | 2324 | NZ  | LYS | B | 161 | 16.427 | 26.941 | 25.152 | 1.00 | 23.30 | B | N |
| ATOM | 2325 | C   | LYS | B | 161 | 13.987 | 23.520 | 19.637 | 1.00 | 19.59 | B | C |
| ATOM | 2326 | O   | LYS | B | 161 | 14.296 | 22.329 | 19.708 | 1.00 | 20.16 | B | O |
| ATOM | 2327 | N   | VAL | B | 162 | 14.471 | 24.336 | 18.709 | 1.00 | 19.67 | B | N |

TABLE 2-continued coordinates for the two molecules in the asymmetric unit of [T287] Aurora A (122–396) in complex with an inhibitor of formula II in space group P2$_1$

| ATOM | 2328 | CA  | VAL | B | 162 | 15.402 | 23.867 | 17.688 | 1.00 | 21.10 | B | C |
|------|------|-----|-----|---|-----|--------|--------|--------|------|-------|---|---|
| ATOM | 2329 | CB  | VAL | B | 162 | 14.945 | 24.292 | 16.276 | 1.00 | 22.26 | B | C |
| ATOM | 2330 | CG1 | VAL | B | 162 | 15.832 | 23.623 | 15.235 | 1.00 | 24.01 | B | C |
| ATOM | 2331 | CG2 | VAL | B | 162 | 13.465 | 23.934 | 16.058 | 1.00 | 22.27 | B | C |
| ATOM | 2332 | C   | VAL | B | 162 | 16.800 | 24.430 | 17.908 | 1.00 | 21.17 | B | C |
| ATOM | 2333 | O   | VAL | B | 162 | 16.993 | 25.642 | 17.848 | 1.00 | 19.86 | B | O |
| ATOM | 2334 | N   | LEU | B | 163 | 17.768 | 23.544 | 18.133 | 1.00 | 21.64 | B | N |
| ATOM | 2335 | CA  | LEU | B | 163 | 19.157 | 23.950 | 18.369 | 1.00 | 20.49 | B | C |
| ATOM | 2336 | CB  | LEU | B | 163 | 19.651 | 23.326 | 19.670 | 1.00 | 20.44 | B | C |
| ATOM | 2337 | CG  | LEU | B | 163 | 18.813 | 23.620 | 20.912 | 1.00 | 22.02 | B | C |
| ATOM | 2338 | CD1 | LEU | B | 163 | 19.087 | 22.573 | 21.978 | 1.00 | 22.74 | B | C |
| ATOM | 2339 | CD2 | LEU | B | 163 | 19.121 | 25.026 | 21.417 | 1.00 | 22.92 | B | C |
| ATOM | 2340 | C   | LEU | B | 163 | 20.094 | 23.542 | 17.234 | 1.00 | 21.79 | B | C |
| ATOM | 2341 | O   | LEU | B | 163 | 19.998 | 22.422 | 16.707 | 1.00 | 22.08 | B | O |
| ATOM | 2342 | N   | PHE | B | 164 | 21.008 | 24.441 | 16.861 | 1.00 | 22.17 | B | N |
| ATOM | 2343 | CA  | PHE | B | 164 | 21.968 | 24.157 | 15.795 | 1.00 | 22.32 | B | C |
| ATOM | 2344 | CB  | PHE | B | 164 | 22.261 | 25.419 | 14.985 | 1.00 | 23.92 | B | C |
| ATOM | 2345 | CG  | PHE | B | 164 | 21.063 | 25.946 | 14.256 | 1.00 | 30.95 | B | C |
| ATOM | 2346 | CD1 | PHE | B | 164 | 20.081 | 26.667 | 14.934 | 1.00 | 30.56 | B | C |
| ATOM | 2347 | GD2 | PHE | B | 164 | 20.880 | 25.668 | 12.903 | 1.00 | 31.82 | B | C |
| ATOM | 2348 | CE1 | PHE | B | 164 | 18.935 | 27.099 | 14.281 | 1.00 | 32.58 | B | C |
| ATOM | 2349 | CE2 | PHE | B | 164 | 19.733 | 26.096 | 12.238 | 1.00 | 34.84 | B | C |
| ATOM | 2350 | CZ  | PHE | B | 164 | 18.758 | 26.813 | 12.930 | 1.00 | 34.24 | B | C |
| ATOM | 2351 | C   | PHE | B | 164 | 23.251 | 23.598 | 16.382 | 1.00 | 22.61 | B | C |
| ATOM | 2352 | O   | PHE | B | 164 | 23.925 | 24.261 | 17.176 | 1.00 | 22.86 | B | O |
| ATOM | 2353 | N   | LYS | B | 165 | 23.582 | 22.371 | 15.994 | 1.00 | 22.67 | B | N |
| ATOM | 2354 | CA  | LYS | B | 165 | 24.777 | 21.711 | 16.511 | 1.00 | 22.73 | B | C |
| ATOM | 2355 | CB  | LYS | B | 165 | 24.982 | 20.360 | 15.827 | 1.00 | 21.42 | B | C |
| ATOM | 2356 | CG  | LYS | B | 165 | 24.153 | 19.240 | 16.419 | 1.00 | 21.02 | B | C |
| ATOM | 2357 | CD  | LYS | B | 165 | 24.153 | 18.010 | 15.506 | 1.00 | 22.54 | B | C |
| ATOM | 2358 | CE  | LYS | B | 165 | 23.243 | 16.926 | 16.062 | 1.00 | 22.64 | B | C |
| ATOM | 2359 | NZ  | LYS | B | 165 | 23.231 | 15.701 | 15.230 | 1.00 | 21.04 | B | N |
| ATOM | 2360 | C   | LYS | B | 165 | 26.051 | 22.533 | 16.388 | 1.00 | 23.20 | B | C |
| ATOM | 2361 | O   | LYS | B | 165 | 26.865 | 22.548 | 17.312 | 1.00 | 21.71 | B | O |
| ATOM | 2362 | N   | ALA | B | 166 | 26.215 | 23.219 | 15.261 | 1.00 | 22.64 | B | N |
| ATOM | 2363 | CA  | ALA | B | 166 | 27.416 | 24.013 | 15.026 | 1.00 | 24.25 | B | C |
| ATOM | 2364 | CB  | ALA | B | 166 | 27.384 | 24.629 | 13.613 | 1.00 | 24.20 | B | C |
| ATOM | 2365 | C   | ALA | B | 166 | 27.636 | 25.098 | 16.072 | 1.00 | 24.80 | B | C |
| ATOM | 2366 | O   | ALA | B | 166 | 28.772 | 25.333 | 16.491 | 1.00 | 24.79 | B | O |
| ATOM | 2367 | N   | GLN | B | 167 | 26.563 | 25.758 | 16.495 | 1.00 | 25.16 | B | N |
| ATOM | 2368 | CA  | GLN | B | 167 | 26.684 | 26.810 | 17.503 | 1.00 | 26.89 | B | C |
| ATOM | 2369 | CB  | GLN | B | 167 | 25.411 | 27.660 | 17.545 | 1.00 | 29.97 | B | C |
| ATOM | 2370 | CG  | GLN | B | 167 | 25.203 | 28.462 | 18.834 | 1.00 | 37.08 | B | C |
| ATOM | 2371 | CD  | GLN | B | 167 | 26.215 | 29.587 | 19.035 | 1.00 | 42.68 | B | C |
| ATOM | 2372 | OE1 | GLN | B | 167 | 27.425 | 29.351 | 19.185 | 1.00 | 43.86 | B | O |
| ATOM | 2373 | NE2 | GLN | B | 167 | 25.719 | 30.824 | 19.042 | 1.00 | 43.02 | B | N |
| ATOM | 2374 | C   | GLN | B | 167 | 26.950 | 26.193 | 18.866 | 1.00 | 26.35 | B | C |
| ATOM | 2375 | O   | GLN | B | 167 | 27.707 | 26.739 | 19.672 | 1.00 | 24.45 | B | O |
| ATOM | 2376 | N   | LEU | B | 168 | 26.334 | 25.041 | 19.111 | 1.00 | 25.56 | B | N |
| ATOM | 2377 | CA  | LEU | B | 168 | 26.501 | 24.339 | 20.374 | 1.00 | 24.45 | B | C |
| ATOM | 2378 | CB  | LEU | B | 168 | 25.605 | 23.091 | 20.428 | 1.00 | 21.23 | B | C |
| ATOM | 2379 | CG  | LEU | B | 168 | 24.076 | 23.257 | 20.548 | 1.00 | 24.32 | B | C |
| ATOM | 2380 | CD1 | LEU | B | 168 | 23.398 | 21.885 | 20.478 | 1.00 | 19.55 | B | C |
| ATOM | 2381 | CD2 | LEU | B | 168 | 23.711 | 23.942 | 21.856 | 1.00 | 19.17 | B | C |
| ATOM | 2382 | C   | LEU | B | 168 | 27.951 | 23.931 | 20.610 | 1.00 | 25.52 | B | C |
| ATOM | 2383 | O   | LEU | B | 168 | 28.501 | 24.192 | 21.674 | 1.00 | 23.62 | B | O |
| ATOM | 2384 | N   | GLU | B | 169 | 28.577 | 23.303 | 19.623 | 1.00 | 27.52 | B | N |
| ATOM | 2385 | CA  | GLU | B | 169 | 29.948 | 22.844 | 19.809 | 1.00 | 32.03 | B | C |
| ATOM | 2386 | CB  | GLU | B | 169 | 30.259 | 21.672 | 18.863 | 1.00 | 32.00 | B | C |
| ATOM | 2387 | CG  | GLU | B | 169 | 29.545 | 21.711 | 17.535 | 1.00 | 35.49 | B | C |
| ATOM | 2388 | CD  | GLU | B | 169 | 29.317 | 20.317 | 16.954 | 1.00 | 35.75 | B | C |
| ATOM | 2389 | OE1 | GLU | B | 169 | 28.662 | 19.485 | 17.621 | 1.00 | 36.56 | B | O |
| ATOM | 2390 | OE2 | GLU | B | 169 | 29.789 | 20.057 | 15.829 | 1.00 | 34.75 | B | O |
| ATOM | 2391 | C   | GLU | B | 169 | 31.007 | 23.924 | 19.703 | 1.00 | 32.42 | B | C |
| ATOM | 2392 | O   | GLU | B | 169 | 32.114 | 23.762 | 20.202 | 1.00 | 34.46 | B | O |
| ATOM | 2393 | N   | LYS | B | 170 | 30.659 | 25.034 | 19.071 | 1.00 | 34.54 | B | N |
| ATOM | 2394 | CA  | LYS | B | 170 | 31.585 | 26.142 | 18.934 | 1.00 | 34.41 | B | C |
| ATOM | 2395 | CB  | LYS | B | 170 | 31.124 | 27.071 | 17.813 | 1.00 | 37.50 | B | C |
| ATOM | 2396 | CG  | LYS | B | 170 | 32.090 | 28.190 | 17.512 | 1.00 | 41.65 | B | C |
| ATOM | 2397 | CD  | LYS | B | 170 | 31.700 | 28.922 | 16.240 | 1.00 | 45.85 | B | C |
| ATOM | 2398 | CE  | LYS | B | 170 | 31.944 | 28.064 | 15.005 | 1.00 | 48.44 | B | C |
| ATOM | 2399 | NZ  | LYS | B | 170 | 33.402 | 27.794 | 14.811 | 1.00 | 48.66 | B | N |
| ATOM | 2400 | C   | LYS | B | 170 | 31.639 | 26.899 | 20.253 | 1.00 | 34.06 | B | C |
| ATOM | 2401 | O   | LYS | B | 170 | 32.694 | 27.395 | 20.651 | 1.00 | 31.09 | B | O |
| ATOM | 2402 | N   | ALA | B | 171 | 30.496 | 26.966 | 20.937 | 1.00 | 33.89 | B | N |
| ATOM | 2403 | CA  | ALA | B | 171 | 30.394 | 27.671 | 22.212 | 1.00 | 34.35 | B | C |

TABLE 2-continued coordinates for the two molecules in the asymmetric unit of [T287] Aurora
A (122–396) in complex with an inhibitor of formula II in space group P2₁

| ATOM | 2404 | CB | ALA | B | 171 | 28.955 | 28.087 | 22.467 | 1.00 | 31.71 | B | C |
|---|---|---|---|---|---|---|---|---|---|---|---|---|
| ATOM | 2405 | C | ALA | B | 171 | 30.914 | 26.869 | 23.398 | 1.00 | 36.33 | B | C |
| ATOM | 2406 | O | ALA | B | 171 | 30.973 | 27.374 | 24.517 | 1.00 | 37.82 | B | O |
| ATOM | 2407 | N | GLY | B | 172 | 31.288 | 25.619 | 23.168 | 1.00 | 37.10 | B | N |
| ATOM | 2408 | CA | GLY | B | 172 | 31.796 | 24.824 | 24.265 | 1.00 | 39.08 | B | C |
| ATOM | 2409 | C | GLY | B | 172 | 31.293 | 23.408 | 24.199 | 1.00 | 41.69 | B | C |
| ATOM | 2410 | O | GLY | B | 172 | 30.945 | 22.814 | 25.231 | 1.00 | 41.29 | B | O |
| ATOM | 2411 | N | VAL | B | 173 | 31.262 | 22.884 | 22.972 | 1.00 | 44.30 | B | N |
| ATOM | 2412 | CA | VAL | B | 173 | 30.807 | 21.528 | 22.670 | 1.00 | 44.96 | B | C |
| ATOM | 2413 | CB | VAL | B | 173 | 31.989 | 20.572 | 22.425 | 1.00 | 46.41 | B | C |
| ATOM | 2414 | CG1 | VAL | B | 173 | 31.476 | 19.285 | 21.791 | 1.00 | 45.74 | B | C |
| ATOM | 2415 | CG2 | VAL | B | 173 | 33.048 | 21.246 | 21.539 | 1.00 | 44.74 | B | C |
| ATOM | 2416 | C | VAL | B | 173 | 29.984 | 20.983 | 23.817 | 1.00 | 46.17 | B | C |
| ATOM | 2417 | O | VAL | B | 173 | 30.498 | 20.247 | 24.667 | 1.00 | 46.81 | B | O |
| ATOM | 2418 | N | GLU | B | 174 | 28.705 | 21.352 | 23.842 | 1.00 | 44.84 | B | N |
| ATOM | 2419 | CA | GLU | B | 174 | 27.841 | 20.912 | 24.911 | 1.00 | 42.70 | B | C |
| ATOM | 2420 | CB | GLU | B | 174 | 26.509 | 21.646 | 24.865 | 1.00 | 43.75 | B | C |
| ATOM | 2421 | CG | GLU | B | 174 | 26.485 | 22.871 | 25.754 | 1.00 | 44.96 | B | C |
| ATOM | 2422 | CD | GLU | B | 174 | 27.483 | 23.929 | 25.329 | 1.00 | 45.73 | B | C |
| ATOM | 2423 | OE1 | GLU | B | 174 | 28.664 | 23.587 | 25.115 | 1.00 | 46.37 | B | O |
| ATOM | 2424 | OE2 | GLU | B | 174 | 27.087 | 25.108 | 25.219 | 1.00 | 45.36 | B | O |
| ATOM | 2425 | C | GLU | B | 174 | 27.611 | 19.420 | 24.997 | 1.00 | 42.19 | B | C |
| ATOM | 2426 | O | GLU | B | 174 | 26.665 | 18.869 | 24.427 | 1.00 | 39.51 | B | O |
| ATOM | 2427 | N | HIS | B | 175 | 28.522 | 18.781 | 25.719 | 1.00 | 41.13 | B | N |
| ATOM | 2428 | CA | HIS | B | 175 | 28.458 | 17.365 | 26.001 | 1.00 | 40.20 | B | C |
| ATOM | 2429 | CB | HIS | B | 175 | 29.845 | 16.864 | 26.435 | 1.00 | 44.57 | B | C |
| ATOM | 2430 | CG | HIS | B | 175 | 29.880 | 15.420 | 26.837 | 1.00 | 49.02 | B | C |
| ATOM | 2431 | CD2 | HIS | B | 175 | 30.422 | 14.337 | 26.228 | 1.00 | 50.48 | B | C |
| ATOM | 2432 | ND1 | HIS | B | 175 | 29.305 | 14.954 | 28.001 | 1.00 | 51.44 | B | N |
| ATOM | 2433 | CE1 | HIS | B | 175 | 29.490 | 13.648 | 28.091 | 1.00 | 51.08 | B | C |
| ATOM | 2434 | NE2 | HIS | B | 175 | 30.165 | 13.249 | 27.027 | 1.00 | 51.29 | B | N |
| ATOM | 2435 | C | HIS | B | 175 | 27.493 | 17.408 | 27.185 | 1.00 | 37.70 | B | C |
| ATOM | 2436 | O | HIS | B | 175 | 26.942 | 16.394 | 27.604 | 1.00 | 37.04 | B | O |
| ATOM | 2437 | N | GLN | B | 176 | 27.282 | 18.621 | 27.692 | 1.00 | 35.01 | B | N |
| ATOM | 2438 | CA | GLN | B | 176 | 26.399 | 18.841 | 28.827 | 1.00 | 36.23 | B | C |
| ATOM | 2439 | CB | GLN | B | 176 | 26.846 | 20.066 | 29.624 | 1.00 | 37.61 | B | C |
| ATOM | 2440 | CG | GLN | B | 176 | 27.133 | 21.297 | 28.819 | 1.00 | 41.69 | B | C |
| ATOM | 2441 | CD | GLN | B | 176 | 27.294 | 22.516 | 29.710 | 1.00 | 46.57 | B | C |
| ATOM | 2442 | OE1 | GLN | B | 176 | 27.841 | 23.549 | 29.298 | 1.00 | 49.05 | B | O |
| ATOM | 2443 | NE2 | GLN | B | 176 | 26.807 | 22.406 | 30.942 | 1.00 | 47.86 | B | N |
| ATOM | 2444 | C | GLN | B | 176 | 24.921 | 18.970 | 28.473 | 1.00 | 34.56 | B | C |
| ATOM | 2445 | O | GLN | B | 176 | 24.063 | 18.678 | 29.299 | 1.00 | 34.08 | B | O |
| ATOM | 2446 | N | LEU | B | 177 | 24.624 | 19.419 | 27.259 | 1.00 | 33.44 | B | N |
| ATOM | 2447 | CA | LEU | B | 177 | 23.240 | 19.533 | 26.824 | 1.00 | 32.62 | B | C |
| ATOM | 2448 | CB | LEU | B | 177 | 23.163 | 20.178 | 25.433 | 1.00 | 33.83 | B | C |
| ATOM | 2449 | CG | LEU | B | 177 | 21.829 | 20.192 | 24.665 | 1.00 | 35.49 | B | C |
| ATOM | 2450 | CD1 | LEU | B | 177 | 21.552 | 18.815 | 24.084 | 1.00 | 35.05 | B | C |
| ATOM | 2451 | CD2 | LEU | B | 177 | 20.698 | 20.638 | 25.581 | 1.00 | 33.78 | B | C |
| ATOM | 2452 | C | LEU | B | 177 | 22.728 | 18.102 | 26.776 | 1.00 | 31.62 | B | C |
| ATOM | 2453 | O | LEU | B | 177 | 21.561 | 17.826 | 27.057 | 1.00 | 30.39 | B | O |
| ATOM | 2454 | N | ARG | B | 178 | 23.624 | 17.188 | 26.425 | 1.00 | 30.82 | B | N |
| ATOM | 2455 | CA | ARG | B | 178 | 23.265 | 15.784 | 26.357 | 1.00 | 32.73 | B | C |
| ATOM | 2456 | CB | ARG | B | 178 | 24.380 | 14.979 | 25.698 | 1.00 | 33.93 | B | C |
| ATOM | 2457 | CG | ARG | B | 178 | 24.492 | 15.194 | 24.207 | 1.00 | 39.47 | B | C |
| ATOM | 2458 | CD | ARG | B | 178 | 25.654 | 14.398 | 23.658 | 1.00 | 44.54 | B | C |
| ATOM | 2459 | NE | ARG | B | 178 | 25.537 | 12.989 | 24.018 | 1.00 | 47.63 | B | N |
| ATOM | 2460 | CZ | ARG | B | 178 | 26.501 | 12.098 | 23.838 | 1.00 | 48.23 | B | C |
| ATOM | 2461 | NH1 | ARG | B | 178 | 27.651 | 12.476 | 23.302 | 1.00 | 49.75 | B | N |
| ATOM | 2462 | NH2 | ARG | B | 178 | 26.316 | 10.835 | 24.192 | 1.00 | 49.72 | B | N |
| ATOM | 2463 | C | ARG | B | 178 | 22.998 | 15.241 | 27.753 | 1.00 | 32.47 | B | C |
| ATOM | 2464 | O | ARG | B | 178 | 21.976 | 14.597 | 27.995 | 1.00 | 33.18 | B | O |
| ATOM | 2465 | N | ARG | B | 179 | 23.912 | 15.506 | 28.676 | 1.00 | 30.61 | B | N |
| ATOM | 2466 | CA | ARG | B | 179 | 23.729 | 15.016 | 30.030 | 1.00 | 31.15 | B | C |
| ATOM | 2467 | CB | ARG | B | 179 | 24.965 | 15.320 | 30.880 | 1.00 | 34.46 | B | C |
| ATOM | 2468 | CG | ARG | B | 179 | 26.228 | 14.641 | 30.359 | 1.00 | 39.50 | B | C |
| ATOM | 2469 | CD | ARG | B | 179 | 26.988 | 13.929 | 31.471 | 1.00 | 43.76 | B | C |
| ATOM | 2470 | NE | ARG | B | 179 | 26.134 | 13.031 | 32.253 | 1.00 | 49.01 | B | N |
| ATOM | 2471 | CZ | ARG | B | 179 | 25.409 | 12.036 | 31.746 | 1.00 | 49.97 | B | C |
| ATOM | 2472 | NH1 | ARG | B | 179 | 25.421 | 11.793 | 30.441 | 1.00 | 51.21 | B | N |
| ATOM | 2473 | NH2 | ARG | B | 179 | 24.668 | 11.280 | 32.547 | 1.00 | 50.28 | B | N |
| ATOM | 2474 | C | ARG | B | 179 | 22.489 | 15.644 | 30.637 | 1.00 | 27.71 | B | C |
| ATOM | 2475 | O | ARG | B | 179 | 21.776 | 15.006 | 31.394 | 1.00 | 26.64 | B | O |
| ATOM | 2476 | N | GLU | B | 180 | 22.228 | 16.896 | 30.279 | 1.00 | 27.23 | B | N |
| ATOM | 2477 | CA | GLU | B | 180 | 21.070 | 17.620 | 30.782 | 1.00 | 26.36 | B | C |
| ATOM | 2478 | CB | GLU | B | 180 | 21.163 | 19.080 | 30.346 | 1.00 | 27.40 | B | C |
| ATOM | 2479 | CG | GLU | B | 180 | 20.452 | 20.047 | 31.271 | 1.00 | 30.43 | B | C |

TABLE 2-continued coordinates for the two molecules in the asymmetric unit of [T287] Aurora
A (122–396) in complex with an inhibitor of formula II in space group P2₁

| ATOM | 2480 | CD | GLU | B | 180 | 20.951 | 19.961 | 32.708 | 1.00 | 33.04 | B | C |
|---|---|---|---|---|---|---|---|---|---|---|---|---|
| ATOM | 2481 | OE1 | GLU | B | 180 | 22.178 | 20.114 | 32.934 | 1.00 | 32.92 | B | O |
| ATOM | 2482 | OE2 | GLU | B | 180 | 20.114 | 19.739 | 33.613 | 1.00 | 32.02 | B | O |
| ATOM | 2483 | C | GLU | B | 180 | 19.746 | 16.997 | 30.296 | 1.00 | 25.78 | B | C |
| ATOM | 2484 | O | GLU | B | 180 | 18.796 | 16.863 | 31.063 | 1.00 | 24.13 | B | O |
| ATOM | 2485 | N | VAL | B | 181 | 19.693 | 16.612 | 29.023 | 1.00 | 25.67 | B | N |
| ATOM | 2486 | CA | VAL | B | 181 | 18.494 | 16.002 | 28.453 | 1.00 | 27.08 | B | C |
| ATOM | 2487 | CB | VAL | B | 181 | 18.693 | 15.717 | 26.936 | 1.00 | 27.03 | B | C |
| ATOM | 2488 | CG1 | VAL | B | 181 | 17.566 | 14.856 | 26.405 | 1.00 | 27.81 | B | C |
| ATOM | 2489 | CG2 | VAL | B | 181 | 18.745 | 17.029 | 26.171 | 1.00 | 22.54 | B | C |
| ATOM | 2490 | C | VAL | B | 181 | 18.155 | 14.703 | 29.188 | 1.00 | 28.77 | B | C |
| ATOM | 2491 | O | VAL | B | 181 | 17.000 | 14.452 | 29.536 | 1.00 | 30.48 | B | O |
| ATOM | 2492 | N | GLU | B | 182 | 19.175 | 13.887 | 29.433 | 1.00 | 30.16 | B | N |
| ATOM | 2493 | CA | GLU | B | 182 | 19.024 | 12.615 | 30.139 | 1.00 | 29.83 | B | C |
| ATOM | 2494 | CB | GLU | B | 182 | 20.394 | 11.937 | 30.231 | 1.00 | 34.09 | B | C |
| ATOM | 2495 | CG | GLU | B | 182 | 20.452 | 10.614 | 30.983 | 1.00 | 40.35 | B | C |
| ATOM | 2496 | CD | GLU | B | 182 | 21.884 | 10.092 | 31.105 | 1.00 | 45.37 | B | C |
| ATOM | 2497 | OE1 | GLU | B | 182 | 22.072 | 8.979 | 31.646 | 1.00 | 47.27 | B | O |
| ATOM | 2498 | OE2 | GLU | B | 182 | 22.826 | 10.798 | 30.657 | 1.00 | 47.17 | B | O |
| ATOM | 2499 | C | GLU | B | 182 | 18.445 | 12.843 | 31.534 | 1.00 | 28.60 | B | C |
| ATOM | 2500 | O | GLU | B | 182 | 17.457 | 12.223 | 31.920 | 1.00 | 28.99 | B | O |
| ATOM | 2501 | N | ILE | B | 183 | 19.060 | 13.741 | 32.290 | 1.00 | 27.98 | B | N |
| ATOM | 2502 | CA | ILE | B | 183 | 18.593 | 14.056 | 33.636 | 1.00 | 28.08 | B | C |
| ATOM | 2503 | CB | ILE | B | 183 | 19.493 | 15.130 | 34.293 | 1.00 | 28.69 | B | C |
| ATOM | 2504 | CG2 | ILE | B | 183 | 18.894 | 15.567 | 35.618 | 1.00 | 27.35 | B | C |
| ATOM | 2505 | CG1 | ILE | B | 183 | 20.910 | 14.586 | 34.484 | 1.00 | 28.95 | B | C |
| ATOM | 2506 | CD1 | ILE | B | 183 | 21.880 | 15.609 | 35.030 | 1.00 | 30.67 | B | C |
| ATOM | 2507 | C | ILE | B | 183 | 17.153 | 14.588 | 33.627 | 1.00 | 28.81 | B | C |
| ATOM | 2508 | O | ILE | B | 183 | 16.275 | 14.072 | 34.321 | 1.00 | 27.77 | B | O |
| ATOM | 2509 | N | GLN | B | 184 | 16.934 | 15.632 | 32.837 | 1.00 | 27.78 | B | N |
| ATOM | 2510 | CA | GLN | B | 184 | 15.635 | 16.283 | 32.721 | 1.00 | 29.40 | B | C |
| ATOM | 2511 | CB | GLN | B | 184 | 15.728 | 17.393 | 31.677 | 1.00 | 29.48 | B | C |
| ATOM | 2512 | CG | GLN | B | 184 | 15.084 | 18.695 | 32.085 | 1.00 | 33.57 | B | C |
| ATOM | 2513 | CD | GLN | B | 184 | 15.767 | 19.331 | 33.274 | 1.00 | 34.49 | B | C |
| ATOM | 2514 | OE1 | GLN | B | 184 | 15.177 | 19.449 | 34.344 | 1.00 | 34.49 | B | O |
| ATOM | 2515 | NE2 | GLN | B | 184 | 17.021 | 19.740 | 33.095 | 1.00 | 36.47 | B | N |
| ATOM | 2516 | C | GLN | B | 184 | 14.474 | 15.349 | 32.360 | 1.00 | 29.74 | B | C |
| ATOM | 2517 | O | GLN | B | 184 | 13.377 | 15.473 | 32.899 | 1.00 | 29.32 | B | O |
| ATOM | 2518 | N | SER | B | 185 | 14.714 | 14.411 | 31.455 | 1.00 | 30.43 | B | N |
| ATOM | 2519 | CA | SER | B | 185 | 13.659 | 13.497 | 31.024 | 1.00 | 31.44 | B | C |
| ATOM | 2520 | CB | SER | B | 185 | 14.123 | 12.710 | 29.801 | 1.00 | 29.48 | B | C |
| ATOM | 2521 | OG | SER | B | 185 | 15.188 | 11.853 | 30.147 | 1.00 | 33.05 | B | O |
| ATOM | 2522 | C | SER | B | 185 | 13.151 | 12.524 | 32.093 | 1.00 | 32.12 | B | C |
| ATOM | 2523 | O | SER | B | 185 | 12.156 | 11.842 | 31.884 | 1.00 | 31.84 | B | O |
| ATOM | 2524 | N | HIS | B | 186 | 13.818 | 12.463 | 33.237 | 1.00 | 33.65 | B | N |
| ATOM | 2525 | CA | HIS | B | 186 | 13.391 | 11.564 | 34.305 | 1.00 | 34.39 | B | C |
| ATOM | 2526 | CB | HIS | B | 186 | 14.582 | 10.731 | 34.781 | 1.00 | 36.84 | B | C |
| ATOM | 2527 | CG | HIS | B | 186 | 15.052 | 9.729 | 33.773 | 1.00 | 39.30 | B | C |
| ATOM | 2528 | CD2 | HIS | B | 186 | 14.363 | 8.961 | 32.893 | 1.00 | 40.21 | B | C |
| ATOM | 2529 | ND1 | HIS | B | 186 | 16.384 | 9.432 | 33.581 | 1.00 | 39.62 | B | N |
| ATOM | 2530 | CE1 | HIS | B | 186 | 16.497 | 8.528 | 32.623 | 1.00 | 42.04 | B | C |
| ATOM | 2531 | NE2 | HIS | B | 186 | 15.286 | 8.225 | 32.189 | 1.00 | 42.20 | B | N |
| ATOM | 2532 | C | HIS | B | 186 | 12.758 | 12.295 | 35.487 | 1.00 | 34.27 | B | C |
| ATOM | 2533 | O | HIS | B | 186 | 12.296 | 11.667 | 36.442 | 1.00 | 34.94 | B | O |
| ATOM | 2534 | N | LEU | B | 187 | 12.745 | 13.621 | 35.423 | 1.00 | 32.72 | B | N |
| ATOM | 2535 | CA | LEU | B | 187 | 12.162 | 14.441 | 36.476 | 1.00 | 31.38 | B | C |
| ATOM | 2536 | CB | LEU | B | 187 | 12.798 | 15.835 | 36.466 | 1.00 | 30.82 | B | C |
| ATOM | 2537 | CG | LEU | B | 187 | 14.074 | 16.108 | 37.274 | 1.00 | 31.43 | B | C |
| ATOM | 2538 | CD1 | LEU | B | 187 | 14.997 | 14.911 | 37.294 | 1.00 | 32.58 | B | C |
| ATOM | 2539 | CD2 | LEU | B | 187 | 14.764 | 17.317 | 36.686 | 1.00 | 31.34 | B | C |
| ATOM | 2540 | C | LEU | B | 187 | 10.659 | 14.569 | 36.248 | 1.00 | 31.86 | B | C |
| ATOM | 2541 | O | LEU | B | 187 | 10.214 | 14.797 | 35.121 | 1.00 | 30.47 | B | O |
| ATOM | 2542 | N | ALA | B | 188 | 9.881 | 14.413 | 37.316 | 1.00 | 31.25 | B | N |
| ATOM | 2543 | CA | ALA | B | 188 | 8.429 | 14.530 | 37.230 | 1.00 | 30.44 | B | C |
| ATOM | 2544 | CB | ALA | B | 188 | 7.789 | 13.148 | 37.091 | 1.00 | 29.88 | B | C |
| ATOM | 2545 | C | ALA | B | 188 | 7.912 | 15.237 | 38.481 | 1.00 | 29.21 | B | C |
| ATOM | 2546 | O | ALA | B | 188 | 7.862 | 14.651 | 39.559 | 1.00 | 28.34 | B | O |
| ATOM | 2547 | N | HIS | B | 189 | 7.538 | 16.504 | 38.319 | 1.00 | 28.72 | B | N |
| ATOM | 2548 | CA | HIS | B | 189 | 7.032 | 17.326 | 39.412 | 1.00 | 27.13 | B | C |
| ATOM | 2549 | CB | HIS | B | 189 | 8.205 | 17.925 | 40.201 | 1.00 | 27.59 | B | C |
| ATOM | 2550 | CG | HIS | B | 189 | 7.799 | 18.662 | 41.442 | 1.00 | 24.39 | B | C |
| ATOM | 2551 | CD2 | HIS | B | 189 | 7.993 | 18.377 | 42.752 | 1.00 | 25.28 | B | C |
| ATOM | 2552 | ND1 | HIS | B | 189 | 7.122 | 19.859 | 41.410 | 1.00 | 26.03 | B | N |
| ATOM | 2553 | CE1 | HIS | B | 189 | 6.919 | 20.283 | 42.646 | 1.00 | 24.93 | B | C |
| ATOM | 2554 | NE2 | HIS | B | 189 | 7.438 | 19.402 | 43.479 | 1.00 | 23.51 | B | N |
| ATOM | 2555 | C | HIS | B | 189 | 6.193 | 18.431 | 38.787 | 1.00 | 26.49 | B | C |

TABLE 2-continued coordinates for the two molecules in the asymmetric unit of [T287] Aurora A (122–396) in complex with an inhibitor of formula II in space group P2₁

| ATOM | 2556 | O | HIS | B | 189 | 6.562 | 18.998 | 37.766 | 1.00 | 26.44 | B | O |
|------|------|-----|-----|---|-----|--------|--------|--------|------|-------|---|---|
| ATOM | 2557 | N | PRO | B | 190 | 5.049 | 18.760 | 39.402 | 1.00 | 26.98 | B | N |
| ATOM | 2558 | CD | PRO | B | 190 | 4.548 | 18.263 | 40.699 | 1.00 | 25.70 | B | C |
| ATOM | 2559 | CA | PRO | B | 190 | 4.177 | 19.807 | 38.863 | 1.00 | 24.70 | B | C |
| ATOM | 2560 | CB | PRO | B | 190 | 2.998 | 19.811 | 39.846 | 1.00 | 25.70 | B | C |
| ATOM | 2561 | CG | PRO | B | 190 | 3.633 | 19.382 | 41.139 | 1.00 | 26.97 | B | C |
| ATOM | 2562 | C | PRO | B | 190 | 4.814 | 21.191 | 38.682 | 1.00 | 24.45 | B | C |
| ATOM | 2563 | O | PRO | B | 190 | 4.378 | 21.966 | 37.832 | 1.00 | 24.60 | B | O |
| ATOM | 2564 | N | ASN | B | 191 | 5.842 | 21.506 | 39.464 | 1.00 | 22.38 | B | N |
| ATOM | 2565 | CA | ASN | B | 191 | 6.481 | 22.809 | 39.346 | 1.00 | 21.54 | B | C |
| ATOM | 2566 | CB | ASN | B | 191 | 6.713 | 23.408 | 40.730 | 1.00 | 21.05 | B | C |
| ATOM | 2567 | CG | ASN | B | 191 | 5.436 | 23.575 | 41.495 | 1.00 | 19.72 | B | C |
| ATOM | 2568 | OD1 | ASN | B | 191 | 4.567 | 24.371 | 41.121 | 1.00 | 19.90 | B | O |
| ATOM | 2569 | ND2 | ASN | B | 191 | 5.299 | 22.815 | 42.571 | 1.00 | 20.48 | B | N |
| ATOM | 2570 | C | ASN | B | 191 | 7.793 | 22.801 | 38.564 | 1.00 | 21.58 | B | C |
| ATOM | 2571 | O | ASN | B | 191 | 8.627 | 23.699 | 38.720 | 1.00 | 19.27 | B | O |
| ATOM | 2572 | N | ILE | B | 192 | 7.964 | 21.787 | 37.722 | 1.00 | 20.97 | B | N |
| ATOM | 2573 | CA | ILE | B | 192 | 9.154 | 21.674 | 36.880 | 1.00 | 21.01 | B | C |
| ATOM | 2574 | CB | ILE | B | 192 | 10.064 | 20.494 | 37.331 | 1.00 | 21.26 | B | C |
| ATOM | 2575 | CG2 | ILE | B | 192 | 11.219 | 20.288 | 36.331 | 1.00 | 19.48 | B | C |
| ATOM | 2576 | CG1 | ILE | B | 192 | 10.613 | 20.770 | 38.733 | 1.00 | 21.57 | B | C |
| ATOM | 2577 | CD1 | ILE | B | 192 | 11.462 | 19.627 | 39.299 | 1.00 | 23.94 | B | C |
| ATOM | 2578 | C | ILE | B | 192 | 8.667 | 21.432 | 35.453 | 1.00 | 19.86 | B | C |
| ATOM | 2579 | O | ILE | B | 192 | 7.908 | 20.497 | 35.210 | 1.00 | 22.96 | B | O |
| ATOM | 2580 | N | LEU | B | 193 | 9.082 | 22.282 | 34.519 | 1.00 | 20.26 | B | N |
| ATOM | 2581 | CA | LEU | B | 193 | 8.669 | 22.142 | 33.124 | 1.00 | 21.42 | B | C |
| ATOM | 2582 | CB | LEU | B | 193 | 9.307 | 23.234 | 32.268 | 1.00 | 22.27 | B | C |
| ATOM | 2583 | CG | LEU | B | 193 | 8.681 | 23.436 | 30.883 | 1.00 | 23.28 | B | C |
| ATOM | 2584 | CD1 | LEU | B | 193 | 7.245 | 23.930 | 31.030 | 1.00 | 21.92 | B | C |
| ATOM | 2585 | CD2 | LEU | B | 193 | 9.495 | 24.445 | 30.101 | 1.00 | 19.52 | B | C |
| ATOM | 2586 | C | LEU | B | 193 | 9.041 | 20.763 | 32.565 | 1.00 | 21.67 | B | C |
| ATOM | 2587 | O | LEU | B | 193 | 10.199 | 20.350 | 32.598 | 1.00 | 18.44 | B | O |
| ATOM | 2588 | N | ARG | B | 194 | 8.041 | 20.069 | 32.036 | 1.00 | 21.75 | B | N |
| ATOM | 2589 | CA | ARG | B | 194 | 8.215 | 18.732 | 31.482 | 1.00 | 23.01 | B | C |
| ATOM | 2590 | CB | ARG | B | 194 | 6.841 | 18.096 | 31.268 | 1.00 | 25.81 | B | C |
| ATOM | 2591 | CG | ARG | B | 194 | 6.788 | 16.596 | 31.448 | 1.00 | 32.81 | B | C |
| ATOM | 2592 | CD | ARG | B | 194 | 6.817 | 16.240 | 32.921 | 1.00 | 37.46 | B | C |
| ATOM | 2593 | NE | ARG | B | 194 | 6.281 | 14.904 | 33.176 | 1.00 | 44.90 | B | N |
| ATOM | 2594 | CZ | ARG | B | 194 | 5.012 | 14.542 | 32.974 | 1.00 | 47.96 | B | C |
| ATOM | 2595 | NH1 | ARG | B | 194 | 4.125 | 15.418 | 32.508 | 1.00 | 48.71 | B | N |
| ATOM | 2596 | NH2 | ARG | B | 194 | 4.626 | 13.299 | 33.247 | 1.00 | 48.22 | B | N |
| ATOM | 2597 | C | ARG | B | 194 | 8.981 | 18.673 | 30.159 | 1.00 | 21.93 | B | C |
| ATOM | 2598 | O | ARG | B | 194 | 8.821 | 19.538 | 29.292 | 1.00 | 19.59 | B | O |
| ATOM | 2599 | N | LEU | B | 195 | 9.819 | 17.647 | 30.021 | 1.00 | 21.33 | B | N |
| ATOM | 2600 | CA | LEU | B | 195 | 10.567 | 17.403 | 28.788 | 1.00 | 22.76 | B | C |
| ATOM | 2601 | CB | LEU | B | 195 | 12.053 | 17.148 | 29.069 | 1.00 | 22.81 | B | C |
| ATOM | 2602 | CG | LEU | B | 195 | 13.078 | 17.437 | 27.959 | 1.00 | 24.02 | B | C |
| ATOM | 2603 | CD1 | LEU | B | 195 | 14.267 | 16.498 | 28.140 | 1.00 | 21.85 | B | C |
| ATOM | 2604 | CD2 | LEU | B | 195 | 12.483 | 17.251 | 26.563 | 1.00 | 23.51 | B | C |
| ATOM | 2605 | C | LEU | B | 195 | 9.921 | 16.119 | 28.274 | 1.00 | 22.36 | B | C |
| ATOM | 2606 | O | LEU | B | 195 | 10.110 | 15.056 | 28.861 | 1.00 | 22.57 | B | O |
| ATOM | 2607 | N | TYR | B | 196 | 9.145 | 16.215 | 27.201 | 1.00 | 22.31 | B | N |
| ATOM | 2608 | CA | TYR | B | 196 | 8.453 | 15.050 | 26.651 | 1.00 | 22.19 | B | C |
| ATOM | 2609 | CB | TYR | B | 196 | 7.281 | 15.490 | 25.768 | 1.00 | 23.58 | B | C |
| ATOM | 2610 | CG | TYR | B | 196 | 6.155 | 16.146 | 26.519 | 1.00 | 23.96 | B | C |
| ATOM | 2611 | CD1 | TYR | B | 196 | 5.772 | 17.460 | 26.238 | 1.00 | 25.04 | B | C |
| ATOM | 2612 | CE1 | TYR | B | 196 | 4.728 | 18.071 | 26.937 | 1.00 | 24.87 | B | C |
| ATOM | 2613 | CD2 | TYR | B | 196 | 5.467 | 15.457 | 27.515 | 1.00 | 25.05 | B | C |
| ATOM | 2614 | CE2 | TYR | B | 196 | 4.426 | 16.056 | 28.217 | 1.00 | 25.56 | B | C |
| ATOM | 2615 | CZ | TYR | B | 196 | 4.062 | 17.361 | 27.923 | 1.00 | 25.01 | B | C |
| ATOM | 2616 | OH | TYR | B | 196 | 3.023 | 17.944 | 28.612 | 1.00 | 29.27 | B | O |
| ATOM | 2617 | C | TYR | B | 196 | 9.333 | 14.108 | 25.851 | 1.00 | 22.57 | B | C |
| ATOM | 2618 | O | TYR | B | 196 | 9.132 | 12.898 | 25.873 | 1.00 | 23.50 | B | O |
| ATOM | 2619 | N | GLY | B | 197 | 10.294 | 14.663 | 25.124 | 1.00 | 22.59 | B | N |
| ATOM | 2620 | CA | GLY | B | 197 | 11.180 | 13.841 | 24.332 | 1.00 | 20.31 | B | C |
| ATOM | 2621 | C | GLY | B | 197 | 12.161 | 14.702 | 23.572 | 1.00 | 23.62 | B | C |
| ATOM | 2622 | O | GLY | B | 197 | 12.220 | 15.919 | 23.772 | 1.00 | 24.47 | B | O |
| ATOM | 2623 | N | TYR | B | 198 | 12.935 | 14.078 | 22.695 | 1.00 | 23.97 | B | N |
| ATOM | 2624 | CA | TYR | B | 198 | 13.903 | 14.810 | 21.900 | 1.00 | 27.71 | B | C |
| ATOM | 2625 | CB | TYR | B | 198 | 15.140 | 15.125 | 22.735 | 1.00 | 31.42 | B | C |
| ATOM | 2626 | CG | TYR | B | 198 | 15.966 | 13.915 | 23.087 | 1.00 | 36.13 | B | C |
| ATOM | 2627 | CD1 | TYR | B | 198 | 17.100 | 13.584 | 22.349 | 1.00 | 37.59 | B | C |
| ATOM | 2628 | CE1 | TYR | B | 198 | 17.863 | 12.466 | 22.667 | 1.00 | 40.01 | B | C |
| ATOM | 2629 | CD2 | TYR | B | 198 | 15.611 | 13.096 | 24.158 | 1.00 | 38.85 | B | C |
| ATOM | 2630 | CE2 | TYR | B | 198 | 16.364 | 11.977 | 24.485 | 1.00 | 40.86 | B | C |
| ATOM | 2631 | CZ | TYR | B | 198 | 17.489 | 11.667 | 23.734 | 1.00 | 41.45 | B | C |

TABLE 2-continued coordinates for the two molecules in the asymmetric unit of [T287] Aurora A (122–396) in complex with an inhibitor of formula II in space group P2$_1$

| ATOM | 2632 | OH | TYR | B | 198 | 18.232 | 10.550 | 24.049 | 1.00 | 46.15 | B | O |
|---|---|---|---|---|---|---|---|---|---|---|---|---|
| ATOM | 2633 | C | TYR | B | 198 | 14.293 | 13.982 | 20.699 | 1.00 | 26.60 | B | C |
| ATOM | 2634 | O | TYR | B | 198 | 13.951 | 12.812 | 20.611 | 1.00 | 26.01 | B | O |
| ATOM | 2635 | N | PHE | B | 199 | 15.000 | 14.599 | 19.767 | 1.00 | 27.65 | B | N |
| ATOM | 2636 | CA | PHE | B | 199 | 15.443 | 13.904 | 18.572 | 1.00 | 27.79 | B | C |
| ATOM | 2637 | CB | PHE | B | 199 | 14.233 | 13.426 | 17.749 | 1.00 | 27.11 | B | C |
| ATOM | 2638 | CG | PHE | B | 199 | 13.388 | 14.540 | 17.161 | 1.00 | 27.89 | B | C |
| ATOM | 2639 | CD1 | PHE | B | 199 | 13.637 | 15.019 | 15.876 | 1.00 | 27.86 | B | C |
| ATOM | 2640 | CD2 | PHE | B | 199 | 12.310 | 15.064 | 17.868 | 1.00 | 27.14 | B | C |
| ATOM | 2641 | CE1 | PHE | B | 199 | 12.824 | 15.996 | 15.301 | 1.00 | 26.93 | B | C |
| ATOM | 2642 | CE2 | PHE | B | 199 | 11.492 | 16.040 | 17.303 | 1.00 | 26.16 | B | C |
| ATOM | 2643 | CZ | PHE | B | 199 | 11.750 | 16.505 | 16.015 | 1.00 | 27.17 | B | C |
| ATOM | 2644 | C | PHE | B | 199 | 16.297 | 14.860 | 17.767 | 1.00 | 28.08 | B | C |
| ATOM | 2645 | O | PHE | B | 199 | 16.345 | 16.049 | 18.073 | 1.00 | 28.24 | B | O |
| ATOM | 2646 | N | HIS | B | 200 | 16.993 | 14.353 | 16.758 | 1.00 | 27.87 | B | N |
| ATOM | 2647 | CA | HIS | B | 200 | 17.806 | 15.238 | 15.938 | 1.00 | 29.75 | B | C |
| ATOM | 2648 | CB | HIS | B | 200 | 19.100 | 15.594 | 16.681 | 1.00 | 33.26 | B | C |
| ATOM | 2649 | CG | HIS | B | 200 | 19.948 | 14.418 | 17.048 | 1.00 | 34.79 | B | C |
| ATOM | 2650 | CD2 | HIS | B | 200 | 21.287 | 14.230 | 16.965 | 1.00 | 36.25 | B | C |
| ATOM | 2651 | ND1 | HIS | B | 200 | 19.439 | 13.288 | 17.648 | 1.00 | 35.92 | B | N |
| ATOM | 2652 | CE1 | HIS | B | 200 | 20.427 | 12.454 | 17.921 | 1.00 | 37.18 | B | C |
| ATOM | 2653 | NE2 | HIS | B | 200 | 21.559 | 13.003 | 17.517 | 1.00 | 36.60 | B | N |
| ATOM | 2654 | C | HIS | B | 200 | 18.116 | 14.715 | 14.538 | 1.00 | 27.95 | B | C |
| ATOM | 2655 | O | HIS | B | 200 | 17.752 | 13.591 | 14.187 | 1.00 | 26.05 | B | O |
| ATOM | 2656 | N | ASP | B | 201 | 18.725 | 15.571 | 13.721 | 1.00 | 26.67 | B | N |
| ATOM | 2657 | CA | ASP | B | 201 | 19.138 | 15.186 | 12.377 | 1.00 | 25.20 | B | C |
| ATOM | 2658 | CB | ASP | B | 201 | 18.335 | 15.916 | 11.282 | 1.00 | 23.68 | B | C |
| ATOM | 2659 | CG | ASP | B | 201 | 18.264 | 17.424 | 11.483 | 1.00 | 25.88 | B | C |
| ATOM | 2660 | OD1 | ASP | B | 201 | 19.294 | 18.047 | 11.802 | 1.00 | 23.44 | B | O |
| ATOM | 2661 | OD2 | ASP | B | 201 | 17.166 | 17.998 | 11.290 | 1.00 | 26.10 | B | O |
| ATOM | 2662 | C | ASP | B | 201 | 20.627 | 15.505 | 12.299 | 1.00 | 24.36 | B | C |
| ATOM | 2663 | O | ASP | B | 201 | 21.263 | 15.653 | 13.339 | 1.00 | 24.08 | B | O |
| ATOM | 2664 | N | ALA | B | 202 | 21.184 | 15.617 | 11.096 | 1.00 | 22.49 | B | N |
| ATOM | 2665 | CA | ALA | B | 202 | 22.615 | 15.887 | 10.946 | 1.00 | 22.92 | B | C |
| ATOM | 2666 | CB | ALA | B | 202 | 23.038 | 15.661 | 9.485 | 1.00 | 21.85 | B | C |
| ATOM | 2667 | C | ALA | B | 202 | 23.106 | 17.263 | 11.420 | 1.00 | 22.02 | B | C |
| ATOM | 2668 | O | ALA | B | 202 | 24.289 | 17.437 | 11.710 | 1.00 | 19.11 | B | O |
| ATOM | 2669 | N | ALA | B | 203 | 22.212 | 18.237 | 11.520 | 1.00 | 21.84 | B | N |
| ATOM | 2670 | CA | ALA | B | 203 | 22.654 | 19.564 | 11.935 | 1.00 | 20.59 | B | C |
| ATOM | 2671 | CB | ALA | B | 203 | 22.661 | 20.502 | 10.718 | 1.00 | 18.98 | B | C |
| ATOM | 2672 | C | ALA | B | 203 | 21.902 | 20.213 | 13.095 | 1.00 | 17.95 | B | C |
| ATOM | 2673 | O | ALA | B | 203 | 22.321 | 21.262 | 13.583 | 1.00 | 19.24 | B | O |
| ATOM | 2674 | N | ARG | B | 204 | 20.825 | 19.595 | 13.568 | 1.00 | 17.86 | B | N |
| ATOM | 2675 | CA | ARG | B | 204 | 20.060 | 20.197 | 14.660 | 1.00 | 19.08 | B | C |
| ATOM | 2676 | CB | ARG | B | 204 | 18.849 | 20.964 | 14.111 | 1.00 | 23.11 | B | C |
| ATOM | 2677 | CG | ARG | B | 204 | 19.083 | 21.702 | 12.813 | 1.00 | 24.65 | B | C |
| ATOM | 2678 | CD | ARG | B | 204 | 17.793 | 22.345 | 12.317 | 1.00 | 31.21 | B | C |
| ATOM | 2679 | NE | ARG | B | 204 | 17.847 | 22.663 | 10.890 | 1.00 | 36.40 | B | N |
| ATOM | 2680 | CZ | ARG | B | 204 | 17.679 | 21.773 | 9.911 | 1.00 | 38.70 | B | C |
| ATOM | 2681 | NH1 | ARG | B | 204 | 17.752 | 22.161 | 8.644 | 1.00 | 41.01 | B | N |
| ATOM | 2682 | NH2 | ARG | B | 204 | 17.419 | 20.500 | 10.191 | 1.00 | 38.76 | B | N |
| ATOM | 2683 | C | ARG | B | 204 | 19.547 | 19.228 | 15.711 | 1.00 | 18.39 | B | C |
| ATOM | 2684 | O | ARG | B | 204 | 19.463 | 18.030 | 15.492 | 1.00 | 18.56 | B | O |
| ATOM | 2685 | N | VAL | B | 205 | 19.199 | 19.767 | 16.870 | 1.00 | 18.68 | B | N |
| ATOM | 2686 | CA | VAL | B | 205 | 18.649 | 18.958 | 17.949 | 1.00 | 18.67 | B | C |
| ATOM | 2687 | CB | VAL | B | 205 | 19.551 | 18.984 | 19.201 | 1.00 | 18.98 | B | C |
| ATOM | 2688 | CG1 | VAL | B | 205 | 18.933 | 18.135 | 20.301 | 1.00 | 19.79 | B | C |
| ATOM | 2689 | CG2 | VAL | B | 205 | 20.947 | 18.472 | 18.852 | 1.00 | 15.84 | B | C |
| ATOM | 2690 | C | VAL | B | 205 | 17.290 | 19.572 | 18.282 | 1.00 | 19.14 | B | C |
| ATOM | 2691 | O | VAL | B | 205 | 17.182 | 20.796 | 18.405 | 1.00 | 21.54 | B | O |
| ATOM | 2692 | N | TYR | B | 206 | 16.263 | 18.731 | 18.396 | 1.00 | 17.89 | B | N |
| ATOM | 2693 | CA | TYR | B | 206 | 14.910 | 19.193 | 18.709 | 1.00 | 19.04 | B | C |
| ATOM | 2694 | CB | TYR | B | 206 | 13.891 | 18.696 | 17.674 | 1.00 | 18.60 | B | C |
| ATOM | 2695 | CG | TYR | B | 206 | 14.228 | 19.017 | 16.240 | 1.00 | 18.39 | B | C |
| ATOM | 2696 | CD1 | TYR | B | 206 | 15.207 | 18.293 | 15.565 | 1.00 | 21.42 | B | C |
| ATOM | 2697 | CE1 | TYR | B | 206 | 15.542 | 18.578 | 14.244 | 1.00 | 21.55 | B | C |
| ATOM | 2698 | CD2 | TYR | B | 206 | 13.576 | 20.052 | 15.555 | 1.00 | 19.46 | B | C |
| ATOM | 2699 | CE2 | TYR | B | 206 | 13.907 | 20.352 | 14.216 | 1.00 | 21.97 | B | C |
| ATOM | 2700 | CZ | TYR | B | 206 | 14.898 | 19.602 | 13.573 | 1.00 | 23.91 | B | C |
| ATOM | 2701 | OH | TYR | B | 206 | 15.267 | 19.858 | 12.269 | 1.00 | 26.45 | B | O |
| ATOM | 2702 | C | TYR | B | 206 | 14.459 | 18.705 | 20.073 | 1.00 | 19.50 | B | C |
| ATOM | 2703 | O | TYR | B | 206 | 14.538 | 17.508 | 20.373 | 1.00 | 21.94 | B | O |
| ATOM | 2704 | N | LEU | B | 207 | 13.985 | 19.633 | 20.897 | 1.00 | 16.85 | B | N |
| ATOM | 2705 | CA | LEU | B | 207 | 13.491 | 19.291 | 22.224 | 1.00 | 17.98 | B | C |
| ATOM | 2706 | CB | LEU | B | 207 | 14.181 | 20.161 | 23.286 | 1.00 | 16.72 | B | C |
| ATOM | 2707 | CG | LEU | B | 207 | 15.722 | 20.138 | 23.321 | 1.00 | 19.44 | B | C |

TABLE 2-continued coordinates for the two molecules in the asymmetric unit of [T287] Aurora
A (122–396) in complex with an inhibitor of formula II in space group P2$_1$

| ATOM | 2708 | CD1 | LEU | B | 207 | 16.216 | 21.031 | 24.461 | 1.00 | 19.09 | B | C |
|---|---|---|---|---|---|---|---|---|---|---|---|---|
| ATOM | 2709 | CD2 | LEU | B | 207 | 16.226 | 18.707 | 23.519 | 1.00 | 19.58 | B | C |
| ATOM | 2710 | C | LEU | B | 207 | 11.973 | 19.535 | 22.225 | 1.00 | 17.04 | B | C |
| ATOM | 2711 | O | LEU | B | 207 | 11.513 | 20.588 | 21.803 | 1.00 | 18.06 | B | O |
| ATOM | 2712 | N | ILE | B | 208 | 11.205 | 18.547 | 22.674 | 1.00 | 18.23 | B | N |
| ATOM | 2713 | CA | ILE | B | 208 | 9.747 | 18.653 | 22.727 | 1.00 | 16.54 | B | C |
| ATOM | 2714 | CB | ILE | B | 208 | 9.093 | 17.336 | 22.272 | 1.00 | 16.55 | B | C |
| ATOM | 2715 | CG2 | ILE | B | 208 | 7.568 | 17.474 | 22.238 | 1.00 | 14.96 | B | C |
| ATOM | 2716 | CG1 | ILE | B | 208 | 9.614 | 16.978 | 20.872 | 1.00 | 20.37 | B | C |
| ATOM | 2717 | CD1 | ILE | B | 208 | 9.149 | 15.613 | 20.347 | 1.00 | 21.43 | B | C |
| ATOM | 2718 | C | ILE | B | 208 | 9.412 | 18.969 | 24.179 | 1.00 | 17.23 | B | C |
| ATOM | 2719 | O | ILE | B | 208 | 9.636 | 18.144 | 25.081 | 1.00 | 16.63 | B | O |
| ATOM | 2720 | N | LEU | B | 209 | 8.871 | 20.166 | 24.401 | 1.00 | 16.12 | B | N |
| ATOM | 2721 | CA | LEU | B | 209 | 8.577 | 20.630 | 25.752 | 1.00 | 17.56 | B | C |
| ATOM | 2722 | CB | LEU | B | 209 | 9.472 | 21.830 | 26.063 | 1.00 | 17.90 | B | C |
| ATOM | 2723 | CG | LEU | B | 209 | 10.978 | 21.577 | 25.959 | 1.00 | 19.46 | B | C |
| ATOM | 2724 | CD1 | LEU | B | 209 | 11.664 | 22.798 | 25.379 | 1.00 | 19.75 | B | C |
| ATOM | 2725 | CD2 | LEU | B | 209 | 11.525 | 21.215 | 27.336 | 1.00 | 19.17 | B | C |
| ATOM | 2726 | C | LEU | B | 209 | 7.144 | 21.018 | 26.084 | 1.00 | 18.62 | B | C |
| ATOM | 2727 | O | LEU | B | 209 | 6.348 | 21.346 | 25.202 | 1.00 | 18.84 | B | O |
| ATOM | 2728 | N | GLU | B | 210 | 6.844 | 20.984 | 27.381 | 1.00 | 16.02 | B | N |
| ATOM | 2729 | CA | GLU | B | 210 | 5.549 | 21.382 | 27.898 | 1.00 | 17.17 | B | C |
| ATOM | 2730 | CB | GLU | B | 210 | 5.496 | 21.128 | 29.409 | 1.00 | 16.24 | B | C |
| ATOM | 2731 | CG | GLU | B | 210 | 4.275 | 21.705 | 30.100 | 1.00 | 17.66 | B | C |
| ATOM | 2732 | CD | GLU | B | 210 | 4.319 | 21.542 | 31.615 | 1.00 | 19.26 | B | C |
| ATOM | 2733 | OE1 | GLU | B | 210 | 3.396 | 22.037 | 32.298 | 1.00 | 19.17 | B | O |
| ATOM | 2734 | OE2 | GLU | B | 210 | 5.273 | 20.919 | 32.126 | 1.00 | 18.51 | B | O |
| ATOM | 2735 | C | GLU | B | 210 | 5.419 | 22.881 | 27.619 | 1.00 | 17.58 | B | C |
| ATOM | 2736 | O | GLU | B | 210 | 6.386 | 23.640 | 27.787 | 1.00 | 17.15 | B | O |
| ATOM | 2737 | N | TYR | B | 211 | 4.239 | 23.301 | 27.177 | 1.00 | 17.46 | B | N |
| ATOM | 2738 | CA | TYR | B | 211 | 3.975 | 24.707 | 26.875 | 1.00 | 17.27 | B | C |
| ATOM | 2739 | CB | TYR | B | 211 | 2.915 | 24.830 | 25.771 | 1.00 | 17.32 | B | C |
| ATOM | 2740 | CG | TYR | B | 211 | 2.598 | 26.265 | 25.406 | 1.00 | 18.99 | B | C |
| ATOM | 2741 | CD1 | TYR | B | 211 | 3.601 | 27.115 | 24.953 | 1.00 | 18.89 | B | C |
| ATOM | 2742 | CE1 | TYR | B | 211 | 3.337 | 28.443 | 24.637 | 1.00 | 18.07 | B | C |
| ATOM | 2743 | CD2 | TYR | B | 211 | 1.300 | 26.783 | 25.536 | 1.00 | 19.53 | B | C |
| ATOM | 2744 | CE2 | TYR | B | 211 | 1.025 | 28.124 | 25.215 | 1.00 | 17.93 | B | C |
| ATOM | 2745 | CZ | TYR | B | 211 | 2.058 | 28.943 | 24.766 | 1.00 | 19.57 | B | C |
| ATOM | 2746 | OH | TYR | B | 211 | 1.837 | 30.268 | 24.435 | 1.00 | 21.28 | B | O |
| ATOM | 2747 | C | TYR | B | 211 | 3.488 | 25.437 | 28.119 | 1.00 | 17.08 | B | C |
| ATOM | 2748 | O | TYR | B | 211 | 2.676 | 24.905 | 28.880 | 1.00 | 20.12 | B | O |
| ATOM | 2749 | N | ALA | B | 212 | 3.977 | 26.657 | 28.315 | 1.00 | 16.19 | B | N |
| ATOM | 2750 | CA | ALA | B | 212 | 3.619 | 27.487 | 29.470 | 1.00 | 16.51 | B | C |
| ATOM | 2751 | CB | ALA | B | 212 | 4.882 | 27.927 | 30.202 | 1.00 | 15.30 | B | C |
| ATOM | 2752 | C | ALA | B | 212 | 2.856 | 28.705 | 28.952 | 1.00 | 17.50 | B | C |
| ATOM | 2753 | O | ALA | B | 212 | 3.450 | 29.726 | 28.596 | 1.00 | 18.16 | B | O |
| ATOM | 2754 | N | PRO | B | 213 | 1.520 | 28.618 | 28.925 | 1.00 | 17.93 | B | N |
| ATOM | 2755 | CD | PRO | B | 213 | 0.728 | 27.494 | 29.458 | 1.00 | 16.26 | B | C |
| ATOM | 2756 | CA | PRO | B | 213 | 0.651 | 29.693 | 28.437 | 1.00 | 18.73 | B | C |
| ATOM | 2757 | CB | PRO | B | 213 | −0.758 | 29.108 | 28.604 | 1.00 | 17.80 | B | C |
| ATOM | 2758 | CG | PRO | B | 213 | −0.609 | 28.146 | 29.724 | 1.00 | 19.64 | B | C |
| ATOM | 2759 | C | PRO | B | 213 | 0.761 | 31.115 | 28.984 | 1.00 | 19.83 | B | C |
| ATOM | 2760 | O | PRO | B | 213 | 0.513 | 32.063 | 28.245 | 1.00 | 20.80 | B | O |
| ATOM | 2761 | N | LEU | B | 214 | 1.128 | 31.288 | 30.250 | 1.00 | 20.66 | B | N |
| ATOM | 2762 | CA | LEU | B | 214 | 1.211 | 32.640 | 30.798 | 1.00 | 20.06 | B | C |
| ATOM | 2763 | CB | LEU | B | 214 | 0.709 | 32.647 | 32.255 | 1.00 | 19.58 | B | C |
| ATOM | 2764 | CG | LEU | B | 214 | −0.812 | 32.790 | 32.467 | 1.00 | 22.04 | B | C |
| ATOM | 2765 | CD1 | LEU | B | 214 | −1.576 | 31.829 | 31.576 | 1.00 | 23.11 | B | C |
| ATOM | 2766 | CD2 | LEU | B | 214 | −1.161 | 32.538 | 33.926 | 1.00 | 22.72 | B | C |
| ATOM | 2767 | C | LEU | B | 214 | 2.572 | 33.346 | 30.686 | 1.00 | 21.48 | B | C |
| ATOM | 2768 | O | LEU | B | 214 | 2.749 | 34.451 | 31.200 | 1.00 | 23.25 | B | O |
| ATOM | 2769 | N | GLY | B | 215 | 3.533 | 32.724 | 30.013 | 1.00 | 21.00 | B | N |
| ATOM | 2770 | CA | GLY | B | 215 | 4.825 | 33.368 | 29.847 | 1.00 | 21.31 | B | C |
| ATOM | 2771 | C | GLY | B | 215 | 5.790 | 33.299 | 31.023 | 1.00 | 23.13 | B | C |
| ATOM | 2772 | O | GLY | B | 215 | 5.657 | 32.448 | 31.904 | 1.00 | 23.73 | B | O |
| ATOM | 2773 | N | THR | B | 216 | 6.758 | 34.214 | 31.042 | 1.00 | 22.29 | B | N |
| ATOM | 2774 | CA | THR | B | 216 | 7.779 | 34.238 | 32.088 | 1.00 | 23.81 | B | C |
| ATOM | 2775 | CB | THR | B | 216 | 9.127 | 34.692 | 31.517 | 1.00 | 23.63 | B | C |
| ATOM | 2776 | OG1 | THR | B | 216 | 9.090 | 36.102 | 31.277 | 1.00 | 25.10 | B | O |
| ATOM | 2777 | CG2 | THR | B | 216 | 9.409 | 33.987 | 30.199 | 1.00 | 22.17 | B | C |
| ATOM | 2778 | C | THR | B | 216 | 7.461 | 35.125 | 33.291 | 1.00 | 23.33 | B | C |
| ATOM | 2779 | O | THR | B | 216 | 6.712 | 36.100 | 33.191 | 1.00 | 20.98 | B | O |
| ATOM | 2780 | N | VAL | B | 217 | 8.036 | 34.774 | 34.435 | 1.00 | 22.90 | B | N |
| ATOM | 2781 | CA | VAL | B | 217 | 7.827 | 35.554 | 35.651 | 1.00 | 24.21 | B | C |
| ATOM | 2782 | CB | VAL | B | 217 | 8.470 | 34.857 | 36.867 | 1.00 | 23.26 | B | C |
| ATOM | 2783 | CG1 | VAL | B | 217 | 8.387 | 35.740 | 38.109 | 1.00 | 22.26 | B | C |

TABLE 2-continued coordinates for the two molecules in the asymmetric unit of [T287] Aurora A (122–396) in complex with an inhibitor of formula II in space group P2₁

| ATOM | 2784 | CG2 | VAL | B | 217 | 7.763 | 33.552 | 37.110 | 1.00 | 22.25 | B | C |
|---|---|---|---|---|---|---|---|---|---|---|---|---|
| ATOM | 2785 | C | VAL | B | 217 | 8.439 | 36.935 | 35.449 | 1.00 | 23.65 | B | C |
| ATOM | 2786 | O | VAL | B | 217 | 7.922 | 37.933 | 35.932 | 1.00 | 23.81 | B | O |
| ATOM | 2787 | N | TYR | B | 218 | 9.536 | 36.967 | 34.708 | 1.00 | 25.98 | B | N |
| ATOM | 2788 | CA | TYR | B | 218 | 10.247 | 38.193 | 34.395 | 1.00 | 29.23 | B | C |
| ATOM | 2789 | CB | TYR | B | 218 | 11.395 | 37.865 | 33.437 | 1.00 | 33.60 | B | C |
| ATOM | 2790 | CG | TYR | B | 218 | 12.225 | 39.040 | 32.974 | 1.00 | 37.23 | B | C |
| ATOM | 2791 | CD1 | TYR | B | 218 | 11.965 | 39.661 | 31.753 | 1.00 | 39.24 | B | C |
| ATOM | 2792 | CE1 | TYR | B | 218 | 12.756 | 40.710 | 31.296 | 1.00 | 40.90 | B | C |
| ATOM | 2793 | CD2 | TYR | B | 218 | 13.296 | 39.503 | 33.733 | 1.00 | 39.21 | B | C |
| ATOM | 2794 | CE2 | TYR | B | 218 | 14.096 | 40.551 | 33.285 | 1.00 | 41.41 | B | C |
| ATOM | 2795 | CZ | TYR | B | 218 | 13.819 | 41.149 | 32.065 | 1.00 | 42.06 | B | C |
| ATOM | 2796 | OH | TYR | B | 218 | 14.609 | 42.175 | 31.607 | 1.00 | 43.77 | B | O |
| ATOM | 2797 | C | TYR | B | 218 | 9.302 | 39.228 | 33.788 | 1.00 | 30.16 | B | C |
| ATOM | 2798 | O | TYR | B | 218 | 9.259 | 40.368 | 34.242 | 1.00 | 31.95 | B | O |
| ATOM | 2799 | N | ALA | B | 219 | 8.540 | 38.831 | 32.770 | 1.00 | 30.65 | B | N |
| ATOM | 2800 | CA | ALA | B | 219 | 7.589 | 39.736 | 32.123 | 1.00 | 29.66 | B | C |
| ATOM | 2801 | CB | ALA | B | 219 | 6.906 | 39.026 | 30.967 | 1.00 | 28.94 | B | C |
| ATOM | 2802 | C | ALA | B | 219 | 6.542 | 40.257 | 33.118 | 1.00 | 29.78 | B | C |
| ATOM | 2803 | O | ALA | B | 219 | 6.199 | 41.438 | 33.110 | 1.00 | 28.08 | B | O |
| ATOM | 2804 | N | GLU | B | 220 | 6.027 | 39.371 | 33.964 | 1.00 | 30.79 | B | N |
| ATOM | 2805 | CA | GLU | B | 220 | 5.037 | 39.753 | 34.968 | 1.00 | 34.09 | B | C |
| ATOM | 2806 | CB | GLU | B | 220 | 4.587 | 38.529 | 35.766 | 1.00 | 36.73 | B | C |
| ATOM | 2807 | CG | GLU | B | 220 | 3.344 | 37.838 | 35.251 | 1.00 | 43.32 | B | C |
| ATOM | 2808 | CD | GLU | B | 220 | 2.073 | 38.618 | 35.542 | 1.00 | 46.85 | B | C |
| ATOM | 2809 | OE1 | GLU | B | 220 | 1.801 | 39.613 | 34.835 | 1.00 | 48.71 | B | O |
| ATOM | 2810 | OE2 | GLU | B | 220 | 1.350 | 38.237 | 36.489 | 1.00 | 48.33 | B | O |
| ATOM | 2811 | C | GLU | B | 220 | 5.618 | 40.785 | 35.934 | 1.00 | 34.92 | B | C |
| ATOM | 2812 | O | GLU | B | 220 | 4.956 | 41.755 | 36.296 | 1.00 | 36.60 | B | O |
| ATOM | 2813 | N | LEU | B | 221 | 6.858 | 40.569 | 36.356 | 1.00 | 34.26 | B | N |
| ATOM | 2814 | CA | LEU | B | 221 | 7.505 | 41.482 | 37.286 | 1.00 | 34.78 | B | C |
| ATOM | 2815 | CB | LEU | B | 221 | 8.920 | 40.995 | 37.621 | 1.00 | 33.24 | B | C |
| ATOM | 2816 | CG | LEU | B | 221 | 9.646 | 41.761 | 38.735 | 1.00 | 32.72 | B | C |
| ATOM | 2817 | CD1 | LEU | B | 221 | 8.807 | 41.773 | 40.010 | 1.00 | 30.46 | B | C |
| ATOM | 2818 | CD2 | LEU | B | 221 | 10.996 | 41.112 | 38.988 | 1.00 | 32.35 | B | C |
| ATOM | 2819 | C | LEU | B | 221 | 7.565 | 42.880 | 36.693 | 1.00 | 34.90 | B | C |
| ATOM | 2820 | O | LEU | B | 221 | 7.275 | 43.864 | 37.374 | 1.00 | 32.14 | B | O |
| ATOM | 2821 | N | GLN | B | 222 | 7.941 | 42.961 | 35.419 | 1.00 | 35.21 | B | N |
| ATOM | 2822 | CA | GLN | B | 222 | 8.026 | 44.241 | 34.735 | 1.00 | 37.12 | B | C |
| ATOM | 2823 | CB | GLN | B | 222 | 8.563 | 44.044 | 33.319 | 1.00 | 39.87 | B | C |
| ATOM | 2824 | CG | GLN | B | 222 | 9.945 | 43.424 | 33.287 | 1.00 | 44.00 | B | C |
| ATOM | 2825 | CD | GLN | B | 222 | 10.690 | 43.723 | 32.004 | 1.00 | 47.25 | B | C |
| ATOM | 2826 | OE1 | GLN | B | 222 | 10.220 | 43.410 | 30.907 | 1.00 | 49.30 | B | O |
| ATOM | 2827 | NE2 | GLN | B | 222 | 11.864 | 44.333 | 32.135 | 1.00 | 48.03 | B | N |
| ATOM | 2828 | C | GLN | B | 222 | 6.684 | 44.972 | 34.687 | 1.00 | 36.68 | B | C |
| ATOM | 2829 | O | GLN | B | 222 | 6.634 | 46.184 | 34.865 | 1.00 | 37.49 | B | O |
| ATOM | 2830 | N | LYS | B | 223 | 5.597 | 44.241 | 34.461 | 1.00 | 35.79 | B | N |
| ATOM | 2831 | CA | LYS | B | 223 | 4.277 | 44.859 | 34.406 | 1.00 | 36.52 | B | C |
| ATOM | 2832 | CB | LYS | B | 223 | 3.237 | 43.868 | 33.875 | 1.00 | 37.92 | B | C |
| ATOM | 2833 | CG | LYS | B | 223 | 3.354 | 43.561 | 32.389 | 1.00 | 39.91 | B | C |
| ATOM | 2834 | CD | LYS | B | 223 | 2.292 | 42.560 | 31.944 | 1.00 | 42.68 | B | C |
| ATOM | 2835 | CE | LYS | B | 223 | 0.886 | 43.140 | 32.033 | 1.00 | 43.66 | B | C |
| ATOM | 2836 | NZ | LYS | B | 223 | 0.693 | 44.275 | 31.079 | 1.00 | 46.03 | B | N |
| ATOM | 2837 | C | LYS | B | 223 | 3.792 | 45.402 | 35.749 | 1.00 | 36.84 | B | C |
| ATOM | 2838 | O | LYS | B | 223 | 3.357 | 46.550 | 35.833 | 1.00 | 38.21 | B | O |
| ATOM | 2839 | N | LEU | B | 224 | 3.860 | 44.580 | 36.795 | 1.00 | 35.10 | B | N |
| ATOM | 2840 | CA | LEU | B | 224 | 3.398 | 44.988 | 38.122 | 1.00 | 33.56 | B | C |
| ATOM | 2841 | CB | LEU | B | 224 | 2.929 | 43.762 | 38.913 | 1.00 | 33.55 | B | C |
| ATOM | 2842 | CG | LEU | B | 224 | 1.871 | 42.852 | 38.282 | 1.00 | 34.89 | B | C |
| ATOM | 2843 | CD1 | LEU | B | 224 | 1.619 | 41.658 | 39.189 | 1.00 | 33.24 | B | C |
| ATOM | 2844 | CD2 | LEU | B | 224 | 0.589 | 43.630 | 38.059 | 1.00 | 34.60 | B | C |
| ATOM | 2845 | C | LEU | B | 224 | 4.452 | 45.735 | 38.939 | 1.00 | 32.05 | B | C |
| ATOM | 2846 | O | LEU | B | 224 | 4.141 | 46.297 | 39.989 | 1.00 | 32.92 | B | O |
| ATOM | 2847 | N | SER | B | 225 | 5.691 | 45.723 | 38.455 | 1.00 | 30.59 | B | N |
| ATOM | 2848 | CA | SER | B | 225 | 6.826 | 46.380 | 39.112 | 1.00 | 31.41 | B | C |
| ATOM | 2849 | CB | SER | B | 225 | 6.449 | 47.792 | 39.549 | 1.00 | 32.21 | B | C |
| ATOM | 2850 | OG | SER | B | 225 | 7.615 | 48.537 | 39.843 | 1.00 | 34.55 | B | O |
| ATOM | 2851 | C | SER | B | 225 | 7.361 | 45.585 | 40.318 | 1.00 | 31.23 | B | C |
| ATOM | 2852 | O | SER | B | 225 | 8.556 | 45.589 | 40.599 | 1.00 | 30.58 | B | O |
| ATOM | 2853 | N | LYS | B | 226 | 6.466 | 44.921 | 41.035 | 1.00 | 30.59 | B | N |
| ATOM | 2854 | CA | LYS | B | 226 | 6.851 | 44.096 | 42.173 | 1.00 | 31.60 | B | C |
| ATOM | 2855 | CB | LYS | B | 226 | 7.535 | 44.924 | 43.273 | 1.00 | 32.62 | B | C |
| ATOM | 2856 | CG | LYS | B | 226 | 6.733 | 46.065 | 43.866 | 1.00 | 33.34 | B | C |
| ATOM | 2857 | CD | LYS | B | 226 | 7.482 | 46.606 | 45.085 | 1.00 | 37.58 | B | C |
| ATOM | 2858 | CE | LYS | B | 226 | 6.839 | 47.858 | 45.658 | 1.00 | 39.62 | B | C |
| ATOM | 2859 | NZ | LYS | B | 226 | 7.074 | 49.049 | 44.786 | 1.00 | 41.42 | B | N |

TABLE 2-continued coordinates for the two molecules in the asymmetric unit of [T287] Aurora
A (122–396) in complex with an inhibitor of formula II in space group P2$_1$

| ATOM | 2860 | C | LYS | B | 226 | 5.620 | 43.400 | 42.707 | 1.00 | 29.47 | B | C |
|---|---|---|---|---|---|---|---|---|---|---|---|---|
| ATOM | 2861 | O | LYS | B | 226 | 4.501 | 43.795 | 42.391 | 1.00 | 29.83 | B | O |
| ATOM | 2862 | N | PHE | B | 227 | 5.821 | 42.355 | 43.500 | 1.00 | 28.21 | B | N |
| ATOM | 2863 | CA | PHE | B | 227 | 4.702 | 41.597 | 44.039 | 1.00 | 26.85 | B | C |
| ATOM | 2864 | CB | PHE | B | 227 | 4.928 | 40.091 | 43.833 | 1.00 | 28.42 | B | C |
| ATOM | 2865 | CG | PHE | B | 227 | 5.401 | 39.718 | 42.453 | 1.00 | 27.26 | B | C |
| ATOM | 2866 | CD1 | PHE | B | 227 | 4.884 | 40.346 | 41.321 | 1.00 | 27.70 | B | C |
| ATOM | 2867 | CD2 | PHE | B | 227 | 6.352 | 38.712 | 42.286 | 1.00 | 27.41 | B | C |
| ATOM | 2868 | CE1 | PHE | B | 227 | 5.308 | 39.976 | 40.041 | 1.00 | 27.47 | B | C |
| ATOM | 2869 | CE2 | PHE | B | 227 | 6.786 | 38.334 | 41.011 | 1.00 | 27.41 | B | C |
| ATOM | 2870 | CZ | PHE | B | 227 | 6.261 | 38.969 | 39.887 | 1.00 | 27.84 | B | C |
| ATOM | 2871 | C | PHE | B | 227 | 4.453 | 41.850 | 45.525 | 1.00 | 26.66 | B | C |
| ATOM | 2872 | O | PHE | B | 227 | 5.307 | 42.385 | 46.229 | 1.00 | 25.45 | B | O |
| ATOM | 2873 | N | ASP | B | 228 | 3.273 | 41.442 | 45.983 | 1.00 | 24.91 | B | N |
| ATOM | 2874 | CA | ASP | B | 228 | 2.870 | 41.576 | 47.375 | 1.00 | 25.21 | B | C |
| ATOM | 2875 | CB | ASP | B | 228 | 1.346 | 41.623 | 47.484 | 1.00 | 25.97 | B | C |
| ATOM | 2876 | CG | ASP | B | 228 | 0.675 | 40.479 | 46.742 | 1.00 | 26.97 | B | C |
| ATOM | 2877 | OD1 | ASP | B | 228 | 0.468 | 40.611 | 45.525 | 1.00 | 33.21 | B | O |
| ATOM | 2878 | OD2 | ASP | B | 228 | 0.373 | 39.440 | 47.359 | 1.00 | 27.04 | B | O |
| ATOM | 2879 | C | ASP | B | 228 | 3.394 | 40.357 | 48.129 | 1.00 | 26.47 | B | C |
| ATOM | 2880 | O | ASP | B | 228 | 3.979 | 39.447 | 47.528 | 1.00 | 26.50 | B | O |
| ATOM | 2881 | N | GLU | B | 229 | 3.158 | 40.327 | 49.436 | 1.00 | 25.93 | B | N |
| ATOM | 2882 | CA | GLU | B | 229 | 3.627 | 39.234 | 50.275 | 1.00 | 25.05 | B | C |
| ATOM | 2883 | CB | GLU | B | 229 | 3.425 | 39.579 | 51.757 | 1.00 | 26.99 | B | C |
| ATOM | 2884 | CG | GLU | B | 229 | 4.230 | 40.789 | 52.233 | 1.00 | 30.82 | B | C |
| ATOM | 2885 | CD | GLU | B | 229 | 4.296 | 40.905 | 53.753 | 1.00 | 31.53 | B | C |
| ATOM | 2886 | OE1 | GLU | B | 229 | 3.239 | 41.053 | 54.403 | 1.00 | 32.47 | B | O |
| ATOM | 2887 | OE2 | GLU | B | 229 | 5.415 | 40.847 | 54.299 | 1.00 | 33.80 | B | O |
| ATOM | 2888 | C | GLU | B | 229 | 2.961 | 37.900 | 49.973 | 1.00 | 25.00 | B | C |
| ATOM | 2889 | O | GLU | B | 229 | 3.624 | 36.855 | 49.985 | 1.00 | 22.64 | B | O |
| ATOM | 2890 | N | GLN | B | 230 | 1.657 | 37.930 | 49.702 | 1.00 | 23.27 | B | N |
| ATOM | 2891 | CA | GLN | B | 230 | 0.925 | 36.698 | 49.420 | 1.00 | 25.73 | B | C |
| ATOM | 2892 | CB | GLN | B | 230 | −0.577 | 36.990 | 49.254 | 1.00 | 30.97 | B | C |
| ATOM | 2893 | CG | GLN | B | 230 | −1.443 | 35.736 | 49.099 | 1.00 | 37.32 | B | C |
| ATOM | 2894 | CD | GLN | B | 230 | −2.902 | 36.043 | 48.773 | 1.00 | 41.26 | B | C |
| ATOM | 2895 | OE1 | GLN | B | 230 | −3.214 | 36.601 | 47.720 | 1.00 | 43.42 | B | O |
| ATOM | 2896 | NE2 | GLN | B | 230 | −3.800 | 35.673 | 49.679 | 1.00 | 43.12 | B | N |
| ATOM | 2897 | C | GLN | B | 230 | 1.477 | 36.003 | 48.173 | 1.00 | 22.96 | B | C |
| ATOM | 2898 | O | GLN | B | 230 | 1.779 | 34.811 | 48.203 | 1.00 | 22.41 | B | O |
| ATOM | 2899 | N | ARG | B | 231 | 1.618 | 36.750 | 47.081 | 1.00 | 21.69 | B | N |
| ATOM | 2900 | CA | ARG | B | 231 | 2.151 | 36.196 | 45.841 | 1.00 | 20.70 | B | C |
| ATOM | 2901 | CB | ARG | B | 231 | 2.067 | 37.237 | 44.720 | 1.00 | 24.11 | B | C |
| ATOM | 2902 | CG | ARG | B | 231 | 2.972 | 36.943 | 43.534 | 1.00 | 29.60 | B | C |
| ATOM | 2903 | CD | ARG | B | 231 | 2.207 | 36.654 | 42.261 | 1.00 | 32.47 | B | C |
| ATOM | 2904 | NE | ARG | B | 231 | 1.381 | 37.776 | 41.827 | 1.00 | 35.86 | B | N |
| ATOM | 2905 | CZ | ARG | B | 231 | 1.031 | 37.992 | 40.562 | 1.00 | 38.81 | B | C |
| ATOM | 2906 | NH1 | ARG | B | 231 | 0.269 | 39.031 | 40.249 | 1.00 | 39.91 | B | N |
| ATOM | 2907 | NH2 | ARG | B | 231 | 1.466 | 37.183 | 39.602 | 1.00 | 38.33 | B | N |
| ATOM | 2908 | C | ARG | B | 231 | 3.606 | 35.719 | 46.001 | 1.00 | 19.50 | B | C |
| ATOM | 2909 | O | ARG | B | 231 | 3.957 | 34.622 | 45.557 | 1.00 | 17.71 | B | O |
| ATOM | 2910 | N | THR | B | 232 | 4.441 | 36.538 | 46.635 | 1.00 | 17.49 | B | N |
| ATOM | 2911 | CA | THR | B | 232 | 5.838 | 36.184 | 46.847 | 1.00 | 16.16 | B | C |
| ATOM | 2912 | CB | THR | B | 232 | 6.612 | 37.312 | 47.576 | 1.00 | 19.54 | B | C |
| ATOM | 2913 | OG1 | THR | B | 232 | 6.597 | 38.504 | 46.782 | 1.00 | 13.78 | B | O |
| ATOM | 2914 | CG2 | THR | B | 232 | 8.082 | 36.879 | 47.834 | 1.00 | 14.78 | B | C |
| ATOM | 2915 | C | THR | B | 232 | 5.956 | 34.904 | 47.682 | 1.00 | 17.18 | B | C |
| ATOM | 2916 | O | THR | B | 232 | 6.672 | 33.984 | 47.307 | 1.00 | 15.09 | B | O |
| ATOM | 2917 | N | ALA | B | 233 | 5.243 | 34.852 | 48.807 | 1.00 | 19.12 | B | N |
| ATOM | 2918 | CA | ALA | B | 233 | 5.264 | 33.684 | 49.695 | 1.00 | 18.94 | B | C |
| ATOM | 2919 | CB | ALA | B | 233 | 4.352 | 33.925 | 50.906 | 1.00 | 17.71 | B | C |
| ATOM | 2920 | C | ALA | B | 233 | 4.828 | 32.407 | 48.966 | 1.00 | 19.02 | B | C |
| ATOM | 2921 | O | ALA | B | 233 | 5.417 | 31.334 | 49.157 | 1.00 | 18.32 | B | O |
| ATOM | 2922 | N | THR | B | 234 | 3.785 | 32.527 | 48.148 | 1.00 | 19.42 | B | N |
| ATOM | 2923 | CA | THR | B | 234 | 3.275 | 31.399 | 47.370 | 1.00 | 18.40 | B | C |
| ATOM | 2924 | CB | THR | B | 234 | 1.975 | 31.784 | 46.620 | 1.00 | 17.88 | B | C |
| ATOM | 2925 | OG1 | THR | B | 234 | 0.965 | 32.134 | 47.575 | 1.00 | 15.16 | B | O |
| ATOM | 2926 | CG2 | THR | B | 234 | 1.480 | 30.618 | 45.762 | 1.00 | 16.22 | B | C |
| ATOM | 2927 | C | THR | B | 234 | 4.329 | 30.932 | 46.364 | 1.00 | 18.28 | B | C |
| ATOM | 2928 | O | THR | B | 234 | 4.550 | 29.735 | 46.196 | 1.00 | 20.75 | B | O |
| ATOM | 2929 | N | TYR | B | 235 | 4.981 | 31.876 | 45.694 | 1.00 | 19.08 | B | N |
| ATOM | 2930 | CA | TYR | B | 235 | 6.034 | 31.540 | 44.736 | 1.00 | 18.92 | B | C |
| ATOM | 2931 | CB | TYR | B | 235 | 6.514 | 32.803 | 44.014 | 1.00 | 19.29 | B | C |
| ATOM | 2932 | CG | TYR | B | 235 | 5.661 | 33.258 | 42.851 | 1.00 | 21.57 | B | C |
| ATOM | 2933 | CD1 | TYR | B | 235 | 4.389 | 32.729 | 42.634 | 1.00 | 23.85 | B | C |
| ATOM | 2934 | CE1 | TYR | B | 235 | 3.589 | 33.176 | 41.579 | 1.00 | 24.93 | B | C |
| ATOM | 2935 | CD2 | TYR | B | 235 | 6.116 | 34.247 | 41.984 | 1.00 | 21.08 | B | C |

TABLE 2-continued coordinates for the two molecules in the asymmetric unit of [T287] Aurora A (122–396) in complex with an inhibitor of formula II in space group P2₁

| ATOM | 2936 | CE2 | TYR | B | 235 | 5.325 | 34.705 | 40.926 | 1.00 | 24.94 | B | C |
|---|---|---|---|---|---|---|---|---|---|---|---|---|
| ATOM | 2937 | CZ | TYR | B | 235 | 4.063 | 34.168 | 40.728 | 1.00 | 26.16 | B | C |
| ATOM | 2938 | OH | TYR | B | 235 | 3.267 | 34.628 | 39.695 | 1.00 | 22.88 | B | O |
| ATOM | 2939 | C | TYR | B | 235 | 7.242 | 30.871 | 45.423 | 1.00 | 18.91 | B | C |
| ATOM | 2940 | O | TYR | B | 235 | 7.855 | 29.956 | 44.869 | 1.00 | 18.47 | B | O |
| ATOM | 2941 | N | ILE | B | 236 | 7.603 | 31.336 | 46.619 | 1.00 | 18.40 | B | N |
| ATOM | 2942 | CA | ILE | B | 236 | 8.745 | 30.741 | 47.321 | 1.00 | 17.73 | B | C |
| ATOM | 2943 | CB | ILE | B | 236 | 9.188 | 31.601 | 48.541 | 1.00 | 18.76 | B | C |
| ATOM | 2944 | CG2 | ILE | B | 236 | 10.387 | 30.945 | 49.254 | 1.00 | 18.52 | B | C |
| ATOM | 2945 | CG1 | ILE | B | 236 | 9.612 | 32.999 | 48.065 | 1.00 | 19.28 | B | C |
| ATOM | 2946 | CD1 | ILE | B | 236 | 10.744 | 32.987 | 47.035 | 1.00 | 16.65 | B | C |
| ATOM | 2947 | C | ILE | B | 236 | 8.407 | 29.322 | 47.781 | 1.00 | 16.37 | B | C |
| ATOM | 2948 | O | ILE | B | 236 | 9.274 | 28.460 | 47.824 | 1.00 | 15.52 | B | O |
| ATOM | 2949 | N | THR | B | 237 | 7.138 | 29.086 | 48.109 | 1.00 | 17.75 | B | N |
| ATOM | 2950 | CA | THR | B | 237 | 6.685 | 27.770 | 48.545 | 1.00 | 18.73 | B | C |
| ATOM | 2951 | CB | THR | B | 237 | 5.203 | 27.813 | 49.028 | 1.00 | 20.81 | B | C |
| ATOM | 2952 | OG1 | THR | B | 237 | 5.124 | 28.585 | 50.224 | 1.00 | 20.67 | B | O |
| ATOM | 2953 | CG2 | THR | B | 237 | 4.677 | 26.420 | 49.334 | 1.00 | 20.82 | B | C |
| ATOM | 2954 | C | THR | B | 237 | 6.818 | 26.764 | 47.410 | 1.00 | 18.80 | B | C |
| ATOM | 2955 | O | THR | B | 237 | 7.425 | 25.710 | 47.576 | 1.00 | 20.21 | B | O |
| ATOM | 2956 | N | GLU | B | 238 | 6.253 | 27.092 | 46.252 | 1.00 | 20.60 | B | N |
| ATOM | 2957 | CA | GLU | B | 238 | 6.320 | 26.199 | 45.099 | 1.00 | 19.19 | B | C |
| ATOM | 2958 | CB | GLU | B | 238 | 5.555 | 26.813 | 43.918 | 1.00 | 20.66 | B | C |
| ATOM | 2959 | CG | GLU | B | 238 | 4.036 | 26.779 | 44.100 | 1.00 | 23.37 | B | C |
| ATOM | 2960 | CD | GLU | B | 238 | 3.313 | 27.786 | 43.224 | 1.00 | 24.80 | B | C |
| ATOM | 2961 | OE1 | GLU | B | 238 | 3.581 | 27.842 | 42.009 | 1.00 | 25.78 | B | O |
| ATOM | 2962 | OE2 | GLU | B | 238 | 2.466 | 28.527 | 43.755 | 1.00 | 28.41 | B | O |
| ATOM | 2963 | C | GLU | B | 238 | 7.767 | 25.917 | 44.705 | 1.00 | 19.31 | B | C |
| ATOM | 2964 | O | GLU | B | 238 | 8.126 | 24.780 | 44.361 | 1.00 | 17.16 | B | O |
| ATOM | 2965 | N | LEU | B | 239 | 8.598 | 26.954 | 44.751 | 1.00 | 18.37 | B | N |
| ATOM | 2966 | CA | LEU | B | 239 | 10.004 | 26.801 | 44.401 | 1.00 | 17.98 | B | C |
| ATOM | 2967 | CB | LEU | B | 239 | 10.690 | 28.166 | 44.357 | 1.00 | 19.30 | B | C |
| ATOM | 2968 | CG | LEU | B | 239 | 10.569 | 28.862 | 43.002 | 1.00 | 22.62 | B | C |
| ATOM | 2969 | CD1 | LEU | B | 239 | 10.915 | 30.346 | 43.126 | 1.00 | 23.53 | B | C |
| ATOM | 2970 | CD2 | LEU | B | 239 | 11.493 | 28.157 | 42.008 | 1.00 | 23.78 | B | C |
| ATOM | 2971 | C | LEU | B | 239 | 10.746 | 25.877 | 45.362 | 1.00 | 18.38 | B | C |
| ATOM | 2972 | O | LEU | B | 239 | 11.517 | 25.025 | 44.926 | 1.00 | 18.06 | B | O |
| ATOM | 2973 | N | ALA | B | 240 | 10.514 | 26.047 | 46.665 | 1.00 | 16.60 | B | N |
| ATOM | 2974 | CA | ALA | B | 240 | 11.180 | 25.214 | 47.668 | 1.00 | 17.68 | B | C |
| ATOM | 2975 | CB | ALA | B | 240 | 10.830 | 25.701 | 49.080 | 1.00 | 16.34 | B | C |
| ATOM | 2976 | C | ALA | B | 240 | 10.777 | 23.750 | 47.496 | 1.00 | 18.39 | B | C |
| ATOM | 2977 | O | ALA | B | 240 | 11.606 | 22.856 | 47.641 | 1.00 | 16.04 | B | O |
| ATOM | 2978 | N | ASN | B | 241 | 9.502 | 23.518 | 47.179 | 1.00 | 19.07 | B | N |
| ATOM | 2979 | CA | ASN | B | 241 | 9.009 | 22.166 | 46.967 | 1.00 | 21.46 | B | C |
| ATOM | 2980 | CB | ASN | B | 241 | 7.517 | 22.167 | 46.602 | 1.00 | 23.76 | B | C |
| ATOM | 2981 | CG | ASN | B | 241 | 6.625 | 22.096 | 47.814 | 1.00 | 28.59 | B | C |
| ATOM | 2982 | OD1 | ASN | B | 241 | 6.917 | 21.367 | 48.759 | 1.00 | 31.92 | B | O |
| ATOM | 2983 | ND2 | ASN | B | 241 | 5.524 | 22.842 | 47.794 | 1.00 | 29.40 | B | N |
| ATOM | 2984 | C | ASN | B | 241 | 9.789 | 21.536 | 45.833 | 1.00 | 21.94 | B | C |
| ATOM | 2985 | O | ASN | B | 241 | 10.282 | 20.408 | 45.951 | 1.00 | 23.36 | B | O |
| ATOM | 2986 | N | ALA | B | 242 | 9.898 | 22.279 | 44.735 | 1.00 | 20.78 | B | N |
| ATOM | 2987 | CA | ALA | B | 242 | 10.614 | 21.816 | 43.553 | 1.00 | 21.85 | B | C |
| ATOM | 2988 | CB | ALA | B | 242 | 10.437 | 22.818 | 42.426 | 1.00 | 18.99 | B | C |
| ATOM | 2989 | C | ALA | B | 242 | 12.105 | 21.567 | 43.820 | 1.00 | 21.42 | B | C |
| ATOM | 2990 | O | ALA | B | 242 | 12.634 | 20.508 | 43.488 | 1.00 | 21.59 | B | O |
| ATOM | 2991 | N | LEU | B | 243 | 12.782 | 22.537 | 44.426 | 1.00 | 22.94 | B | N |
| ATOM | 2992 | CA | LEU | B | 243 | 14.209 | 22.383 | 44.730 | 1.00 | 21.96 | B | C |
| ATOM | 2993 | CB | LEU | B | 243 | 14.751 | 23.669 | 45.360 | 1.00 | 19.53 | B | C |
| ATOM | 2994 | CG | LEU | B | 243 | 14.744 | 24.896 | 44.439 | 1.00 | 20.66 | B | C |
| ATOM | 2995 | CD1 | LEU | B | 243 | 15.174 | 26.127 | 45.213 | 1.00 | 20.26 | B | C |
| ATOM | 2996 | CD2 | LEU | B | 243 | 15.674 | 24.656 | 43.266 | 1.00 | 20.88 | B | C |
| ATOM | 2997 | C | LEU | B | 243 | 14.457 | 21.196 | 45.668 | 1.00 | 21.93 | B | C |
| ATOM | 2998 | O | LEU | B | 243 | 15.449 | 20.469 | 45.535 | 1.00 | 20.07 | B | O |
| ATOM | 2999 | N | SER | B | 244 | 13.558 | 21.014 | 46.626 | 1.00 | 22.84 | B | N |
| ATOM | 3000 | CA | SER | B | 244 | 13.676 | 19.913 | 47.572 | 1.00 | 25.72 | B | C |
| ATOM | 3001 | CB | SER | B | 244 | 12.528 | 19.966 | 48.582 | 1.00 | 26.38 | B | C |
| ATOM | 3002 | OG | SER | B | 244 | 12.707 | 18.992 | 49.589 | 1.00 | 31.74 | B | O |
| ATOM | 3003 | C | SER | B | 244 | 13.646 | 18.594 | 46.800 | 1.00 | 26.65 | B | C |
| ATOM | 3004 | O | SER | B | 244 | 14.497 | 17.725 | 47.001 | 1.00 | 28.75 | B | O |
| ATOM | 3005 | N | TYR | B | 245 | 12.667 | 18.450 | 45.912 | 1.00 | 25.41 | B | N |
| ATOM | 3006 | CA | TYR | B | 245 | 12.545 | 17.246 | 45.101 | 1.00 | 26.59 | B | C |
| ATOM | 3007 | CB | TYR | B | 245 | 11.297 | 17.347 | 44.210 | 1.00 | 28.10 | B | C |
| ATOM | 3008 | CG | TYR | B | 245 | 11.234 | 16.369 | 43.050 | 1.00 | 29.48 | B | C |
| ATOM | 3009 | CD1 | TYR | B | 245 | 11.789 | 16.695 | 41.808 | 1.00 | 27.01 | B | C |
| ATOM | 3010 | CE1 | TYR | B | 245 | 11.746 | 15.806 | 40.740 | 1.00 | 25.91 | B | C |
| ATOM | 3011 | CD2 | TYR | B | 245 | 10.625 | 15.113 | 43.193 | 1.00 | 29.43 | B | C |

TABLE 2-continued coordinates for the two molecules in the asymmetric unit of [T287] Aurora A (122–396) in complex with an inhibitor of formula II in space group P2$_1$

| ATOM | 3012 | CE2 | TYR | B | 245 | 10.576 | 14.210 | 42.124 | 1.00 | 29.19 | B | C |
|---|---|---|---|---|---|---|---|---|---|---|---|---|
| ATOM | 3013 | CZ | TYR | B | 245 | 11.144 | 14.568 | 40.900 | 1.00 | 27.94 | B | C |
| ATOM | 3014 | OH | TYR | B | 245 | 11.131 | 13.687 | 39.842 | 1.00 | 26.95 | B | O |
| ATOM | 3015 | C | TYR | B | 245 | 13.808 | 17.026 | 44.261 | 1.00 | 27.59 | B | C |
| ATOM | 3016 | O | TYR | B | 245 | 14.272 | 15.897 | 44.117 | 1.00 | 27.11 | B | O |
| ATOM | 3017 | N | CYS | B | 246 | 14.372 | 18.099 | 43.711 | 1.00 | 27.30 | B | N |
| ATOM | 3018 | CA | CYS | B | 246 | 15.586 | 17.965 | 42.907 | 1.00 | 27.67 | B | C |
| ATOM | 3019 | CB | CYS | B | 246 | 15.926 | 19.284 | 42.202 | 1.00 | 27.42 | B | C |
| ATOM | 3020 | SG | CYS | B | 246 | 14.898 | 19.706 | 40.755 | 1.00 | 29.37 | B | S |
| ATOM | 3021 | C | CYS | B | 246 | 16.787 | 17.518 | 43.753 | 1.00 | 26.99 | B | C |
| ATOM | 3022 | O | CYS | B | 246 | 17.568 | 16.670 | 43.333 | 1.00 | 24.30 | B | O |
| ATOM | 3023 | N | HIS | B | 247 | 16.938 | 18.097 | 44.940 | 1.00 | 27.86 | B | N |
| ATOM | 3024 | CA | HIS | B | 247 | 18.048 | 17.734 | 45.813 | 1.00 | 28.63 | B | C |
| ATOM | 3025 | CB | HIS | B | 247 | 18.007 | 18.546 | 47.116 | 1.00 | 27.63 | B | C |
| ATOM | 3026 | CG | HIS | B | 247 | 18.519 | 19.950 | 46.976 | 1.00 | 27.06 | B | C |
| ATOM | 3027 | CD2 | HIS | B | 247 | 18.746 | 20.716 | 45.882 | 1.00 | 26.78 | B | C |
| ATOM | 3028 | ND1 | HIS | B | 247 | 18.873 | 20.724 | 48.062 | 1.00 | 26.58 | B | N |
| ATOM | 3029 | CE1 | HIS | B | 247 | 19.299 | 21.902 | 47.643 | 1.00 | 24.28 | B | C |
| ATOM | 3030 | NE2 | HIS | B | 247 | 19.232 | 21.923 | 46.325 | 1.00 | 24.21 | B | N |
| ATOM | 3031 | C | HIS | B | 247 | 18.006 | 16.241 | 46.128 | 1.00 | 30.30 | B | C |
| ATOM | 3032 | O | HIS | B | 247 | 19.046 | 15.594 | 46.243 | 1.00 | 29.75 | B | O |
| ATOM | 3033 | N | SER | B | 248 | 16.801 | 15.691 | 46.245 | 1.00 | 31.77 | B | N |
| ATOM | 3034 | CA | SER | B | 248 | 16.641 | 14.275 | 46.550 | 1.00 | 34.48 | B | C |
| ATOM | 3035 | CB | SER | B | 248 | 15.169 | 13.943 | 46.824 | 1.00 | 34.54 | B | C |
| ATOM | 3036 | OG | SER | B | 248 | 14.419 | 13.874 | 45.621 | 1.00 | 34.42 | B | O |
| ATOM | 3037 | C | SER | B | 248 | 17.166 | 13.396 | 45.417 | 1.00 | 36.24 | B | C |
| ATOM | 3038 | O | SER | B | 248 | 17.527 | 12.239 | 45.640 | 1.00 | 39.13 | B | O |
| ATOM | 3039 | N | LYS | B | 249 | 17.206 | 13.937 | 44.205 | 1.00 | 37.49 | B | N |
| ATOM | 3040 | CA | LYS | B | 249 | 17.714 | 13.183 | 43.065 | 1.00 | 38.33 | B | C |
| ATOM | 3041 | CB | LYS | B | 249 | 16.752 | 13.291 | 41.882 | 1.00 | 39.56 | B | C |
| ATOM | 3042 | CG | LYS | B | 249 | 15.480 | 12.470 | 42.075 | 1.00 | 41.09 | B | C |
| ATOM | 3043 | CD | LYS | B | 249 | 14.692 | 12.348 | 40.783 | 1.00 | 42.87 | B | C |
| ATOM | 3044 | CE | LYS | B | 249 | 13.544 | 11.345 | 40.903 | 1.00 | 44.69 | B | C |
| ATOM | 3045 | NZ | LYS | B | 249 | 14.008 | 9.940 | 41.115 | 1.00 | 43.80 | B | N |
| ATOM | 3046 | C | LYS | B | 249 | 19.110 | 13.649 | 42.667 | 1.00 | 38.25 | B | C |
| ATOM | 3047 | O | LYS | B | 249 | 19.535 | 13.500 | 41.520 | 1.00 | 38.18 | B | O |
| ATOM | 3048 | N | ALA | B | 250 | 19.823 | 14.208 | 43.639 | 1.00 | 38.25 | B | N |
| ATOM | 3049 | CA | ALA | B | 250 | 21.180 | 14.693 | 43.429 | 1.00 | 38.88 | B | C |
| ATOM | 3050 | CB | ALA | B | 250 | 22.128 | 13.506 | 43.260 | 1.00 | 37.35 | B | C |
| ATOM | 3051 | C | ALA | B | 250 | 21.294 | 15.642 | 42.234 | 1.00 | 39.66 | B | C |
| ATOM | 3052 | O | ALA | B | 250 | 22.256 | 15.586 | 41.469 | 1.00 | 39.73 | B | O |
| ATOM | 3053 | N | VAL | B | 251 | 20.312 | 16.521 | 42.077 | 1.00 | 40.68 | B | N |
| ATOM | 3054 | CA | VAL | B | 251 | 20.331 | 17.475 | 40.976 | 1.00 | 41.44 | B | C |
| ATOM | 3055 | CB | VAL | B | 251 | 19.009 | 17.448 | 40.197 | 1.00 | 39.71 | B | C |
| ATOM | 3056 | CG1 | VAL | B | 251 | 18.996 | 18.543 | 39.156 | 1.00 | 36.93 | B | C |
| ATOM | 3057 | CG2 | VAL | B | 251 | 18.833 | 16.099 | 39.542 | 1.00 | 39.66 | B | C |
| ATOM | 3058 | C | VAL | B | 251 | 20.575 | 18.887 | 41.487 | 1.00 | 43.36 | B | C |
| ATOM | 3059 | O | VAL | B | 251 | 19.857 | 19.361 | 42.361 | 1.00 | 43.18 | B | O |
| ATOM | 3060 | N | ALA | B | 252 | 21.594 | 19.572 | 41.411 | 1.00 | 47.23 | B | N |
| ATOM | 3061 | CA | ALA | B | 252 | 21.800 | 20.930 | 41.937 | 1.00 | 51.57 | B | C |
| ATOM | 3062 | CB | ALA | B | 252 | 23.072 | 20.979 | 42.781 | 1.00 | 50.06 | B | C |
| ATOM | 3063 | C | ALA | B | 252 | 21.867 | 21.974 | 40.811 | 1.00 | 55.17 | B | C |
| ATOM | 3064 | O | ALA | B | 252 | 22.516 | 21.755 | 39.786 | 1.00 | 55.31 | B | O |
| ATOM | 3065 | N | HIS | B | 253 | 21.201 | 23.110 | 41.025 | 1.00 | 59.25 | B | N |
| ATOM | 3066 | CA | HIS | B | 253 | 21.127 | 24.196 | 40.039 | 1.00 | 62.40 | B | C |
| ATOM | 3067 | CB | HIS | B | 253 | 19.928 | 25.100 | 40.346 | 1.00 | 63.38 | B | C |
| ATOM | 3068 | CG | HIS | B | 253 | 18.626 | 24.569 | 39.838 | 1.00 | 65.58 | B | C |
| ATOM | 3069 | CD2 | HIS | B | 253 | 17.728 | 25.093 | 38.970 | 1.00 | 65.78 | B | C |
| ATOM | 3070 | ND1 | HIS | B | 253 | 18.131 | 23.335 | 40.205 | 1.00 | 66.21 | B | N |
| ATOM | 3071 | CE1 | HIS | B | 253 | 16.985 | 23.122 | 39.583 | 1.00 | 66.24 | B | C |
| ATOM | 3072 | NE2 | HIS | B | 253 | 16.718 | 24.173 | 38.828 | 1.00 | 66.35 | B | N |
| ATOM | 3073 | C | HIS | B | 253 | 22.343 | 25.091 | 39.812 | 1.00 | 64.23 | B | C |
| ATOM | 3074 | O | HIS | B | 253 | 23.157 | 24.827 | 38.924 | 1.00 | 64.24 | B | O |
| ATOM | 3075 | N | ARG | B | 254 | 22.431 | 26.162 | 40.603 | 1.00 | 66.29 | B | N |
| ATOM | 3076 | CA | ARG | B | 254 | 23.501 | 27.162 | 40.503 | 1.00 | 67.93 | B | C |
| ATOM | 3077 | CB | ARG | B | 254 | 24.829 | 26.507 | 40.106 | 1.00 | 69.34 | B | C |
| ATOM | 3078 | CG | ARG | B | 254 | 25.429 | 25.629 | 41.199 | 1.00 | 72.18 | B | C |
| ATOM | 3079 | CD | ARG | B | 254 | 26.435 | 24.626 | 40.649 | 1.00 | 73.87 | B | C |
| ATOM | 3080 | NE | ARG | B | 254 | 27.423 | 25.232 | 39.760 | 1.00 | 76.14 | B | N |
| ATOM | 3081 | CZ | ARG | B | 254 | 28.423 | 24.559 | 39.197 | 1.00 | 77.32 | B | C |
| ATOM | 3082 | NH1 | ARG | B | 254 | 28.566 | 23.259 | 39.435 | 1.00 | 77.53 | B | N |
| ATOM | 3083 | NH2 | ARG | B | 254 | 29.275 | 25.180 | 38.391 | 1.00 | 77.47 | B | N |
| ATOM | 3084 | C | ARG | B | 254 | 23.093 | 28.203 | 39.455 | 1.00 | 68.10 | B | C |
| ATOM | 3085 | O | ARG | B | 254 | 23.941 | 28.818 | 38.805 | 1.00 | 68.48 | B | O |
| ATOM | 3086 | N | ASP | B | 255 | 21.779 | 28.383 | 39.311 | 1.00 | 67.94 | B | N |
| ATOM | 3087 | CA | ASP | B | 255 | 21.181 | 29.321 | 38.358 | 1.00 | 66.09 | B | C |

TABLE 2-continued coordinates for the two molecules in the asymmetric unit of [T287] Aurora A (122–396) in complex with an inhibitor of formula II in space group P2₁

| ATOM | 3088 | CB  | ASP | B | 255 | 21.768 | 29.117 | 36.960 | 1.00 | 68.18 B | C |
|------|------|-----|-----|---|-----|--------|--------|--------|------|---------|---|
| ATOM | 3089 | CG  | ASP | B | 255 | 20.978 | 29.848 | 35.891 | 1.00 | 70.20 B | C |
| ATOM | 3090 | OD1 | ASP | B | 255 | 20.977 | 31.098 | 35.906 | 1.00 | 70.85 B | O |
| ATOM | 3091 | OD2 | ASP | B | 255 | 20.346 | 29.176 | 35.045 | 1.00 | 70.61 B | O |
| ATOM | 3092 | C   | ASP | B | 255 | 19.670 | 29.086 | 38.290 | 1.00 | 64.02 B | C |
| ATOM | 3093 | O   | ASP | B | 255 | 19.224 | 27.980 | 37.966 | 1.00 | 63.85 B | O |
| ATOM | 3094 | N   | ILE | B | 256 | 18.887 | 30.123 | 38.587 | 1.00 | 60.24 B | N |
| ATOM | 3095 | CA  | ILE | B | 256 | 17.432 | 30.007 | 38.557 | 1.00 | 56.06 B | C |
| ATOM | 3096 | CB  | ILE | B | 256 | 16.938 | 29.251 | 39.813 | 1.00 | 56.48 B | C |
| ATOM | 3097 | CG2 | ILE | B | 256 | 17.097 | 30.123 | 41.051 | 1.00 | 57.30 B | C |
| ATOM | 3098 | CG1 | ILE | B | 256 | 15.483 | 28.833 | 39.637 | 1.00 | 56.77 B | C |
| ATOM | 3099 | CD1 | ILE | B | 256 | 15.012 | 27.833 | 40.671 | 1.00 | 57.42 B | C |
| ATOM | 3100 | C   | ILE | B | 256 | 16.727 | 31.371 | 38.444 | 1.00 | 52.46 B | C |
| ATOM | 3101 | O   | ILE | B | 256 | 15.769 | 31.661 | 39.154 | 1.00 | 51.61 B | O |
| ATOM | 3102 | N   | LYS | B | 257 | 17.209 | 32.193 | 37.521 | 1.00 | 48.41 B | N |
| ATOM | 3103 | CA  | LYS | B | 257 | 16.684 | 33.536 | 37.258 | 1.00 | 44.89 B | C |
| ATOM | 3104 | CB  | LYS | B | 257 | 17.469 | 34.142 | 36.094 | 1.00 | 45.52 B | C |
| ATOM | 3105 | CG  | LYS | B | 257 | 18.981 | 34.051 | 36.249 | 1.00 | 48.52 B | C |
| ATOM | 3106 | CD  | LYS | B | 257 | 19.703 | 34.586 | 35.017 | 1.00 | 50.54 B | C |
| ATOM | 3107 | CE  | LYS | B | 257 | 19.499 | 33.695 | 33.791 | 1.00 | 50.70 B | C |
| ATOM | 3108 | NZ  | LYS | B | 257 | 20.251 | 32.406 | 33.875 | 1.00 | 51.10 B | N |
| ATOM | 3109 | C   | LYS | B | 257 | 15.177 | 33.614 | 36.941 | 1.00 | 40.75 B | C |
| ATOM | 3110 | O   | LYS | B | 257 | 14.548 | 32.614 | 36.614 | 1.00 | 40.52 B | O |
| ATOM | 3111 | N   | PRO | B | 258 | 14.480 | 34.397 | 36.931 | 1.00 | 37.08 B | N |
| ATOM | 3112 | CD  | PRO | B | 258 | 15.445 | 35.391 | 37.431 | 1.00 | 36.34 B | C |
| ATOM | 3113 | CA  | PRO | B | 258 | 13.167 | 35.015 | 36.690 | 1.00 | 35.17 B | C |
| ATOM | 3114 | CB  | PRO | B | 258 | 13.397 | 36.489 | 37.038 | 1.00 | 34.26 B | C |
| ATOM | 3115 | CG  | PRO | B | 258 | 14.544 | 36.448 | 38.017 | 1.00 | 33.40 B | C |
| ATOM | 3116 | C   | PRO | B | 258 | 12.770 | 34.825 | 35.227 | 1.00 | 34.61 B | C |
| ATOM | 3117 | O   | PRO | B | 258 | 11.604 | 34.576 | 34.908 | 1.00 | 31.39 B | O |
| ATOM | 3118 | N   | GLU | B | 259 | 13.757 | 34.954 | 34.346 | 1.00 | 33.54 B | N |
| ATOM | 3119 | CA  | GLU | B | 259 | 13.540 | 34.769 | 32.918 | 1.00 | 34.62 B | C |
| ATOM | 3120 | CB  | GLU | B | 259 | 14.706 | 35.332 | 32.100 | 1.00 | 37.22 B | C |
| ATOM | 3121 | CG  | GLU | B | 259 | 15.143 | 36.745 | 32.442 | 1.00 | 41.67 B | C |
| ATOM | 3122 | CD  | GLU | B | 259 | 15.934 | 36.826 | 33.735 | 1.00 | 44.39 B | C |
| ATOM | 3123 | OE1 | GLU | B | 259 | 16.564 | 37.874 | 33.978 | 1.00 | 46.55 B | O |
| ATOM | 3124 | OE2 | GLU | B | 259 | 15.924 | 35.851 | 34.515 | 1.00 | 46.90 B | O |
| ATOM | 3125 | C   | GLU | B | 259 | 13.469 | 33.265 | 32.678 | 1.00 | 34.06 B | C |
| ATOM | 3126 | O   | GLU | B | 259 | 13.004 | 32.812 | 31.632 | 1.00 | 34.68 B | O |
| ATOM | 3127 | N   | ASN | B | 260 | 13.943 | 32.492 | 33.652 | 1.00 | 31.75 B | N |
| ATOM | 3128 | CA  | ASN | B | 260 | 13.941 | 31.042 | 33.527 | 1.00 | 30.54 B | C |
| ATOM | 3129 | CB  | ASN | B | 260 | 15.262 | 30.455 | 34.035 | 1.00 | 34.15 B | C |
| ATOM | 3130 | CG  | ASN | B | 260 | 16.474 | 31.178 | 33.478 | 1.00 | 39.70 B | C |
| ATOM | 3131 | OD1 | ASN | B | 260 | 16.454 | 31.681 | 32.347 | 1.00 | 41.30 B | O |
| ATOM | 3132 | ND2 | ASN | B | 260 | 17.545 | 31.226 | 34.265 | 1.00 | 40.33 B | N |
| ATOM | 3133 | C   | ASN | B | 260 | 12.785 | 30.413 | 34.284 | 1.00 | 27.70 B | C |
| ATOM | 3134 | O   | ASN | B | 260 | 12.723 | 29.194 | 34.423 | 1.00 | 28.09 B | O |
| ATOM | 3135 | N   | LEU | B | 261 | 11.879 | 31.244 | 34.783 | 1.00 | 23.87 B | N |
| ATOM | 3136 | CA  | LEU | B | 261 | 10.715 | 30.748 | 35.511 | 1.00 | 23.63 B | C |
| ATOM | 3137 | CB  | LEU | B | 261 | 10.636 | 31.393 | 36.904 | 1.00 | 23.52 B | C |
| ATOM | 3138 | CG  | LEU | B | 261 | 11.859 | 31.157 | 37.802 | 1.00 | 23.80 B | C |
| ATOM | 3139 | CD1 | LEU | B | 261 | 11.784 | 32.065 | 39.013 | 1.00 | 23.16 B | C |
| ATOM | 3140 | CD2 | LEU | B | 261 | 11.918 | 29.696 | 38.233 | 1.00 | 23.15 B | C |
| ATOM | 3141 | C   | LEU | B | 261 | 9.486  | 31.094 | 34.683 | 1.00 | 22.79 B | C |
| ATOM | 3142 | O   | LEU | B | 261 | 9.248  | 32.259 | 34.360 | 1.00 | 23.35 B | O |
| ATOM | 3143 | N   | LEU | B | 262 | 8.720  | 30.072 | 34.329 | 1.00 | 21.85 B | N |
| ATOM | 3144 | CA  | LEU | B | 262 | 7.530  | 30.240 | 33.503 | 1.00 | 20.81 B | C |
| ATOM | 3145 | CB  | LEU | B | 262 | 7.583  | 29.241 | 32.338 | 1.00 | 18.28 B | C |
| ATOM | 3146 | CG  | LEU | B | 262 | 8.805  | 29.444 | 31.427 | 1.00 | 20.74 B | C |
| ATOM | 3147 | CD1 | LEU | B | 262 | 9.022  | 28.247 | 30.528 | 1.00 | 17.18 B | C |
| ATOM | 3148 | CD2 | LEU | B | 262 | 8.594  | 30.704 | 30.600 | 1.00 | 23.22 B | C |
| ATOM | 3149 | C   | LEU | B | 262 | 6.260  | 30.050 | 34.324 | 1.00 | 20.95 B | C |
| ATOM | 3150 | O   | LEU | B | 262 | 6.320  | 29.607 | 35.468 | 1.00 | 21.65 B | O |
| ATOM | 3151 | N   | LEU | B | 263 | 5.118  | 30.385 | 33.731 | 1.00 | 20.04 B | N |
| ATOM | 3152 | CA  | LEU | B | 263 | 3.818  | 30.291 | 34.401 | 1.00 | 19.89 B | C |
| ATOM | 3153 | CB  | LEU | B | 263 | 3.199  | 31.682 | 34.542 | 1.00 | 19.96 B | C |
| ATOM | 3154 | CG  | LEU | B | 263 | 3.895  | 32.673 | 35.485 | 1.00 | 22.61 B | C |
| ATOM | 3155 | CD1 | LEU | B | 263 | 3.332  | 34.074 | 35.269 | 1.00 | 19.88 B | C |
| ATOM | 3156 | CD2 | LEU | B | 263 | 3.689  | 32.218 | 36.938 | 1.00 | 19.42 B | C |
| ATOM | 3157 | C   | LEU | B | 263 | 2.828  | 29.405 | 33.667 | 1.00 | 20.69 B | C |
| ATOM | 3158 | O   | LEU | B | 263 | 2.555  | 29.607 | 32.477 | 1.00 | 19.05 B | O |
| ATOM | 3159 | N   | GLY | B | 264 | 2.285  | 28.434 | 34.390 | 1.00 | 20.39 B | N |
| ATOM | 3160 | CA  | GLY | B | 264 | 1.318  | 27.531 | 33.810 | 1.00 | 22.81 B | C |
| ATOM | 3161 | C   | GLY | B | 264 | −0.058 | 28.166 | 33.723 | 1.00 | 23.93 B | C |
| ATOM | 3162 | O   | GLY | B | 264 | −0.267 | 29.307 | 34.146 | 1.00 | 23.55 B | O |
| ATOM | 3163 | N   | SER | B | 265 | −0.996 | 27.406 | 33.178 | 1.00 | 26.43 B | N |

TABLE 2-continued coordinates for the two molecules in the asymmetric unit of [T287] Aurora A (122–396) in complex with an inhibitor of formula II in space group P2$_1$

| ATOM | 3164 | CA  | SER | B | 265 | −2.375 | 27.846 | 33.002 | 1.00 | 29.74 B | C |
|------|------|-----|-----|---|-----|--------|--------|--------|------|---------|---|
| ATOM | 3165 | CB  | SER | B | 265 | −3.224 | 26.687 | 32.478 | 1.00 | 30.89 B | C |
| ATOM | 3166 | OG  | SER | B | 265 | −4.593 | 27.054 | 32.458 | 1.00 | 37.32 B | O |
| ATOM | 3167 | C   | SER | B | 265 | −3.026 | 28.398 | 34.267 | 1.00 | 30.10 B | C |
| ATOM | 3168 | O   | SER | B | 265 | −3.786 | 29.356 | 34.203 | 1.00 | 31.27 B | O |
| ATOM | 3169 | N   | ALA | B | 266 | −2.738 | 27.790 | 35.411 | 1.00 | 29.46 B | N |
| ATOM | 3170 | CA  | ALA | B | 266 | −3.319 | 28.239 | 36.670 | 1.00 | 28.49 B | C |
| ATOM | 3171 | CB  | ALA | B | 266 | −3.645 | 27.040 | 37.546 | 1.00 | 27.90 B | C |
| ATOM | 3172 | C   | ALA | B | 266 | −2.424 | 29.202 | 37.433 | 1.00 | 27.49 B | C |
| ATOM | 3173 | O   | ALA | B | 266 | −2.673 | 29.486 | 38.594 | 1.00 | 26.71 B | O |
| ATOM | 3174 | N   | GLY | B | 267 | −1.380 | 29.704 | 36.785 | 1.00 | 28.52 B | N |
| ATOM | 3175 | CA  | GLY | B | 267 | −0.485 | 30.630 | 37.458 | 1.00 | 27.29 B | C |
| ATOM | 3176 | C   | GLY | B | 267 | 0.556  | 29.951 | 38.335 | 1.00 | 26.61 B | C |
| ATOM | 3177 | O   | GLY | B | 267 | 1.155  | 30.591 | 39.203 | 1.00 | 27.45 B | O |
| ATOM | 3178 | N   | GLU | B | 268 | 0.780  | 28.660 | 38.117 | 1.00 | 25.29 B | N |
| ATOM | 3179 | CA  | GLU | B | 268 | 1.766  | 27.924 | 38.905 | 1.00 | 26.30 B | C |
| ATOM | 3180 | CB  | GLU | B | 268 | 1.409  | 26.433 | 38.967 | 1.00 | 27.43 B | C |
| ATOM | 3181 | CG  | GLU | B | 268 | 0.012  | 26.107 | 38.488 | 1.00 | 34.47 B | C |
| ATOM | 3182 | CD  | GLU | B | 268 | −0.087 | 26.008 | 36.976 | 1.00 | 35.53 B | C |
| ATOM | 3183 | OE1 | GLU | B | 268 | 0.297  | 24.958 | 36.423 | 1.00 | 38.92 B | O |
| ATOM | 3184 | OE2 | GLU | B | 268 | −0.546 | 26.979 | 36.339 | 1.00 | 38.49 B | O |
| ATOM | 3185 | C   | GLU | B | 268 | 3.154  | 28.083 | 38.287 | 1.00 | 24.38 B | C |
| ATOM | 3186 | O   | GLU | B | 268 | 3.300  | 28.062 | 37.063 | 1.00 | 21.68 B | O |
| ATOM | 3187 | N   | LEU | B | 269 | 4.171  | 28.250 | 39.129 | 1.00 | 23.82 B | N |
| ATOM | 3188 | CA  | LEU | B | 269 | 5.542  | 28.398 | 38.634 | 1.00 | 21.61 B | C |
| ATOM | 3189 | CB  | LEU | B | 269 | 6.492  | 28.808 | 39.761 | 1.00 | 24.33 B | C |
| ATOM | 3190 | CG  | LEU | B | 269 | 6.545  | 30.246 | 40.265 | 1.00 | 25.70 B | C |
| ATOM | 3191 | CD1 | LEU | B | 269 | 7.693  | 30.382 | 41.252 | 1.00 | 24.92 B | C |
| ATOM | 3192 | CD2 | LEU | B | 269 | 6.751  | 31.198 | 39.103 | 1.00 | 27.39 B | C |
| ATOM | 3193 | C   | LEU | B | 269 | 6.061  | 27.099 | 38.034 | 1.00 | 19.77 B | C |
| ATOM | 3194 | O   | LEU | B | 269 | 5.703  | 26.015 | 38.485 | 1.00 | 19.34 B | O |
| ATOM | 3195 | N   | LYS | B | 270 | 6.909  | 27.222 | 37.017 | 1.00 | 19.92 B | N |
| ATOM | 3196 | CA  | LYS | B | 270 | 7.525  | 26.074 | 36.356 | 1.00 | 20.30 B | C |
| ATOM | 3197 | CB  | LYS | B | 270 | 6.902  | 25.836 | 34.972 | 1.00 | 18.33 B | C |
| ATOM | 3198 | CG  | LYS | B | 270 | 5.393  | 25.615 | 34.964 | 1.00 | 18.74 B | C |
| ATOM | 3199 | CD  | LYS | B | 270 | 5.012  | 24.155 | 35.137 | 1.00 | 15.50 B | C |
| ATOM | 3200 | CE  | LYS | B | 270 | 3.491  | 23.994 | 35.128 | 1.00 | 18.10 B | C |
| ATOM | 3201 | NZ  | LYS | B | 270 | 3.046  | 22.575 | 35.077 | 1.00 | 15.24 B | N |
| ATOM | 3202 | C   | LYS | B | 270 | 9.019  | 26.383 | 36.178 | 1.00 | 20.49 B | C |
| ATOM | 3203 | O   | LYS | B | 270 | 9.373  | 27.374 | 35.550 | 1.00 | 18.08 B | O |
| ATOM | 3204 | N   | ILE | B | 271 | 9.889  | 25.545 | 36.737 | 1.00 | 21.09 B | N |
| ATOM | 3205 | CA  | ILE | B | 271 | 11.329 | 25.756 | 36.587 | 1.00 | 20.68 B | C |
| ATOM | 3206 | CB  | ILE | B | 271 | 12.133 | 25.016 | 37.674 | 1.00 | 21.21 B | C |
| ATOM | 3207 | CG2 | ILE | B | 271 | 13.640 | 25.176 | 37.413 | 1.00 | 19.34 B | C |
| ATOM | 3208 | CG1 | ILE | B | 271 | 11.761 | 25.553 | 39.060 | 1.00 | 23.24 B | C |
| ATOM | 3209 | CD1 | ILE | B | 271 | 12.514 | 24.863 | 40.210 | 1.00 | 24.09 B | C |
| ATOM | 3210 | C   | ILE | B | 271 | 11.754 | 25.207 | 35.224 | 1.00 | 20.59 B | C |
| ATOM | 3211 | O   | ILE | B | 271 | 11.482 | 24.051 | 34.911 | 1.00 | 19.44 B | O |
| ATOM | 3212 | N   | ALA | B | 272 | 12.410 | 26.034 | 34.416 | 1.00 | 19.34 B | N |
| ATOM | 3213 | CA  | ALA | B | 272 | 12.858 | 25.598 | 33.095 | 1.00 | 24.16 B | C |
| ATOM | 3214 | CB  | ALA | B | 272 | 12.404 | 26.594 | 32.037 | 1.00 | 20.99 B | C |
| ATOM | 3215 | C   | ALA | B | 272 | 14.384 | 25.434 | 33.039 | 1.00 | 26.77 B | C |
| ATOM | 3216 | O   | ALA | B | 272 | 15.106 | 26.155 | 33.723 | 1.00 | 27.46 B | O |
| ATOM | 3217 | N   | ASP | B | 273 | 14.843 | 24.478 | 32.225 | 1.00 | 29.94 B | N |
| ATOM | 3218 | CA  | ASP | B | 273 | 16.265 | 24.150 | 32.014 | 1.00 | 32.45 B | C |
| ATOM | 3219 | CB  | ASP | B | 273 | 17.153 | 25.351 | 32.319 | 1.00 | 33.94 B | C |
| ATOM | 3220 | CG  | ASP | B | 273 | 17.622 | 26.038 | 31.068 | 1.00 | 38.34 B | C |
| ATOM | 3221 | OD1 | ASP | B | 273 | 18.171 | 27.165 | 31.162 | 1.00 | 41.51 B | O |
| ATOM | 3222 | OD2 | ASP | B | 273 | 17.439 | 25.436 | 29.986 | 1.00 | 36.50 B | O |
| ATOM | 3223 | C   | ASP | B | 273 | 16.799 | 22.930 | 32.767 | 1.00 | 34.27 B | C |
| ATOM | 3224 | O   | ASP | B | 273 | 17.928 | 22.472 | 32.518 | 1.00 | 34.48 B | O |
| ATOM | 3225 | N   | GLY | B | 290 | 22.452 | 32.822 | 36.840 | 1.00 | 57.41 B | N |
| ATOM | 3226 | CA  | GLY | B | 290 | 22.919 | 33.188 | 35.513 | 1.00 | 56.55 B | C |
| ATOM | 3227 | C   | GLY | B | 290 | 23.992 | 34.260 | 35.563 | 1.00 | 56.09 B | C |
| ATOM | 3228 | O   | GLY | B | 290 | 25.185 | 33.954 | 35.650 | 1.00 | 56.35 B | O |
| ATOM | 3229 | N   | THR | B | 291 | 23.572 | 35.522 | 35.508 | 1.00 | 54.56 B | N |
| ATOM | 3230 | CA  | THR | B | 291 | 24.511 | 36.633 | 35.555 | 1.00 | 52.44 B | C |
| ATOM | 3231 | CB  | THR | B | 291 | 23.813 | 37.967 | 35.195 | 1.00 | 53.95 B | C |
| ATOM | 3232 | OG1 | THR | B | 291 | 22.687 | 38.172 | 36.056 | 1.00 | 54.88 B | O |
| ATOM | 3233 | CG2 | THR | B | 291 | 23.338 | 37.946 | 33.746 | 1.00 | 55.03 B | C |
| ATOM | 3234 | C   | THR | B | 291 | 25.140 | 36.738 | 36.945 | 1.00 | 50.11 B | C |
| ATOM | 3235 | O   | THR | B | 291 | 24.840 | 35.940 | 37.840 | 1.00 | 47.96 B | O |
| ATOM | 3236 | N   | LEU | B | 292 | 26.010 | 37.727 | 37.123 | 1.00 | 47.85 B | N |
| ATOM | 3237 | CA  | LEU | B | 292 | 26.695 | 37.926 | 38.395 | 1.00 | 46.13 B | C |
| ATOM | 3238 | CB  | LEU | B | 292 | 27.664 | 39.109 | 38.280 | 1.00 | 46.70 B | C |
| ATOM | 3239 | CG  | LEU | B | 292 | 28.706 | 39.250 | 39.393 | 1.00 | 47.14 B | C |

TABLE 2-continued coordinates for the two molecules in the asymmetric unit of [T287] Aurora
A (122–396) in complex with an inhibitor of formula II in space group P2$_1$

| ATOM | 3240 | CD1 | LEU | B | 292 | 29.422 | 37.921 | 39.596 | 1.00 | 46.68 B | C |
|---|---|---|---|---|---|---|---|---|---|---|---|
| ATOM | 3241 | CD2 | LEU | B | 292 | 29.704 | 40.342 | 39.030 | 1.00 | 46.77 B | C |
| ATOM | 3242 | C | LEU | B | 292 | 25.740 | 38.143 | 39.573 | 1.00 | 44.02 B | C |
| ATOM | 3243 | O | LEU | B | 292 | 25.967 | 37.638 | 40.675 | 1.00 | 43.84 B | O |
| ATOM | 3244 | N | ASP | B | 293 | 24.663 | 38.879 | 39.330 | 1.00 | 41.14 B | N |
| ATOM | 3245 | CA | ASP | B | 293 | 23.687 | 39.172 | 40.371 | 1.00 | 40.18 B | C |
| ATOM | 3246 | CB | ASP | B | 293 | 22.551 | 40.010 | 39.789 | 1.00 | 40.75 B | C |
| ATOM | 3247 | CG | ASP | B | 293 | 22.969 | 41.428 | 39.508 | 1.00 | 39.93 B | C |
| ATOM | 3248 | OD1 | ASP | B | 293 | 23.770 | 41.635 | 38.578 | 1.00 | 43.70 B | O |
| ATOM | 3249 | OD2 | ASP | B | 293 | 22.510 | 42.336 | 40.227 | 1.00 | 42.04 B | O |
| ATOM | 3250 | C | ASP | B | 293 | 23.084 | 37.986 | 41.124 | 1.00 | 38.77 B | C |
| ATOM | 3251 | O | ASP | B | 293 | 22.442 | 38.175 | 42.157 | 1.00 | 36.99 B | O |
| ATOM | 3252 | N | TYR | B | 294 | 23.288 | 36.770 | 40.628 | 1.00 | 38.33 B | N |
| ATOM | 3253 | CA | TYR | B | 294 | 22.704 | 35.607 | 41.284 | 1.00 | 36.46 B | C |
| ATOM | 3254 | CB | TYR | B | 294 | 21.721 | 34.923 | 40.324 | 1.00 | 37.01 B | C |
| ATOM | 3255 | CG | TYR | B | 294 | 20.645 | 35.862 | 39.813 | 1.00 | 36.29 B | C |
| ATOM | 3256 | CD1 | TYR | B | 294 | 20.894 | 36.732 | 38.747 | 1.00 | 36.77 B | C |
| ATOM | 3257 | CE1 | TYR | B | 294 | 19.932 | 37.650 | 38.324 | 1.00 | 35.17 B | C |
| ATOM | 3258 | CD2 | TYR | B | 294 | 19.405 | 35.931 | 40.440 | 1.00 | 33.86 B | C |
| ATOM | 3259 | CE2 | TYR | B | 294 | 18.438 | 36.841 | 40.029 | 1.00 | 34.67 B | C |
| ATOM | 3260 | CZ | TYR | B | 294 | 18.707 | 37.700 | 38.974 | 1.00 | 36.81 B | C |
| ATOM | 3261 | OH | TYR | B | 294 | 17.747 | 38.614 | 38.586 | 1.00 | 37.64 B | O |
| ATOM | 3262 | C | TYR | B | 294 | 23.674 | 34.573 | 41.855 | 1.00 | 35.29 B | C |
| ATOM | 3263 | O | TYR | B | 294 | 23.241 | 33.612 | 42.482 | 1.00 | 33.83 B | O |
| ATOM | 3264 | N | LEU | B | 295 | 24.975 | 34.768 | 41.664 | 1.00 | 34.16 B | N |
| ATOM | 3265 | CA | LEU | B | 295 | 25.946 | 33.804 | 42.180 | 1.00 | 34.73 B | C |
| ATOM | 3266 | CB | LEU | B | 295 | 27.191 | 33.790 | 41.287 | 1.00 | 35.44 B | C |
| ATOM | 3267 | CG | LEU | B | 295 | 26.941 | 33.402 | 39.822 | 1.00 | 37.31 B | C |
| ATOM | 3268 | CD1 | LEU | B | 295 | 28.232 | 33.537 | 39.015 | 1.00 | 38.09 B | C |
| ATOM | 3269 | CD2 | LEU | B | 295 | 26.409 | 31.974 | 39.754 | 1.00 | 37.09 B | C |
| ATOM | 3270 | C | LEU | B | 295 | 26.340 | 34.071 | 43.635 | 1.00 | 33.23 B | C |
| ATOM | 3271 | O | LEU | B | 295 | 26.485 | 35.220 | 44.045 | 1.00 | 33.47 B | O |
| ATOM | 3272 | N | PRO | B | 296 | 26.501 | 33.003 | 44.438 | 1.00 | 32.82 B | N |
| ATOM | 3273 | CD | PRO | B | 296 | 26.174 | 31.603 | 44.099 | 1.00 | 32.14 B | C |
| ATOM | 3274 | CA | PRO | B | 296 | 26.877 | 33.123 | 45.852 | 1.00 | 32.58 B | C |
| ATOM | 3275 | CB | PRO | B | 296 | 26.408 | 31.796 | 46.442 | 1.00 | 30.74 B | C |
| ATOM | 3276 | CG | PRO | B | 296 | 26.654 | 30.841 | 45.321 | 1.00 | 30.81 B | C |
| ATOM | 3277 | C | PRO | B | 296 | 28.380 | 33.355 | 46.069 | 1.00 | 34.00 B | C |
| ATOM | 3278 | O | PRO | B | 296 | 29.185 | 33.190 | 45.150 | 1.00 | 32.17 B | O |
| ATOM | 3279 | N | PRO | B | 297 | 28.771 | 33.744 | 47.297 | 1.00 | 35.08 B | N |
| ATOM | 3280 | CD | PRO | B | 297 | 27.894 | 34.068 | 48.438 | 1.00 | 34.25 B | C |
| ATOM | 3281 | CA | PRO | B | 297 | 30.174 | 33.999 | 47.639 | 1.00 | 36.33 B | C |
| ATOM | 3282 | CB | PRO | B | 297 | 30.111 | 34.293 | 49.137 | 1.00 | 34.76 B | C |
| ATOM | 3283 | CG | PRO | B | 297 | 28.777 | 34.948 | 49.287 | 1.00 | 34.10 B | C |
| ATOM | 3284 | C | PRO | B | 297 | 31.128 | 32.840 | 47.314 | 1.00 | 37.57 B | C |
| ATOM | 3285 | O | PRO | B | 297 | 32.097 | 33.021 | 46.583 | 1.00 | 39.23 B | O |
| ATOM | 3286 | N | GLU | B | 298 | 30.847 | 31.654 | 47.848 | 1.00 | 38.80 B | N |
| ATOM | 3287 | CA | GLU | B | 298 | 31.709 | 30.491 | 47.626 | 1.00 | 40.63 B | C |
| ATOM | 3288 | CB | GLU | B | 298 | 31.108 | 29.232 | 48.260 | 1.00 | 39.54 B | C |
| ATOM | 3289 | CG | GLU | B | 298 | 29.823 | 28.761 | 47.590 | 1.00 | 38.57 B | C |
| ATOM | 3290 | CD | GLU | B | 298 | 28.592 | 29.251 | 48.313 | 1.00 | 37.66 B | C |
| ATOM | 3291 | OE1 | GLU | B | 298 | 28.601 | 30.406 | 48.795 | 1.00 | 38.14 B | O |
| ATOM | 3292 | OE2 | GLU | B | 298 | 27.618 | 28.481 | 48.400 | 1.00 | 36.41 B | O |
| ATOM | 3293 | C | GLU | B | 298 | 32.016 | 30.187 | 46.164 | 1.00 | 42.36 B | C |
| ATOM | 3294 | O | GLU | B | 298 | 32.873 | 29.355 | 45.874 | 1.00 | 42.42 B | O |
| ATOM | 3295 | N | MET | B | 299 | 31.317 | 30.837 | 45.241 | 1.00 | 44.46 B | N |
| ATOM | 3296 | CA | MET | B | 299 | 31.572 | 30.589 | 43.830 | 1.00 | 46.93 B | C |
| ATOM | 3297 | CB | MET | B | 299 | 30.262 | 30.454 | 43.054 | 1.00 | 47.22 B | C |
| ATOM | 3298 | CG | MET | B | 299 | 29.494 | 29.190 | 43.410 | 1.00 | 49.38 B | C |
| ATOM | 3299 | SD | MET | B | 299 | 28.411 | 28.637 | 42.093 | 1.00 | 51.57 B | S |
| ATOM | 3300 | CE | MET | B | 299 | 29.502 | 27.513 | 41.247 | 1.00 | 53.08 B | C |
| ATOM | 3301 | C | MET | B | 299 | 32.447 | 31.662 | 43.212 | 1.00 | 47.79 B | C |
| ATOM | 3302 | O | MET | B | 299 | 33.416 | 31.350 | 42.522 | 1.00 | 48.57 B | O |
| ATOM | 3303 | N | ILE | B | 300 | 32.118 | 32.926 | 43.457 | 1.00 | 48.73 B | N |
| ATOM | 3304 | CA | ILE | B | 300 | 32.930 | 34.004 | 42.914 | 1.00 | 49.57 B | C |
| ATOM | 3305 | CB | ILE | B | 300 | 32.190 | 35.362 | 42.968 | 1.00 | 49.76 B | C |
| ATOM | 3306 | CG2 | ILE | B | 300 | 30.896 | 35.273 | 42.171 | 1.00 | 49.66 B | C |
| ATOM | 3307 | CG1 | ILE | B | 300 | 31.904 | 35.761 | 44.416 | 1.00 | 48.39 B | C |
| ATOM | 3308 | CD1 | ILE | B | 300 | 31.295 | 37.143 | 44.540 | 1.00 | 47.07 B | C |
| ATOM | 3309 | C | ILE | B | 300 | 34.243 | 34.096 | 43.697 | 1.00 | 50.74 B | C |
| ATOM | 3310 | O | ILE | B | 300 | 35.253 | 34.571 | 43.177 | 1.00 | 50.30 B | O |
| ATOM | 3311 | N | GLU | B | 301 | 34.226 | 33.630 | 44.943 | 1.00 | 52.24 B | N |
| ATOM | 3312 | CA | GLU | B | 301 | 35.424 | 33.648 | 45.776 | 1.00 | 54.57 B | C |
| ATOM | 3313 | CB | GLU | B | 301 | 35.058 | 33.596 | 47.267 | 1.00 | 55.69 B | C |
| ATOM | 3314 | CG | GLU | B | 301 | 34.210 | 34.770 | 47.737 | 1.00 | 58.62 B | C |
| ATOM | 3315 | CD | GLU | B | 301 | 34.020 | 34.806 | 49.247 | 1.00 | 59.50 B | C |

TABLE 2-continued coordinates for the two molecules in the asymmetric unit of [T287] Aurora A (122–396) in complex with an inhibitor of formula II in space group P2₁

| ATOM | 3316 | OE1 | GLU | B | 301 | 33.827 | 33.731 | 49.855 | 1.00 | 60.80 | B | O |
|---|---|---|---|---|---|---|---|---|---|---|---|---|
| ATOM | 3317 | OE2 | GLU | B | 301 | 34.046 | 35.915 | 49.823 | 1.00 | 59.81 | B | O |
| ATOM | 3318 | C | GLU | B | 301 | 36.309 | 32.456 | 45.421 | 1.00 | 55.44 | B | C |
| ATOM | 3319 | O | GLU | B | 301 | 37.419 | 32.322 | 45.936 | 1.00 | 55.50 | B | O |
| ATOM | 3320 | N | GLY | B | 302 | 35.804 | 31.590 | 44.544 | 1.00 | 55.63 | B | N |
| ATOM | 3321 | CA | GLY | B | 302 | 36.567 | 30.429 | 44.119 | 1.00 | 56.55 | B | C |
| ATOM | 3322 | C | GLY | B | 302 | 36.457 | 29.193 | 44.995 | 1.00 | 57.16 | B | C |
| ATOM | 3323 | O | GLY | B | 302 | 36.823 | 28.100 | 44.563 | 1.00 | 57.49 | B | O |
| ATOM | 3324 | N | ARG | B | 303 | 35.966 | 29.359 | 46.221 | 1.00 | 57.72 | B | N |
| ATOM | 3325 | CA | ARG | B | 303 | 35.808 | 28.241 | 47.149 | 1.00 | 57.79 | B | C |
| ATOM | 3326 | CB | ARG | B | 303 | 35.094 | 28.702 | 48.419 | 1.00 | 58.72 | B | C |
| ATOM | 3327 | CG | ARG | B | 303 | 35.855 | 29.706 | 49.257 | 1.00 | 61.00 | B | C |
| ATOM | 3328 | CD | ARG | B | 303 | 34.963 | 30.239 | 50.366 | 1.00 | 62.94 | B | C |
| ATOM | 3329 | NE | ARG | B | 303 | 35.680 | 31.094 | 51.309 | 1.00 | 64.60 | B | N |
| ATOM | 3330 | CZ | ARG | B | 303 | 36.606 | 30.661 | 52.160 | 1.00 | 65.49 | B | C |
| ATOM | 3331 | NH1 | ARG | B | 303 | 37.203 | 31.514 | 52.982 | 1.00 | 65.70 | B | N |
| ATOM | 3332 | NH2 | ARG | B | 303 | 36.936 | 29.376 | 52.191 | 1.00 | 65.53 | B | N |
| ATOM | 3333 | C | ARG | B | 303 | 34.995 | 27.119 | 46.517 | 1.00 | 58.00 | B | C |
| ATOM | 3334 | O | ARG | B | 303 | 34.586 | 27.209 | 45.358 | 1.00 | 58.81 | B | O |
| ATOM | 3335 | N | MET | B | 304 | 34.758 | 26.060 | 47.284 | 1.00 | 57.39 | B | N |
| ATOM | 3336 | CA | MET | B | 304 | 33.974 | 24.934 | 46.792 | 1.00 | 56.99 | B | C |
| ATOM | 3337 | CB | MET | B | 304 | 34.389 | 23.647 | 47.508 | 1.00 | 59.63 | B | C |
| ATOM | 3338 | CG | MET | B | 304 | 34.471 | 22.435 | 46.594 | 1.00 | 63.14 | B | C |
| ATOM | 3339 | SD | MET | B | 304 | 32.911 | 22.046 | 45.769 | 1.00 | 67.12 | B | S |
| ATOM | 3340 | CE | MET | B | 304 | 32.278 | 20.749 | 46.851 | 1.00 | 66.78 | B | C |
| ATOM | 3341 | C | MET | B | 304 | 32.504 | 25.247 | 47.072 | 1.00 | 54.74 | B | C |
| ATOM | 3342 | O | MET | B | 304 | 32.197 | 26.264 | 47.691 | 1.00 | 53.70 | B | O |
| ATOM | 3343 | N | HIS | B | 305 | 31.600 | 24.382 | 46.618 | 1.00 | 52.40 | B | N |
| ATOM | 3344 | CA | HIS | B | 305 | 30.170 | 24.598 | 46.826 | 1.00 | 49.37 | B | C |
| ATOM | 3345 | CB | HIS | B | 305 | 29.638 | 25.583 | 45.791 | 1.00 | 49.86 | B | C |
| ATOM | 3346 | CG | HIS | B | 305 | 29.857 | 25.138 | 44.380 | 1.00 | 51.90 | B | C |
| ATOM | 3347 | CD2 | HIS | B | 305 | 28.986 | 24.712 | 43.434 | 1.00 | 52.04 | B | C |
| ATOM | 3348 | ND1 | HIS | B | 305 | 31.110 | 25.069 | 43.809 | 1.00 | 51.78 | B | N |
| ATOM | 3349 | CE1 | HIS | B | 305 | 31.000 | 24.619 | 42.571 | 1.00 | 53.53 | B | C |
| ATOM | 3350 | NE2 | HIS | B | 305 | 29.723 | 24.395 | 42.319 | 1.00 | 53.06 | B | N |
| ATOM | 3351 | C | HIS | B | 305 | 29.347 | 23.312 | 46.750 | 1.00 | 46.97 | B | C |
| ATOM | 3352 | O | HIS | B | 305 | 29.791 | 22.296 | 46.208 | 1.00 | 46.30 | B | O |
| ATOM | 3353 | N | ASP | B | 306 | 28.135 | 23.372 | 47.289 | 1.00 | 43.16 | B | N |
| ATOM | 3354 | CA | ASP | B | 306 | 27.246 | 22.224 | 47.279 | 1.00 | 40.92 | B | C |
| ATOM | 3355 | CB | ASP | B | 306 | 27.405 | 21.433 | 48.586 | 1.00 | 40.71 | B | C |
| ATOM | 3356 | CG | ASP | B | 306 | 26.952 | 22.210 | 49.805 | 1.00 | 40.75 | B | C |
| ATOM | 3357 | OD1 | ASP | B | 306 | 26.828 | 23.449 | 49.725 | 1.00 | 40.70 | B | O |
| ATOM | 3358 | OD2 | ASP | B | 306 | 26.729 | 21.574 | 50.853 | 1.00 | 42.16 | B | O |
| ATOM | 3359 | C | ASP | B | 306 | 25.797 | 22.670 | 47.077 | 1.00 | 39.86 | B | C |
| ATOM | 3360 | O | ASP | B | 306 | 25.545 | 23.734 | 46.505 | 1.00 | 39.27 | B | O |
| ATOM | 3361 | N | GLU | B | 307 | 24.851 | 21.858 | 47.542 | 1.00 | 37.39 | B | N |
| ATOM | 3362 | CA | GLU | B | 307 | 23.437 | 22.179 | 47.392 | 1.00 | 35.90 | B | C |
| ATOM | 3363 | CB | GLU | B | 307 | 22.562 | 21.048 | 47.939 | 1.00 | 37.19 | B | C |
| ATOM | 3364 | CG | GLU | B | 307 | 23.310 | 19.796 | 48.370 | 1.00 | 42.69 | B | C |
| ATOM | 3365 | CD | GLU | B | 307 | 23.978 | 19.942 | 49.723 | 1.00 | 43.86 | B | C |
| ATOM | 3366 | OE1 | GLU | B | 307 | 23.275 | 20.245 | 50.713 | 1.00 | 46.08 | B | O |
| ATOM | 3367 | OE2 | GLU | B | 307 | 25.205 | 19.747 | 49.798 | 1.00 | 45.78 | B | O |
| ATOM | 3368 | C | GLU | B | 307 | 23.049 | 23.484 | 48.083 | 1.00 | 34.05 | B | C |
| ATOM | 3369 | O | GLU | B | 307 | 21.948 | 24.005 | 47.862 | 1.00 | 30.38 | B | O |
| ATOM | 3370 | N | LYS | B | 308 | 23.953 | 24.017 | 48.905 | 1.00 | 29.97 | B | N |
| ATOM | 3371 | CA | LYS | B | 308 | 23.660 | 25.247 | 49.632 | 1.00 | 27.77 | B | C |
| ATOM | 3372 | CB | LYS | B | 308 | 24.706 | 25.485 | 50.723 | 1.00 | 29.00 | B | C |
| ATOM | 3373 | CG | LYS | B | 308 | 24.669 | 24.472 | 51.857 | 1.00 | 30.48 | B | C |
| ATOM | 3374 | CD | LYS | B | 308 | 23.346 | 24.521 | 52.605 | 1.00 | 31.68 | B | C |
| ATOM | 3375 | CE | LYS | B | 308 | 23.442 | 23.788 | 53.921 | 1.00 | 32.64 | B | C |
| ATOM | 3376 | NZ | LYS | B | 308 | 22.194 | 23.897 | 54.726 | 1.00 | 32.70 | B | N |
| ATOM | 3377 | C | LYS | B | 308 | 23.536 | 26.485 | 48.743 | 1.00 | 25.47 | B | C |
| ATOM | 3378 | O | LYS | B | 308 | 23.007 | 27.504 | 49.177 | 1.00 | 23.55 | B | O |
| ATOM | 3379 | N | VAL | B | 309 | 24.011 | 26.405 | 47.504 | 1.00 | 23.68 | B | N |
| ATOM | 3380 | CA | VAL | B | 309 | 23.894 | 27.549 | 46.612 | 1.00 | 23.94 | B | C |
| ATOM | 3381 | CB | VAL | B | 309 | 24.666 | 27.334 | 45.284 | 1.00 | 23.56 | B | C |
| ATOM | 3382 | CG1 | VAL | B | 309 | 26.147 | 27.135 | 45.572 | 1.00 | 26.07 | B | C |
| ATOM | 3383 | CG2 | VAL | B | 309 | 24.101 | 26.148 | 44.528 | 1.00 | 23.94 | B | C |
| ATOM | 3384 | C | VAL | B | 309 | 22.423 | 27.853 | 46.291 | 1.00 | 24.19 | B | C |
| ATOM | 3385 | O | VAL | B | 309 | 22.051 | 29.017 | 46.139 | 1.00 | 25.34 | B | O |
| ATOM | 3386 | N | ASP | B | 310 | 21.589 | 26.815 | 46.197 | 1.00 | 23.71 | B | N |
| ATOM | 3387 | CA | ASP | B | 310 | 20.169 | 27.007 | 45.897 | 1.00 | 22.68 | B | C |
| ATOM | 3388 | CB | ASP | B | 310 | 19.454 | 25.656 | 45.690 | 1.00 | 23.58 | B | C |
| ATOM | 3389 | CG | ASP | B | 310 | 19.924 | 24.934 | 44.434 | 1.00 | 27.55 | B | C |
| ATOM | 3390 | OD1 | ASP | B | 310 | 20.273 | 25.612 | 43.445 | 1.00 | 28.81 | B | O |
| ATOM | 3391 | OD2 | ASP | B | 310 | 19.936 | 23.688 | 44.419 | 1.00 | 31.31 | B | O |

TABLE 2-continued coordinates for the two molecules in the asymmetric unit of [T287] Aurora
A (122–396) in complex with an inhibitor of formula II in space group P2₁

| ATOM | 3392 | C   | ASP | B | 310 | 19.466 | 27.816 | 46.983 | 1.00 | 21.05 B | C |
| ---- | ---- | --- | --- | - | --- | ------ | ------ | ------ | ---- | ------- | - |
| ATOM | 3393 | O   | ASP | B | 310 | 18.512 | 28.545 | 46.701 | 1.00 | 20.77 B | O |
| ATOM | 3394 | N   | LEU | B | 311 | 19.935 | 27.690 | 48.222 | 1.00 | 20.13 B | N |
| ATOM | 3395 | CA  | LEU | B | 311 | 19.353 | 28.444 | 49.327 | 1.00 | 19.16 B | C |
| ATOM | 3396 | CB  | LEU | B | 311 | 19.885 | 27.942 | 50.676 | 1.00 | 19.21 B | C |
| ATOM | 3397 | CG  | LEU | B | 311 | 19.208 | 26.743 | 51.357 | 1.00 | 21.60 B | C |
| ATOM | 3398 | CD1 | LEU | B | 311 | 17.737 | 27.054 | 51.572 | 1.00 | 20.35 B | C |
| ATOM | 3399 | CD2 | LEU | B | 311 | 19.360 | 25.484 | 50.528 | 1.00 | 19.65 B | C |
| ATOM | 3400 | C   | LEU | B | 311 | 19.664 | 29.934 | 49.174 | 1.00 | 19.50 B | C |
| ATOM | 3401 | O   | LEU | B | 311 | 18.853 | 30.791 | 49.530 | 1.00 | 17.78 B | O |
| ATOM | 3402 | N   | TRP | B | 312 | 20.848 | 30.245 | 48.653 | 1.00 | 20.26 B | N |
| ATOM | 3403 | CA  | TRP | B | 312 | 21.226 | 31.634 | 48.452 | 1.00 | 19.28 B | C |
| ATOM | 3404 | CB  | TRP | B | 312 | 22.716 | 31.729 | 48.109 | 1.00 | 20.45 B | C |
| ATOM | 3405 | CG  | TRP | B | 312 | 23.156 | 33.064 | 47.620 | 1.00 | 18.65 B | C |
| ATOM | 3406 | CD2 | TRP | B | 312 | 23.784 | 34.092 | 48.390 | 1.00 | 19.00 B | C |
| ATOM | 3407 | CE2 | TRP | B | 312 | 24.034 | 35.176 | 47.515 | 1.00 | 18.21 B | C |
| ATOM | 3408 | CE3 | TRP | B | 312 | 24.161 | 34.205 | 49.733 | 1.00 | 20.36 B | C |
| ATOM | 3409 | CD1 | TRP | B | 312 | 23.048 | 33.551 | 46.344 | 1.00 | 20.44 B | C |
| ATOM | 3410 | NE1 | TRP | B | 312 | 23.574 | 34.820 | 46.274 | 1.00 | 19.77 B | N |
| ATOM | 3411 | CZ2 | TRP | B | 312 | 24.646 | 36.354 | 47.940 | 1.00 | 18.87 B | C |
| ATOM | 3412 | CZ3 | TRP | B | 312 | 24.771 | 35.379 | 50.157 | 1.00 | 19.61 B | C |
| ATOM | 3413 | CH2 | TRP | B | 312 | 25.007 | 36.438 | 49.260 | 1.00 | 21.25 B | C |
| ATOM | 3414 | C   | TRP | B | 312 | 20.389 | 32.206 | 47.326 | 1.00 | 20.24 B | C |
| ATOM | 3415 | O   | TRP | B | 312 | 19.903 | 33.334 | 47.408 | 1.00 | 18.37 B | O |
| ATOM | 3416 | N   | SER | B | 313 | 20.236 | 31.421 | 46.263 | 1.00 | 20.08 B | N |
| ATOM | 3417 | CA  | SER | B | 313 | 19.455 | 31.845 | 45.113 | 1.00 | 19.43 B | C |
| ATOM | 3418 | CB  | SER | B | 313 | 19.460 | 30.760 | 44.037 | 1.00 | 20.79 B | C |
| ATOM | 3419 | OG  | SER | B | 313 | 20.741 | 30.657 | 43.448 | 1.00 | 24.62 B | O |
| ATOM | 3420 | C   | SER | B | 313 | 18.024 | 32.156 | 45.502 | 1.00 | 19.39 B | C |
| ATOM | 3421 | O   | SER | B | 313 | 17.403 | 33.035 | 44.920 | 1.00 | 18.50 B | O |
| ATOM | 3422 | N   | LEU | B | 314 | 17.512 | 31.442 | 46.498 | 1.00 | 19.22 B | N |
| ATOM | 3423 | CA  | LEU | B | 314 | 16.141 | 31.641 | 46.960 | 1.00 | 19.58 B | C |
| ATOM | 3424 | CB  | LEU | B | 314 | 15.737 | 30.476 | 47.871 | 1.00 | 20.69 B | C |
| ATOM | 3425 | CG  | LEU | B | 314 | 14.276 | 30.024 | 47.987 | 1.00 | 23.50 B | C |
| ATOM | 3426 | CD1 | LEU | B | 314 | 13.682 | 29.761 | 46.608 | 1.00 | 20.26 B | C |
| ATOM | 3427 | CD2 | LEU | B | 314 | 14.215 | 28.758 | 48.843 | 1.00 | 20.22 B | C |
| ATOM | 3428 | C   | LEU | B | 314 | 16.021 | 32.976 | 47.693 | 1.00 | 19.00 B | C |
| ATOM | 3429 | O   | LEU | B | 314 | 14.973 | 33.637 | 47.632 | 1.00 | 20.65 B | O |
| ATOM | 3430 | N   | GLY | B | 315 | 17.097 | 33.372 | 48.375 | 1.00 | 17.95 B | N |
| ATOM | 3431 | CA  | GLY | B | 315 | 17.112 | 34.638 | 49.097 | 1.00 | 14.32 B | C |
| ATOM | 3432 | C   | GLY | B | 315 | 17.085 | 35.805 | 48.120 | 1.00 | 15.06 B | C |
| ATOM | 3433 | O   | GLY | B | 315 | 16.308 | 36.753 | 48.270 | 1.00 | 15.06 B | O |
| ATOM | 3434 | N   | VAL | B | 316 | 17.930 | 35.728 | 47.098 | 1.00 | 15.22 B | N |
| ATOM | 3435 | CA  | VAL | B | 316 | 17.996 | 36.775 | 46.090 | 1.00 | 15.50 B | C |
| ATOM | 3436 | CB  | VAL | B | 316 | 19.115 | 36.487 | 45.050 | 1.00 | 17.46 B | C |
| ATOM | 3437 | CG1 | VAL | B | 316 | 19.005 | 37.470 | 43.858 | 1.00 | 15.92 B | C |
| ATOM | 3438 | CG2 | VAL | B | 316 | 20.492 | 36.626 | 45.715 | 1.00 | 15.82 B | C |
| ATOM | 3439 | C   | VAL | B | 316 | 16.651 | 36.899 | 45.387 | 1.00 | 15.41 B | C |
| ATOM | 3440 | O   | VAL | B | 316 | 16.152 | 38.004 | 45.193 | 1.00 | 18.18 B | O |
| ATOM | 3441 | N   | LEU | B | 317 | 16.063 | 35.764 | 45.020 | 1.00 | 15.83 B | N |
| ATOM | 3442 | CA  | LEU | B | 317 | 14.762 | 35.729 | 44.350 | 1.00 | 17.96 B | C |
| ATOM | 3443 | CB  | LEU | B | 317 | 14.399 | 34.276 | 44.019 | 1.00 | 22.63 B | C |
| ATOM | 3444 | CG  | LEU | B | 317 | 14.200 | 33.825 | 42.569 | 1.00 | 28.46 B | C |
| ATOM | 3445 | CD1 | LEU | B | 317 | 15.254 | 34.441 | 41.657 | 1.00 | 30.81 B | C |
| ATOM | 3446 | CD2 | LEU | B | 317 | 14.273 | 32.299 | 42.512 | 1.00 | 30.80 B | C |
| ATOM | 3447 | C   | LEU | B | 317 | 13.653 | 36.359 | 45.204 | 1.00 | 17.12 B | C |
| ATOM | 3448 | O   | LEU | B | 317 | 12.877 | 37.184 | 44.721 | 1.00 | 17.94 B | O |
| ATOM | 3449 | N   | CYS | B | 318 | 13.575 | 35.961 | 46.472 | 1.00 | 15.77 B | N |
| ATOM | 3450 | CA  | CYS | B | 318 | 12.569 | 36.494 | 47.386 | 1.00 | 13.11 B | C |
| ATOM | 3451 | CB  | CYS | B | 318 | 12.718 | 35.837 | 48.762 | 1.00 | 12.76 B | C |
| ATOM | 3452 | SG  | CYS | B | 318 | 11.422 | 36.262 | 49.915 | 1.00 | 14.06 B | S |
| ATOM | 3453 | C   | CYS | B | 318 | 12.683 | 38.017 | 47.521 | 1.00 | 14.34 B | C |
| ATOM | 3454 | O   | CYS | B | 318 | 11.672 | 38.730 | 47.550 | 1.00 | 17.24 B | O |
| ATOM | 3455 | N   | TYR | B | 319 | 13.913 | 38.513 | 47.611 | 1.00 | 15.07 B | N |
| ATOM | 3456 | CA  | TYR | B | 319 | 14.149 | 39.950 | 47.726 | 1.00 | 15.31 B | C |
| ATOM | 3457 | CB  | TYR | B | 319 | 15.642 | 40.217 | 47.992 | 1.00 | 17.63 B | C |
| ATOM | 3458 | CG  | TYR | B | 319 | 16.029 | 41.679 | 48.141 | 1.00 | 18.67 B | C |
| ATOM | 3459 | CD1 | TYR | B | 319 | 16.103 | 42.524 | 47.032 | 1.00 | 20.95 B | C |
| ATOM | 3460 | CE1 | TYR | B | 319 | 16.465 | 43.878 | 47.172 | 1.00 | 22.71 B | C |
| ATOM | 3461 | CD2 | TYR | B | 319 | 16.327 | 42.215 | 49.398 | 1.00 | 21.26 B | C |
| ATOM | 3462 | CE2 | TYR | B | 319 | 16.687 | 43.560 | 49.552 | 1.00 | 22.44 B | C |
| ATOM | 3463 | CZ  | TYR | B | 319 | 16.752 | 44.384 | 48.436 | 1.00 | 23.40 B | C |
| ATOM | 3464 | OH  | TYR | B | 319 | 17.074 | 45.713 | 48.592 | 1.00 | 22.93 B | O |
| ATOM | 3465 | C   | TYR | B | 319 | 13.719 | 40.650 | 46.430 | 1.00 | 15.75 B | C |
| ATOM | 3466 | O   | TYR | B | 319 | 13.009 | 41.655 | 46.461 | 1.00 | 15.99 B | O |
| ATOM | 3467 | N   | GLU | B | 320 | 14.156 | 40.125 | 45.289 | 1.00 | 14.73 B | N |

TABLE 2-continued coordinates for the two molecules in the asymmetric unit of [T287] Aurora
A (122–396) in complex with an inhibitor of formula II in space group P2₁

| ATOM | 3468 | CA  | GLU | B | 320 | 13.782 | 40.736 | 44.021 | 1.00 | 17.64 | B | C |
|------|------|-----|-----|---|-----|--------|--------|--------|------|-------|---|---|
| ATOM | 3469 | CB  | GLU | B | 320 | 14.463 | 40.031 | 42.853 | 1.00 | 17.46 | B | C |
| ATOM | 3470 | CG  | GLU | B | 320 | 14.174 | 40.726 | 41.542 | 1.00 | 22.76 | B | C |
| ATOM | 3471 | CD  | GLU | B | 320 | 15.125 | 40.341 | 40.423 | 1.00 | 26.48 | B | C |
| ATOM | 3472 | OE1 | GLU | B | 320 | 15.023 | 40.974 | 39.359 | 1.00 | 28.28 | B | O |
| ATOM | 3473 | OE2 | GLU | B | 320 | 15.967 | 39.426 | 40.592 | 1.00 | 26.81 | B | O |
| ATOM | 3474 | C   | GLU | B | 320 | 12.264 | 40.748 | 43.811 | 1.00 | 17.10 | B | C |
| ATOM | 3475 | O   | GLU | B | 320 | 11.719 | 41.682 | 43.237 | 1.00 | 20.22 | B | O |
| ATOM | 3476 | N   | PHE | B | 321 | 11.573 | 39.720 | 44.276 | 1.00 | 17.49 | B | N |
| ATOM | 3477 | CA  | PHE | B | 321 | 10.126 | 39.703 | 44.121 | 1.00 | 18.22 | B | C |
| ATOM | 3478 | CB  | PHE | B | 321 | 9.524  | 38.385 | 44.622 | 1.00 | 18.69 | B | C |
| ATOM | 3479 | CG  | PHE | B | 321 | 9.701  | 37.231 | 43.683 | 1.00 | 21.02 | B | C |
| ATOM | 3480 | CD1 | PHE | B | 321 | 10.056 | 37.439 | 42.351 | 1.00 | 21.40 | B | C |
| ATOM | 3481 | CD2 | PHE | B | 321 | 9.498  | 35.930 | 44.126 | 1.00 | 22.14 | B | C |
| ATOM | 3482 | CE1 | PHE | B | 321 | 10.209 | 36.366 | 41.479 | 1.00 | 21.40 | B | C |
| ATOM | 3483 | CE2 | PHE | B | 321 | 9.648  | 34.853 | 43.260 | 1.00 | 23.29 | B | C |
| ATOM | 3484 | CZ  | PHE | B | 321 | 10.006 | 35.073 | 41.935 | 1.00 | 22.08 | B | C |
| ATOM | 3485 | C   | PHE | B | 321 | 9.469  | 40.841 | 44.887 | 1.00 | 20.00 | B | C |
| ATOM | 3486 | O   | PHE | B | 321 | 8.563  | 41.499 | 44.375 | 1.00 | 19.40 | B | O |
| ATOM | 3487 | N   | LEU | B | 322 | 9.919  | 41.057 | 46.123 | 1.00 | 20.34 | B | N |
| ATOM | 3488 | CA  | LEU | B | 322 | 9.351  | 42.089 | 46.991 | 1.00 | 21.70 | B | C |
| ATOM | 3489 | CB  | LEU | B | 322 | 9.645  | 41.760 | 48.459 | 1.00 | 20.38 | B | C |
| ATOM | 3490 | CG  | LEU | B | 322 | 8.924  | 40.530 | 49.008 | 1.00 | 20.56 | B | C |
| ATOM | 3491 | CD1 | LEU | B | 322 | 9.485  | 40.164 | 50.385 | 1.00 | 21.26 | B | C |
| ATOM | 3492 | CD2 | LEU | B | 322 | 7.427  | 40.822 | 49.085 | 1.00 | 17.17 | B | C |
| ATOM | 3493 | C   | LEU | B | 322 | 9.796  | 43.516 | 46.719 | 1.00 | 22.34 | B | C |
| ATOM | 3494 | O   | LEU | B | 322 | 9.027  | 44.451 | 46.927 | 1.00 | 23.00 | B | O |
| ATOM | 3495 | N   | VAL | B | 323 | 11.024 | 43.679 | 46.247 | 1.00 | 22.63 | B | N |
| ATOM | 3496 | CA  | VAL | B | 323 | 11.571 | 45.006 | 45.994 | 1.00 | 24.72 | B | C |
| ATOM | 3497 | CB  | VAL | B | 323 | 13.034 | 45.072 | 46.495 | 1.00 | 22.95 | B | C |
| ATOM | 3498 | CG1 | VAL | B | 323 | 13.655 | 46.414 | 46.172 | 1.00 | 24.04 | B | C |
| ATOM | 3499 | CG2 | VAL | B | 323 | 13.054 | 44.856 | 48.002 | 1.00 | 23.23 | B | C |
| ATOM | 3500 | C   | VAL | B | 323 | 11.486 | 45.443 | 44.535 | 1.00 | 25.81 | B | C |
| ATOM | 3501 | O   | VAL | B | 323 | 11.200 | 46.606 | 44.245 | 1.00 | 26.53 | B | O |
| ATOM | 3502 | N   | GLY | B | 324 | 11.730 | 44.516 | 43.617 | 1.00 | 25.39 | B | N |
| ATOM | 3503 | CA  | GLY | B | 324 | 11.651 | 44.857 | 42.213 | 1.00 | 25.94 | B | C |
| ATOM | 3504 | C   | GLY | B | 324 | 12.980 | 44.762 | 41.508 | 1.00 | 26.51 | B | C |
| ATOM | 3505 | O   | GLY | B | 324 | 13.024 | 44.751 | 40.282 | 1.00 | 27.88 | B | O |
| ATOM | 3506 | N   | LYS | B | 325 | 14.062 | 44.709 | 42.281 | 1.00 | 27.18 | B | N |
| ATOM | 3507 | CA  | LYS | B | 325 | 15.407 | 44.599 | 41.732 | 1.00 | 28.30 | B | C |
| ATOM | 3508 | CB  | LYS | B | 325 | 16.040 | 45.985 | 41.573 | 1.00 | 32.53 | B | C |
| ATOM | 3509 | CG  | LYS | B | 325 | 16.057 | 46.809 | 42.843 | 1.00 | 36.71 | B | C |
| ATOM | 3510 | CD  | LYS | B | 325 | 16.678 | 48.183 | 42.605 | 1.00 | 41.59 | B | C |
| ATOM | 3511 | CE  | LYS | B | 325 | 16.621 | 49.053 | 43.864 | 1.00 | 44.11 | B | C |
| ATOM | 3512 | NZ  | LYS | B | 325 | 17.286 | 48.415 | 45.044 | 1.00 | 44.74 | B | N |
| ATOM | 3513 | C   | LYS | B | 325 | 16.259 | 43.749 | 42.666 | 1.00 | 28.12 | B | C |
| ATOM | 3514 | O   | LYS | B | 325 | 15.940 | 43.606 | 43.845 | 1.00 | 26.18 | B | O |
| ATOM | 3515 | N   | PRO | B | 326 | 17.348 | 43.160 | 42.147 | 1.00 | 26.86 | B | N |
| ATOM | 3516 | CD  | PRO | B | 326 | 17.790 | 43.134 | 40.742 | 1.00 | 26.79 | B | C |
| ATOM | 3517 | CA  | PRO | B | 326 | 18.212 | 42.330 | 42.991 | 1.00 | 26.22 | B | C |
| ATOM | 3518 | CB  | PRO | B | 326 | 19.137 | 41.653 | 41.979 | 1.00 | 27.30 | B | C |
| ATOM | 3519 | CG  | PRO | B | 326 | 19.215 | 42.656 | 40.863 | 1.00 | 26.62 | B | C |
| ATOM | 3520 | C   | PRO | B | 326 | 18.952 | 43.159 | 44.048 | 1.00 | 25.76 | B | C |
| ATOM | 3521 | O   | PRO | B | 326 | 19.249 | 44.330 | 43.838 | 1.00 | 24.87 | B | O |
| ATOM | 3522 | N   | PRO | B | 327 | 19.257 | 42.546 | 45.201 | 1.00 | 25.19 | B | N |
| ATOM | 3523 | CD  | PRO | B | 327 | 19.005 | 41.111 | 45.435 | 1.00 | 24.23 | B | C |
| ATOM | 3524 | CA  | PRO | B | 327 | 19.945 | 43.148 | 46.350 | 1.00 | 24.63 | B | C |
| ATOM | 3525 | CB  | PRO | B | 327 | 19.864 | 42.046 | 47.407 | 1.00 | 23.95 | B | C |
| ATOM | 3526 | CG  | PRO | B | 327 | 19.947 | 40.801 | 46.589 | 1.00 | 24.61 | B | C |
| ATOM | 3527 | C   | PRO | B | 327 | 21.376 | 43.684 | 46.198 | 1.00 | 25.54 | B | C |
| ATOM | 3528 | O   | PRO | B | 327 | 21.766 | 44.598 | 46.917 | 1.00 | 23.51 | B | O |
| ATOM | 3529 | N   | PHE | B | 328 | 22.158 | 43.128 | 45.280 | 1.00 | 27.17 | B | N |
| ATOM | 3530 | CA  | PHE | B | 328 | 23.540 | 43.572 | 45.107 | 1.00 | 27.57 | B | C |
| ATOM | 3531 | CB  | PHE | B | 328 | 24.480 | 42.365 | 45.205 | 1.00 | 24.24 | B | C |
| ATOM | 3532 | CG  | PHE | B | 328 | 24.257 | 41.519 | 46.432 | 1.00 | 23.37 | B | C |
| ATOM | 3533 | CD1 | PHE | B | 328 | 24.674 | 41.964 | 47.694 | 1.00 | 21.17 | B | C |
| ATOM | 3534 | CD2 | PHE | B | 328 | 23.609 | 40.286 | 46.334 | 1.00 | 20.04 | B | C |
| ATOM | 3535 | CE1 | PHE | B | 328 | 24.449 | 41.195 | 48.832 | 1.00 | 19.30 | B | C |
| ATOM | 3536 | CE2 | PHE | B | 328 | 23.377 | 39.505 | 47.465 | 1.00 | 21.16 | B | C |
| ATOM | 3537 | CZ  | PHE | B | 328 | 23.801 | 39.963 | 48.725 | 1.00 | 21.41 | B | C |
| ATOM | 3538 | C   | PHE | B | 328 | 23.778 | 44.306 | 43.786 | 1.00 | 30.91 | B | C |
| ATOM | 3539 | O   | PHE | B | 328 | 24.920 | 44.593 | 43.424 | 1.00 | 29.74 | B | O |
| ATOM | 3540 | N   | GLU | B | 329 | 22.699 | 44.617 | 43.073 | 1.00 | 35.49 | B | N |
| ATOM | 3541 | CA  | GLU | B | 329 | 22.809 | 45.312 | 41.792 | 1.00 | 39.40 | B | C |
| ATOM | 3542 | CB  | GLU | B | 329 | 21.422 | 45.680 | 41.257 | 1.00 | 40.82 | B | C |
| ATOM | 3543 | CG  | GLU | B | 329 | 21.439 | 46.221 | 39.829 | 1.00 | 44.77 | B | C |

TABLE 2-continued coordinates for the two molecules in the asymmetric unit of [T287] Aurora
A (122–396) in complex with an inhibitor of formula II in space group P2₁

| ATOM | 3544 | CD | GLU | B | 329 | 20.104 | 46.816 | 39.401 | 1.00 | 45.81 | B | C |
|------|------|-----|-----|---|-----|--------|--------|--------|------|-------|---|---|
| ATOM | 3545 | OE1 | GLU | B | 329 | 19.695 | 47.839 | 39.986 | 1.00 | 46.10 | B | O |
| ATOM | 3546 | OE2 | GLU | B | 329 | 19.465 | 46.262 | 38.480 | 1.00 | 47.31 | B | O |
| ATOM | 3547 | C | GLU | B | 329 | 23.643 | 46.579 | 41.920 | 1.00 | 41.08 | B | C |
| ATOM | 3548 | O | GLU | B | 329 | 23.353 | 47.444 | 42.740 | 1.00 | 40.70 | B | O |
| ATOM | 3549 | N | ALA | B | 330 | 24.686 | 46.678 | 41.106 | 1.00 | 43.84 | B | N |
| ATOM | 3550 | CA | ALA | B | 330 | 25.554 | 47.848 | 41.120 | 1.00 | 46.89 | B | C |
| ATOM | 3551 | CB | ALA | B | 330 | 26.943 | 47.469 | 41.610 | 1.00 | 45.55 | B | C |
| ATOM | 3552 | C | ALA | B | 330 | 25.633 | 48.417 | 39.709 | 1.00 | 49.66 | B | C |
| ATOM | 3553 | O | ALA | B | 330 | 25.028 | 47.884 | 38.776 | 1.00 | 50.00 | B | O |
| ATOM | 3554 | N | ASN | B | 331 | 26.382 | 49.500 | 39.556 | 1.00 | 52.10 | B | N |
| ATOM | 3555 | CA | ASN | B | 331 | 26.531 | 50.134 | 38.256 | 1.00 | 54.10 | B | C |
| ATOM | 3556 | CB | ASN | B | 331 | 26.785 | 51.634 | 38.436 | 1.00 | 55.63 | B | C |
| ATOM | 3557 | CG | ASN | B | 331 | 26.419 | 52.446 | 37.205 | 1.00 | 57.22 | B | C |
| ATOM | 3558 | OD1 | ASN | B | 331 | 26.304 | 53.671 | 37.271 | 1.00 | 57.48 | B | O |
| ATOM | 3559 | ND2 | ASN | B | 331 | 26.240 | 51.768 | 36.074 | 1.00 | 58.16 | B | N |
| ATOM | 3560 | C | ASN | B | 331 | 27.691 | 49.481 | 37.513 | 1.00 | 54.40 | B | C |
| ATOM | 3561 | O | ASN | B | 331 | 27.748 | 49.517 | 36.286 | 1.00 | 54.29 | B | O |
| ATOM | 3562 | N | THR | B | 332 | 28.602 | 48.867 | 38.266 | 1.00 | 55.19 | B | N |
| ATOM | 3563 | CA | THR | B | 332 | 29.761 | 48.202 | 37.676 | 1.00 | 55.71 | B | C |
| ATOM | 3564 | CB | THR | B | 332 | 31.056 | 49.020 | 37.908 | 1.00 | 55.73 | B | C |
| ATOM | 3565 | OG1 | THR | B | 332 | 32.189 | 48.248 | 37.491 | 1.00 | 56.87 | B | O |
| ATOM | 3566 | CG2 | THR | B | 332 | 31.210 | 49.385 | 39.371 | 1.00 | 55.37 | B | C |
| ATOM | 3567 | C | THR | B | 332 | 29.977 | 46.787 | 38.206 | 1.00 | 56.55 | B | C |
| ATOM | 3568 | O | THR | B | 332 | 29.604 | 46.466 | 39.337 | 1.00 | 57.13 | B | O |
| ATOM | 3569 | N | TYR | B | 333 | 30.587 | 45.945 | 37.377 | 1.00 | 56.97 | B | N |
| ATOM | 3570 | CA | TYR | B | 333 | 30.861 | 44.558 | 37.739 | 1.00 | 56.81 | B | C |
| ATOM | 3571 | CB | TYR | B | 333 | 31.623 | 43.848 | 36.610 | 1.00 | 58.85 | B | C |
| ATOM | 3572 | CG | TYR | B | 333 | 30.984 | 43.930 | 35.233 | 1.00 | 62.30 | B | C |
| ATOM | 3573 | CD1 | TYR | B | 333 | 31.675 | 43.490 | 34.099 | 1.00 | 62.80 | B | C |
| ATOM | 3574 | CE1 | TYR | B | 333 | 31.103 | 43.563 | 32.826 | 1.00 | 63.19 | B | C |
| ATOM | 3575 | CD2 | TYR | B | 333 | 29.695 | 44.446 | 35.057 | 1.00 | 63.26 | B | C |
| ATOM | 3576 | CE2 | TYR | B | 333 | 29.114 | 44.521 | 33.786 | 1.00 | 63.66 | B | C |
| ATOM | 3577 | CZ | TYR | B | 333 | 29.825 | 44.079 | 32.678 | 1.00 | 63.50 | B | C |
| ATOM | 3578 | OH | TYR | B | 333 | 29.257 | 44.153 | 31.425 | 1.00 | 63.78 | B | O |
| ATOM | 3579 | C | TYR | B | 333 | 31.697 | 44.484 | 39.012 | 1.00 | 55.92 | B | C |
| ATOM | 3580 | O | TYR | B | 333 | 31.351 | 43.770 | 39.950 | 1.00 | 56.04 | B | O |
| ATOM | 3581 | N | GLN | B | 334 | 32.802 | 45.224 | 39.033 | 1.00 | 55.18 | B | N |
| ATOM | 3582 | CA | GLN | B | 334 | 33.711 | 45.227 | 40.176 | 1.00 | 54.38 | B | C |
| ATOM | 3583 | CB | GLN | B | 334 | 34.871 | 46.203 | 39.925 | 1.00 | 55.19 | B | C |
| ATOM | 3584 | CG | GLN | B | 334 | 34.482 | 47.678 | 39.879 | 1.00 | 57.42 | B | C |
| ATOM | 3585 | CD | GLN | B | 334 | 35.599 | 48.566 | 39.340 | 1.00 | 59.56 | B | C |
| ATOM | 3586 | OE1 | GLN | B | 334 | 36.756 | 48.459 | 39.759 | 1.00 | 60.33 | B | O |
| ATOM | 3587 | NE2 | GLN | B | 334 | 35.253 | 49.454 | 38.409 | 1.00 | 59.33 | B | N |
| ATOM | 3588 | C | GLN | B | 334 | 32.998 | 45.572 | 41.478 | 1.00 | 53.11 | B | C |
| ATOM | 3589 | O | GLN | B | 334 | 33.352 | 45.067 | 42.544 | 1.00 | 52.68 | B | O |
| ATOM | 3590 | N | GLU | B | 335 | 31.986 | 46.427 | 41.386 | 1.00 | 51.38 | B | N |
| ATOM | 3591 | CA | GLU | B | 335 | 31.226 | 46.826 | 42.561 | 1.00 | 50.81 | B | C |
| ATOM | 3592 | CB | GLU | B | 335 | 30.428 | 48.098 | 42.257 | 1.00 | 51.54 | B | C |
| ATOM | 3593 | CG | GLU | B | 335 | 29.750 | 48.707 | 43.470 | 1.00 | 54.47 | B | C |
| ATOM | 3594 | CD | GLU | B | 335 | 30.722 | 48.982 | 44.607 | 1.00 | 56.00 | B | C |
| ATOM | 3595 | OE1 | GLU | B | 335 | 30.265 | 49.435 | 45.681 | 1.00 | 55.50 | B | O |
| ATOM | 3596 | OE2 | GLU | B | 335 | 31.939 | 48.745 | 44.429 | 1.00 | 56.77 | B | O |
| ATOM | 3597 | C | GLU | B | 335 | 30.287 | 45.693 | 42.997 | 1.00 | 49.24 | B | C |
| ATOM | 3598 | O | GLU | B | 335 | 30.247 | 45.321 | 44.171 | 1.00 | 48.26 | B | O |
| ATOM | 3599 | N | THR | B | 336 | 29.543 | 45.144 | 42.042 | 1.00 | 47.63 | B | N |
| ATOM | 3600 | CA | THR | B | 336 | 28.622 | 44.046 | 42.318 | 1.00 | 46.12 | B | C |
| ATOM | 3601 | CB | THR | B | 336 | 28.002 | 43.497 | 41.013 | 1.00 | 45.85 | B | C |
| ATOM | 3602 | OG1 | THR | B | 336 | 27.289 | 44.548 | 40.347 | 1.00 | 47.48 | B | O |
| ATOM | 3603 | CG2 | THR | B | 336 | 27.046 | 42.345 | 41.308 | 1.00 | 44.35 | B | C |
| ATOM | 3604 | C | THR | B | 336 | 29.394 | 42.922 | 43.001 | 1.00 | 45.04 | B | C |
| ATOM | 3605 | O | THR | B | 336 | 28.916 | 42.313 | 43.963 | 1.00 | 44.35 | B | O |
| ATOM | 3606 | N | TYR | B | 337 | 30.594 | 42.665 | 42.494 | 1.00 | 42.84 | B | N |
| ATOM | 3607 | CA | TYR | B | 337 | 31.465 | 41.625 | 43.025 | 1.00 | 42.44 | B | C |
| ATOM | 3608 | CB | TYR | B | 337 | 32.784 | 41.606 | 42.251 | 1.00 | 45.11 | B | C |
| ATOM | 3609 | CG | TYR | B | 337 | 33.675 | 40.446 | 42.624 | 1.00 | 47.49 | B | C |
| ATOM | 3610 | CD1 | TYR | B | 337 | 33.639 | 39.258 | 41.901 | 1.00 | 48.63 | B | C |
| ATOM | 3611 | CE1 | TYR | B | 337 | 34.421 | 38.166 | 42.273 | 1.00 | 51.33 | B | C |
| ATOM | 3612 | CD2 | TYR | B | 337 | 34.520 | 40.520 | 43.733 | 1.00 | 49.23 | B | C |
| ATOM | 3613 | CE2 | TYR | B | 337 | 35.302 | 39.439 | 44.114 | 1.00 | 50.54 | B | C |
| ATOM | 3614 | CZ | TYR | B | 337 | 35.247 | 38.263 | 43.380 | 1.00 | 51.96 | B | C |
| ATOM | 3615 | OH | TYR | B | 337 | 36.005 | 37.179 | 43.761 | 1.00 | 54.44 | B | O |
| ATOM | 3616 | C | TYR | B | 337 | 31.769 | 41.809 | 44.513 | 1.00 | 41.13 | B | C |
| ATOM | 3617 | O | TYR | B | 337 | 31.759 | 40.843 | 45.276 | 1.00 | 40.24 | B | O |
| ATOM | 3618 | N | LYS | B | 338 | 32.048 | 43.050 | 44.909 | 1.00 | 40.20 | B | N |
| ATOM | 3619 | CA | LYS | B | 338 | 32.371 | 43.390 | 46.296 | 1.00 | 38.23 | B | C |

TABLE 2-continued coordinates for the two molecules in the asymmetric unit of [T287] Aurora
A (122–396) in complex with an inhibitor of formula II in space group P2₁

| ATOM | 3620 | CB | LYS | B | 338 | 32.833 | 44.850 | 46.388 | 1.00 | 41.59 B | C |
|------|------|------|------|---|-----|--------|--------|--------|------|---------|---|
| ATOM | 3621 | CG | LYS | B | 338 | 34.123 | 45.176 | 45.644 | 1.00 | 44.66 B | C |
| ATOM | 3622 | CD | LYS | B | 338 | 34.527 | 46.631 | 45.891 | 1.00 | 48.09 B | C |
| ATOM | 3623 | CE | LYS | B | 338 | 35.874 | 46.981 | 45.256 | 1.00 | 48.00 B | C |
| ATOM | 3624 | NZ | LYS | B | 338 | 35.838 | 46.925 | 43.765 | 1.00 | 51.10 B | N |
| ATOM | 3625 | C | LYS | B | 338 | 31.205 | 43.191 | 47.262 | 1.00 | 35.20 B | C |
| ATOM | 3626 | O | LYS | B | 338 | 31.339 | 42.526 | 48.291 | 1.00 | 32.57 B | O |
| ATOM | 3627 | N | ARG | B | 339 | 30.063 | 43.783 | 46.923 | 1.00 | 33.78 B | N |
| ATOM | 3628 | CA | ARG | B | 339 | 28.868 | 43.694 | 47.758 | 1.00 | 32.18 B | C |
| ATOM | 3629 | CB | ARG | B | 339 | 27.741 | 44.499 | 47.125 | 1.00 | 34.50 B | C |
| ATOM | 3630 | CG | ARG | B | 339 | 28.069 | 45.975 | 46.971 | 1.00 | 34.49 B | C |
| ATOM | 3631 | CD | ARG | B | 339 | 26.849 | 46.753 | 46.513 | 1.00 | 37.43 B | C |
| ATOM | 3632 | NE | ARG | B | 339 | 27.183 | 48.140 | 46.215 | 1.00 | 39.07 B | N |
| ATOM | 3633 | CZ | ARG | B | 339 | 26.318 | 49.042 | 45.768 | 1.00 | 40.69 B | C |
| ATOM | 3634 | NH1 | ARG | B | 339 | 25.052 | 48.714 | 45.563 | 1.00 | 41.15 B | N |
| ATOM | 3635 | NH2 | ARG | B | 339 | 26.723 | 50.278 | 45.524 | 1.00 | 42.78 B | N |
| ATOM | 3636 | C | ARG | B | 339 | 28.424 | 42.255 | 48.005 | 1.00 | 30.59 B | C |
| ATOM | 3637 | O | ARG | B | 339 | 27.998 | 41.916 | 49.106 | 1.00 | 30.06 B | O |
| ATOM | 3638 | N | ILE | B | 340 | 28.531 | 41.411 | 46.983 | 1.00 | 28.84 B | N |
| ATOM | 3639 | CA | ILE | B | 340 | 28.172 | 40.005 | 47.113 | 1.00 | 28.23 B | C |
| ATOM | 3640 | CB | ILE | B | 340 | 28.265 | 39.284 | 45.746 | 1.00 | 29.04 B | C |
| ATOM | 3641 | CG2 | ILE | B | 340 | 28.191 | 37.777 | 45.932 | 1.00 | 27.61 B | C |
| ATOM | 3642 | CG1 | ILE | B | 340 | 27.143 | 39.778 | 44.828 | 1.00 | 29.93 B | C |
| ATOM | 3643 | CD1 | ILE | B | 340 | 27.294 | 39.344 | 43.379 | 1.00 | 30.36 B | C |
| ATOM | 3644 | C | ILE | B | 340 | 29.149 | 39.362 | 48.094 | 1.00 | 28.00 B | C |
| ATOM | 3645 | O | ILE | B | 340 | 28.746 | 38.760 | 49.092 | 1.00 | 28.08 B | O |
| ATOM | 3646 | N | SER | B | 341 | 30.437 | 39.511 | 47.806 | 1.00 | 27.83 B | N |
| ATOM | 3647 | CA | SER | B | 341 | 31.500 | 38.971 | 48.647 | 1.00 | 27.74 B | C |
| ATOM | 3648 | CB | SER | B | 341 | 32.869 | 39.405 | 48.099 | 1.00 | 29.39 B | C |
| ATOM | 3649 | OG | SER | B | 341 | 33.904 | 39.101 | 49.023 | 1.00 | 31.17 B | O |
| ATOM | 3650 | C | SER | B | 341 | 31.390 | 39.394 | 50.115 | 1.00 | 26.62 B | C |
| ATOM | 3651 | O | SER | B | 341 | 31.581 | 38.576 | 51.019 | 1.00 | 26.60 B | O |
| ATOM | 3652 | N | ARG | B | 342 | 31.095 | 40.670 | 50.349 | 1.00 | 26.86 B | N |
| ATOM | 3653 | CA | ARG | B | 342 | 30.967 | 41.190 | 51.713 | 1.00 | 27.32 B | C |
| ATOM | 3654 | CB | ARG | B | 342 | 31.486 | 42.635 | 51.786 | 1.00 | 30.87 B | C |
| ATOM | 3655 | CG | ARG | B | 342 | 32.988 | 42.792 | 51.559 | 1.00 | 34.75 B | C |
| ATOM | 3656 | CD | ARG | B | 342 | 33.407 | 44.264 | 51.585 | 1.00 | 38.59 B | C |
| ATOM | 3657 | NE | ARG | B | 342 | 34.861 | 44.410 | 51.496 | 1.00 | 44.23 B | N |
| ATOM | 3658 | CZ | ARG | B | 342 | 35.518 | 45.568 | 51.542 | 1.00 | 45.71 B | C |
| ATOM | 3659 | NH1 | ARG | B | 342 | 36.842 | 45.574 | 51.450 | 1.00 | 47.72 B | N |
| ATOM | 3660 | NH2 | ARG | B | 342 | 34.862 | 46.717 | 51.678 | 1.00 | 45.74 B | N |
| ATOM | 3661 | C | ARG | B | 342 | 29.525 | 41.157 | 52.232 | 1.00 | 26.65 B | C |
| ATOM | 3662 | O | ARG | B | 342 | 29.249 | 41.651 | 53.324 | 1.00 | 24.28 B | O |
| ATOM | 3663 | N | VAL | B | 343 | 28.615 | 40.578 | 51.449 | 1.00 | 25.25 B | N |
| ATOM | 3664 | CA | VAL | B | 343 | 27.201 | 40.491 | 51.825 | 1.00 | 23.45 B | C |
| ATOM | 3665 | CB | VAL | B | 343 | 26.964 | 39.453 | 52.942 | 1.00 | 22.70 B | C |
| ATOM | 3666 | CG1 | VAL | B | 343 | 25.475 | 39.151 | 53.038 | 1.00 | 26.95 B | C |
| ATOM | 3667 | CG2 | VAL | B | 343 | 27.744 | 38.182 | 52.667 | 1.00 | 24.45 B | C |
| ATOM | 3668 | C | VAL | B | 343 | 26.667 | 41.834 | 52.319 | 1.00 | 22.20 B | C |
| ATOM | 3669 | O | VAL | B | 343 | 26.236 | 41.958 | 53.463 | 1.00 | 22.42 B | O |
| ATOM | 3670 | N | GLU | B | 344 | 26.702 | 42.841 | 51.461 | 1.00 | 20.93 B | N |
| ATOM | 3671 | CA | GLU | B | 344 | 26.224 | 44.163 | 51.836 | 1.00 | 19.95 B | C |
| ATOM | 3672 | CB | GLU | B | 344 | 27.317 | 45.217 | 51.593 | 1.00 | 21.95 B | C |
| ATOM | 3673 | CG | GLU | B | 344 | 28.483 | 45.077 | 52.579 | 1.00 | 26.85 B | C |
| ATOM | 3674 | CD | GLU | B | 344 | 29.731 | 45.844 | 52.177 | 1.00 | 29.55 B | C |
| ATOM | 3675 | OE1 | GLU | B | 344 | 30.643 | 45.948 | 53.029 | 1.00 | 31.16 B | O |
| ATOM | 3676 | OE2 | GLU | B | 344 | 29.811 | 46.331 | 51.021 | 1.00 | 29.15 B | O |
| ATOM | 3677 | C | GLU | B | 344 | 24.970 | 44.500 | 51.054 | 1.00 | 19.08 B | C |
| ATOM | 3678 | O | GLU | B | 344 | 25.007 | 44.692 | 49.832 | 1.00 | 15.34 B | O |
| ATOM | 3679 | N | PHE | B | 345 | 23.859 | 44.555 | 51.778 | 1.00 | 16.62 B | N |
| ATOM | 3680 | CA | PHE | B | 345 | 22.572 | 44.858 | 51.188 | 1.00 | 19.25 B | C |
| ATOM | 3681 | CB | PHE | B | 345 | 21.938 | 43.576 | 50.615 | 1.00 | 17.18 B | C |
| ATOM | 3682 | CG | PHE | B | 345 | 21.524 | 42.574 | 51.661 | 1.00 | 17.47 B | C |
| ATOM | 3683 | CD1 | PHE | B | 345 | 20.271 | 42.645 | 52.253 | 1.00 | 18.52 B | C |
| ATOM | 3684 | CD2 | PHE | B | 345 | 22.394 | 41.561 | 52.060 | 1.00 | 19.11 B | C |
| ATOM | 3685 | CE1 | PHE | B | 345 | 19.884 | 41.725 | 53.225 | 1.00 | 18.14 B | C |
| ATOM | 3686 | CE2 | PHE | B | 345 | 22.015 | 40.634 | 53.039 | 1.00 | 20.48 B | C |
| ATOM | 3687 | CZ | PHE | B | 345 | 20.758 | 40.719 | 53.620 | 1.00 | 19.36 B | C |
| ATOM | 3688 | C | PHE | B | 345 | 21.673 | 45.470 | 52.253 | 1.00 | 18.97 B | C |
| ATOM | 3689 | O | PHE | B | 345 | 21.857 | 45.229 | 53.450 | 1.00 | 19.32 B | O |
| ATOM | 3690 | N | THR | B | 346 | 20.714 | 46.275 | 51.811 | 1.00 | 19.42 B | N |
| ATOM | 3691 | CA | THR | B | 346 | 19.775 | 46.917 | 52.715 | 1.00 | 19.27 B | C |
| ATOM | 3692 | CB | THR | B | 346 | 20.082 | 48.424 | 52.857 | 1.00 | 19.00 B | C |
| ATOM | 3693 | OG1 | THR | B | 346 | 20.109 | 49.030 | 51.564 | 1.00 | 20.30 B | O |
| ATOM | 3694 | CG2 | THR | B | 346 | 21.437 | 48.635 | 53.539 | 1.00 | 18.82 B | C |
| ATOM | 3695 | C | THR | B | 346 | 18.350 | 46.704 | 52.197 | 1.00 | 19.39 B | C |

TABLE 2-continued coordinates for the two molecules in the asymmetric unit of [T287] Aurora
A (122–396) in complex with an inhibitor of formula II in space group P2₁

| ATOM | 3696 | O   | THR | B | 346 | 18.163 | 46.200 | 51.095 | 1.00 | 20.35 | B | O |
|------|------|-----|-----|---|-----|--------|--------|--------|------|-------|---|---|
| ATOM | 3697 | N   | PHE | B | 347 | 17.364 | 47.086 | 53.003 | 1.00 | 20.32 | B | N |
| ATOM | 3698 | CA  | PHE | B | 347 | 15.941 | 46.925 | 52.689 | 1.00 | 22.26 | B | C |
| ATOM | 3699 | CB  | PHE | B | 347 | 15.239 | 46.134 | 53.801 | 1.00 | 19.26 | B | C |
| ATOM | 3700 | CG  | PHE | B | 347 | 15.710 | 44.715 | 53.954 | 1.00 | 22.00 | B | C |
| ATOM | 3701 | CD1 | PHE | B | 347 | 15.318 | 43.731 | 53.050 | 1.00 | 20.34 | B | C |
| ATOM | 3702 | CD2 | PHE | B | 347 | 16.521 | 44.352 | 55.029 | 1.00 | 19.14 | B | C |
| ATOM | 3703 | CE1 | PHE | B | 347 | 15.723 | 42.411 | 53.217 | 1.00 | 18.46 | B | C |
| ATOM | 3704 | CE2 | PHE | B | 347 | 16.930 | 43.037 | 55.202 | 1.00 | 16.81 | B | C |
| ATOM | 3705 | CZ  | PHE | B | 347 | 16.529 | 42.062 | 54.293 | 1.00 | 16.52 | B | C |
| ATOM | 3706 | C   | PHE | B | 347 | 15.180 | 48.246 | 52.572 | 1.00 | 23.77 | B | C |
| ATOM | 3707 | O   | PHE | B | 347 | 15.384 | 49.166 | 53.364 | 1.00 | 24.75 | B | O |
| ATOM | 3708 | N   | PRO | B | 348 | 14.280 | 48.353 | 51.590 | 1.00 | 26.17 | B | N |
| ATOM | 3709 | CD  | PRO | B | 348 | 14.032 | 47.471 | 50.438 | 1.00 | 27.03 | B | C |
| ATOM | 3710 | CA  | PRO | B | 348 | 13.519 | 49.602 | 51.474 | 1.00 | 27.72 | B | C |
| ATOM | 3711 | CB  | PRO | B | 348 | 12.702 | 49.393 | 50.198 | 1.00 | 28.07 | B | C |
| ATOM | 3712 | CG  | PRO | B | 348 | 13.561 | 48.455 | 49.394 | 1.00 | 28.17 | B | C |
| ATOM | 3713 | C   | PRO | B | 348 | 12.629 | 49.609 | 52.727 | 1.00 | 29.25 | B | C |
| ATOM | 3714 | O   | PRO | B | 348 | 12.262 | 48.546 | 53.232 | 1.00 | 29.40 | B | O |
| ATOM | 3715 | N   | ASP | B | 349 | 12.265 | 50.784 | 53.220 | 1.00 | 30.11 | B | N |
| ATOM | 3716 | CA  | ASP | B | 349 | 11.453 | 50.864 | 54.426 | 1.00 | 30.67 | B | C |
| ATOM | 3717 | CB  | ASP | B | 349 | 11.199 | 52.329 | 54.785 | 1.00 | 35.47 | B | C |
| ATOM | 3718 | CG  | ASP | B | 349 | 12.486 | 53.141 | 54.863 | 1.00 | 39.29 | B | C |
| ATOM | 3719 | OD1 | ASP | B | 349 | 13.519 | 52.592 | 55.315 | 1.00 | 40.71 | B | O |
| ATOM | 3720 | OD2 | ASP | B | 349 | 12.463 | 54.334 | 54.483 | 1.00 | 42.81 | B | O |
| ATOM | 3721 | C   | ASP | B | 349 | 10.127 | 50.105 | 54.428 | 1.00 | 30.99 | B | C |
| ATOM | 3722 | O   | ASP | B | 349 | 9.639  | 49.729 | 55.501 | 1.00 | 31.13 | B | O |
| ATOM | 3723 | N   | PHE | B | 350 | 9.539  | 49.858 | 53.256 | 1.00 | 28.24 | B | N |
| ATOM | 3724 | CA  | PHE | B | 350 | 8.256  | 49.153 | 53.225 | 1.00 | 24.82 | B | C |
| ATOM | 3725 | CB  | PHE | B | 350 | 7.496  | 49.459 | 51.920 | 1.00 | 21.72 | B | C |
| ATOM | 3726 | CG  | PHE | B | 350 | 8.175  | 48.964 | 50.670 | 1.00 | 20.48 | B | C |
| ATOM | 3727 | CD1 | PHE | B | 350 | 8.133  | 47.616 | 50.323 | 1.00 | 20.47 | B | C |
| ATOM | 3728 | CD2 | PHE | B | 350 | 8.836  | 49.853 | 49.825 | 1.00 | 18.76 | B | C |
| ATOM | 3729 | CE1 | PHE | B | 350 | 8.741  | 47.156 | 49.145 | 1.00 | 19.61 | B | C |
| ATOM | 3730 | CE2 | PHE | B | 350 | 9.447  | 49.412 | 48.649 | 1.00 | 20.75 | B | C |
| ATOM | 3731 | CZ  | PHE | B | 350 | 9.400  | 48.057 | 48.305 | 1.00 | 22.07 | B | C |
| ATOM | 3732 | C   | PHE | B | 350 | 8.327  | 47.637 | 53.442 | 1.00 | 25.64 | B | C |
| ATOM | 3733 | O   | PHE | B | 350 | 7.293  | 47.002 | 53.660 | 1.00 | 25.56 | B | O |
| ATOM | 3734 | N   | VAL | B | 351 | 9.523  | 47.050 | 53.386 | 1.00 | 23.17 | B | N |
| ATOM | 3735 | CA  | VAL | B | 351 | 9.643  | 45.604 | 53.586 | 1.00 | 21.29 | B | C |
| ATOM | 3736 | CB  | VAL | B | 351 | 11.012 | 45.072 | 53.124 | 1.00 | 18.96 | B | C |
| ATOM | 3737 | CG1 | VAL | B | 351 | 11.060 | 43.564 | 53.314 | 1.00 | 18.55 | B | C |
| ATOM | 3738 | CG2 | VAL | B | 351 | 11.244 | 45.423 | 51.663 | 1.00 | 15.50 | B | C |
| ATOM | 3739 | C   | VAL | B | 351 | 9.429  | 45.215 | 55.052 | 1.00 | 21.74 | B | C |
| ATOM | 3740 | O   | VAL | B | 351 | 10.054 | 45.772 | 55.949 | 1.00 | 20.28 | B | O |
| ATOM | 3741 | N   | THR | B | 352 | 8.535  | 44.254 | 55.273 | 1.00 | 22.77 | B | N |
| ATOM | 3742 | CA  | THR | B | 352 | 8.186  | 43.776 | 56.609 | 1.00 | 23.82 | B | C |
| ATOM | 3743 | CB  | THR | B | 352 | 6.918  | 42.899 | 56.523 | 1.00 | 25.23 | B | C |
| ATOM | 3744 | OG1 | THR | B | 352 | 5.829  | 43.705 | 56.054 | 1.00 | 27.41 | B | O |
| ATOM | 3745 | CG2 | THR | B | 352 | 6.555  | 42.331 | 57.872 | 1.00 | 27.51 | B | C |
| ATOM | 3746 | C   | THR | B | 352 | 9.304  | 43.017 | 57.343 | 1.00 | 22.96 | B | C |
| ATOM | 3747 | O   | THR | B | 352 | 10.213 | 42.463 | 56.718 | 1.00 | 23.44 | B | O |
| ATOM | 3748 | N   | ALA | B | 353 | 9.228  | 42.998 | 58.674 | 1.00 | 22.56 | B | N |
| ATOM | 3749 | CA  | ALA | B | 353 | 10.233 | 42.334 | 59.502 | 1.00 | 19.72 | B | C |
| ATOM | 3750 | CB  | ALA | B | 353 | 10.018 | 42.682 | 60.984 | 1.00 | 21.49 | B | C |
| ATOM | 3751 | C   | ALA | B | 353 | 10.230 | 40.825 | 59.305 | 1.00 | 18.37 | B | C |
| ATOM | 3752 | O   | ALA | B | 353 | 11.270 | 40.184 | 59.390 | 1.00 | 17.81 | B | O |
| ATOM | 3753 | N   | GLY | B | 354 | 9.061  | 40.252 | 59.043 | 1.00 | 17.83 | B | N |
| ATOM | 3754 | CA  | GLY | B | 354 | 9.002  | 38.820 | 58.807 | 1.00 | 14.69 | B | C |
| ATOM | 3755 | C   | GLY | B | 354 | 9.749  | 38.486 | 57.524 | 1.00 | 15.67 | B | C |
| ATOM | 3756 | O   | GLY | B | 354 | 10.484 | 37.497 | 57.449 | 1.00 | 15.82 | B | O |
| ATOM | 3757 | N   | ALA | B | 355 | 9.571  | 39.318 | 56.503 | 1.00 | 14.39 | B | N |
| ATOM | 3758 | CA  | ALA | B | 355 | 10.241 | 39.091 | 55.227 | 1.00 | 16.28 | B | C |
| ATOM | 3759 | CB  | ALA | B | 355 | 9.683  | 40.047 | 54.163 | 1.00 | 14.46 | B | C |
| ATOM | 3760 | C   | ALA | B | 355 | 11.759 | 39.285 | 55.374 | 1.00 | 16.62 | B | C |
| ATOM | 3761 | O   | ALA | B | 355 | 12.541 | 38.560 | 54.778 | 1.00 | 18.69 | B | O |
| ATOM | 3762 | N   | ARG | B | 356 | 12.162 | 40.266 | 56.175 | 1.00 | 18.54 | B | N |
| ATOM | 3763 | CA  | ARG | B | 356 | 13.571 | 40.558 | 56.397 | 1.00 | 18.70 | B | C |
| ATOM | 3764 | CB  | ARG | B | 356 | 13.703 | 41.894 | 57.138 | 1.00 | 19.52 | B | C |
| ATOM | 3765 | CG  | ARG | B | 356 | 13.122 | 43.053 | 56.343 | 1.00 | 21.00 | B | C |
| ATOM | 3766 | CD  | ARG | B | 356 | 12.584 | 44.189 | 57.208 | 1.00 | 21.75 | B | C |
| ATOM | 3767 | NE  | ARG | B | 356 | 13.576 | 45.223 | 57.463 | 1.00 | 25.09 | B | N |
| ATOM | 3768 | CZ  | ARG | B | 356 | 13.435 | 46.503 | 57.130 | 1.00 | 20.74 | B | C |
| ATOM | 3769 | NH1 | ARG | B | 356 | 12.340 | 46.921 | 56.528 | 1.00 | 23.41 | B | N |
| ATOM | 3770 | NH2 | ARG | B | 356 | 14.400 | 47.363 | 57.394 | 1.00 | 19.75 | B | N |
| ATOM | 3771 | C   | ARG | B | 356 | 14.266 | 39.436 | 57.168 | 1.00 | 20.44 | B | C |

TABLE 2-continued coordinates for the two molecules in the asymmetric unit of [T287] Aurora A (122–396) in complex with an inhibitor of formula II in space group P2₁

| ATOM | 3772 | O   | ARG | B | 356 | 15.449 | 39.156 | 56.951 | 1.00 | 21.10 | B | O |
|------|------|-----|-----|---|-----|--------|--------|--------|------|-------|---|---|
| ATOM | 3773 | N   | ASP | B | 357 | 13.546 | 38.786 | 58.076 | 1.00 | 20.86 | B | N |
| ATOM | 3774 | CA  | ASP | B | 357 | 14.164 | 37.698 | 58.819 | 1.00 | 18.80 | B | C |
| ATOM | 3775 | CB  | ASP | B | 357 | 13.259 | 37.204 | 59.938 | 1.00 | 20.18 | B | C |
| ATOM | 3776 | CG  | ASP | B | 357 | 13.911 | 36.098 | 60.740 | 1.00 | 19.17 | B | C |
| ATOM | 3777 | OD1 | ASP | B | 357 | 14.805 | 36.415 | 61.543 | 1.00 | 20.57 | B | O |
| ATOM | 3778 | OD2 | ASP | B | 357 | 13.552 | 34.918 | 60.555 | 1.00 | 21.02 | B | O |
| ATOM | 3779 | C   | ASP | B | 357 | 14.465 | 36.530 | 57.887 | 1.00 | 18.01 | B | C |
| ATOM | 3780 | O   | ASP | B | 357 | 15.539 | 35.937 | 57.941 | 1.00 | 19.94 | B | O |
| ATOM | 3781 | N   | LEU | B | 358 | 13.508 | 36.199 | 57.029 | 1.00 | 18.45 | B | N |
| ATOM | 3782 | CA  | LEU | B | 358 | 13.696 | 35.101 | 56.087 | 1.00 | 17.99 | B | C |
| ATOM | 3783 | CB  | LEU | B | 358 | 12.442 | 34.900 | 55.231 | 1.00 | 17.24 | B | C |
| ATOM | 3784 | CG  | LEU | B | 358 | 12.619 | 33.829 | 54.153 | 1.00 | 18.71 | B | C |
| ATOM | 3785 | CD1 | LEU | B | 358 | 12.858 | 32.466 | 54.819 | 1.00 | 17.61 | B | C |
| ATOM | 3786 | CD2 | LEU | B | 358 | 11.396 | 33.791 | 53.254 | 1.00 | 20.87 | B | C |
| ATOM | 3787 | C   | LEU | B | 358 | 14.879 | 35.357 | 55.161 | 1.00 | 17.62 | B | C |
| ATOM | 3788 | O   | LEU | B | 358 | 15.745 | 34.499 | 54.986 | 1.00 | 17.62 | B | O |
| ATOM | 3789 | N   | ILE | B | 359 | 14.906 | 36.543 | 54.565 | 1.00 | 16.22 | B | N |
| ATOM | 3790 | CA  | ILE | B | 359 | 15.976 | 36.891 | 53.640 | 1.00 | 19.15 | B | C |
| ATOM | 3791 | CB  | ILE | B | 359 | 15.684 | 38.236 | 52.940 | 1.00 | 18.39 | B | C |
| ATOM | 3792 | CG2 | ILE | B | 359 | 16.848 | 38.610 | 52.036 | 1.00 | 17.22 | B | C |
| ATOM | 3793 | CG1 | ILE | B | 359 | 14.387 | 38.117 | 52.129 | 1.00 | 20.22 | B | C |
| ATOM | 3794 | CD1 | ILE | B | 359 | 13.872 | 39.439 | 51.528 | 1.00 | 22.11 | B | C |
| ATOM | 3795 | C   | ILE | B | 359 | 17.363 | 36.947 | 54.282 | 1.00 | 17.31 | B | C |
| ATOM | 3796 | O   | ILE | B | 359 | 18.359 | 36.611 | 53.640 | 1.00 | 16.11 | B | O |
| ATOM | 3797 | N   | SER | B | 360 | 17.433 | 37.364 | 55.543 | 1.00 | 16.97 | B | N |
| ATOM | 3798 | CA  | SER | B | 360 | 18.725 | 37.447 | 56.213 | 1.00 | 18.07 | B | C |
| ATOM | 3799 | CB  | SER | B | 360 | 18.615 | 38.316 | 57.466 | 1.00 | 18.16 | B | C |
| ATOM | 3800 | OG  | SER | B | 360 | 18.402 | 39.669 | 57.111 | 1.00 | 17.16 | B | O |
| ATOM | 3801 | C   | SER | B | 360 | 19.267 | 36.060 | 56.573 | 1.00 | 19.03 | B | C |
| ATOM | 3802 | O   | SER | B | 360 | 20.480 | 35.874 | 56.711 | 1.00 | 18.93 | B | O |
| ATOM | 3803 | N   | ARG | B | 361 | 18.369 | 35.088 | 56.716 | 1.00 | 19.00 | B | N |
| ATOM | 3804 | CA  | ARG | B | 361 | 18.775 | 33.730 | 57.040 | 1.00 | 20.67 | B | C |
| ATOM | 3805 | CB  | ARG | B | 361 | 17.630 | 33.003 | 57.742 | 1.00 | 25.65 | B | C |
| ATOM | 3806 | CG  | ARG | B | 361 | 17.160 | 33.726 | 58.993 | 1.00 | 31.87 | B | C |
| ATOM | 3807 | CD  | ARG | B | 361 | 16.083 | 32.947 | 59.716 | 1.00 | 38.15 | B | C |
| ATOM | 3808 | NE  | ARG | B | 361 | 16.529 | 31.589 | 59.998 | 1.00 | 44.86 | B | N |
| ATOM | 3809 | CZ  | ARG | B | 361 | 15.896 | 30.743 | 60.804 | 1.00 | 48.17 | B | C |
| ATOM | 3810 | NH1 | ARG | B | 361 | 14.779 | 31.116 | 61.419 | 1.00 | 47.35 | B | N |
| ATOM | 3811 | NH2 | ARG | B | 361 | 16.382 | 29.521 | 60.993 | 1.00 | 48.87 | B | N |
| ATOM | 3812 | C   | ARG | B | 361 | 19.211 | 32.974 | 55.785 | 1.00 | 21.43 | B | C |
| ATOM | 3813 | O   | ARG | B | 361 | 19.994 | 32.024 | 55.855 | 1.00 | 22.60 | B | O |
| ATOM | 3814 | N   | LEU | B | 362 | 18.721 | 33.407 | 54.628 | 1.00 | 20.42 | B | N |
| ATOM | 3815 | CA  | LEU | B | 362 | 19.087 | 32.763 | 53.375 | 1.00 | 18.53 | B | C |
| ATOM | 3816 | CB  | LEU | B | 362 | 17.949 | 32.888 | 52.362 | 1.00 | 17.29 | B | C |
| ATOM | 3817 | CG  | LEU | B | 362 | 16.665 | 32.103 | 52.653 | 1.00 | 15.10 | B | C |
| ATOM | 3818 | CD1 | LEU | B | 362 | 15.621 | 32.437 | 51.611 | 1.00 | 15.28 | B | C |
| ATOM | 3819 | CD2 | LEU | B | 362 | 16.961 | 30.596 | 52.650 | 1.00 | 14.06 | B | C |
| ATOM | 3820 | C   | LEU | B | 362 | 20.364 | 33.370 | 52.794 | 1.00 | 20.19 | B | C |
| ATOM | 3821 | O   | LEU | B | 362 | 21.117 | 32.695 | 52.090 | 1.00 | 19.39 | B | O |
| ATOM | 3822 | N   | LEU | B | 363 | 20.614 | 34.640 | 53.098 | 1.00 | 19.15 | B | N |
| ATOM | 3823 | CA  | LEU | B | 363 | 21.793 | 35.310 | 52.565 | 1.00 | 21.61 | B | C |
| ATOM | 3824 | CB  | LEU | B | 363 | 21.421 | 36.728 | 52.121 | 1.00 | 21.25 | B | C |
| ATOM | 3825 | CG  | LEU | B | 363 | 20.391 | 36.784 | 50.986 | 1.00 | 22.02 | B | C |
| ATOM | 3826 | CD1 | LEU | B | 363 | 20.063 | 38.228 | 50.677 | 1.00 | 21.41 | B | C |
| ATOM | 3827 | CD2 | LEU | B | 363 | 20.941 | 36.079 | 49.732 | 1.00 | 21.42 | B | C |
| ATOM | 3828 | C   | LEU | B | 363 | 22.970 | 35.345 | 53.545 | 1.00 | 23.78 | B | C |
| ATOM | 3829 | O   | LEU | B | 363 | 23.443 | 36.421 | 53.931 | 1.00 | 25.25 | B | O |
| ATOM | 3830 | N   | LYS | B | 364 | 23.425 | 34.158 | 53.939 | 1.00 | 22.72 | B | N |
| ATOM | 3831 | CA  | LYS | B | 364 | 24.546 | 34.004 | 54.860 | 1.00 | 25.21 | B | C |
| ATOM | 3832 | CB  | LYS | B | 364 | 24.296 | 32.822 | 55.812 | 1.00 | 26.10 | B | C |
| ATOM | 3833 | CG  | LYS | B | 364 | 23.328 | 33.116 | 56.964 | 1.00 | 28.20 | B | C |
| ATOM | 3834 | CD  | LYS | B | 364 | 23.970 | 34.044 | 57.987 | 1.00 | 30.83 | B | C |
| ATOM | 3835 | CE  | LYS | B | 364 | 22.964 | 34.630 | 58.974 | 1.00 | 33.43 | B | C |
| ATOM | 3836 | NZ  | LYS | B | 364 | 22.367 | 33.622 | 59.900 | 1.00 | 36.33 | B | N |
| ATOM | 3837 | C   | LYS | B | 364 | 25.831 | 33.766 | 54.062 | 1.00 | 25.33 | B | C |
| ATOM | 3838 | O   | LYS | B | 364 | 25.850 | 32.987 | 53.102 | 1.00 | 24.66 | B | O |
| ATOM | 3839 | N   | HIS | B | 365 | 26.904 | 34.444 | 54.455 | 1.00 | 25.93 | B | N |
| ATOM | 3840 | CA  | HIS | B | 365 | 28.175 | 34.296 | 53.763 | 1.00 | 26.63 | B | C |
| ATOM | 3841 | CB  | HIS | B | 365 | 29.261 | 35.141 | 54.424 | 1.00 | 25.92 | B | C |
| ATOM | 3842 | CG  | HIS | B | 365 | 30.590 | 35.009 | 53.756 | 1.00 | 26.63 | B | C |
| ATOM | 3843 | CD2 | HIS | B | 365 | 31.646 | 34.202 | 54.022 | 1.00 | 25.39 | B | C |
| ATOM | 3844 | ND1 | HIS | B | 365 | 30.909 | 35.688 | 52.598 | 1.00 | 28.19 | B | N |
| ATOM | 3845 | CE1 | HIS | B | 365 | 32.103 | 35.303 | 52.179 | 1.00 | 27.11 | B | C |
| ATOM | 3846 | NE2 | HIS | B | 365 | 32.569 | 34.401 | 53.024 | 1.00 | 26.10 | B | N |
| ATOM | 3847 | C   | HIS | B | 365 | 28.636 | 32.845 | 53.757 | 1.00 | 26.18 | B | C |

TABLE 2-continued coordinates for the two molecules in the asymmetric unit of [T287] Aurora
A (122–396) in complex with an inhibitor of formula II in space group P2$_1$

| ATOM | 3848 | O   | HIS | B | 365 | 29.112 | 32.338 | 52.747 | 1.00 | 27.21 | B | O |
|------|------|-----|-----|---|-----|--------|--------|--------|------|-------|---|---|
| ATOM | 3849 | N   | ASN | B | 366 | 28.504 | 32.195 | 54.907 | 1.00 | 27.62 | B | N |
| ATOM | 3850 | CA  | ASN | B | 366 | 28.902 | 30.804 | 55.076 | 1.00 | 29.77 | B | C |
| ATOM | 3851 | CB  | ASN | B | 366 | 29.442 | 30.620 | 56.493 | 1.00 | 31.38 | B | C |
| ATOM | 3852 | CG  | ASN | B | 366 | 29.794 | 29.190 | 56.802 | 1.00 | 35.31 | B | C |
| ATOM | 3853 | OD1 | ASN | B | 366 | 30.346 | 28.480 | 55.963 | 1.00 | 38.20 | B | O |
| ATOM | 3854 | ND2 | ASN | B | 366 | 29.491 | 28.757 | 58.020 | 1.00 | 37.60 | B | N |
| ATOM | 3855 | C   | ASN | B | 366 | 27.716 | 29.862 | 54.805 | 1.00 | 28.07 | B | C |
| ATOM | 3856 | O   | ASN | B | 366 | 26.771 | 29.793 | 55.583 | 1.00 | 26.33 | B | O |
| ATOM | 3857 | N   | PRO | B | 367 | 27.765 | 29.121 | 53.690 | 1.00 | 29.03 | B | N |
| ATOM | 3858 | CD  | PRO | B | 367 | 28.937 | 29.001 | 52.804 | 1.00 | 29.75 | B | C |
| ATOM | 3859 | CA  | PRO | B | 367 | 26.711 | 28.182 | 53.285 | 1.00 | 29.22 | B | C |
| ATOM | 3860 | CB  | PRO | B | 367 | 27.283 | 27.542 | 52.017 | 1.00 | 27.84 | B | C |
| ATOM | 3861 | CG  | PRO | B | 367 | 28.755 | 27.619 | 52.224 | 1.00 | 29.93 | B | C |
| ATOM | 3862 | C   | PRO | B | 367 | 26.285 | 27.148 | 54.323 | 1.00 | 29.89 | B | C |
| ATOM | 3863 | O   | PRO | B | 367 | 25.132 | 26.715 | 54.332 | 1.00 | 30.60 | B | O |
| ATOM | 3864 | N   | SER | B | 368 | 27.202 | 26.754 | 55.198 | 1.00 | 30.30 | B | N |
| ATOM | 3865 | CA  | SER | B | 368 | 26.871 | 25.762 | 56.208 | 1.00 | 31.18 | B | C |
| ATOM | 3866 | CB  | SER | B | 368 | 28.141 | 25.252 | 56.905 | 1.00 | 32.85 | B | C |
| ATOM | 3867 | OG  | SER | B | 368 | 28.550 | 26.132 | 57.939 | 1.00 | 35.93 | B | O |
| ATOM | 3868 | C   | SER | B | 368 | 25.907 | 26.345 | 57.233 | 1.00 | 30.31 | B | C |
| ATOM | 3869 | O   | SER | B | 368 | 25.268 | 25.613 | 57.975 | 1.00 | 30.36 | B | O |
| ATOM | 3870 | N   | GLN | B | 369 | 25.797 | 27.667 | 57.264 | 1.00 | 31.55 | B | N |
| ATOM | 3871 | CA  | GLN | B | 369 | 24.897 | 28.333 | 58.200 | 1.00 | 32.07 | B | C |
| ATOM | 3872 | CB  | GLN | B | 369 | 25.505 | 29.665 | 58.656 | 1.00 | 36.11 | B | C |
| ATOM | 3873 | CG  | GLN | B | 369 | 26.848 | 29.518 | 59.359 | 1.00 | 42.42 | B | C |
| ATOM | 3874 | CD  | GLN | B | 369 | 27.376 | 30.837 | 59.891 | 1.00 | 45.10 | B | C |
| ATOM | 3875 | OE1 | GLN | B | 369 | 26.768 | 31.454 | 60.766 | 1.00 | 48.57 | B | O |
| ATOM | 3876 | NE2 | GLN | B | 369 | 28.511 | 31.279 | 59.361 | 1.00 | 46.32 | B | N |
| ATOM | 3877 | C   | GLN | B | 369 | 23.506 | 28.581 | 57.618 | 1.00 | 29.24 | B | C |
| ATOM | 3878 | O   | GLN | B | 369 | 22.607 | 29.029 | 58.323 | 1.00 | 28.91 | B | O |
| ATOM | 3879 | N   | ARG | B | 370 | 23.330 | 28.301 | 56.331 | 1.00 | 27.41 | B | N |
| ATOM | 3880 | CA  | ARG | B | 370 | 22.036 | 28.496 | 55.675 | 1.00 | 25.29 | B | C |
| ATOM | 3881 | CB  | ARG | B | 370 | 22.230 | 28.548 | 54.157 | 1.00 | 23.14 | B | C |
| ATOM | 3882 | CG  | ARG | B | 370 | 23.078 | 29.715 | 53.698 | 1.00 | 17.66 | B | C |
| ATOM | 3883 | CD  | ARG | B | 370 | 23.530 | 29.546 | 52.268 | 1.00 | 21.09 | B | C |
| ATOM | 3884 | NE  | ARG | B | 370 | 24.615 | 30.468 | 51.956 | 1.00 | 20.83 | B | N |
| ATOM | 3885 | CZ  | ARG | B | 370 | 25.404 | 30.365 | 50.895 | 1.00 | 22.00 | B | C |
| ATOM | 3886 | NH1 | ARG | B | 370 | 25.235 | 29.372 | 50.029 | 1.00 | 21.78 | B | N |
| ATOM | 3887 | NH2 | ARG | B | 370 | 26.365 | 31.262 | 50.698 | 1.00 | 23.58 | B | N |
| ATOM | 3888 | C   | ARG | B | 370 | 21.096 | 27.348 | 56.048 | 1.00 | 24.43 | B | C |
| ATOM | 3889 | O   | ARG | B | 370 | 21.533 | 26.214 | 56.209 | 1.00 | 25.53 | B | O |
| ATOM | 3890 | N   | PRO | B | 371 | 19.789 | 27.625 | 56.177 | 1.00 | 25.63 | B | N |
| ATOM | 3891 | CD  | PRO | B | 371 | 19.116 | 28.920 | 55.965 | 1.00 | 25.62 | B | C |
| ATOM | 3892 | CA  | PRO | B | 371 | 18.816 | 26.584 | 56.538 | 1.00 | 25.56 | B | C |
| ATOM | 3893 | CB  | PRO | B | 371 | 17.561 | 27.392 | 56.860 | 1.00 | 25.65 | B | C |
| ATOM | 3894 | CG  | PRO | B | 371 | 17.649 | 28.519 | 55.882 | 1.00 | 24.95 | B | C |
| ATOM | 3895 | C   | PRO | B | 371 | 18.551 | 25.529 | 55.461 | 1.00 | 25.92 | B | C |
| ATOM | 3896 | O   | PRO | B | 371 | 18.942 | 25.689 | 54.308 | 1.00 | 27.40 | B | O |
| ATOM | 3897 | N   | MET | B | 372 | 17.893 | 24.444 | 55.853 | 1.00 | 27.14 | B | N |
| ATOM | 3898 | CA  | MET | B | 372 | 17.533 | 23.391 | 54.911 | 1.00 | 27.45 | B | C |
| ATOM | 3899 | CB  | MET | B | 372 | 17.344 | 22.053 | 55.623 | 1.00 | 29.21 | B | C |
| ATOM | 3900 | CG  | MET | B | 372 | 18.607 | 21.462 | 56.225 | 1.00 | 32.29 | B | C |
| ATOM | 3901 | SD  | MET | B | 372 | 18.257 | 19.888 | 57.038 | 1.00 | 38.80 | B | S |
| ATOM | 3902 | CE  | MET | B | 372 | 18.599 | 18.751 | 55.690 | 1.00 | 36.16 | B | C |
| ATOM | 3903 | C   | MET | B | 372 | 16.206 | 23.820 | 54.305 | 1.00 | 26.36 | B | C |
| ATOM | 3904 | O   | MET | B | 372 | 15.471 | 24.590 | 54.922 | 1.00 | 27.49 | B | O |
| ATOM | 3905 | N   | LEU | B | 373 | 15.901 | 23.323 | 53.108 | 1.00 | 24.23 | B | N |
| ATOM | 3906 | CA  | LEU | B | 373 | 14.657 | 23.663 | 52.423 | 1.00 | 22.39 | B | C |
| ATOM | 3907 | CB  | LEU | B | 373 | 14.528 | 22.850 | 51.132 | 1.00 | 22.84 | B | C |
| ATOM | 3908 | CG  | LEU | B | 373 | 15.511 | 23.250 | 50.032 | 1.00 | 24.40 | B | C |
| ATOM | 3909 | CD1 | LEU | B | 373 | 15.332 | 22.333 | 48.825 | 1.00 | 26.89 | B | C |
| ATOM | 3910 | CD2 | LEU | B | 373 | 15.282 | 24.716 | 49.638 | 1.00 | 24.98 | B | C |
| ATOM | 3911 | C   | LEU | B | 373 | 13.412 | 23.470 | 53.272 | 1.00 | 20.58 | B | C |
| ATOM | 3912 | O   | LEU | B | 373 | 12.488 | 24.280 | 53.212 | 1.00 | 22.00 | B | O |
| ATOM | 3913 | N   | ALA | B | 374 | 13.393 | 22.409 | 54.071 | 1.00 | 21.21 | B | N |
| ATOM | 3914 | CA  | ALA | B | 374 | 12.249 | 22.111 | 54.936 | 1.00 | 23.10 | B | C |
| ATOM | 3915 | CB  | ALA | B | 374 | 12.423 | 20.733 | 55.580 | 1.00 | 26.30 | B | C |
| ATOM | 3916 | C   | ALA | B | 374 | 12.033 | 23.168 | 56.019 | 1.00 | 23.37 | B | C |
| ATOM | 3917 | O   | ALA | B | 374 | 10.916 | 23.353 | 56.496 | 1.00 | 23.95 | B | O |
| ATOM | 3918 | N   | GLU | B | 375 | 13.102 | 23.854 | 56.410 | 1.00 | 22.62 | B | N |
| ATOM | 3919 | CA  | GLU | B | 375 | 13.007 | 24.891 | 57.426 | 1.00 | 22.21 | B | C |
| ATOM | 3920 | CB  | GLU | B | 375 | 14.394 | 25.218 | 57.984 | 1.00 | 23.52 | B | C |
| ATOM | 3921 | CG  | GLU | B | 375 | 15.035 | 24.067 | 58.761 | 1.00 | 27.91 | B | C |
| ATOM | 3922 | CD  | GLU | B | 375 | 16.465 | 24.369 | 59.174 | 1.00 | 29.27 | B | C |
| ATOM | 3923 | OE1 | GLU | B | 375 | 16.666 | 25.158 | 60.120 | 1.00 | 31.60 | B | O |

TABLE 2-continued coordinates for the two molecules in the asymmetric unit of [T287] Aurora A (122–396) in complex with an inhibitor of formula II in space group P2₁

| ATOM | 3924 | OE2 | GLU | B | 375 | 17.389 | 23.826 | 58.538 | 1.00 | 29.51 | B | O |
|---|---|---|---|---|---|---|---|---|---|---|---|---|
| ATOM | 3925 | C | GLU | B | 375 | 12.380 | 26.139 | 56.823 | 1.00 | 22.31 | B | C |
| ATOM | 3926 | O | GLU | B | 375 | 11.661 | 26.874 | 57.497 | 1.00 | 20.94 | B | O |
| ATOM | 3927 | N | VAL | B | 376 | 12.664 | 26.376 | 55.545 | 1.00 | 21.78 | B | N |
| ATOM | 3928 | CA | VAL | B | 376 | 12.106 | 27.526 | 54.840 | 1.00 | 21.13 | B | C |
| ATOM | 3929 | CB | VAL | B | 376 | 12.666 | 27.613 | 53.394 | 1.00 | 18.71 | B | C |
| ATOM | 3930 | CG1 | VAL | B | 376 | 11.973 | 28.725 | 52.634 | 1.00 | 17.37 | B | C |
| ATOM | 3931 | CG2 | VAL | B | 376 | 14.176 | 27.854 | 53.429 | 1.00 | 15.43 | B | C |
| ATOM | 3932 | C | VAL | B | 376 | 10.582 | 27.378 | 54.777 | 1.00 | 22.45 | B | C |
| ATOM | 3933 | O | VAL | B | 376 | 9.841 | 28.336 | 55.006 | 1.00 | 22.60 | B | O |
| ATOM | 3934 | N | LEU | B | 377 | 10.133 | 26.163 | 54.478 | 1.00 | 22.30 | B | N |
| ATOM | 3935 | CA | LEU | B | 377 | 8.715 | 25.857 | 54.366 | 1.00 | 26.34 | B | C |
| ATOM | 3936 | CB | LEU | B | 377 | 8.533 | 24.449 | 53.785 | 1.00 | 26.41 | B | C |
| ATOM | 3937 | CG | LEU | B | 377 | 9.025 | 24.299 | 52.343 | 1.00 | 27.84 | B | C |
| ATOM | 3938 | CD1 | LEU | B | 377 | 9.044 | 22.837 | 51.924 | 1.00 | 27.54 | B | C |
| ATOM | 3939 | CD2 | LEU | B | 377 | 8.115 | 25.105 | 51.431 | 1.00 | 26.87 | B | C |
| ATOM | 3940 | C | LEU | B | 377 | 7.976 | 25.971 | 55.693 | 1.00 | 27.31 | B | C |
| ATOM | 3941 | O | LEU | B | 377 | 6.752 | 25.965 | 55.719 | 1.00 | 28.00 | B | O |
| ATOM | 3942 | N | GLU | B | 378 | 8.722 | 26.069 | 56.788 | 1.00 | 27.51 | B | N |
| ATOM | 3943 | CA | GLU | B | 378 | 8.126 | 26.189 | 58.113 | 1.00 | 28.70 | B | C |
| ATOM | 3944 | CB | GLU | B | 378 | 8.796 | 25.221 | 59.100 | 1.00 | 33.15 | B | C |
| ATOM | 3945 | CG | GLU | B | 378 | 8.265 | 23.796 | 59.082 | 1.00 | 39.47 | B | C |
| ATOM | 3946 | CD | GLU | B | 378 | 9.030 | 22.878 | 60.036 | 1.00 | 44.38 | B | C |
| ATOM | 3947 | OE1 | GLU | B | 378 | 8.545 | 21.758 | 60.311 | 1.00 | 47.53 | B | O |
| ATOM | 3948 | OE2 | GLU | B | 378 | 10.119 | 23.271 | 60.506 | 1.00 | 44.23 | B | O |
| ATOM | 3949 | C | GLU | B | 378 | 8.252 | 27.601 | 58.659 | 1.00 | 26.28 | B | C |
| ATOM | 3950 | O | GLU | B | 378 | 7.780 | 27.886 | 59.752 | 1.00 | 26.40 | B | O |
| ATOM | 3951 | N | HIS | B | 379 | 8.891 | 28.491 | 57.915 | 1.00 | 23.55 | B | N |
| ATOM | 3952 | CA | HIS | B | 379 | 9.045 | 29.852 | 58.405 | 1.00 | 22.18 | B | C |
| ATOM | 3953 | CB | HIS | B | 379 | 9.891 | 30.671 | 57.438 | 1.00 | 18.53 | B | C |
| ATOM | 3954 | CG | HIS | B | 379 | 10.310 | 31.999 | 57.984 | 1.00 | 20.37 | B | C |
| ATOM | 3955 | CD2 | HIS | B | 379 | 11.503 | 32.430 | 58.455 | 1.00 | 16.86 | B | C |
| ATOM | 3956 | ND1 | HIS | B | 379 | 9.437 | 33.058 | 58.121 | 1.00 | 18.83 | B | N |
| ATOM | 3957 | CE1 | HIS | B | 379 | 10.076 | 34.084 | 58.653 | 1.00 | 19.47 | B | C |
| ATOM | 3958 | NE2 | HIS | B | 379 | 11.330 | 33.729 | 58.864 | 1.00 | 20.07 | B | N |
| ATOM | 3959 | C | HIS | B | 379 | 7.672 | 30.488 | 58.604 | 1.00 | 22.39 | B | C |
| ATOM | 3960 | O | HIS | B | 379 | 6.784 | 30.339 | 57.760 | 1.00 | 24.30 | B | O |
| ATOM | 3961 | N | PRO | B | 380 | 7.477 | 31.199 | 59.734 | 1.00 | 21.58 | B | N |
| ATOM | 3962 | CD | PRO | B | 380 | 8.461 | 31.340 | 60.818 | 1.00 | 20.38 | B | C |
| ATOM | 3963 | CA | PRO | B | 380 | 6.218 | 31.870 | 60.091 | 1.00 | 20.86 | B | C |
| ATOM | 3964 | CB | PRO | B | 380 | 6.521 | 32.487 | 61.458 | 1.00 | 22.72 | B | C |
| ATOM | 3965 | CG | PRO | B | 380 | 7.574 | 31.573 | 62.013 | 1.00 | 23.24 | B | C |
| ATOM | 3966 | C | PRO | B | 380 | 5.697 | 32.910 | 59.095 | 1.00 | 21.33 | B | C |
| ATOM | 3967 | O | PRO | B | 380 | 4.483 | 33.127 | 59.013 | 1.00 | 17.95 | B | O |
| ATOM | 3968 | N | TRP | B | 381 | 6.599 | 33.560 | 58.355 | 1.00 | 19.60 | B | N |
| ATOM | 3969 | CA | TRP | B | 381 | 6.183 | 34.555 | 57.365 | 1.00 | 19.09 | B | C |
| ATOM | 3970 | CB | TRP | B | 381 | 7.373 | 35.392 | 56.893 | 1.00 | 19.18 | B | C |
| ATOM | 3971 | CG | TRP | B | 381 | 7.000 | 36.467 | 55.892 | 1.00 | 20.21 | B | C |
| ATOM | 3972 | CD2 | TRP | B | 381 | 7.254 | 36.450 | 54.478 | 1.00 | 18.07 | B | C |
| ATOM | 3973 | CE2 | TRP | B | 381 | 6.688 | 37.629 | 53.935 | 1.00 | 18.87 | B | C |
| ATOM | 3974 | CE3 | TRP | B | 381 | 7.901 | 35.554 | 53.619 | 1.00 | 19.02 | B | C |
| ATOM | 3975 | CD1 | TRP | B | 381 | 6.316 | 37.630 | 56.142 | 1.00 | 18.93 | B | C |
| ATOM | 3976 | NE1 | TRP | B | 381 | 6.126 | 38.331 | 54.970 | 1.00 | 16.23 | B | N |
| ATOM | 3977 | CZ2 | TRP | B | 381 | 6.748 | 37.929 | 52.570 | 1.00 | 16.90 | B | C |
| ATOM | 3978 | CZ3 | TRP | B | 381 | 7.962 | 35.855 | 52.251 | 1.00 | 18.05 | B | C |
| ATOM | 3979 | CH2 | TRP | B | 381 | 7.386 | 37.034 | 51.747 | 1.00 | 17.42 | B | C |
| ATOM | 3980 | C | TRP | B | 381 | 5.572 | 33.809 | 56.171 | 1.00 | 20.19 | B | C |
| ATOM | 3981 | O | TRP | B | 381 | 4.562 | 34.233 | 55.600 | 1.00 | 16.91 | B | O |
| ATOM | 3982 | N | ILE | B | 382 | 6.199 | 32.699 | 55.801 | 1.00 | 18.76 | B | N |
| ATOM | 3983 | CA | ILE | B | 382 | 5.719 | 31.887 | 54.695 | 1.00 | 22.56 | B | C |
| ATOM | 3984 | CB | ILE | B | 382 | 6.766 | 30.844 | 54.318 | 1.00 | 22.31 | B | C |
| ATOM | 3985 | CG2 | ILE | B | 382 | 6.139 | 29.747 | 53.486 | 1.00 | 22.37 | B | C |
| ATOM | 3986 | CG1 | ILE | B | 382 | 7.908 | 31.529 | 53.573 | 1.00 | 23.31 | B | C |
| ATOM | 3987 | CD1 | ILE | B | 382 | 9.066 | 30.636 | 53.321 | 1.00 | 29.66 | B | C |
| ATOM | 3988 | C | ILE | B | 382 | 4.395 | 31.181 | 55.019 | 1.00 | 24.58 | B | C |
| ATOM | 3989 | O | ILE | B | 382 | 3.447 | 31.210 | 54.230 | 1.00 | 23.86 | B | O |
| ATOM | 3990 | N | THR | B | 383 | 4.348 | 30.543 | 56.183 | 1.00 | 25.64 | B | N |
| ATOM | 3991 | CA | THR | B | 383 | 3.167 | 29.825 | 56.640 | 1.00 | 25.76 | B | C |
| ATOM | 3992 | CB | THR | B | 383 | 3.462 | 29.123 | 57.982 | 1.00 | 25.87 | B | C |
| ATOM | 3993 | OG1 | THR | B | 383 | 4.162 | 27.896 | 57.732 | 1.00 | 31.20 | B | O |
| ATOM | 3994 | CG2 | THR | B | 383 | 2.196 | 28.841 | 58.734 | 1.00 | 28.47 | B | C |
| ATOM | 3995 | C | THR | B | 383 | 1.966 | 30.746 | 56.812 | 1.00 | 26.92 | B | C |
| ATOM | 3996 | O | THR | B | 383 | 0.817 | 30.336 | 56.615 | 1.00 | 27.54 | B | O |
| ATOM | 3997 | N | ALA | B | 384 | 2.234 | 31.994 | 57.175 | 1.00 | 26.10 | B | N |
| ATOM | 3998 | CA | ALA | B | 384 | 1.170 | 32.961 | 57.396 | 1.00 | 27.17 | B | C |
| ATOM | 3999 | CB | ALA | B | 384 | 1.653 | 34.053 | 58.326 | 1.00 | 25.11 | B | C |

TABLE 2-continued coordinates for the two molecules in the asymmetric unit of [T287] Aurora A (122–396) in complex with an inhibitor of formula II in space group P2₁

| | | | | | | | | | | |
|---|---|---|---|---|---|---|---|---|---|---|
| ATOM | 4000 | C | ALA | B | 384 | 0.635 | 33.584 | 56.119 | 1.00 | 28.32 B C |
| ATOM | 4001 | O | ALA | B | 384 | −0.550 | 33.900 | 56.022 | 1.00 | 27.86 B O |
| ATOM | 4002 | N | ASN | B | 385 | 1.503 | 33.756 | 55.134 | 1.00 | 29.11 B N |
| ATOM | 4003 | CA | ASN | B | 385 | 1.090 | 34.392 | 53.898 | 1.00 | 32.57 B C |
| ATOM | 4004 | CB | ASN | B | 385 | 2.128 | 35.451 | 53.541 | 1.00 | 27.65 B C |
| ATOM | 4005 | CG | ASN | B | 385 | 2.247 | 36.512 | 54.625 | 1.00 | 26.99 B C |
| ATOM | 4006 | OD1 | ASN | B | 385 | 1.328 | 37.303 | 54.829 | 1.00 | 25.20 B O |
| ATOM | 4007 | ND2 | ASN | B | 385 | 3.367 | 36.517 | 55.342 | 1.00 | 23.02 B N |
| ATOM | 4008 | C | ASN | B | 385 | 0.807 | 33.447 | 52.735 | 1.00 | 35.05 B C |
| ATOM | 4009 | O | ASN | B | 385 | 0.812 | 33.859 | 51.580 | 1.00 | 35.34 B O |
| ATOM | 4010 | N | SER | B | 386 | 0.527 | 32.190 | 53.078 | 1.00 | 40.53 B N |
| ATOM | 4011 | CA | SER | B | 386 | 0.201 | 31.117 | 52.138 | 1.00 | 44.93 B C |
| ATOM | 4012 | CB | SER | B | 386 | −0.537 | 31.661 | 50.910 | 1.00 | 45.41 B C |
| ATOM | 4013 | OG | SER | B | 386 | −0.956 | 30.611 | 50.055 | 1.00 | 45.89 B O |
| ATOM | 4014 | C | SER | B | 386 | 1.436 | 30.343 | 51.701 | 1.00 | 48.13 B C |
| ATOM | 4015 | O | SER | B | 386 | 2.357 | 30.904 | 51.108 | 1.00 | 48.75 B O |
| ATOM | 4016 | N | SER | B | 387 | 1.435 | 29.046 | 52.006 | 1.00 | 51.11 B N |
| ATOM | 4017 | CA | SER | B | 387 | 2.536 | 28.143 | 51.673 | 1.00 | 52.94 B C |
| ATOM | 4018 | CB | SER | B | 387 | 3.430 | 27.924 | 52.898 | 1.00 | 52.84 B C |
| ATOM | 4019 | OG | SER | B | 387 | 4.439 | 26.960 | 52.630 | 1.00 | 53.68 B O |
| ATOM | 4020 | C | SER | B | 387 | 2.022 | 26.788 | 51.181 | 1.00 | 53.55 B C |
| ATOM | 4021 | O | SER | B | 387 | 2.221 | 25.788 | 51.903 | 1.00 | 56.01 B O |
| ATOM | 4022 | OXT | SER | B | 387 | 1.426 | 26.735 | 50.087 | 1.00 | 52.55 B O |
| TER | 4023 | | SER | B | 387 | | | | | |
| ATOM | 4024 | C1 | FRA | Z | 1 | 21.364 | 83.849 | 79.751 | 1.00 | 28.06 Z C |
| ATOM | 4025 | C2 | FRA | Z | 1 | 21.204 | 82.482 | 80.488 | 1.00 | 28.48 Z C |
| ATOM | 4026 | C3 | FRA | Z | 1 | 20.089 | 81.594 | 79.848 | 1.00 | 28.20 Z C |
| ATOM | 4027 | C4 | FRA | Z | 1 | 20.171 | 81.530 | 78.286 | 1.00 | 29.96 Z C |
| ATOM | 4028 | C5 | FRA | Z | 1 | 20.403 | 82.931 | 77.637 | 1.00 | 26.40 Z C |
| ATOM | 4029 | N6 | FRA | Z | 1 | 21.562 | 83.678 | 78.268 | 1.00 | 26.70 Z N |
| ATOM | 4030 | C7 | FRA | Z | 1 | 21.844 | 85.007 | 77.590 | 1.00 | 26.79 Z C |
| ATOM | 4031 | C8 | FRA | Z | 1 | 22.091 | 84.946 | 76.062 | 1.00 | 22.84 Z C |
| ATOM | 4032 | C9 | FRA | Z | 1 | 21.703 | 86.217 | 75.301 | 1.00 | 22.28 Z C |
| ATOM | 4033 | O10 | FRA | Z | 1 | 22.186 | 86.127 | 73.930 | 1.00 | 21.29 Z O |
| ATOM | 4034 | C11 | FRA | Z | 1 | 22.294 | 87.227 | 73.066 | 1.00 | 20.50 Z C |
| ATOM | 4035 | C12 | FRA | Z | 1 | 22.781 | 87.073 | 71.728 | 1.00 | 19.83 Z C |
| ATOM | 4036 | C13 | FRA | Z | 1 | 22.881 | 88.197 | 70.870 | 1.00 | 17.71 Z C |
| ATOM | 4037 | C14 | FRA | Z | 1 | 22.506 | 89.483 | 71.312 | 1.00 | 15.27 Z C |
| ATOM | 4038 | C15 | FRA | Z | 1 | 22.005 | 89.651 | 72.695 | 1.00 | 16.51 Z C |
| ATOM | 4039 | C16 | FRA | Z | 1 | 21.911 | 88.516 | 73.537 | 1.00 | 18.78 Z C |
| ATOM | 4040 | N17 | FRA | Z | 1 | 21.634 | 90.872 | 73.162 | 1.00 | 18.92 Z N |
| ATOM | 4041 | C18 | FRA | Z | 1 | 21.733 | 91.911 | 72.347 | 1.00 | 15.67 Z C |
| ATOM | 4042 | N19 | FRA | Z | 1 | 22.169 | 91.877 | 71.088 | 1.00 | 16.81 Z N |
| ATOM | 4043 | C20 | FRA | Z | 1 | 22.560 | 90.693 | 70.539 | 1.00 | 16.78 Z C |
| ATOM | 4044 | N21 | FRA | Z | 1 | 23.025 | 90.704 | 69.148 | 1.00 | 16.94 Z N |
| ATOM | 4045 | C22 | FRA | Z | 1 | 23.001 | 91.757 | 68.180 | 1.00 | 18.96 Z C |
| ATOM | 4046 | C23 | FRA | Z | 1 | 24.061 | 91.923 | 67.246 | 1.00 | 17.20 Z C |
| ATOM | 4047 | N24 | FRA | Z | 1 | 24.042 | 92.933 | 66.367 | 1.00 | 19.55 Z N |
| ATOM | 4048 | C25 | FRA | Z | 1 | 22.992 | 93.783 | 66.394 | 1.00 | 18.00 Z C |
| ATOM | 4049 | N26 | FRA | Z | 1 | 21.955 | 93.708 | 67.214 | 1.00 | 17.17 Z N |
| ATOM | 4050 | C27 | FRA | Z | 1 | 21.936 | 92.724 | 68.097 | 1.00 | 18.78 Z C |
| ATOM | 4051 | N28 | FRA | Z | 1 | 23.043 | 94.876 | 65.467 | 1.00 | 22.15 Z N |
| ATOM | 4052 | C29 | FRA | Z | 1 | 23.696 | 95.214 | 64.346 | 1.00 | 20.72 Z C |
| ATOM | 4053 | C30 | FRA | Z | 1 | 23.352 | 96.585 | 63.786 | 1.00 | 19.36 Z C |
| ATOM | 4054 | C31 | FRA | Z | 1 | 22.405 | 97.470 | 64.411 | 1.00 | 17.69 Z C |
| ATOM | 4055 | C32 | FRA | Z | 1 | 22.122 | 98.742 | 63.860 | 1.00 | 20.12 Z C |
| ATOM | 4056 | C33 | FRA | Z | 1 | 22.776 | 99.153 | 62.676 | 1.00 | 17.24 Z C |
| ATOM | 4057 | C34 | FRA | Z | 1 | 23.710 | 98.303 | 62.042 | 1.00 | 17.77 Z C |
| ATOM | 4058 | C35 | FRA | Z | 1 | 23.998 | 97.035 | 62.589 | 1.00 | 17.80 Z C |
| ATOM | 4059 | O36 | FRA | Z | 1 | 24.531 | 94.448 | 63.824 | 1.00 | 21.83 Z O |
| ATOM | 4060 | O37 | FRA | Z | 1 | 23.170 | 85.827 | 71.240 | 1.00 | 20.79 Z O |
| ATOM | 4061 | C38 | FRA | Z | 1 | 22.679 | 85.375 | 69.951 | 1.00 | 26.55 Z C |
| ATOM | 4062 | O39 | FRA | Z | 1 | 23.466 | 84.677 | 75.820 | 1.00 | 24.51 Z O |
| TER | 4063 | | FRA | Z | 1 | | | | | |
| ATOM | 4064 | C1 | FRA | Y | 1 | 1.515 | 35.986 | 27.679 | 1.00 | 36.52 Y C |
| ATOM | 4065 | C2 | FRA | Y | 1 | 0.608 | 36.976 | 26.867 | 1.00 | 37.59 Y C |
| ATOM | 4066 | C3 | FRA | Y | 1 | −0.401 | 36.230 | 25.961 | 1.00 | 36.15 Y C |
| ATOM | 4067 | C4 | FRA | Y | 1 | 0.319 | 35.193 | 25.054 | 1.00 | 37.83 Y C |
| ATOM | 4068 | C5 | FRA | Y | 1 | 1.177 | 34.183 | 25.879 | 1.00 | 36.12 Y C |
| ATOM | 4069 | N6 | FRA | Y | 1 | 2.132 | 34.827 | 26.897 | 1.00 | 36.16 Y N |
| ATOM | 4070 | C7 | FRA | Y | 1 | 3.479 | 35.234 | 26.297 | 1.00 | 37.30 Y C |
| ATOM | 4071 | C8 | FRA | Y | 1 | 4.332 | 34.189 | 25.489 | 1.00 | 32.04 Y C |
| ATOM | 4072 | C9 | FRA | Y | 1 | 4.647 | 32.852 | 26.202 | 1.00 | 29.29 Y C |
| ATOM | 4073 | O10 | FRA | Y | 1 | 6.097 | 32.795 | 26.275 | 1.00 | 25.58 Y O |
| ATOM | 4074 | C11 | FRA | Y | 1 | 6.903 | 31.673 | 26.442 | 1.00 | 20.22 Y C |
| ATOM | 4075 | C12 | FRA | Y | 1 | 8.327 | 31.834 | 26.469 | 1.00 | 19.90 Y C |

TABLE 2-continued coordinates for the two molecules in the asymmetric unit of [T287] Aurora A (122–396) in complex with an inhibitor of formula II in space group P2$_1$

| | | | | | | | | | | | |
|---|---|---|---|---|---|---|---|---|---|---|---|
| ATOM | 4076 | C13 | FRA | Y | 1 | 9.170 | 30.706 | 26.629 | 1.00 | 18.27 | Y C |
| ATOM | 4077 | C14 | FRA | Y | 1 | 8.622 | 29.412 | 26.769 | 1.00 | 16.62 | Y C |
| ATOM | 4078 | C15 | FRA | Y | 1 | 7.143 | 29.247 | 26.749 | 1.00 | 16.07 | Y C |
| ATOM | 4079 | C16 | FRA | Y | 1 | 6.320 | 30.391 | 26.580 | 1.00 | 17.70 | Y C |
| ATOM | 4080 | N17 | FRA | Y | 1 | 6.583 | 28.029 | 26.887 | 1.00 | 17.71 | Y N |
| ATOM | 4081 | C18 | FRA | Y | 1 | 7.389 | 26.981 | 27.040 | 1.00 | 17.21 | Y C |
| ATOM | 4082 | N19 | FRA | Y | 1 | 8.725 | 27.007 | 27.067 | 1.00 | 17.12 | Y N |
| ATOM | 4083 | C20 | FRA | Y | 1 | 9.371 | 28.193 | 26.934 | 1.00 | 17.89 | Y C |
| ATOM | 4084 | N21 | FRA | Y | 1 | 10.845 | 28.199 | 26.966 | 1.00 | 19.44 | Y N |
| ATOM | 4085 | C22 | FRA | Y | 1 | 11.804 | 27.160 | 27.225 | 1.00 | 17.92 | Y C |
| ATOM | 4086 | C23 | FRA | Y | 1 | 13.046 | 27.089 | 26.514 | 1.00 | 17.84 | Y C |
| ATOM | 4087 | N24 | FRA | Y | 1 | 13.927 | 26.091 | 26.750 | 1.00 | 17.67 | Y N |
| ATOM | 4088 | C25 | FRA | Y | 1 | 13.591 | 25.172 | 27.677 | 1.00 | 19.86 | Y C |
| ATOM | 4089 | N26 | FRA | Y | 1 | 12.465 | 25.164 | 28.390 | 1.00 | 22.22 | Y N |
| ATOM | 4090 | C27 | FRA | Y | 1 | 11.584 | 26.130 | 28.180 | 1.00 | 20.19 | Y C |
| ATOM | 4091 | N28 | FRA | Y | 1 | 14.520 | 24.102 | 27.878 | 1.00 | 21.17 | Y N |
| ATOM | 4092 | C29 | FRA | Y | 1 | 15.769 | 23.800 | 27.502 | 1.00 | 20.01 | Y C |
| ATOM | 4093 | C30 | FRA | Y | 1 | 16.310 | 22.465 | 27.980 | 1.00 | 19.29 | Y C |
| ATOM | 4094 | C31 | FRA | Y | 1 | 15.545 | 21.551 | 28.783 | 1.00 | 19.61 | Y C |
| ATOM | 4095 | C32 | FRA | Y | 1 | 16.081 | 20.315 | 29.195 | 1.00 | 21.23 | Y C |
| ATOM | 4096 | C33 | FRA | Y | 1 | 17.394 | 19.964 | 28.819 | 1.00 | 18.14 | Y C |
| ATOM | 4097 | C34 | FRA | Y | 1 | 18.172 | 20.843 | 28.033 | 1.00 | 19.61 | Y C |
| ATOM | 4098 | C35 | FRA | Y | 1 | 17.642 | 22.083 | 27.612 | 1.00 | 19.21 | Y C |
| ATOM | 4099 | O36 | FRA | Y | 1 | 16.421 | 24.575 | 26.797 | 1.00 | 19.90 | Y O |
| ATOM | 4100 | O37 | FRA | Y | 1 | 8.904 | 33.109 | 26.339 | 1.00 | 21.63 | Y O |
| ATOM | 4101 | C38 | FRA | Y | 1 | 10.186 | 33.273 | 25.678 | 1.00 | 23.16 | Y C |
| ATOM | 4102 | O39 | FRA | Y | 1 | 3.746 | 33.908 | 24.230 | 1.00 | 36.52 | Y O |
| TER | 4103 | | FRA | Y | 1 | | | | | | |
| ATOM | 4104 | O | HOH | E | 1 | −2.816 | 80.929 | 50.812 | 1.00 | 19.03 | E O |
| ATOM | 4105 | O | HOH | E | 2 | 3.978 | 72.365 | 54.056 | 1.00 | 19.03 | E O |
| ATOM | 4106 | O | HOH | E | 3 | 13.505 | 98.252 | 72.880 | 1.00 | 19.36 | E O |
| ATOM | 4107 | O | HOH | E | 4 | 28.293 | 104.582 | 83.681 | 1.00 | 21.47 | E O |
| ATOM | 4108 | O | HOH | E | 6 | 6.360 | 44.178 | 47.881 | 1.00 | 23.42 | E O |
| ATOM | 4109 | O | HOH | E | 7 | 1.770 | 73.865 | 68.162 | 1.00 | 20.46 | E O |
| ATOM | 4110 | O | HOH | E | 8 | 8.297 | 17.524 | 35.431 | 1.00 | 28.17 | E O |
| ATOM | 4111 | O | HOH | E | 9 | 4.373 | 82.422 | 53.549 | 1.00 | 66.83 | E O |
| ATOM | 4112 | O | HOH | E | 10 | 9.876 | 77.587 | 53.891 | 1.00 | 15.33 | E O |
| ATOM | 4113 | O | HOH | E | 11 | 13.114 | 23.318 | 30.599 | 1.00 | 23.68 | E O |
| ATOM | 4114 | O | HOH | E | 12 | 7.067 | 14.767 | 42.081 | 1.00 | 41.33 | E O |
| ATOM | 4115 | O | HOH | E | 13 | 15.665 | 28.507 | 29.364 | 1.00 | 35.38 | E O |
| ATOM | 4116 | O | HOH | E | 14 | 8.724 | 81.834 | 51.911 | 1.00 | 15.54 | E O |
| ATOM | 4117 | O | HOH | E | 15 | 21.092 | 27.236 | 30.877 | 1.00 | 29.72 | E O |
| ATOM | 4118 | O | HOH | E | 16 | 4.235 | 23.958 | 10.152 | 1.00 | 18.27 | E O |
| ATOM | 4119 | O | HOH | E | 17 | 21.990 | 41.088 | 42.974 | 1.00 | 32.56 | E O |
| ATOM | 4120 | O | HOH | E | 18 | 20.666 | 46.477 | 48.657 | 1.00 | 22.11 | E O |
| ATOM | 4121 | O | HOH | E | 19 | 12.394 | 30.572 | 26.200 | 1.00 | 25.85 | E O |
| ATOM | 4122 | O | HOH | E | 20 | 24.458 | 88.275 | 67.914 | 1.00 | 18.95 | E O |
| ATOM | 4123 | O | HOH | E | 21 | 16.023 | 94.041 | 76.489 | 1.00 | 18.64 | E O |
| ATOM | 4124 | O | HOH | E | 22 | −3.046 | 75.441 | 65.884 | 1.00 | 19.92 | E O |
| ATOM | 4125 | O | HOH | E | 24 | 13.742 | 101.239 | 70.093 | 1.00 | 20.42 | E O |
| ATOM | 4126 | O | HOH | E | 25 | 2.139 | 79.403 | 76.859 | 1.00 | 24.59 | E O |
| ATOM | 4127 | O | HOH | E | 26 | −0.923 | 97.738 | 56.694 | 1.00 | 26.97 | E O |
| ATOM | 4128 | O | HOH | E | 27 | 27.493 | 25.824 | 48.659 | 1.00 | 25.58 | E O |
| ATOM | 4129 | O | HOH | E | 28 | −3.060 | 85.100 | 45.284 | 1.00 | 28.40 | E O |
| ATOM | 4130 | O | HOH | E | 29 | 2.126 | 21.471 | 26.630 | 1.00 | 18.24 | E O |
| ATOM | 4131 | O | HOH | E | 30 | 19.055 | 98.237 | 66.551 | 1.00 | 26.93 | E O |
| ATOM | 4132 | O | HOH | E | 31 | 5.015 | 20.070 | 34.897 | 1.00 | 27.21 | E O |
| ATOM | 4133 | O | HOH | E | 32 | 20.699 | 97.163 | 78.060 | 1.00 | 20.06 | E O |
| ATOM | 4134 | O | HOH | E | 33 | 19.905 | 95.504 | 66.214 | 1.00 | 16.74 | E O |
| ATOM | 4135 | O | HOH | E | 34 | 26.799 | 36.524 | 56.357 | 1.00 | 23.12 | E O |
| ATOM | 4136 | O | HOH | E | 35 | 7.281 | 42.459 | 52.886 | 1.00 | 27.29 | E O |
| ATOM | 4137 | O | HOH | E | 36 | −5.229 | 82.177 | 76.134 | 1.00 | 17.35 | E O |
| ATOM | 4138 | O | HOH | E | 37 | 16.156 | 81.681 | 74.210 | 1.00 | 33.58 | E O |
| ATOM | 4139 | O | HOH | E | 38 | 17.171 | 26.456 | 35.298 | 1.00 | 26.63 | E O |
| ATOM | 4140 | O | HOH | E | 41 | 10.220 | 96.211 | 76.240 | 1.00 | 36.39 | E O |
| ATOM | 4141 | O | HOH | E | 42 | 21.575 | 87.342 | 80.619 | 1.00 | 26.03 | E O |
| ATOM | 4142 | O | HOH | E | 43 | −2.344 | 82.211 | 46.311 | 1.00 | 33.39 | E O |
| ATOM | 4143 | O | HOH | E | 44 | 1.411 | 102.153 | 63.920 | 1.00 | 40.99 | E O |
| ATOM | 4144 | O | HOH | E | 45 | 22.412 | 37.472 | 55.894 | 1.00 | 36.08 | E O |
| ATOM | 4145 | O | HOH | E | 46 | 2.300 | 24.457 | 31.665 | 1.00 | 23.22 | E O |
| ATOM | 4146 | O | HOH | E | 47 | 13.621 | 22.599 | 34.360 | 1.00 | 23.98 | E O |
| ATOM | 4147 | O | HOH | E | 48 | 15.081 | 50.361 | 55.761 | 1.00 | 28.43 | E O |
| ATOM | 4148 | O | HOH | E | 49 | 14.580 | 93.564 | 78.622 | 1.00 | 24.96 | E O |
| ATOM | 4149 | O | HOH | E | 50 | 26.890 | 18.450 | 12.611 | 1.00 | 42.82 | E O |
| ATOM | 4150 | O | HOH | E | 51 | 9.227 | 107.514 | 67.012 | 1.00 | 41.46 | E O |
| ATOM | 4151 | O | HOH | E | 52 | 34.558 | 108.086 | 67.299 | 1.00 | 37.65 | E O |

TABLE 2-continued coordinates for the two molecules in the asymmetric unit of [T287] Aurora A (122–396) in complex with an inhibitor of formula II in space group P2$_1$

| | | | | | | | | | | | |
|---|---|---|---|---|---|---|---|---|---|---|---|
| ATOM | 4152 | O | HOH | E | 53 | 10.050 | 90.871 | 55.783 | 1.00 | 29.24 | E | O |
| ATOM | 4153 | O | HOH | E | 54 | 7.944 | 16.482 | 49.236 | 1.00 | 41.77 | E | O |
| ATOM | 4154 | O | HOH | E | 55 | 13.318 | 100.169 | 53.864 | 1.00 | 42.27 | E | O |
| ATOM | 4155 | O | HOH | E | 56 | 7.437 | 71.694 | 56.237 | 1.00 | 34.69 | E | O |
| ATOM | 4156 | O | HOH | E | 57 | −0.370 | 31.293 | 25.399 | 1.00 | 22.63 | E | O |
| ATOM | 4157 | O | HOH | E | 58 | 6.282 | 69.233 | 70.952 | 1.00 | 40.32 | E | O |
| ATOM | 4158 | O | HOH | E | 59 | 16.826 | 72.690 | 51.895 | 1.00 | 39.22 | E | O |
| ATOM | 4159 | O | HOH | E | 60 | 26.960 | 20.330 | 32.431 | 1.00 | 46.00 | E | O |
| ATOM | 4160 | O | HOH | E | 61 | 24.484 | 34.166 | 17.080 | 1.00 | 57.71 | E | O |
| ATOM | 4161 | O | HOH | E | 62 | 15.070 | 29.732 | 24.722 | 1.00 | 36.63 | E | O |
| ATOM | 4162 | O | HOH | E | 63 | 2.410 | 82.045 | 76.883 | 1.00 | 31.15 | E | O |
| ATOM | 4163 | O | HOH | E | 64 | 20.509 | 17.863 | 8.881 | 1.00 | 34.06 | E | O |
| ATOM | 4164 | O | HOH | E | 65 | 9.108 | 18.512 | 47.676 | 1.00 | 36.58 | E | O |
| ATOM | 4165 | O | HOH | E | 66 | −4.442 | 94.264 | 72.560 | 1.00 | 35.02 | E | O |
| ATOM | 4166 | O | HOH | E | 67 | 4.615 | 73.935 | 73.283 | 1.00 | 34.26 | E | O |
| ATOM | 4167 | O | HOH | E | 68 | 20.674 | 96.637 | 81.076 | 1.00 | 32.24 | E | O |
| ATOM | 4168 | O | HOH | E | 69 | 6.012 | 84.836 | 76.526 | 1.00 | 39.65 | E | O |
| ATOM | 4169 | O | HOH | E | 70 | 18.931 | 64.756 | 50.070 | 1.00 | 41.17 | E | O |
| ATOM | 4170 | O | HOH | E | 71 | 1.034 | 33.236 | 39.187 | 1.00 | 32.26 | E | O |
| ATOM | 4171 | O | HOH | E | 72 | −3.531 | 21.419 | 23.837 | 1.00 | 33.17 | E | O |
| ATOM | 4172 | O | HOH | E | 73 | 35.386 | 104.215 | 87.572 | 1.00 | 48.96 | E | O |
| ATOM | 4173 | O | HOH | E | 74 | 17.897 | 25.522 | 63.076 | 1.00 | 45.88 | E | O |
| ATOM | 4174 | O | HOH | E | 75 | 21.283 | 17.561 | 47.461 | 1.00 | 37.66 | E | O |
| ATOM | 4175 | O | HOH | E | 76 | −11.086 | 90.035 | 66.851 | 1.00 | 30.87 | E | O |
| ATOM | 4176 | O | HOH | E | 77 | 11.320 | 20.363 | 58.814 | 1.00 | 46.67 | E | O |
| ATOM | 4177 | O | HOH | E | 78 | −6.338 | 85.994 | 41.967 | 1.00 | 51.31 | E | O |
| ATOM | 4178 | O | HOH | E | 79 | 3.655 | 87.067 | 43.145 | 1.00 | 39.38 | E | O |
| ATOM | 4179 | O | HOH | E | 81 | 7.253 | 86.756 | 37.906 | 1.00 | 59.51 | E | O |
| ATOM | 4180 | O | HOH | E | 82 | 23.816 | 46.171 | 47.749 | 1.00 | 28.26 | E | O |
| ATOM | 4181 | O | HOH | E | 83 | −2.313 | 31.734 | 47.707 | 1.00 | 41.05 | E | O |
| ATOM | 4182 | O | HOH | E | 84 | 11.459 | 17.532 | 33.022 | 1.00 | 35.50 | E | O |
| ATOM | 4183 | O | HOH | E | 85 | 1.163 | 30.110 | 41.773 | 1.00 | 28.95 | E | O |
| ATOM | 4184 | O | HOH | E | 86 | 6.404 | 108.929 | 60.380 | 1.00 | 44.61 | E | O |
| ATOM | 4185 | O | HOH | E | 87 | 6.970 | 44.481 | 59.964 | 1.00 | 33.00 | E | O |
| ATOM | 4186 | O | HOH | E | 88 | 6.136 | 40.362 | 59.850 | 1.00 | 35.96 | E | O |
| ATOM | 4187 | O | HOH | E | 89 | 8.854 | 36.982 | 12.914 | 1.00 | 51.29 | E | O |
| ATOM | 4188 | O | HOH | E | 90 | 14.894 | 17.557 | 10.137 | 1.00 | 29.07 | E | O |
| ATOM | 4189 | O | HOH | E | 91 | 3.598 | 70.913 | 41.429 | 1.00 | 37.85 | E | O |
| ATOM | 4190 | O | HOH | E | 92 | 15.660 | 96.593 | 64.706 | 1.00 | 34.79 | E | O |
| ATOM | 4191 | O | HOH | E | 93 | −1.289 | 22.000 | 25.700 | 1.00 | 53.85 | E | O |
| ATOM | 4192 | O | HOH | E | 94 | 18.658 | 94.873 | 78.816 | 1.00 | 34.79 | E | O |
| ATOM | 4193 | O | HOH | E | 95 | 24.030 | 37.111 | 44.167 | 1.00 | 31.33 | E | O |
| ATOM | 4194 | O | HOH | E | 96 | 24.327 | 108.825 | 70.586 | 1.00 | 43.44 | E | O |
| ATOM | 4195 | O | HOH | E | 97 | 17.453 | 29.940 | 39.065 | 1.00 | 62.04 | E | O |
| ATOM | 4196 | O | HOH | E | 98 | −10.095 | 77.380 | 58.416 | 1.00 | 32.83 | E | O |
| ATOM | 4197 | O | HOH | E | 99 | 1.372 | 41.175 | 43.439 | 1.00 | 30.57 | E | O |
| ATOM | 4198 | O | HOH | E | 100 | 13.220 | 40.977 | 61.050 | 1.00 | 25.13 | E | O |
| ATOM | 4199 | O | HOH | E | 101 | 20.635 | 23.766 | 29.311 | 1.00 | 36.67 | E | O |
| ATOM | 4200 | O | HOH | E | 102 | 6.907 | 103.740 | 69.211 | 1.00 | 39.48 | E | O |
| ATOM | 4201 | O | HOH | E | 103 | 29.965 | 20.328 | 27.392 | 1.00 | 35.16 | E | O |
| ATOM | 4202 | O | HOH | E | 104 | −5.202 | 80.206 | 74.097 | 1.00 | 29.87 | E | O |
| ATOM | 4203 | O | HOH | E | 105 | −0.936 | 62.297 | 61.894 | 1.00 | 42.93 | E | O |
| ATOM | 4204 | O | HOH | E | 106 | 36.982 | 102.874 | 54.415 | 1.00 | 36.76 | E | O |
| ATOM | 4205 | O | HOH | E | 107 | 5.889 | 102.017 | 53.094 | 1.00 | 63.79 | E | O |
| ATOM | 4206 | O | HOH | E | 108 | 39.219 | 43.505 | 52.395 | 1.00 | 38.65 | E | O |
| TER | 4207 | | HOH | E | 108 | | | | | | | |
| END | | | | | | | | | | | | |

The shape of the ATP binding pocket is defined by the atomic coordinates of the atoms in the amino-acid residues in Tables 1 and 2. Table 1 lists the atomic coordinates for [T287D] Aurora A(122–396) catalytic domain, together with the AMP-PNP molecule, in Protein Data Bank (PDB) format, as determined from the first crystalline form. Table 2-lists the atomic coordinates for the two independent molecules of the GSHM-[T287D]Aurora A (122–400) catalytic domain, together with the inhibitor of formula II, in PDB format, as determined from the second crystalline form. The atomic coordinates are listed in those lines that begin with the code ATOM or HETATM, one atom per line. Following the code are: the unique atom number; the atom name; the amino acid residue name; the protein chain identifier; the amino acid residue number; the atomic coordinates x, y, and z in orthogonal Angstrom space; the atomic occupancy factor; the atomic temperature factor; the chain identifier; and the atom type. The atomic coordinates of the ATP analogue AMP-PNP carry the residue name of -ANP. Solvent water molecules carry the residue name of HOH, and a citrate and a bound phosphate derived from the crystallisation buffer carry the residue name of FRA. In the inhibitor complex the inhibitor molecules carry the residue name of FRA.

It is possible to reproduce the shape of the [T287D] Aurora A active site binding pocket through carrying out similar structure determinations with minor variations in the experimental conditions (including variations in construct such as mutants, variants and homologues, variations in crystallisation conditions, crystal form, trial model used in molecular replacement, etc.). Different experiments may give rise to apparently different co-ordinates, but those in the art will realise that two apparently different sets of coordinates for the same or similar proteins can be shown to be equivalent by superposition of the molecules. For example, the coordinates in Tables 1 and 2 are different numerically. But following superposition they can be seen to describe the same molecule. It will be appreciated that, according to accepted practice, the atomic coordinates may vary within certain limits due to experimental variation. Such variation includes standard experimental error (coordinates determined for the same construct may vary somewhat, for example within 0.3 Å) and other variation (for example, coordinates of Aurora mutants, variants, or homologues). The co-ordinates of the active site ATP binding site may also differ upon introduction of a different small molecule inhibitor, where flexible portions of the binding site adopt a new conformation specific to a type of inhibitor. For example, following superposition, the protein coordinates in Table 1 are seen to be marginally different to those in Table 2, as a result of flexible portions of the protein being influenced by the presence of a different inhibitor. This constitutes a modification of the active site ATP binding site rather than the creation of a new site. Those in the art will realise that kinases in general have flexible active sites, and adopt a number of biologically relevant conformations related to the state of catalytic activation. Therefore, for the purposes of differentiating the shape of the active site ATP-binding pocket from that in other kinases, the binding pocket is best defined by a subset of amino acids that are least affected by flexible protein responses to inhibitor binding. Thus, a protein can be said to have the Aurora active site described here if, following superposition, the positions of all atoms in the active site residues in set B, i.e. Arg136, Leu138, Gly139, Val146, Ala159, Lys161, Leu163, Ile183, Gln184, Leu193, Leu195, Leu207, Leu209, Glu210, Tyr211, Ala212, Pro213, Leu214, Gly215, Thr216, Arg219, Glu259, Asn260 and Leu262 or their equivalents, are within a root mean square deviation of 1.0 Å of the coordinates of these amino acid residues given in Tables 1 and 2. An equivalent residue is an amino acid residue in any Aurora mutant, variant, or homologue that occurs at one of the amino acid sequence positions in Tables 1 or 2—if the residue is not identical, only the N, Cα, Cβ, C, O atoms may be sensibly included in the rmsd calculation. It is also understood that if equivalent residues are not present in a particular variant or homologue, then they are omitted from the calculation of the average distance.

The criterion of 1.0 Å is intended to be large enough to allow the types of variations described above, yet small enough to discriminate between the active sites of Aurora kinases and other kinases. That this criterion is reasonable is illustrated in Table 3, which compares [T287D]Aurora A to one of the most closely related kinases, PKA.

TABLE 3 rms deviations in Å between all atoms of set B amino acids in the active site. The top row refers to the PDB codes for 6 entries of a different kinase, protein kinase A (PKA). The bold numbers refer to the Tables 1 and 2 which contain Aurora coordinates. Thus, when independent structure determinations of Aurora are compared (1-2, 1-3, 2-3) the rmsd is less than 1 Å, whereas when Aurora is compared to PKA (6 independent structures) the rmsd is greater than 1 Å.

|     |      |       | 1 atp | 1 13r | 1 bx6 | 1 apm | 1 ydt | 1 cmk |
|-----|------|-------|-------|-------|-------|-------|-------|-------|
| 1-2 | 0.85 | 1-PKA | 1.32  | 1.32  | 1.29  | 1.24  | 1.28  | 1.17  |
| 1-3 | 0.67 | 2-PKA | 1.19  | 1.14  | 1.08  | 1.13  | 1.13  | 1.13  |
| 2-3 | 0.42 | 3-PKA | 1.14  | 1.08  | 1.09  | 1.08  | 1.10  | 1.21  |

Thus, according to a further aspect of the invention, we provide the shape of the active site ATP binding pocket in Aurora protein kinase as defined by the atomic coordinates given in Tables 1 and 2 or by equivalent coordinates. Equivalent coordinates are those for which the subset of least flexible residues (set B) have atomic positions on average within 1.0 Å of those in the Aurora active site ATP binding pocket as defined by the coordinates in Tables 1 and 2.

According to a further aspect of the invention we provide a method to determine or design the three-dimensional structure of a crystal form of Aurora (including Aurora A homologues, variants, mutants, and inhibitor complexes) by using a particular Aurora A catalytic domain structure. The atomic co-ordinates of an Aurora A crystal may be used to model the structure of a second Aurora crystal by difference Fourier or molecular replacement methods.

The crystal structure of the Aurora A kinase catalytic domain described herein can be used to model the three-dimensional structures of other Aurora kinases. Furthermore, alternative methods of determining three-dimensional structure that do not rely on X-ray diffraction techniques and thus do not require crystallization of the protein, such as NMR techniques, are simplified if a model of the structure is available for refinement using the additional data gathered by the alternative technique. Thus, definition of the three-dimensional structure of the catalytic domain of Aurora A kinase enables one of skill in the art to determine the structure of the catalytic domains of other Aurora kinases.

Knowledge of the three-dimensional structure of the catalytic domain of Aurora A kinase provides a means for investigating the mechanism of action of the protein and tools for identifying inhibitors of its function. Knowledge of the three-dimensional structure of the catalytic domain of Aurora A kinase allows one to design molecules capable of binding thereto, including molecules which are capable of inhibiting (partially or completely) the activity of Aurora A kinase.

Illustrative crystalline forms of polypeptides of this invention having various physicochemical characteristics are disclosed herein. Preferred crystalline forms invention are capable of diffracting x-rays to a resolution of better than about 3.5 Å, and more preferably to a resolution of 3.0 Å or better, and even more preferably to a resolution of 2.2 Å or better, and are useful for determining the three-dimensional structure of the material.

Crystalline compositions of this invention specifically include those in which the crystals comprise Aurora kinase family proteins characterized by the structural coordinates set forth in any of the accompanying tables or characterized by coordinates having a root mean square deviation therefrom, with respect to backbone atoms of amino acids given in the Tables, of 1.5 Å or less. Crystalline compositions of this invention also include those in which the crystals comprise Aurora kinase family proteins characterized by having a binding site defined by the x,y,z-coordinates of atoms in the set of amino acid residues (set A) given by the list Arg136, Leu138, Gly139, Lys140, Gly141, Val146, Lys161, Leu163, Val177, Glu180, Val181, Ile183, Gln184, Leu193, Leu195, Leu207, Leu209, Glu210, Tyr211, Ala212, Pro213, Leu214, Gly215, Thr216, Arg219, Glu259, Asn260, Leu262, Ala272, Asp273, Phe274, Gly275, Trp276, Ser277, Val278, and His279, the atomic coordinates being listed in Tables 1 and 2. Further, crystalline forms of polypeptides of this invention also include those in which the crystals comprise Aurora kinase family proteins in which the binding site is defined by the x,y,z-coordinates of atoms in the set of amino acid residues (set B) given by the list Arg136, Leu138, Gly139, Val146, Ala159, Lys161, Leu163, Ile183, Gln184, Leu193, Leu195, Leu207, Leu209, Glu210, Tyr211, Ala212, Pro213, Leu214, Gly215, Thr216, Arg219, Glu259, Asn260 and Leu262 or their equivalent, are within a root mean square deviation of 1.0 Å of the coordinates of these amino acid residues given in Tables 1 and 2.

Structural coordinates of a crystalline composition of this invention may be stored in a machine-readable form on a machine-readable storage medium, such as a computer hard drive, diskette, DAT tape, for display as a three-dimensional shape or for other uses involving computer-assisted manipulation of, or computation based on, the structural coordinates or the three-dimensional structures they define. For example, data defining the three dimensional structure of a protein of the Aurora kinase family, or portions or structurally similar homologues of such proteins, may be stored in a machine-readable storage medium and displayed as a three-dimensional representation of the protein structure, typically using a computer capable of reading the data from said storage medium and programmed with instructions for creating the representation from such data. This invention thus encompasses a machine, such as a computer, having a memory which contains data representing the structural coordinates of a crystalline composition of this invention, such as the coordinates set forth in Tables 1 and 2, together with additional optional data and instructions for manipulating such data. Such data may be used for a variety of purposes, such as the elucidation of other related structures and drug discovery.

For example, a first set of such machine readable data may be combined with a second set of machine-readable data using a machine programmed with instructions for using the first data set and the second data set to determine at least a portion of the coordinates corresponding to the second set of machine-readable data. For instance, the first set of data may comprise a Fourier transform of at least a portion of the coordinates for Aurora kinase proteins set forth in Tables 1 and 2, while the second data set may comprise X-ray diffraction data of a molecule or molecular complex.

More specifically, one of the objects of this invention is to provide three-dimensional structural information on new complexes of Aurora kinase family members (e.g., complexed with an ATP analogue or an inhibitor, such as a synthetic inhibitor), new Aurora kinase family members and variants of any of the foregoing. The structural coordinates of a crystalline composition of this invention, or portions thereof, can be used to solve, e.g. by molecular replacement, the three dimensional structure of a crystalline form of such a polypeptide or polypeptide complex. Doing so involves obtaining x-ray diffraction data for crystals of the polypeptide or polypeptide complex (e.g., in complex with an ATP analogue or an inhibitor, such as a synthetic inhibitor) for which one wishes to determine the three dimensional structure. The three-dimensional structure of that polypeptide or complex is determined by analyzing the x-ray diffraction data using molecular replacement techniques with reference to the structural coordinates provided. For example, molecular replacement can use a molecule having a known structure as a starting point to model the structure of an unknown crystalline sample. This technique is based on the principle that two molecules which have similar structures, orientations and positions in the unit cell diffract similarly. The term "molecular replacement" refers to a method that involves generating a preliminary model of a crystal whose atomic coordinates are not known, by orienting and positioning a related molecule whose atomic coordinates are known. Phases are then calculated from this model and combined with observed amplitudes to give an approximate Fourier synthesis of the structure whose coordinates are unknown. Molecular replacement involves positioning the known structure in the unit cell in the same location and orientation as the unknown structure. Once positioned, the atoms of the known structure in the unit cell are used to calculate the structure factors that would result from a hypothetical diffraction experiment. This involves rotating the known structure in the six dimensions (three angular and three spatial dimensions) until alignment of the known structure with the experimental data is achieved. This approximate structure can be refined to yield a more accurate and often higher resolution structure using various refinement techniques. For instance, the resultant model for the structure defined by the experimental data may be subjected to rigid body refinement in which the model is subjected to limited additional rotation in the six dimensions yielding positioning shifts of under about 5%. The refined model may then be further refined using other known refinement methods.

For example, one may use molecular replacement to exploit a set of coordinates such as set forth in Table 1 or Table 2 to determine the structure of the catalytic domain of Aurora kinase in complex with other than ATP-PNP or the inhibitor of formula II.

The present invention also relates to designing and, optionally producing, a homologue of Aurora kinase, such as a homologue of Aurora kinase A, that mimics the three-dimensional structure of the Aurora kinase. The method comprises:
  (i) determining the three-dimensional coordinates of atoms of an Aurora kinase;
  (ii) providing a computer having a memory means, a data input means, a visual display means, said memory means containing three-dimensional molecular simulation software operable to retrieve co-ordinate data from said memory means and to display a three-dimensional representation of a molecule on said visual display means and being operable to produce a modified three-dimensional homologue representation responsive to operator-selected changes to the structure of the Aurora kinase and to display the three-dimensional representation of the modified three-dimensional homologue;
  (iii) inputting three-dimensional co-ordinate data of atoms of Aurora kinase into the computer and storing said data in the memory means;
  (iv) inputting into the data input means of said computer at least one operator-selected change in structure of the Aurora kinase;
  (v) executing said molecular simulation software to produce a modified three-dimensional molecular representation of the homologue structure;

(vi) displaying the three-dimensional representation of the homologue on said visual display means, whereby changes in three-dimensional structure of the Aurora kinase resulting from changes on structure can be visually monitored;

(vii) repeating steps (iv) through (vi) to produce a multiplicity of homologues; and (viii) selecting a homologue structure represented by a three-dimensional representation wherein the three-dimensional configuration and spatial arrangements of the kinase catalytic domain remain substantially preserved, thereby producing a homologue of Aurora kinase that mimics the three-dimensional structure of the Aurora kinase.

The present invention also relates to a method of producing a modulator of Aurora kinase (particularly inhibitors), such as a modulator of Aurora kinase A. The method comprises identifying a compound or molecule or designing a compound or molecule that fits into the active site ATP binding pocket of the Aurora kinase, wherein the ATP binding pocket is defined by (a) Arg136, Leu138, Gly139, Lys140, Gly141, Val146, Lys161, Leu163, Val177, Glu180, Val181, Ile183, Gln184, Leu193, Leu195, Leu207, Leu209, Glu210, Tyr211, Ala212, Pro213, Leu214, Gly215, Thr216, Arg219, Glu259, Asn260, Leu262, Ala272, Asp273, Phe274, Gly275, Trp276, Ser277, Val278, and His279, the atomic coordinates being listed in Tables 1 and 2 or (b) the x,y,z-coordinates of atoms in the set of amino acid residues (set B) given by the list Arg136, Leu138, Gly139, Val146, Ala159, Lys161, Leu163, Ile183, Gln184, Leu193, Leu195, Leu207, Leu209, Glu210, Tyr211, Ala212, Pro213, Leu214, Gly215, Thr216, Arg219, Glu259, Asn260 and Leu262, each having coordinates as described in Tables 1 and 2, thereby producing a modulator of Aurora kinase.

Another object of the invention is to provide a method for determining the three-dimensional structure of the catalytic domain of an Aurora kinase protein, or the catalytic domain of an Aurora kinase protein in complex with an inhibitor, using homology modeling techniques and structural coordinates for a composition of this invention. Homology modeling involves constructing a model of an unknown structure using structural coordinates of one or more related proteins, protein domains and/or subdomains. Homology modeling may be conducted by fitting common or homologous portions of the protein or peptide whose three dimensional structure is to be solved to the three dimensional structure of homologous structural elements. This approach can be used to rebuild part or all of a three dimensional structure with replacement of amino acids (or other components) by those of the related structure to be solved. For example, using the structural coordinates of the catalytic domain of an Aurora kinase in complex with AMP-PNP or the inhibitor of formula II, it is possible to determine the three dimensional structure of the catalytic domain of another Aurora kinase protein through the use of homology modeling. Those coordinates may be stored, displayed, manipulated and otherwise used in like fashion as the Aurora kinase coordinates of Tables 1–2.

Thus, crystalline compositions of this invention provide a starting material for use in solving the three-dimensional structure of other Aurora kinase polypeptides.

By way of further example, the structure defined by the machine readable data may be computationally evaluated for its ability to associate with various chemical entities. The term "chemical entity", as used herein, refers to chemical compounds, complexes of at least two chemical compounds, and fragments of such compounds or complexes.

For instance, a first set of machine-readable data defining the three-dimensional structure of an Aurora kinase family protein, or a portion or complex thereof, is combined with a second set of machine-readable data defining the structure of a chemical entity or moiety of interest using a machine programmed with instructions for evaluating the ability of the chemical entity or moiety to associate with the Aurora kinase family protein or portion or complex thereof and/or the location and/or orientation of such association. Such methods provide insight into the location, orientation and energetics of association of the Aurora kinase family protein with such chemical entities. Chemical entities that associate or interact with an Aurora kinase may inhibit its interaction with naturally occurring ligands for the protein and may inhibit biological functions mediated by such interaction. Such chemical entities are drug candidates.

The protein structure encoded by the data may be displayed in a graphical format permitting visual inspection of the structure, as well as visual inspection of the structure's association with chemical entities. Alternatively, more quantitative or computational methods may be used. For example, one method of this invention for evaluating the ability of a chemical entity to associate with any of the molecules or molecular complexes set forth herein comprises the steps of: a) employing computational means to perform a fitting operation between the chemical entity and a binding pocket or other surface feature of the molecule or molecular complex; and b) analyzing the results of the fitting operation to quantify the association between the chemical entity and the binding pocket.

This invention further provides for the use of the structural coordinates of a crystalline composition of this invention, or portions thereof, to identify reactive amino acids, such as cysteine residues, within the three-dimensional structure, such as within or adjacent to the catalytic domain; to generate and visualize a molecular surface, such as a water-accessible surface or a surface comprising the space-filling van der Waals surface of all atoms; to calculate and visualize the size and shape of surface features of the protein or complex, e.g., ligand binding pockets; to locate potential H-bond donors and acceptors within the three-dimensional structure, preferably within or adjacent to a ligand binding site; to calculate regions of hydrophobicity and hydrophilicity within the three-dimensional structure, preferably within or adjacent to a ligand binding site; and to calculate and visualize regions on or adjacent to the protein surface of favorable interaction energies with respect to selected functional groups of interest (e.g. amino, hydroxyl, carboxyl, methylene, alkyl, alkenyl, aromatic carbon, aromatic rings, heteroaromatic rings, substituted and unsubstituted phosphates, substituted and unsubstituted phosphonates, substituted and unsubstituted fluoro and difluorophosphonates; etc.). One may use the foregoing approaches for characterizing the protein and its interactions with moieties of potential ligands to design or select compounds capable of specific covalent attachment to reactive amino acids (e.g., cysteine) and to design or select compounds of complementary characteristics (e.g., size, shape, charge, hydrophobicity/hydrophilicity, ability to participate in hydrogen bonding, etc.) to surface features of the protein, a set of which may be preselected. Using the structural coordinates, one may also predict or calculate the orientation, binding constant or relative affinity of a given ligand to the protein in the complexed state, and use that information to design or select compounds of improved affinity.

In such cases, the structural coordinates of the Aurora kinase family protein, or portion or complex thereof, are entered in machine readable form into a machine programmed with instructions for carrying out the desired operation and containing any necessary additional data (e.g. data defining structural and/or functional characteristics of a potential ligand or moiety thereof, defining molecular characteristics of the various amino acids).

One method of this invention provides for selecting from a database of chemical structures a molecular compound capable of binding to an Aurora kinase family protein (e.g., coordinates defining the three dimensional structure of an Aurora kinase family protein or a portion thereof). Points associated with the three dimensional structure (structural coordinates) of a crystalline form of Aurora A kinase catalytic domain are characterized with respect to the favorability of interactions with one or more functional groups. A database of chemical structures is then searched for candidate compounds containing one or more functional groups disposed for favorable interaction with the protein based on the prior characterization. Compounds having structures which best fit the points of favorable interaction with the three dimensional structure are thus identified.

It is often preferred, although not required, that such searching be conducted with the aid of a computer. In that case a first set of machine-readable data defining the three-dimensional structure of an Aurora kinase family protein, or a portion or complex thereof, is combined with a second set of machine readable data defining one or more moieties or functional groups of interest, using a machine programmed with instructions for identifying preferred locations for favorable interaction between the functional group(s) and atoms of the protein. A third set of data, which defines the location(s) of favorable interaction between protein and functional group(s) is generated. The third set of data is then combined with a fourth set of data defining the three-dimensional structures of one or more chemical entities using a machine programmed with instructions for identifying chemical entities containing functional groups to best fit the locations of their respective favorable interaction with the protein.

Compounds of the structures selected or designed by any of the foregoing means may be tested for their ability to bind to an Aurora kinase family protein, inhibit the binding of an Aurora kinase family protein to a natural or non-natural ligand therefor, and/or inhibit a biological function mediated by an Aurora kinase family member.

The new crystal may be a crystal of a homologue, variant, mutant, or inhibitor complex of Aurora. The shape of the Aurora active site binding pocket in the new crystal model is an equivalent shape to that of the first. The active site binding pocket of the original Aurora A crystal is defined by the amino acid residues of set A and their atomic coordinates as given in Tables 1 and 2. Equivalent shape is defined as having an rmsd of less than 1 Å upon superposition of the subset of least flexible amino acid residues (set B).

Thus, the invention provides a method to determine or design the three dimensional structure of a crystal form of Aurora by difference Fourier or Molecular Replacement, using the coordinates (Tables 1 and 2) of an Aurora A crystal to model the structure of a new Aurora crystal wherein the active site ATP binding region is equivalent to that in the first crystal. The method may be carried out as follows. An Aurora protein (wild type, mutant, variant or homologue) is purified and crystallised as a pure protein or in complex with an inhibitor compound. This crystal may have the same crystal form (same protein packing) as one of the crystal structures defined by Tables 1 and 2, or it may have a different crystal form (different protein packing). By taking diffraction measurements of the crystal and using the atomic coordinates in Tables 1 or 2 (or equivalent coordinates), it is possible to work out the structure of the crystal by the known methods of difference Fourier (same packing) or molecular replacement (different packing). This invention covers the use in drug design of the active site ATP binding pocket in any new crystal since this will be equivalent to that in the original crystal.

The invention further provides Aurora A proteins (including homologues, variants and mutants) designed by the above method. The Aurora A proteins may have identical properties to wild type Aurora A or may have one or more different properties compared to wild type Aurora A.

According to a further aspect of the invention, we provide a method to select or design chemical modulators (preferably inhibitors) of Aurora by using the Aurora A catalytic domain structure (including that of homologues, variants, mutants, and inhibitor complexes) and the shape of the active site ATP binding pocket (or an equivalent shape as previously defined). Information from the three dimensional atomic coordinates of the AMP-PNP molecule and its spatial orientation in relation to the three dimensional atomic coordinates of the Aurora A catalytic domain is used as a tool to design Aurora modulators (preferably inhibitors). In addition, information from the three dimensional atomic coordinates of the inhibitor molecule of formula II and its spatial orientation in relation to the three dimensional atomic coordinates of the Aurora A catalytic domain is used as tool to design Aurora modulators (preferably inhibitors). Small-molecule modulators of Aurora may be selected or designed to fit into the shape of the active site binding pocket.

Knowledge of the structural determinants that account for the difference in substrate specificity between Aurora A and other kinases, such as PKA, provides a foundation for the design of highly specific modulators of the Aurora A enzyme.

Structural differences at the ATP binding pocket between Aurora and other kinases (defined by differences in the atomic coordinates of residues in the ATP pocket) may be used to design selective Aurora A modulators.

According to a further aspect of the invention, use of the coordinates of the Aurora A catalytic domain (Tables 1 and 2) to locate other pockets for interaction by small molecule modulators that affect Aurora activity is claimed. Such pockets may overlap with the active site ATP binding pocket or be completely independent. The three-dimensional structure of Aurora A kinase is an essential tool in the discovery of any such pockets that provide an alternative for modulator interaction to the active site ATP binding pocket.

As described above, the Aurora A crystal structure may be used in the rational design of drugs which modulate (preferably inhibit) the action of Aurora. These Aurora modulators may be used to prevent or treat the undesirable physical and pharmacological consequences of inappropriate Aurora activity.

The present invention will now be described with reference to the following non-limiting Examples.

Definition of Terms

In the Description (including the Examples) the following terms are used:

The term "atomic co-ordinates" refers to mathematical co-ordinates corresponding to the positions of every atom derived from mathematical equations related to the diffraction patterns obtained from a monochromatic beam of X-rays illuminating a crystal. The diffraction data are used to calculate an electron density map of the repeating unit of the crystal. The electron density maps are used to establish the positions of the individual atoms within the unit cell of the crystal. Those of skill in the art understand that a set of atomic co-ordinates determined by X-ray crystallography is not without standard error or experimental variation.

The term "unit cell" refers to the basic building block from which the entire volume of a crystal may be constructed.

The term "space group" refers to the arrangement of symmetry elements within a unit cell.

The term "molecular replacement" refers to a method that involves generating a preliminary model of a crystal whose atomic co-ordinates are not known, by orienting and positioning a related molecule whose atomic co-ordinates are known. Phases are then calculated from this model and combined with observed amplitudes to give an approximate Fourier synthesis of the structure whose co-ordinates are unknown.

EXAMPLE 1

Production of the Kinase Catalytic Domain of Aurora A Molecular Biology

In order to obtain a polypeptide (or protein) that can be utilised for determination of the three dimensional (tertiary) structure of Aurora A, DNA encoding Aurora A may be obtained by total gene synthesis or by cloning. This DNA may then be expressed in a suitable expression system to obtain a polypeptide that can be subjected to techniques to determine its three dimensional structure.

In this case, the human Aurora A gene carrying an artificially induced mutation (GAT to ACT in nucleotides 862–864, taking the A of the initial ATG in the open reading frame of the gene to be +1) encoding for a threonine to aspartate (T to D using the single letter amino acid code) mutation of amino acid 287 (taking the first amino acid immediately after the initial methionine as amino acid number one) formed the basis of the expression construct used in these studies. This [T287D]Aurora A mutant was a gift of Dr. Jim Bischoff, SUGEN Inc. Since the full length [T287D]Aurora A protein expressed in $E.$ $coli$ was poorly soluble and aggregated on purification, a truncated mutant form was generated. The regions encoding for amino acids 94 to the stop codon of [T287D] Aurora A was amplified using the polymerase chain reaction (PCR). The 5' PCR primer (5'GATCGATCGGATCCACCCAAAAGAG-CAAGCAGCCC 3'; SEQ ID NO.: 1) carried a spacer region (to allow efficient cleavage by restriction endonuclease), the BamH1 restriction endonuclease recognition sequence and sequence corresponding to the bases 283–301. The 3' primer (5' TGACGCTAGGATCCCCTAAGACT-GTTTGCTAGCTGATTC 3'; SEQ ID NO.: 2) carried a spacer region, BamH1 recognition sequence and 3' end of the Aurora A (bases 1189–1212) sequence including the stop codon. PCR products were purified and cloned in to the pCR-Script vector (Stratagene) using the pCR-Script AMP cloning kit (Stratagene. product # 211188) according to manufacturers directions. The pCR-Script vector carrying the [T287D] Aurora A (94–402) sequence was digested with BamH1, the digestion products resolved by agarose gel electrophoresis and the DNA fragment corresponding to the [T287D] Aurora A (94–402) sequence excised and purified using a Qiagen QIAquick kit (Qiagen product #28704). This fragment was then ligated into the vector pTB375NBSE, which had previously been cut with BamH1. (Details of the methods for the assembly of recombinant DNA molecules can be found in standard texts, for example Sambrook et al. 1989, Molecular Cloning—A Laboratory Manual, $2^{nd}$ Edition, Cold Spring hbor Laboratory Press and Ausubel et al. 1999, Current Protocols in Molecular Biology, John Wiley and Sons Inc). The pTB375NBSE vector is derived from pAT153, which is a mobilization-minus derivative of pBR322. The inserted genes were under the control of a bacteriophage T7 promoter and therefore requires expression of the T7 polymerase in trans for efficient transcription in $E.$ $coli$. The plasmid encodes tetracyline resistance for selection.

The ligation reactions were transfected in-to TOP10 competent $E.$ $coli$ (Invitrogen product #C4040-10) and $E.$ $coli$ carrying the pTB375NBSE recombinant vectors identified by their ability to grow on media containing tetracycline. Plasmid DNA was extracted from these bacteria and subjected to digestion with the restriction endonuclease EcoR1 to identify those carrying the [T287D] Aurora A (94–402) sequence. The identity of the insert was then confirmed by dideoxy chain termination DNA sequencing prior to protein expression.

pTB375NBSE carries the initiation codon (ATG) 3' to the T7 promoter and also the following sequence up to and including the BamH1 restriction endonuclease recognition site:

```
                                          (SEQ ID NO.: 3)
5' . . . ATG GGC CAT CAT CAT CAT CAT CAC GGA
TCC . . . 3'
```

Sequences inserted into the BamH1 site "in frame" with the initiation codon will therefore be expressed as a fusion protein with the following N-terminal fusion:

```
                                          (SEQ ID NO.: 4)
   (N-terminal) MGHHHHHHGS . . . (C-terminal)
```

The fusion of 6 histidines to proteins is commonly used to provide a "tag" for protein purification, usually by affinity for metal ions such as nickel. Since the [T287D] Aurora A sequence coding for amino acids 94–402 was inserted in to the BamH1 site, the plasmid encodes for the following protein (using the standard single letter amino acid code):

```
MGHHHHHHGSTQKSKQPLPSAPENNPEEELASKQKNEESKKRQWALEDFEIG    (SEQ ID NO.: 5)

RPLGKGKFGNVYLAREKQSKFILALKVLFKAQLEKAGVEHQLRREVEIQSHL

RHPNILRLYGYFHDATRVYLILEYAPLGTVYRELQKLSKFDEQRTATYITELA

NALSYCHSKRVIHRDIKPENLLLGSAGELKIADFGWSVHAPSSRRTDLCGTLD

YLPPEMIEGRMHDEKVDLWSLGVLCYEFLVGKPPFEANTYQETYKRISRVEF
```

-continued

```
TFPDFVTEGARDLISRLLKHNPSQRPMLREVLEHPWITANSSKPSNCQNKESA

SKQS.
```

This protein will be referred to in the text as MG-6His-GS-[T287D]Aurora A(94-402).

Based on the limited proteolysis studies (described later in Example 1), two additional truncated mutant forms of the Aurora A protein were also generated. The regions encoding for amino acids 113–400 and 122–400 of [T287D]Aurora A were amplified using the polymerase chain reaction (PCR). The 5' PCR primers (5'CATATGCTGGCATCAAAACAGAAAAATG 3' (SEQ ID NO.: 6) for 113–400 of [T287D]Aurora A or 5'CATATGTCAAAAAAGAGGCAGTGGGC 3'(SEQ ID NO.: 7) for 122–400 of [T287D]Aurora A) carried a NdeI restriction endonuclease recognition sequence. A single 3' primer (5'GGATCCTCATTTGCTAGCTGATTCTTTGTTTTGG 3'(SEQ ID NO.: 8)) was used for both constructs and carries a BamH1 recognition sequence and 3' end of the Aurora A sequence following the stop codon. PCR products were purified and cloned into the pCR-Script vector (Stratagene) using the pCR-Script AMP cloning kit (Stratagene. product #211188) according to manufacturers instructions and transfected into the E. coli strain DH5□ (Invitrogen product #18258-012). The E. coli colonies containing the recombinant pPCR-Script [T287D]Aurora A(113–400) or pPCRscript [T287D]Aurora A(122–400) were identified by colony PCR screening using the primers T3 (5'AATTAACCCTCACTAAAGGG 3' (SEQ ID NO.: 9)) and T7pro (5'TAATACGACTCACTATAGGG 3' (SEQ ID NO.: 10)) hybridising specifically on either side of the pPCR script vector cloning site. The pPCR-Script vectors carrying the [T287D]Aurora A(113–400) or [T287D]Aurora A(122–400) sequence were prepared from E. coli and were digested with Nde1 and BamH1, the digestion products resolved by agarose gel electrophoresis. The fragments containing the [T287D]Aurora A(113–400) or [T287D]Aurora(122–400) were ligated into the expression vector pET28a (Novagen product #69864-3) between the Nde1 and BamH1 restriction sites. The inserted genes were cloned in frame with a sequence coding for a 6 histidine tag followed by a sequence encoding a thrombin protease cleavage site (see below for a complete description). The inserted genes are under the control of a bacteriophage T7 promoter and therefore require expression of the T7 polymerase in trans for efficient transcription in E. coli. The plasmid encodes kanamycin resistance for selection.

The ligation reactions were transfected into DH5 □ competent E. coli and the bacteria carrying the pET28a-[T287D]Aurora A(113–400) or pET28a-[T287D]Aurora A(122–400) recombinant vectors were identified by their ability to grow on media containing kanamycin. Plasmid DNAs were extracted from these bacteria and subjected to digestion with the restriction endonucleases Nde1 and BamH1 to identify those carrying the [T287D]Aurora A(113–400) or [T287D]Aurora A(122–400) sequences. The identity of the insert was then confirmed by dideoxy chain termination DNA sequencing prior to protein expression.

pET28a carries the initiation codon (ATG) 3' to the T7 promoter and also the following sequence up to and including the Nde1 restriction endonuclease recognition site:

```
                                          (SEQ ID NO.: 11)
5' . . . ATG GGC AGC AGC CAT CAT CAT CAT CAT CAC

AGC AGC GGC CTG GTG CCG CGC GGC AGC CAT ATG . . .

3'
```

Sequences inserted into the Nde1 site "in frame" with the initiation codon will therefore be expressed as a fusion protein with the following N-terminal fusion (using the standard single letter amino acid code):

```
                                          (SEQ ID NO.: 12)
(N-terminal) MGSSHHHHHHSSGLVPRGSHM . . .
(C-terminal)
```

The fusion of 6 histidines to proteins is commonly used to provide a "tag" for protein purification, usually by affinity for metal ions such as nickel. The motif "LVPRGS" (SEQ ID NO.: 13) corresponds to a specific thrombin protease cleavage site that allows the proteolytic removal of the sequence "MGSSHHHHHHSSGLVPR" (SEQ ID NO.: 14) after incubation of the protein with thrombin. Since the [T287D]Aurora A sequences coding for amino acids 113–400 and 122–400 were inserted into the Nde 1 site, the plasmid encodes for the following protein (using the standard single letter amino acid code):

```
[T287D]Aurora A(113-400)
MGSSHHHHHHSSGLVPRGSHMLASKQKNEESKKRQWALEDFEIGRPLGKGK     (SEQ ID NO.: 15)

FGNVYLAREKQSKFILALKVLFKAQLEKAGVEHQLRREVEIQSHLRHPNILRL

YGYFHDATRVYLILEYAPLGTVYRELQKLSKFDEQRTATYITELANALSYCHS

KRVIHRDIKPENLLLGSAGELKIADFGWSVHAPSSRRTDLCGTLDYLPPEMIEG

RMHDEKVDLWSLGVLCYEFLVGKPPFEANTYQETYKRISRVEFTFPDFVTEG

ARDLISRLLKHNPSQRPMLREVLEHPWITANSSKPSNCQNKESASK
```

This protein will be referred to in the text as MGSS-6His-SSGLVPRGSHM-[T287D]Aurora A(113–400)

```
[T287D]Aurora A(122-400)
MGSSHHHHHHSSGLVPRGSHMSKKRQWALEDFEIGRPLGKGKFGNVYLARE     (SEQ ID NO.: 16)

KQSKFILALKVLFKAQLEKAGVEHQLRREVEIQSHLRHPNILRLYGYFHDATR

VYLILEYAPLGTVYRELQKLSKFDEQRTATYITELANALSYCHSKRVIHRDIKP

ENLLLGSAGELKIADFGWSVHAPSSRRTDLCGTLDYLPPEMIEGRMHDEKVD

LWSLGVLCYEFLVGKPPFEANTYQETYKRISRVEFTFPDFVTEGARDLISRLLK

HNPSQRPMLREVLEHPWITANSSKPSNCQNKESASK
```

This protein will be referred to in the text as MGSS-6His-SSGLVPRGSHM-[T287D]Aurora A(122–400)

Protein Expression pTB375NBSE carrying the [T287D] Aurora A (94–402) sequence were transfected into *E. coli* BL21(DE3) pLys S (genotype: B F⁻ dcm ompT hsdS($r_B^-m_B^-$) gal □(DE3) [pLysS Camʳ]). The strain was grown for 16 h (LB medium containing tetracycline (10 µg/mL) and chloramphenicol (34 µg/mL) at 30° C. in shake flasks to $OD_{550nm}$~5. This culture was inoculated into high biomass medium containing tetracycline (10 µg/mL) and chloramphenicol (34 µg/mL), in a 20 L fermenter (B. Braun, Melsungen, Germany). Cells were grown aerobically in fed batch culture at 30° C., pH 6.7 with dissolved oxygen tension maintained at 50% air saturation. Expression of 6His-[T287D] Aurora A (94–402) was induced 12 hours post inoculation ($OD_{550nm}$~13) with 0.40 mM isopropyl-β-D-thiogalactopyranoside (IPTG), and cells harvested 3.0 hours later ($OD_{550nm}$~33) by batch centrifugation (7,000×g at 4° C. for 30 min).

pET28a carrying the [T287D]Aurora A(122–400) sequence was transfected into *E coli* DS410 (DE3) (a derivative of the original minicell-producing strain P678–54). The strain was grown for 30 h (M9 glucose medium containing kanamycin (25 µg/mL) at 37° C. in shake flasks to $OD_{550nm}$~1.4. This culture was inoculated into high biomass medium containing kanamycin (25 µg/mL) in a 20 L fermenter (B. Braun, Melsungen, Germany). Cells were grown aerobically in fed batch culture at 30° C., pH 6.7 with dissolved oxygen tension maintained at 50% air saturation. Expression of MGSS-6His-SSGLVPRG-SHM-[T287D]Aurora A(122–400) (SEQ ID NO.: 16) was induced 16 hours post inoculation ($OD_{550nm}$~19) with 0.10 mM isopropyl-β-D-thiogalactopyranoside (IPTG), and cells harvested 23 hours later ($OD_{550nm}$~26) by batch centrifugation (7,000×g at 4° C. for 30 min).

Definition of Kinase Domain Fragment

MG-6His-GS-[T287D]Aurora A(94–402) (SEQ ID NO.: 4) was purified from *E. coli* cell paste by Ni-NTA Agarose chromatography followed by size exclusion chromatography. The solution properties of this protein were found to be unfavourable for structural studies. Limited proteolysis of MG-6His-GS-[T287D]Aurora A(94–402) (SEQ ID NO.: 4) was used to identify fragments of the Aurora A kinase domain with superior solution properties. Aliquots of MG-6His-GS-[T287D]Aurora A(94–402) (SEQ ID NO.: 4) were subjected to proteolytic digestion with trypsin, thermolysin or endoproteinase Glu-C (V8). Protein fragments were identified by analysis with Coomassie-stained SDS PAGE, electrospray mass spectrometry (ESMS) and N-terminal sequencing. Cleavage and purification was performed at sufficient scale to produce appropriate quantities of [T287D]Aurora A (122–396) for crystallisation, as detailed below. Characterization of these fragments of Aurora A was used to design additional constructs, including MGSS-6His-SSGLVPRGSHM-[T287D]Aurora-A(122–400) (SEQ ID NO.: 16). The molecular biology procedures used to generate MGSS-6His-SSGLVPRGSHM-[T287D]Aurora-A (122–400) (SEQ ID NO.: 16) are given in the Molecular Biology section of Example 1.

Lysis of *E. coli* Containing MG-6His-GS-[T287D]Aurora A(94–402)

The following procedures were performed at 4° C. unless otherwise stated. *E. coli* cell paste (200 g) was resuspended using a Kinematica PT6000 homogeniser (Kinematica GMBH, Basel, Switzerland) in 1.01 of lysis buffer (40 mM HEPES, 200 mM NaCl, 2 mM imidazole, 2 mM 2-mercaptoethanol, 1 mM benzamidine, pH 7.4). The cells were lysed using an Avestin EmulsiFlex ñC5 (Avestin, Inc., Ottawa, Canada), using a single pass at an average pressure of 10,000 psi. The resulting lysate was centrifuged at 17,000×g (average) for 90 min before aspirating the supernatant and discarding the pellet.

Lysis of *E. coli* Containing MG-6His-GS-[T287D]Aurora A(94–402)

The following procedures were performed at 4° C. unless otherwise stated. *E. coli* cell paste (200 g) was resuspended using a Kinematica PT6000 homogeniser (Kinematica GMBH, Basel, Switzerland) in 1.01 of lysis buffer (40 mM HEPES, 200 mM NaCl, 2 mM imidazole, 2 mM 2-mercaptoethanol, 1 mM benzamidine, pH 7.4). The cells were lysed using an Avestin EmulsiFlex ñC5 (Avestin, Inc., Ottawa, Canada), using a single pass at an average pressure of 10,000 psi. The resulting lysate was centrifuged at 17,000×g (average) for 90 min before aspirating the supernatant and discarding the pellet.

The following procedures were performed at 4° C. unless otherwise stated. A 26 mm diameter chromatography column packed with 25 mL Qiagen Ni NTA-Agarose (Qiagen GMBH, Hilden, Germany) was equilibrated with 10 column volumes of lysis buffer before loading lysate supernatant containing MG-6His-GS-[T287D]Aurora A(94–402) (SEQ ID NO.: 4) onto the column at a flow rate of 0.9 mL/min. Using a flow rate of 2.0 mL/min the column was washed with 10 column volumes of wash buffer (40 mM HEPES, 20 mM imidazole, 2 mM 2-mercaptoethanol, pH 7.5) to remove weakly bound or non-specifically bound impurities. Elution of bound protein was effected using elution buffer (40 mM HEPES, 400 mM imidazole, 2 mM 2-mercaptoethanol, pH 7.5) at 2.0 mL/min. Eluted material was flowed through a second chromatography column (26 mm diameter, packed with 25 mL Pharmacia Q Sepharose Fast Flow (Amersham Pharmacia Biotech, Uppsala, Sweden) previously equilibrated with 10 column volumes of wash buffer). Fractions of 10.0 mL were collected, and after analysis by Coomassie-stained SDS PAGE, those fractions containing significant amounts of MG-6His-GS-[T287D]Aurora A(94–402) were pooled. At this stage the pool (approximately 200 mL) was stored in an airtight container at 4° C. for up to seven days.

From this stage forward, all procedures were carried out at room temperature, unless otherwise stated. A Pharmacia HiPrep 16/60 Sephacryl S-100 pre-packed size exclusion column was equilibrated in running buffer (40 mM HEPES pH7.5, 350 mM NaCl, 2 mM dithiothreitol (DTT)). The column was run at a flowrate of 1.0 mL/min. A 10 mL sample of the MG-6His-GS-[T287D]Aurora A(94–402) (SEQ ID NO.: 4) pool was centrifuged (31,000×g, 4° C., 60 min) and loaded onto the column. The fractions (2.0 mL) were analysed by Coomassie-stained SDS PAGE, and those containing MG-6His-GS-[T287D]Aurora A(94–402) (SEQ ID NO.: 4) were pooled.

Limited proteolysis at room temperature was carried out on the size exclusion chromatography-purified pool of MG-6His-GS-[T287D]Aurora A(94–402) (SEQ ID NO.: 4), whose concentration was 1 mg/mL. Using a mass ratio of 1 part protease to 100 parts MG-6His-GS-[T287D]Aurora A(94–402) (SEQ ID NO.: 4), endoproteinase Glu-C from Staphylococcus aureus V8 (Boehringer Mannheim UK, Lewes, Sussex, UK) was added to the pool. Proteolysis was allowed to continue for between 3 and 7 h.

A chromatography column was packed with a mixture of Pharmacia Sephacryl S-100 HR and Pharmacia Q-Sepharose high performance in the ratio of 9:1 v/v respectively (referred to as 'the S-100/Q column'). The column volume was 130 mL. It was equilibrated and run in S-100/Q running buffer (40 mM HEPES pH7.5, 50 mM NaCl, 2 mM dithiothreitol) at a flowrate of 1.0 mL/min. A sample of the proteolysed pool (8 mL) was loaded onto the S-100/Q column and 2.0 mL fractions were collected. Fractions were analysed by Coomassie-stained SDS PAGE, and those containing significant quantities of pure [T287D] Aurora A(122–396) were pooled. A sample of the pool was analysed by LC-ESMS using a Micromass LCT in conjunction with a Waters Alliance HPLC (Micromass, Manchester, UK). A further sample of the pool was subjected to N-terminal sequencing. Once the identity of the cleaved protein had been confirmed as [T287D]Aurora A(122–396), it was submitted for crystallisation.

Preparation of GSHM-[T287D]Aurora A(122–400)

The following procedures were performed at 4° C. unless otherwise stated. A 26 mm diameter chromatography column packed with 15 mL Qiagen Ni NTA-Agarose (Qiagen GMBH, Hilden, Germany) was equilibrated with 10 column volumes of lysis buffer before loading lysate supernatant containing MGSS-6His-SSGLVPRGSHM-[T287D]Aurora-A(122–400) (SEQ ID NO.: 16) onto the column at a flow rate of 1.0 mL/min. Using a flow rate of 2.0 mL/min the column was washed with 7 column volumes of wash buffer (40 mM HEPES, 200 mM NaCl, 10 mM $MgCl_2$, 20 mM imidazole, 2 mM 2-mercaptoethanol, pH 7.5) to remove weakly bound or non-specifically bound impurities. Elution of bound protein was effected using elution buffer (40 mM HEPES, 400 mM imidazole, 10 mM $MgCl_2$, 2 mM 2-mercaptoethanol, pH 7.5) at 2.0 mL/min. Fractions of 10.0 mL were collected, and after analysis by Coomassie-stained SDS PAGE, those fractions containing significant amounts of MGSS-6His-SSGLVPRGSHM-[T287D]Aurora-A (122–400) (SEQ ID NO.: 16) were pooled.

From this stage in the purification onward, all procedures were carried out at room temperature unless otherwise stated. A Pharmacia HiPrep 26/10 Fast Desalting pre-packed column was equilibrated in running buffer (40 mM HEPES pH7.4, 150 mM NaCl, 2 mM 2-mercaptoethanol). The column was run at a flowrate of 3.0 mL/min. A 10 mL sample of the MGSS-6His-SSGLVPRGSHM-[T287D]Aurora-A(122–400) (SEQ ID NO.: 16) pool was filtered (0.22 μm) and loaded onto the column. Fractions were collected, and those containing the most concentrated amounts of MGSS-6His-SSGLVPRGSHM-[T287D]Aurora-A (122–400) (SEQ ID NO.: 16) were pooled.

Bovine thrombin (500 units, Amersham Pharmacia Biotech) was added to the pool of 50 mg (+/−20%) of purified MGSS-6His-SSGLVPRGSHM-[T287D]Aurora-A (122–400) (SEQ ID NO.: 16) whose concentration was 1 mg/mL. Specific proteolytic cleavage was allowed to proceed to completion at 4° C., producing the truncated mutant GSHM-[T287D]Aurora A(122–400).

A Pharmacia HiPrep 16/60 Sephacryl S-100 pre-packed size exclusion column was equilibrated in running buffer (40 mM HEPES pH7.4, 50 mM NaCl, 1 mM dithiothreitol). The column was run at a flowrate of 1.0 mL/min. A 10 mL sample of the GSHM-[T287D]Aurora A(122–400) pool was filtered (0.22 μm) and loaded onto the column. Fractions (2.0 mL) were analysed by Coomassie-stained SDS PAGE, and those containing GSHM-[T287D]Aurora A(122–400) were pooled, and submitted for crystallisation.

Analysis

For SDS PAGE all samples were diluted in Laemmli buffer containing □-mercaptoethanol, boiled for 2 minutes and loaded onto a 8–16% gradient, 1.5 mm thickness×10 well NOVEX gel (NOVEX, San Diego, Calif.). Gels were stained with Coomassie blue R-250. Edman degradation was carried out on a Perkin Elmer 477A peptide sequencer (Applied Biosystems, Foster City, Calif.) with on-line detection of PTH amino acids. Mass spectra were acquired using a Micromass LCT with electrospray source (Micromass, Manchester, UK) and on-line Waters 2790 Alliance delivery system (Waters, Milford, Mass.). Protein was loaded directly on to a Phenomenex Jupiter 5μ C5 300_150×2.00 mm reverse phase column equilibrated in Milli Q water (Millipore, Bedford, Mass.), 2.7% acetonitrile, 0.1% trifluoroacetic acid, and the column was developed with a 2.7% to 90% acetonitrile gradient over 30 minutes at a flowrate of 80 μl/min. A fraction (approximately 25%) of the eluted proteins passed into the mass spectrometer.

EXAMPLE 2

Crystallisation of [T287D] Aurora A Catalytic Domain Constructs

The [T287D] Aurora A(122–396):AMPPNP complex was crystallized at 15° C. by the method of hanging-drop vapour diffusion. The protein [T287D] Aurora A (122–396) was concentrated to ~10 mg/mL solution (in 40 mM HEPES pH 7.4, 2 mM DTT, 50 mM NaCl), 5 mM AMP-PNP was then added to this solution and the complex was incubated on ice for 30 minutes. Prior to setting up crystallization trials this complex solution was microfuged for 10 minutes. The drops contained a 1:1 by volume mixture of complex solution and reservoir buffer (0.2M $K_2HPO_4$, 1.6M $NaH_2PO_4$, 0.1M phosphate/citrate buffer pH 3.8) giving a final 4 μl drop volume. The [T287D] Aurora(122–396)-AMP-PNP crystals belong to space group $P3_221$ with unit cell dimensions a=b=86.55 Å, c=78.34 Å, and α=β=90°, γ=120°, and contain 1 complex molecule per asymmetric unit. Before data collection, the crystals were transferred briefly (for about 20 seconds) to a cryobuffer containing 0.2M $K_2HPO_4$, 1.6M $NaH_2PO_4$, 0.1M phosphate citrate pH 3.8, 30% glycerol before being cooled to 100 K in a nitrogen gas stream.

The GSHM-[T287D] Aurora A(122–400) complex with the chemically synthesized inhibitor of formula II was crystallized as follows. Preparation of compound of formula II is described under example 19 in patent publication number WO 01/21597, publication date 29 Mar., 2001 (application number PCT/GB00/03593, international filing date 19 Sep., 2000). The compound was added at 5 mM to a solution containing protein (GSHM-[T287D] Aurora A(122–400) at 10 mg/ml, 40 mM HEPES pH7.5, 50 mM NaCl, and 1 mM 2-mercaptoethanol. Drops were formed by mixing 1:1 volumes of protein complex solution and a reservoir solution containing 22% PEG 4000 and 0.2M ammonium sulphate. Crystallisation was achieved by hanging drop vapour diffusion at 15° C. Data were collected at room temperature from a crystal mounted in a capillary. The crystal could be translated in the X-ray beam to allow multiple exposures. The Aurora A-inhibitor crystals are of space group $P2_1$ with unit cell dimensions a=52.6, b=88.4, c=67.8 Å, α=γ=90 and β=90.01°, and contain two complex molecules in the asymmetric unit.

EXAMPLE 3

Structure Determination of [T287D] Aurora A Catalytic Constructs

Diffraction data were collected at beamline PX9.6 at the SRS, Daresbury on an ADSC Quantum 4 CCD detector. The data were indexed and integrated with the program Mosflm and scaled with the program SCALA (CCP4). Molecular replacement and rigid body refinement to a resolution of 3.0 Å were carried out using the program AMoRe. A search model was derived from mouse PKA, truncating the model at residues 32 to 310 and replacing all non-identical residues with Ala. 5% of the data were reserved at this stage as a cross-validation set and the initial model underwent torsion angle simulated annealing in the program CNX using a maximum likelihood target and an overall anisotropic temperature factor correction. The model then underwent iterative rounds of manual rebuilding and simulated annealing until the working R-factor fell below 30%, at which point restrained isotropic individual temperature factor refinement was carried out. Concurrent building of both inhibitor complexes with the same Aurora protein in different crystal forms proved very instructive when it came to clarification of regions that were difficult to interpret. Further iterative rebuilding and addition of waters was carried out until the free R factor converged.

Crystallographic data and refinement statistics are given in tables 4 and 5.

TABLE 4

Aurora-AMPPNP complex data and refinement statistics.

| | |
|---|---|
| Space Group | $P3_221$ |
| Cell constants | a = b = 86.55, c = 78.34 Å α = β = 90, γ = 120° |
| Reflections | 62278 |
| Independent Reflections | 17003 |

TABLE 4-continued

Aurora-AMPPNP complex data and refinement statistics.

| | |
|---|---|
| $R_{sym}$ (2.25–2.2 Å) | 3.6% (32.6%) |
| Resolution (Å) | 38–2.2 |
| I/sigI (2.25–2.2 Å) | 19.3 (3.0) |
| Completeness (2.25–2.2 Å) | 97.1% (83.2%) |
| $R_{(free)}$, $R_{(work)}$ | 23%, 28% |
| Rmsd (bond lengths) | 0.006 |
| Rmsd (bond angles) | 1.2 |

TABLE 5

Aurora-inhibitor complex data and refinement statistics:

| | |
|---|---|
| Space Group | $P2_1$ |
| Cell constants | a = 52.6, b = 88.4, c = 67.8 Å □ = □ = 90, β = 90.01° |
| Reflections | 36664 |
| Independent Reflections | 26294 |
| $R_{sym}$ (2.25–2.1 Å) | 6.6% (30.5%) |
| Resolution (Å) | 52–2.1 |
| I/sigI (2.25–2.1 Å) | 7 (2.1) |
| Completeness (2.25–2.1 Å) | 72.5% (25.5%) |
| $R_{(free)}$, $R_{(work)}$ | 22%, 27% |
| Rmsd (bond lengths) | 0.019 |
| Rmsd (bond angles) | 1.8 |

EXAMPLE 4

Description of the Structure of Aurora A Kinase

The structure of [T287D] Aurora A (122–396) in a binary complex with the ATP analogue AMP-PNP has been solved to a resolution of 2.2 Å. The structure of GSHM-[T287D] Aurora A(122–400) in a binary complex with the synthetic inhibitor of formula II has been solved to a resolution of 2.1 Å. The structures contain the residues of the kinase catalytic domain. The kinase domain of [T287D] Aurora A shows the bilobal structure characteristic of protein kinases with the ATP and inhibitor binding site situated between the two lobes. The N-terminal domain (lobe) comprises a twisted β-sheet and a single kinked helix. The C-terminal lobe comprises mainly helices but also includes a small region of β-sheet. Parts of the polypeptide chain are disordered. In particular, the activation loop, residues 279 to 290 containing the T287D substitution, is not visible in the electron density. The disordered nature of the activation loop is a common feature in kinase crystal structures.

Figure 3:
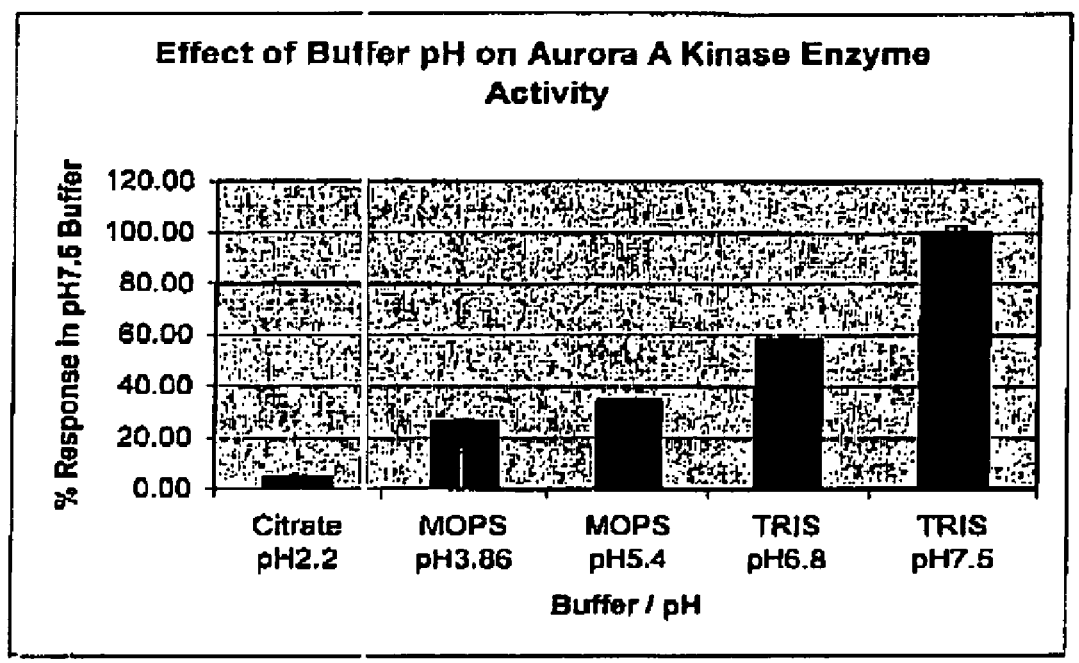
FIG. 3 is a graph of the activity of [T287D]Aurora A as a function of pH.

The structure adopts a conformation typical of catalytically inactive kinases, despite the introduction of the constitutively active mutation, T287D. It is thought that the acidic pH at which the crystallisation experiments were carried out will result in the introduced aspartate being protonated, and thus no longer able to mimic the phosphorylated threonine in the wild-type activated protein. The kinase activity of the mutant enzyme towards a peptide substrate was measured at varying pH values, as shown in FIG. 3, and indeed, activity is significantly reduced falls as the pH is lowered.

The inactive conformation seen in our [T287D] Aurora A complexes is clearly capable of binding the inhibitor of formula II and the ATP analogue, and therefore allows structure-based design, which needs to make allowances for the flexibility and conformational changes that the kinase may undergo, for example, between its active and inactive states. In the case of the inhibitor, the inactive conformation may be forced by the steric bulk of the inhibitor.

Aurora A is quite closely related to the cyclic AMP-dependent protein kinase, also known as PKA, and the structures superpose with an overall rmsd of 1.4 Å. The ATP binding cleft of Aurora A is more extended than the equivalent cleft in PKA on account of a shift in the position of a helix, formed by residues 174 to 182 in the N-terminal lobe. In the structure of [T287D] Aurora A, the helix is displaced approximately 3 Å away from the ATP binding pocket compared with the equivalent helix in PKA, thus extending the length of the cleft between the two lobes. The extended cleft can be exploited by elongated inhibitor molecules such as that of formula II and may be key to the design of specific inhibitors. The conserved DFG motif (Asp273Phe274Glu275) preceding the activation loop is apparent in the electron density. This region contains an aspartate residue necessary for catalysis. The glycine-rich loop, which is important for ATP binding in all kinases, shows good electron density throughout the main chain atoms, although the temperature factors are quite high, indicating significant mobility of the loop. However, the density for the side chains of some residues, such as Phe 143, is poor, and these are likely to adopt multiple conformations.

The AMP-PNP molecule adopts a dual conformation (FIG. 1). The adenine ring and ribose moiety in both conformations occupy similar locations with respect to the kinase molecule. Classical hydrogen-bonding interactions are made between the adenine ring and the hinge region of Aurora A. These are between N6 of the adenine ring and the main chain oxygen of Glu 210 and between N1 of the adenine ring and the main chain nitrogen of Ala 212. The differences in the two conformations arise from torsion angle differences between the ribose ring and the phosphate groups and also in torsion angles of phosphorus-oxygen bonds. In one conformation, the β-phosphate group forms a hydrogen bond to a water molecule, which, in turn, forms a hydrogen bond to Asp 273. In the other conformation, the β-phosphate forms hydrogen bonds with Ser 277 and Gln 260. In both conformations the α-phosphate forms a salt-bridge with Lys 161, and also forms a hydrogen bond with the main chain nitrogen of Val 278. No electron density for the γ-phosphate is present in either conformation suggesting a high degree of disorder. This disorder of the γ-phosphate has also been seen in other crystal structures, for example that of Checkpoint kinase.

The molecule of formula II also binds in the ATP binding site in the cleft between the two domains in the Aurora A kinase molecule. The molecule of formula II adopts an extended conformation, which demonstrates the extent of the available binding pocket (FIG. 2b). A classical kinase (adenine-mimetic) inhibitor hydrogen bond interaction with the main chain peptides is made between N(17) in the inhibitor and the amide of amino acid residue 212. The piperidine moiety of the inhibitor extends into solvent (on the left in FIG. 2b). At the other extreme of the inhibitor (right end in FIG. 2b) the benzoyl moiety fits into a hydrophobic pocket formed by residues Leu163, Leu181, Leu195, Leu207 and Trp276. This inhibitor represents a more interesting start point for design than AMPPNP since protein regions more remote from the ATP location are explored, and this may help achieve specificity.

What we claim is:

1. A crystalline form of a human Aurora A kinase polypeptide consisting of the catalytic domain of human Aurora A kinase comprising-amino acids 22 to 296 of SEQ ID NO:16, wherein said amino acids are equivalent to amino acids 122 to 396 of full length human Aurora A kinase, which is complexed with an Aurora A kinase inhibitor, wherein the inhibitor is

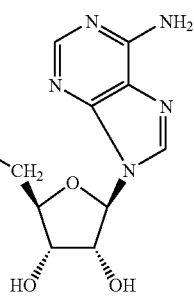

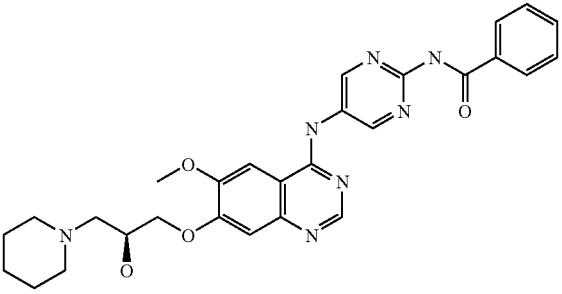

Chiral and wherein the crystalline form is further characterized as having the space group of P3$_2$21 and comprises the unit cell dimensions of a=b=86.55 Å, c=78.34 Å, α=β=90° and γ=120°.

2. A crystalline form of a human Aurora A kinase polypeptide consisting of the catalytic domain of human Aurora A kinase comprising-amino acids 22 to 300 of SEQ ID NO:16, wherein said amino acids are equivalent to amino acids 122 to 400 of full length human Aurora A kinase, which is complexed with an Aurora A kinase inhibitor, wherein the inhibitor is and wherein the crystalline form is further characterized as having the space group of P2$_1$ and comprises the unit cell dimensions of a=52.6 Å, b=88.4 Å, c=67.8 Å, α=γ=90° and β=90.01°.

3. A crystalline form according to claim 1 or claim 2, wherein the catalytic domain comprises a binding site, wherein the binding site is defined by the x,y,z-coordinates of atoms in the set of amino acid residues given by the list: Arg136, Leu138, Gly139, Lys140, Gly141, Val146, Ala159, Lys161, Leu163, Val177, Glu180, Val181, Ile183, Gln184, Leu193, Leu195, Leu207, Leu209, Glu210, Tyr211, Ala212, Pro213, Leu214, Gly215, Thr216, Arg219, Glu259, Asn260, Leu262, Ala272, Asp273, Phe274, Gly275, Trp276, Ser277, Val278, and His279, wherein the atomic coordinates are listed in Tables 1 and 2; or wherein the binding site is defined by the x,y,z-coordinates of atoms in the set of amino acid residues given by the list: Arg136, Leu138, Gly139, Val146, Ala159, Lys161, Leu163, Ile183, Gln184, Leu193, Leu207, Leu209, Glu210, Tyr211, Ala212, Pro213, Leu214, Gly215, Thr216, Arg219, Glu259, Asn260 and Leu262, and wherein the x,y,z-coordinates are within a root mean square deviation of not more than 1.0 Å of the coordinates listed in Tables 1 and 2.

* * * * *

SEQUENCE LISTING

<160> NUMBER OF SEQ ID NOS: 16

<210> SEQ ID NO 1
<211> LENGTH: 35
<212> TYPE: DNA
<213> ORGANISM: Unknown
<220> FEATURE:
<223> OTHER INFORMATION: 5' PCR primer

<400> SEQUENCE: 1
gatcgatcgg atccacccaa aagagcaagc agccc                              35

<210> SEQ ID NO 2
<211> LENGTH: 39
<212> TYPE: DNA
<213> ORGANISM: Unknown
<220> FEATURE:
<223> OTHER INFORMATION: 3' PCR primer

<400> SEQUENCE: 2
tgacgctagg atcccctaag actgtttgct agctgattc                          39

<210> SEQ ID NO 3
<211> LENGTH: 30
<212> TYPE: DNA
<213> ORGANISM: Unknown
<220> FEATURE:
<223> OTHER INFORMATION: pTB375NBSE subsequence

<400> SEQUENCE: 3
atgggccatc atcatcatca tcacggatcc 30

<210> SEQ ID NO 4
<211> LENGTH: 10
<212> TYPE: PRT
<213> ORGANISM: Unknown
<220> FEATURE:
<223> OTHER INFORMATION: Tag for protein purification

<400> SEQUENCE: 4

Met Gly His His His His His Gly Ser
1               5                   10

<210> SEQ ID NO 5
<211> LENGTH: 319
<212> TYPE: PRT
<213> ORGANISM: Artificial Sequence
<220> FEATURE:
<223> OTHER INFORMATION: MG-6His-GS-[T287D]Aurora A(94-402)

<400> SEQUENCE: 5

Met Gly His His His His His Gly Ser Thr Gln Lys Ser Lys Gln
1               5                   10                  15

Pro Leu Pro Ser Ala Pro Glu Asn Asn Pro Glu Glu Glu Leu Ala Ser
            20                  25                  30

Lys Gln Lys Asn Glu Gly Ser Lys Lys Arg Gln Trp Ala Leu Glu Asp
        35                  40                  45

Phe Glu Ile Gly Arg Pro Leu Gly Lys Gly Lys Phe Gly Asn Val Tyr
50                  55                  60

Leu Ala Arg Glu Lys Gln Ser Lys Phe Ile Leu Ala Leu Lys Val Leu
65                  70                  75                  80

Phe Lys Ala Gln Leu Glu Lys Ala Gly Val Glu His Gln Leu Arg Arg
                85                  90                  95

Glu Val Glu Ile Gln Ser His Leu Arg His Pro Asn Ile Leu Arg Leu
            100                 105                 110

Tyr Gly Tyr Phe His Asp Ala Thr Arg Val Tyr Leu Ile Leu Glu Tyr
        115                 120                 125

Ala Pro Leu Gly Thr Val Tyr Arg Glu Leu Gln Lys Leu Ser Lys Phe
    130                 135                 140

Asp Glu Gln Arg Thr Ala Thr Tyr Ile Thr Glu Leu Ala Asn Ala Leu
145                 150                 155                 160

Ser Tyr Cys His Ser Lys Arg Val Ile His Arg Asp Ile Lys Pro Glu
                165                 170                 175

Asn Leu Leu Leu Gly Ser Ala Gly Glu Leu Lys Ile Ala Asp Phe Gly
            180                 185                 190

Trp Ser Val His Ala Pro Ser Ser Arg Arg Thr Asp Leu Cys Gly Thr
        195                 200                 205

Leu Asp Tyr Leu Pro Pro Glu Met Ile Glu Gly Arg Met His Asp Glu
    210                 215                 220

Lys Val Asp Leu Trp Ser Leu Gly Val Leu Cys Tyr Glu Phe Leu Val
225                 230                 235                 240

Gly Lys Pro Pro Phe Glu Ala Asn Thr Tyr Gln Glu Thr Tyr Lys Arg
                245                 250                 255

Ile Ser Arg Val Glu Phe Thr Phe Pro Asp Phe Val Thr Glu Gly Ala
            260                 265                 270

Arg Asp Leu Ile Ser Arg Leu Leu Lys His Asn Pro Ser Gln Arg Pro
        275                 280                 285

Met Leu Arg Glu Val Leu Glu His Pro Trp Ile Thr Ala Asn Ser Ser
    290                 295                 300

Lys Pro Ser Asn Cys Gln Asn Lys Glu Ser Ala Ser Lys Gln Ser
305                 310                 315

<210> SEQ ID NO 6
<211> LENGTH: 28
<212> TYPE: DNA
<213> ORGANISM: Unknown
<220> FEATURE:
<223> OTHER INFORMATION: 5' PCR primer

<400> SEQUENCE: 6
catatgctgg catcaaaaca gaaaaatg                                28

<210> SEQ ID NO 7
<211> LENGTH: 26
<212> TYPE: DNA
<213> ORGANISM: Unknown
<220> FEATURE:
<223> OTHER INFORMATION: 5' PCR primer

<400> SEQUENCE: 7
catatgtcaa aaagaggca gtgggc                                  26

<210> SEQ ID NO 8
<211> LENGTH: 34
<212> TYPE: DNA
<213> ORGANISM: Unknown
<220> FEATURE:
<223> OTHER INFORMATION: 3' primer

<400> SEQUENCE: 8
ggatcctcat ttgctagctg attctttgtt ttgg                        34

<210> SEQ ID NO 9
<211> LENGTH: 20
<212> TYPE: DNA
<213> ORGANISM: Unknown
<220> FEATURE:
<223> OTHER INFORMATION: Primer T3

<400> SEQUENCE: 9
aattaaccct cactaaaggg                                        20

<210> SEQ ID NO 10
<211> LENGTH: 20
<212> TYPE: DNA
<213> ORGANISM: Unknown
<220> FEATURE:
<223> OTHER INFORMATION: Primer T7pro

<400> SEQUENCE: 10
taatacgact cactataggg                                        20

<210> SEQ ID NO 11
<211> LENGTH: 63
<212> TYPE: DNA
<213> ORGANISM: Unknown
<220> FEATURE:
<223> OTHER INFORMATION: pET28a subsequence

<400> SEQUENCE: 11
atgggcagca gccatcatca tcatcatcac agcagcggcc tggtgccgcg cggcagccat    60
atg                                                                  63

<210> SEQ ID NO 12
<211> LENGTH: 21
<212> TYPE: PRT
<213> ORGANISM: Unknown
<220> FEATURE:
<223> OTHER INFORMATION: pET28a subsequence

<400> SEQUENCE: 12

Met Gly Ser Ser His His His His His His Ser Ser Gly Leu Val Pro
1               5                   10                  15

Arg Gly Ser His Met
            20

<210> SEQ ID NO 13
<211> LENGTH: 6
<212> TYPE: PRT
<213> ORGANISM: Unknown
<220> FEATURE:
<223> OTHER INFORMATION: cleavage site

<400> SEQUENCE: 13

Leu Val Pro Arg Gly Ser
1               5

<210> SEQ ID NO 14
<211> LENGTH: 17
<212> TYPE: PRT
<213> ORGANISM: Unknown
<220> FEATURE:
<223> OTHER INFORMATION: excised sequence

<400> SEQUENCE: 14

Met Gly Ser Ser His His His His His His Ser Ser Gly Leu Val Pro
1               5                   10                  15

Arg

<210> SEQ ID NO 15
<211> LENGTH: 309
<212> TYPE: PRT
<213> ORGANISM: Artificial Sequence
<220> FEATURE:
<223> OTHER INFORMATION: MGSS-6His-SSGLVPRGSHM-[T287D]Aurora A(113-400)

<400> SEQUENCE: 15

Met Gly Ser Ser His His His His His His Ser Ser Gly Leu Val Pro
1               5                   10                  15

Arg Gly Ser His Met Leu Ala Ser Lys Gln Lys Asn Glu Glu Ser Lys
            20                  25                  30

Lys Arg Gln Trp Ala Leu Glu Asp Phe Glu Ile Gly Arg Pro Leu Gly
        35                  40                  45

Lys Gly Lys Phe Gly Asn Val Tyr Leu Ala Arg Glu Lys Gln Ser Lys
    50                  55                  60

Phe Ile Leu Ala Leu Lys Val Leu Phe Lys Ala Gln Leu Glu Lys Ala
65                  70                  75                  80

Gly Val Glu His Gln Leu Arg Arg Glu Val Glu Ile Gln Ser His Leu
                85                  90                  95

Arg His Pro Asn Ile Leu Arg Leu Tyr Gly Tyr Phe His Asp Ala Thr
            100                 105                 110

Arg Val Tyr Leu Ile Leu Glu Tyr Ala Pro Leu Gly Thr Val Tyr Arg
        115                 120                 125

-continued

```
Glu Leu Gln Lys Leu Ser Lys Phe Asp Glu Gln Arg Thr Ala Thr Tyr
    130                 135                 140

Ile Thr Glu Leu Ala Asn Ala Leu Ser Tyr Cys His Ser Lys Arg Val
145                 150                 155                 160

Ile His Arg Asp Ile Lys Pro Glu Asn Leu Leu Leu Gly Ser Ala Gly
                165                 170                 175

Glu Leu Lys Ile Ala Asp Phe Gly Trp Ser Val His Ala Pro Ser Ser
            180                 185                 190

Arg Arg Thr Asp Leu Cys Gly Thr Leu Asp Tyr Leu Pro Pro Glu Met
        195                 200                 205

Ile Glu Gly Arg Met His Asp Glu Lys Val Asp Leu Trp Ser Leu Gly
    210                 215                 220

Val Leu Cys Tyr Glu Phe Leu Val Gly Lys Pro Pro Phe Glu Ala Asn
225                 230                 235                 240

Thr Tyr Gln Glu Thr Tyr Lys Arg Ile Ser Arg Val Glu Phe Thr Phe
                245                 250                 255

Pro Asp Phe Val Thr Glu Gly Ala Arg Asp Leu Ile Ser Arg Leu Leu
            260                 265                 270

Lys His Asn Pro Ser Gln Arg Pro Met Leu Arg Glu Val Leu Glu His
        275                 280                 285

Pro Trp Ile Thr Ala Asn Ser Ser Lys Pro Ser Asn Cys Gln Asn Lys
    290                 295                 300

Glu Ser Ala Ser Lys
305

<210> SEQ ID NO 16
<211> LENGTH: 300
<212> TYPE: PRT
<213> ORGANISM: Artificial Sequence
<220> FEATURE:
<223> OTHER INFORMATION: MGSS-6His-SSGLVPRGSHM-[T287D]Aurora A(122-400)

<400> SEQUENCE: 16

Met Gly Ser Ser His His His His His His Ser Ser Gly Leu Val Pro
1               5                   10                  15

Arg Gly Ser His Met Ser Lys Lys Arg Gln Trp Ala Leu Glu Asp Phe
            20                  25                  30

Glu Ile Gly Arg Pro Leu Gly Lys Gly Lys Phe Gly Asn Val Tyr Leu
        35                  40                  45

Ala Arg Glu Lys Gln Ser Lys Phe Ile Leu Ala Leu Lys Val Leu Phe
    50                  55                  60

Lys Ala Gln Leu Glu Lys Ala Gly Val Glu His Gln Leu Arg Arg Glu
65                  70                  75                  80

Val Glu Ile Gln Ser His Leu Arg His Pro Asn Ile Leu Arg Leu Tyr
                85                  90                  95

Gly Tyr Phe His Asp Ala Thr Arg Val Tyr Leu Ile Leu Glu Tyr Ala
            100                 105                 110

Pro Leu Gly Thr Val Tyr Arg Glu Leu Gln Lys Leu Ser Lys Phe Asp
        115                 120                 125

Glu Gln Arg Thr Ala Thr Tyr Ile Thr Glu Leu Ala Asn Ala Leu Ser
    130                 135                 140

Tyr Cys His Ser Lys Arg Val Ile His Arg Asp Ile Lys Pro Glu Asn
145                 150                 155                 160

Leu Leu Leu Gly Ser Ala Gly Glu Leu Lys Ile Ala Asp Phe Gly Trp
                165                 170                 175
```

-continued

```
Ser Val His Ala Pro Ser Ser Arg Arg Thr Asp Leu Cys Gly Thr Leu
            180                 185                 190

Asp Tyr Leu Pro Pro Glu Met Ile Glu Gly Arg Met His Asp Glu Lys
        195                 200                 205

Val Asp Leu Trp Ser Leu Gly Val Leu Cys Tyr Glu Phe Leu Val Gly
    210                 215                 220

Lys Pro Pro Phe Glu Ala Asn Thr Tyr Gln Glu Thr Tyr Lys Arg Ile
225                 230                 235                 240

Ser Arg Val Glu Phe Thr Phe Pro Asp Phe Val Thr Glu Gly Ala Arg
                245                 250                 255

Asp Leu Ile Ser Arg Leu Leu Lys His Asn Pro Ser Gln Arg Pro Met
                260                 265                 270

Leu Arg Glu Val Leu Glu His Pro Trp Ile Thr Ala Asn Ser Ser Lys
        275                 280                 285

Pro Ser Asn Cys Gln Asn Lys Glu Ser Ala Ser Lys
        290                 295                 300
```